US010473643B2

(12) United States Patent
Housey et al.

(10) Patent No.: US 10,473,643 B2
(45) Date of Patent: Nov. 12, 2019

(54) COMPOUNDS AND METHODS OF IDENTIFYING, SYNTHESIZING, OPTIMIZING AND PROFILING PROTEIN MODULATORS

(71) Applicant: HMI Medical Innovations, LLC, Southfield, MI (US)

(72) Inventors: Gerard M. Housey, Southfield, MI (US); Monica E. Balash, Farmington Hills, MI (US)

(73) Assignee: HMI Medical Innovations, LLC, Southfield, MI (US)

( * ) Notice: Subject to any disclaimer, the term of this patent is extended or adjusted under 35 U.S.C. 154(b) by 0 days.

(21) Appl. No.: 16/003,516

(22) Filed: Jun. 8, 2018

(65) Prior Publication Data

US 2018/0356395 A1 Dec. 13, 2018

Related U.S. Application Data

(60) Continuation of application No. 15/462,115, filed on Mar. 17, 2017, now Pat. No. 10,018,619, which is a division of application No. 14/958,222, filed on Dec. 3, 2015, now Pat. No. 9,645,137, which is a division of application No. 13/873,740, filed on Apr. 30, 2013, now Pat. No. 9,222,933, which is a continuation of application No. 11/604,109, filed on Nov. 24, 2006, now Pat. No. 8,431,110, which is a continuation-in-part of application No. PCT/US2006/033890, filed on Aug. 29, 2006, which is a continuation-in-part of application No. PCT/US2005/018412, filed on May 23, 2005.

(60) Provisional application No. 60/739,477, filed on Nov. 23, 2005, provisional application No. 60/739,476, filed on Nov. 23, 2005, provisional application No. 60/741,767, filed on Dec. 2, 2005, provisional application No. 60/751,030, filed on Dec. 16, 2005, provisional application No. 60/783,106, filed on Mar. 13, 2006, provisional application No. 60/785,904, filed on Mar. 23, 2006, provisional application No. 60/785,817, filed on Mar. 23, 2006, provisional application No. 60/789,379, filed on Apr. 4, 2006.

(51) Int. Cl.
*G01N 33/50* (2006.01)
*C12Q 1/48* (2006.01)

(52) U.S. Cl.
CPC .......... *G01N 33/502* (2013.01); *C12Q 1/485* (2013.01); *G01N 33/5026* (2013.01); *G01N 33/5044* (2013.01); *G01N 2500/10* (2013.01)

(58) Field of Classification Search
CPC .................................................. G01N 33/502
See application file for complete search history.

(56) References Cited

U.S. PATENT DOCUMENTS

| | | | |
|---|---|---|---|
| 3,647,858 | A | 3/1972 | Hinkley et al. |
| 3,887,699 | A | 6/1975 | Yolles |
| 3,940,486 | A | 2/1976 | Fitzi |
| 4,180,662 | A | 12/1979 | Pfister et al. |
| 4,233,299 | A | 11/1980 | Trummlitz et al. |
| 4,480,038 | A | 10/1984 | Cheng |
| 4,500,637 | A | 2/1985 | Neville et al. |
| 4,532,204 | A | 7/1985 | Crespi et al. |
| 4,569,916 | A | 2/1986 | Penman et al. |
| 4,695,459 | A | 9/1987 | Steinman et al. |
| 4,701,406 | A | 10/1987 | Chou |
| 4,714,613 | A | 12/1987 | Shouval et al. |
| 4,736,866 | A | 4/1988 | Leder et al. |
| 4,761,371 | A | 8/1988 | Bell et al. |
| 4,857,637 | A | 8/1989 | Hammonds et al. |
| 4,859,585 | A | 8/1989 | Sonnenschein et al. |
| 4,859,609 | A | 8/1989 | Dull et al. |
| 4,910,132 | A | 3/1990 | Knight et al. |
| 4,929,616 | A | 5/1990 | Binder et al. |
| 4,980,281 | A | 12/1990 | Housey |
| 4,981,784 | A | 1/1991 | Evans et al. |
| 4,981,790 | A | 1/1991 | Haseltine et al. |
| 4,985,352 | A | 1/1991 | Julius et al. |
| 5,030,576 | A | 7/1991 | Dull et al. |
| 5,057,417 | A | 10/1991 | Hammonds et al. |

(Continued)

FOREIGN PATENT DOCUMENTS

| | | | |
|---|---|---|---|
| AU | 2004251641 | A1 | 6/2005 |
| AU | 2005244745 | A1 | 12/2005 |

(Continued)

OTHER PUBLICATIONS

International Preliminary Report on Patentability dated Jul. 2, 2008 in PCT/US2006/045394.

(Continued)

*Primary Examiner* — Paul V Ward

(74) *Attorney, Agent, or Firm* — Mueting, Raasch & Gebhardt, P.A.

(57) ABSTRACT

This invention relates to methods of identifying, synthesizing, optimizing and profiling compounds that are inhibitors or activators of proteins, both naturally occurring endogenous proteins as well as certain variant forms of endogenous proteins, and novel methods of identifying such variants. The method accelerates the identification and development of compounds as potential therapeutically effective drugs by simplifying the pharmaceutical discovery and creation process through improvements in hit identification, lead optimization, biological profiling, and rapid elimination of toxic compounds. Implementation results in overall cost reductions in the drug discovery process resulting from the corresponding increases in efficiency.

23 Claims, 17 Drawing Sheets

(56) References Cited

U.S. PATENT DOCUMENTS

| | | | |
|---|---|---|---|
| 5,138,072 | A | 8/1992 | Wagner |
| 5,145,842 | A | 9/1992 | Driedger et al. |
| 5,260,200 | A | 11/1993 | Kahn et al. |
| 5,266,464 | A | 11/1993 | Housey |
| 5,380,738 | A | 1/1995 | Norman et al. |
| 5,424,185 | A | 6/1995 | Lam et al. |
| 5,506,107 | A | 4/1996 | Cunningham et al. |
| 5,578,590 | A | 11/1996 | Grunicke et al. |
| 5,665,543 | A | 9/1997 | Foulkes et al. |
| 5,688,655 | A | 11/1997 | Housey |
| 5,741,641 | A | 4/1998 | Smart et al. |
| 5,821,072 | A | 10/1998 | Schwartz et al. |
| 5,858,701 | A | 1/1999 | White et al. |
| 5,877,007 | A | 3/1999 | Housey |
| 6,004,931 | A | 12/1999 | Cunningham et al. |
| 6,043,211 | A | 3/2000 | Williams et al. |
| 6,110,737 | A | 8/2000 | Escobedo et al. |
| 6,290,929 | B1 | 9/2001 | Camden |
| 6,660,737 | B2 | 12/2003 | Almstead et al. |
| 7,112,680 | B2 | 9/2006 | Hofmann et al. |
| 2003/0162222 | A1 | 8/2003 | Warmuth et al. |

FOREIGN PATENT DOCUMENTS

| | | | |
|---|---|---|---|
| CA | 1176565 | | 10/1984 |
| EA | 0158277 | A2 | 10/1985 |
| EP | 0058481 | A1 | 8/1982 |
| EP | 0133988 | A2 | 4/1985 |
| EP | 0171496 | A2 | 2/1986 |
| EP | 0214709 | A2 | 4/1986 |
| EP | 0184087 | A2 | 6/1986 |
| EP | 0187041 | A1 | 7/1986 |
| EP | 0219106 | A2 | 4/1987 |
| EP | 0246882 | A2 | 11/1987 |
| EP | 0247557 | A2 | 12/1987 |
| EP | 0249390 | A2 | 12/1987 |
| EP | 0251612 | A2 | 1/1988 |
| EP | 0325849 | B1 | 8/1989 |
| EP | 0327369 | A2 | 8/1989 |
| EP | 0194276 | B1 | 8/1993 |
| EP | 0695547 | A1 | 2/1996 |
| WO | WO 86/04613 | | 8/1986 |
| WO | WO 88/03168 | | 5/1988 |
| WO | WO 89/03687 | | 5/1989 |
| WO | WO 89/07654 | | 8/1989 |
| WO | WO 94/13635 | | 6/1994 |
| WO | WO 94/15932 | | 7/1994 |
| WO | WO 94/23714 | | 10/1994 |
| WO | WO 94/26731 | | 11/1994 |
| WO | WO 94/27980 | | 12/1994 |
| WO | WO 2001/094340 | A1 | 12/2001 |
| WO | WO 2002/009715 | A2 | 2/2002 |
| WO | WO 2002/102976 | | 6/2002 |
| WO | WO 2003/030909 | A1 | 4/2003 |
| WO | WO 2003/049698 | A2 | 6/2003 |
| WO | WO 2003/075828 | A2 | 9/2003 |
| WO | WO 2005/037801 | A1 | 4/2005 |
| WO | WO 2005/115992 | | 5/2005 |

OTHER PUBLICATIONS

Search Report dated Sep. 22, 2010 in related European Patent Application No. 05754265.6.

Australian patent application No. 567572, an English language version of EP 0133988, submitted on Apr. 14, 2011.

Australian publication No. AU-4105985, an English language version of EP 0158277, submitted on Apr. 14, 2011.

Office Action dated Jun. 30, 2011 in U.S. Appl. U.S. Appl. No. 12/085,484.

Response filed Dec. 30, 2011 in U.S. Appl. No. 12/085,484.

International Search Report and Written Opinion from PCT/US06/45394 filed Nov. 24, 2006.

Response to Written Opinion filed Feb. 7, 2008 in PCT/US06/45394.

IPRP from PCT/US06/45394 filed Nov. 24, 2006.

Office Action dated Feb. 1, 2012 in U.S. Appl. No. 12/085,484.

Acquafreda, D., et al, "Procarbazine, CCNU and Vincristine, also known as PCV," internet citation Feb. 26, 2002.

Adcock, I.M., et al., "Mechanisms of Steroid Action and Resistance in Inflammation", Journal of Endocrinology, vol. 178 (Sep. 2003) pp. 347-355.

Akiyama, S., et al., "Isolation and genetic characterization of human KB cell lines resistant to multiple drugs." Somat Cell Mol Genet (1985), vol. 11(2), pp. 117-126.

Akiyama, S., et al., "Synthetic isoprenoid photoaffinity labeling of P glycoprotein specific to multidrug resistant cells." Mol. Pharmacol. (1989), vol. 36, pp. 730-735.

Alberts, T., "Molecular Biology of the Cell," 3rd ed. (Garland Publishing, NY, USA 1994) p. 1072.

Alberts, T., "Molecular Biology of the Cell," 3rd ed. (Garland Publishing, NY, USA 1994) pp. 1264-1265.

Allen, P.B., et al., "An Activating Mutation in the ATP Binding Site of the ABL Kinase Domain", The Journal of Biological Chemistry, vol. 271 (Aug. 9, 1996) pp. 19585-19591.

Ammann, A.J., et al., "Acquired immune dysfunction in homosexual men: immunologic profiles." Clin. Immunol. Immunopathol. (1983), vol. 27(3), pp. 315-325.

Angehrn, P., "Antibacterial properties of carumonam (Ro 17 2301, AMA 1080), a new sulfonated monocyclic beta lactam antibiotic." Chemotherapy (1985), vol. 31, pp. 440-450.

Armelin, H.A., et al., "Functional role for c myc in mitogenic response to platelet derived growth factor." Nature (1984), vol. 310, pp. 655-660.

Ashendel, C.L., "The phorbol ester receptor: a phospholipid regulated protein kinase." Biochim. Biophys. Acta (1985), vol. 822, pp. 219-242.

Ashkenazi, A., et al., "An M2 muscarinic receptor subtype coupled to both adenylyl cyclase and phosphoinositide turnover." Science (1987), vol. 238, pp. 672-675.

Ayusawa, D., et al., "Selection of mammalian thymidine auxotrophic cell mutants defective in thymidylate synthase by their reduced sensitivity to methotrexate." Somatic Cell Genet (1981), vol. 7, pp. 523-534.

Ayusawa, D., et al., "Single step selection of mouse FM3A cell mutants defective in thymidylate synthetase." Somatic Cell Genet. (1980), vol. 6, pp. 261-270.

Balzarini, J., et al., "Murine mammary FM3A carcinoma cells transformed with the herpes simplex virus type 1 thymidine kinase gene are highly sensitive to the growth-inhibitory properties of (E)-5-(2-bromovinyl)-2'-deoxyuridine and related compounds." FEBS Lett. (1985), vol. 185, pp. 95-100.

Balzarini, J., et al., "Strategies for the measurement of the inhibitory effects of thymidine analogs on the activity of thymidylate synthase in intact murine leukemia L1210 cells." Biochim Biophys Acta (1984), vol. 785, pp. 36-45.

Balzarini, J., et al., "Thymidylate synthetase deficient mouse FM3A mammary carcinoma cell line as a tool for studying the thymidine salvage pathway and the incorporation of thymidine analogues into host cell DNA." Biochem. J. (1984), vol. 217, pp. 245-252.

Balzarini, J., et al., "Thymidylate synthase is the principal target enzyme for the cytostatic activity of (E) 5 (2 bromovinyl) 2' deoxyuridine against murine mammary carcinoma (FM3A) cells transformed with the herpes simplex virus type 1 or type 2 thymidine kinase gene." Mol. Pharmacol. (1987), vol. 32, pp. 410-416.

Balzarini, J., et al., "Thymidylate synthetase positive and negative murine mammary FM3A carcinoma cells as a useful system for detecting thymidylate synthetase inhibitors." FEBS Lett. (1984), vol. 173, pp. 227-232.

Bardon, S., et al., "The antiproliferative effect of tamoxifen in breast cancer cells: mediation by the estrogen receptor." Mol. Cell. Endocrinol. (1984), vol. 35, pp. 89-96.

Bardon, S., et al., "RU486, a progestin and glucocorticoid antagonist, inhibits the growth of breast cancer cells via the progesterone receptor." J. Clin. Endocrinol. Metab. (1985), vol. 60, pp. 692-697.

(56) References Cited

OTHER PUBLICATIONS

Barre Sinoussi, F., et al., "Isolation of a T lymphotropic retrovirus from a patient at risk for acquired immune deficiency syndrome (AIDS)." Science (1983) vol. 220(4599), pp. 868-871.
Barthe, C., et al., "Roots of Clinical Resistance to STI-571 Cancer Therapy", Science, vol. 293 (Sep. 21, 2001) pp. 2163a.
Bartus, H.R., et al., "Improved genetically modified *Escherichia coli* strain for prescreening antineoplastic agents." Antimicrob. Agents Chemother. (1984), vol. 25, pp. 622-625.
*Bayer Ag* v. *Housey Pharm., Inc.* (D. Del. Nov. 12, 2002).
Beck, W.T., et al., "Altered surface membrane glycoproteins in Vinca alkaloid resistant human leukemic lymphoblasts." Cancer Res. (1979), vol. 39(6 Pt 1), pp. 2070-2076.
Beck, W.T., "Cellular pharmacology of Vinca alkaloid resistance and its circumvention." Adv. Enzyme Regul. (1984), vol. 22, pp. 207-227.
Beck, W.T., et al., "Reversal of Vinca alkaloid resistance but not multiple drug resistance in human leukemic cells by verapamil." Cancer Res. (1986), vol. 46, pp. 778-784.
Bender, P.E., et al., "5,6 Diaryl 2,3 dihydroimidazo[2,1 b]thiazoles: a new class of immunoregulatory antiinflammatory agents." J. Med. Chem. (1985), vol. 28, pp. 1169-1177.
Berge, S.M., et al., "Pharmaceutical salts", Journal of Pharmaceutical Science, vol. 66:1 (Jan. 1977), pp. 1-19.
Berkow, R.L., et al., "The effect of a protein kinase C inhibitor, H 7, on human neutrophil oxidative burst and degranulation." J. Leukoc. Biol. (1987), vol. 41, pp. 441-446.
Berridge, M.J., et al., "Lithium amplifies agonist dependent phosphatidylinositol responses in brain and salivary glands." Biochem. J. (1982), vol. 206, pp. 587-595.
Bignami, M., et al., "Tumor promoters enhance v myc induced focus formation in mammalian cell lines." Ann. N. Y. Acad. Sci. (1987), vol. 511, pp. 343-349.
Binder, D., et al., "Analogues and derivatives of tenoxicam. 1. Synthesis and antiinflammatory activity of analogues with different residues on the ring nitrogen and the amide nitrogen." J. Med. Chem. (1987), vol. 30, pp. 678-682.
Blythin, D.J., et al., "Antiinflammatory activity of substituted 6 hydroxypyrimido[2,1 f]purine-2,4,8(1H,3H,9H) triones. Atypical nonsteroidal antiinflammatory agents." J. Med. Chem. (1986), vol. 29, pp. 1099 1113.
Bollag, G.E., et al., "Protein kinase C directly phosphorylates the insulin receptor in vitro and reduces its protein tyrosine kinase activity." Proc. Natl. Acad. Sci. USA (1986), vol. 83, pp. 5822-5824.
Bolstad, B.M., et al., "A Comparison of Normalization Methods for High Density Oligonucleotide Array Data Based on Variance and Bias", Bioinformatics, vol. 19, Jan. 22, 2003), pp. 185-193.
Boreiko, C., et al., "Effect of 12 O tetradecanoylphorbol 13 acetate on the morphology and growth of C3H/10T1/2 mouse embryo cells." Cancer Res. (1980), vol. 40, pp. 4709-4716.
Boschelli, D. M., et al., "Synthesis and Tyrosine Kinase Inhibitory Activity of a Series of 2-Amino-8H-pyrido[2,3,-d] pyrimidines: Identification of Potent, Selective Platelet-Derived Growth Factor Receptor Tyrosine Kinase Inhibitors", J. Med. Chem. (1998), vol. 41, pp. 4365-4377.
Boulianne, G.L., et al., "Production of functional chimaeric mouse/human antibody." Nature (1984), vol. 312(5995), pp. 643-646.
Bowen, D.L., et al., "Immunopathogenesis of the acquired immunodeficiency syndrome." Ann. Intern. Med. (1985), vol. 103, pp. 704-709.
Bradford, M.M., et al., "A rapid and sensitive method for the quantitation of microgram quantities of protein utilizing the principle of protein-dye binding." Anal. Biochem. (1976), vol. 72, pp. 248-254.
Brandt, S.J., et al., "Distinct patterns of expression of different protein kinase C mRNAs in rat tissues." Cell (1987), vol. 49:57-63.
Branford, S., et al., "High Frequency of Point Mutations Clustered Within the Adenosine Triphosphate-Binding Region of BCR/ABL in Patients with Chronic Myeloid Leukemia or Ph-positive Acute Lymphoblastic Leukemia Who Develop Imatinib (STI571) Resistance", Blood, vol. 99 (May 1, 2002) pp. 3472-3475.
Brann, M.R., et al., "Expression of a cloned muscarinic receptor in A9 L cells." Mol. Pharmacol. (1987), vol. 32, 450-455.
Breshears, S.R., et al., "Purines, VIII: The Aminolysis of Certain Chlorosubstituted Purines", Journal of the American Chemical Society, vol. 81 (Jul. 20, 1959), pp. 3789-3792).
Brooks, K.H., et al., "Recombinant IL 2 but not recombinant interferon gamma stimulates both proliferation and IgM secretion in a Ly 1+ clone of neoplastic murine B cells (BCL1)." J. Immunol. (1986), vol. 137, pp. 3205-3210.
Burbaum, J.J., et al., "A paradigm for drug discovery employing encoded combinatorial libraries", Proceedings of the National Academy of Science U S A, vol. 92 (Jun. 20, 1995) pp. 6027-6031.
Buzas, A., et al., "Sur la chlorosulfonylation du thiophene et de quelques uns de ses derives substitues." Bulletin De la Societe Francaise de Cancerologie (1960) pp. 793-803.
Camper, S.A., et al., "Hormonal regulation of the bovine prolactin promoter in rat pituitary tumor cells." J. Biol. Chem. (1985), vol. 260, 12246-12251.
Capps, T.M., et al., "Identification and Synthesis of a Unique Disulfide Dimeric Metabolite of Primisulfuron-methyl in the Mouse", Journal of Agricultural and Food Chemistry, vol. 41, (1993), pp. 2411-2415.
Carter, T.A., et al., "Inhibition of drug-resistant mutants of ABL, KIT, and EGF receptor kinases", Proceedings of the National Academy of Science U S A, vol. 102 (Aug. 2, 2005) pp. 11011-11016.
Catino, J.J., et al., "A microtitre cytotoxicity assay useful for the discovery of fermentation derived antitumor agents." Cancer Chemother. Pharmacol. (1985), vol. 15, pp. 240-243.
Chakrabarty, S., et al., "Restoration of normal growth control and membrane antigen composition in malignant cells by N,N dimethylformamide." Cancer Res. (1984) vol. 44, pp. 2181-2185.
Chanh, T.C., et al., "Induction of anti HIV neutralizing antibodies by synthetic peptides." EMBO J. (1986), vol. 5, pp. 3065-3071.
Chen, C.J., et al., "Internal duplication and homology with bacterial transport proteins in the mdrl (P glycoprotein) gene from multidrug resistant human cells." Cell (1986), vol. 47, pp. 381-389.
Chen, Y.C., et al., "Properties of mammalian cells transformed by temperature sensitive mutants of avian sarcoma virus." Cell (1977), vol. 11, pp. 513-521.
Chen, W.T., et al., "Regulation of fibronectin receptor distribution by transformation, exogenous fibronectin, and synthetic peptides." J. Cell Biol. (1986), vol. 103, pp. 1649-1661.
Chiaini, J., et al., "Excretion and metabolism of a nonsteroidal antiinflammatory agent, 4 hydroxy 2 methyl 2H 1,2 benzothiazine-3 carboxanilide 1,1 dioxide, in rat, dog, monkey, and man." J. Med. Chem. (1971), vol. 14, pp. 1175-1177.
Chomczynski, P., et al., "Single step method of RNA isolation by acid guanidinium thiocyanate phenol chloroform extraction." Anal. Biochem. (1987), vol. 162, pp. 156-159.
Chou, C.K., et al., "Human insulin receptors mutated at the ATP binding site lack protein tyrosine kinase activity and fail to mediate postreceptor effects of insulin." J. Biol. Chem. (1987), vol. 262, pp. 1842-1847.
Ciardiello, F., et al, "Selective growth sensitivity to 4-cis-hydroxy-L-proline of rodent transformed cell lines and human tumor cell lines in vitro." Proc. AACR (1987), vol. 28, p. 65, Abstract 260.
Clauser, E., et al., "The human insulin receptor cDNA: a new tool to study the function of this receptor." J. Recept. Res. (1987), vol. 7, pp. 377-404.
Cole, S.P.C., et al., "The EBV-Hybridoma Technique and its Application to Human Lung Cancer." In: Monoclonal Antibodies and Cancer Therapy, pp. 77-96 (R. Reisfeld & S. Sell, eds., Alan R. Liss, N.Y. 1985).
Collard, J.G., et al., "Invasive and metastatic potential induced by ras transfection into mouse BW5147 T lymphoma cells." Cancer Res. (1987), vol. 47, pp. 754-759.
Connan, G., et al., "Focus formation in rat fibroblasts exposed to a tumour promoter after transfer of polyoma plt and myc oncogenes." Nature (1985), vol. 314, pp. 277-279.

(56) References Cited

OTHER PUBLICATIONS

Consonni, R., et al., "Reactivity of 2-Methyl-4-(1-pyrrolidinyl)-2H-1,2-benzothiazine 1,1-dioxide towards p-Toluenesulphonyl Azide." J. Heterocyclic Chem. (1990), vol. 27, pp. 427-430.
Corbin, A. S., et al., "Analysis of the Structural Basis of Specificity of Inhibition of the Abl Kinase by STI571", The Journal of Biological Chemistry, vol. 277 (Aug. 30, 2002) pp. 32214-32219.
Cornwell, M.M., et al, "Certain calcium channel blockers bind specifically to multidrug resistant human KB carcinoma membrane vesicles and inhibit drug binding to P glycoprotein." J. Biol. Chem. (1987), vol. 262, pp. 2166-2170.
Cornwell, M.M., et al., "Increased vinblastine binding to membrane vesicles from multidrug resistant KB cells." J. Biol. Chem. (1986), vol. 261, pp. 7921-7928.
Cornwell, M.M., et al., "Membrane vesicles from multidrug resistant human cancer cells contain a specific 150 to 170 kDa protein detected by photoaffinity labeling." Proc. Natl. Acad. Sci. USA (1986), vol. 83, pp. 3847-3850.
Coussens, L., et al, "Multiple, distinct forms of bovine and human protein kinase C suggest diversity in cellular signaling pathways." Science (1986), vol. 233, pp. 859-866.
Crofford, L.J., "COX 1 and COX 2 tissue expression: implications and predictions." J. Rheumatol. (1997) 24 Suppl 49, pp. 15-19.
Croop, J.M., et al., "Genetics of multidrug resistance: relationship of a cloned gene to the complete multidrug resistant phenotype." Cancer Res. (1987), vol. 47, pp. 5982-5988.
Crossman, L.C., et al., "A single nucleotide polymorphism in the coding region of ABL and its effects on sensitivity to imatinib", Leukemia, vol. 19, (2005), pp. 1859-1862.
Cunningham Rundles, "Serum suppression of lymphocyte activation in vitro in acquired immunodeficiency disease." J. Clin. Immunol. (1983), vol. 3, pp. 156-165.
Cuttitta, F., et al., "Bombesin like peptides can function as autocrine growth factors in human small cell lung cancer." Nature (1985), vol. 316(6031), pp. 823-826.
Dailey, L., et al., "Sequences in the polyomavirus DNA regulatory region involved in viral DNA replication and early gene expression." J. Virol (1985), vol. 54, pp. 739-749.
Daley, G.Q., et al., "The CML specific P210 bcr/abl protein, unlike v abl, does not transform NIH/3T3 fibroblasts." Science (1987), vol. 237:532-535.
Daley, G. Q., et al., "Induction of Chronic Myelogenous Leukemia in Mice by the P210 $^{brc/abl}$ Gene of the Philadelphia Chromosome", Science, vol. 247 (Feb. 16, 1990) pp. 824-830.
Dalgleish, A.G., et al., "The CD4 (T4) antigen is an essential component of the receptor for the AIDS retrovirus." Nature (1984), vol. 312 (5996), pp. 763-776.
Dano, K., "Active outward transport of daunomycin in resistant Ehrlich ascites tumor cells." Biochim Biophys Acta. (1973), vol. 323, pp. 466-483.
Darnell, J.E., et al., Molecular Cell Biology, Scientific American Books, Inc. (1986), p. 143.
Davies, T., "Magic bullets." Nature (1981), vol. 289(5793), pp. 12-13.
Davis, R.J., et al., "Platelet derived growth factor mimics phorbol diester action on epidermal growth factor receptor phosphorylation at threonine 654." Proc. Natl. Acad. Sci. USA (1985), vol. 82, pp. 4080-4084.
Davis, T.L., "The Mechanism of Reactions in the Urea Series", Proceedings of the National Academy of Sciences of the United States of America, vol. 11 (1925), pp. 68-73.
Dean, M., et al., "Role of myc in the abrogation of IL3 dependence of myeloid FDC P1 cells." Oncogene Res. (1987), vol. 1, pp. 279-296.
Debouck, C., et al., "Human immunodeficiency virus protease expressed in *Escherichia coli* exhibits autoprocessing and specific maturation of the gag precursor." Proc. Natl. Acad. Sci. USA (1987), vol. 84, pp. 8903-8906.
De Brabander, M., et al., "A new culture model facilitating rapid quantitative testing of mitotic spindle inhibition in mammalian cells." J. Natl. Cancer. Inst. (1976), vol. 56, pp. 357-363.
De Clercq, E., et al., "Potent activity of 5 fluoro 2' deoxyuridine and related compounds against thymidine kinase deficient (TK) herpes simplex virus: targeted at thymidylate synthase." Mol. Pharmacol. (1987), vol. 32, pp. 286-292.
De Clercq, E., et al., "Thymidylate synthetase as target enzyme for the inhibitory activity of 5 substituted 2' deoxyuridines on mouse leukemia L1210 cell growth." Mol. Pharmacol. (1981), vol. 19, pp. 321-330.
Delclos, K.B., et al., "Specific labeling of mouse brain membrane phospholipids with [20 3H]phorbol 12 p azidobenzoate 13 benzoate, a photolabile phorbol ester." Proc. Natl. Acad. Sci. USA (1983), vol. 80, pp. 3054-3058.
Depper, J.M., et al., Blockade of the interleukin 2 receptor by anti Tac antibody: inhibition of human lymphocyte activation. J. Immunol. (1983), vol. 131, pp. 690-696.
Desantis, R., et al., "NIH 3T3 cells transfected with human tumor DNA lose the transformed phenotype when treated with swainsonine." Biochem. Biophys. Res. Commun. (1987) vol. 142, pp. 348-353.
Di Fiore, P.P., et al., "erbB 2 is a potent oncogene when overexpressed in NIH/3T3 cells." Science (1987), vol. 237, pp. 178-182.
Di Fiore, P.P., et al., "Overexpression of the human EGF receptor confers an EGF dependent transformed phenotype to NIH 3T3 cells." Cell (1987), vol. 51, pp. 1063-1070.
Dixon, R.A., et al., "Cloning of the gene and cDNA for mammalian beta adrenergic receptor and homology with rhodopsin." Nature (1986), vol. 321(6065), pp. 75-79.
Dixon, R.A. et al., "Ligand binding to the beta adrenergic receptor involves its rhodopsin like core." Nature (1987), vol. 326, pp. 73-77.
Dixon, R.A., et al., "Structural features required for ligand binding to the beta adrenergic receptor." EMBO J. (1987), vol. 6, pp. 3269-3275.
Dotto, G.P., et al., "Specific growth response of ras transformed embryo fibroblasts to tumour promoters." Nature (1985), vol. 318, pp. 472-475.
Drebin, J.A., et al., "Down modulation of an oncogene protein product and reversion of the transformed phenotype by monoclonal antibodies." Cell (1985), vol. 41, pp. 695-706.
Druege, P.M., et al., "Introduction of estrogen responsiveness into mammalian cell lines." Nucleic Acids Res. (1986), vol. 14, pp. 9329 9337.
Druker, B.J., et al., "Activity of a Specific Inhibitor of the BCR-ABL Tyrosine Kinase in the Blast Crisis of Chronic Myeloid Leukemia and Acute Lymphoblastic Leukemia with the Philadelphia Chromosome", The New England Journal of Medicine, vol. 344 (Apr. 5, 2001) pp. 1038-1042.
Druker, B. J., et al., "Effects of a Selective Inhibitor of the Abl Tyrosine Kinase on the Growth of Bcr-Abl Positive Cells", Nature Medicine, vol. 2 (May 1996) pp. 561-566.
Druker, B. J., et al., "Efficacy and Safety of a Specific Inhibitor of the BCR-ABL Tyrosine Kinase in Chronic Myeloid Leukemia", The New England Journal of Medicine, vol. 344 (Apr. 5, 2001) pp. 1031-1037.
Dutta-Roy, A.K., et al., "Prostacyclin stimulation of the activation of blood coagulation factor X by platelets." Science (1986), vol. 231(4736), pp. 385-388.
Easmon, J., et al, "2-Benzoxazolyl and 2-Benzimidazolyl Hydrazones Derived from 2-Acetylpyridine: A Novel Class of Antitumor Agents", Int. J. Cancer (2001), vol. 94, pp. 89-96.
Ebeling, J.G., et al., "Diacylglycerols mimic phorbol diester induction of leukemic cell differentiation." Proc. Natl. Acad. Sci. USA (1985), vol. 82, pp. 815-819.
Ebina, Y., et al., "Expression of a functional human insulin receptor from a cloned cDNA in Chinese hamster ovary cells." Proc. Natl. Acad. Sci. USA (1985), vol. 82, pp. 8014-8018.
Ebina, Y., et al., "Replacement of lysine residue 1030 in the putative ATP binding region of the insulin receptor abolishes insulin and antibody stimulated glucose uptake and receptor kinase activity." Proc. Natl. Acad. Sci. USA (1987), vol. 84(3), pp. 704-708.

(56) References Cited

OTHER PUBLICATIONS

Elespuru, R.K., et al., "Biochemical prophage induction assay: a rapid test for antitumor agents that interact with DNA." Cancer Res. (1983), vol. 43, pp. 2819-2830.
Elespuru, R.K., et al., "A colorimetric assay of lysogenic induction designed for screening potential carcinogenic and carcinostatic agents." Environ. Mutagen. (1979), vol. 1, pp. 65-78.
Ellis, L., et al., "Replacement of insulin receptor tyrosine residues 1162 and 1163 compromises insulin stimulated kinase activity and uptake of 2 deoxyglucose." Cell (1986), vol. 45, pp. 721-732.
Elroy Stein, O., et al., "Overproduction of human Cu/Zn superoxide dismutase in transfected cells: extenuation of paraquat mediated cytotoxicity and enhancement of lipid peroxidation." EMBO J. (1986), vol. 5, pp. 615-622.
Erikson, R.L., et al., "Molecular events in cells transformed by Rous Sarcoma virus." J. Cell Biol. (1980), vol. 87, pp. 319-325.
Erikson, R.L., "Towards a biochemical description of malignant transformation. Identification and functional characterization of the Rous sarcoma virus transforming gene product." Cancer (1984), vol. 53, pp. 2041-2045.
Escobedo, J.A., et al., "Platelet derived growth factor receptors expressed by cDNA transfection couple to a diverse group of cellular responses associated with cell proliferation." J. Biol. Chem. (1988), vol. 263, pp. 1482-1487.
Faderl, S., et al., "The Biology of Chronic Myeloid Leukemia", The New England Journal of Medicine, vol. 341 (Jul. 15, 1999) pp. 164-172.
Fairbanks, K.P., et al., "Effects of mevinolin and mevalonate on cell growth in several transformed cell lines." J. Cell. Physiol. (1986), pp. 127, pp. 216-222.
Farmerie, W.G., et al., "Expression and processing of the AIDS virus reverse transcriptase in *Escherichia coli*." Science (1987), vol. 236, pp. 305-308.
Fauci, A.S., "Immunologic abnormalities in the acquired immunodeficiency syndrome (AIDS)." Clin. Res. (1984), vol. 32, pp. 491-499.
Feramisco, J.R., et al., "Transient reversion of ras oncogene induced cell transformation by antibodies specific for amino acid 12 of ras protein." Nature (1985), vol. 314(6012), pp. 639-642.
Fisher, P.B., et al., "Modulation of differentiation in murine and human cells by interferon and phorbol ester tumor promoters." In: Pigment Cell 1985. Biological, Molecular and Clinical Aspects of Pigmentation (Bagnara, J., Klaus, S.N., Paul, E. & Schartl, M. eds., University of Tokyo Press) p. 325-332.
Fisher, P.B., et al., "Interactions between initiating chemical carcinogens, tumor promoters, and adenovirus in cell transformation." Teratog. Carcinog. Mutagen. (1980) vol. 1, pp. 245-257.
Fojo, A., et al., "Reduced drug accumulation in multiply drug resistant human KB carcinoma cell lines" Cancer Res. (1985), vol. 45, pp. 3002-3007.
Fojo, A.T., et al., "Amplification of DNA sequences in human multidrug resistant KB carcinoma cells." Proc. Natl. Acad. Sci. USA. (1985), vol. 82, pp. 7661-7665.
Fojo, A., et al., "Molecular biology of drug resistance." Breast Cancer Res. Treat. (1987), vol. 9, pp. 5-16.
Fontana, S., et al., "Expression of major histocompatibility complex class I antigens in normal and transformed rat thyroid epithelial cell lines." Cancer Res. (1987), vol. 47, pp. 4178-4183.
Fraga, C.A.M., et al., "The synthesis of a new benzothiazine derivative, related to oxicams, synthesized from natural safrole." J. Heterocyclic Chem (1992), vol. 29, pp. 1667-1669.
Fraser, C.M., et al., "Continuous high density expression of human beta 2 adrenergic receptors in a mouse cell line previously lacking beta receptors." J. Biol. Chem. (1987), vol. 262, pp. 14843-14846.
Freedman, V.H., et al. "Cellular tumorigenicity in nude mice: correlation with cell growth in semi solid medium." Cell (1974), vol. 3, pp. 355-359.
Freeman, A.E., et al., "Morphological transformation of rat embryo cells induced by dimethylnitrosamine and murine lukemia viruses." J. Natl. Cancer Inst. (1970), vol. 44, pp. 65-78.
Friis, R.R., et al., "Phenotypes of Rous sarcoma virus transformed fibroblasts: an argument for a multifunctional Src gene product." Med. Microbiol. Immunol. (Berl). (1977), vol. 164, pp. 155-165.
Fu, J.Y., et al., "The induction and suppression of prostaglandin H2 synthase (cyclooxygenase) in human monocytes." J. Biol. Chem. (1990), vol. 265(28), pp. 16737-16740.
Fukazawa, H., et al., "Effects of herbimycin A and various SH-reagents on p60v-src kinase activity in vitro." Biochem Biophys Res Commun. (1990), vol. 173(1), pp. 276-282.
Fukazawa, H., et al., "Specific inhibition of cytoplasmic protein tyrosine kinases by herbimycin A in vitro." Biochem. Pharmacol. (1991), vol. 42(9), pp. 1661-1671.
Fukazawa, H., et al., "Labeling of v Src and BCR ABL tyrosine kinases with [14C]herbimycin A and its use in the elucidation of the kinase inactivation mechanism." FEBS Lett. (1994), vol. 340, pp. 155-158.
Fukuda, K., et al., "Molecular distinction between muscarinic acetylcholine receptor subtypes." Nature (1987), vol. 327, pp. 623-625.
Fulton, R.J., et al., "Purification of ricin A1, A2, and B chains and characterization of their toxicity." J. Biol. Chem. (1986), vol. 261, pp. 5314-5319.
Fung, M.S.C., et al., "Monoclonal antibodies that neutralize HIV-1 virions and inhibit syncytium formation by infected cells." Bio/technology (1987), vol. 5, pp. 940-946.
Gallick et al., "Specific Reduction in SRC Kinase Activity in HT 29 Humal Colorectal Carcinomal Cells Correlates with Growth Inhibition by Interperon and Tumor Necrosis Factor." UCLA Symposia on Melecular & Cellular Biology Abstract D 207, Jan. 17 Jan. 30, 1988.
Gallo, R.C., et al., "Frequent detection and isolation of cytopathic retroviruses (HTLV III) from patients with AIDS and at risk for AIDS." Science (1984), vol. 224(4648), pp. 500-503.
Gambacorti-Passerini, C., et al., "Role of $\alpha$1 Acid Glycoprotein in the In Vivo Resistance of Human BCR-ABL$^+$. Leukemic Cells to the Abl Inhibitor STI571", Journal of the National Cancer Institute, vol. 92 (Oct. 18, 2000) pp. 1641-1650.
Gerlach, J.H., et al., "Homology between P glycoprotein and a bacterial haemolysin transport protein suggests a model for multidrug resistance." Nature (1986), vol. 324(6096), pp. 485-489.
Gherzi, R., et al., "Reevaluation of the evidence that an antibody to the insulin receptor is insulinmimetic without activating the protein tyrosine kinase activity of the receptor." J. Biol. Chem. (1987), vol. 262, pp. 16900 16905.
Giguere, V., et al., "Functional domains of the human glucocorticoid receptor." Cell (1986), vol. 46, pp. 645-652.
Gill, G.N., et al., "Regulatory features of the epidermal growth factor receptor." J. Cell. Physiol. Suppl. (1987) , vol. 5, pp. 35-41.
Gill, G.N., et al., "Monoclonal anti epidermal growth factor receptor antibodies which are inhibitors of epidermal growth factor binding and antagonists of epidermal growth factor binding and antagonists of epidermal growth factor stimulated tyrosine protein kinase activity." J. Biol. Chem. (1984), vol. 259, pp. 7755-7760.
Gineinah, M.M., et al., "Synthesis and Antiinflammatory Screening of Some Quinazoline and Quinazolyl-4-oxoquinazoline Derivatives", Archiv der Pharmizie—Pharmaceutical and Medicinal Chemistry, vol. 335 (2002), pp. 556-562.
Glick, M.C., et al., "Glycosylation changes in membrane glycoproteins after transfection of NIH 3T3 with human tumor DNA." Prog. Clin. Biol. Res. (1985) 175:229-237.
Gohji, K., et al., "Enhanced inhibition of colony formation of human renal cell carcinoma in soft agar by the combination of alpha difluoromethylornithine and recombinant gamma interferon." Cancer Res. (1986), vol. 46, pp. 6264-6268.
Gooding, L.R., et al., "Antibody and cellular detection of SV40 T-antigenic determinants on the surfaces of transformed cells." In Levine, A.J. et al. (Eds), Cancer Cells 1: The Transformed Phenotype pp. 263-269. (Cold Spring Harbor Laboratory, Cold Spring Harbor, N.Y. 1984).
Goodman & Gilman, The Pharmacological Basis of Therapeutics, 9th ed. (1996) Chapter 2.

(56) References Cited

OTHER PUBLICATIONS

Goodnow, R.A., Jr., et al., "Library design practices for success in lead generation with small molecule libraries", Combinatorial Chemistry and High Throughput Screening, vol. 6 (Nov. 2003) pp. 649-660.
Goto, R., et al., "Characteristics of D leucine uptake by mouse Ehrlich ascites tumor cells." J. Biochem. (1979) (Tokyo), vol. 86, pp. 363-369.
Gorre, M.E., et al., "Clinical Resistance to STI-571 Cancer Therapy Caused by BCR-ABL Gene Mutation or Amplification", Science, vol. 293 (Aug. 3, 2001) pp. 876-880.
Gould, K.L., et al., "Protein kinase C phosphorylates pp60src at a novel site." Cell (1985), vol. 42, pp. 849-857.
Goustin, A.S., et al., "Growth factors and cancer." Cancer Res. (1986), vol. 46, pp. 1015-1029.
Grabau, C.L., "Genetic and biochemical characterization of the lipid protein interactions of pyruvate oxidase." U. of Illinois Ph.D. Dissertation (1987).
Graham, F.L., et al., "A new technique for the assay of infectivity of human adenovirus 5 DNA." Virology (1973), vol. 52, pp. 456-467.
Green, S., et al., "Human oestrogen receptor cDNA: sequence, expression and homology to v erb A." Nature (1986), vol. 320(6058), pp. 134-139.
Grieveson, A.P.H., "Enhancement of extracellular enzyme secretion in Bacillus lichenformis NCIB 6346." Ph.D. Dissertation (1987).
Gros, P., et al., "Chromosome mediated gene transfer of multidrug resistance." Mol. Cell Biol. (1986), vol. 6, pp. 3785-3790.
Gros, P., et al., "Isolation and expression of a complementary DNA that confers multidrug resistance." Nature (1986) , vol. 323(6090), pp. 728-731.
Gros, P., et al., "Mammalian multidrug resistance gene: complete cDNA sequence indicates strong homology to bacterial transport proteins." Cell (1986), vol. 47, pp. 371-380.
Guadagno, T.M., et al., "A link between cyclin A expression and adhesion-dependent cell cycle progression." Science (1993), vol. 262(5139), pp. 1572-1575.
Guillem, J.G., et al., "Altered levels of protein kinase C and Ca2+ dependent protein kinases in human colon carcinomas." Cancer Res. (1987), vol. 47, pp. 2036-2039.
Gunter, K.C., et al., "Functional expression of the murine Thy 1.2 gene in transfected human T cells." J. Exp. Med. (1986), vol. 163, pp. 285-300.
Hakomori, S., "Tumor associated carbohydrate antigens." Annu. Rev. Immunol. (1984), vol. 2, pp. 103-126.
Hall, I. H., et al., "Investigations on the Mechanism of Action of the Novel Antitumor Agents 2-Benzothiazolyl, 2-Benzoxazolyl and 2-Benzimidazolyl Hydrazones Derived from 2-Acetylpyridine", Arch. Phar., Med. Chem. (1999),vol. 332, pp. 115-123.
Hallek, M., et al., "Signal transduction of interleukin-6 involves tyrosine phosphorylation of multiple cytosolic proteins and activation of Src-family kinases Fyn, Hck, and Lyn in multiple myeloma cell lines." Exp Hematol. (1997), vol. 25(13), pp. 1367-1377.
Hamada, H., et al., "Functional role for the 170 to 180 kDa glycoprotein specific to drug resistant tumor cells as revealed by monoclonal antibodies." Proc. Natl. Acad. Sci. U S A. (1986), vol. 83, pp. 7785-7789.
Hanke, J.H., et al., "Discovery of a novel, potent, and Src family-selective tyrosine kinase inhibitor. Study of Lck- and FynT-dependent T cell activation", Journal of Biological Chemistry, vol. 271 (Jan. 1996) pp. 695-701.
Hapel, A.J., et al., "Generation of an autocrine leukaemia using a retroviral expression vector carrying the interleukin 3 gene." Lymphokine Res. (1986), vol. 5:249-254.
Hibshoosh, H., et al., "Effects of overexpression of ornithine decarboxylase (ODC) on growth control and oncogene-induced cell transformation." Oncogene (1991), vol. 6(5), pp. 739-743.
Hillova, J., et al., "Loss of the oncogene from human H ras 1 transfected NIH/3T3 cells grown in the presence of excess methionine." J. Natl. Cancer Inst. (1986), vol. 77, pp. 721-732.
Hofmann, W. K., et al., "$Ph^+$ Acute Lymphoblastic Leukemia Resistant to the Tyrosine Kinase Inhibitor STI571 has a Unique BCR-ABL Gene Mutation", Blood, vol. 99 (Mar. 1, 2002) pp. 1860-1862.
Honegger, A.M., et al., "A mutant epidermal growth factor receptor with defective protein tyrosine kinase is unable to stimulate proto oncogene expression and DNA synthesis." Mol. Cell. Biol. (1987), vol. 7, pp. 4568-4571.
Horgan, K. et al., "Inhibition of protein kinase C mediated signal transduction by tamoxifen. Importance for antitumour activity." Biochem. Pharmacol. (1986), vol. 35, pp. 4463-4465.
Hori, M., et al., "Antibiotics Inhibiting Oncogene Functions." Gann Monograph on Cancer Research (1989), vol. 36, pp. 193-201.
Horowitz, A.D., et al., "Identification of receptors for phorbol ester tumor promoters in intact mammalian cells and of an inhibitor of receptor binding in biologic fluids." Proc. Natl. Acad. Sci. USA (1981), vol. 78, pp. 2315-2319.
Horwich, A.L., et al., "Expression of amplified DNA sequences for ornithine transcarbamylase in HeLa cells: arginine residues may be required for mitochondrial import of enzyme precursor." J. Cell. Biol. (1985), vol. 100, pp. 1515-1521.
Hou, Y.Y., et al., "C-kit Gene Mutation in Human Gastrointestinal Stromal Tumors", World Journal of Gastroenterology, vol. 10 (May 1, 2004) pp. 1310-1314.
Housey, G.M., et al., "Altered Growth Control and Enhanced Morphologic Response to Tumor Promoters in Rat Fibroblasts Stably Overproducing Protein Kinase C." In: Journal of Cellular Biochemistry, Supplement 12A: UCLA Symposia on Molecular & Cellular Biology, (Jan. 17-Jan. 30, 1988), Abstract C224, Alan R. Liss, Inc., New York, p. 105.
Housey, G.M., et al., "Expression of long terminal repeat (LTR) sequences in carcinogen induced murine skin carcinomas." Biochem. Biophys. Res. Commun. (1985), vol. 127, pp. 391-398.
Housey, G. M., et al. "Isolation and nucleotide sequence analysis of cDNA clones from rat brain using oligonucleotide probes to protein kinase C and protein kinase A." In: Journal of Cellular Biochemistry, Supplement 10C: UCLA Symposia on Molecular & Cellular Biology, Abstract L95, Alan R. Liss, Inc., New York, p. 132, (1986).
Housey, G.M., et al., "Isolation of cDNA clones encoding protein kinase C: evidence for a protein kinase C related gene family." Proc. Natl. Acad. Sci. USA (1987), vol. 84, pp. 1065-1069.
Housey, G.M., et al., "Overproduction of protein kinase C causes disordered growth control in rat fibroblasts." Cell (Feb. 12, 1988), vol. 52, pp. 343-354.
Housey, G.M., "The Role of Protein Kinase C in Growth Control and Tumor Promotion", Ph.D. Dissertation, (1988).
Housey, G.M., et al., "Structural and functional studies of protein kinase C. Adv. Exp." Med. Biol. (1988), vol. 234, pp. 127-140.
Hsiao, W.L.W., et al., "Oncogene induced transformation of C3H 10T1/2 cells is enhanced by tumor promoters." Science (1984), vol. 226, pp. 552-555.
Hsiao, W.L.W., et al., "Oncogene induced transformation of a rat embryo fibroblast cell line is enhanced by tumor promoters." Mol. Cell. Biol. (1986), vol. 6:1943-1950.
Hsiao, W.L.W., et al., "Tumor promoters and a serum factor enhance expression of the transformed phenotype in rat 6 fibroblasts transfected with an activated oncogene." In: Journal of Cellular Biochemistry, Supplement 10C: UCLA Symposia on Molecular & Cellular Biology, Abstract L155, Alan R. Liss, Inc., New York, p. 152. (1986).
Hsiao, W.L., et al., "A factor present in fetal calf serum enhances oncogene induced transformation of rodent fibroblasts." Mol. Cell Biol. (1987), vol. 7, pp. 3380-3385.
Hsyu, P.H., et al., "Pharmacokinetics and cyclooxygenase inhibition of itazigrel in normal volunteers after single oral doses." J. Pharm. Sci. (1994), vol. 83, pp. 1747-1750.
Huang, J.S., et al., "Transforming protein of simian sarcoma virus stimulates autocrine growth of SSV transformed cells through PDGF cell surface receptors." Cell 1984), vol. 39, pp. 79-87.
Huang, K.P., et al., "Isozymic forms of rat brain Ca2+ activated and phospholipid dependent protein kinase." Proc. Natl. Acad. Sci. USA (1986) vol. 83, pp. 8535-8539.
Huang, M.T., et al., "Inhibitory Effects of Caffeic Acid Phenethyl Ester (CAPE) on 12-0-tetradecanoylphorbol-13-acetate-induced tumor

(56) References Cited

OTHER PUBLICATIONS promotion in mouse skin and the synthesis of DNA, RNA and protein in HeLa Cells", Carcinogenesie (1996), vol. 17:4, pp. 761-765.
Huberman, E., et al, Callaham, M.F. (1979) Induction of terminal differentiation in human promyelocytic leukemia cells by tumor promoting agents. Proc. Natl. Acad. Sci. USA 76:1293-1297.
Hudziak, R.M., et al., "Increased expression of the putative growth factor receptor p185HER2 causes transformation and tumorigenesis of NIH 3T3 cells." Proc. Natl. Acad. Sci. USA (1987), vol. 84, pp. 7159-7163.
Huisgen, R., et al., "Diphenyl-nitrilimin und seine 1,3-dipolaren additionen an alkene und alkine." Tetrahedron (1962), vol. 17, pp. 3-29. (in German with English abstract).
Hunter, T., et al., "Protein kinase C phosphorylation of the EGF receptor at a threonine residue close to the cytoplasmic face of the plasma membrane." Nature (1984), vol. 311:480-483.
Huron, D. R., et al., "A Novel Pyridopyrimidine Inhibitor of Abl Kinase is a Picomolar Inhibitor of Bcr-abl-driven K562 Cells and is Effective against STI571-resistant Bcr-abl Mutants", Clinical Cancer Research (Apr. 2003) vol. 9, pp. 1267-1273.
Ikeda, T., et al., "Anti-allergic and anti-inflammatory actions of 2'-(tetrazole-5-yl) 4-hydroxy-2-methyl-2H-1,2-benzothiazine 1,1-dioxide." Bioorg. Med. Chem. Lett. (1992), vol. 2, pp. 709-714.
Inaba, M., et al., "Reversal of multidrug resistance by non antitumor anthracycline analogs." Gann (1984), vol. 75, pp. 1049-1052.
Ingram, V.M., "Sequence Methods." Meth. Enzymol. (1963), vol. 6, pp. 831-848.
Jaken, S., et al., "Purification and characterization of three types of protein kinase C from rabbit brain cytosol." Proc. Natl. Acad. Sci. USA (1987), vol. 84, pp. 4418-4422.
Jeng, A.Y., et al., "Phosphorylation of ras oncogene product by protein kinase C." Biochem. Biophys. Res. Commun. (1987), vol. 145, pp. 782-788.
Jenkins, F.J., et al., "Effect of ribavirin on Rous sarcoma virus transformation." Antimicrob. Agents Chemother. (1981), vol. 19, pp. 364-368.
Jetten, A.M., et al., "Differential response to retinoic acid of Syrian hamster embryo fibroblasts expressing v src or v Ha ras oncogenes." Mol. Cell. Biol. (1986), vol. 6, pp. 3341-3348.
Jetten, A.M., et al., "Inhibition of ornithine decarboxylase by retinoic acid and difluoromethylornithine in relation to their effects on differentiation and proliferation." Exp. Cell Res. (1985), vol. 156, pp. 221-230.
Johnson, M.D., et al., "Molecular cloning of gene sequences regulated by tumor promoters and mitogens through protein kinase." C. Mol. Cell. Biol. (1987), vol. 7, pp. 2821-2829.
Johnson, M.D., et al., Role of protein kinase C in regulation of gene expression and relevance to tumor promotion.' Environ. Health. Perspect. (1987), vol. 76, pp. 89-95.
Johnsson, A., et al., "Antibodies against platelet derived growth factor inhibit acute transformation by simian sarcoma virus." Nature (1985), vol. 317, pp. 438-440.
Juliano, R.L., et al., "A surface glycoprotein modulating drug permeability in Chinese hamster ovary cell mutants." Biochim Biophys Acta. (1976), vol. 455, pp. 152-162.
Julius, D., et al., "Ectopic expression of the serotonin 1c receptor and the triggering of malignant transformation." Science (1989), vol. 244, pp. 1057-1062.
Julius, D., et al., "Molecular characterization of a functional cDNA encoding the serotonin 1c receptor." Science (1988), vol. 241, pp. 558-564.
Jung Testas, I., et al., "Effects of steroid hormones and antihormones in cultured cells." Exp. Clin. Endocrinol. (1985), vol. 86, pp. 151-164.
Kahana, C., et al., "Isolation of cloned cDNA encoding mammalian ornithine decarboxylase." Proc. Natl. Acad. Sci. USA (1984), vol. 81, pp. 3645-3649.
Kahana, C., et al., "Nucleotide sequence of murine ornithine decarboxylase mRNA." Proc. Natl. Acad. Sci. USA (1985), vol. 82, pp. 1673-1677.
Kahn, C.R., et al., "The insulin receptor and the molecular mechanism of insulin action." J. Clin. Invest. (1988), vol. 82, pp. 1151-1156.
Kajikawa, N., et al., "Ca2+ dependent neutral protease and proteolytic activation of Ca2+ activated, phospholipid dependent protein kinase." Methods. Enzymol. (1983), vol. 102, pp. 279-290.
Kamata, N., et al., "Growth inhibitory effects of epidermal growth factor and overexpression of its receptors on human squamous cell carcinomas in culture." Cancer Res. (1986), vol. 46, pp. 1648-1653.
Kara, J., et al., "9 (S) (2,3 Dihydroxypropyl)adenine inhibits the transformation of chick embryo fibroblasts infected with Rous sarcoma virus: Evidence for inhibition of enzymatic activity of isolated cellular protein kinases by the drug." FEBS Lett. (1979), vol. 107, pp. 187-192.
Kartner, N., et al., "Cell surface P glycoprotein associated with multidrug resistance in mammalian cell lines." Science (1983), vol. 221, pp. 1285-1288.
Kartner, N., et al., "Detection of P glycoprotein in multidrug resistant cell lines by monoclonal antibodies." Nature (1985), vol. 316(6031), pp. 820 823.
Kasuga, M., et al., "Insulin stimulates the phosphorylation of the 95,000 dalton subunit of its own receptor." Science (1982), vol. 215, pp. 185-187.
Kavanagh, T.J., et al., "Characterization of a human teratocarcinoma cell assay for inhibitors of metabolic cooperation." Cancer Res. (1986), vol. 46, pp. 1359-1366.
Kawamoto, S., et al. "1 (5 Isoquinolinesulfonyl) 2 methylpiperazine (H 7) is a selective inhibitor of protein kinase C in rabbit platelets." Biochem. Biophys. Res. Commun. (1984), vol. 125, pp. 258-264.
Kerkelä, R., et al., "Cardiotoxicity of the cancer therapeutic agent imatinib mesylate", Nature Medicine, vol. 12 (Aug. 2006) pp. 908-916.
Kikkawa, U., et al., "Calcium activated, phospholipid dependent protein kinase from rat brain. Subcellular distribution, purification, and properties." J. Biol. Chem. (1982) 257, pp. 13341-13348.
Kikkawa, U., et al., "Protein Kinase C and the Mechanism of Action of Tumor Promoters." in Levine, A.J. et al. (Eds), Cancer Cells 1: The Transformed Phenotype, pp. 239-244. (Cold Spring Harbor Laboratory, Cold Spring Harbor, N.Y. 1984).
Kimura, S., et al., "NS-187, A Potent and Selective Dual Bcr-Abl/Lyn Tyrosine Kinase Inhibitor, is a Novel Agent for Imatinib-Resistant Leukemia", Blood, (2005), vol. 106, pp. 3948-3954.
Kirschmeier, P.T., et al., "Construction and characterization of a retroviral vector demonstrating efficient expression of cloned cDNA sequences." DNA (1988), vol. 7, pp. 219-225.
Kirstein, et al. "Tumor necrosis factor stimulates proliferation of human gastrosarcoma cells and transcription of Myc messenger RNA." UCLA Symposia on Molecular & Cellular Biology Abstract D 209, Jan. 17 Jan. 30, 1988.
Klatzmann, D., et al., "HIV infection: facts and hypotheses." Immunol. Today (1986), vol. 7, pp. 291-296.
Klatzmann, D., et al., "T lymphocyte T4 molecule behaves as the receptor for human retrovirus LAV." Nature (1984), vol. 312(5996), pp. 767-768.
Klohs, W.D., et al., "Resistance to anthrapyrazoles and anthracyclines in multidrug resistant P388 murine leukemia cells: reversal by calcium blockers and calmodulin antagonists." Cancer Res. (1986), vol. 46, pp. 4352-4356.
Knight, Z.A., et al., "Features of Selective Kinase Inhibitors", Chemistry and Biology, vol. 12 (Jun. 2005) pp. 621-637.
Knopf, J.L., et al., "Cloning and expression of multiple protein kinase C cDNAs." Cell (1986), vol. 46, pp. 491-502.
Knowles, P.P., et al., "Purification of immunotoxins containing ricin A chain and abrin A chain using blue sepharose CL 6B." Anal. Biochem. (1987), vol. 160, pp. 440-443.
Kobilka, B.K., et al., "Functional activity and regulation of human β2 adrenergic receptors expressed in Xenopus oocytes." J. Biol. Chem. (1987), vol. 262, pp. 15796-15802.

(56) References Cited

OTHER PUBLICATIONS

Koenig, S., et al., "Detection of AIDS virus in macrophages in brain tissue from AIDS patients with encephalopathy." Science (1986), vol. 233(4768), pp. 1089-1093.
Kohler, G., et al., "Derivation of specific antibody producing tissue culture and tumor lines by cell fusion." Eur. J. Immunol. (1976), vol. 6, pp. 511-519.
Kolata, G., Why do cancer cells resist drugs? Science (1986), vol. 231(4735), pp. 220-221.
Koprowski, H., et al., "Human anti idiotype antibodies in cancer patients: Is the modulation of the immune response beneficial for the patient?" Proc. Natl. Acad. Sci. USA (1984), vol. 81, pp. 216-219.
Kraft, A.S., et al. Characterization of cytosolic calcium activated phospholipid dependent protein kinase activity in embryonal carcinoma cells. Effect of retinoic acid induced differentiation of F9 cells to parietal endoderm. (1983), J. Biol. Chem. vol. 258, pp. 9178-9183.
Kraft, A.S., et al., "Differing modulation of protein kinase C by bryostatin 1 and phorbol esters in JB6 mouse epidermal cells." J. Biol. Chem. (1988), vol. 263 pp. 8437-8442.
Kraft, A.S., et al., "Overexpression of protein kinase C beta 1 is not sufficient to induce factor independence in the interleukin-3-dependent myeloid cell line FDC-P1." Oncogene (1990), vol. 5(8), pp. 1243-1246.
Krauss, R.S., et al., "Disturbances in growth control and gene expression in a C3H/10T1/2 cell line that stably overproduces protein kinase C." Oncogene (1989), vol. 4, pp. 991-998.
Kronke, M., et al., "Adult T cell leukemia: a potential target for ricin A chain immunotoxins." Blood (1985), vol. 65, pp. 1416-1421.
Kronke, M., et al., "Selective killing of human T lymphotropic virus I infected leukemic T cells by monoclonal anti interleukin 2 receptor antibody ricin A chain conjugates: potentiation by ammonium chloride and monensin." Cancer Res. (1986), vol. 46, pp. 3295-3298.
Krishan, A., et al., "Flow cytometric monitoring of cellular anthracycline accumulation in murine leukemic cells." Cancer Res. (1986), 46(4 Pt 1), pp. 1768-1773.
Kuczek, T., et al., "Tumor cell heterogeneity: divided colony assay for measuring drug response." Proc. Natl. Acad. Sci. USA (1987), vol. 84, pp. 4490-4494.
Kuwano, M., et al., "Techniques to reverse or circumvent drug resistance in vitro." Prog. Clin. Biol. Res. (1986), vol. 223, pp. 163-171.
La Rosee, P., et al., "Activity of the Bcr-Abl Kinase Inhibitor PD180970 Against Clinically Relevant Bcr-Abl Isoforms That Cause Resistance to Imatinib Mesylate (Gleevec, STI-571)", Cancer Research, vol. 62 (Dec. 15, 2002) pp. 7149-7153.
Laemmli, U. K., "Cleavage of Structural Proteins during the Assembly of the Head of Bacteriophage T4." Nature (1970), vol. 227, pp. 680-685.
Laker, C., et al., "Autocrine stimulation after transfer of the granulocyte/macrophage colony stimulating factor gene and autonomous growth are distinct but interdependent steps in the oncogenic pathway." Proc. Natl. Acad. Sci. USA (1987), vol. 84, pp. 8458 8462.
Lane, H.C., et al., "Abnormalities of B cell activation and immunoregulation in patients with the acquired immunodeficiency syndrome." N. Eng. J. Med. (1983), vol. 309, pp. 453-458.
Lane, H.C., et al., "Qualitative analysis of immune function in patients with the acquired immunodeficiency syndrome. Evidence for a selective defect in soluble antigen recognition." N. Engl. J. Med. (1985), vol. 313, pp. 79-84.
Lang, R.A., et al., "Expression of a hemopoietic growth factor cDNA in a factor dependent cell line results in autonomous growth and tumorigenicity." Cell (1985) vol. 43, pp. 531-542.
Langer, R., "Controlled release of macromolecules." Chemtech (1982), vol. 12, pp. 98-105.
Lasky, L.A., et al., "Neutralization of the AIDS retrovirus by antibodies to a recombinant envelope glycoprotein." Science (1986), vol. 233(4760), pp. 209-212.
Latham, H.G., Jr., et al., "Amino- and Guanidino-Phenylglucosides", Journal of Organic Chemistry, vol. 15 (1950), pp. 884-889.
Le Coutre, P., et al., "Induction of Resistance to the Abelson Inhibitor STI571 in Human Leukemic Cells Through Gene Amplification", Blood, vol. 95 (Mar. 1, 2000) pp. 1758-1766.
Leach, K.L., et al., Characterization of a specific phorbol ester aporeceptor in mouse brain cytosol. Proc. Natl. Acad. Sci. USA (1983), vol. 80, pp. 4208-4212.
Lee, F., et al., "Isolation of cDNA for a human granulocyte macrophage colony stimulating factor by functional expression in mammalian cells." Proc. Natl. Acad. Sci. USA (1985), vol. 82, pp. 4360-4364.
Lee, S. P., et al., "Inhibitory Effect of Methyl Caffeate on Fos-Jun-DNA Complex Formation and Suppression of Cancer Cell Growth", Bull Korean Chem. Soc. (2001), vol. 22:10, pp. 1131-1135.
Leonard, G.D., et al., "The Role of ABC Transporters in Clinical Practice", The Oncologist, vol. 8 (2003) pp. 411-424.
Lerner, R.A., "Tapping the immunological repertoire to produce antibodies of predetermined specificity." Nature (1982), vol. 299(5884), pp. 592-596.
Lester, H.A., "Heterologous expression of excitability proteins: route to more specific drugs?" Science (1988), vol. 241(4869), pp. 1057-1063.
Levy, J.A., et al., "AIDS associated retroviruses (ARV) can productively infect other cells besides human T helper cells." Virology (1985), vol. 147, pp. 441-448.
Lippman, S.M., et al., "Retinoids as preventive and therapeutic anticancer agents (Part I)." Cancer Treat. Rep. (1987), vol. 71, pp. 391-405.
Livneh, E., et al., "Reconstitution of human epidermal growth factor receptors and its deletion mutants in cultured hamster cells." J. Biol. Chem. (1986), vol. 261, pp. 12490-12497.
Lombardino, J.G., et al., "Antiinflammatory 3,4 dihydro 2 alkyl 3 oxo-2H 1,2 benzothiazine 4 carboxamide 1,1 dioxides." J. Med. Chem. (1971), vol. 14, pp. 973-977.
Lombardino, J.G., et al., "New synthetic approaches to 3-carboxamides of 4-hydroxy-2H-1,2-benzothiazine 1,1-dioxide." J. Heterocyclic. Chem. (1976), vol. 1, pp. 333-335.
Lombardino, J.G., et al., "Preparation and antiinflammatory activity of some nonacidic trisubstituted imidazoles." J. Med. Chem. (1974), vol. 17, pp. 1182-1188.
Lombardino, J.G., et al., "Synthesis and antiinflammatory activity of some 3-carboxamides of 2-alkyl-4-hydroxy-2H-1,2-benzothiazine 1,1-dioxide." J. Med. Chem. (1971), vol. 14, pp. 1171-1175.
Lombardino, J.G., "Synthesis and antiinflammatory activity of metabolites of piroxicam." J. Med. Chem. (1981), vol. 24, pp. 39-42.
Long, S.D., et al., "Protease inhibitor antipain suppresses 12 O tetradecanoyl phorbol 13 acetate induction of plasminogen activator in transformable mouse embryo fibroblasts." Carcinogenesis (1981), vol. 2, pp. 933-936.
Loosfelt, H., et al., "Cloning and sequence analysis of rabbit progesterone receptor complementary DNA." Proc. Natl. Acad. Sci. USA (1986), vol. 83, pp. 9045-9049.
Loutfy, M.R., et al., "Salvage Antiretroviral Therapy in HIV Infection", Expert Opinion, vol. 3 (Feb. 2002) pp. 81-90.
Lusky, M., et al. "Inhibition of SV40 replication in simian cells by specific pBR322 DNA sequences." Nature (1981), vol. 293:79-81.
Lyerly, H.K., et al., "Human T cell lymphotropic virus IIIB glycoprotein (gp120) bound to CD4 determinants on normal lymphocytes and expressed by infected cells serves as target for immune attack." Proc. Natl. Acad. Sci. USA (1987), vol. 84, pp. 4601-4605.
Lynch, T.J., et al., "Activating Mutations in the Epidermal Growth Factor Receptor Underlying Responsiveness of Non-Small-Cell Lung Cancer to Gefitinib", The New England Journal of Medicine, vol. 350 (May 20, 2004) pp. 2129-2139.
Macleod, C.L., et al., "EGF induces cell cycle arrest of A431 human epidermoid carcinoma cells." J. Cell. Physiol. (1986), vol. 127, pp. 175-182.
Maddon, P.J., et al., "The T4 gene encodes the AIDS virus receptor and is expressed in the immune system and the brain." Cell (1986), vol. 47, pp. 333-348.

(56) References Cited

OTHER PUBLICATIONS

Mahon, F. X., et al., "Selection and Characterization of BCR-ABL Positive Cell Lines with Differential Sensitivity to the Tyrosine Kinase Inhibitor STI571: Diverse Mechanisms of Resistance", Blood, vol. 96 (Aug. 1, 2000) pp. 1070-1079.
Maier, P., et al., "A two parameter flow cytometry protocol for the detection and characterization of the clastogenic, cytostatic and cytotoxic activities of chemicals." Mutat. Res. (1986), vol. 164, pp. 369-379.
Makowske, M., et al., "A cDNA encoding protein kinase C identifies two species of mRNA in brain and GH3 cells." J. Biol. Chem. (1986) 261:13389-13392.
Mann, R., et al., "Construction of a retrovirus packaging mutant and its use to produce helper free defective retrovirus." Cell (1983), vol. 33, pp. 153-159.
Mansky, L.M., et al., "Lower in Vivo Mutation Rate of Human Immunodeficiency Virus Type 1 than that Predicted from the Fidelity of Purified Reverse Transcriptase", Journal of Virology, vol. 69 (Aug. 1995), pp. 5087-5094.
Marshall, J.R., et al., "Experimental Study of Some Potentially Tautomeric 2- and 4(6)-Substituted Pyrimidines", Journal of the Chemical Society, (1951) pp. 1004-1017.
Marx, J., "Why a New Cancer Drug Works Well in Some Patients", Science, vol. 304 (Apr. 30, 2004) pp. 658-659.
Masui, T., et al., "Type beta transforming growth factor is the primary differentiation inducing serum factor for normal human bronchial epithelial cells." Proc. Natl. Acad. Sci. USA (1986), vol. 83, pp. 2438-2442.
Matthews, J.T., et al., "12 O tetradecanoylphorbol 13 acetate stimulates phosphorylation of the 58,000 Mr form of polyomavirus middle T antigen in vivo: implications for a possible role of protein kinase C in middle T function." J. Virol. (1986), vol. 58(2), pp. 239-246.
Mayer, T.U., et al., "Small Molecule Inhibitor of Mitotic Spindle Bipolarity Identified in a Phenotype-Based Screen", Science, vol. 286 (Oct. 29, 1999), pp. 971-974.
McConlogue, L., et al., "Multiple mechanisms are responsible for altered expression of ornithine decarboxylase in overproducing variant cells." Mol. Cell. Biol. (1986), vol. 6, pp. 2865-2871.
McDougal, J.S., et al., "Binding of HTLV III/LAV to T4+ T cells by a complex of the 110K viral protein and the T4 molecule." Science (1986), vol. 231(4736), pp. 382-385.
McDougal, J.S., et al, "Binding of the human retrovirus HTLV III/LAV/ARV/HIV to the CD4 (T4) molecule: conformation dependence, epitope mapping, antibody inhibition, and potential for idiotypic mimicry." J. Immunol. (1986), vol. 137, pp. 2937-2944.
Mehra, V., et al., "Efficient mapping of protein antigenic determinants." Proc. Natl. Acad. Sci. USA (1986), vol. 83, pp. 7013-7017.
Meijlink, F., et al., "Removal of a 67 base pair sequence in the noncoding region of protooncogene fos converts it to a transforming gene." Proc. Natl. Acad. Sci. USA (1985), vol. 82:4987-4991.
Melo J.V., et al., "P190BCR-ABL chronic myeloid leukaemia: the missing link with chronic myelomonocytic leukaemia?" Leukemia, vol. 8 (Jan. 1994) pp. 208-211.
Metcalf, D., "The granulocyte macrophage colony stimulating factors." Science (1985), vol. 229, pp. 16-22.
Metcalf, D., et al., "The in vitro behavior of hemopoietic cells transformed by polyoma middle T antigen parallels that of primary human myeloid leukemic cells." EMBO J. (1987), vol. 6, pp. 3703-3709.
Modrow, S., et al., "Computer assisted analysis of envelope protein sequences of seven human immunodeficiency virus isolates: prediction of antigenic epitopes in conserved and variable regions." J. Virol. (1987), vol. 61, pp. 570-578.
Moolten, F.L., "Tumor chemosensitivity conferred by inserted herpes thymidine kinase genes: paradigm for a prospective cancer control strategy." Cancer Res. (1986), vol. 46, pp. 5276-5281.
Morrison, S.L., et al., "Chimeric human antibody molecules: mouse antigen binding domains with human constant region domains." Proc. Natl. Acad. Sci. USA (1984), vol. 81, pp. 6851-6855.
Mougneau, E., et al., "Biological activities of v myc and rearranged c myc oncogenes in rat fibroblast cells in culture." Proc. Natl. Acad. Sci. USA (1984), vol. 81, pp. 5758-5762.
Müller, O., et al., "Identification of Potent Ras Signaling Inhibitors by Pathway-Selective Phenotype-Based Screening", Angewandte Chemie—International Edition, vol. 43(4), (Jan. 16, 2004), pp. 450-454. Published online Jan. 14, 2004.
Müller, O., et al., "Identification of Potent Ras Signaling Inhibitors by Pathway-Selective Phenotype-Based Screening", Angewandte Chemie, vol. 116(4), (Jan. 16, 2004), pp. 456-460. Published online Jan. 14, 2004.
Murphy, L.C., et al., "Differential effects of tamoxifen and analogs with nonbasic side chains on cell proliferation in vitro." Endocrinology (1984), vol. 116, pp. 1071-1078.
Murray, H.W., et al., "Impaired production of lymphokines and immune (gamma) interferon in the acquired immunodeficiency syndrome." N. Engl. J. Med. (1984), vol. 310(14), pp. 883-889.
Mutschler, E., Effects of Pharmaceutical Preparations (1975) pp. 231-235. (with translation).
Nair, M.D., et al., "Syntheses and Reactions of Condensed Isoquinolines—Imidazo, Pyrimido, Triazolo, and Tetrazolo Isoquinolines", Indian Journal of Chemistry, vol. 5, (Sep. 1967), pp. 403-408.
Nakadate, T., et al., "Inhibition of 12 O tetradecanoylphorbol 13 acetate induced tumor promotion and epidermal ornithine decarboxylase activity in mouse skin by palmitoylcarnitine." Cancer Res. (1986), vol. 46, pp. 1589-1593.
Nakagawa, M., et al., "Reversal of multidrug resistance by synthetic isoprenoids in the KB human cancer cell line." Cancer Res. (1986), vol. 46, pp. 4453-4457.
Nakamura, G.R., et al., "Monoclonal Antibodies to the Extracellular Domain of HIV-1IIIB gp160 that Neutralize Infectivity, Block Binding to CD4, and React with Diverse Isolates." AIDS Res. and Human Retroviruses (1992), vol. 8(11), pp. 1875-1885.
Nepom, G.T., et al., "Induction of immunity to a human tumor marker by in vivo administration of anti idiotypic antibodies in mice." Proc. Natl. Acad. Sci. USA (1984), vol. 81, pp. 2864-2867.
Neuberger, M.S., et al., "Recombinant antibodies possessing novel effector functions." Nature (1984), vol. 312(5995), pp. 604-608.
Nichols, E.J., et al., "Transformation by the oncogene v fms: the effects of castanospermine on transformation related parameters." Exp. Cell Res. (1987), vol. 173, pp. 486-495.
Nishikawa, M., et al., "1 (5 Isoquinolinesulfonyl) 2 methylpiperazine(H 7), a potent inhibitor of protein kinases, inhibits the differentiation of HL 60 cells induced by phorbol diester." Life Sci. (1986) , vol. 39, pp. 1101-1107.
Nishizuka, Y., "The role of protein kinase C in cell surface signal transduction and tumour promotion." Nature (1984), vol. 308, pp. 693-698.
Nishizuka, Y., "Studies and perspectives of protein kinase C." Science (1986), vol. 233, pp. 305-312.
Noble, M.E.M., et al., "Protein Kinase Inhibitors: Insights into Drug Design from Structure", Science, vol. 303 (Mar. 19, 2004) pp. 1800-1805.
Noda, M., et al., "Expression of functional sodium channels from cloned cDNA." Nature (1986), vol. 322, pp. 826-828.
Noguchi, S., et al., "Expression of functional (Na+ + K+)-ATPase from cloned cDNAs." FEBSLett. (1987), vol. 225, pp. 27-32.
O'Brian, C.A., et al., "Protein kinase C phosphorylates the synthetic peptide Arg Arg Lys Ala Ser Gly Pro Pro Val in the presence of phospholipid plus either Ca2+ or a phorbol ester tumor promoter." Biochem. Biophys. Res. Commun. (1984), vol. 124, pp. 296-302.
O'Brian, C.A., et al., "Studies on protein kinase C and their relevance to tumor promotion. In Levine, A.J. et al. (Eds), Cancer Cells 3: Growth Factors and Transformation pp. 359-363." (Cold Spring Harbor Laboratory, Cold Spring Harbor, N.Y. 1985).
O'Brian, C.A., et al., "Inhibition of protein kinase C by tamoxifen." Cancer Res. (1985), vol. 45, pp. 2462-2465.
O'Brian, C.A., et al., "Current concepts of tumor promotion by phorbol esters and related compounds." In: New Insights into Cell and Membrane Transport Processes (1986) (Poste, G. and Crooke, S. T., eds., Plenum Publishing Co., New York, NY) pp. 261-274.

(56) References Cited

OTHER PUBLICATIONS

O'Brian, C.A., et al., "Triphenylethylenes: a new class of protein kinase C inhibitors." J. Natl. Cancer Inst. (1986), vol. 76, pp. 1243-1246.
O'Brian, et al., "Specific and Direct Binding of Protein Kinase C to an Immobilized Tamoxifen Analogue", Cancer Research, 1988, vol. 48, pp. 3626-3629.
O'Hara, C.J., et al., "Cells resistant to cytotoxic drugs are recognized by monoclonal antibody." J. Clin. Immunol. (1984), vol. 4, pp. 403-411.
O'Hare, T., et al., "Inhibition of wild-type and mutant Bcr-Abl by AP23464, a potent ATP-based oncogenic protein kinase inhibitor: implications for CML", Blood, vol. 104:8 (Oct. 15, 2004) pp. 2532-2539.
Oi, V.T., et al., "Immunoglobulin-producing hybrid cell lines." In: Selected Methods in Cellular Immunology (Mishell, B.B. and Shiigi, S.M., eds., W.H. Freeman & Co., San Francisco, CA), (1980) pp. 351-372.
Ogawara, H., et al., "A specific inhibitor for tyrosine protein kinase from Pseudomonas." J. Antibiot. (1986) (Tokyo), vol. 39, pp. 606-608.
Ohno, S., et al., "Tissue specific expression of three distinct types of rabbit protein kinase C." Nature (1987), vol. 325, pp. 161-166.
Okuda, K., et al., "p210BCR/ABL, p190BCR/ABL, and TEL/ABL activate similar signal transduction pathways in hematopoietic cell lines", Oncogene (1996), vol. 13:6, pp. 1147-1152.
Ono, Y., et al., "Expression and properties of two types of protein kinase C: alternative splicing from a single gene." Science (1987), vol. 236, pp. 1116-1120.
Ono, Y., et al., "Two types of complementary DNAs of rat brain protein kinase C. Heterogeneity determined by alternative splicing." FEBS Lett. (1986), vol. 206, pp. 347-352.
Paez, J.G., et al., "EGFR Mutations in Lung Cancer: Correlation with Clinical Response to Gefitinib Therapy", Sciencexpress (Apr. 29, 2004) pp. 1-4.
Palaszynski, E.W., et al., "Evidence for specific receptors for interleukin 3 on lymphokine dependent cell lines established from long term bone marrow cultures." J. Immunol. (1984), vol. 132, pp. 1872-1878.
Parker, P.J., et al., "The complete primary structure of protein kinase C the major phorbol ester receptor." Science (1986), vol. 233, pp. 853-859.
Pastan, et al. "Multidrug resistance." UCLA Symposia on Molecular & Cellular Biology Abstract A13, Jan. 1986.
Pauwels, R., et al., "Sensitive and rapid assay on MT 4 cells for detection of antiviral compounds against the AIDS virus." J. Virol. Methods (1987), vol. 16, pp. 171-185.
Pellerano, C., et al, "Sistemi Chelanti Tridentati N-N-N Quali Potenziali Agenti Antitumorali", Farmco (1985) vol. 40:9 pp. 645-654. (with English translation).
Perez, P., et al., "Specific targeting of cytotoxic T cells by anti T3 linked to anti target cell antibody." Nature (1985), vol. 316(6026), pp. 354-356.
Perkins, A.S., et al., "Design of a retrovirus derived vector for expression and transduction of exogenous genes in mammalian cells." Mol. Cell. Biol. (1983), vol. 3, pp. 1123-1132.
Persons, D.A., et al., "Altered growth regulation and enhanced tumorigenicity of NIH 3T3 fibroblasts transfected with protein kinase C I cDNA." Cell (1988), vol. 52, pp. 447-458.
Pontremoli, S., et al., "Phosphorylation and proteolytic modification of specific cytoskeletal proteins in human neutrophils stimulated by phorbol 12 myristate 13 acetate." Proc. Natl. Acad. Sci. USA (1987), vol. 84, pp. 3604-3608.
Popovic, M., et al., "Detection, isolation, and continuous production of cytopathic retroviruses (HTLV III) from patients with AIDS and pre AIDS." Science (1984), vol. 224(4648), pp. 497-500.
Prescott, B., et al, "Potential Antitumor Agents: Derivatives of 2-Hydrazino-5-nitropyridine", J. Pharm. Sci. (1970), vol. 59:1, pp. 101-104.
Pritchett, D.B., et al., "Structure and functional expression of cloned rat serotonin 5HT 2 receptor." EMBO J. (1988), vol. 7, pp. 4135-4140.
Prywes, R., et al., "Mutations in the cytoplasmic domain of EGF receptor affect EGF binding and receptor internalization." EMBO J. (1986), vol. 5, pp. 2179-2190.
Putney, S.D., et al., "HTLV III/LAV neutralizing antibodies to an *E. coli* produced fragment of the virus envelope." Science (1986), vol. 234(4782), pp. 1392-1395.
Quillardet, P., et al., "SOS chromotest, a direct assay of induction of an SOS function in *Escherichia coli* K 12 to measure genotoxicity." Proc. Natl. Acad. Sci. USA (1982), vol. 79, pp. 5971-5975.
Racker, E., et al., "Glycolysis and methylaminoisobutyrate uptake in rat 1 cells transfected with ras or myc oncogenes." Proc. Natl. Acad. Sci. USA (1985), vol. 82, pp. 3535-3538.
Rahaingoson, F., et al., "On epot synthesis of furyl α-bromoketones from furyl ketones using the A-162 Br3-resin/CH3NO2 system." Synth. Comm. (1992), vol. 22, pp. 1923-1927.
Ravandi F., et al., "Chronic myelogenous leukaemia with p185(BCR/ABL) expression: characteristics and clinical significance", British Journal of Haematology, vol. 107 (Dec. 1999) pp. 581-586.
Ratner, L., et al., "Complete nucleotide sequence of the AIDS virus, HTLV III." Nature (1985), vol. 313(6000), pp. 277-284.
Reddel, R.R., et al., "Differential sensitivity of human breast cancer cell lines to the growth inhibitory effects of tamoxifen." Cancer Res. (1985) , vol. 45, pp. 1525-1531.
Reddy, E.P., et al., "Complete nucleotide sequence and organization of the Moloney murine sarcoma virus genome." Science (1981), vol. 214(4519), pp. 445-450.
Reinecke, M.G., et al., "An improved synthesis of thiophene-2,3-dicarboxylic acid by sequential carboxylation." Synthesis (Apr. 1980), pp. 327-329.
Richert, N., et al., "Inhibition of the transformation specific kinase in ASV transformed cells by N alpha tosyl L lysyl chloromethyl ketone." Cell (1979), vol. 18, pp. 369-374.
Riedel, H., et al., "A chimeric, ligand binding v erbB/EGF receptor retains transforming potential." Science (1987), vol. 236, pp. 197-200.
Riordan, J.R., et al., "Amplification of P glycoprotein genes in multidrug resistant mammalian cell lines." Nature (1985), vol. 316(6031), pp. 817-819.
Rizzino, A., et al., "Induction and modulation of anchorage independent growth by platelet derived growth factor, fibroblast growth factor, and transforming growth factor beta." Cancer Res. (1986), vol. 46, pp. 2816-2820.
Roberts, A.B., et al., "Selective inhibition of the anchorage independent growth of myc transfected fibroblasts by retinoic acid." Nature (1985), vol. 315(6016), pp. 237-239.
Robey, W.G., et al., "Prospect for prevention of human immunodeficiency virus infection: purified 120 kDa envelope glycoprotein induces neutralizing antibody." Proc. Natl. Acad. Sci. USA (1986), vol. 83, pp. 7023-7027.
Roninson, I.B., et al., "Amplification of specific DNA sequences correlates with multi drug resistance in Chinese hamster cells." Nature (1984), vol. 309(5969), pp. 626-628.
Roninson, I.B., et al., "Isolation of human mdr DNA sequences amplified in multidrug resistant KB carcinoma cells." Proc. Natl. Acad. Sci. USA (1986), vol. 83, pp. 4538-4542.
Roninson, I.B., et al., "Mdr gene amplification in multidrug-resistant cells." In: Journal of Cellular Biochemistry, Supplement 10A: UCLA Symposia on Molecular & Cellular Biology (1986), Abstract A18, Alan R. Liss, Inc., New York, p. 12.
Roninson, I.B., "Molecular mechanism of multidrug resistance in tumor cells." Clin. Physiol. Biochem. (1987), vol. 5, pp. 140-151.
Rook, A.H., et al., "Interleukin 2 enhances the depressed natural killer and cytomegalovirus specific cytotoxic activities of lymphocytes from patients with the acquired immune deficiency syndrome." J. Clin. Invest. (1983), vol. 72, pp. 398-403.
Rosenthal, A., et al., "Expression in rat fibroblasts of a human transforming growth factor alpha cDNA results in transformation." Cell (1986), vol. 46, pp. 301-309.
Roth, C.W., et al., "Rous sarcoma virus transformed cells are resistant to cyclic AMP." J. Cell Physiol. (1982), vol. 111, pp. 42-48.

(56) References Cited

OTHER PUBLICATIONS

Rovera, G., et al., "Human promyelocytic leukemia cells in culture differentiate into macrophage like cells when treated with a phorbol diester." Proc. Natl. Acad. Sci. USA. (1979), vol. 76, pp. 2779-2783.
Roy, S.K., et al., "High performance immunosorbent purification of recombinant leukocyte A interferon", J. Chromatogr. (1984), vol. 303, pp. 225-228.
Rubin, L.A., et al., "Reconstitution of a functional interleukin 2 receptor in a nonlymphoid cell." J. Immunol. (1987), vol. 139, pp. 2355-2360.
Safa, A.R., et al., "Identification of the multidrug resistance related membrane glycoprotein as an acceptor for calcium channel blockers." J. Biol. Chem. (1987), vol. 262, pp. 7884-7888.
Safa, A.R., "Photoaffinity labeling of the multidrug resistance related P glycoprotein with photoactive analogs of verapamil." Proc. Natl. Acad. Sci. USA. (1988), vol. 85, pp. 7187-7191.
Said, M. M., "Synthesis of some new 1, 2,4,-triazine derivatives and evaluation of their antimicrobial and cytotoxic actvitives", Egyptian J. Bio. Sci. (2003) vol. 11, pp. 46-59.
Sakai, Y., et al., "Pharmacological characterization of serotonin receptor induced by rat brain messenger RNA in Xenopus oocytes." Brain Res. (1986), vol. 362, pp. 199-203.
Salomon, D.S., et al., "Loss of growth responsiveness to epidermal growth factor and enhanced production of alpha transforming growth factors in ras transformed mouse mammary epithelial cells." J. Cell. Physiol. (1987), vol. 130, pp. 397-409.
Samid, D., et al., "Biochemical correlates of phenotypic reversion in interferon treated mouse cells transformed by a human oncogene." Biochem. Biophys. Res. Commun. (1984), vol. 119, pp. 21-28.
Samid, D., et al., "Development of transformed phenotype induced by a human ras oncogene is inhibited by interferon." Biochem. Biophys. Res. Commun. (1985), vol. 126, pp. 509-516.
Sandstrom, E.G., et al., "Inhibition of human T-cell lymphotropic virus type III in vitro by phosphonoformate." Lancet (1985), vol. 1(8444), pp. 1480-1482.
Sarngadharan, M.G., et al., "Antibodies reactive with human T lymphotropic retroviruses (HTLV III) in the serum of patients with AIDS." Science (1984), vol. 224(4648), pp. 506-508.
Sawyers, C.L., "Chronic Myeloid Leukemia", The New England Journal of Medicine, vol. 340 (Apr. 29,1999) pp. 1330-1340.
Schaeffer, W.I., et al., "Efficient detection of soft agar grown colonies using a tetrazolium salt." Cancer Lett. (1976), vol. 1, pp. 259-262.
Schindler, T., et al., "Structural Mechanism for STI-571 Inhibition of Abelson Tyrosine Kinase", Science, vol. 289 (Sep. 15, 2000) pp. 1938-1942.
Schleicher, R.L. et al., "Inhibition of hamster melanoma growth by estrogen." Cancer Res. (1987), vol. 47, pp. 453-459.
Senechal, K., et al., "The CRKL Adaptor Protein Transforms Fibroblasts and Functions in Transformation by the BCR-ABL Onocogene", The Journal of Biological Chemistry, vol. 271 (Sep. 20, 1996) pp. 23255-23261.
Senechal, K., et al., "Structural Requirements for Function of the Crkl Adapter Protein in Fibroblasts and Hematopoietic Cells", Molecular and Cellular Biology, vol. 18 (Sep. 1998) pp. 5082-5090.
Senga, T., et al., "Clustered cysteine residues in the kinase domain of v-Src: critical role for protein stability, cell transformation and sensitivity to herbimycin A." Oncogene (2000), vol. 19(2), pp. 273-279.
Schupbach, J., et al., "Serological analysis of a subgroup of human T lymphotropic retroviruses (HTLV III) associated with AIDS." Science (1984), vol. 224(4648), pp. 503-505.
Schweigerer, L., et al., "Capillary endothelial cells express basic fibroblast growth factor, a mitogen that promotes their own growth." Nature (1987), vol. 325(6101), pp. 257-259.
Shah, D.M., et al., "Engineering herbicide tolerance in transgenic plants." Science (1986), vol. 233, pp. 478-481.
Shah, N. P., et al., "Overriding Imatinib Resistance with a Novel ABL Kinase Inhibitor", Science, vol. 305, (Jul. 16, 2004), pp. 399-401.
Shalaby, M.R., et al., "The effects of human immunodeficiency virus recombinant envelope glycoprotein on immune cell functions in vitro." Cell. Immunol. (1987), vol. 110, pp. 140-148.
Shearer, B.G., "Conformationally Restricted Arginine Analogues as Inhibitors of Human Nitric Oxide Synthase", Bioorganic and Medicinal Chemistry Letters, vol. 7 (Jul. 8, 1997), pp. 1763-1768.
Shen, D.W., et al., "Human multidrug resistant cell lines: increased mdrl expression can precede gene amplification." Science (1986), vol. 232(4750), pp. 643-645.
Shen, D.W., et al., "Multiple drug resistant human KB carcinoma cells independently selected for high level resistance to colchicine, adriamycin, or vinblastine show changes in expression of specific proteins." J. Biol. Chem. (1986), vol. 261, pp. 7762-7770.
Shiroki, K., et al., "Expression of the E4 gene is required for establishment of soft agar colony forming rat cell lines transformed by the adenovirus 12 E1 gene." J. Virol. (1984), vol. 50, pp. 854-863.
Sibley, D.R., et al., "Regulation of transmembrane signaling by receptor phosphorylation." Cell (1987) , vol. 48, pp. 913-922.
Sidman, K.R., et al., "Controlled release of macromolecules and pharmaceuticals from synthetic polypeptides based on glutamic acid." Biopolymers (1983), vol. 22(1), pp. 547-556.
Siegel, J.P., et al., "Sera from patients with the acquired immunodeficiency syndrome inhibit production of interleukin 2 by normal lymphocytes." J. Clin. Invest. (1985), vol. 75, pp. 1957-1964.
Sistonen, L., et al., "Dose effects of transfected c Ha rasVal 12 oncogene in transformed cell clones." Exp. Cell Res. (1987), vol. 168, pp. 518-530.
Skovsgaard, T., et al., "Chemosensitizers counteracting acquired resistance to anthracyclines and vinca alkaloids in vivo. A new treatment principle." Cancer Treat. (1984), Rev. 11 Suppl A:63-72.
Smith, D.H., et al., "Blocking of HIV 1 infectivity by a soluble, secreted form of the CD4 antigen." Science (1987), vol. 238(4834), pp. 1704-1707.
Sorrentino, V., et al., "Potentiation of growth factor activity by exogenous c myc expression." Proc. Natl. Acad. Sci. USA (1986), vol. 83, pp. 8167-8171.
Stabel, S., et al. "Protein kinase C—structural and functional characterization." In: Journal of Cellular Biochemistry, Supplement 10C: UCLA Symposia on Molecular & Cellular Biology, (1986) Abstract L318, Alan R. Liss, Inc., New York, p. 206.
Stabel, S., et al., "Quantitation of protein kinase C by immunoblot expression in different cell lines and response to phorbol esters." J. Cell. Physiol. (1987), vol. 130, pp. 111-117.
Stahl, R.E., et al., "Immunologic abnormalities in homosexual men. Relationship to Kaposi's sarcoma." Am. J. Med. (1982), vol. 73(2), pp. 171-178.
Steinkamp, J.A., et al., "Phagocytosis: flow cytometric quantitation with fluorescent microspheres." Science (1982) , vol. 215(4528), pp. 64-66.
Stern, D.F., et al., "Differential responsiveness of myc and ras transfected cells to growth factors: selective stimulation of myc transfected cells by epidermal growth factor." Mol. Cell. Biol. (1986), vol. 6, pp. 870-877.
Storer, R.D., et al., "Malignant transformation of a preneoplastic hamster epidermal cell line by the EJ c Ha ras oncogene." Cancer Res. (1986), vol. 46, pp. 1458-1464.
Strader, C.D., et al., "Beta adrenergic receptor subtype is an intrinsic property of the receptor gene product." Mol. Pharmacol. (1987), vol. 32, pp. 179-183.
Strader, C.D., et al., "The carboxyl terminus of the hamster beta adrenergic receptor expressed in mouse L cells is not required for receptor sequestration." Cell (1987), vol. 49, pp. 855-863.
Strader, C.D., et al., "Identification of residues required for ligand binding to the beta adrenergic receptor." Proc. Natl. Acad. Sci. USA. (1987), vol. 84, pp. 4384-4388.
Strader, C.D., et al., "Mutations that uncouple the beta adrenergic receptor from Gs and increase agonist affinity." J. Biol. Chem. (1987), vol. 262, pp. 16439-16443.
Stryer, L., (1981) Biochemistry, pp. 854-855.

(56) References Cited

OTHER PUBLICATIONS

Stumpo, D.J., et al., "Identification of c fos sequences involved in induction by insulin and phorbol esters." J. Biol. Chem. (1988), vol. 263, pp. 1611-1614.
Sullivan, L.M., et al., "An anticatalytic monoclonal antibody to avian plasminogen activator: its effect on behavior of RSV transformed chick fibroblasts." Cell (1986), vol. 45, pp. 905-915.
Tagliaferri, P., et al., "Effects of ouabain on NIH/3T3 cells transformed with retroviral oncogenes and on human tumor cell lines." Int. J. Cancer (1987), vol. 40, pp. 653-658.
Takahashi, T., et al., "A physiological study on acetylcholine receptor expressed in Xenopus oocytes from cloned cDNAs." J. Physiol. (1985) (Paris) vol. 80, pp. 229-232.
Takeda, S., et al., "Construction of chimaeric processed immunoglobulin genes containing mouse variable and human constant region sequences." Nature (1985), vol. 314(6010), pp. 452-454.
Takeuchi, M., et al., "An in vitro screening method for antitumor and/or antitumorigenic substances involving the transformation of chick embryo fibroblasts infected with Rous sarcoma virus." J. Antibiot. (1984) (Tokyo), vol. 37, pp. 235-238.
Tanaka, A., et al., "Antiplatelet agents based on cyclooxygenase inhibition without ulcerogenesis. Evaluation and synthesis of 4,5 bis(4 methoxyphenyl) 2 substituted thiazoles." J. Med. Chem. (1994), vol. 37, pp. 1189-1199.
Tanaka, K., et al, "Pharmacological studies of the new antiinflammatory agent 3 formylamino-7 methylsulfonylamino 6 phenoxy 4' 1 benzopyran 4 one. 2nd communication: effect on the arachidonic acid cascades." Arzneimittelforschung (1992), vol. 42, pp. 945-950.
Taparowsky, E., et al., "Activation of the T24 bladder carcinoma transforming gene is linked to a single amino acid change." Nature (1982), vol. 300(5894), pp. 762-765.
Thalacker, F.W., et al., "Specific induction of secreted proteins by transforming growth factor beta and 12 O tetradecanoylphorbol 13 acetate. Relationship with an inhibitor of plasminogen activator." J. Biol. Chem. (1987), vol. 262, pp. 2283-2290.
Thorpe, P.E., et al., "Modification of the carbohydrate in ricin with metaperiodate cyanoborohydride mixtures. Effects on toxicity and in vivo distribution." Eur. J. Biochem. (1985), vol. 147, pp. 197-206.
Tipping, AJ., et al., "Efficacy of dual-specific Bcr-Abl and Src-family kinase inhibitors in cells sensitive and resistant to imatinib mesylate", Leukemia, vol. 18 (Aug. 2004) pp. 1352-1356.
Tseng, et al., Prevention of anchorage independent colony growth of inducible EJ ras oncogene transfected RAT 1 fibroblasts by drugs that interact with the poly (ADP ribose) polymerase system. (1986) Abstract. Clin Res (1986). vol. 34(1).
Tseng, A., Jr., et al., Prevention of tumorigenesis of oncogene transformed rat fibroblasts with DNA site inhibitors of poly(ADP ribose) polymerase. Proc. Natl. Acad. Sci. USA (1987), vol. 84, pp. 1107-1111.
Tsuruo, T., et al., "Enhancement of vincristine and adriamycin induced cytotoxicity by verapamil in P388 leukemia and its sublines resistant to vincristine and adriamycin." Biochem. Pharmacol. (1982), vol. pp. 31, pp. 3138-3140.
Tsuruo, T., et al., "Overcoming of vincristine resistance in P388 leukemia in vivo and in vitro through enhanced cytotoxicity of vincristine and vinblastine by verapamil." Cancer Res. (1981), vol. 41, pp. 1967-1972.
Tsuruo, T., et al., "Potentiation of antitumor agents by calcium channel blockers with special reference to cross resistance patterns." Cancer Chemother. Pharmacol. (1985), vol. 15, pp. 16-19.
Tsuruo, T., et al., "Potentiation of vincristine and Adriamycin effects in human hemopoietic tumor cell lines by calcium antagonists and calmodulin inhibitors." Cancer Res. (1983), vol. 43, pp. 2267-2272.
Ueda, K., et al., "Expression of a full length cDNA for the human "MDR1" gene confers resistance to colchicine, doxorubicin, and vinblastine." Proc. Natl. Acad. Sci. USA (1987), vol. 84, pp. 3004-3008.
Ueda, K., et al., "The mdr1 gene, responsible for multidrug resistance, codes for P glycoprotein." Biochem. Biophys. Res. Commun. (1986), vol. 141, pp. 956-962.
Uehara, Y., et al., "An approach to developing anti tumor agents by using the cells expressing particular oncogenes." Taisha (1987), vol. 24, pp. 197-203. (in Japanese with accompanying English translation).
Uehara, Y., Cancer gene inhibitor and its screening. Oncologia (1986), vol. 19, pp. 90-93. (in Japanese with accompanying English translation).
Uehara, Y., et al., "Differential sensitivity of RSVts (temperature sensitive Rous sarcoma virus) infected rat kidney cells to nucleoside antibiotics at permissive and non permissive temperatures." Biochem. J. (1985), vol. 232, pp. 825-831.
Uehara, Y., et al., "Increased sensitivity to oxanosine, a novel nucleoside antibiotic, of rat kidney cells upon expression of the integrated viral src gene." Cancer Res. (1985), vol. 45, pp. 5230-5234.
Uehara, Y., et al., "Inhibition of transforming activity of tyrosine kinase oncogenes by herbimycin A." Virology (1988), vol. 164, pp. 294-298.
Uehara, Y., et al., "Irreversible inhibition of v src tyrosine kinase activity by herbimycin A and its abrogation by sulfhydryl compounds." Biochem. Biophys. Res. Commun. (1989), vol. 163, pp. 803-809.
Uehara, Y., et al., "Mechanism of reversion of Rous sarcoma virus transformation by herbimycin A: reduction of total phosphotyrosine levels due to reduced kinase activity and increased turnover of p60v src1." Cancer Res. (1989), vol. 49, pp. 780-785.
Uehara, Y., et al., "Morphological changes from 'transformed' to 'normal' by benzoquinoid ansamycins accompany the inhibition of pp60src in rat kidney cells infected with srcts-Rous Sarcoma Virus." Recent Adv. Chemother., Proc. Int. Congr. Chemother., 14th, vol.: Anticancer Sect. 1 (Ishigami, Joji, ed., Univ. Tokyo, 1985), pp. 219-220.
Uehara, Y., et al., "Phenotypic change from transformed to normal induced by benzoquinonoid ansamycins accompanies inactivation of p60src in rat kidney cells infected with Rous sarcoma virus." Mol. Cell. Biol. (1986), vol. 6, pp. 2198-2206.
Uehara, Y., et al., "Screening of agents which convert 'transformed morphology' of Rous sarcoma virus infected rat kidney cells to 'normal morphology': identification of an active agent as herbimycin and its inhibition of intracellular src kinase." Jpn. J. Cancer Res. (1985), vol. 76, pp. 672-675.
Uehara, Y., et al., "Specific increase in thymidine transport at a permissive temperature in the rat kidney cells infected with srcts Rous sarcoma virus." Biochem. Biophys. Res. Commun. (1984), vol. 125, pp. 129-134.
Uehara, Y., et al., "Use and selectivity of herbimycin A as inhibitor of protein-tyrosine kinases." Methods Enzymol. (1991), vol. 201:370-9.
Ullrich, A., et al., "Human epidermal growth factor receptor cDNA sequence and aberrant expression of the amplified gene in A431 epidermoid carcinoma cells." Nature (1984), vol. 309, pp. 418-425.
Umbach, J.A., et al., "Expression of an omega-conotoxin-sensitive calcium channel in Xenopus oocytes injected with mRNA from Torpedo electric lobe." Proc. Natl. Acad. Sci. USA (1987), vol. 84, pp. 5464-5468.
Umezawa, H., et al., "Studies on a new epidermal growth factor-receptor kinase inhibitor, erbstatin, produced by MH435 hF3." J. Antibiot. (1986) (Tokyo), vol. 39, pp. 170-173.
Vane, J., "Towards a better aspirin." Nature (1994), vol. 367(6460), pp. 215-216.
Verma, A.K., et al, "Involvement of protein kinase C activation in ornithine decarboxylase gene expression in primary culture of newborn mouse epidermal cells and in skin tumor promotion by 12 O tetradecanoylphorbol 13 acetate." Cancer Res. (1986) vol. 46, pp. 6149-6155.
Vilmer, E., et al., "Isolation of new lymphotropic retrovirus from two siblings with haemophilia B, one with AIDS." Lancet (1984), vol. 1(8380), pp. 753-757.
Vitetta, E.S., et al., "Redesigning nature's poisons to create anti tumor reagents." Science (1987), vol. 238(4830), pp. 1098-1104.

(56) References Cited

OTHER PUBLICATIONS

Von Hoff, D.D. et al., "Use of a radiometric system to screen for antineoplastic agents: correlation with a human tumor cloning system." Cancer Res. (1985), vol. 45, pp. 4032-4038.
Von Bubnoff, N., et al., "BCR-ABL Gene Mutations in Relation to Clinical Resistance of Philadelphia-Chromosome-Positive Leukemia to STI571: A Prospective Study", The Lancet, vol. 359 (Feb. 9, 2002) pp. 487-491.
Von Bubnoff, N., et al., "A cell-based screen for resistance of Bcr-Abl positive leukemia identifies the mutation pattern for PD166326, an alternative Abl kinase inhibitor", Blood, vol. 105 (Feb. 15, 2005) pp. 1652-1659.
Von Bubnoff, N., et al., "Inhibition of Wild-Type and Mutant Bcr-Abl by Pyrido-Pyrimidine-Type Small Molecule Kinase Inhibitors", Cancer Research (Oct. 1, 2003) vol. 63. pp. 6395-6404.
Von Hoff, D.D., et al., "Use of a radiometric system to screen for antineoplastic agents: correlation with a human tumor cloning system." Cancer Res. (1985), vol. 45, pp. 4032-4038.
Von Meyenburg, K., et al., "Proton conduction by subunit a of the membrane-bound ATP synthase of *Escherichia coli* revealed after induced overproduction." EMBO J. (1985), vol. 4, pp. 2357-2363.
Wakai, T., et al., "Late Resistance to Imatinib Therapy in a Metastatic Gastrointestinal Stromal Tumour is Associated With a Second KIT Mutation", British Journal of Cancer, vol. 90 (Jun. 1, 2004) pp. 2059-2061.
Walton, G.M., et al., "A three step purification procedure for protein kinase C: characterization of the purified enzyme." Anal. Biochem. (1987), vol. 161, pp. 425-437.
Weigel, U., et al., "Mutant Proteins of Human Interleukin 2: Renaturation Yield, Proliferative Activity and Receptor Binding", European Journal of Biochemistry, vol. 180 (Mar. 15, 1989) pp. 295-300.
Weinstein, I.B., Growth factors, oncogenes, and multistage carcinogenesis. J. Cell. Biochem. (1987), vol. 33, pp. 213-224.
Weinstein, I.B., et al., "Initial cellular targets and eventual genomic changes in multistage carcinogenesis." In: Models, Mechanisms and Etiology of Tumour Promotion (Borzsonyi, M., Lapis, K., Day, N.E., Yamasaki, H. eds., International Agency for Research on Cancer, Lyon, France, 1984) pp. 277-297.
Weinstein, I.B., et al., "Molecular mechanisms in multistage chemical carcinogenesis." In: Biochemical Basis of Carcinogenesis (Greim, H., Jung, R., Kramer, M., Marquardt, H., Oesch, F. eds., Raven Press, New York, NY 1984) pp. 193-212.
Weinstein, I.B., et al., "Multistage carcinogenesis involves multiple genes and multiple mechanisms." J. Cell. Physiol. (1984), Suppl. 3, pp. 127-137.
Weinstein, I.B., et al., "Multistage carcinogenesis involves multiple genes and multiple mechanisms." In Levine, A.J. et al. (Eds), Cancer Cells 1: The Transformed Phenotype pp. 229-237 (Cold Spring Harbor Laboratory, Cold Spring Harbor, N.Y. 1984).
Weinstein I.B., et al., "Studies on the mechanism of action of protein kinase C and the isolation of molecular clones encoding the enzyme." Symp. Fundam. Cancer Res. (1987), vol. 39, pp. 173-183.
Weisberg E., "Characterization of AMN107, a selective inhibitor of native and mutant Bcr-Abl", Cancer Cell, vol. 7 (Feb. 2005) pp. 129-141.
Weisberg E., et al., "Histone deacetylase inhibitor NVP-LAQ824 has significant activity against myeloid leukemia cells in vitro and in vivo", Leukemia, vol. 18 (Dec. 2004) pp. 1951-1963.
Weisberg, E., et al., "Mechanism of Resistance to the ABL Tyrosine Kinase Inhibitor STI 571 in BCR/ABL-Transformed Hematopoietic Cell Lines", Blood, vol. 95 (Jun. 1, 2000) pp. 3498-3505.
Weiss, A., et al., "Role of T3 surface molecules in human T cell activation: T3 dependent activation results in an increase in cytoplasmic free calcium." Proc. Natl. Acad. Sci. USA (1984), vol. 81, pp. 4169-4173.
Weltman, J.K., et al., "Rapid screening with indirect immunotoxin for monoclonal antibodies against human small cell lung cancer." Cancer Res. (1987), vol. 47, pp. 5552-5556.
White, M.F., et al., "Mutation of the Insulin Receptor at Tyrosine 960 Inhibits Signal Transmission but Does Not Affect Its Tyrosine Kinase Activity", Cell, vol. 54 (Aug. 26, 1988) pp. 641-649.
Wigler, M., et al., "Transfer of purified herpes virus thymidine kinase gene to cultured mouse cells." Cell (1977), vol. 11, pp. 223-232.
Willey, J.C., et al., "Relationship of ornithine decarboxylase activity and cAMP metabolism to proliferation of normal human bronchial epithelial cells." J. Cell. Physiol. (1985), vol. 124, pp. 207-212.
Willingham, M.C., et al., "Single cell analysis of daunomycin uptake and efflux in multidrug resistant and sensitive KB cells: effects of verapamil and other drugs." Cancer Res. (1986), vol. 46, pp. 5941-5946.
Winsiewski, C.L., et al., "Characterization of Potent Inhibitors of the Bcr-Abl and the c-Kit Receptor Tyrosine Kinases", Cancer Research (2002), vol. 62, pp. 4244-4255.
Wood, P.A., et al., "Expression of human argininosuccinate synthetase after retroviral mediated gene transfer." Somat. Cell Mol. Genet. (1986), vol. 12, pp. 493-500.
Woodgett, J.R., et al., "Substrate specificity of protein kinase C. Use of synthetic peptides corresponding to physiological sites as probes for substrate recognition requirements." Eur. J. Biochem. (1986), vol. 161, pp. 177-184.
Work, T.S., et al., Work E., Laboratory Techniques in Biochemistry and Molecular Biology, Elsevier Biomedical Press (1982).
Wu, M.T., et al., "Annelated Piperazinyl-7,8-dihydro-6H-thiopyrano[3,2-d]pyrimidines", Journal of Heterocyclic Chemistry, vol. 27 (1990), pp. 1559-1563.
Xue Y., et al. "Study on the anti-carcinogenic effects of three compounds in Kaempferia galangal L", Journal of Hygiene Research (2002), vol. 31:4, pp. 247-251. [with English translation].
Yamamoto, K.R., et al., Alberts, B.M. "Steroid receptors: elements for modulation of eukaryotic transcription." Annu. Rev. Biochem . (1976), vol. 45, pp. 721-746.
Yanovich, S., et al., "Effects of verapamil on daunomycin cellular retention and cytotoxicity in P388 leukemic cells." Cancer Res. (1984), vol. 44, pp. 1743-1747.
Yokota, T., et al., "Isolation and characterization of a mouse cDNA clone that expresses mast cell growth factor activity in monkey cells." Proc. Natl. Acad. Sci. USA (1984), vol. 81, pp. 1070-1074.
Young, R.A., et al, "Dissection of *Mycobacterium tuberculosis* antigens using recombinant DNA." Proc. Natl. Acad. Sci. USA. (1985), vol. 82(9), pp. 2583-2587.
Young, S., et al., "Down regulation of protein kinase C is due to an increased rate of degradation." Biochem. J. (1987), vol. 244, pp. 775-779.
Yoshikawa, M., et al., "Analysis of proteolytic processing during specific antigen presentation." Cell. Immunol. (1987), vol. 110, pp. 431-435.
Yu, V.C., et al., A human neuroblastoma cell line expresses mu and delta opioid receptor sites.: J. Biol. Chem. (1986), vol. 261, pp. 1065-1070.

wt P210

| | No Treatment | 10 μM STI-571 |
|---|---|---|
| Relative Band Intensity* | 100 | 43.8 |
| % Inhibition | 0 | 56.2 |

T315I

| | No Treatment | 100 μM STI-571 | 50 μM STI-571 | 10 μM STI-571 | C 2 |
|---|---|---|---|---|---|
| Relative Band Intensity* | 100 | 100 | 100 | 100 | 35.3 |
| % Inhibition | 0 | 0 | 0 | 0 | 64.7 |

COMPOUNDS AND METHODS OF IDENTIFYING, SYNTHESIZING, OPTIMIZING AND PROFILING PROTEIN MODULATORS

CROSS-REFERENCE TO RELATED APPLICATIONS

This application is a continuation of U.S. Ser. No. 15/462,115, filed Mar. 17, 2017, which is a divisional of U.S. Ser. No. 14/958,222, filed Dec. 3, 2015, now U.S. Pat. No. 9,645,137, which is a divisional of U.S. Ser. No. 13/873,740, filed Apr. 30, 2013, now U.S. Pat. No. 9,222,933, which is a continuation of U.S. Ser. No. 11/604,109, filed Nov. 24, 2006, now U.S. Pat. No. 8,431,110, which is a continuation-in-part of PCT International Application PCT/US06/33890, filed Aug. 29, 2006, which is a continuation in part of PCT/US2005/18412, filed May 23, 2005, and claims priority to U.S. Ser. No. 60/739,477, filed Nov. 23, 2005, U.S. Ser. No. 60/739,476, filed Nov. 23, 2005, U.S. Ser. No. 60/741,767, filed Dec. 2, 2005, U.S. Ser. No. 60/751,030, filed Dec. 16, 2005, U.S. Ser. No. 60/783,106, filed Mar. 13, 2006, U.S. Ser. No. 60/785,904, filed Mar. 23, 2006, U.S. Ser. No. 60/785,817, filed Mar. 23, 2006, and U.S. Ser. No. 60/789,379, filed Apr. 4, 2006, each of which is incorporated herein by reference.

FIELD OF THE INVENTION

This invention relates to methods of identifying, synthesizing, optimizing and profiling compounds that are inhibitors or activators of proteins, both naturally occurring endogenous proteins as well as certain variant forms of endogenous proteins, and novel methods of identifying such variants. The method accelerates the identification and development of compounds as potential therapeutically effective drugs by simplifying the pharmaceutical discovery and creation process through improvements in hit identification, lead optimization, biological profiling, and rapid elimination of toxic compounds. Implementation results in overall cost reductions in the drug discovery process resulting from the corresponding increases in efficiency.

BACKGROUND OF THE INVENTION

Important components of modern new drug discovery/creation methods that are directed towards a selected protein target present in a human cell include:

1. identification of "hit" compounds which inhibit or activate the selected target protein. (A hit is defined for these purposes as a compound that scores positively in a given assay and may posess some of the effects and pharmacological properties that the investigator desires. In modern pharmaceutical research, however, hits are virtually never final clinical candidates without substantial further modification);

2. selection of a lead compound upon which to base further studies and refinements of the initial hit compound;

3. optimization of a lead compound (whose chemical structure is either related to or identical to the original hit compound) by making a series of chemical modifications designed primarily to improve the inhibitory or activating properties of the lead compound with respect to the target protein, but which may also improve bioavailability, plasma half-life, or reduce toxicity;

4. profiling the spectrum of biological activity of a given lead compound (including an optimized lead) in order to determine its relative specificity and selectivity for the chosen target protein as compared to other non-target proteins, some of which may be closely related to the target protein itself (such as other members of a protein family);

5. preclinical in-vitro and in-vivo animal studies designed to evaluate dosing ranges, carcinogenicity, absorption, distribution, metabolism, excretion, pharmacokinetics, oral bioavailability (if desired), pharmacodynamics, toxicity, and related parameters;

6. clinical trials in healthy volunteers and in patients afflicted with the disease for which the potential therapeutic treatment is thought to be beneficial.

This invention is directed toward a novel approach which substantially improves steps 1-4 as given above. The method can also be used to create and optimize compounds that are substantially more effective and less toxic than typical experimental drugs that have been identified, optimized or profiled using standard, less sophisticated approaches that are currently in use.

The methodology described herein has been developed as part of an intensive effort to develop advanced new pharmaceutical technologies that convert the "drug discovery" process into one more accurately described as a "drug creation" process by inventing predictable, reliable methodologies that provide the skilled investigator with the necessary tools to create new drugs that target specific proteins of importance in human disease while reducing the time and immense costs associated with the drug discovery/development process.

The progressive development of drug resistance in a patient is the hallmark of chronic treatment with many classes of drugs, especially in the therapeutic areas of cancer and infectious diseases. Molecular mechanisms have been identified which mediate certain types of drug resistance phenomena, whereas in other cases the mechanisms of acquired as well as de novo resistance remain unknown today.

One mechanism of induced (acquired) drug resistance originally thought to be relevant in the area of cancer therapy involves increased expression of a protein known as P-glycoprotein (P-gp). P-gp is located in the cell membrane and functions as a drug efflux pump. The protein is capable of pumping toxic chemical agents, including many classical anti-cancer drugs, out of the cell. Consequently, upregulation of P-glycoprotein usually results in resistance to multiple drugs. Upregulation of P-glycoprotein in tumor cells may represent a defense mechanism which has evolved in mammalian cells to prevent damage from toxic chemical agents. Other related drug resistance proteins have now been identified with similar functions to P-gp, including multi-drug-resistance-associated protein family members such as MRP1 and ABCG2. In any event, with the advent of the development of compounds that are specific for a given target protein, and less toxic, the importance of P-glycoprotein and related ATP-binding cassette (ABC) transporter proteins in clinically significant drug resistance has lessened.

Another possible molecular mechanism of acquired drug resistance is that alternative signal pathways are responsible for continued survival and metabolism of cells, even though the original drug is still effective against its target. Furthermore, alterations in intracellular metabolism of the drug can lead to loss of therapeutic efficacy as well. In addition, changes in gene expression as well as gene amplification events can occur, resulting in increased or decreased expression of a given target protein and frequently requiring increasing dosages of the drug to maintain the same effects. (Adcock and Lane, 2003)

Mutation induced drug resistance is a frequently occurring event in the infectious disease area. For example, several drugs have been developed that inhibit either the viral reverse transcriptase or the viral protease encoded in the human immunodeficiency (HIV) viral genome. It is well established in the literature that repeated treatment of HIV-infected AIDS patients using, for example, a reverse transcriptase inhibitor eventually gives rise to mutant forms of the virus that have reduced sensitivity to the drug. Mutations that have arisen in the gene encoding reverse transcriptase render the mutant form of the enzyme less affected by the drug.

The appearance of drug resistance during the course of HIV treatment is not surprising considering the rate at which errors are introduced into the HIV genome. The HIV reverse transcriptase enzyme is known to be particularly error prone, with a forward mutation rate of about $3.4\times10^{-5}$ mutations per base pair per replication cycle (Mansky et al., *J. Virol.* 69:5087-94 (1995)). However, analogous mutation rates for endogenous genes encoded in mammalian cells are more than an order of magnitude lower.

New evidence shows that drug resistance can also arise from a mutational event involving the gene encoding the drug target (Gone et al., Science, 2001; PCT/US02/18729). In this case, exposure of the patient to a specific therapeutic substance such as a given cancer drug that targets a specific protein-of-interest (POI, or "target" protein) may be followed by the outgrowth of a group of cells harboring a mutation occurring in the gene encoding the protein that is the target of the therapeutic substance. Whether the outgrowth of this population of cells results from a small percentage of pre-existing cells in the patient which already harbor a mutation which gives rise to a drug-resistant POI, or whether such mutations arise de novo during or following exposure of the animal or human being to a therapeutic agent capable of activating or inhibiting said POI, is presently unknown. In either case, such mutation events may result in a mutated protein (defined below as a theramutein) which is less affected, or perhaps completely unaffected, by said therapeutic substance.

Chronic myelogenous leukemia (CML) is characterized by excess proliferation of myeloid progenitors that retain the capacity for differentiation during the stable or chronic phase of the disease. Multiple lines of evidence have established deregulation of the Abl tyrosine kinase as the causative oncogene in certain forms of CML. The deregulation is commonly associated with a chromosomal translocation known as the Philadelphia chromosome (Ph), which results in expression of a fusion protein comprised of the BCR gene product fused to the Abelson tyrosine kinase, thus forming $p210^{Bcr\text{-}Abl}$ which has tyrosine kinase activity. A related fusion protein, termed $p190^{Bcr\text{-}Abl}$, that arises from a different breakpoint in the BCR gene, has been shown to occur in patients with Philadelphia chromosome positive (Ph+) Acute Lymphoblastic Leukemia (ALL) (Melo, 1994; Ravandi et al., 1999). Transformation appears to result from activation of multiple signal pathways including those involving RAS, MYC, and JUN. Imatinib mesylate ("STI-571" or "Gleevec®") is a 2-phenylamino pyrimidine that targets the ATP binding site of the kinase domain of Abl (Druker et al, NEJM 2001, p. 1038). Subsequently it has also been found by other methods to be an inhibitor of platelet-derived growth factor (PDGF) β receptor, and the Kit tyrosine kinase, the latter of which is involved in the development of gastrointestinal stromal tumors (see below).

Until recently, it had not been observed that during the course of treatment with a specific inhibitor of a given endogenous cellular protein that a mutation in its corresponding endogenous gene could lead to the expression of protein variants whose cellular functioning was resistant to the inhibitor. Work by Charles Sawyers and colleagues (Gorre et al., Science 293:876-80 (2001); PCT/US02/18729) demonstrated for the first time that treatment of a patient with a drug capable of inhibiting the $p210^{Bcr\text{-}Abl}$ tyrosine kinase (i.e., STI-571) could be followed by the emergence of a clinically significant population of cells within said patient harboring a mutation in the gene encoding the $p210^{Bcr\text{-}Abl}$ cancer causing target protein which contains the Abelson tyrosine kinase domain. Various such mutations gave rise to mutant forms of $p210^{Bcr\text{-}Abl}$ which were less responsive to Gleevec treatment than was the original cancer causing version. Notably, the mutations that emerged conferred upon the mutant protein a relative resistance to the effects of the protein kinase inhibitor drug, while maintaining a certain degree of the original substrate specificity of the mutant protein kinase. Prior to the work of Gorre et al., it was generally believed by those skilled in the art that the types of resistance that would be observed in patients exposed to a compound which inhibited the Abelson protein kinase, such as STI-571, would have resulted from one or more of the other mechanisms of resistance listed above, or by some other as yet unknown mechanism, but that in any event said resistance would involve a target (protein or otherwise) which was distinct from the drug's target POI.

Accordingly, the ability to treat clinically relevant resistant mutant forms of proteins that are otherwise the targets of an existing therapy would be extremely useful. Such mutated proteins (theramuteins as defined below) are beginning to be recognized and understood to be important targets in recurring cancers, and will become important in other diseases as well. There exists a need for therapeutic agents that are active against such drug resistant variant forms of cellular proteins that may arise before, during or following normally effective drug therapies. A key purpose of this invention is to provide a generalizable methodology that the skilled investigator may utilize to identify hits from high throughput screening (HTS) systems, create and optimize lead compounds, and profile the spectrum of biological activity of such compounds, all without reliance upon older methods such as cell free radioligand binding assays and the like. An additional key purpose of this invention is to provide compounds that may serve as potential therapeutic agents useful in overcoming mutation-induced drug resistance in endogenously occurring proteins.

BRIEF SUMMARY OF THE INVENTION

The method described herein involves the generation of a cellular response-based drug discovery and creation system that utilizes modulations of a defined, pre-determined characteristic of a cell termed a phenoresponse as a tool to measure the ability of a given compound (chemical agent, modulator) to activate or inhibit a selected target protein. Through the iterative application of this process, the methodology described herein may be utilized to identify protein modulators (as herein defined), perform lead optimization on such modulators, and biologically profile the target protein specificity and selectivity of such modulators.

The invention described herein may be utilized with any target protein and any eukaryotic cell type, provided however that an essential element of the invention which is termed the phenoresponse is first identified and utilized according to the teachings herein. One embodiment of the method provides the skilled investigator with the ability to identify inhibitors or activators of a selected target protein. Another embodiment allows the skilled investigator to do rapid lead optimization studies in order to arrive at a potential clinical candidate compound. Still another embodiment provides the skilled investigator with the ability to design compounds possessing a desired degree of specificity for a given target protein as well as selectivity for that protein relative to distinct yet closely related family members of the target protein that may exist with certain targets.

Improvement of the therapeutic efficacy of a compound, including an already approved medication, is an important recurring problem in pharmaceutical research. A commonly utilized approach is to start with known chemical structure and make additional chemical modifications to the structure for the purpose of improving its potency, specificity (for the target protein), or other parameter relevant to its therapeutic efficacy in the patient. In some cases the starting structure may be a known drug. In other instances it may simply be an initial screening hit identified either using a cell-free or primary cell-based screening assay. In still other instances, the compound may be an initial chemical structure defined in its minimal terms based upon a screening hit or other model structure, and frequently termed a "scaffold". For the purposes of this invention, a scaffold is defined as a chemical structure with one or more side chains or ring substituents that have been removed relative to a representative compound that otherwise shares the same scaffold. By way of example, the third compound in Table 4 may be thought of as a scaffold.

An important contribution of the present invention is the use of the phenoresponse, taken together with determination of the cellular specificity of a first compound relative to a second compound in order to determine whether the first compound exhibits an improved cellular specificity relative to the second compound. This approach, reported for the first time in the invention described herein, represents a fundamental advance over the prior art. The prior art relies upon cell-free assay systems utilizing purified or recombinantly produced proteins for assaying the activity of a compound, and compares the effect of a given compound on a target protein with its effects on other proteins generally related (closely or distantly) to the target protein. Numerous examples of this type of prior art approach are found in the literature, including Hanke et. al., 1996, Warmuth et. al., US 2003/0162222 A1, Knight and Shokat, 2005, and references therein. Such older types of cell-free approaches are markedly less effective or completely ineffective as compared to the present invention in identifying and optimizing the cellular specificity and therapeutic efficacy of a given scaffold. The substantial improvement of the present invention results from at least three key elements.

First, the concept of the phenoresponse, when utilized together with the measurement of the cellular specificity of a given compound (as measured for example by determination of its CSG), provides a system which allows the identification of compounds that may interact with the target protein in an improved, more functionally effective manner.

Second, the present invention provides a method of identifying compounds that are also capable of interacting with other cellular components distinct from the target protein (which include but are not limited to upstream or downstream components of a signal transduction pathway involving the target protein such as monomeric or multi-subunit proteins, protein complexes, protein/nucleic acid complexes, and the like), that are functional in the specific signal transduction pathways or peripheral to the signal transduction pathways in which the target protein functions within the cell, to promote the disease state of interest such as a selected form of human cancer. Due to the complexity of the signal transduction cascades present in the cells of higher ordered organisms such as humans, the current state of the art is incapable of complete knowledge regarding all of the mechanism in which a given target protein functions within the cell.

Third, the present invention eliminates compounds that cross react with other non-target proteins that do NOT participate in the signal transduction pathways that underlie the disease state in which the target protein functions. This ability of the present invention to eliminate such compounds (which will have untoward side effects in the patient) arises from the direct comparative measurement of the cellular specificity of the compound using the phenoresponse, which inherently eliminates effects upon the control cell. If the effect of a given test compound results in a reduced cellular specificity as compared to the reference compound, the compound can be eliminated immediately. Whether the test compound is less effective against the target protein, or cross-reacts with other non-target proteins that do not participate in the signal transduction pathways of the target protein that modulate the phenoresponse linked to the target protein, or is simply cytotoxic, is irrelevant and only of academic interest. The essential point is that the test compound will be a less effective therapeutic and can be eliminated from further consideration. This saves the skilled investigator time and effort in evaluating variant chemical structures. It is important for the reader to recognize that compounds that may be very potent and highly effective against the target in cell-free assay systems may nevertheless show relatively low CSG determinations and may therefore be rapidly eliminated, saving time and precious resources.

The aforementioned key advantages of the present invention are nowhere to be found in the prior art, and provide the essential improvements of the present invention over the prior art. These advantages are applicable to all potential therapeutic target proteins, but are especially important in the case of the intractable, highly drug resistant target proteins known as theramuteins (WO 2005/115992).

As a result of the use of this invention, the problem of improving and optimizing a given compound relative to other less effective compounds is greatly simplified and enhanced. The skilled investigator simply begins with a first compound, whether it be an approved drug, a screening hit, or a basic scaffold which is known to inhibit or activate the protein of interest, and uses this first compound as an starting point for reference purposes. Additional compounds that are analogs, homologs, isomers, and the like, of the first compound (also referred to herein as the "starting compound" or "reference compound") are then synthesized using basic methods of medicinal chemistry synthesis which are now standard in the art. Some of these chemical synthesis methods have already been referred to in other sections herein, and the reader may also refer to Burbaum et al., 1995 and Goodnow et al., 2003 as general references for such procedures. Once the additional compounds are synthesized, the skilled investigator then proceeds to use the methods of the invention rather than the prior art method of constantly referring to the results obtained with cell-free assays by testing the new compounds on both the target protein and an array of other non-target proteins in an attempt to minimize the cross-reactivity of the compound with other proteins. Instead, through the use of this invention, the skilled investigator may guide the improvement of the chemical structure of the starting compound through direct reference to the results obtained from determinations of the CSG of each compound to be tested using the phenoresponse-based cellular assay system of the present invention. Most importantly, continuous reliance upon the results of cell-free, purified protein assays, including "kinase panels" as referenced above in Hanke et al. (1996) and Knight and Shokat (2005) is eliminated in its entirety, and yet the compounds that result from the implementation of the present method are superior to those obtained by the older methods, as shown by the activities of the compounds identified herein that are effective against the highly drug-resistant theramutein p210 Bcr-Abl T315I, as shown in Table 4. Nothing limits the skilled investigator to independently test any resulting compounds in a cell-free system for independent verification if so desired, but this is in no way required in order to practice the invention.

Prior to this invention, it has not been demonstrated that a cellular response; based drug discovery system is capable of identifying and rank ordering inhibitors or activators of a selected target protein without prior reference to a cell-free, purified protein ligand binding assay or enzyme assay (when the target protein is an enzyme) in order to establish that the compounds under investigation are actually binding to the target protein.

These results demonstrate, for the first time, the use of a cellular response-based assay system as a primary tool to identify inhibitors or activators of a given target protein from compounds that score positively in a high-throughput screen (HTS). These results also demonstrate that once a hit or lead compound capable of activating or inhibiting a given target protein is identified (by any method, including the embodiments disclosed herein or via classical cell-free HTS methods), said compound may also be chemically optimized (i.e. lead optimization may be performed on said compound) entirely using the phenoresponse-based cellular assay system without subsequent dependence upon a cell-free purified protein assay system to independently verify/confirm that the inhibitory or activating ability of each subsequent compound synthesized during the lead optimization process. This embodiment alone saves the skilled investigator a substantial amount of time, effort and significant laboratory resources that would normally be spent on generating and independently confirming inhibitory or activating properties using classical cell-free purified protein assays, radioligand binding assays, and the like.

The method is demonstrated herein using a specific mutated form of a cancer-causing protein involved in the development and progression of chronic myelogenous leukemia (CML). This protein, termed the Abelson protein kinase, in its cancer causing form is a known target for certain tyrosine kinase inhibitors such as imatinib mesylate. However, as discussed in detail below, this target protein can arise in a patient in a mutated form that becomes resistant to the inhibitory effects of imatinib. Such forms of the Abelson kinase are termed theramuteins. In an embodiment of the invention, suitable lead compounds capable of inhibiting or activating a given theramutein are identified. In another embodiment of this invention, a lead compound is optimized. The method is effective for the identification of hits, for lead optimization of such hits (regardless of how such hits were initially identified), and for biological profiling of compounds directed towards non-theramutein endogenous target proteins. The general utility of the method is demonstrated using a theramutein consisting of a mutated form of the Abelson kinase harboring a T315I mutation that confers a high degree of drag resistance.

This invention further relates to agents that are inhibitors or activators of variant forms of proteins. The invention also relates to agents that are inhibitors or activators of certain variant forms of endogenous proteins. Of particular interest are inhibitors and activators of endogenous protein variants, encoded by genes which have mutated, which variants often arise or are at least first identified as having arisen following exposure to a chemical agent which is known to be an inhibitor or activator of the corresponding unmutated endogenous protein. Such protein variants (mutant proteins) are herein termed "theramuteins," and may occur either spontaneously in an organism (and be pre-existing mutations in some cases), or said mutants may arise as a result of selective pressure which results when the organism is treated with a given chemical agent capable of inhibiting the non-mutated form of said theramutein (herein termed a "prototheramutein"). It will be understood that in some cases a prototheramutein may be a "wild type" form of a POI (e.g., a protein that gives rise to a disease due to disregulation). In other cases, the prototheramutein will be a disease causing variant of a "wild type" protein, having already mutated and thereby contributing to the development of the diseased state as a result of said prior mutation. One example of the latter type of prototheramutein is the $P210^{BCR\text{-}ABL}$ oncoprotein, and a mutant form of this protein harboring a threonine (T) to isoleucine (I) mutation at position 315 is termed $P210^{BCR\text{-}ABL\text{-}T315I}$ and is one example of a theramutein. As used herein, the designation "$P210^{BCR\text{-}ABL}$" is synonymous with the term "$p210^{Bcr\text{-}Abl}$", the "wild-type Bcr-Abl protein", and the like.

Theramuteins are a rare class of endogenous proteins that harbor mutations that render said proteins resistant to drugs that are known to inhibit or activate in a therapeutically effective manner their non-mutated counterparts. The endogenous genes encoding a few such proteins are presently known to exhibit such mutations under certain circumstances. In one embodiment, this invention is directed toward compositions that inhibit certain drug-resistant mutants (theramuteins) of the Abelson tyrosine kinase protein, originally termed P210-Bcr-Abl in the literature, that is involved in the development of chronic myelogenous leukemia.

The present method is particularly directed toward the identification of specific inhibitors or specific activators of proteins. Use of the term "specific" in the context of the terms "inhibitor" or "activator" (see definitions below) means that said inhibitor or activator binds to the protein and inhibits or activates the cellular functioning of the protein without also binding to and activating or inhibiting a wide variety of other proteins or non-protein targets in the cell. The skilled investigator is well aware that there is a certain degree of variability in the medical literature with respect to the concept of a specific inhibitor or a specific activator, and of the related concept of target protein "specificity" when discussing the actions of inhibitors or activators of a protein. Accordingly, for the purposes of this invention, a substance is a specific inhibitor or a specific activator of a given protein if said substance is capable of inhibiting or activating said protein at a given concentration such that a corresponding phenoresponse is modulated in the appropriate manner, without having an appreciable effect at the same given concentration upon the phenoresponse (if any) of a corresponding control cell that essentially does not express either the protein.

In certain embodiments, a substance may be a modulator of two closely related proteins such as a prototheramutein and one of its corresponding theramuteins. In other embodiments, in addition to being a modulator of the prototheramutein and theramutein, a substance may also modulate the activities of proteins that have similar functions. As discussed above, in addition to inhibiting the $p210^{Bcr\text{-}Abl}$ tyrosine kinase, imatinib mesylate is also capable of inhibiting the c-kit oncogene product (also a tyrosine kinase) which is overexpressed in certain gastrointestinal stromal tumors, as well as the PDGF β receptor (also a tyrosine kinase), which is expressed in certain chronic myelomonocytic leukemias (CMML). Such a compound is sometimes termed a "moderately specific" inhibitor.

The invention also provides a general method that can be used to identify substances that will activate or inhibit a theramutein, to the same extent, and preferably to an even greater extent than a known drug substance is capable of inhibiting the corresponding "wild type" form of that protein. (The skilled artisan is well aware, however, that said "wild type" forms of such proteins may have already mutated in the course of giving rise to the corresponding disease in which said protein participates.)

In a preferred embodiment, the present invention provides inhibitors of the $p210^{BCR\text{-}ABL\text{-}T315I}$ theramutein having the formula I (I)

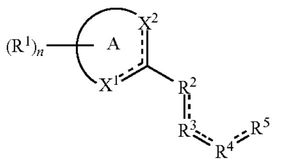

wherein:

ring A is a 5-, 6-, or 7-membered ring or a 7- to 12-membered fused bicyclic ring;

$X^1$ is selected from N, N—$R^0$ or C—$R^1$;

$X^2$ is selected from N, N—$R^0$ or C—$R^1$;

the dotted lines represent optional double bonds;

each $R^1$ is independently selected from the group consisting of H, alkyl, cycloalkyl, alkenyl, alkynyl, aralkyl, CN, $CF_3$, $NO_2$, $OR^{11}$, $—(CH_2)_pC(O)(CH_2)_qR^{11}$, $—(CH_2)_pC(O)N(R^{12})(R^{13})$, $—(CH_2)_pC(O)O(CH_2)_qR^{11}$, $—(CH_2)_pN(R^{11})(CH_2)_qC(O)R^{11}$, $—(CH_2)_pN(R^{12})(R^{13})$, $—(CH_2)_pN(R^{11})(CH_2)_qR^{11}$, $—N(R^{11})SO_2R^{11}$, $—OC(O)N(R^{12})(R^{13})$, $—SO_2N(R^{12})(R^{13})$, halo, aryl, and a heterocyclic ring, and additionally or alternatively, two $R^1$ groups on adjacent ring atoms form a 5- or 6-membered fused ring which contains from 0 to 3 heteroatoms;

n is 0 to 6, each $R^{11}$ is independently selected from H, alkyl, cycloalkyl, alkenyl, alkynyl, aralkyl, aryl, and a heterocyclic ring;

each $R^{12}$ and $R^{13}$ are independently selected from H, alkyl, cycloalkyl, alkenyl, alkynyl, aralkyl, aryl, and a heterocyclic ring; or $R^{12}$ and $R^{13}$ may be taken together with the nitrogen to which they are attached form a 5- to 7-membered ring which may optionally contain a further heteroatom; wherein the 5- to 7-membered ring may optionally be substituted with one to three substituents that are independently selected from alkyl, cycloalkyl, alkenyl, alkynyl, aralkyl, CN, $CF_3$, $NO_2$, $OR^0$, $CO_2R^0$, $C(O)R^0$, halo, aryl, and a heterocyclic ring;

p is 0 to 4;

q is 0 to 4;

$R^2$ is selected from $—CR^{21}{}_a—$, $—NR^{22}{}_b—$, and $—(C{=}R^{23})—$;

each $R^{21}$ is independently selected from H, halo, $—NH_2$, $—N(H)(C_{1\text{-}3}\ alkyl)$, $—N(C_{1\text{-}3}\ alkyl)_2$, $—O—(C_{1\text{-}3}\ alkyl)$, OH and $C_{1\text{-}3}$ alkyl;

each $R^{22}$ is independently selected from H and $C_{1\text{-}3}$ alkyl;

$R^{23}$ is selected from O, S, N—$R^0$, and N—$OR^0$;

$R^3$ is selected from $—CR^{31}{}_c—$, $—NR^{32}{}_d—$, $—SO_2—$, and $—(C{=}R^{33})—$;

each $R^{31}$ group is selected from H, halo, $—NH_2$, $—N(H)(R^0)$, $—N(R^0)_2$, $—O—R^0$, OH and $C_{1\text{-}3}$ alkyl;

each $R^{32}$ group is selected from H, alkyl, cycloalkyl, alkenyl, alkynyl, aralkyl, $CO_2R^0$, $C(O)R^0$, aryl, and a heterocyclic ring;

$R^{33}$ is selected from O, S, N—$R^{34}$, and N—$OR^0$;

$R^{34}$ is selected from H, $NO_2$, CN, alkyl, cycloalkyl, alkenyl, alkynyl, aralkyl, aryl and a heterocyclic ring;

$R^4$ is selected from $—CR^{41}{}_e—$, $—NR^{42}{}_f$, $—(C{=}R^{43})—$, $—SO_2—$, and —O—;

each $R^{41}$ is selected from H, alkyl, cycloalkyl, alkenyl, alkynyl, $CO_2R^0$, $C(O)R^0$, aralkyl, aryl, and a heterocyclic ring;

each $R^{42}$ group is selected from H, alkyl, cycloalkyl, alkenyl, alkynyl, aralkyl, $CO_2R^0$, $C(O)R^0$, aryl, and a heterocyclic ring;

each $R^{43}$ is selected from O, S, N—$R^0$, and N—$OR^0$;

with the provisos that when $R^2$ is $NR^{22}{}_b—$ and $R^4$ is $—NR^{42}{}_f—$, then $R^3$ is not $—NR^{32}{}_d—$; that both $R^3$ and $R^4$ are not simultaneously selected from $—(C{=}R^{33})—$ and $—(C{=}R^{43})—$, respectively; and that $R^3$ and $R^4$ are not simultaneously selected from $—SO_2—$;

$R^5$ is selected from —Y—$R^6$ and —Z—$R^7$;

Y is selected from a chemical bond, O, $NR^0$, $R^6$ is selected from alkyl, cycloalkyl, alkenyl, alkynyl, aralkyl, aryl, and a heterocyclic ring;

Z is a hydrocarbon chain having from 1 to 4 carbon atoms, and optionally substituted with one or more of halo, alkyl, cycloalkyl, alkenyl; alkynyl, aralkyl, $CO_2R^0$, $C(O)R^0$, $C(O)N(R^0)_2$, CN, $CF_3$, $N(R^0)_2$, $NO_2$, and $OR^0$;

$R^7$ is H or is selected from aryl and a heterocyclic ring;

each $R^0$ is independently selected from H, alkyl, cycloalkyl, aralkyl, aryl and a heterocyclic ring;

a is 1 or 2;

b is 0 or 1;

c is 1 or 2;

d is 0 or 1;

e is 1 or 2; and f is 0 or 1.

The invention provides for a fundamentally new way of treating cancer and other diseases where treatment with an existing drug compound, by whatever mechanism, is followed by identifiable (clinically significant) theramutein-mediated drug resistance, by providing alternative drugs that can be administered as theramuteins arise and are identified as such (Wakai et al., 2004, reports an example wherein a theramutein may arise during the course of an on-going treatment regimen), or preemptively before the outgrowth of clinically significant populations of theramutein expressing cells. Further, where a drug treatment for a particular disease is less effective in a subset of individuals that express a certain theramutein of a protein that the drug targets, the invention enables the tailoring of treatments for those subjects by providing alternative drug substances that will be effective against said theramutein.

The invention provides a method of determining whether a chemical agent is at least as effective a modulator of a theramutein in a cell as a known substance is a modulator of a corresponding prototheramutein. One embodiment of the method involves contacting a control cell that expresses the prototheramutein and is capable of exhibiting a responsive phenotypic characteristic (linked to the functioning of the prototheramutein in the cell) with the known modulator of the prototheramutein, contacting a test cell that expresses the theramutein and is also capable of exhibiting the responsive phenotypic characteristic (linked to the functioning of the theramutein in the cell) with the chemical agent, and comparing the response of the treated test cell with the response of the treated control cell; to determine that the chemical agent is at least as effective a modulator of the theramutein as the known substance is a modulator of the prototheramutein. In certain other embodiments, one type of control cell may not express the prototheramutein at all. In other embodiments, the control cell may express about the same amount of the prototheramutein as the test cell expresses of the theramutein. In still other embodiments, the control cell may be capable of exhibiting the responsive phenotypic characteristic to about the same extent as the test cell under certain conditions. In additional embodiments, the test cell may express a given protein, whereas the control cell expresses little or essentially none of the protein.

Proteins of the invention that are of particular interest are those involved in regulatory function, such as enzymes, protein kinases, tyrosine kinases, receptor tyrosine kinases, serine threonine protein kinases, dual specificity protein kinases, proteases, matrix metalloproteinases, phosphatases, cell cycle control proteins, docking proteins such as the IRS family members, cell-surface receptors, G-proteins, ion channels, DNA- and RNA-binding proteins, polymerases, and the like. No limitation is intended on the type of theramutein or other protein that may be used in the invention. At the present time, three theramuteins are known: BCR-ABL, c-Kit, and EGFR.

Any responsive phenotypic characteristic that can be linked to the presence of the protein (including, e.g., a theramutein or prototheramutein) in the cell can be employed for use in the method, including, for example, growth or culture properties, the phosphorylation state (or other modification) of a substrate of the theramutein, and any type of transient characteristic of the cell, as will be defined and discussed in detail.

DETAILED DESCRIPTION OF THE INVENTION

Figure 1:
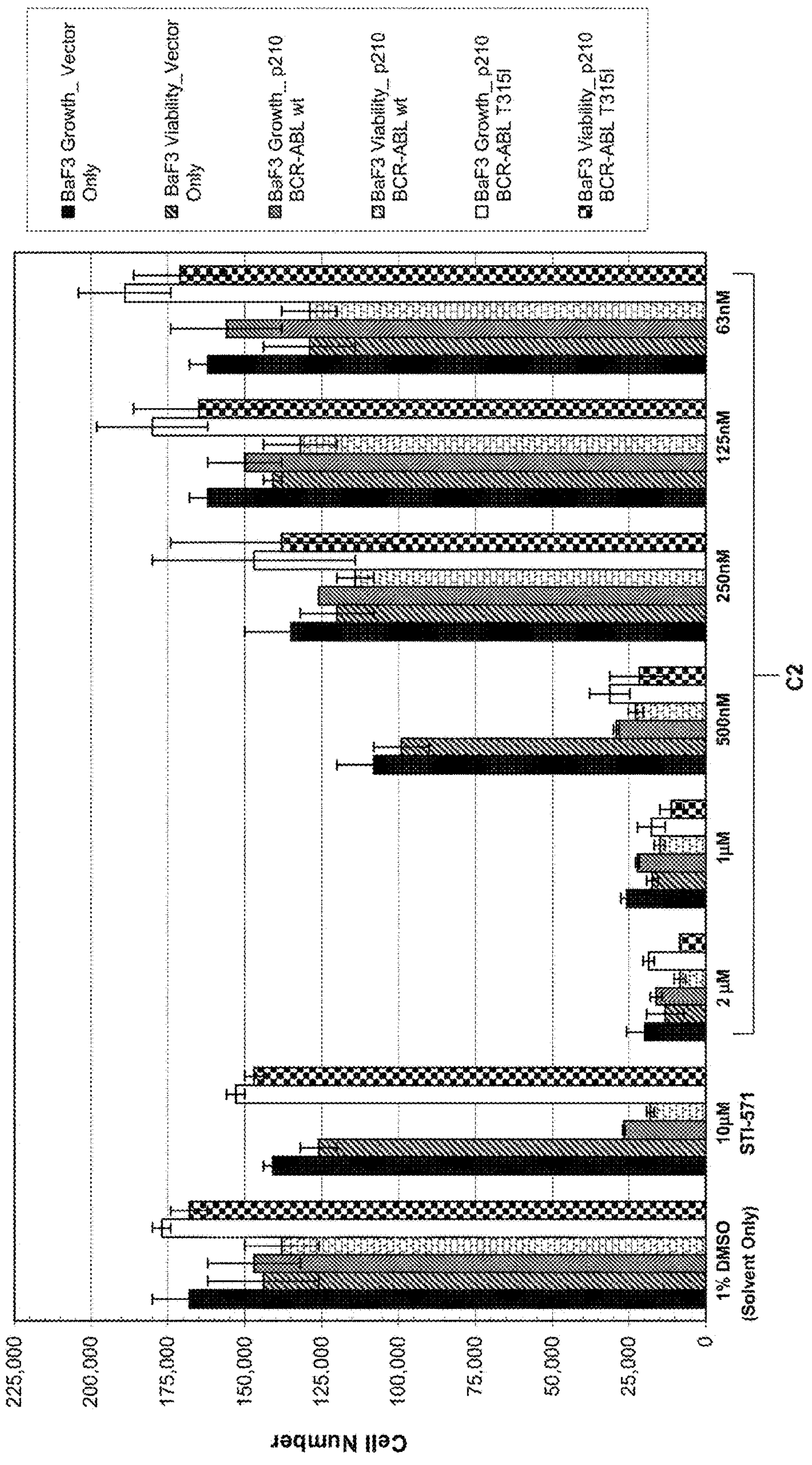
FIG. 1 shows the effect on growth and viability of different concentrations of Compound 2 (C2) for non-transformed vector control Ba/F3 cells (which are IL-3 dependent) as well as Ba/F3 cells expressing the "wild type" $p210^{Bcr\text{-}Abl}$ (designated $p210^{Bcr\text{-}Abl\text{-}wt}$), and Ba/F3 cells expressing the $p210^{Bcr\text{-}Abl\text{-}T315I}$ drug resistant mutant. Cell counts and viability were determined on an automated cell counter as discussed in detail in the specification. Cell counts are shown by the solid color bars; cell viability is shown by the hashed bars. Note that STI-571 potently inhibits growth of the P210 cell line (grey bar) whereas it is unable to inhibit the growth of the T315I cell line (white bar) even at 10 μM concentration. 500 nM C2 shows the largest specificity gap within this dose-response series. Compare STI-571 at 10 μM to C2 at 500 nM on the T315I cell line (white bars). Abbreviations: DMSO: dimethylsulfoxide (solvent used for drug dissolution).

The term "halo" or "halogen" as used herein includes fluorine, chlorine, bromine and iodine.

The term "alkyl" as used herein contemplates substituted and unsubstituted, straight and branched chain alkyl radicals having from 1 to 6 carbon atoms. Preferred alkyl groups include methyl, ethyl, propyl, isopropyl, butyl, isobutyl, tert-butyl, and the like. Additionally, the alkyl group may be optionally substituted with one or more substituents selected from halo, CN, $CO_2R$, C(O)R, $C(O)NR_2$, $NR_2$, cyclic-amino, $NO_2$, and OR.

The term "cycloalkyl" as used herein contemplates substituted and unsubstituted cyclic alkyl radicals. Preferred cycloalkyl groups are those with a single ring containing 3 to 7 carbon atoms and include cyclopropyl, cyclopentyl, cyclohexyl, and the like. Other cycloalkyl groups may be selected from $C_7$ to $C_{10}$ bicyclic systems or from $C_9$ to $C_{14}$ tricyclic systems. Additionally, the cycloalkyl group may be optionally substituted with one or more substituents selected from halo, CN, $CO_2R$, C(O)R, $C(O)NR_2$, $NR_2$, cyclic-amino, $NO_2$, and OR.

The term "alkenyl" as used herein contemplates substituted and unsubstituted, straight and branched chain alkene radicals. Preferred alkenyl groups are those containing two to six carbon atoms. Additionally, the alkenyl group may be optionally substituted with one or more substituents selected from halo, CN, $CO_2R$, C(O)R, $C(O)NR_2$, $NR_2$, cyclic-amino, $NO_2$, and OR.

The term "alkynyl" as used herein contemplates substituted and unsubstituted, straight and branched chain alkyne radicals. Preferred alkynyl groups are those containing two to six carbon atoms. Additionally, the alkynyl group may be optionally substituted with one or more substituents selected from halo, CN, $CO_2R$, C(O)R, $C(O)NR_2$, $NR_2$, cyclic-amino, $NO_2$, and OR.

The term "aralkyl" as used herein contemplates an alkyl group which has as a substituent an aromatic group, which aromatic group may be substituted and unsubstituted. The aralkyl group may be optionally substituted on the aryl with one or more substituents selected from halo, CN, $CF_3$, $NR_2$, cyclic-amino, $NO_2$, OR, $CF_3$, $—(CH_2)_xR$, $—(CH_2)_xC(O)(CH_2)_yR$, $—(CH_2)_xC(O)N(R')(R'')$, $—(CH_2)_xC(O)O(CH_2)_yR$, $—(CH_2)_xN(R')(R'')$, $—N(R)SO_2R$, $—O(CH_2)_xC(O)N(R'R'')$, $—SO_2N(R')(R'')$, $—(CH_2)_xN(R)—(CH_2)_y—R$, $—(CH_2)_xN(R)—C(O)—(CH_2)_y—R$, $—(CH_2)_xN(R)—C(O)—O—(CH_2)_y—R$, $—(CH_2)_xC(O)—N(R)—(CH_2)_y—R$, $—(CH_2)_xC(O)N(R)—(CH_2)_y—R$, $—O—(CH_2)_xC(O)—N(R)—(CH_2)_y—R$, substituted and unsubstituted alkyl, substituted and unsubstituted cycloalkyl, substituted and unsubstituted aralkyl, substituted and unsubstituted alkenyl, substituted and unsubstituted alkynyl, substituted and unsubstituted aryl, and a substituted and unsubstituted heterocyclic ring, wherein the substituted alkyl, substituted cycloalkyl, substituted aralkyl, substituted alkenyl, substituted alkynyl, substituted aryl, and substituted heterocyclic ring may be substituted with one of more halo, CN, $CF_3$, $CO_2R$, C(O)R, $C(O)NR_2$, $NR_2$, cyclic-amino, $NO_2$, and OR.

The term "heterocyclic group" or "heterocyclic ring" as used herein contemplates aromatic and non-aromatic cyclic radicals having at least one heteroatom as a ring member. Preferred heterocyclic groups are those containing 5 or 6 ring atoms which includes at least one hetero atom, and includes cyclic amines such as morpholino, piperidino, pyrrolidino, and the like, and cyclic ethers, such as tetrahydrofuran, tetrahydropyran, and the like. Aromatic heterocyclic groups, also termed "heteroaryl" groups contemplates single-ring hetero-aromatic groups that may include from one to three heteroatoms, for example, pyrrole, furan, thiophene, imidazole, oxazole, thiazole, triazole, pyrazole, pyridine, pyrazine, pyridazine, pyrimidine, and the like. The term heteroaryl also includes polycyclic hetero-aromatic systems having two or more rings in which two atoms are common to two adjoining rings (the rings are "fused") wherein at least one of the rings is a heteroaryl, e.g., the other rings can be cycloalkyls, cycloalkenyls, aryl, heterocycles and/or heteroaryls. Examples of polycyclic heteroaromatic systems include quinoline, isoquinoline, tetrahydroisoquinoline, quinoxaline, quinaxoline, benzimidazole, benzofuran, purine, imidazopyridine, benzotriazole, and the like. Additionally, the heterocyclic groups may be optionally substituted with halo, CN, $CF_3$, $NR_2$, cyclic-amino, $NO_2$, OR, $CF_3$, $—(CH_2)_xC(O)(CH_2)_yR$, $—(CH_2)_xC(O)N(R'R'')$, $—(CH_2)_xC(O)O(CH_2)_yR$, $—(CH_2)_xN(R'R'')$, $—N(R)SO_2R$, $—O(CH_2)_xC(O)N(R')(R'')$, $—SO_2N(R')(R'')$, $—(CH_2)_xN(R)—(CH_2)_y—R$, $—(CH_2)_xN(R)—C(O)—(CH_2)_y—R$, $—(CH_2)_xN(R)—C(O)—O—(CH_2)_y—R$, $—(CH_2)_xC(O)—N(R)—(CH_2)_y—R$, $—(CH_2)_xC(O)N(R)—(CH_2)_y—R$, $—O—(CH_2)_xC(O)—N(R)—(CH_2)_y—R$, substituted and unsubstituted alkyl, substituted and unsubstituted cycloalkyl, substituted and unsubstituted aralkyl, substituted and unsubstituted alkenyl, substituted and unsubstituted alkynyl, substituted and unsubstituted aryl, and a substituted and unsubstituted heterocyclic ring, wherein the substituted alkyl, substituted cycloalkyl, substituted aralkyl, substituted alkenyl, substituted alkynyl, substituted aryl, and substituted heterocyclic ring may be substituted with one of more halo, CN, $CF_3$, $CO_2R$, C(O)R, $C(O)NR_2$, $NR_2$, cyclic-amino, $NO_2$, and OR.

The term "cyclic-amino" as used herein contemplates aromatic and non-aromatic cyclic radicals having at least one nitrogen as a ring member. Preferred cyclic amino groups are those containing 5 or 6 ring atoms, which includes at least one nitrogen, and includes morpholino, piperidino, pyrrolidino, piperazino, imidazole, oxazole, thiazole, triazole, pyrazole, pyridine, pyrazine, pyridazine, pyrimidine and the like. Additionally, the cyclic-amino may be optionally substituted with halo, CN, $CF_3$, $NR_2$, $NO_2$, OR, $CF_3$, substituted and unsubstituted alkyl, substituted and unsubstituted cycloalkyl, substituted and unsubstituted aralkyl, substituted and unsubstituted alkenyl, substituted and unsubstituted alkynyl, substituted and unsubstituted aryl, and a substituted and unsubstituted heterocyclic ring, wherein the substituted alkyl, substituted cycloalkyl, substituted aralkyl, substituted alkenyl, substituted alkynyl, substituted aryl, and substituted heterocyclic ring may be substituted with one or more of halo, CN, $CF_3$, $CO_2R$, C(O)R, $C(O)NR_2$, $NR_2$, $NO_2$, and OR.

The term "aryl" or "aromatic group" as used herein contemplates single-ring aromatic groups (for example, phenyl, pyridyl, pyrazole, etc.) and polycyclic ring systems (naphthyl, quinoline, etc.). The polycyclic rings may have two or more rings in which two atoms are common to two adjoining rings (the rings are "fused") wherein at least one of the rings is aromatic, e.g., the other rings can be cycloalkyls, cycloalkenyls, aryl, heterocycles and/or heteroaryls. Additionally, the aryl groups may be optionally substituted with one or more substituents selected from halo, CN, $CF_3$, $NR_2$, cyclic-amino, $NO_2$, OR, $CF_3$, $—(CH_2)_xC(O)(CH_2)_yR$, $—(CH_2)_xC(O)N(R')(R'')$, $—(CH_2)_xC(O)O(CH_2)_yR$, $—(CH_2)_xN(R')(R'')$, $—N(R)SO_2R$, $—O(CH_2)_xC(O)N(R')(R'')$, $—SO_2N(R')(R'')$, $—(CH_2)_xN(R)—(CH_2)_y—R$, $—(CH_2)_xN(R)—C(O)—(CH_2)_y—R$, $—(CH_2)_xN(R)—C$ $(O)—O—(CH_2)_y—R$, $—(CH_2)_y—C(O)—N(R)—(CH_2)_y—R$, $—CH_2)_xC(O)N(R)—(CH_2)_y—R$, $—O—(CH_2)_xC(O)—N(R)—(CH_2)_y—R$, substituted and unsubstituted alkyl, substituted and unsubstituted cycloalkyl, substituted and unsubstituted aralkyl, substituted and unsubstituted alkenyl, substituted and unsubstituted alkynyl, substituted and unsubstituted aryl, and a substituted and unsubstituted heterocyclic ring, wherein the substituted alkyl, substituted cycloalkyl, substituted aralkyl, substituted alkenyl, substituted alkynyl, substituted aryl, and substituted heterocyclic ring may be substituted with one of more halo, CN, $CF_3$, $CO_2R$, C(O)R, $C(O)NR_2$, $NR_2$, cyclic-amino, $NO_2$, and OR.

The term "heteroatom", particularly as a ring heteroatom, refers to N, O, and S.

Each R is independently selected from H, substituted and unsubstituted alkyl, substituted and unsubstituted cycloalkyl, substituted and unsubstituted aralkyl, substituted and unsubstituted aryl and a substituted and unsubstituted heterocyclic ring, wherein the substituted alkyl, substituted cycloalkyl, substituted aralkyl, substituted aryl and substituted heterocyclic ring may be substituted with one or more halo, CN, $CF_3$, OH, $CO_2H$, $NO_2$, $C_{1-6}$alkyl, $—O—(C_{1-6}alkyl)$, $—NH_2$, $—NH(C_{1-6}alkyl)$ and $—N(C_{1-6}alkyl)_2$. Each R' and R" are independently selected from H, or substituted and unsubstituted alkyl, substituted and unsubstituted cycloalkyl, substituted and unsubstituted aralkyl, substituted and unsubstituted aryl and a substituted and unsubstituted heterocyclic ring, wherein the substituted alkyl, substituted cycloalkyl, substituted aralkyl, substituted aryl and substituted heterocyclic ring may be substituted with one or more halo, CN, $CF_3$, OH, $CO_2H$, $NO_2$, $C_{1-6}$alkyl, $—O—(C_{1-6}alkyl)$, $—NH_2$, $—NH(C_{1-6}\ alkyl)$ and $—N(C_{1-6}alkyl)_2$; or R' and R" may be taken together with the nitrogen to which they are attached form a 5- to 7-membered ring which may optionally contain up to three further heteroatoms, which heteroatoms may be substituted by $C_{1-6}$alkyl. Each x and each y are independently selected from 0 to 4.

In a preferred embodiment, the present invention provides inhibitors of the $p_{210}^{BCR-ABL-T315I}$ theramutein having the formula I (I)

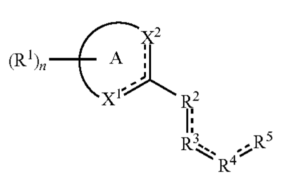

wherein:

ring A is a 5-, 6-, or 7-membered ring or a 7- to 12-membered fused bicyclic ring;

$X^1$ is selected from N, $N—R^0$ or $C—R^1$;

$X^2$ is selected from N, $N—R^0$ or $C—R^1$;

the dotted lines represent optional double bonds;

each $R^1$ is independently selected from the group consisting of H, alkyl, cycloalkyl, alkenyl, alkynyl, aralkyl, CN, $CF_3$, $NO_2$, $OR^{11}$, $—(CH_2)_pC(O)(CH_2)_qR^{11}$, $—(CH_2)_pC(O)N(R^{12})(R^{13})$, $—(CH_2)_pC(O)O(CH_2)_qR^{11}$, $—(CH_2)_pN(R^{11})(CH_2)_qC(O)R^{11}$, $—(CH_2)_pN(R^{12})(R^{13})$, $—N(R^{11})SO_2R^{11}$, $—OC(O)N(R^{12})(R^{13})$, $—SO_2N(R^{12})(R^{13})$, halo, aryl, and a heterocyclic ring, and additionally or alternatively, two $R^1$ groups on adjacent ring atoms form a 5- or 6-membered fused ring which contains from, 0 to 3 heteroatoms;

n is 0 to 6, each $R^{11}$ is independently selected from H, alkyl, cycloalkyl, alkenyl, alkynyl, aralkyl, aryl, and a heterocyclic ring;

each $R^{12}$ and $R^{13}$ are independently selected from H, alkyl, cycloalkyl, alkenyl, alkynyl, aralkyl, aryl, and a heterocyclic ring; or $R^{12}$ and $R^{13}$ may be taken together with the nitrogen to which they are attached form a 5- to 7-membered ring which may optionally contain a further heteroatom; wherein the 5- to 7-membered ring may optionally be substituted with one to three substituents that are independently selected from alkyl, cycloalkyl, alkenyl, alkynyl, aralkyl, CN, $CF_3$, $NO_2$, $OR^0$, $CO_2R^0$, $C(O)R^0$, halo, aryl, and a heterocyclic ring;

p is 0 to 4;

q is 0 to 4;

$R^2$ is selected from $—CR^{21}_a—$, $—NR^{22}_b—$, and $—(C{=}R^{23})—$;

each $R^{21}$ is independently selected from H, halo, $—NH_2$, $—N(H)(C_{1-3}\ alkyl)$, $—N(C_{1-3}\ alkyl)_2$, $—O—(C_{1-3}\ alkyl)$, OH and $C_{1-3}$ alkyl;

each $R^{22}$ is independently selected from H and $C_{1-3}$ alkyl;

$R^{23}$ is selected from O, S, $N—R^0$, and $N—OR^0$;

$R^3$ is selected from $—CR^{31}_c$, $—NR^{32}_d—$, $—SO_2—$, and $—(C{=}R^{33})—$;

each $R^{31}$ group is selected from H, halo, $—NH_2$, $—N(H)(R^0)$, $—N(R^0)_2$, $—O—R^0$, OH and $C_{1-3}$ alkyl;

each $R^{32}$ group is selected from H, alkyl, cycloalkyl, alkenyl, alkynyl, aralkyl, $CO_2R^0$, $C(O)R^0$, aryl; and a heterocyclic ring;

$R^{33}$ is selected from O, S, $N—R^{34}$, and $N—OR^0$;

$R^{34}$ is selected from H, $NO_2$, CN, alkyl, cycloalkyl, alkenyl, alkynyl, aralkyl, aryl and a heterocyclic ring;

$R^4$ is selected from $—CR^{41}_e—$, $—NR^{42}_f—$, $—(C{=}R^{43})—$, $—SO_2—$, and $—O—$;

each $R^{41}$ is selected from H, alkyl, cycloalkyl, alkenyl, alkynyl, $CO_2R^0$, $C(O)R^0$, aralkyl, aryl, and a heterocyclic ring;

each $R^{42}$ group is selected from H, alkyl, cycloalkyl, alkenyl, alkynyl, aralkyl, $CO_2R^0$, $C(O)R^0$, aryl, and a heterocyclic ring;

each $R^{43}$ is selected from O, S, $N—R^0$, and $N—OR^0$;

with the provisos that when $R^2$ is $—NR^{22}_b—$ and $R^4$ is $—NR^{42}_f—$, then $R^3$ is not $—NR^{32}_d—$; that both $R^3$ and $R^4$ are not simultaneously selected from $—(C{=}R^{33})—$ and $—(C{=}R^{43})—$, respectively; and that $R^3$ and $R^4$ are not simultaneously selected from $—SO_2—$;

$R^5$ is selected from $—Y—R^6$ and $—Z—R^7$;

Y is selected from a chemical bond, O, $NR^0$, $R^6$ is selected from alkyl, cycloalkyl, alkenyl, alkynyl, aralkyl, aryl, and a heterocyclic ring;

Z is a hydrocarbon chain having from 1 to 4 carbon atoms, and optionally substituted with one or more of halo, alkyl, cycloalkyl, alkenyl, alkynyl, aralkyl, $CO_2R^0$, $C(O)R^0$, $C(O)N(R^0)_2$, CN, $CF_3$, $N(R^0)_2$, $NO_2$, and $OR^0$;

$R^7$ is H or is selected from aryl and a heterocyclic ring;

each $R^0$ is independently selected from H, alkyl, cycloalkyl, aralkyl, aryl and a heterocyclic ring;

a is 1 or 2;

b is 0 or 1;

c is 1 or 2;

d is 0 or 1;

e is 1 or 2; and f is 0 or 1.

An important component and conceptual teaching of the Invention described herein is that neither the $R^2$ nor the $R^3$ positions of the compounds of this invention are members of any aromatic or non-aromatic ring structure. We have discovered that compounds having the $R^2$ and/or the $R^3$ positions as members of any aromatic or non-aromatic ring structure do not effectively inhibit the T315I theramutein, whereas the compounds of the invention that lack such a ring component at these positions, in addition to having other preferred chemical groups, are potent inhibitors of the T315I theramutein.

In preferred embodiments of the invention, ring A is an aromatic ring.

In preferred embodiments of the invention, $X^1$ or $X^2$ is N. In another preferred embodiment, both $X^1$ and $X^2$ are N. In particularly preferred embodiments of the invention Ring A is a pyridine ring or a pyrimidine ring. In still further preferred embodiments, Ring A is selected from the structures provided below:

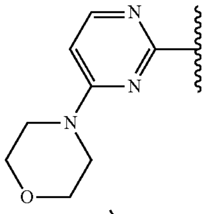

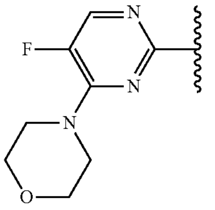

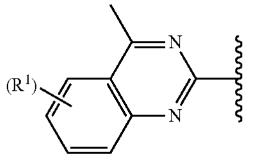

In preferred embodiments of the invention, $R^5$ is a group having the formula

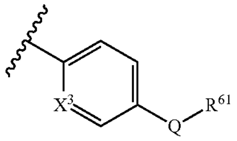

wherein:

$X^3$ is N or CH;

$R^{61}$ is selected from aryl and a heterocyclic ring;

Q is selected from a chemical bond or a group having the formula —O—, —$(CH_2)_i$—, —$(CH_2)_iC(O)(CH_2)_j$—, —$(CH_2)_i$—$N(R^{62})$—$(CH_2)_i$—, —$(CH_2)_iC(O)$—$N(R^{62})$—$(CH_2)_j$—, —$(CH_2)_iC(O)O(CH_2)_j$—, —$(CH_2)_iN(R^{62})C(O)$—$(CH_2)_j$—, —$(CH_2)_iOC(O)N(R^{62})$—$(CH_2)_j$—, and —O—$(CH_2)_i$—$C(O)N(R^{62})$—$(CH_2)_j$—;

$R^{62}$ is selected from H, alkyl, aryl, and a heterocyclic ring;

each $R^0$ is independently selected from H, alkyl, cycloalkyl, aralkyl, aryl and a heterocyclic ring;

h is 0 to 4;

i is 0 to 4; and j is 0 to 4.

In further preferred embodiments of the invention, $R^5$ is a group having the formula

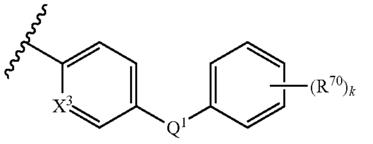

wherein:

$X^3$ is N or CH;

$Q^1$ is selected from a chemical bond or a group having the formula —O—, —$CH_2$—, —NH—, —C(O)—NH—, —C(O)O—, —NH—C(O)—, —OC(O)NH—, and —O—C(O)NH—;

each $R^{70}$ is selected from halo, alkyl, CN, $N(R^{71})_2$, cyclic-amino, $NO_2$, $OR^{71}$, and $CF_3$, each $R^{71}$ is selected from H, alkyl, aryl, aralkyl and a heterocyclic ring; and k is 0 to 4.

In further preferred embodiments of the invention, $R^5$ is a group having the formula

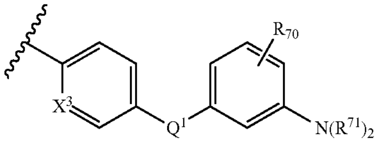

wherein $X^3$ is N or CH;

$Q^1$ is selected from a chemical bond or a group having the formula —O—, —$CH_2$—, —NH—, —C(O)—NH—, —C(O)O—, —NH—C(O)—, —OC(O)NH—, and —O—C(O)NH—;

$R^{70}$ is selected from halo, alkyl, CN, $N(R^{71})_2$, cyclic-amino, $NO_2$, $OR^{71}$, and $CF_3$; and each $R^{71}$ is selected from H, alkyl, aryl, aralkyl and a heterocyclic ring.

In particularly preferred embodiments one or more of the following selections is made: $Q^1$ is —NH—; $X^3$ is N; each $R^{71}$ is independently selected from H, methyl, and ethyl, and preferably each $R^{71}$ is methyl; and/or $R^{70}$ is selected from OH, $OCH_3$, halo, and $CF_3$.

In a preferred embodiment, if $R^2$ or $R^4$ is selected to be —$NR^{22}{}_b$— or —$NR^{42}$— respectively, then $R^{31}$ is not selected from halo, —$NH_2$, —$N(H)(R^0)$, —$N(R^0)_2$, —O—$R^0$, or OH.

In a further preferred embodiment, the present invention provides inhibitors of the $P210^{BCR-ABL-T315I}$ theramutein having the formula $I_a$ ($I_a$)

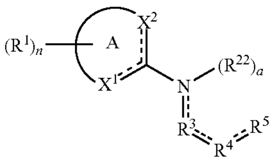

wherein:

ring A is a 5-, 6-, or 7-membered ring or a 7- to 12-membered fused bicyclic ring;

$X^1$ is selected from N, N—$R^0$ or C—$R^1$;

$X^2$ is selected from N, N—$R^0$ or C—$R^1$;

the dotted lines represent optional double bonds;

each $R^1$ is independently selected from the group consisting of H, alkyl, cycloalkyl, alkenyl, alkynyl, aralkyl, CN, $CF_3$, $NO_2$, $OR^{11}$, —$(CH_2)_pC(O)(CH_2)_qR^{11}$, —$(CH_2)_pC(O)N(R^{12})(R^{13})$, —$(CH_2)_pC(O)O(CH_2)_qR^{11}$, —$(CH_2)_pN(R^{11})(CH_2)_qC(O)R^{11}$, —$(CH_2)_pN(R^{12})(R^{13})$, —$N(R^{11})SO_2R^{11}$, —$OC(O)N(R^{12})(R^{13})$, —$SO_2N(R^{12})(R^{13})$, halo, aryl, and a heterocyclic ring, and additionally or alternatively, two $R^1$ groups on adjacent ring atoms form a 5- or 6-membered fused ring which contains from 0 to 3 heteroatoms;

n is 0 to 6, each $R^{11}$ is independently selected from H, alkyl, cycloalkyl, alkenyl, alkynyl, aralkyl, aryl, and a heterocyclic ring;

each $R^{12}$ and $R^{13}$ are independently selected from H, alkyl, cycloalkyl, alkenyl, alkynyl, aralkyl, aryl, and a heterocyclic ring; or $R^{12}$ and $R^{13}$ may be taken together with the nitrogen to which they are attached form a 5- to 7-membered ring which may optionally contain a further heteroatom; wherein the 5- to 7-membered ring may optionally be substituted with one to three substituents that are independently selected from alkyl, cycloalkyl, alkenyl, alkynyl, aralkyl, CN, $CF_3$, $NO_2$, $OR^0$, $CO_2R^0$, $C(O)R^0$, halo, aryl, and a heterocyclic ring;

p is 0 to 4;

q is 0 to 4;

each $R^{22}$ is independently selected from H and $C_{1-3}$ alkyl;

$R^3$ is selected from —$CR^{31}{}_c$—, —$NR^{32}{}_d$—, —$SO_2$—, and —$(C{=}R^{33})$—;

each $R^{31}$ group is selected from H, halo, —$NH_2$, —$N(H)(R^0)$, —$N(R^0)_2$, —O—$R^0$, OH and $C_{1-3}$ alkyl;

each $R^{32}$ group is selected from H, alkyl, cycloalkyl, alkenyl, alkynyl, aralkyl, $CO_2R^0$, $C(O)R^0$, aryl, and a heterocyclic ring;

$R^{33}$ is selected from O, S, N—$R^{34}$, and N—$OR^0$;

$R^{34}$ is selected from H, $NO_2$, CN, alkyl, cycloalkyl, alkenyl, alkynyl, aralkyl, aryl and a heterocyclic ring;

$R^4$ is selected from —$CR^{41}{}_e$—, —$NR^{42}{}_f$—, —$(C{=}R^{43})$—, —$SO_2$—, and -O—;

each $R^{41}$ is selected from H, alkyl, cycloalkyl, alkenyl, alkynyl, $CO_2R^0$, $C(O)R^0$, aralkyl, aryl, and a heterocyclic ring;

each $R^{42}$ group is selected from H, alkyl, cycloalkyl, alkenyl, alkynyl, aralkyl, $CO_2R^0$, $C(O)R^0$, aryl, and a heterocyclic ring;

each $R^{43}$ is selected from O, S, N—$R^0$, and N—$OR^0$;

with the provisos that when $R^4$ is —$NR^4{}_f$— then $R^3$ is not —$NR^{32}{}_d$—; and that both $R^3$ and $R^4$ are not simultaneously selected from —$(C{=}R^{33})$— and —$(C{=}R^{43})$—, respectively; and that $R^3$ and $R^4$ are not simultaneously selected from —$SO_2$—;

$R^5$ is selected from —Y—$R^6$ and —Z—$R^7$;

Y is selected from a chemical bond, O, N—$R^0$, $R^6$ is selected from alkyl, cycloalkyl, alkenyl, alkynyl, aralkyl, aryl, and a heterocyclic ring;

Z is a hydrocarbon chain having from 1 to 4 carbon atoms, and optionally substituted with one or more of halo, alkyl, cycloalkyl, alkenyl, alkynyl, aralkyl, $CO_2R^0$, $C(O)R^0$), $C(O)N(R^0)_2$, CN, $CF_3$, $N(R^0)_2$, $NO_2$, and $OR^0$;

$R^7$ is H or is selected from aryl and a heterocyclic ring;

each $R^0$ is independently selected from H, alkyl, cycloalkyl, aralkyl, aryl and a heterocyclic ring;

a is 1 or 2;

b is 0 or 1;

c is 1 or 2;

d is 0 or 1;

e is 1 or 2; and f is 0 or 1.

In a further preferred embodiment, the present invention provides inhibitors of the P210$^{BCR-ABL-T315I}$ theramutein having the formula $I_b$ ($I_b$)

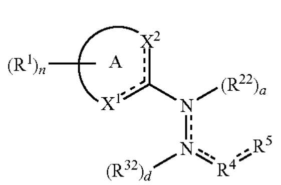

wherein:

ring A is a 5-, 6-, or 7-membered ring or a 7- to 12-membered fused bicyclic ring;

$X^1$ is selected from N, N—$R^0$ or C—$R^1$;

$X^2$ is selected from N, N—$R^0$ or C—$R^1$;

the dotted lines represent optional double bonds;

each $R^1$ is independently selected from the group consisting of H, alkyl, cycloalkyl, alkenyl, alkynyl, aralkyl, CN, $CF_3$, $NO_2$, $OR^{11}$, —$(CH_2)_pC(O)(CH_2)_qR^{11}$, —$(CH_2)_pC(O)N(R^{12})(R^{13})$, —$(CH_2)_pC(O)O(CH_2)_qR^{11}$, —$(CH_2)_pN(R^{11})(CH_2)_qC(O)R^{11}$, —$(CH_2)_pN(R^{12})(R^{13})$, —$N(R^{11})SO_2R^{11}$, —$OC(O)N(R^{12})(R^{13})$, —$SO_2NR^{12})(R^{13})$, halo, aryl, and a heterocyclic ring, and additionally or alternatively, two $R^1$ groups on adjacent ring atoms form a 5- or 6-membered fused ring which contains from 0 to 3 heteroatoms;

n is 0 to 6, each $R^{11}$ is independently selected from H, alkyl, cycloalkyl, alkenyl, alkynyl, aralkyl, aryl, and a heterocyclic ring;

each $R^{12}$ and $R^{13}$ are independently selected from H, alkyl, cycloalkyl, alkenyl, alkynyl, aralkyl, aryl, and a heterocyclic ring; or $R^{12}$ and $R^{13}$ may be taken together with the nitrogen to which they are attached form a 5- to 7-membered ring which may optionally contain a further heteroatom; wherein the 5- to 7-membered ring may optionally be substituted with one to three substituents that are independently selected from alkyl, cycloalkyl, alkenyl, alkynyl, aralkyl, CN, $CF_3$, $NO_2$, $OR^0$, $CO_2R^0$, $C(O)R^0$, halo, aryl, and a heterocyclic ring;

p is 0 to 4;

q is 0 to 4;

each $R^{22}$ is independently selected from H and $C_{1-3}$ alkyl;

each $R^{32}$ group is selected from H, alkyl, cycloalkyl, alkenyl, alkynyl, aralkyl, $CO_2R^0$, $C(O)R^0$, aryl, and a heterocyclic ring;

$R^4$ is selected from —$CR^{41}{}_e$—, —$(C{=}R^{43})$—, —$SO_2$—, and —O—;

each $R^{41}$ is selected from H, alkyl, cycloalkyl, alkenyl, alkynyl, $CO_2R^0$, $C(O)R^0$, aralkyl, aryl, and a heterocyclic ring;

each $R^{43}$ is selected from O, S, N—$R^0$, and N—$OR^0$;

$R^5$ is selected from —Y—$R^6$ and —Z—$R^7$;

Y is selected from a chemical bond, O, N—$R^0$, $R^6$ is selected from alkyl, cycloalkyl, alkenyl, alkynyl, aralkyl, aryl, and a heterocyclic ring;

Z is a hydrocarbon chain having from 1 to 4 carbon atoms, and optionally substituted with one or more of halo, alkyl, cycloalkyl, alkenyl, alkynyl, aralkyl, $CO_2R^0$, $C(O)R^0$, $C(O)N(R^0)_2$, CN, $CF_3$, $N(R)_2$, $NO_2$, and $OR^0$;

$R^7$ is H or is selected from aryl and a heterocyclic ring;

each $R^0$ is independently selected from H, alkyl, cycloalkyl, aralkyl, aryl and a heterocyclic ring;

a is 1 or 2;

b is 0 or 1;

c is 1 or 2;

d is 0 or 1;

e is 1 or 2; and f is 0 or 1.

In a further preferred embodiment, the present invention provides inhibitors of the $P210^{BCR-ABL-T315I}$ theramutein having the formula ($I_c$)

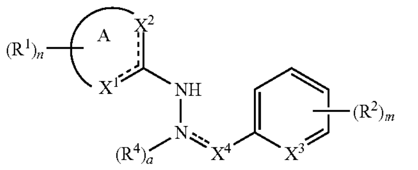

wherein ring A is a 5-, 6-, or 7-membered ring or a 7- to 12-membered fused bicyclic ring;

$X^1$ is selected from N, N—$R^0$ or C—$R^1$;

$X^2$ is selected from N, N—$R^0$ or C—$R^1$;

the dotted lines represent optional double bonds;

each $R^1$ is independently selected from the group consisting of H, alkyl, cycloalkyl, alkenyl, alkynyl, aralkyl, CN, $CF_3$, $NO_2$, $OR^{11}$, —$(CH_2)_pC(O)(CH_2)_qR^{11}$, —$(CH_2)_pC(O)N(R^{12})(R^{13})$, —$(CH_2)_pC(O)O(CH_2)_qR^{11}$, —$(CH_2)_pN(R^{11})(CH_2)_qC(O)R^{11}$, —$(CH_2)_pN(R^{12})(R^{13})$, —$N(R^{11})SO_2R^{11}$, —$OC(O)N(R^{12})(R^{13})$, —$SO_2N(R^{12})(R^{13})$, halo, aryl, and a heterocyclic ring, and additionally or alternatively, two $R^1$ groups on adjacent ring atoms form a 5- or 6-membered fused ring which contains from 0 to 3 heteroatoms;

n is 0 to 6, each $R^{11}$ is independently selected from H, alkyl, cycloalkyl, alkenyl, alkynyl, aralkyl, aryl, and a heterocyclic ring;

each $R^{12}$ and $R^{13}$ are independently selected from H, alkyl, cycloalkyl, alkenyl, alkynyl, aralkyl, aryl, and a heterocyclic ring; or $R^{12}$ and $R^{13}$ may be taken together with the nitrogen to which they are attached form a 5- to 7-membered ring which may optionally contain a further heteroatom, wherein the 5- to 7-membered ring may optionally be substituted with one to three substituents that are independently selected from alkyl, cycloalkyl, alkenyl, alkynyl, aralkyl, CN, $CF_3$, $NO_2$, $OR^0$, $CO_2R^0$, $C(O)R^0$, halo, aryl, and a heterocyclic ring;

p is 0 to 4;

q is 0 to 4;

$X^3$ is N, CH or C—$R^2$;

each $R^2$ is independently selected from the group consisting of alkyl, cycloalkyl, alkenyl, alkynyl, aralkyl, CN, $CF_3$, $NO_2$, $OR^{21}$, —$(CH_2)_rC(O)(CH_2)_sR^{21}$, —$(CH_2)_rC(O)N(R^{22})(R^{23})$, —$(CH_2)_xC(O)O(CH_2)$, $R^{21}$, —$(CH_2)_rN(R^{21})C(O)R^{21}$, —$(CH_2)_rN(R^{22})(R^{23})$, —$N(R^{21})SO_2R^{21}$, —$OC(O)N(R^{22})(R^{23})$, —$SO_2N(R^{22})(R^{23})$, halo, aryl, and a heterocyclic ring, and additionally or alternatively, two $R^2$ groups on adjacent ring atoms form a 5- or 6-membered fused ring which contains from 0 to 3 heteroatoms;

$R^{21}$ is selected from H, alkyl, cycloalkyl; alkenyl, alkynyl, aralkyl, aryl, and a heterocyclic ring;

$R^{22}$ and $R^{23}$ are independently selected from H, alkyl, cycloalkyl, alkenyl, alkynyl, aralkyl, aryl, and a heterocyclic ring; or $R^{22}$ and $R^{23}$ may be taken together with the nitrogen to which they are attached form a 5- to 7-membered ring which may optionally contain a further heteroatom, wherein the 5- to 7-membered ring may optionally be substituted with one to three substituents that are independently selected from alkyl, cycloalkyl, alkenyl, alkynyl, aralkyl, CN, $CF_3$, $NO_2$, $OR^0$, $CO_2R^0$, $C(O)R^0$, halo, aryl, and a heterocyclic ring;

r is 0 to 4;

s is 0 to 4;

m is 0 to 4;

$R^4$ is selected from H, alkyl, cycloalkyl, alkenyl, alkynyl, aralkyl, $CO_2R^0$, $C(O)R^0$, aryl, and a heterocyclic ring;

a is 0 or 1;

$X^4$ is selected from

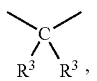,
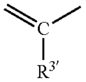
and
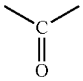
;

each $R^3$ is independently selected from the group consisting of H, —$N(R^0)_2$, alkyl, cycloalkyl, alkenyl, alkynyl, $CO_2R^0$, $C(O)R^0$, aralkyl, aryl, and a heterocyclic ring, $R^{3'}$ is selected from H, —$N(R^0)_2$, alkyl, cycloalkyl, aralkyl, aryl and a heterocyclic ring, and each $R^0$ is independently selected from H, alkyl, cycloalkyl, aralkyl, aryl and a heterocyclic ring.

In preferred embodiments of the invention, $R^2$, $R^3$ and $R^4$ of formula I are selected to give the following chemical groups:

—$N(R^{22})$—N═$C(R^{41})$—
—$N(R^{22})$—$N(R^{32})$—C(═O)—
—$N(R^{22})$—$N(R^{32})$—$C(R^{41})(R^{41})$—
$N(R^{22})$—$C(R^{31})(R^{31})$—$C(R^{41})(R^{41})$
—$N(R^{22})$—$C(R^{31})(R^{31})$—C(═O)—
—N═N—$C(R^{41})(R^{41})$—
$C(R^{21})$═C═$C(R^{41})$—
$C(R^{21})$═$C(R^{31})$—C(═O)—
$C(R^{21})$═$C(R^{31})$—$C(R^{41})(R^{41})$—
—$C(R^{21})(R^{21})$—$C(R^{31})$—$C(R^{41})$—
$C(R^{21})(R^{21})$—$C(R^{31})(R^{31})$—C(═O)—
$C(R^{21})(R^{21})$—$C(R^{31})(R^{31})$—$C(R^{41})(R^{41})$
$C(R^{21})(R^{21})$—$N(R^{32})$—C(═O)—
—$C(R^{21})(R^{21})$—$NR^{32})$—$C(R^{41})(R^{41})$—
—$N(R^{22})$—C(═O)—$C(R^{41})(R^{41})$—
—$N(R^{22})$—C(═O)—$N(R^{41})$—
—$N(R^{22})$—C(═O)—O—
$C(R^{21})(R^{21})$—C(═O)—$C(R^{41})(R^{41})$—
$C(R^{21})(R^{21})$—C(═O)—$N(R^{42})$—
—$N(R^{22})$—C(═$NR^{34}$)—$N(R^{42})$—
C(═O)—$N(R^{32})$—$N(R^{42})$.

Particularly preferred chemical groups for $R^2$, $R^3$ and $R^4$ include:

—$N(R^{22})$—N═$C(R^{41})$—

—$N(R^{22})$—$N(R^{32})$—C(═O)—

—$N(R^{22})$—$C(R^{31})(R^{31})$—$C(R^{41})(R^{41})$—

—$N(R^{22})$—$C(R^{31})(R^{31})$—C(═O)—

—$C(R^{21})(R^{21})$—C(═O)—$C(R^{41})(R^{41})$—

—$C(R^{21})(R^{21})$—C(═O)—$N(R^{42})$—

—$N(R^{22})$—C(═$NR^{34}$)—$N(R^{42})$—

—C(—O)—$N(R^{32})$—$N(R^{42})$.

In further preferred embodiment, $R^6$ or $R^7$ is an aryl group, which may be optionally substituted. Particularly preferred aryl groups include substituted or unsubstituted phenyl and pyridyl. In additional or alternative embodiments, it is preferred that the substituents $R^{21}$ and $R^{22}$ are independently selected from groups which have small steric bulk and are preferably selected from H and $CH_3$, and more preferably are H.

In a further preferred embodiment, the present invention provides inhibitors of the $P210^{BCR\text{-}ABL\text{-}T315I}$ theramutein having the formula II (II)

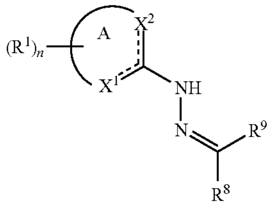

wherein ring A is a 5-, 6-, or 7-membered ring or a 7- to 12-membered fused bicyclic ring;

$X^1$ is selected from N, N—$R^0$ or C—$R^1$;

$X^2$ is selected from N, N—$R^0$ or C—$R^1$;

the dotted lines represent optional double bonds;

each $R^1$ is independently selected from the group consisting of H, alkyl, cycloalkyl, alkenyl, alkynyl, aralkyl, CN, $CF_3$, $NO_2$, $OR^{11}$, —$(CH_2)_pC(O)(CH_2)_qR^{11}$, —$(CH_2)_pC(O)N(R^{12})(R^{13})$, —$(CH_2)_pC(O)O(CH_2)_qR^{11}$, —$(CH_2)_pN(R^{11})(CH_2)_qC(O)R^{11}$, —$(CH_2)_pN(R^{12})(R^{13})$, —$N(R^{11})SO_2R^{11}$, —$OC(O)N(R^{12})(R^{13})$, —$SO_2N(R^{12})(R^{13})$, halo, aryl, and a heterocyclic ring, and additionally or alternatively, two $R^1$ groups on adjacent ring atoms form a 5- or 6-membered fused ring which contains from 0 to 3 heteroatoms;

n is 0 to 6, each $R^{11}$ is independently selected from H, alkyl, cycloalkyl, alkenyl, alkynyl, aryl, and a heterocyclic ring;

each $R^{12}$ and $R^{13}$ are independently selected from H, alkyl, cycloalkyl, alkenyl, alkynyl, aralkyl, aryl, and a heterocyclic ring; or $R^{12}$ and $R^{13}$ may be taken together with the nitrogen to which they are attached form a 5- to 7-membered ring which may optionally contain a further heteroatom; wherein the 5- to 7-membered ring may optionally be substituted with one to three substituents that are independently selected from alkyl, cycloalkyl, alkenyl, alkynyl, aralkyl, CN, $CF_3$, $NO_2$, $OR^0$, $CO_2R^0$, $C(O)R^0$, halo, aryl, and a heterocyclic ring;

p is 0 to 4;

q is 0 to 4;

$R^8$ is selected from the group consisting of is selected from H, alkyl, cycloalkyl, alkenyl, alkynyl, $CO_2R^0$, $C(O)R^0$, aralkyl, aryl, and a heterocyclic ring;

$R^9$ is selected from —Y—$R^6$ and —Z—$R^7$;

Y is selected from a chemical bond, O, N—$R^0$, $R^6$ is selected from alkyl, cycloalkyl, alkenyl, alkynyl, aralkyl, aryl, and a heterocyclic ring;

Z is a hydrocarbon chain having from 1 to 4 carbon atoms, and optionally substituted with one or more of halo, alkyl, cycloalkyl, alkenyl, alkynyl, aralkyl, $CO_2R^0$, $C(O)R^0$, $C(O)N(R^0)_2$, CN, $CF_3$, $N(R^0)_2$, $NO_2$, and $OR^0$;

$R^7$ is H or is selected from aryl and a heterocyclic ring; and each $R^0$ is independently selected from H, alkyl, cycloalkyl, aralkyl, aryl and a heterocyclic ring.

In a further preferred embodiment, the present invention provides inhibitors of the $P210^{BCR\text{-}ABL\text{-}T315I}$ theramutein having the formula $II_a$ ($II_a$)

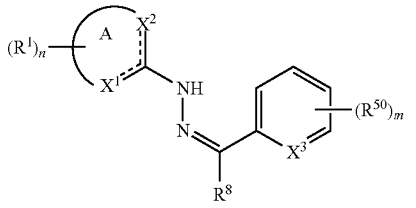

wherein ring A is a 5-, 6-, or 7-membered ring or a 7- to 12-membered fused bicyclic ring;

$X^1$ is selected from N, N—$R^0$ or C—$R^1$;

$X^2$ is selected from N, N—$R^0$ or C—$R^1$;

the dotted lines represent optional double bonds;

each $R^1$ is independently selected from the group consisting of H, alkyl, cycloalkyl, alkenyl, alkynyl, aralkyl, CN, $CF_3$, $NO_2$, $OR^{11}$, —$(CH_2)_pC(O)(CH_2)_qR^{11}$, —$(CH_2)_pC(O)N(R^{12})(R^{13})$, —$(CH_2)_pC(O)O(CH_2)_qR^{11}$, —$(CH_2)_pN(R^{11})C(O)R^{11}$, —$(CH_2)_pN(R^{12})(R^{13})$, —$N(R^{11})SO_2R^{11}$, —$OC(O)N(R^{12})(R^{13})$, —$SO_2N(R^{12})(R^{13})$, halo, aryl, and a heterocyclic ring, and additionally or alternatively, two $R^1$ groups on adjacent ring atoms form a 5- or 6-membered fused ring which contains from 0 to 3 heteroatoms;

n is 0 to 6, each $R^{11}$ is independently selected from H, alkyl, cycloalkyl, alkenyl, alkynyl, aralkyl, aryl, and a heterocyclic ring;

each $R^{12}$ and $R^{13}$ are independently selected from H, alkyl, cycloalkyl, alkenyl, alkynyl, aralkyl, aryl, and a heterocyclic ring; or $R^{12}$ and $R^{13}$ may be taken together with the nitrogen to which they are attached form a 5- to 7-membered ring which may optionally contain a further heteroatom, wherein the 5- to 7-membered ring may optionally be substituted with one to three substituents that are independently selected from alkyl, cycloalkyl, alkenyl, alkynyl, aralkyl, CN, $CF_3$, $NO_2$, $OR^0$, $CO_2R^0$, $C(O)R^0$, halo, aryl, and a heterocyclic ring;

p is 0 to 4;

q is 0 to 4;

$R^8$ is selected from the group consisting of is selected from H, alkyl, cycloalkyl, alkenyl, alkynyl, $CO_2R^0$, $C(O)R^0$, aralkyl, aryl, and a heterocyclic ring;

$X^3$ is N, CH or C—$R^{50}$;

each $R^{50}$ is independently selected from the group consisting of alkyl, cycloalkyl, alkenyl, alkynyl, aralkyl, CN, $CF_3$, $NO_2$, $OR^{51}$, —$(CH_2)_rC(O)(CH_2)_sR^{51}$, —$(CH_2)_xC(O)N(R^{52})(R^{53})$, —$(CH_2)_rC(O)O(CH_2)_sR^{51}$, —$(CH_2)_rN(R^{51})C(O)R^{51}$, —$(CH_2)_rN(R^{52})(R^{53})$, —$N(R^{51})SO_2R^{51}$, —$OC(O)N(R^{52})(R^{53})$, —$SO_2N(R^{52})(R^{53})$, halo, aryl, and a heterocyclic ring, and additionally or alternatively, two $R^{50}$ groups on adjacent ring atoms form a 5- or 6-membered fused ring which contains from 0 to 3 heteroatoms;

$R^{51}$ is selected from H, alkyl, cycloalkyl, alkenyl, alkynyl, aralkyl, aryl, and a heterocyclic ring;

$R^{52}$ and $R^{53}$ are independently selected from H, alkyl, cycloalkyl, alkenyl, alkynyl, aralkyl, aryl, and a heterocyclic ring; or $R^{52}$ and $R^{53}$ may be taken together with the nitrogen to which they are attached form a 5- to 7-membered ring which may optionally contain a further heteroatom, wherein the 5- to 7-membered ring may optionally be substituted with one to three substituents that are independently selected from alkyl, cycloalkyl, alkenyl, alkynyl, aralkyl, CN, $CF_3$, $NO_2$, $OR^0$, $CO_2R^0$, $C(O)R^0$, halo, aryl, and a heterocyclic ring;

r is 0 to 4;

s is 0 to 4;

m is 0 to 4; and each $R^0$ is independently selected from H, alkyl, cycloalkyl, aralkyl, aryl and a heterocyclic ring.

In a further preferred embodiment, the present invention provides inhibitors of the $p210^{BCR\text{-}ABL\text{-}T315I}$ theramutein having the formula $II_b$ ($II_b$)

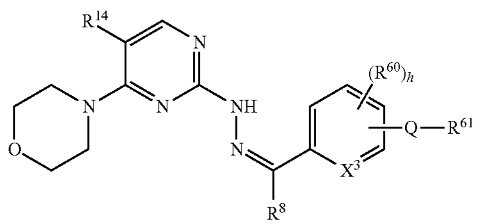

wherein:

$R^{14}$ is selected from H and F;

$R^8$ is selected from the group consisting of is selected from H, alkyl, cycloalkyl, alkenyl, alkynyl, $CO_2R^0$, $C(O)R^0$, aralkyl, aryl, and a heterocyclic ring;

$X^3$ is N, CH or C—$R^{60}$;

each $R^{60}$ is independently selected from the group consisting of alkyl, cycloalkyl, alkenyl, alkynyl, aralkyl, CN, $CF_3$, $NO_2$, $OR^0$, halo, aryl, and a heterocyclic ring;

$R^{61}$ is selected from aryl and a heterocyclic ring;

Q is selected from a chemical bond or a group having the formula —O—, —$(CH_2)_i$, —$(CH_2)_iC(O)(CH_2)_j$—, —$(CH_2)_i$—$N(R^{62})$—$(CH_2)_j$, —$(CH_2)_iC(O)$—$N(R^{62})$—$(CH_2)_j$—, —$(CH_2)_iC(O)O(CH_2)_j$—, —$(CH_2)_iN(R^{62})C(O)$—$(CH_2)_j$, —$(CH_2)_iOC(O)N(R^{62})$—$(CH_2)_j$—, and —O—$(CH_2)_i$—$C(O)N(R^{62})$—$(CH_2)_j$—;

$R^{62}$ is selected from H, alkyl, aryl, and a heterocyclic ring;

each $R^0$ is independently selected from H, alkyl, cycloalkyl, aralkyl, aryl and a heterocyclic ring;

h is 0 to 4;

i is 0 to 4; and j is 0 to 4.

In preferred embodiments of compounds of the formula $II_b$, $R^{60}$ is selected from halo, $CF_3$, and OH. In other preferred embodiments, $R^8$ is selected from H and $CH_3$.

In preferred embodiments of compounds of the formula $II_b$, $X^3$ is N. In further preferred embodiments, Q is selected to be —$(CH_2)_i$—$N(R^{62})$—$(CH_2)_j$—, and particularly in preferred embodiments, Q is —$N(R^{62})$—.

In a further preferred embodiment, the present invention provides inhibitors of the $P210^{BCR\text{-}ABL\text{-}T315I}$ theramutein having the formula $II_c$

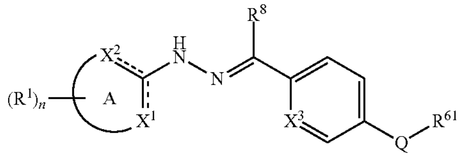

wherein:

ring A is a 5-, 6-, or 7-membered ring or a 7- to 12-membered fused bicyclic ring;

$X^1$ is selected from N, N—$R^0$ or C—$R^1$;

$X^2$ is selected from N, N—$R^0$ or C—$R^1$;

the dotted lines represent optional double bonds;

each $R^1$ is independently selected from the group consisting of H, alkyl, cycloalkyl, alkenyl, alkynyl, aralkyl, CN, $CF_3$, $NO_2$, $OR^{11}$, —$(CH_2)_pC(O)(CH_2)_qR^{11}$, —$(CH_2)_pC(O)N(R^{12})(R^{13})$, —$(CH_2)_pC(O)O(CH_2)_qR^{11}$, —$(CH_2)_pN(R^{11})C(O)R^{11}$, —$(CH_2)_pN(R^{12})(R^{13})$, —$N(R^{11})SO_2R^{11}$, —$OC(O)N(R^{12})(R^{13})$, —$SO_2N(R^{12})(R^{13})$, halo, aryl, and a heterocyclic ring, and additionally or alternatively, two $R^1$ groups on adjacent ring atoms form a 5- or 6-membered fused ring which contains from 0 to 3 heteroatoms;

n is 0 to 6, each $R^{11}$ is independently selected from H, alkyl, cycloalkyl, alkenyl, alkynyl, aralkyl, aryl, and a heterocyclic ring;

each $R^{12}$ and $R^{13}$ are independently selected from H, alkyl, cycloalkyl, alkenyl, alkynyl, aralkyl, aryl, and a heterocyclic ring; or $R^{12}$ and $R^{13}$ may be taken together with the nitrogen to which they are attached form a 5- to 7-membered ring which may optionally contain a further heteroatom, wherein the 5- to 7-membered ring may optionally be substituted with one to three substituents that are independently selected from alkyl, cycloalkyl, alkenyl, alkynyl, aralkyl, CN, $CF_3$, $NO_2$, $OR^0$, $CO_2R^0$, $C(O)R^0$, halo, aryl, and a heterocyclic ring;

p is 0 to 4;

q is 0 to 4;

$R^8$ is selected from H and methyl;

$X^3$ is N or CH;

$R^{61}$ is selected from aryl and a heterocyclic ring;

Q is selected from a chemical bond or a group having the formula —O—, —$(CH_2)_i$—, —$(CH_2)_iC(O)(CH_2)_j$—, —$(CH_2)_i$—$N(R^{62})$—$(CH_2)_j$—, —$(CH_2)_iC(O)$—$N(R^{62})$—$(CH_2)_j$—, —$(CH_2)_i$—$C(O)O(CH_2)_j$—, —$(CH_2)_iN(R^{62})C(O)$—$(CH_2)_j$—, —$(CH_2)_iOC(O)N(R^{62})$—$(CH_2)_j$—, and —O—$(CH_2)_i$—$C(O)N(R^{62})$—$(CH_2)_j$—;

$R^{62}$ is selected from H, alkyl, aryl, and a heterocyclic ring;

each $R^0$ is independently selected from H, alkyl, cycloalkyl, aralkyl, aryl and a heterocyclic ring;

h is 0 to 4;

i is 0 to 4; and j is 0 to 4.

In a further preferred embodiment, the present invention provides inhibitors of the $P210^{BCR-ABL-T315I}$ theramutein having the formula $II_d$

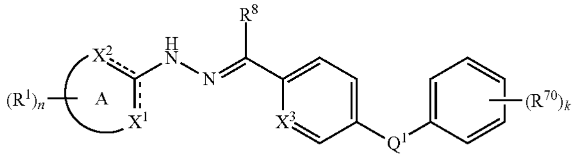

wherein:

ring A is a 5-, 6-, or 7-membered ring or a 7- to 12-membered fused bicyclic ring;

$X^1$ is selected from N, N—$R^0$ or C—$R^1$;

$X^2$ is selected from N, N—$R^0$ or C—$R^1$;

the dotted lines represent optional double bonds;

each $R^1$ is independently selected from the group consisting of H, alkyl, cycloalkyl, alkenyl, alkynyl, aralkyl, CN, $CF_3$, $NO_2$, $OR^{11}$, —$(CH_2)_pC(O)(CH_2)_qR^{11}$, —$(CH_2)_pC(O)N(R^{12})(R^{13})$, —$(CH_2)_pC(O)O(CH_2)_qR^{11}$, —$(CH_2)_pN(R^{11})C(O)R^{11}$, —$(CH_2)_pN(R^{12})(R^{13})$, —$N(R^{11})SO_2R^{11}$, —$OC(O)N(R^{12})(R^{13})$, —$SO_2N(R^{12})(R^{13})$, halo, aryl, and a heterocyclic ring, and additionally or alternatively, two $R^1$ groups on adjacent ring atoms form a 5- or 6-membered fused ring which contains from 0 to 3 heteroatoms;

n is 0 to 6, each $R^{11}$ is independently selected from H, alkyl, cycloalkyl, alkenyl, alkynyl, aralkyl, aryl, and a heterocyclic ring;

each $R^{12}$ and $R^{13}$ are independently selected from H, alkyl, cycloalkyl, alkenyl, alkynyl, aralkyl, aryl, and a heterocyclic ring; or $R^{12}$ and $R^{13}$ may be taken together with the nitrogen to which they are attached form a 5- to 7-membered ring which may optionally contain a further heteroatom, wherein the 5- to 7-membered ring may optionally be substituted with one to three substituents that are independently selected from alkyl, cycloalkyl, alkenyl, alkynyl, aralkyl, CN, $CF_3$, $NO_2$, $OR^0$, $CO_2R^0$, $C(O)R^0$, halo, aryl, and a heterocyclic ring;

p is 0 to 4;

q is 0 to 4;

each $R^0$ is independently selected from H, alkyl, cycloalkyl, aralkyl, aryl and a heterocyclic ring;

$R^8$ is selected from H and $CH_3$;

$X^3$ is N or CH;

$Q^1$ is selected from a chemical bond or a group having the formula —O—, —$CH_2$—, —NH—, —C(O)—NH—, —C(O)O—, —NH—C(O)—, —OC(O)NH—, and —O—C(O)NH—;

each $R^{70}$ is selected from halo, alkyl, CN, $N(R^{71})_2$, cyclic-amino, $NO_2$, $OR^{71}$, and $CF_3$, each $R^{71}$ is selected from H, alkyl, aryl, aralkyl and a heterocyclic ring; and k is 0 to 4.

In a further preferred embodiment, the present invention provides inhibitors of the $P210^{BCR-ABL-T315I}$ theramutein having the formula $II_e$

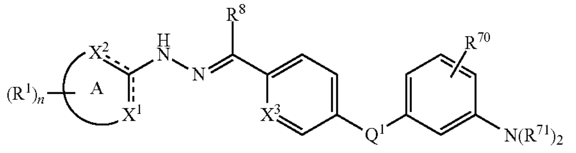

wherein:

ring A is a 5-, 6-, or 7-membered ring or a 7- to 12-membered fused bicyclic ring;

$X^1$ is selected from N, N—$R^0$ or C—$R^1$;

$X^2$ is selected from N, N—$R^0$ or C—$R^1$;

the dotted lines represent optional double bonds;

each $R^1$ is independently selected from the group consisting of H, alkyl, cycloalkyl, alkenyl, alkynyl, aralkyl, CN, $CF_3$, $NO_2$, $OR^{11}$, —$(CH_2)_pC(O)(CH_2)_qR^{11}$, —$(CH_2)_pC(O)NR^{12})(R^{13})$, —$(CH_2)_pC(O)O(CH_2)_qR^{11}$, —$(CH_2)_pN(R^{11})C(O)R^{11}$, —$(CH_2)_pN(R^{12})(R^{13})$, —$N(R^{11})SO_2R^{11}$, —$OC(O)N(R^{12})(R^{13})$, —$SO_2N(R^{12})(R^{13})$, halo, aryl, and a heterocyclic ring, and additionally or alternatively, two $R^1$ groups on adjacent ring atoms form a 5- or 6-membered fused ring which contains from 0 to 3 heteroatoms;

n is 0 to 6, each $R^{11}$ is independently selected from H, alkyl, cycloalkyl, alkenyl, alkynyl, aralkyl, aryl, and a heterocyclic ring;

each $R^{12}$ and $R^{13}$ are independently selected from H, alkyl, cycloalkyl, alkenyl, alkynyl, aralkyl, aryl, and a heterocyclic ring; or $R^{12}$ and $R^{13}$ may be taken together with the nitrogen to which they are attached form a 5- to 7-membered ring which may optionally contain a further heteroatom, wherein the 5- to 7-membered ring may optionally be substituted with one to three substituents that are independently selected from alkyl, cycloalkyl, alkenyl, alkynyl, aralkyl, CN, $CF_3$, $NO_2$, $OR^0$, $CO_2R^0$, $C(O)R^0$, halo, aryl, and a heterocyclic ring;

p is 0 to 4;

q is 0 to 4;

each $R^0$ is independently selected from H, alkyl, cycloalkyl, aralkyl, aryl and a heterocyclic ring;

$R^8$ is selected from H and $CH_3$;

$X^3$ is N or CH;

$Q^1$ is selected from a chemical bond or a group having the formula —O—, —$CH_2$—, —NH—, —C(O)—NH—, —C(O)O—, —NH—C(O)—, —OC(O)NH—, and —O—C(O)NH—;

each $R^{70}$ is selected from halo, alkyl, CN, $N(R^{71})_2$, cyclic-amino, $NO_2$, $OR^{71}$, and $CF_3$; and each $R^{71}$ is selected from H and alkyl.

In a further preferred embodiment, the present invention provides inhibitors of the $P210^{BCR-ABL-T315I}$ theramutein having the formula $II_f$

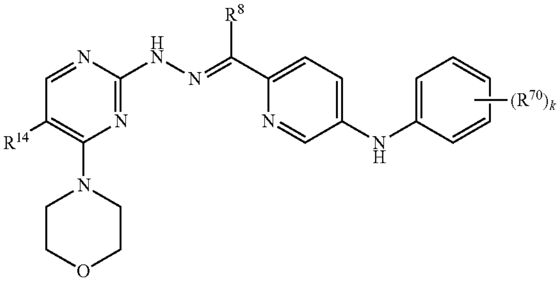

wherein
$R^{14}$ is selected from H and F;
$R^8$ is selected from H and $CH_3$;
each $R^{70}$ is selected from halo, alkyl, CN, $N(R^{71})_2$, cyclic-amino, $NO_2$, $OR^{71}$, and $CF_3$,
each $R^{71}$ is selected from H, alkyl, aryl, aralkyl and a heterocyclic ring; and
k is 0 to 4.
Exemplary compounds of the formula II, $II_a$, $II_b$, $II_c$, $II_d$, $II_e$ or $II_f$ includes the following structures:
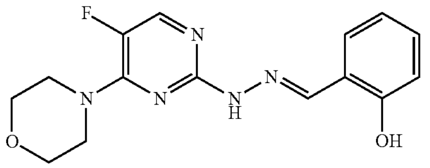
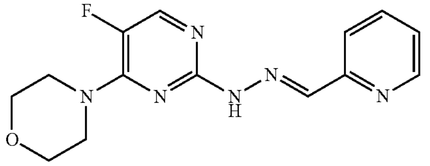
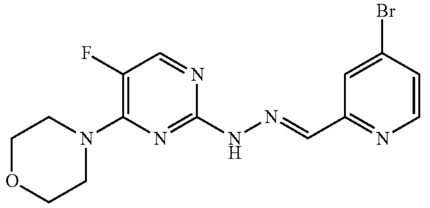
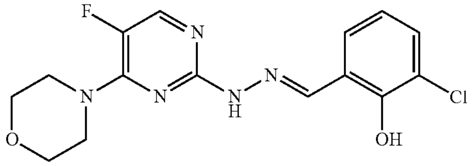
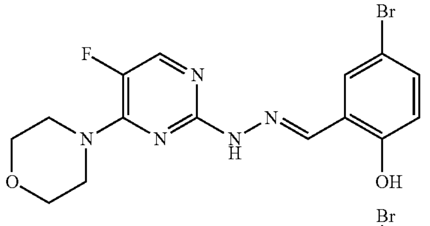
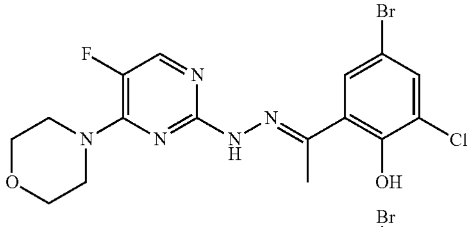
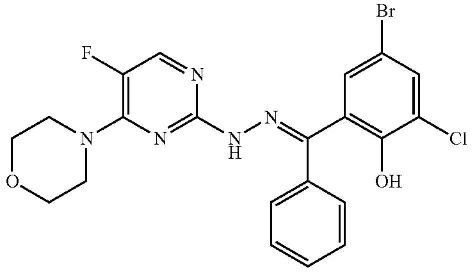
-continued
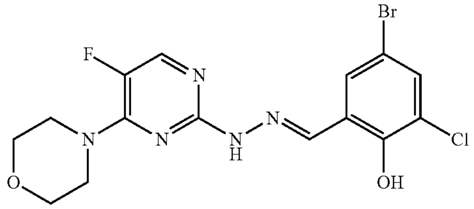
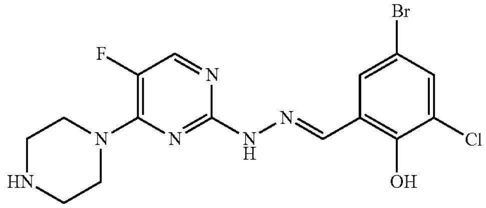
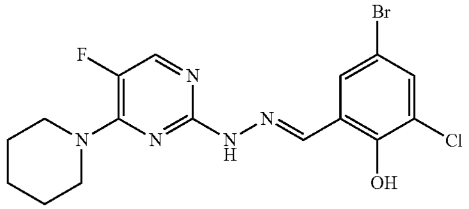
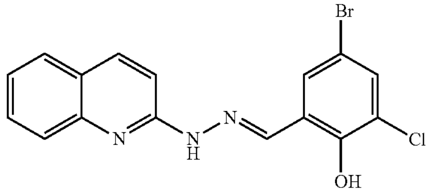
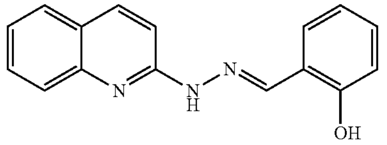
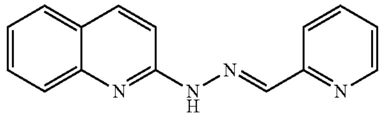
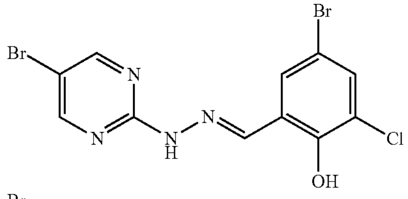
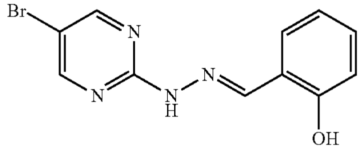
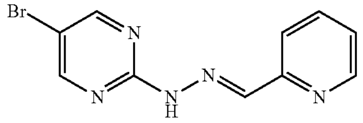
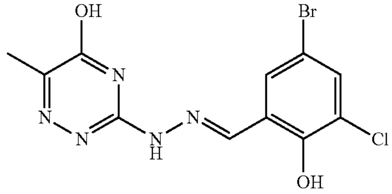

-continued
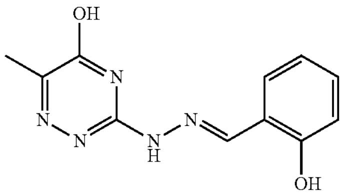
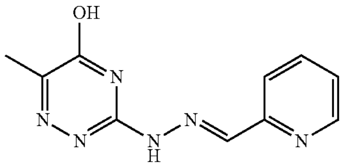
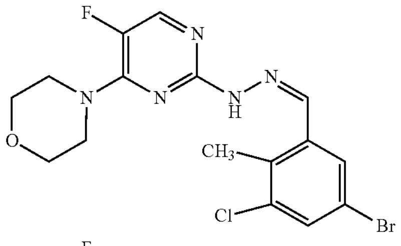
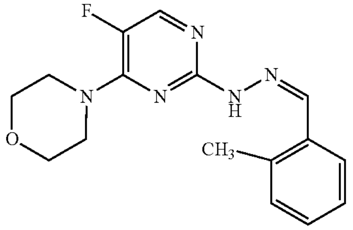
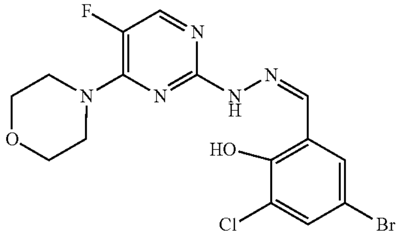
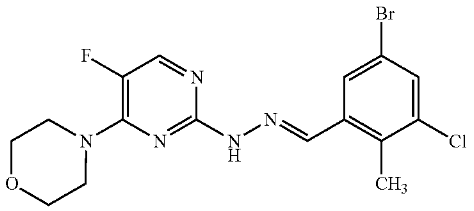
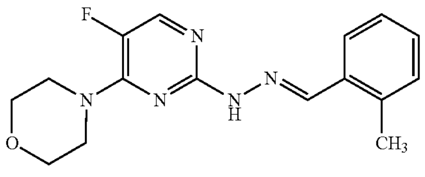
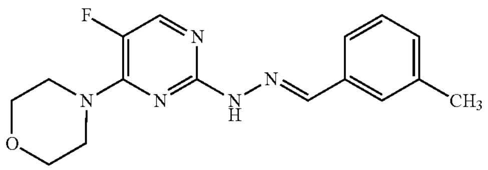
-continued
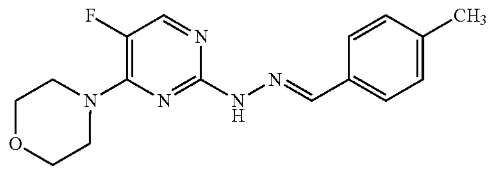
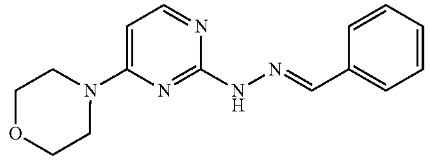
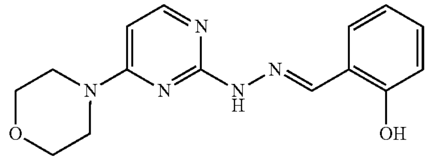
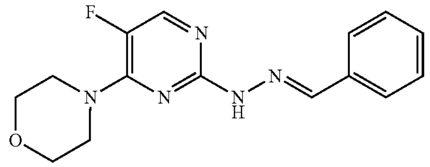
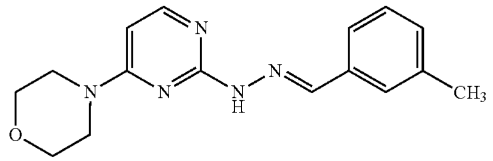
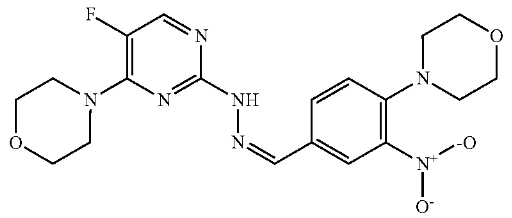
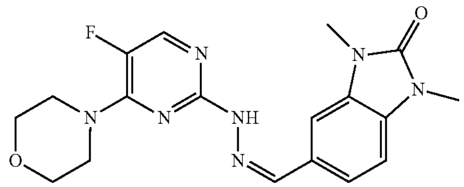
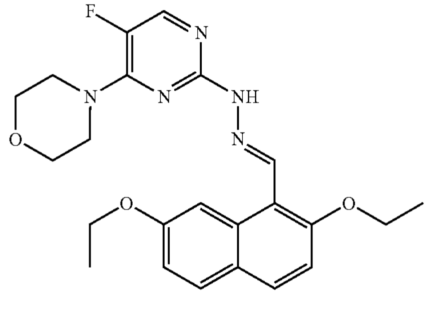

-continued
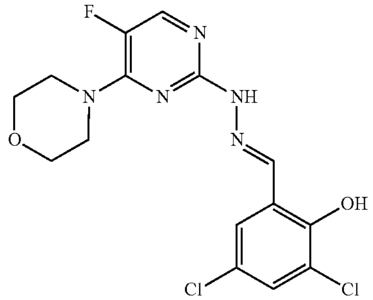
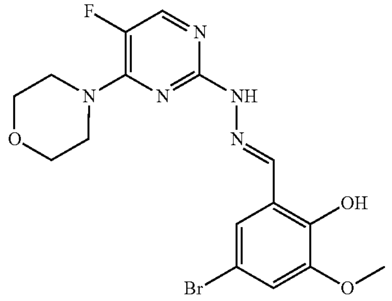
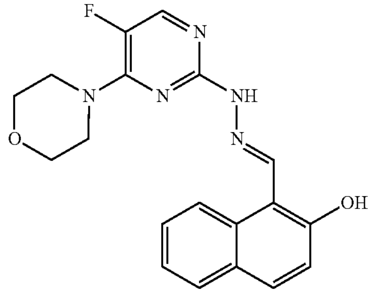
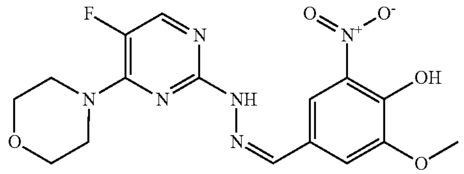
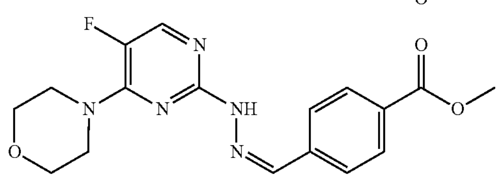
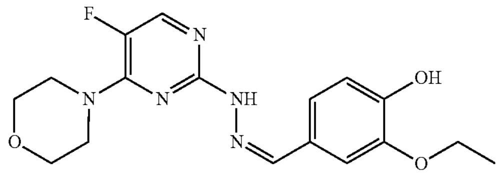
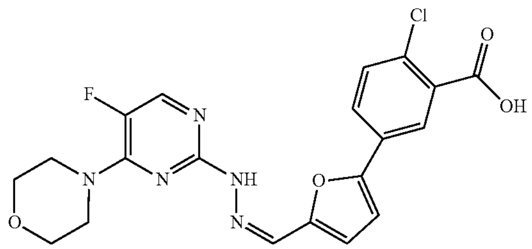
-continued
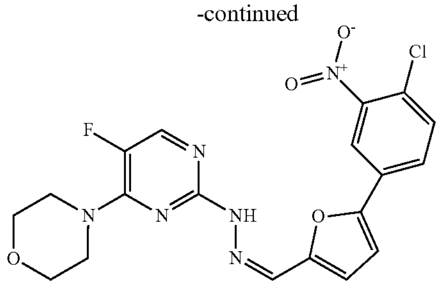
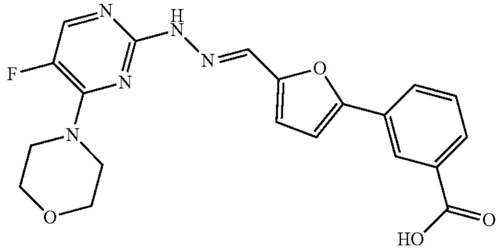
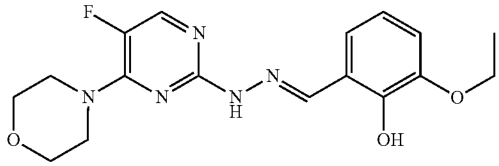
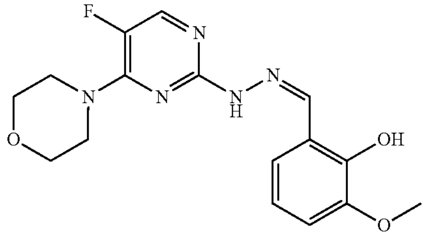
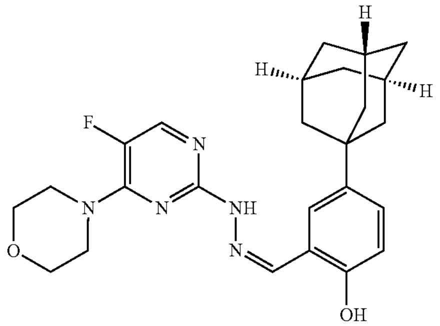
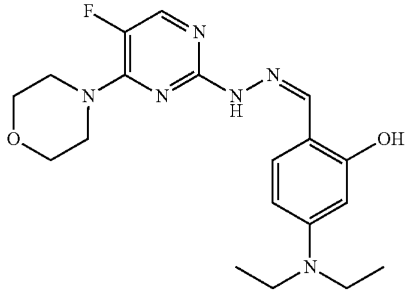
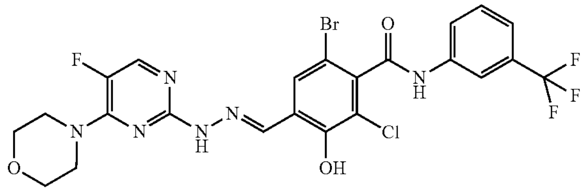

-continued
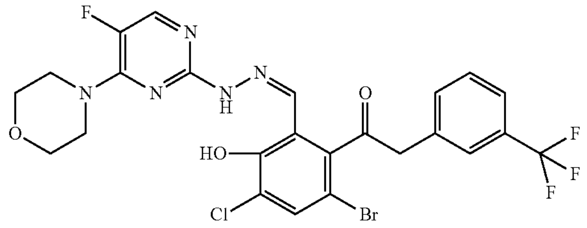
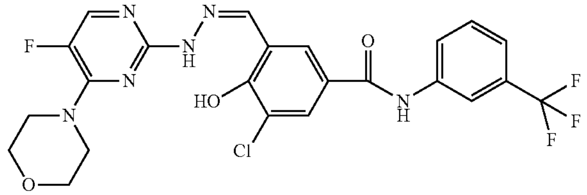
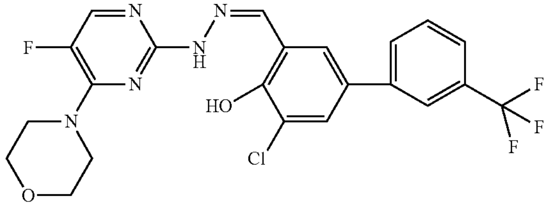
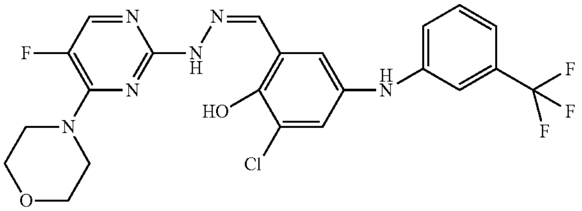
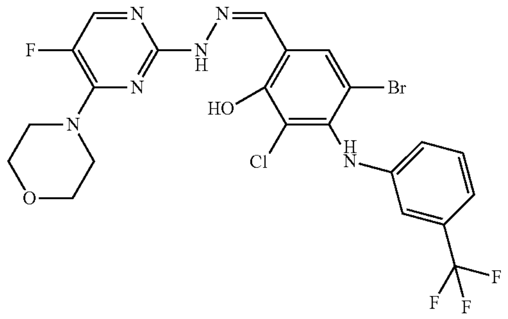
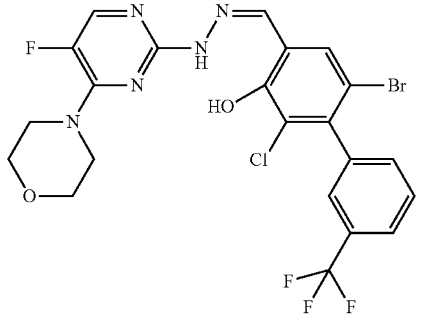
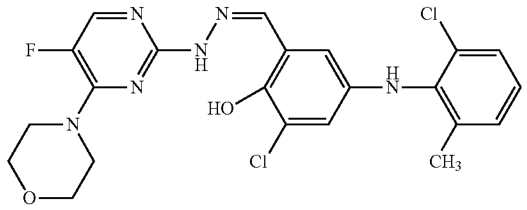
-continued
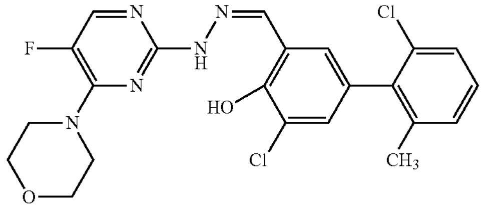
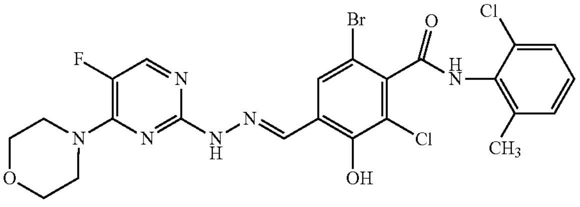
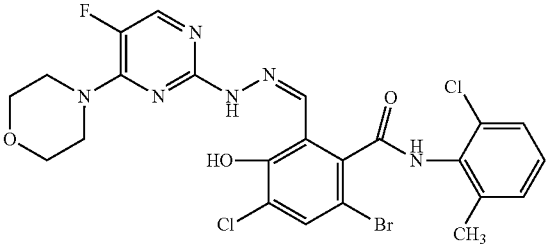
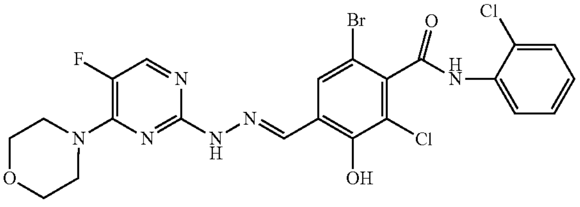
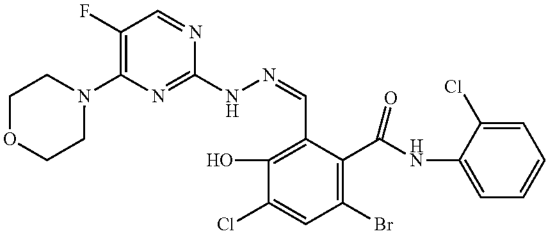
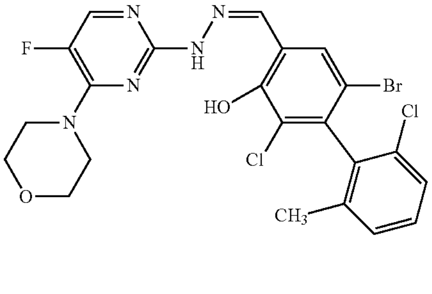
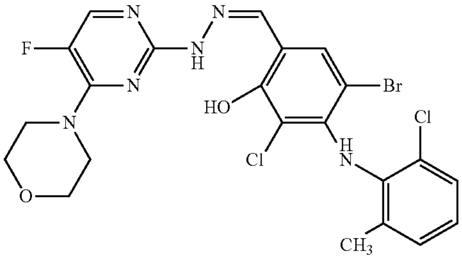

-continued
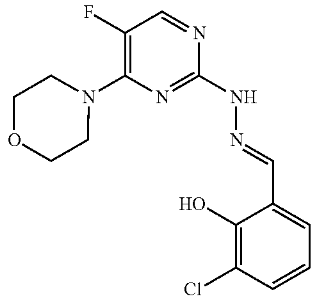
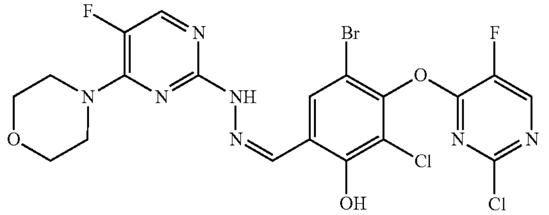
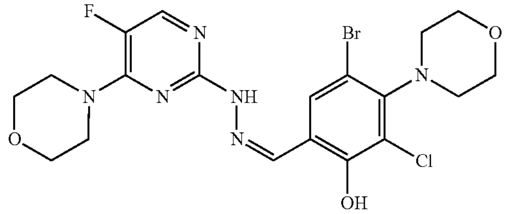
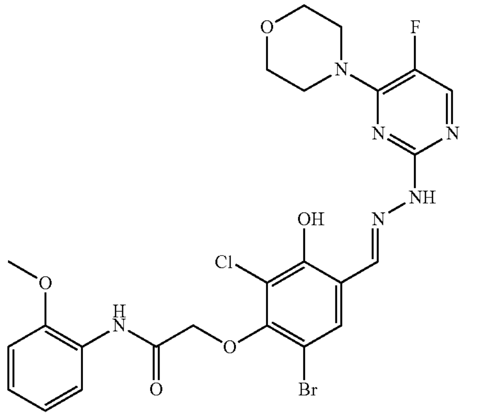
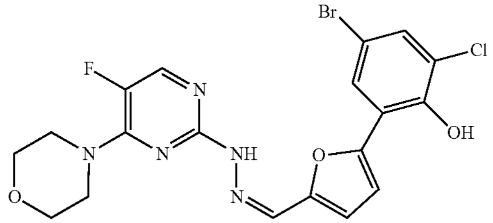
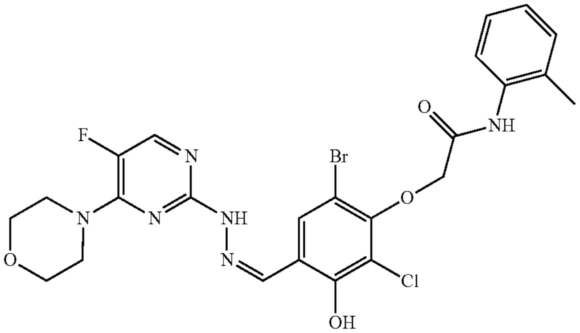
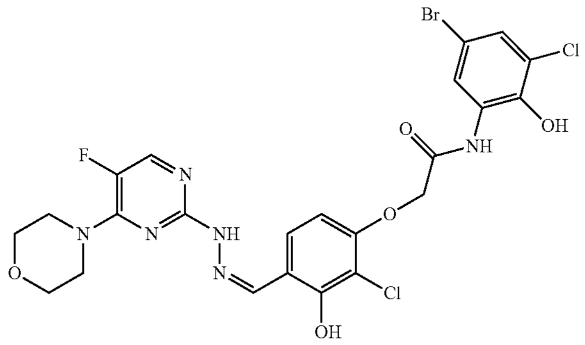
-continued
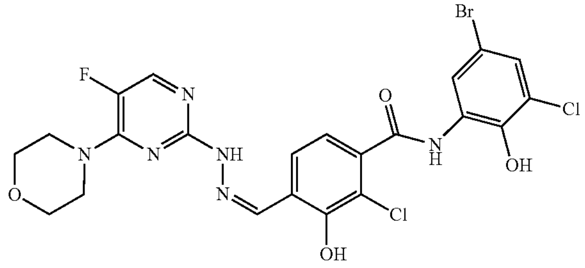
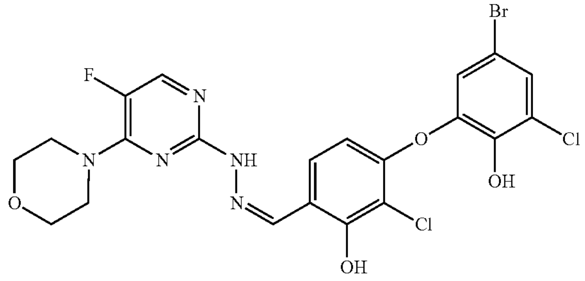
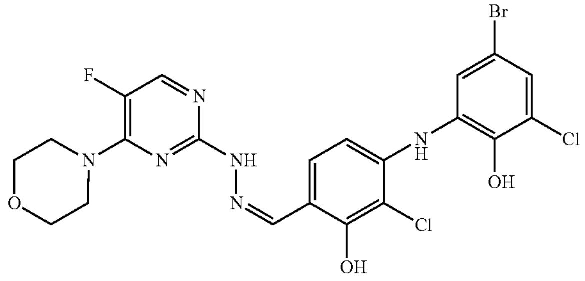
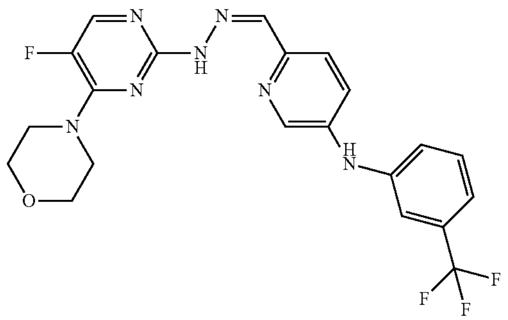

-continued
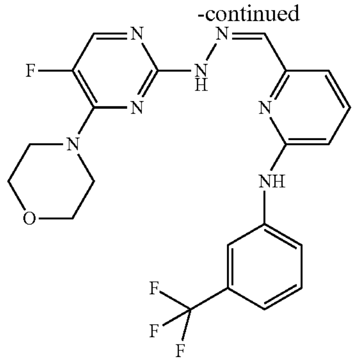
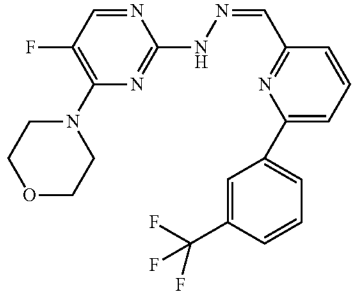
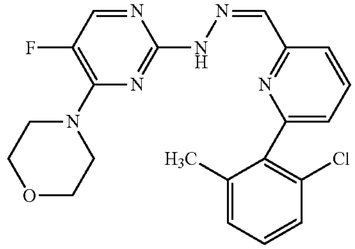
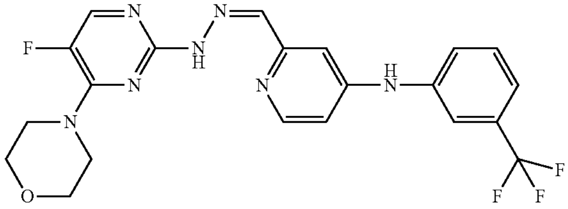
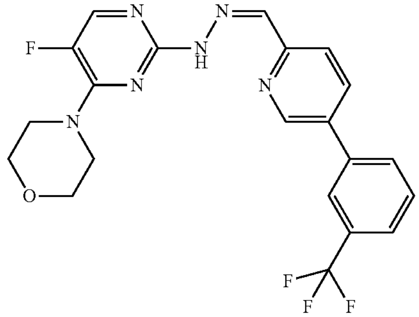
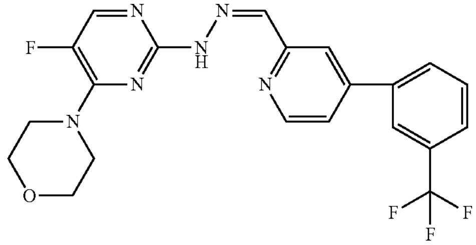
-continued
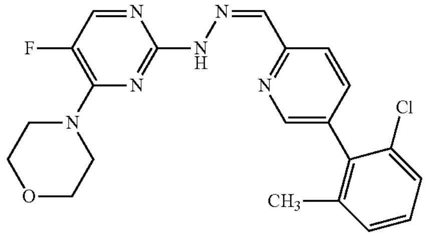
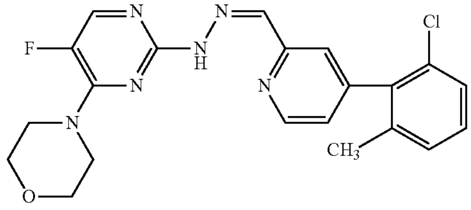
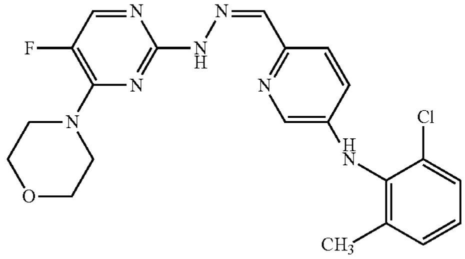
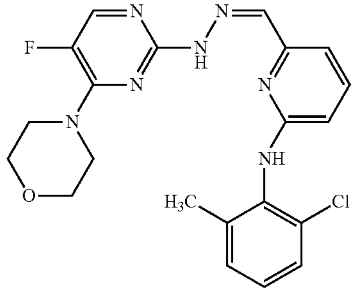
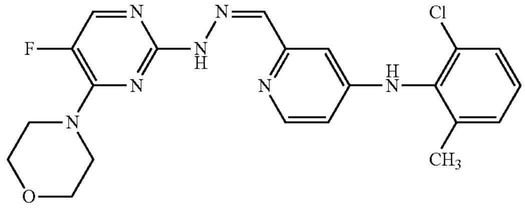
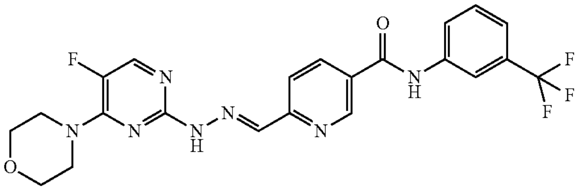
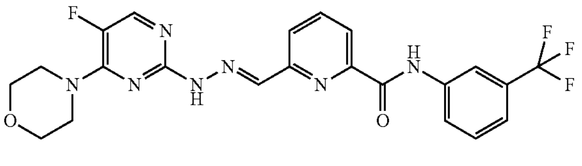

-continued
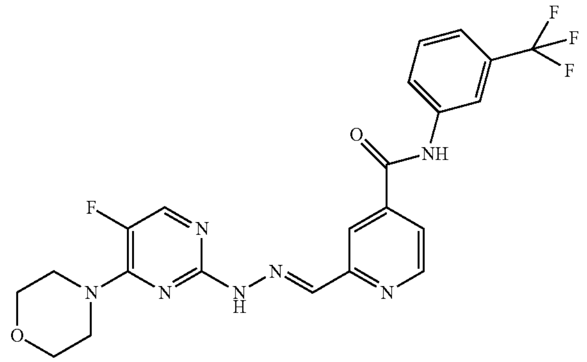
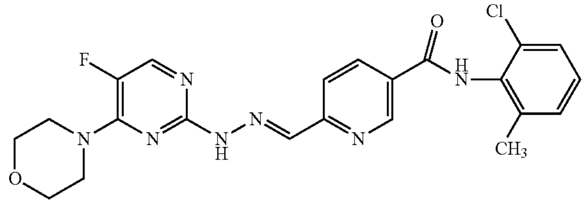
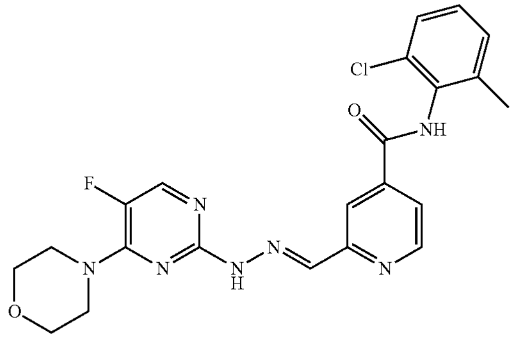
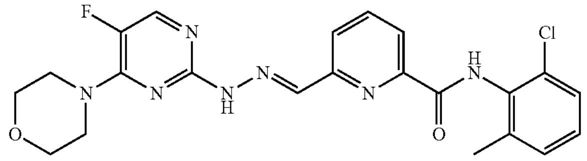
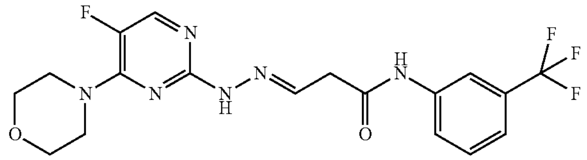
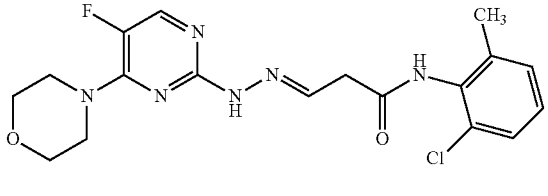
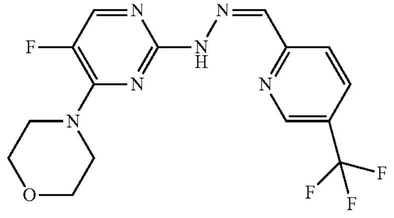
-continued
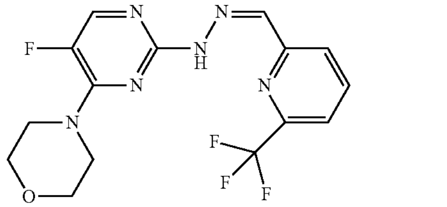
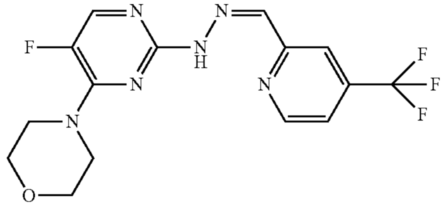
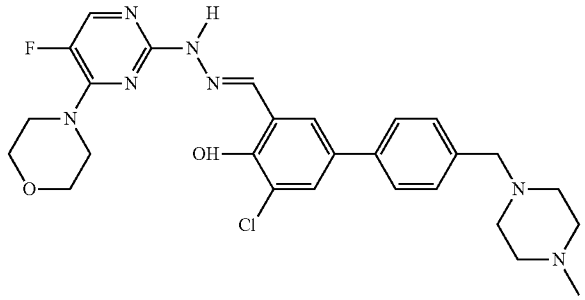
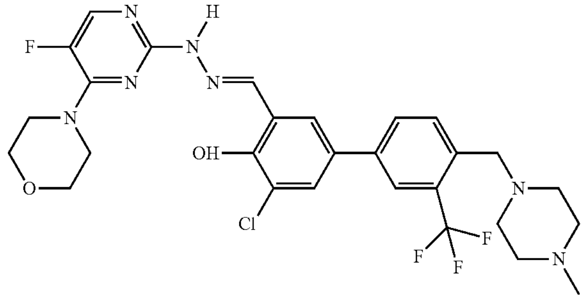
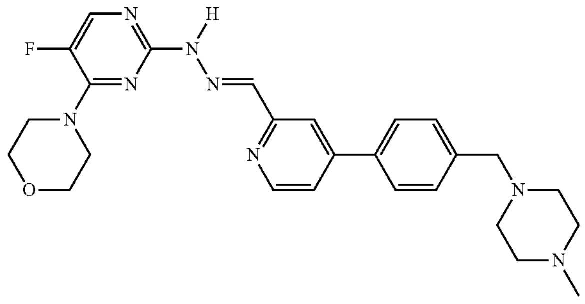
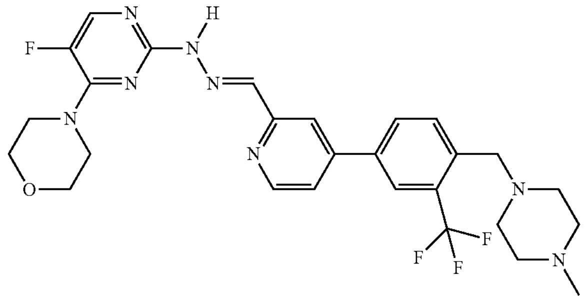

-continued
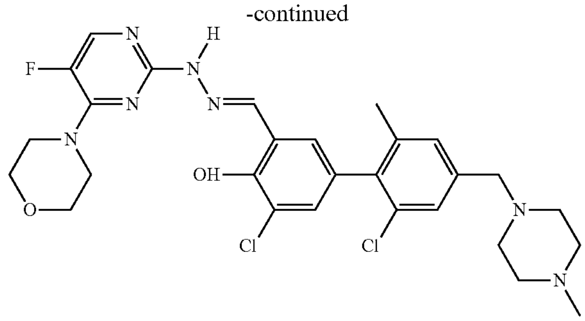
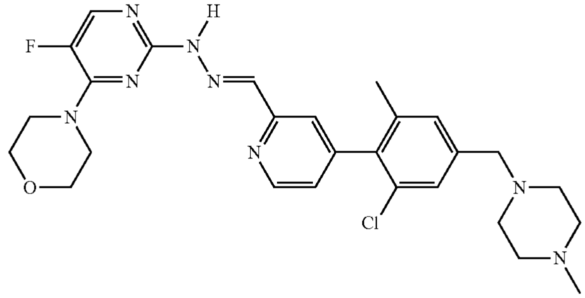
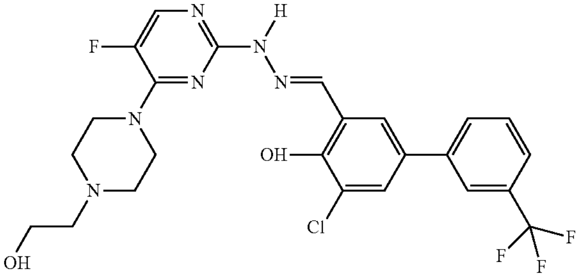
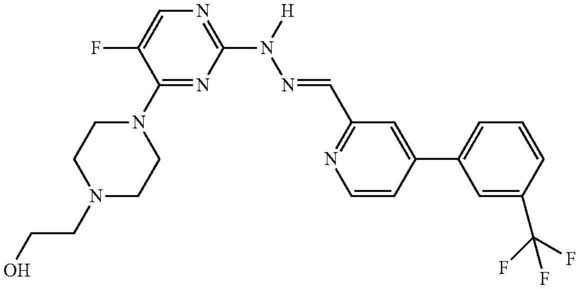
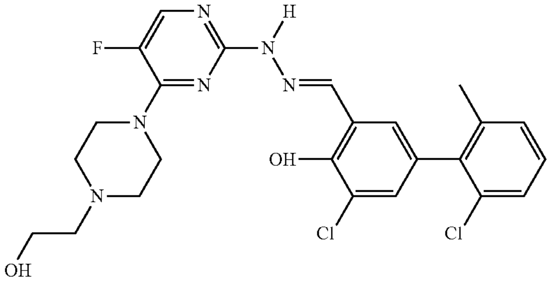
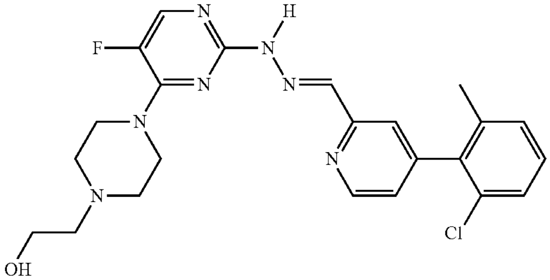
-continued
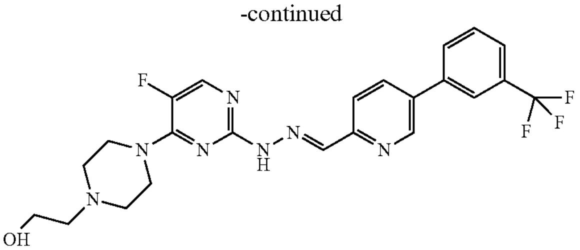
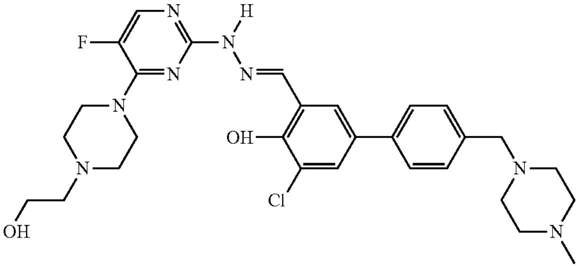
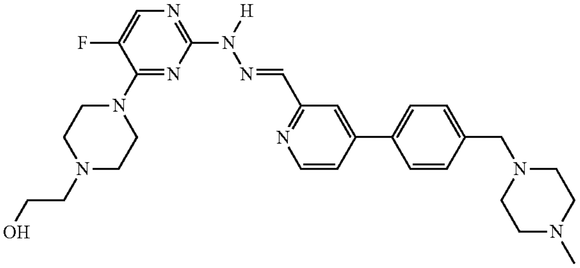
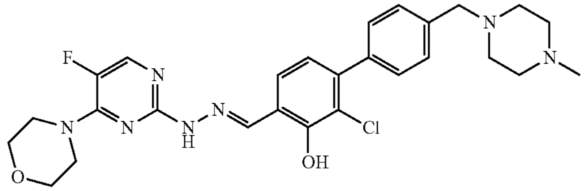
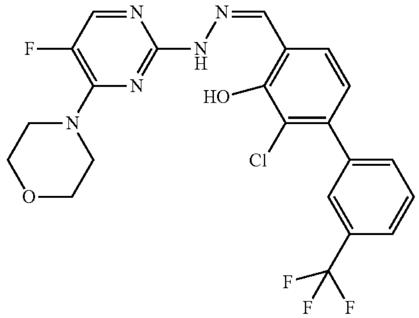
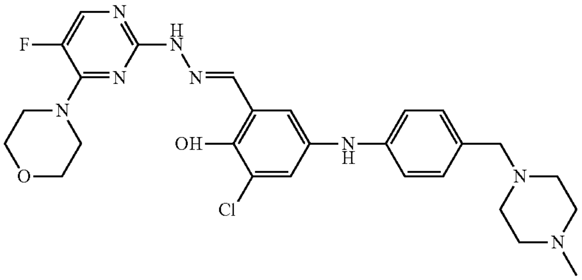

-continued
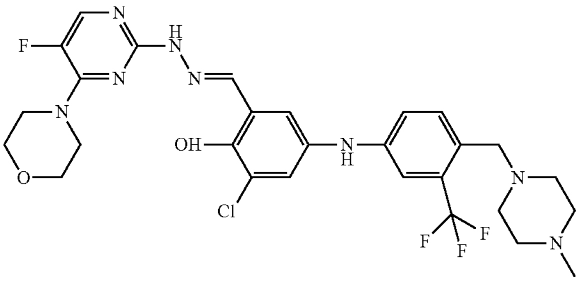
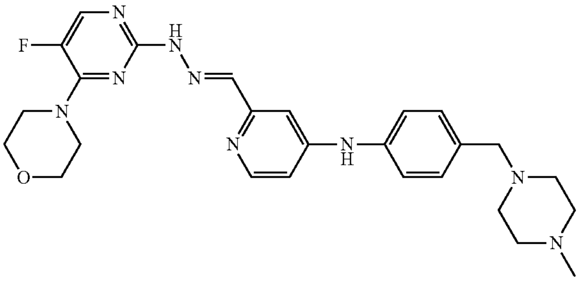
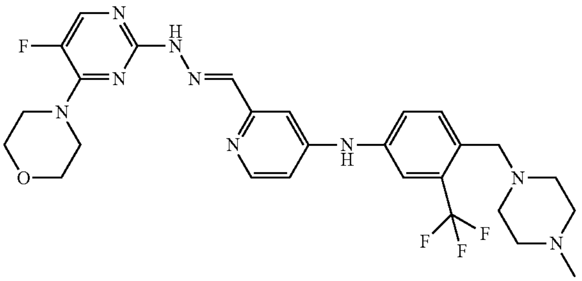
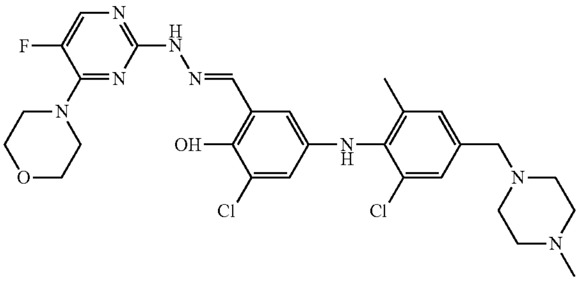
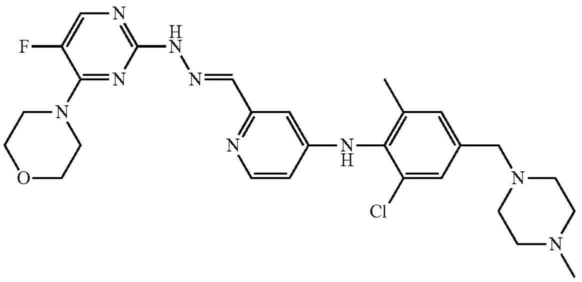
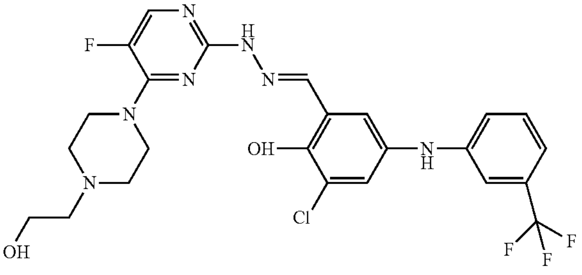
-continued
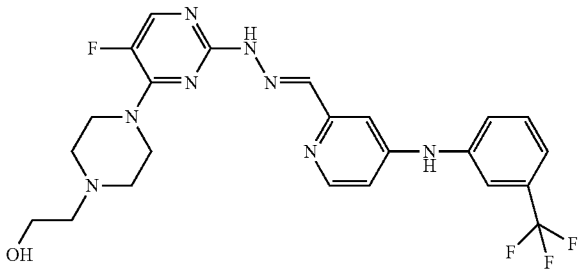
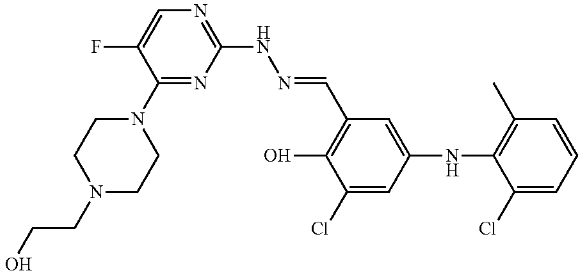
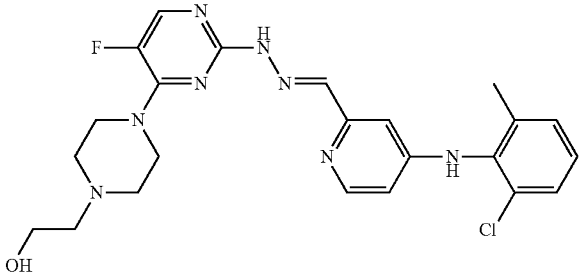
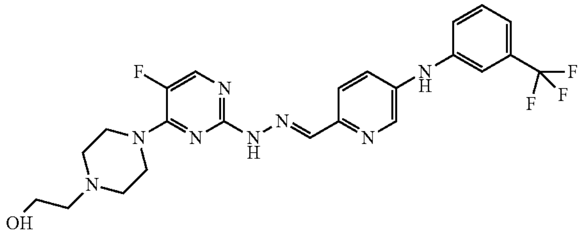
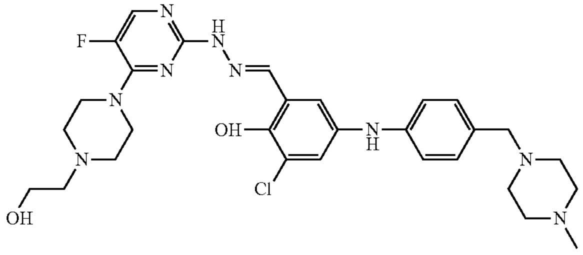
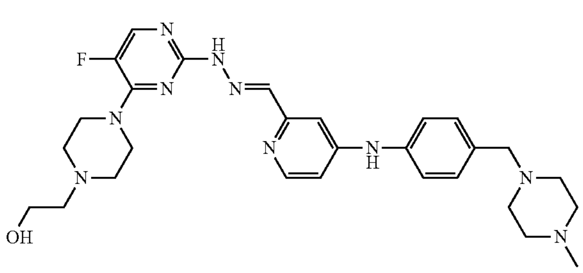

-continued
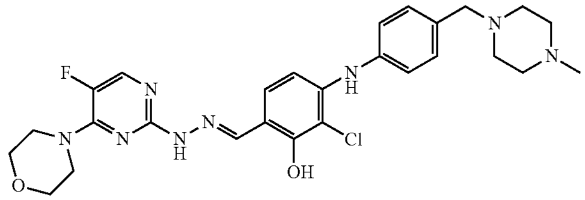
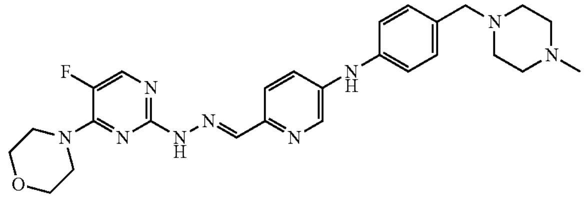
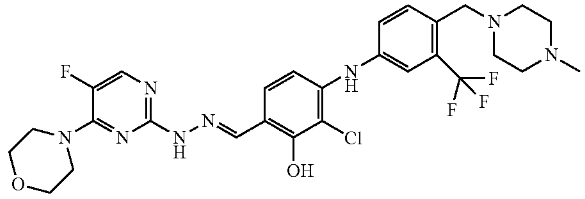
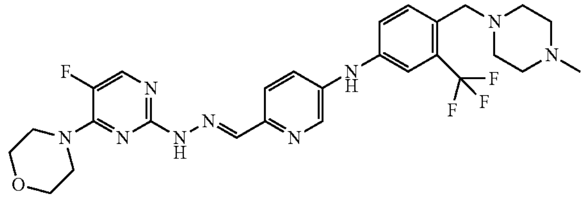
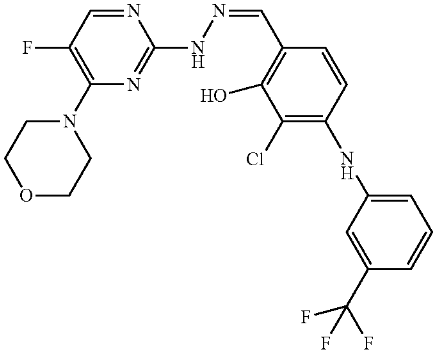
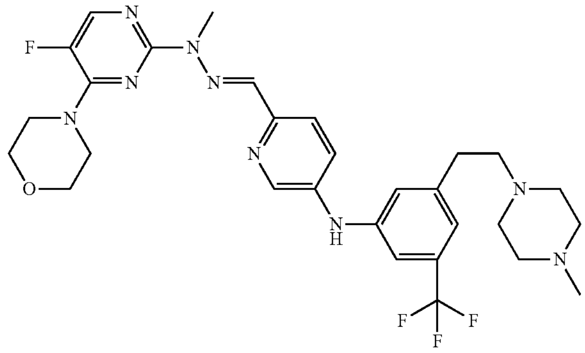
-continued
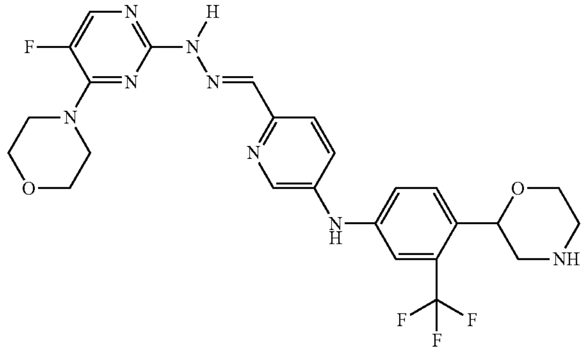
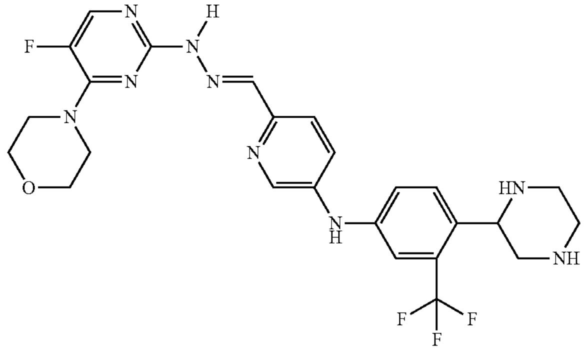
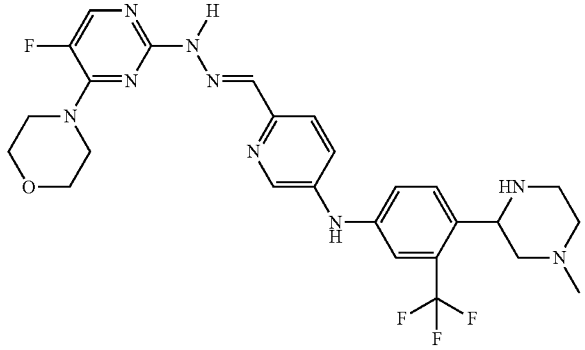
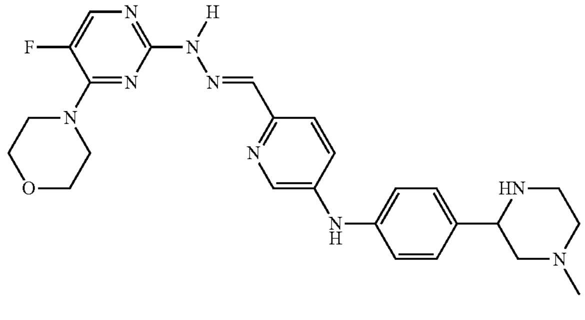
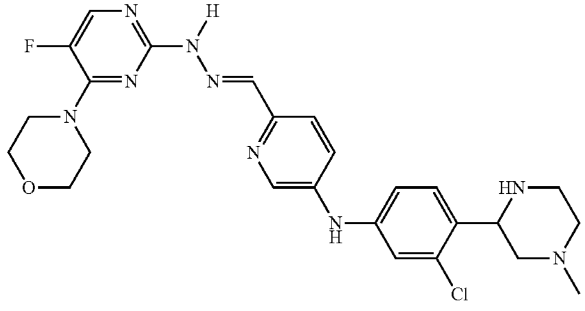

-continued
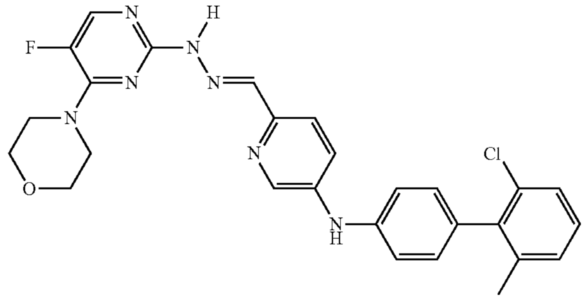
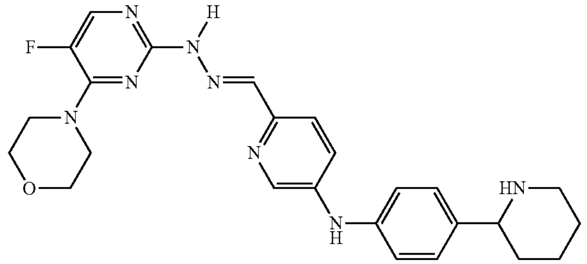
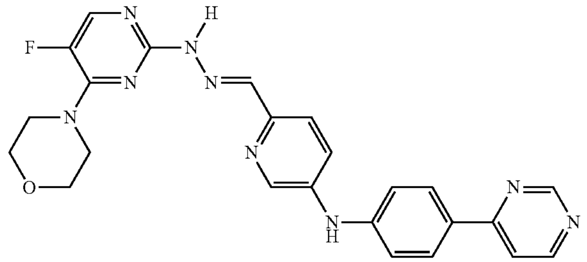
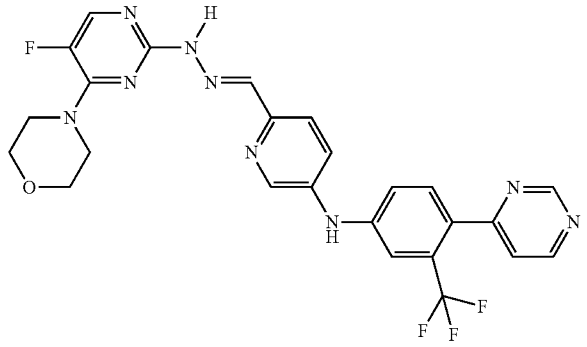
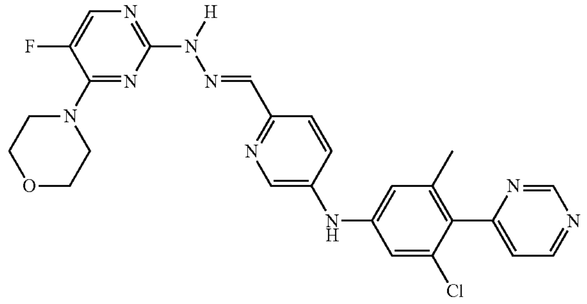
-continued
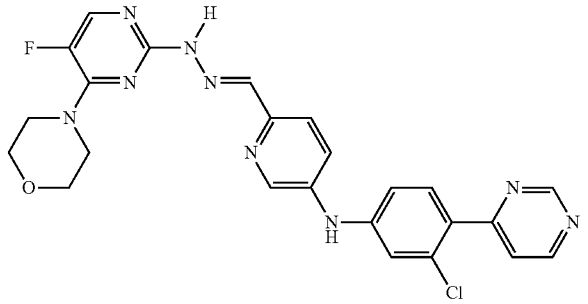
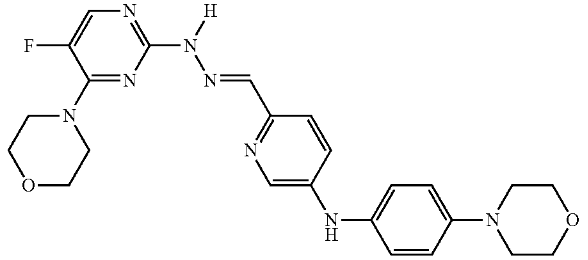
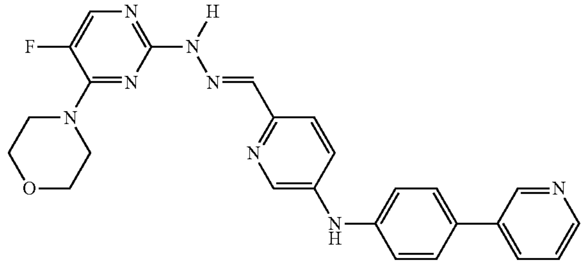
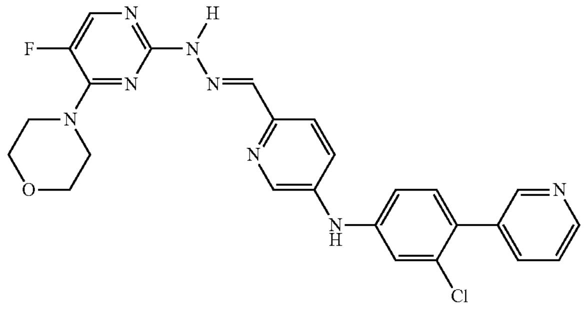
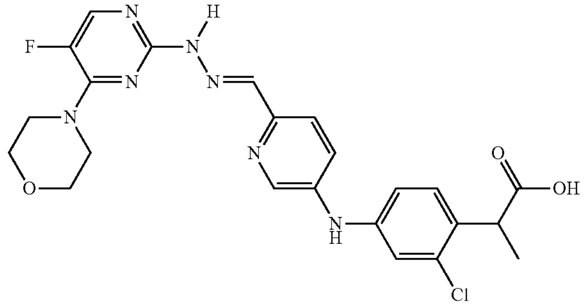
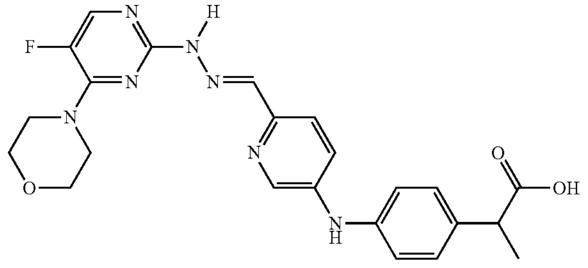

-continued
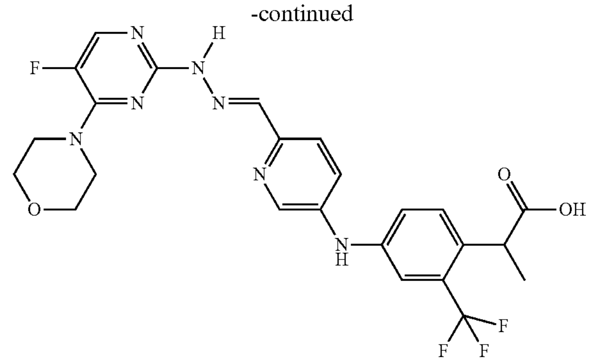
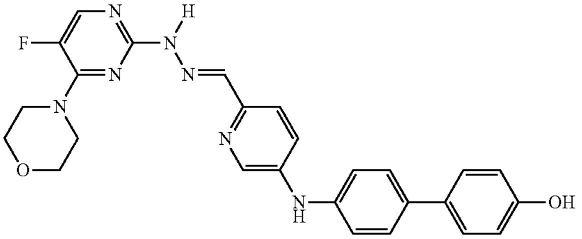
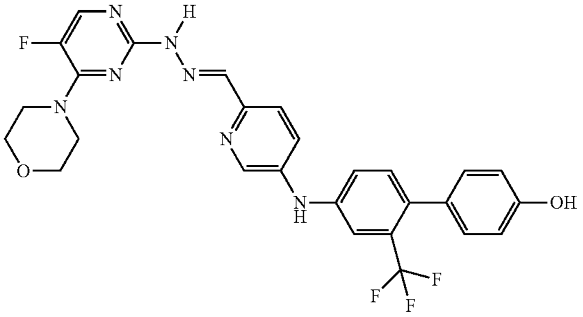
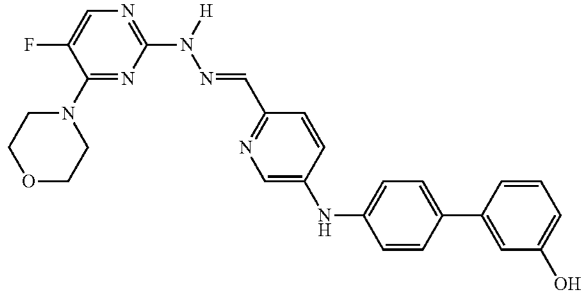
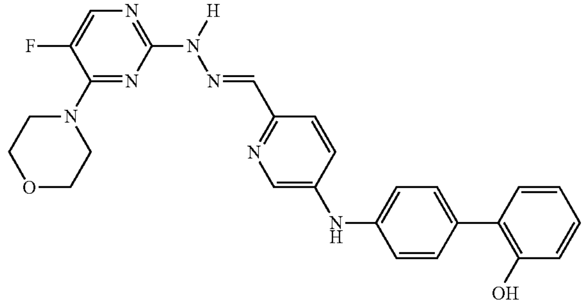
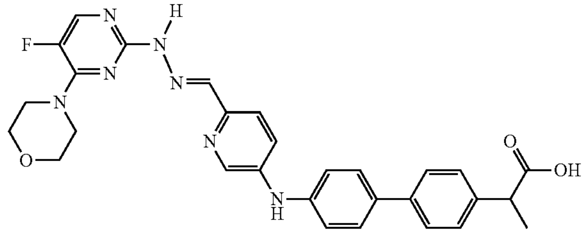
-continued
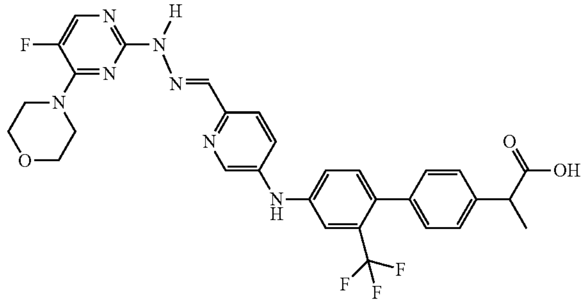
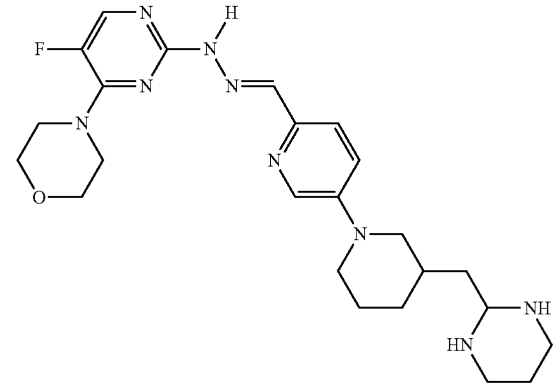
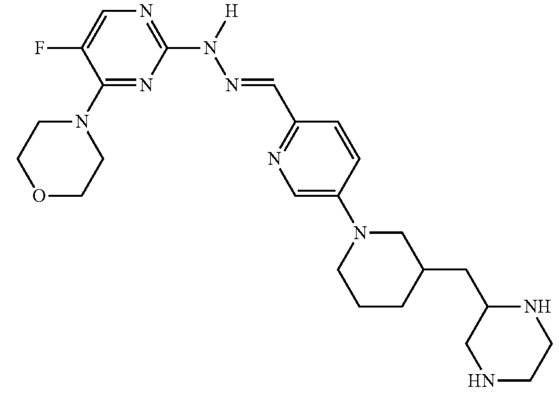
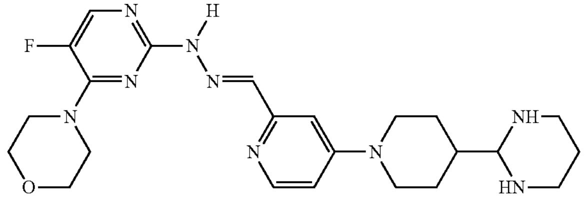
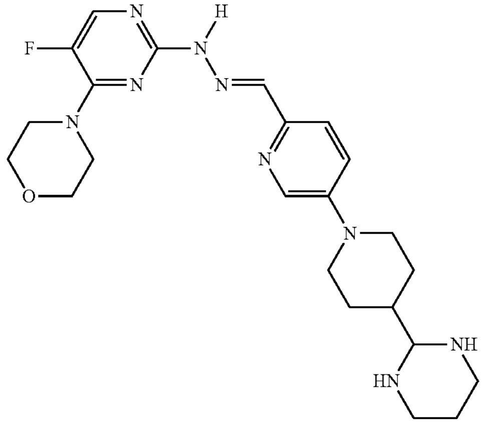

-continued
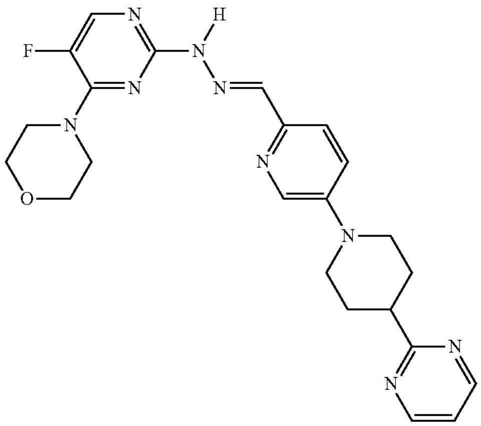
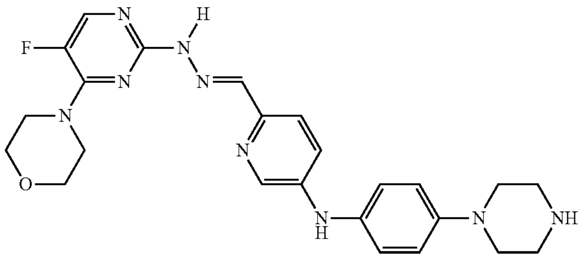
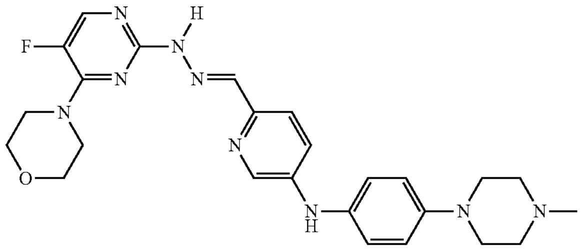
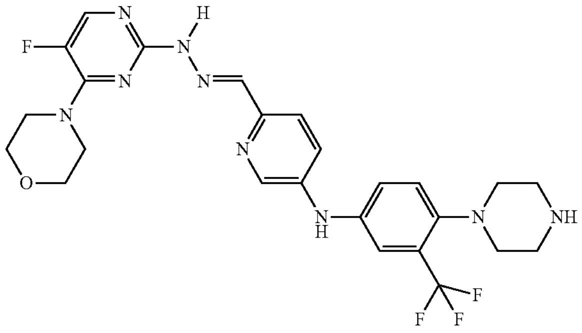
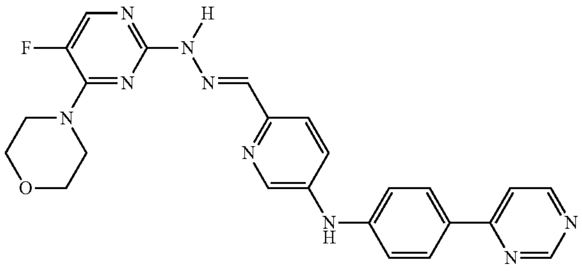
-continued
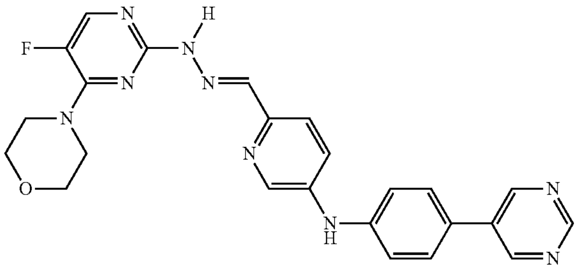
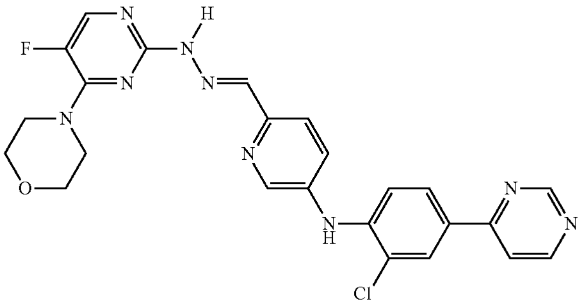
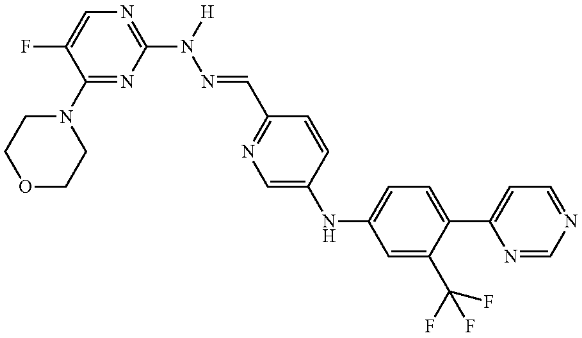
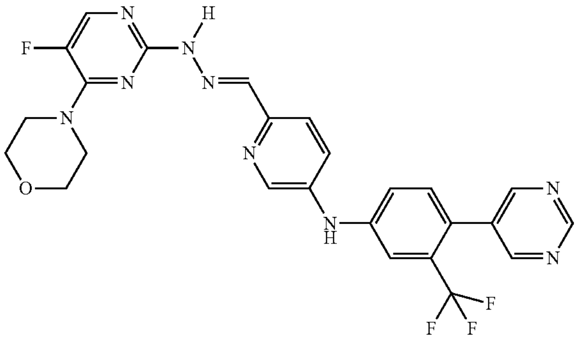
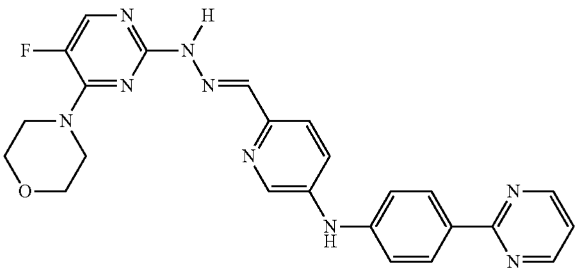

-continued
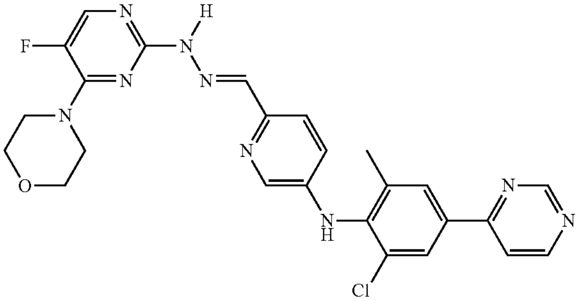
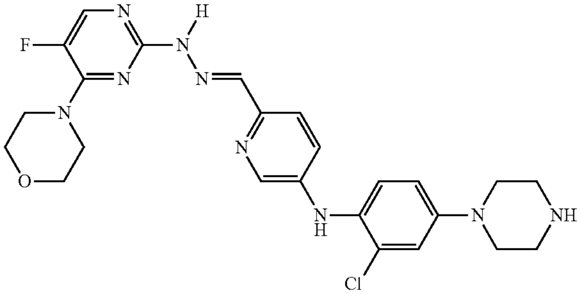
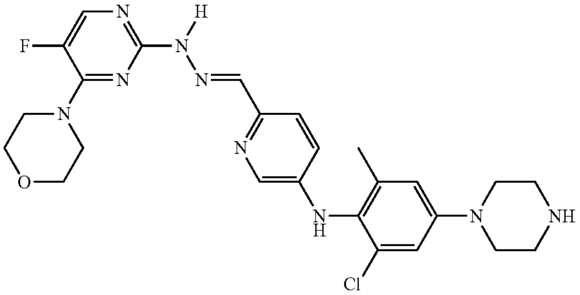
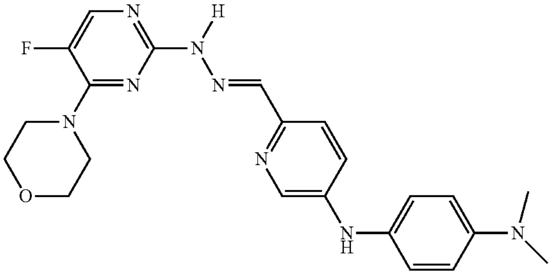
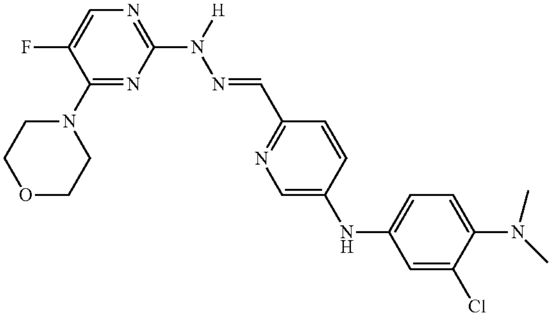
-continued
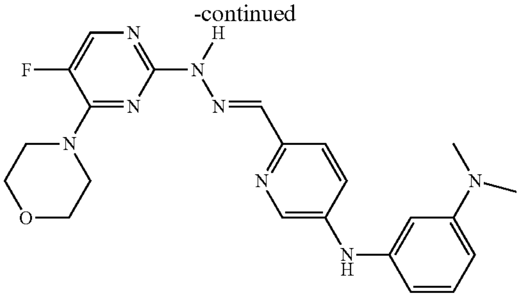
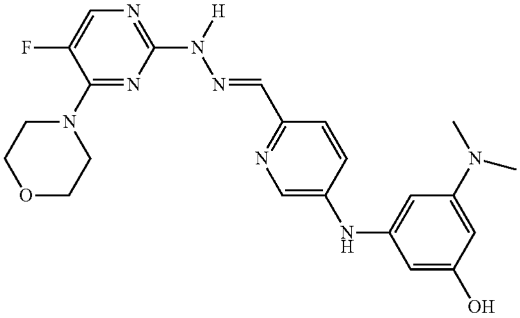
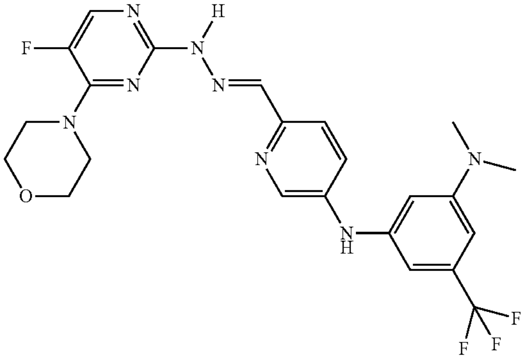
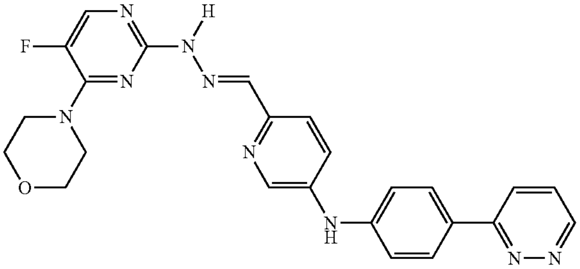
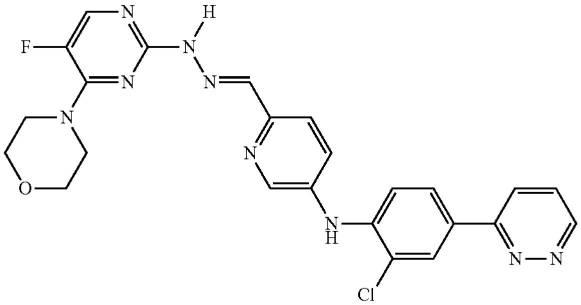

-continued
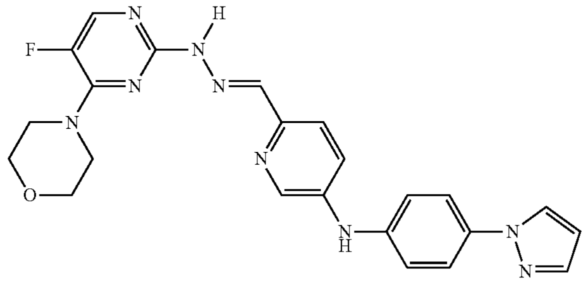
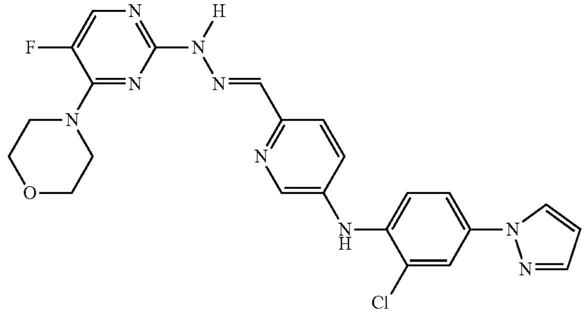
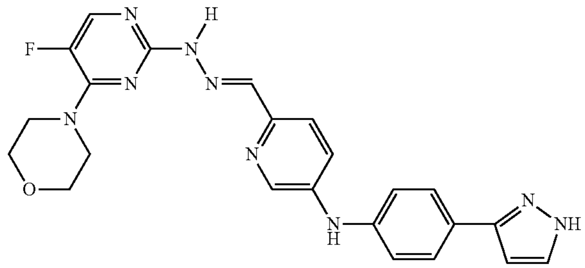
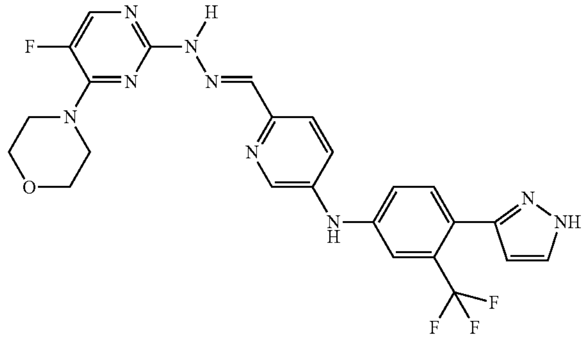
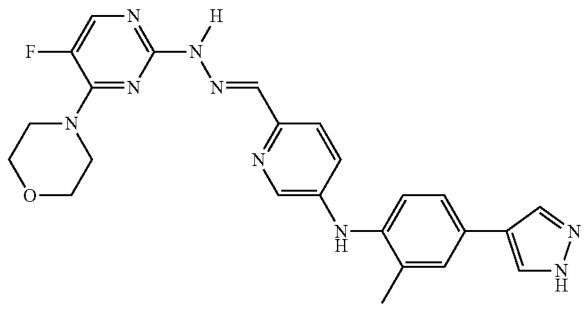
-continued
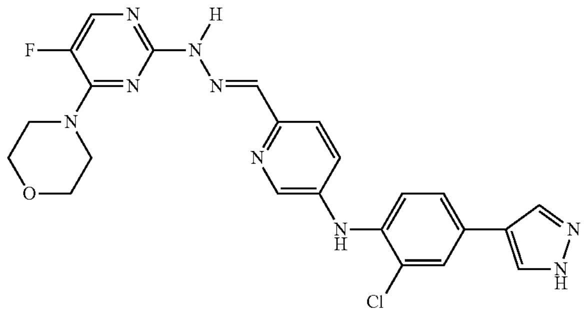
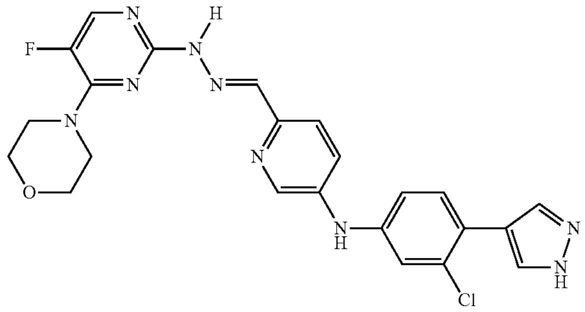
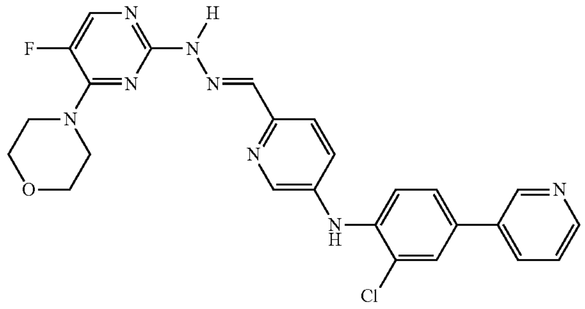
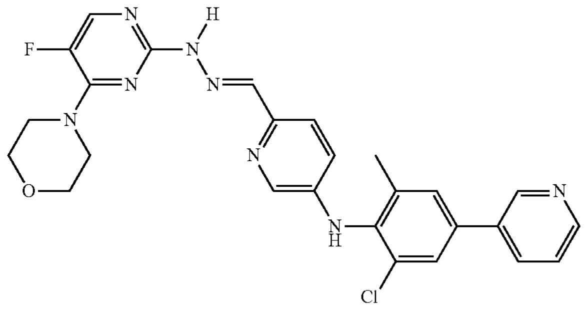
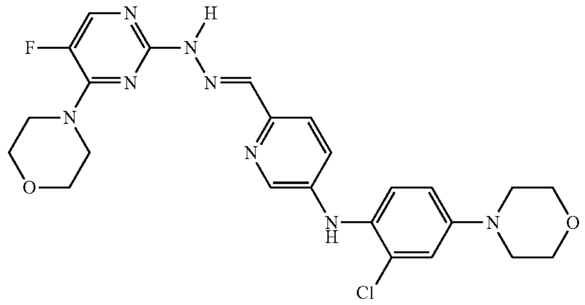

-continued
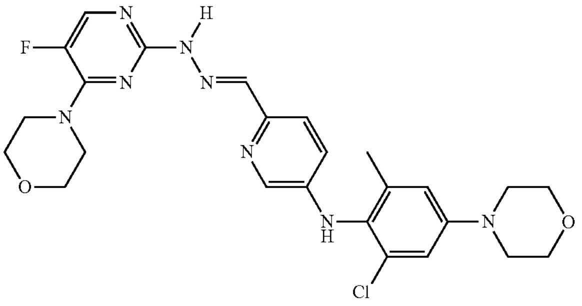
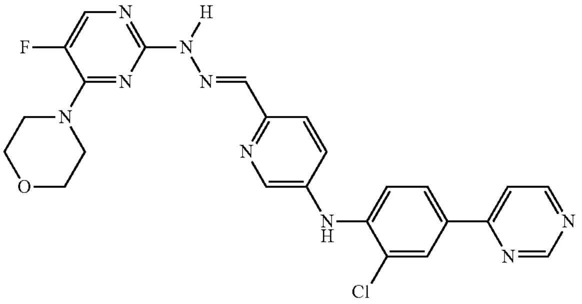
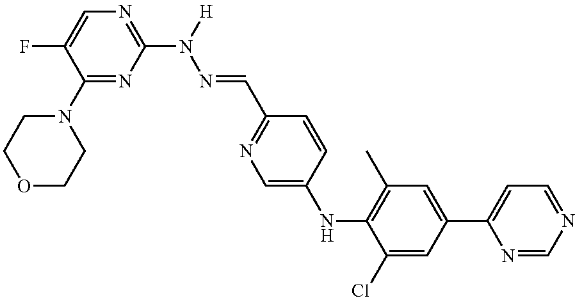
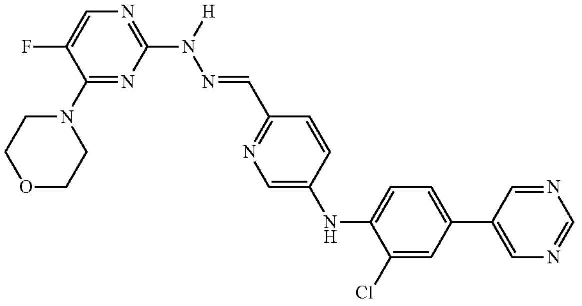
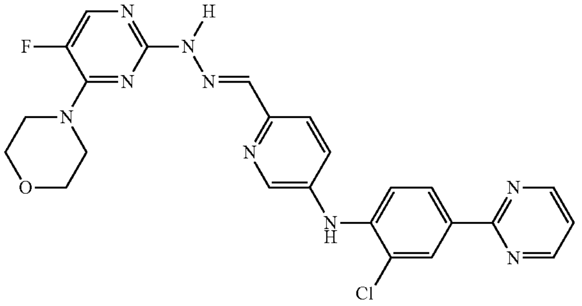
-continued
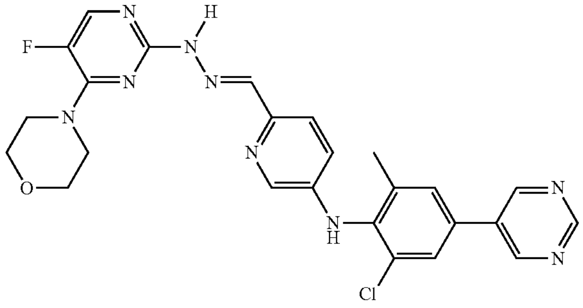
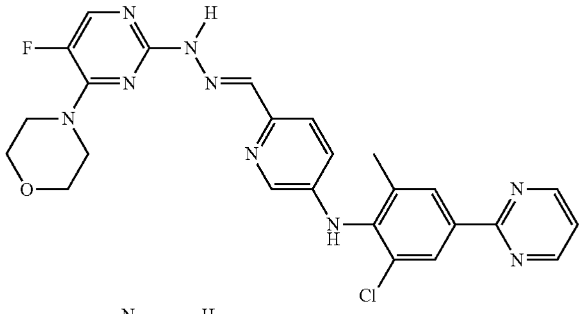
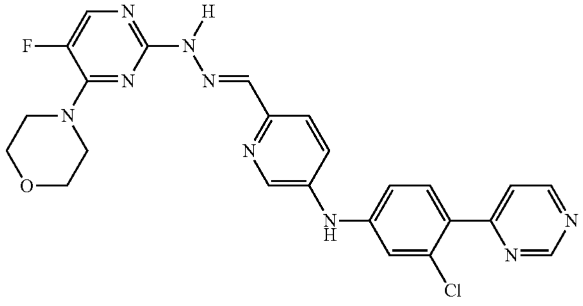
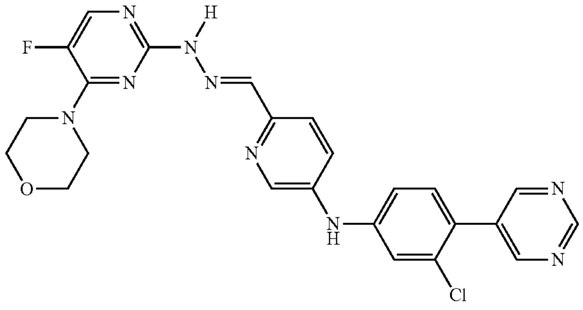
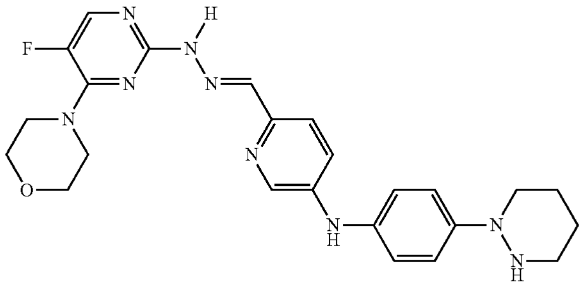

-continued
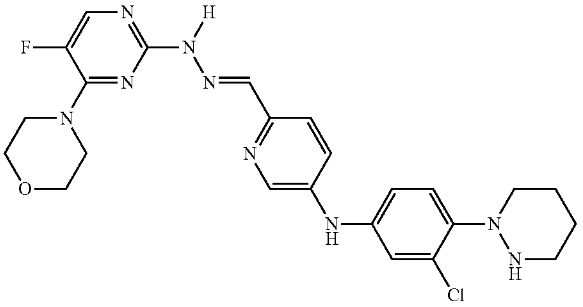
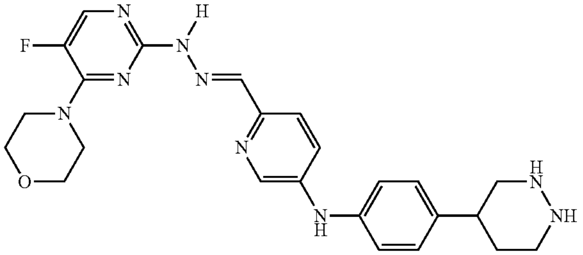
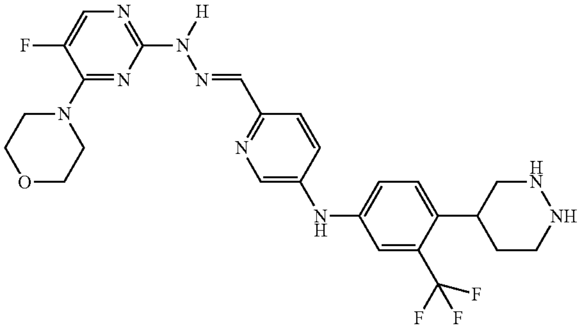
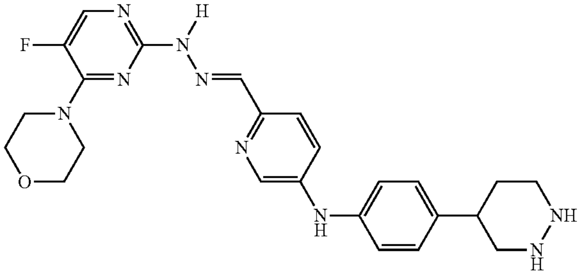
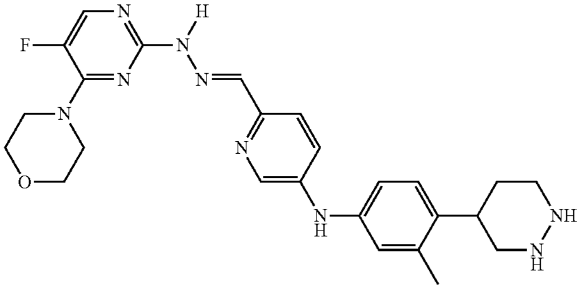
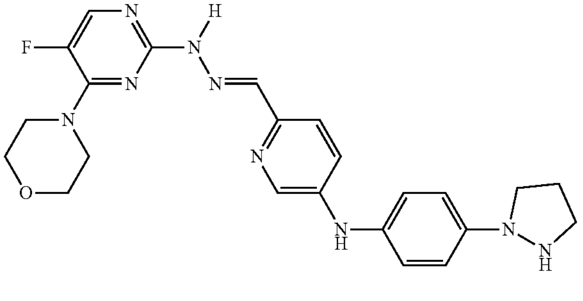
-continued
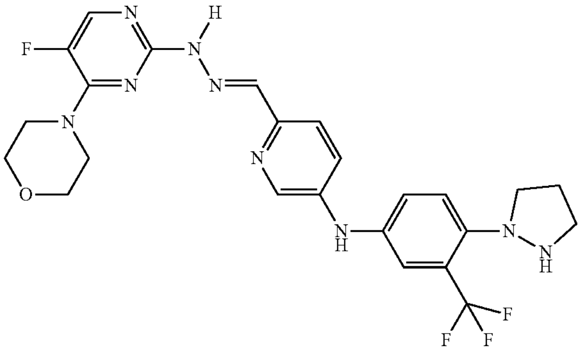
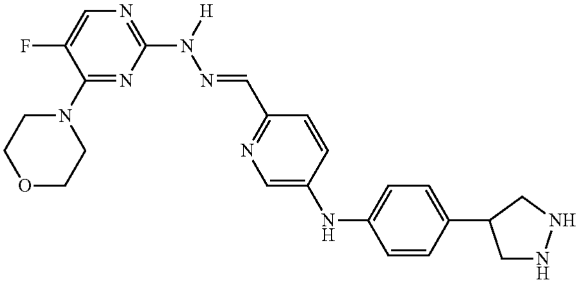
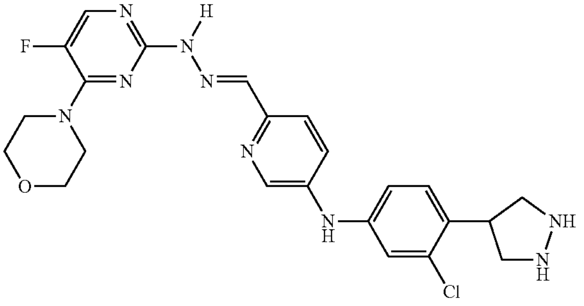
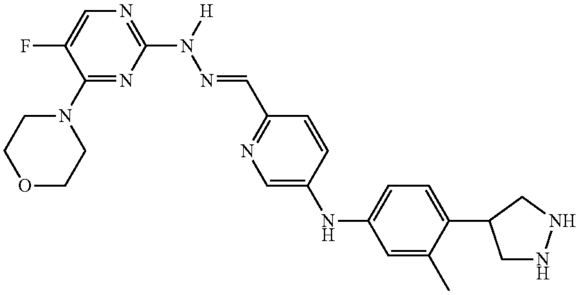
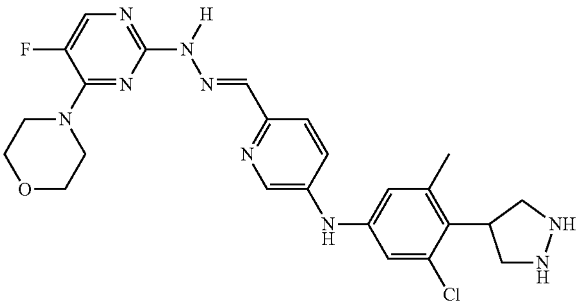

-continued
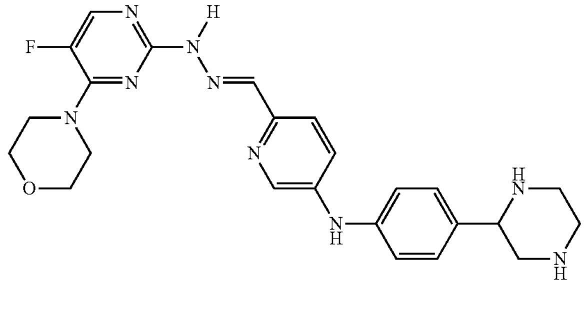
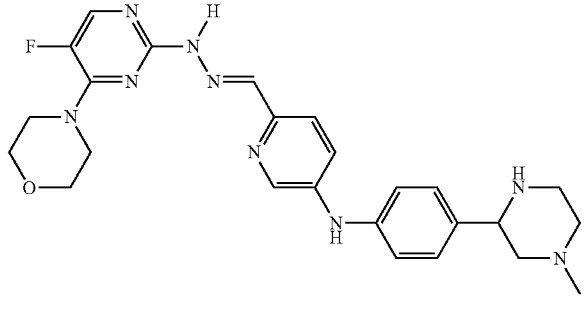
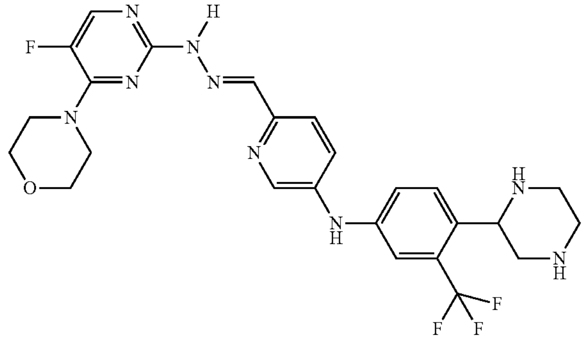
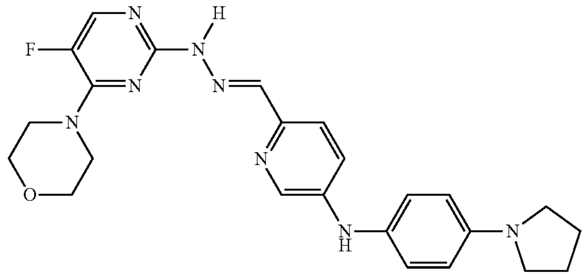
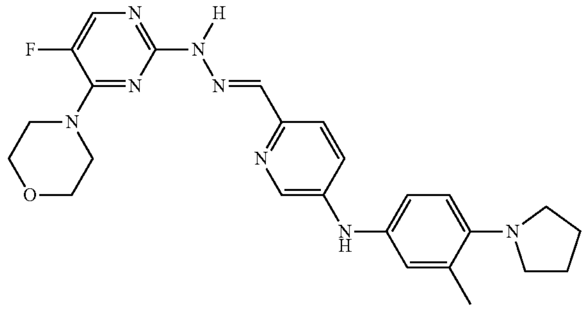
-continued
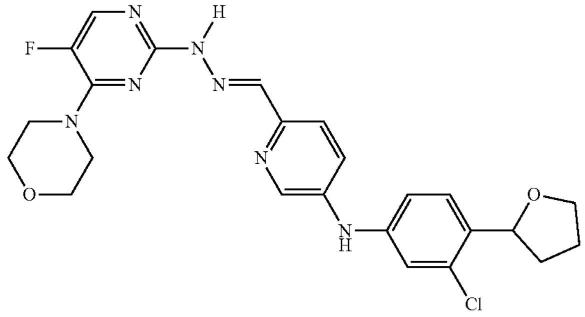
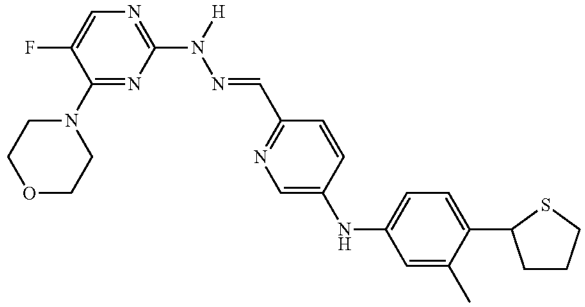
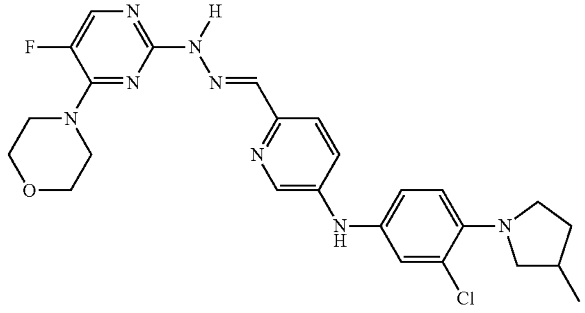
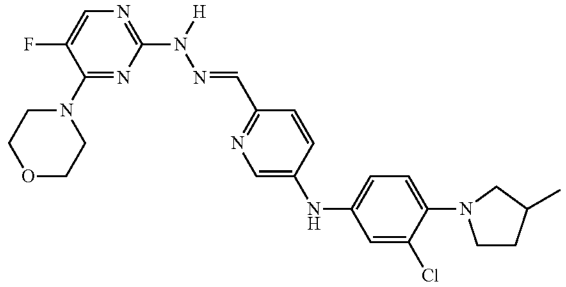
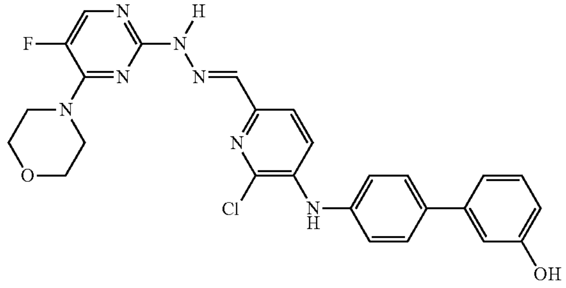

-continued
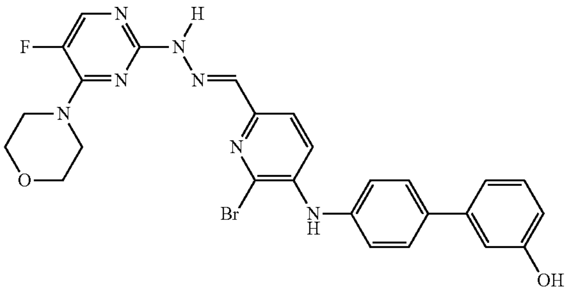
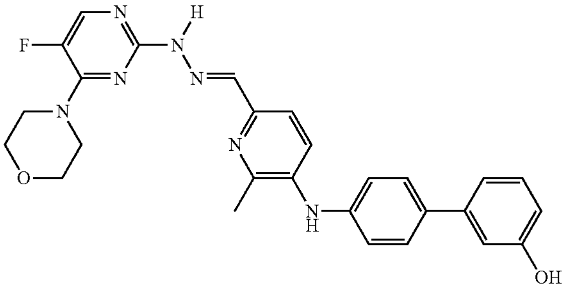
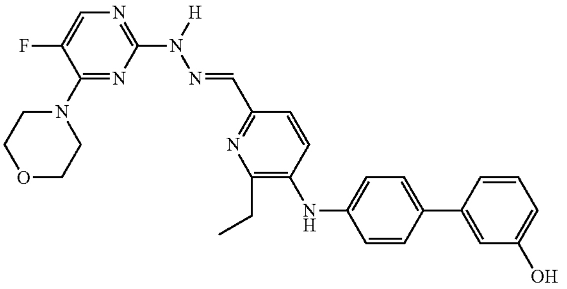
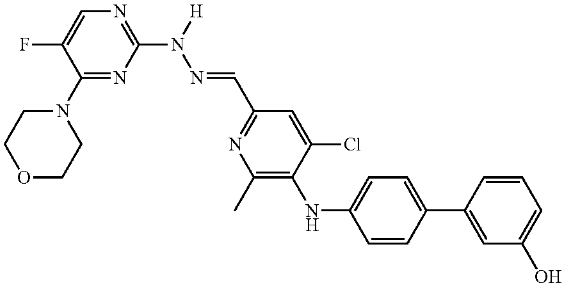
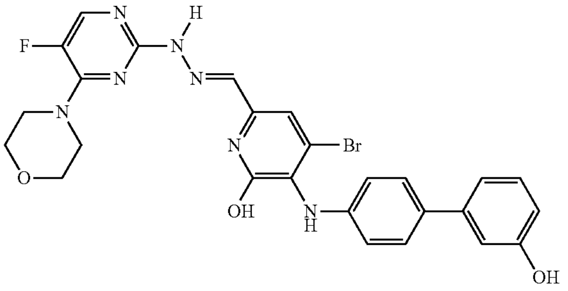
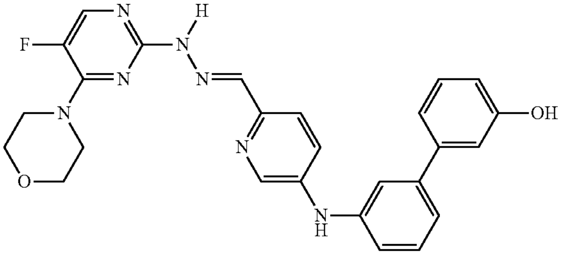
-continued
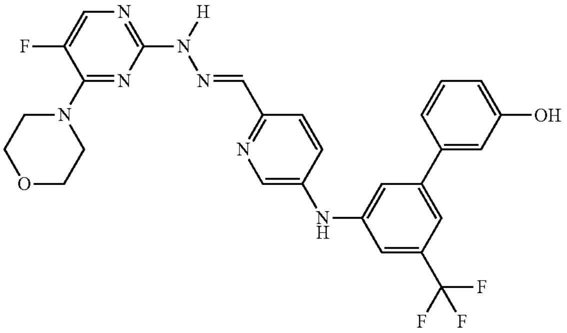
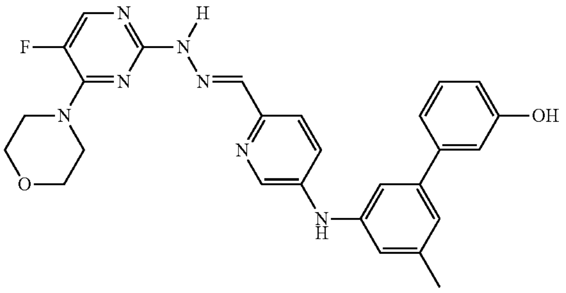
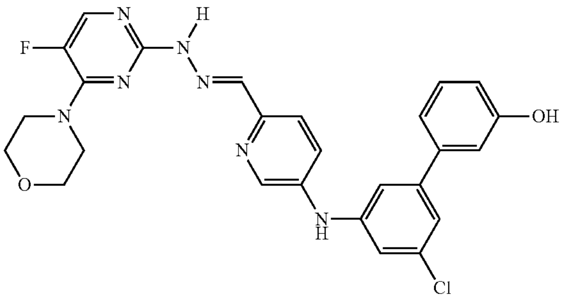
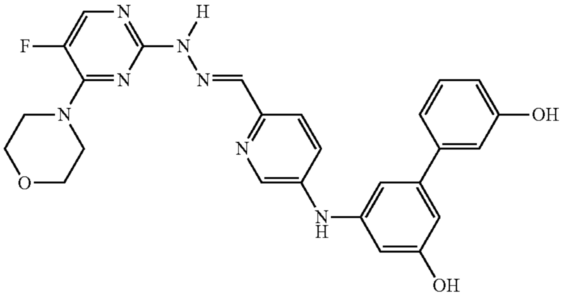
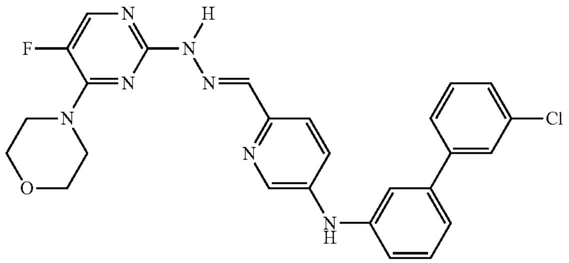

-continued
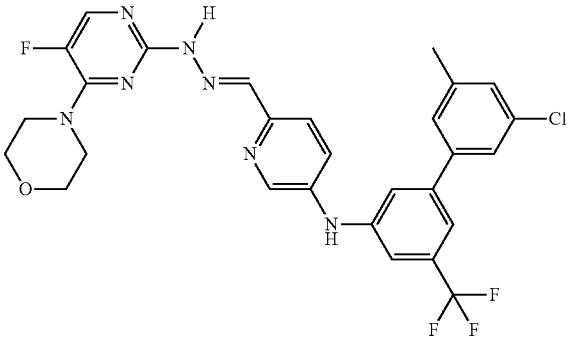
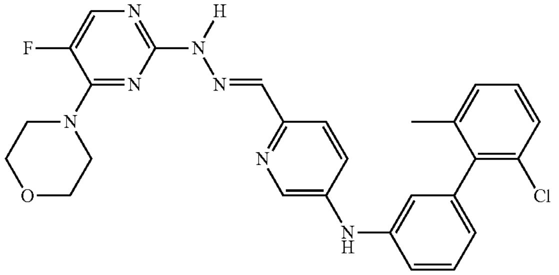
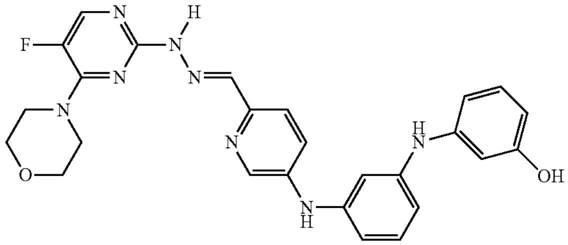
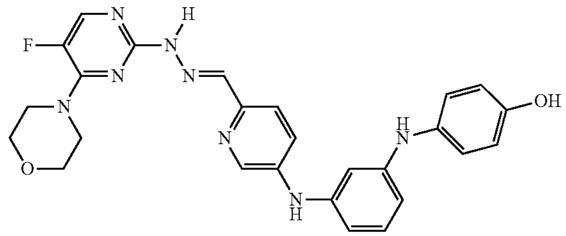
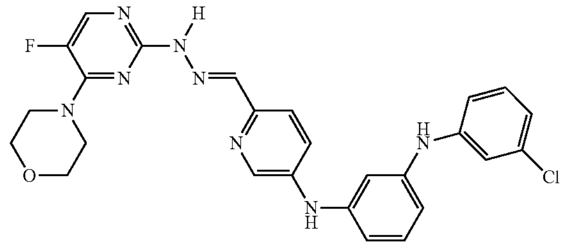
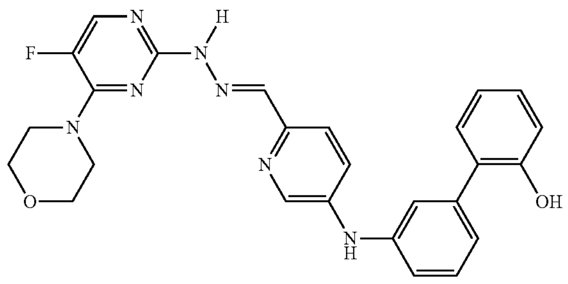
-continued
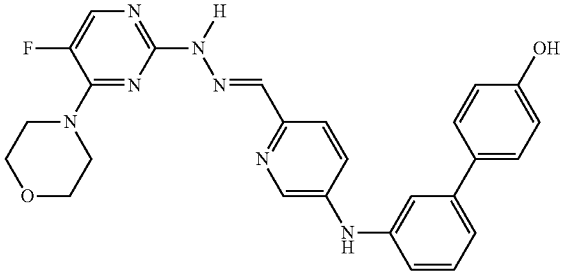
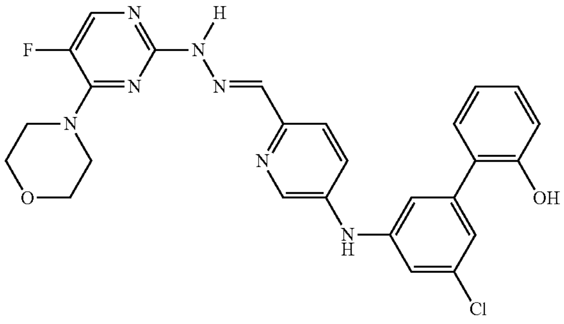
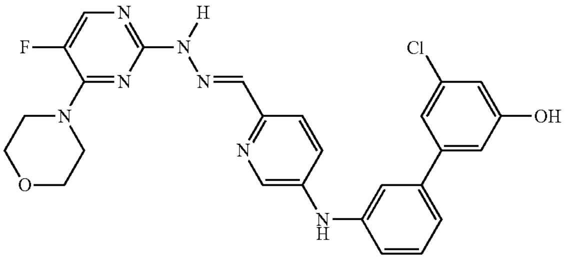
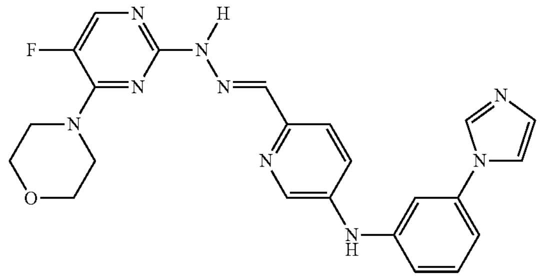
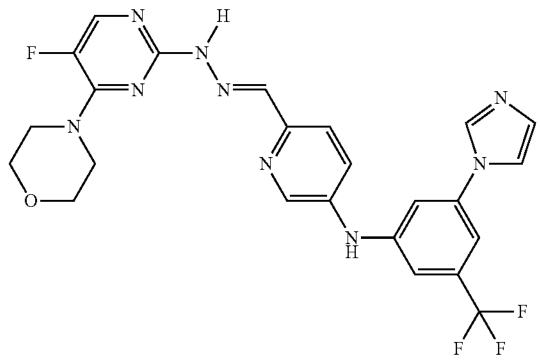

-continued
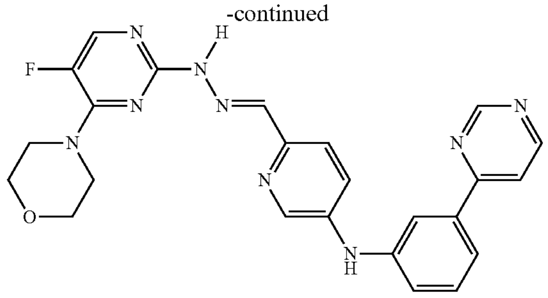
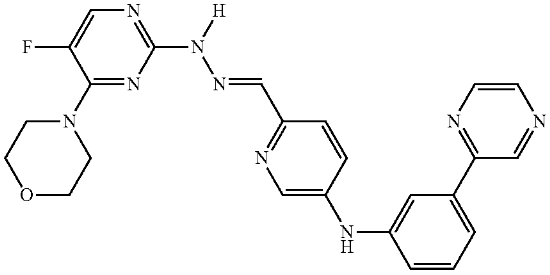
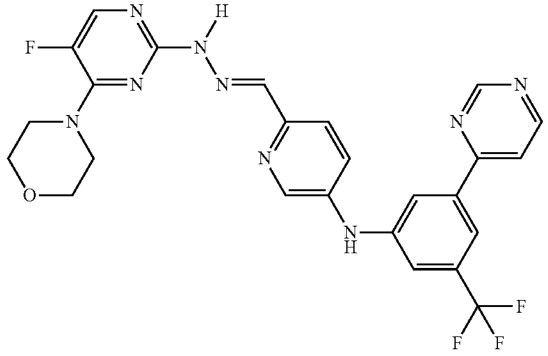
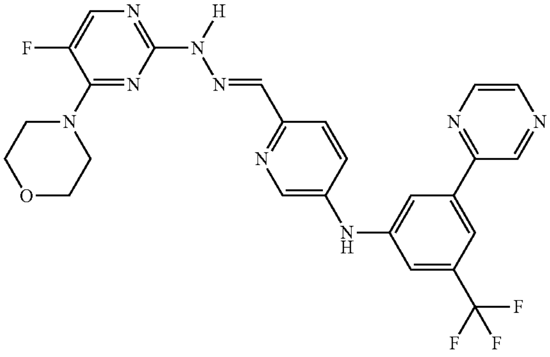
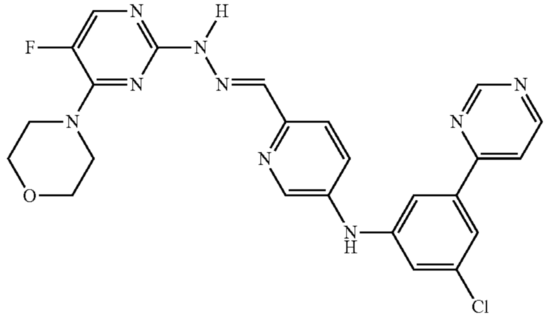
-continued
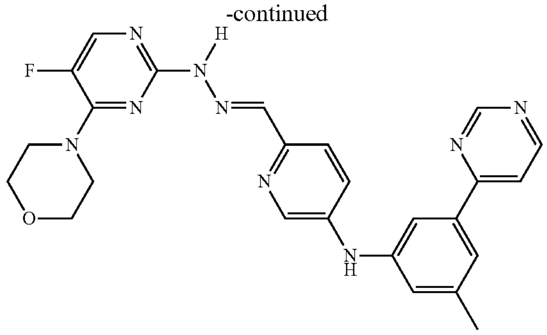
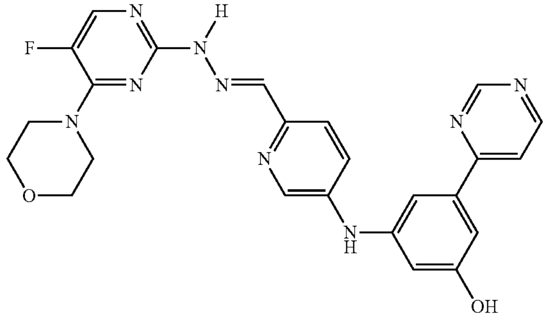
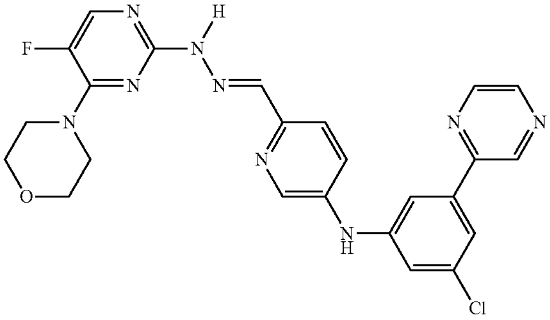
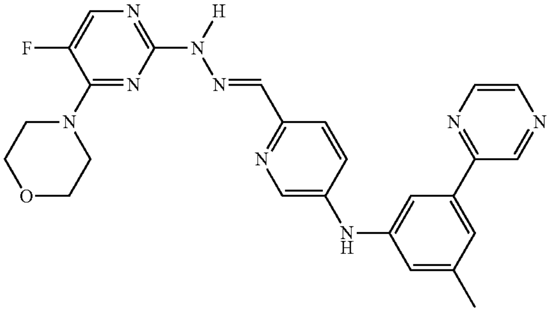
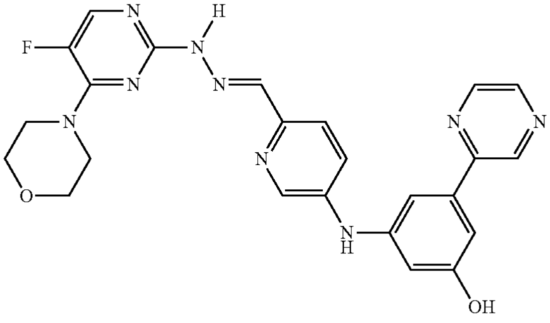

-continued
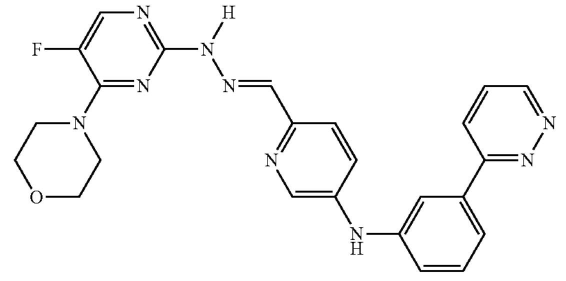
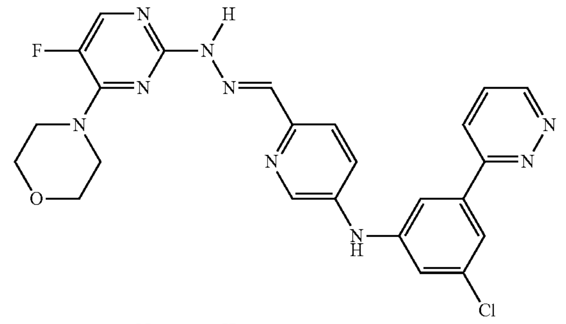
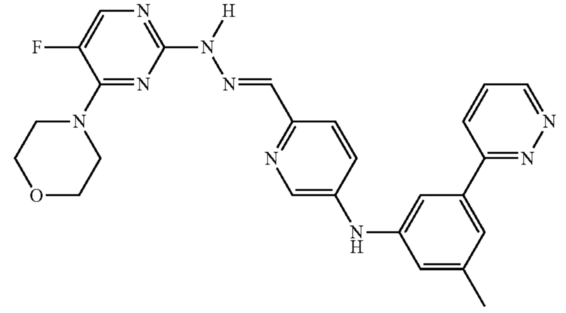
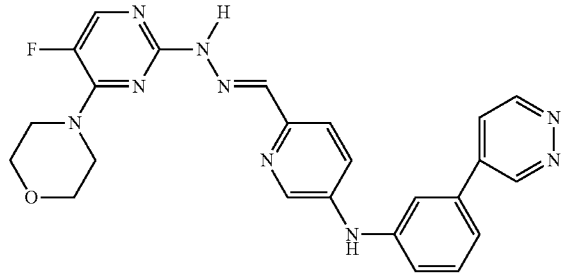
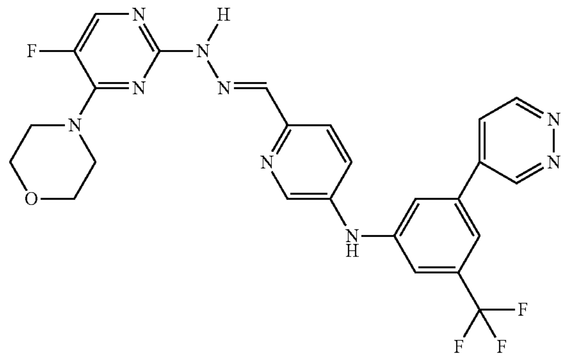
-continued
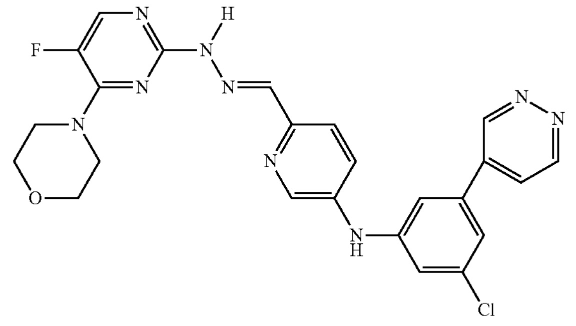
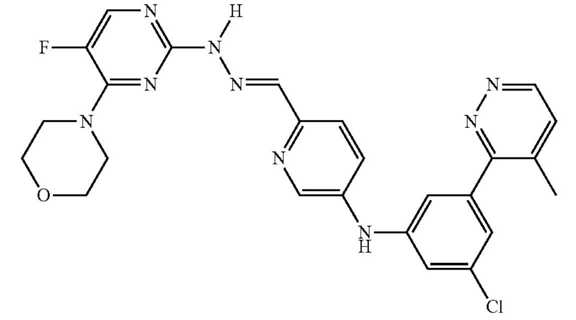
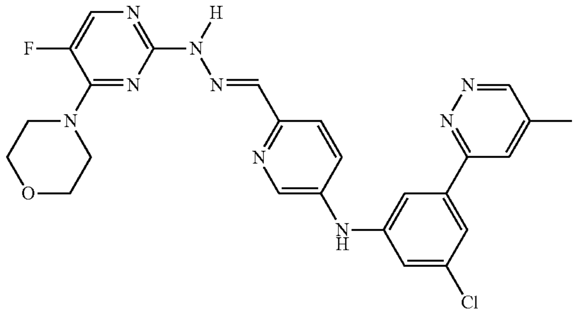
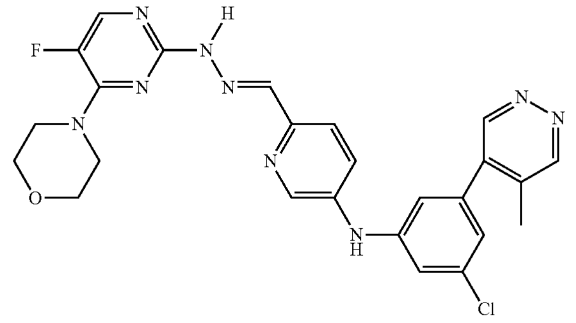
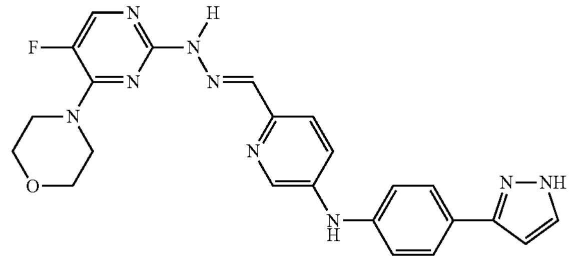

-continued
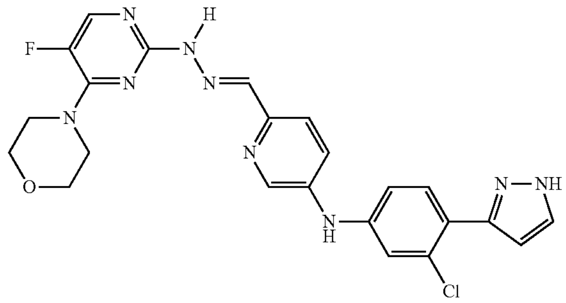
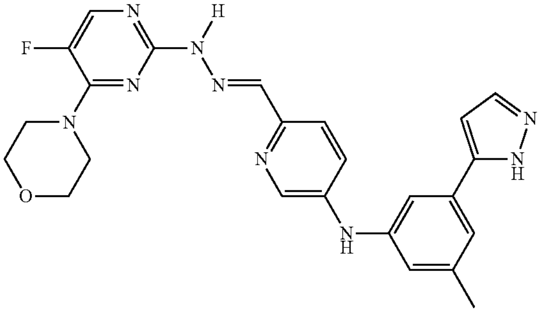
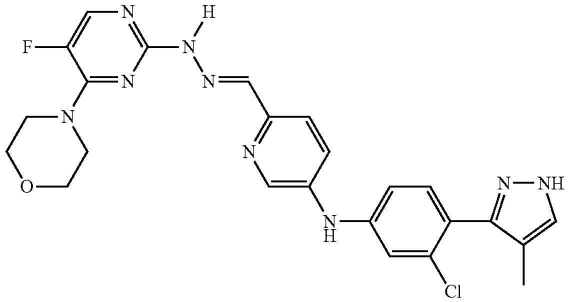
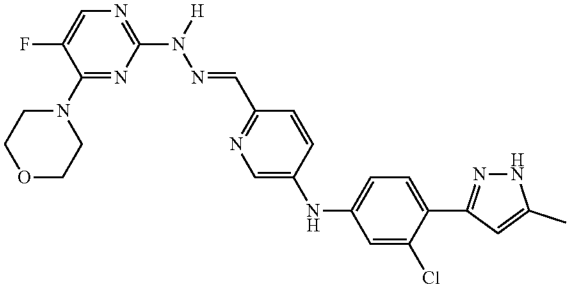
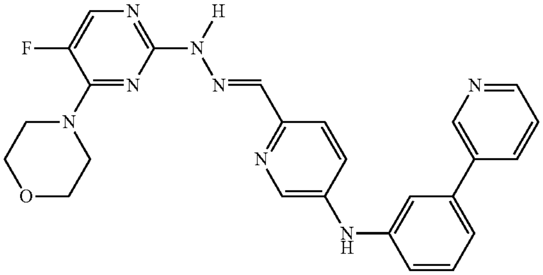
-continued
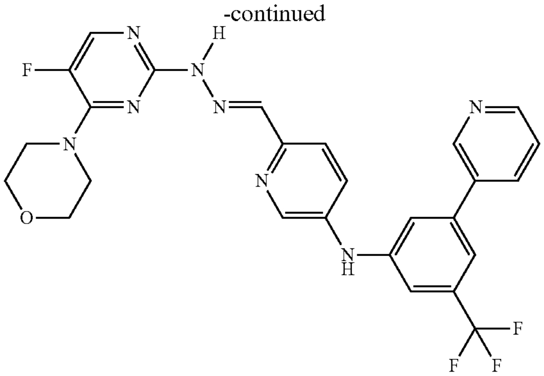
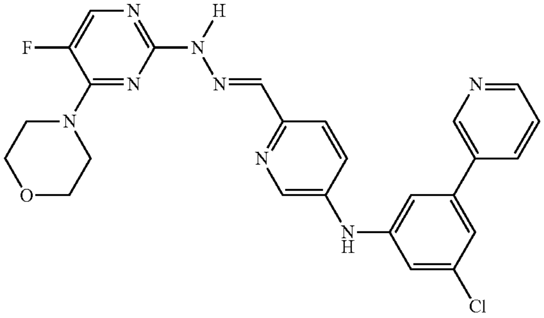
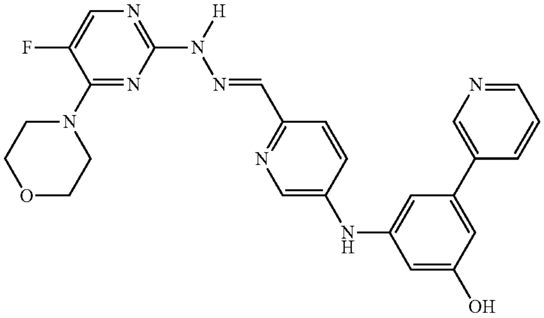
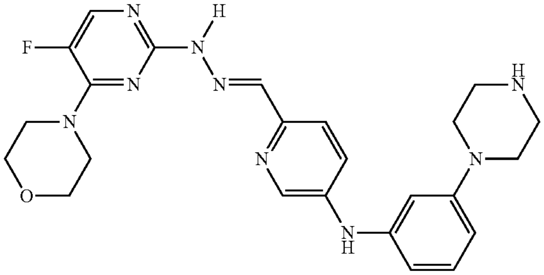
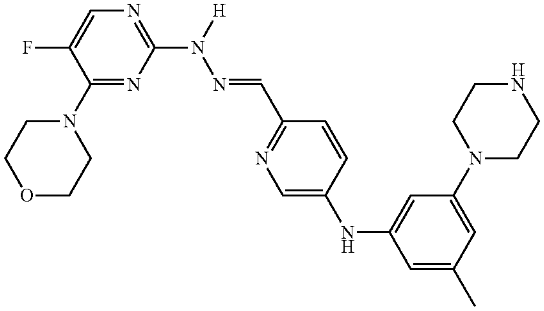

-continued
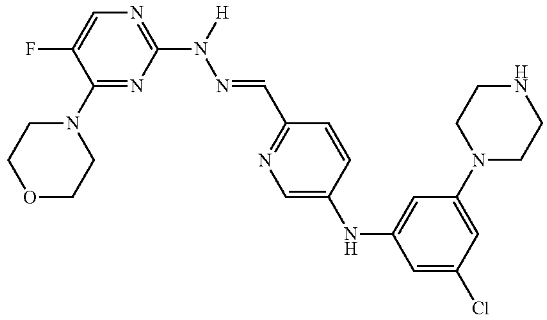
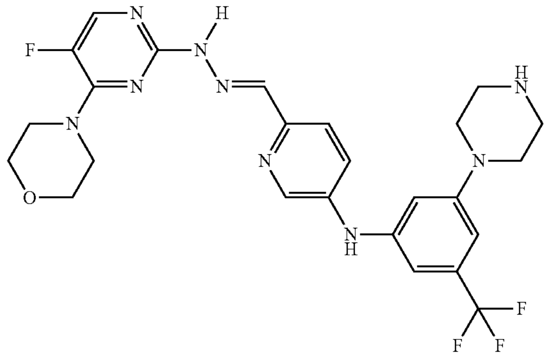
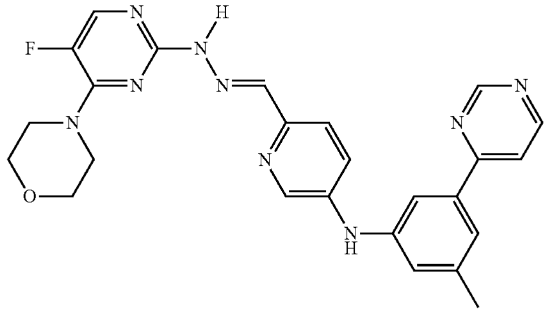
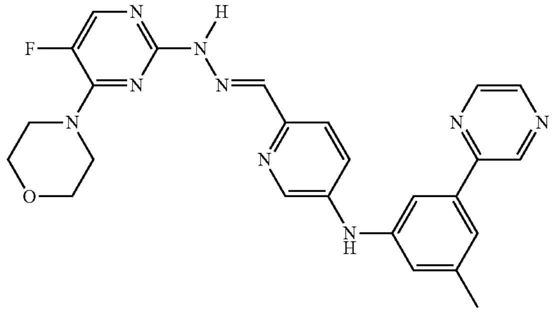
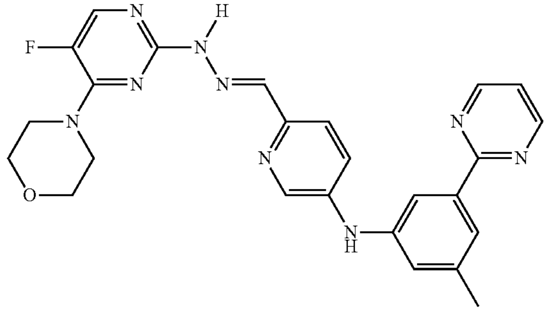
-continued
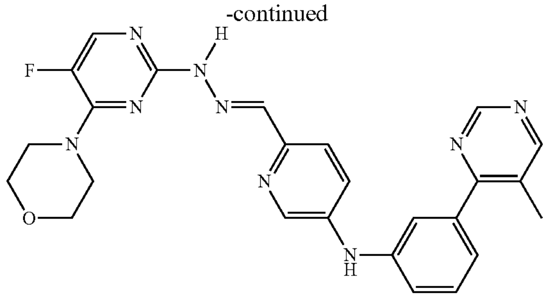
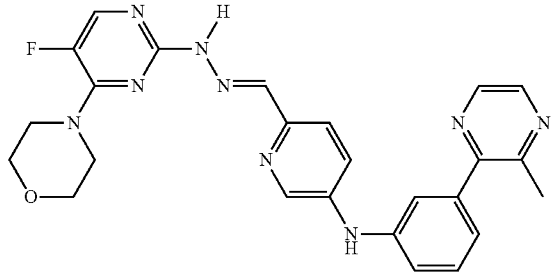
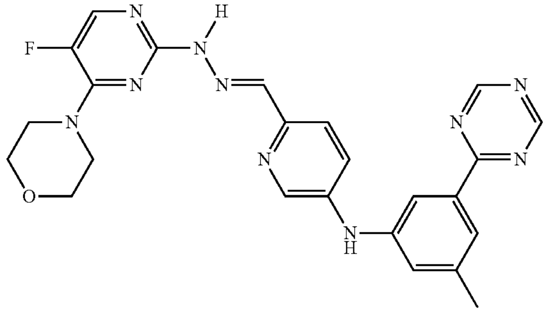
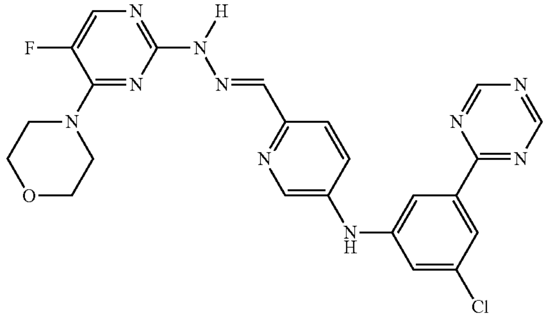
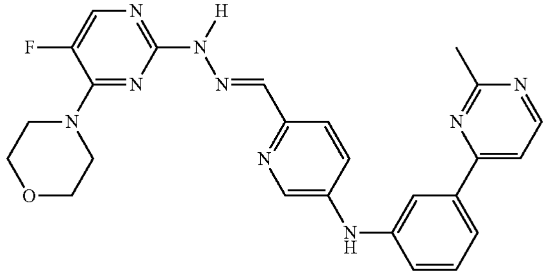
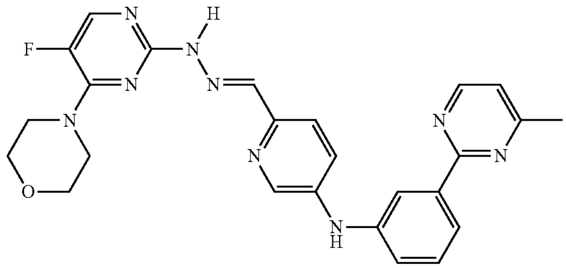

-continued
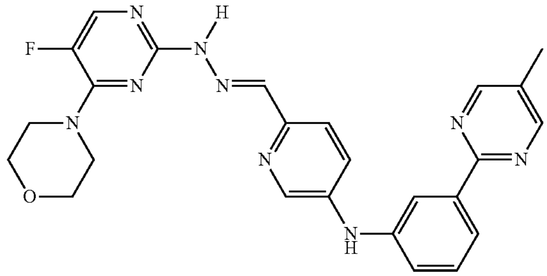
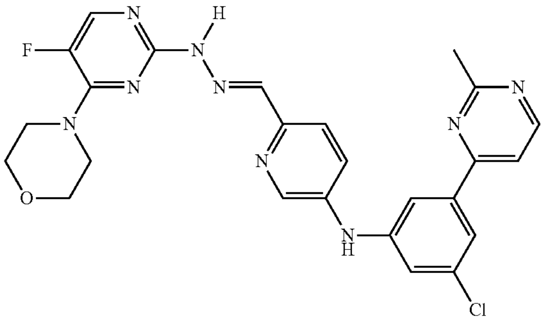
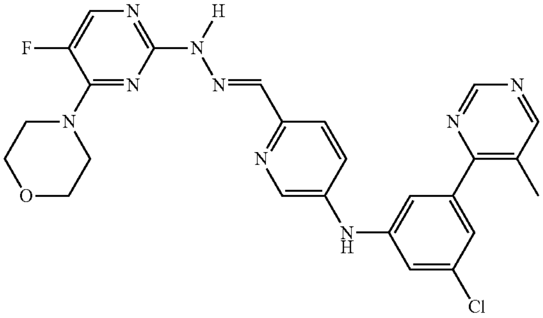
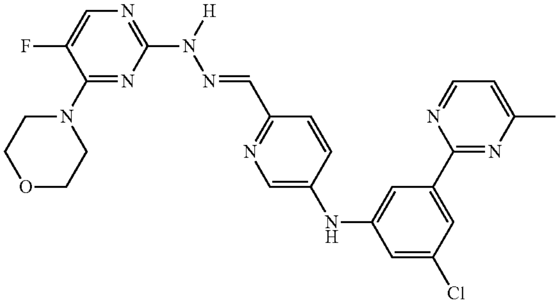
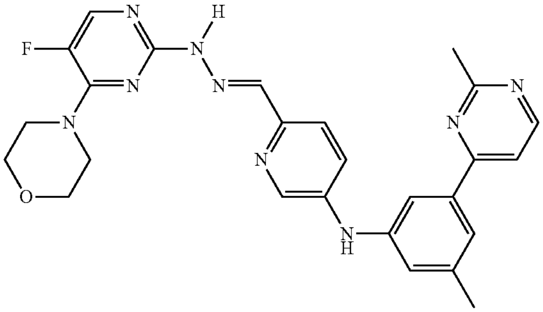
-continued
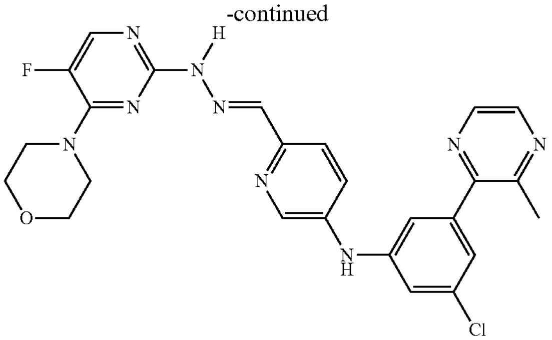
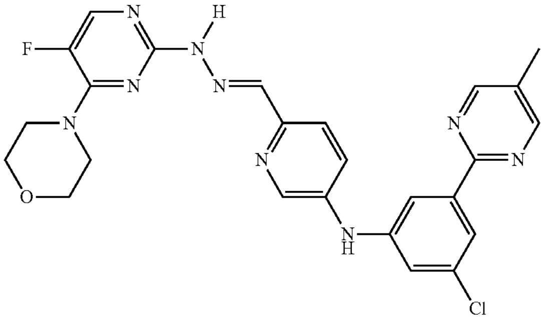
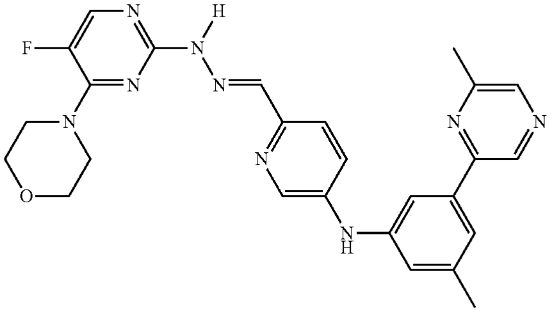
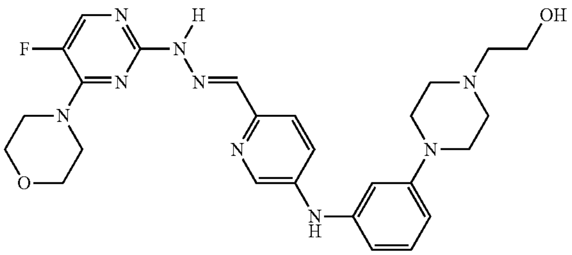
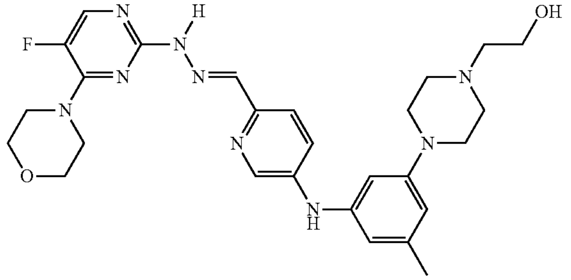

-continued
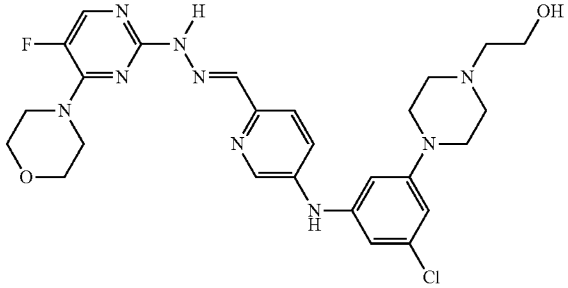
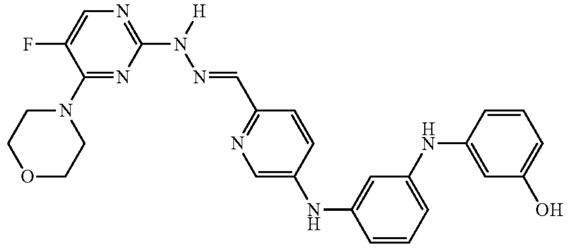
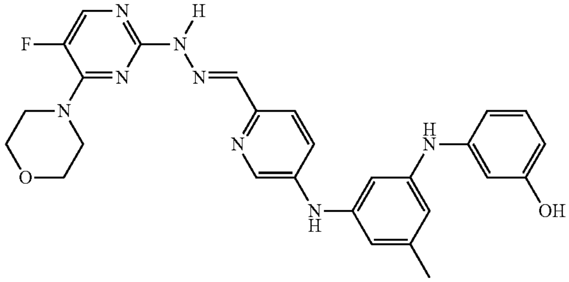
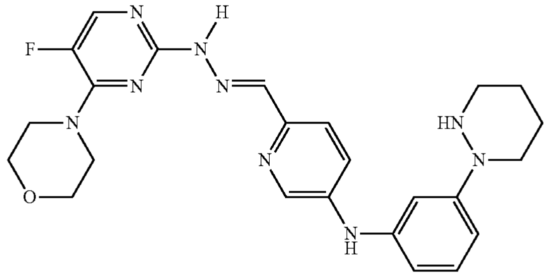
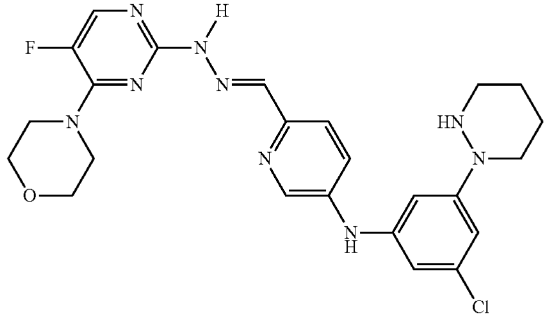
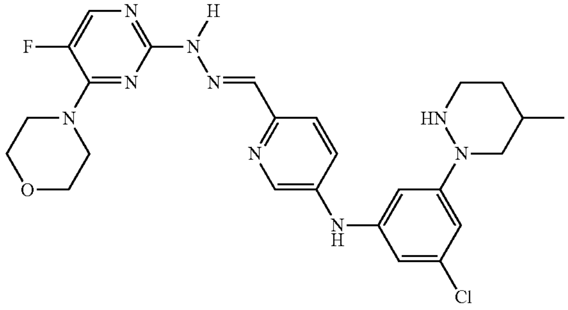
-continued
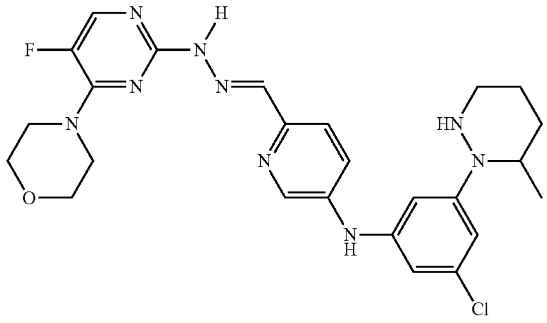
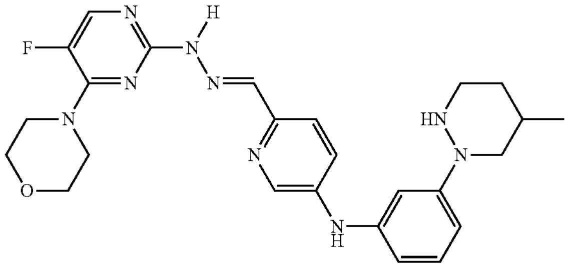
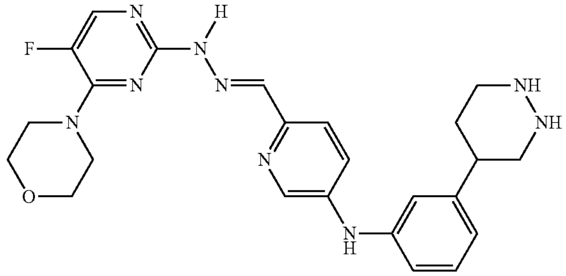
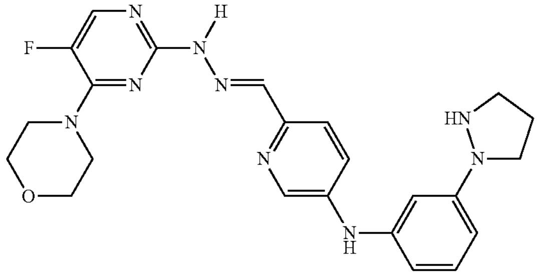
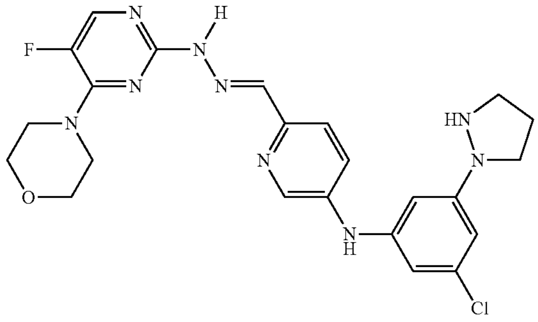

-continued
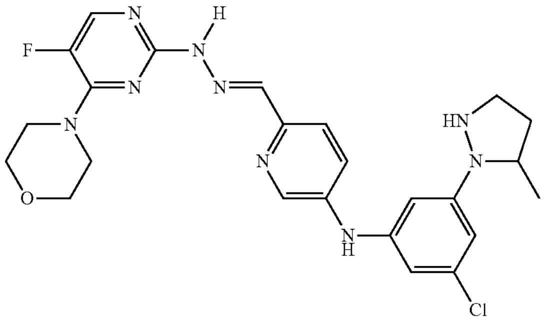
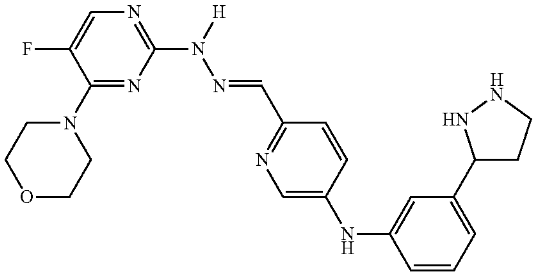
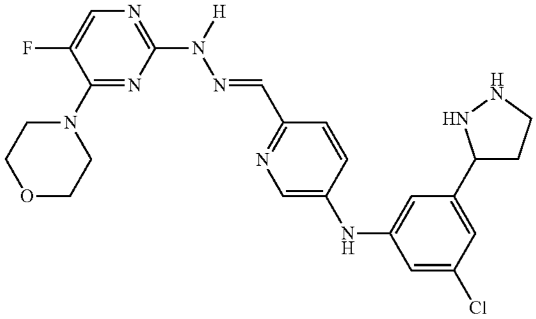
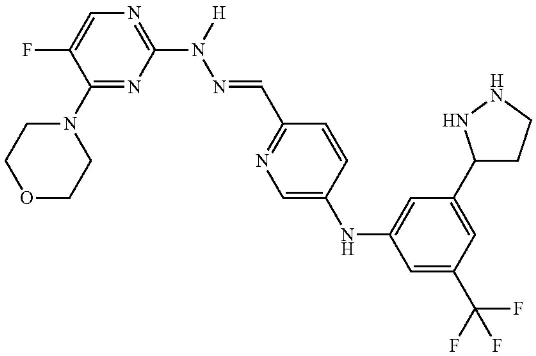
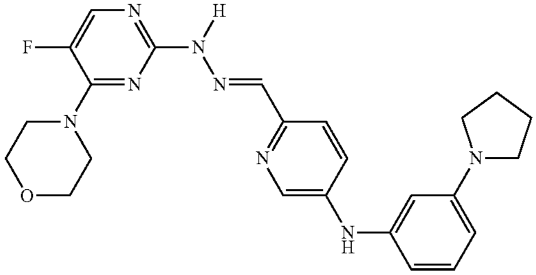
-continued
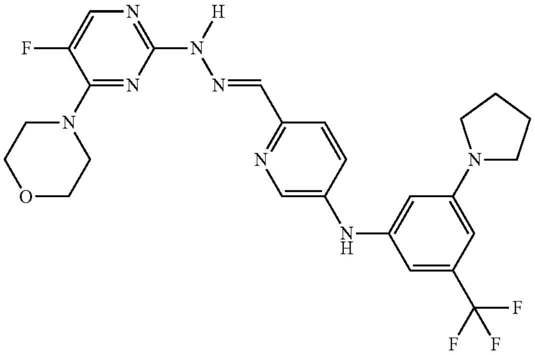
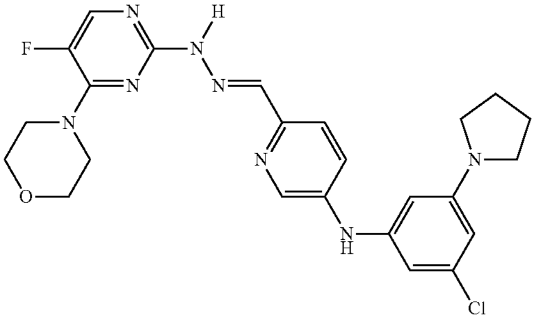
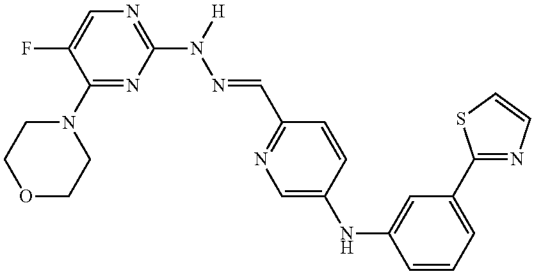
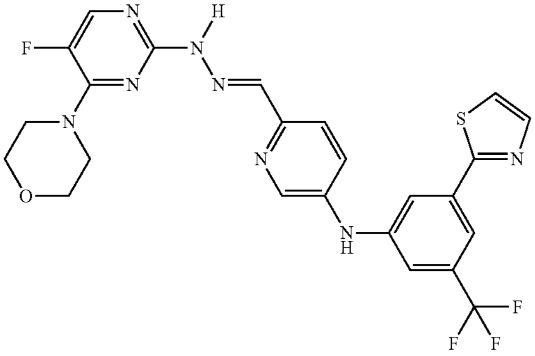
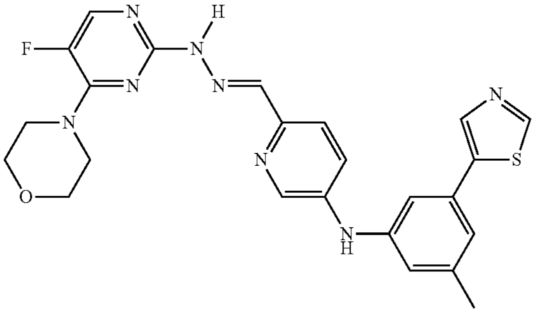

-continued
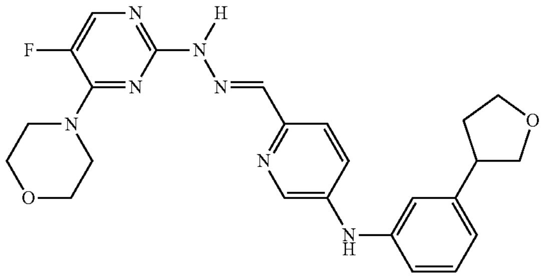
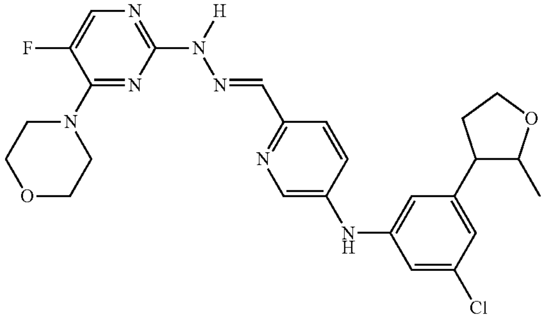
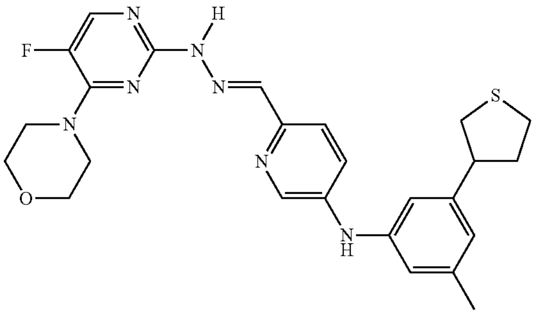
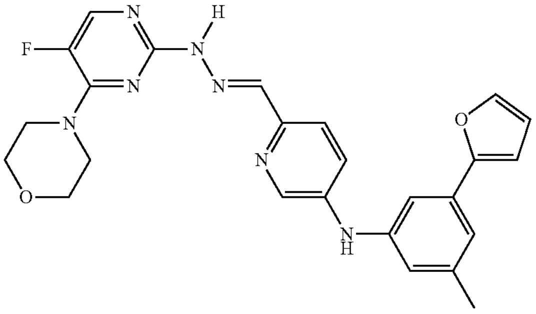
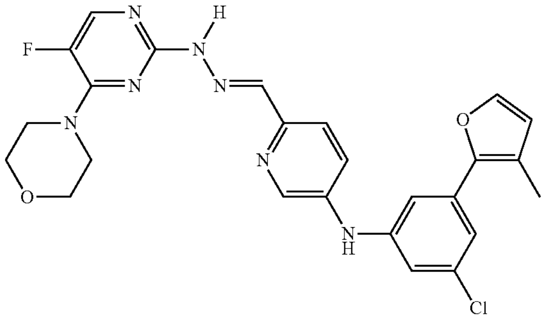
-continued
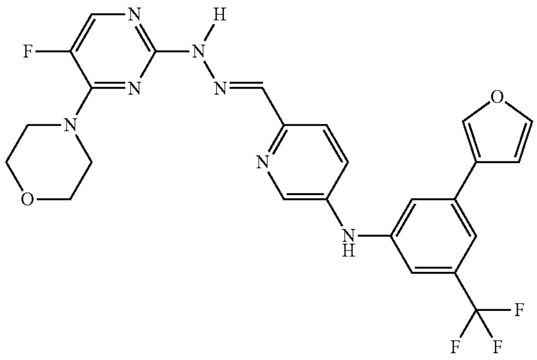
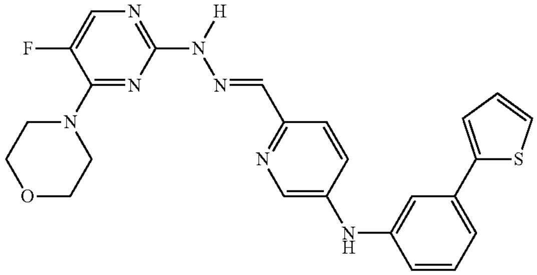
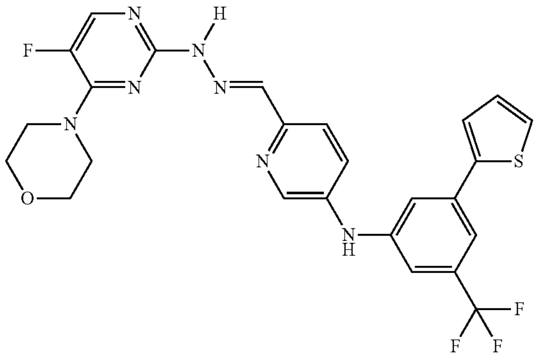
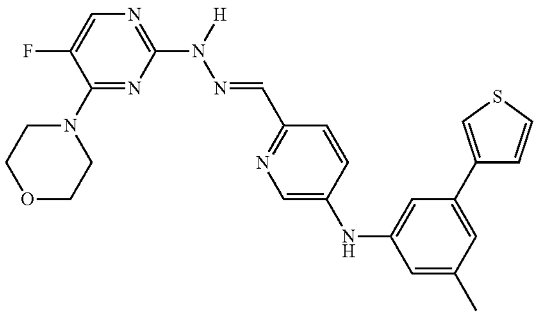
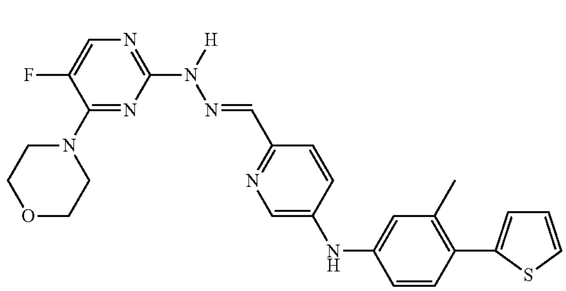

-continued
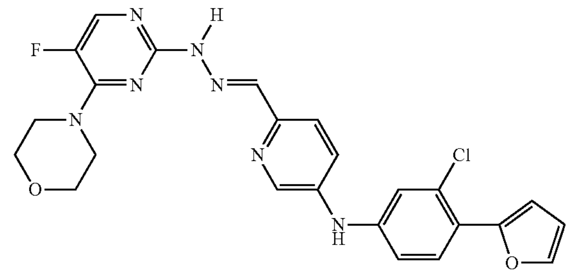
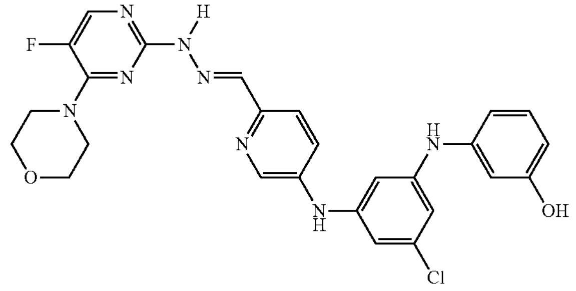
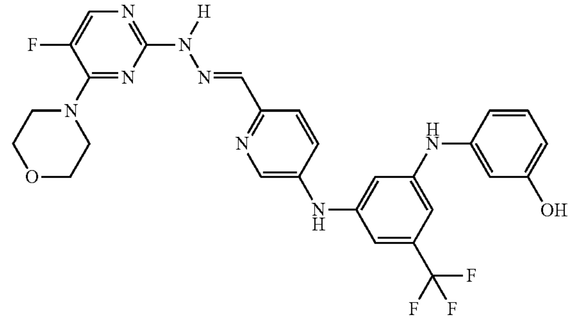
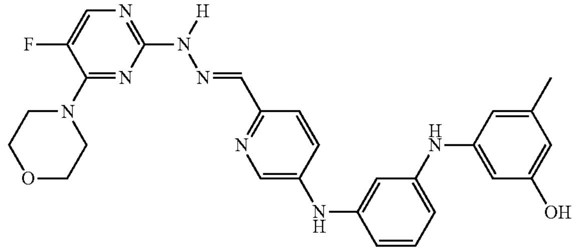
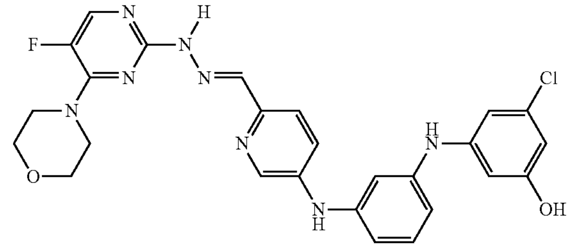
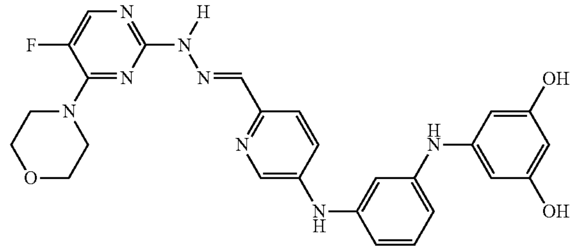
-continued
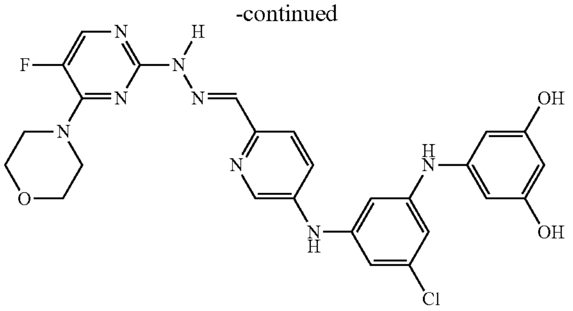
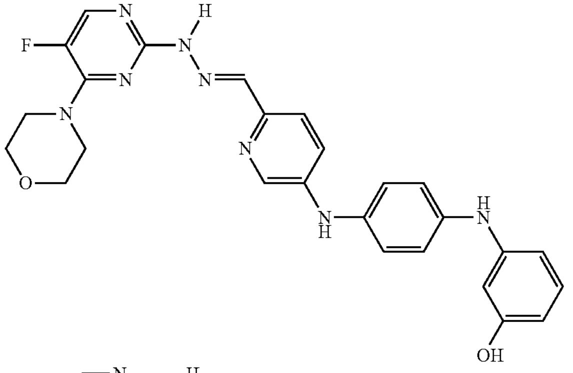
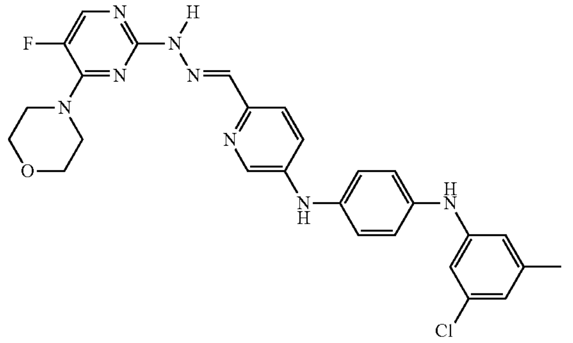
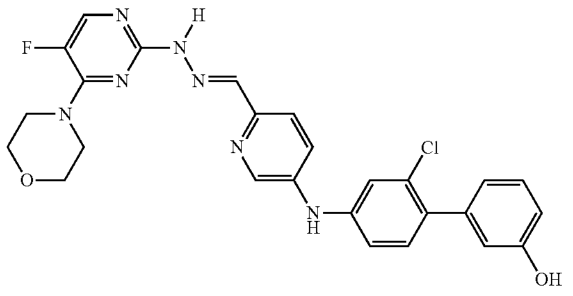
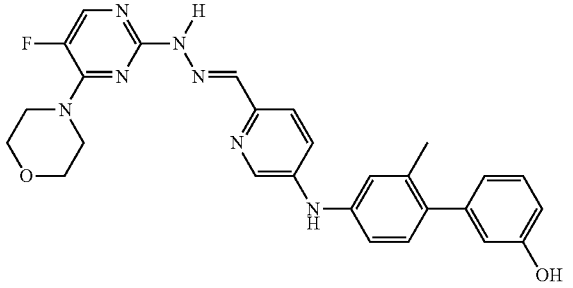

-continued
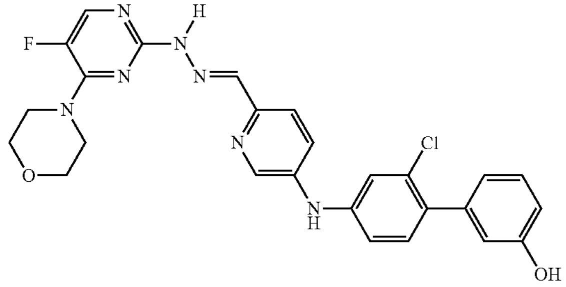
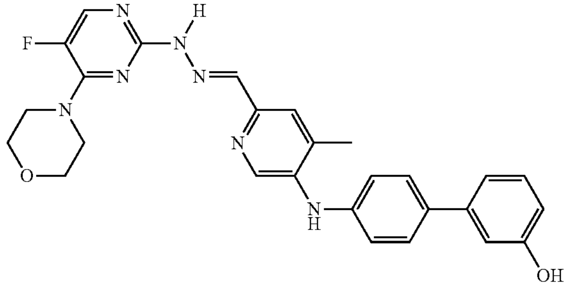
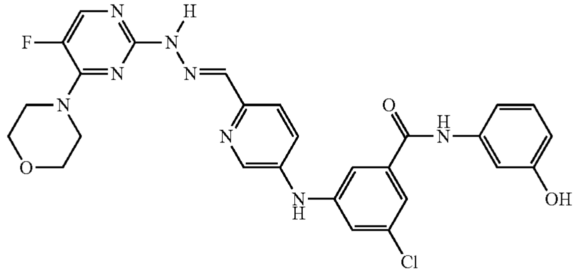
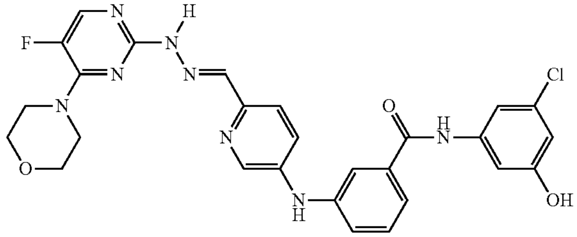
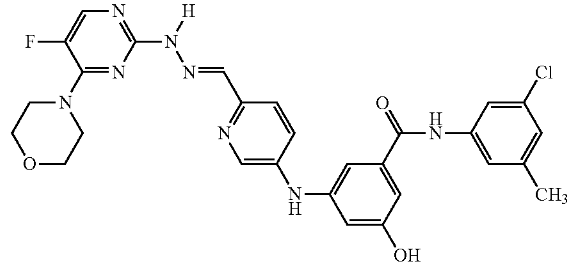
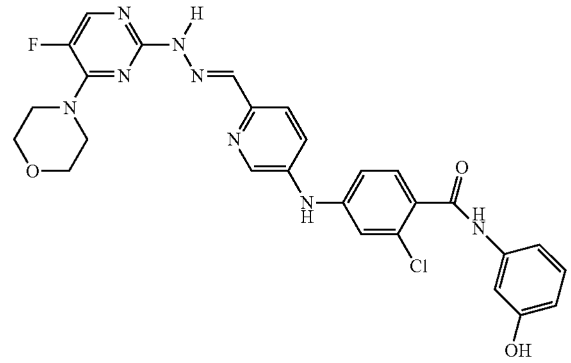
-continued
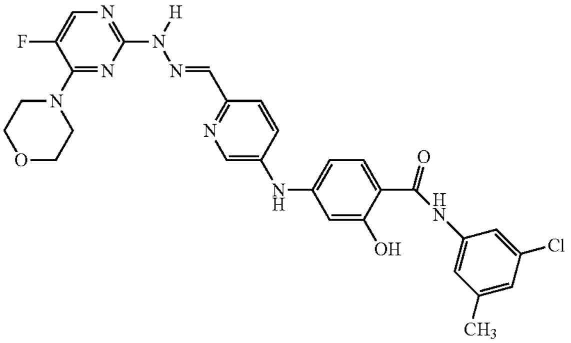
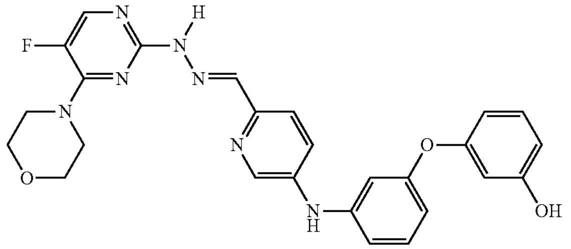
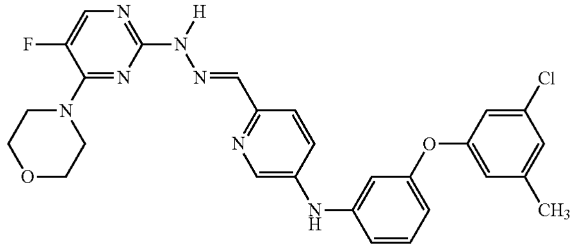
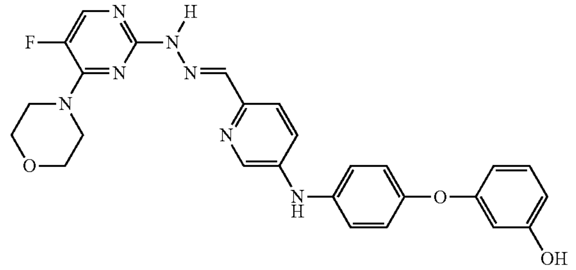
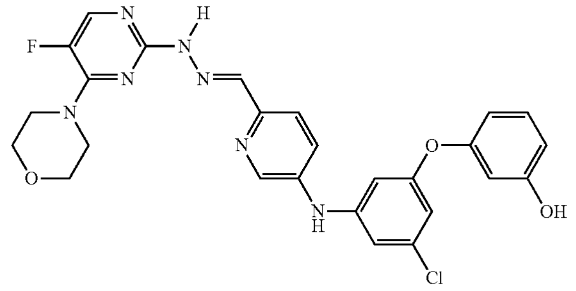
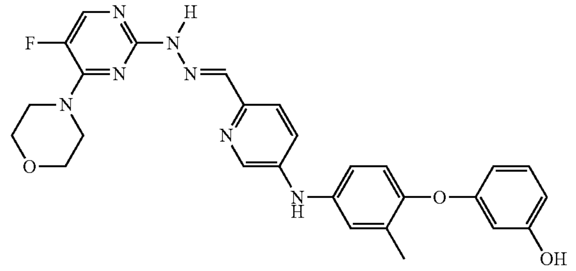

-continued
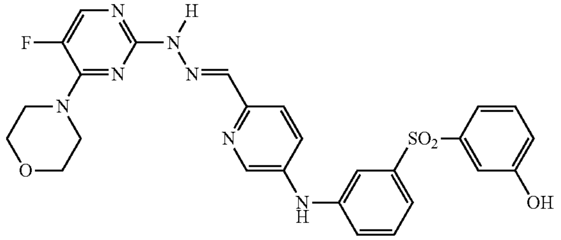
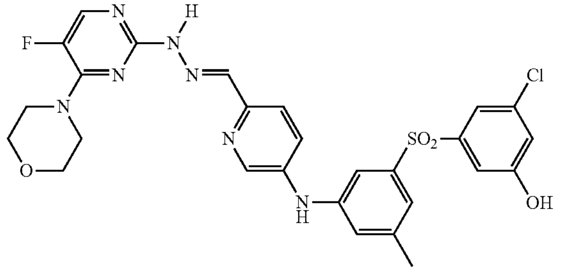
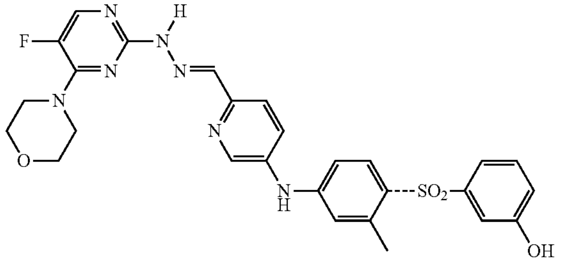
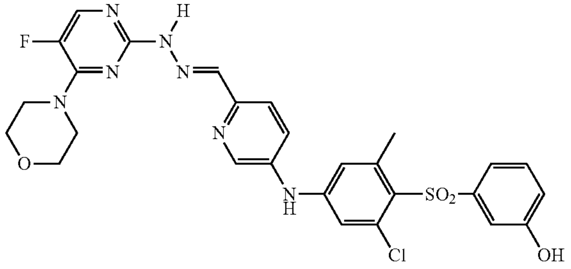
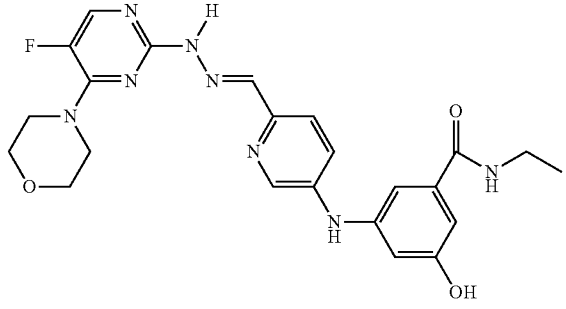
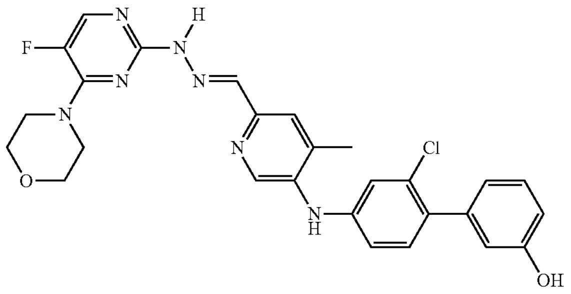
-continued
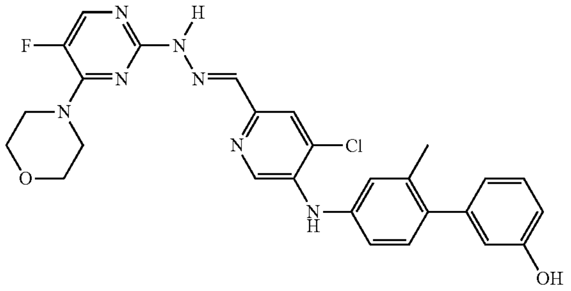
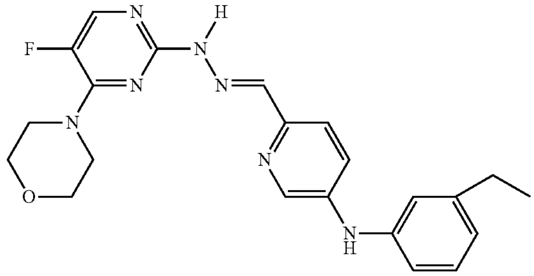
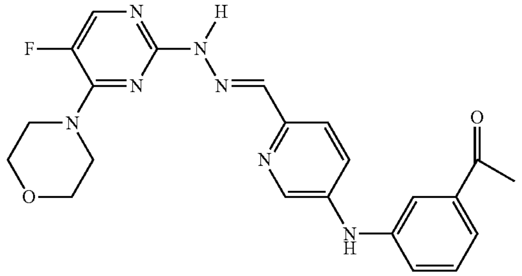
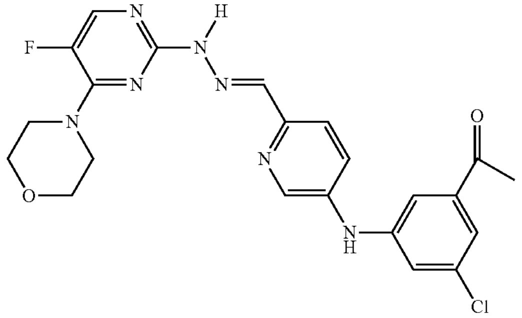
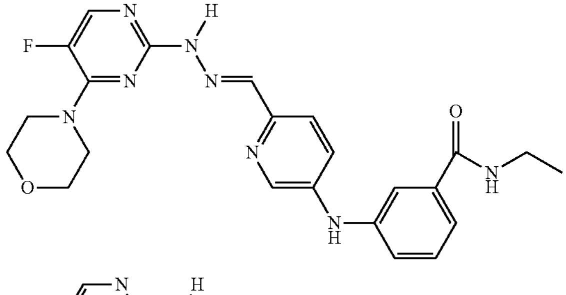
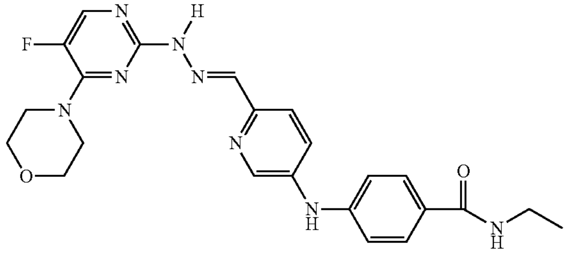

-continued
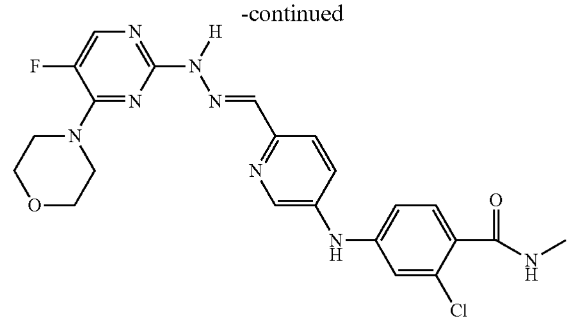
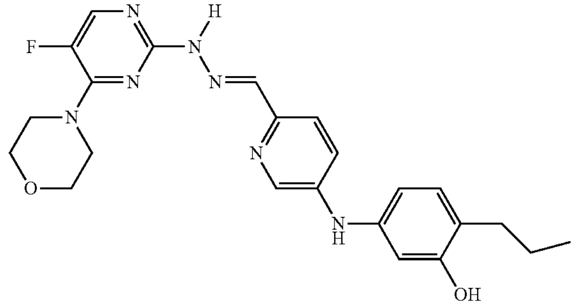
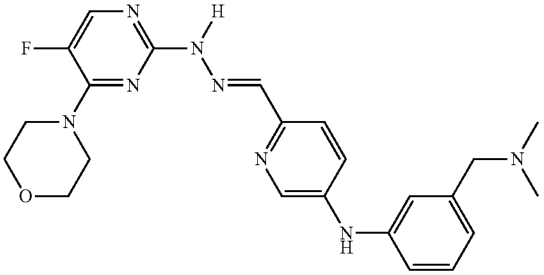
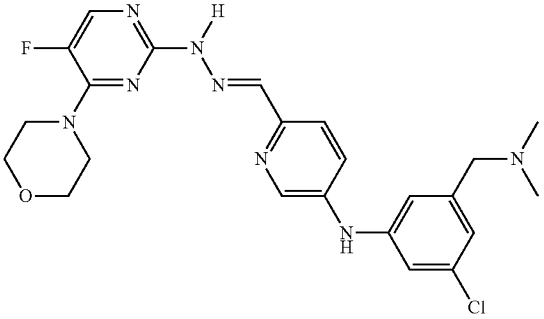
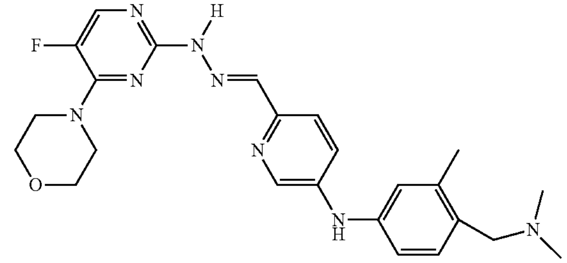
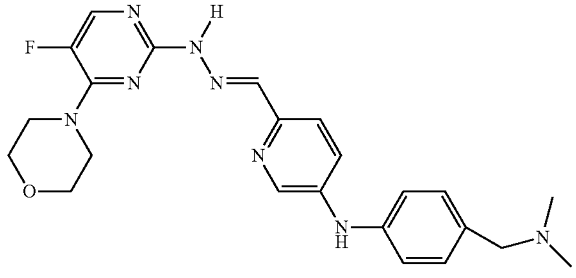
-continued
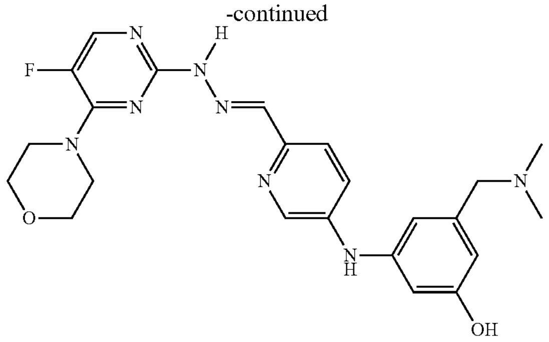
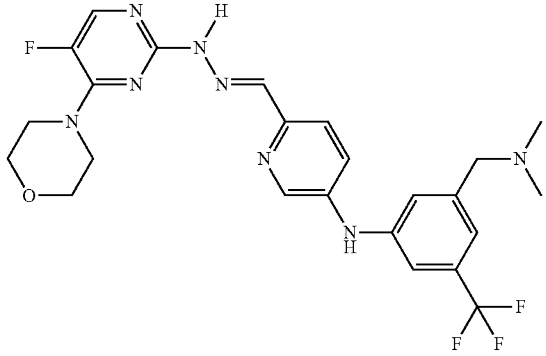
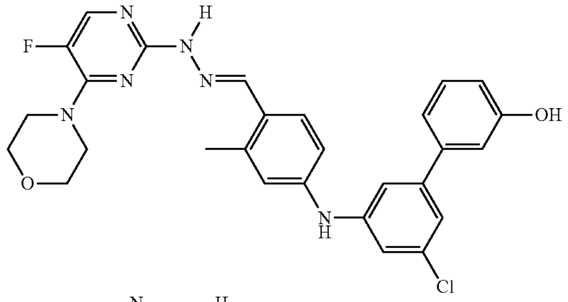
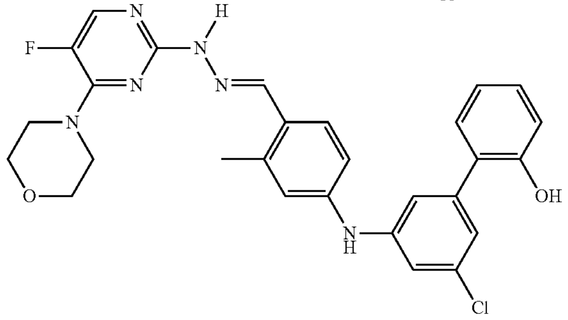
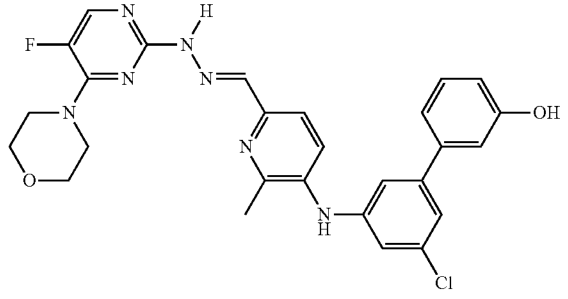

-continued
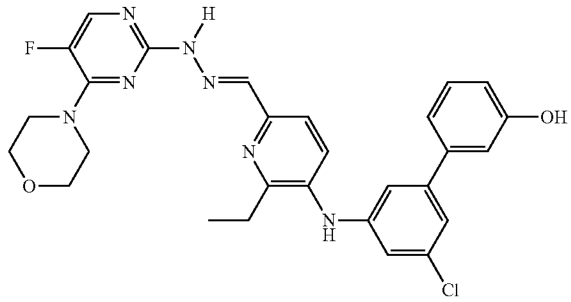
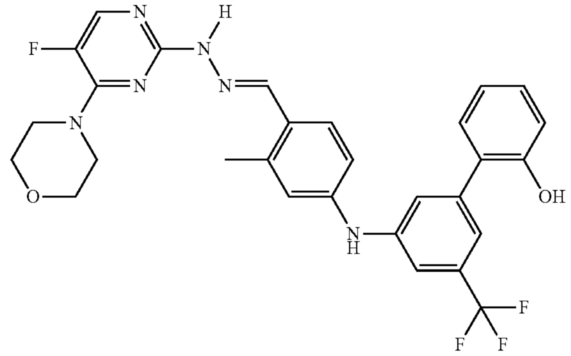
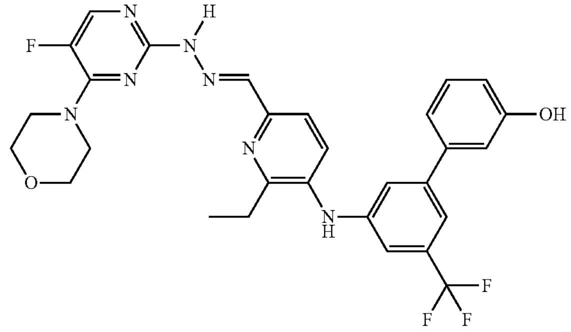
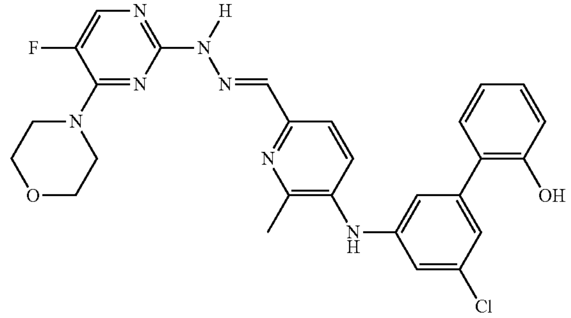
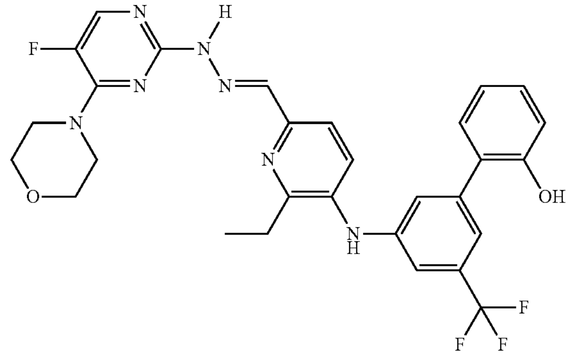
-continued
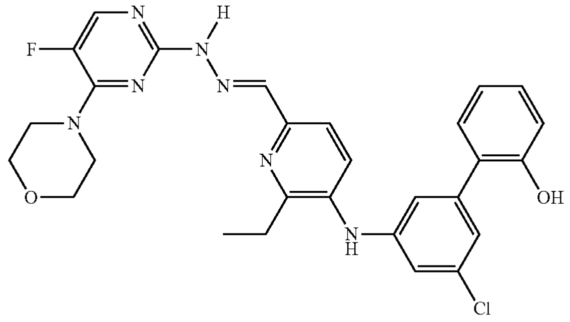
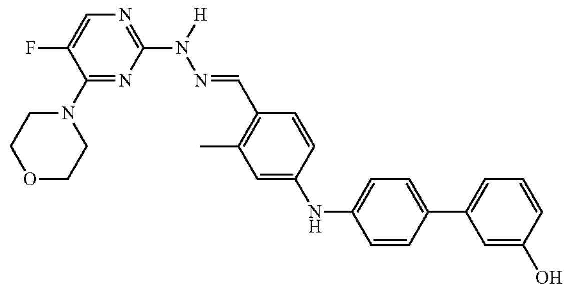
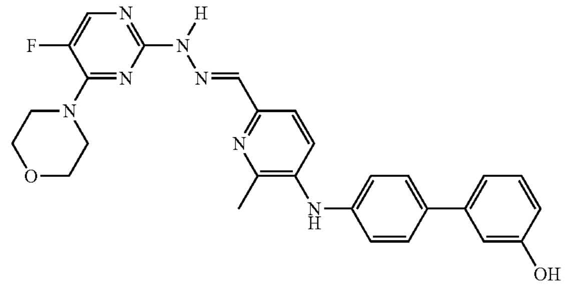
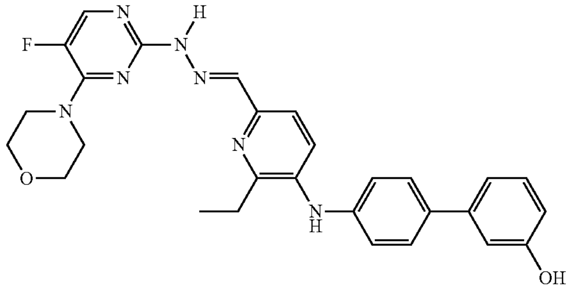
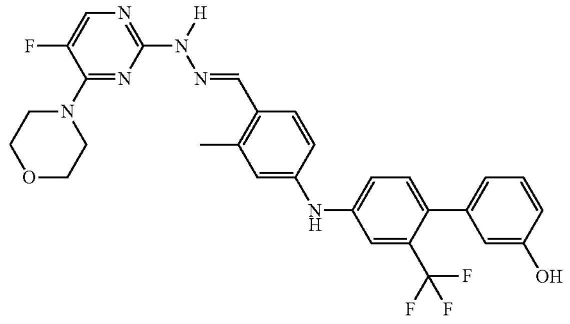

-continued
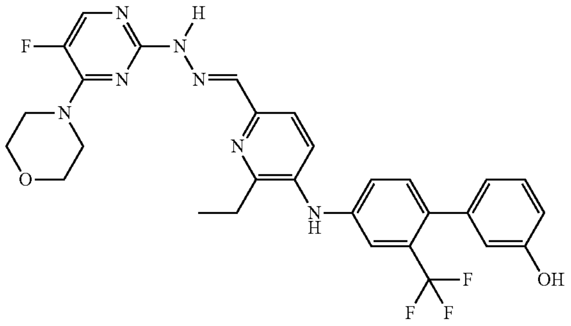
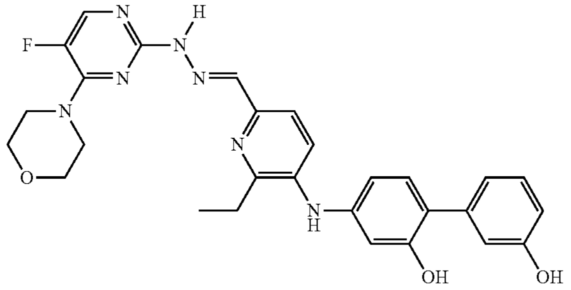
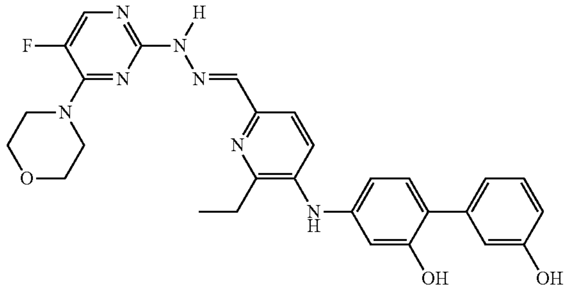
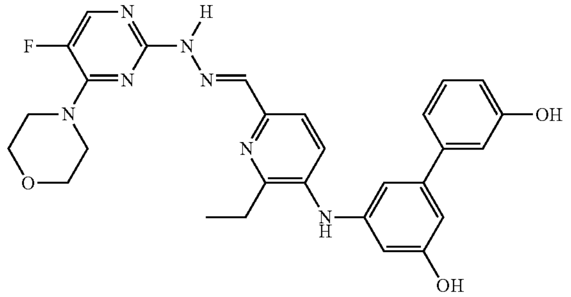
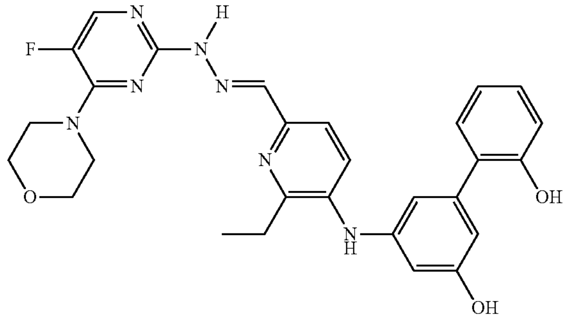
-continued
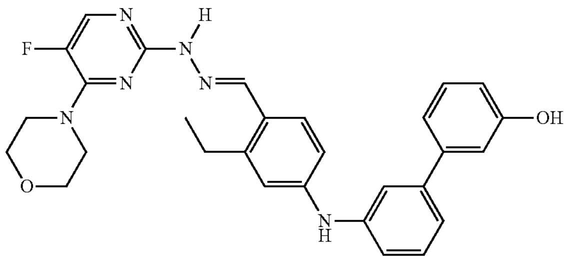
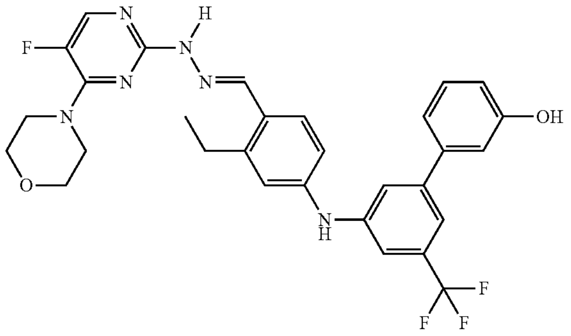
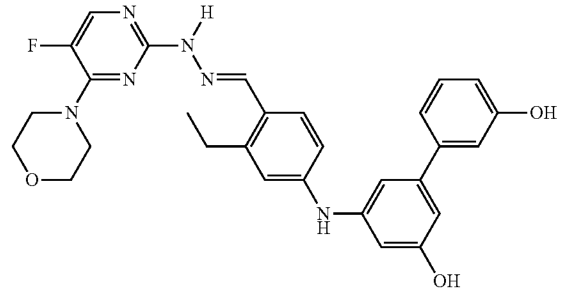
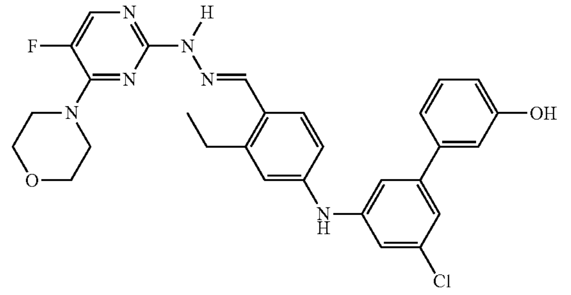
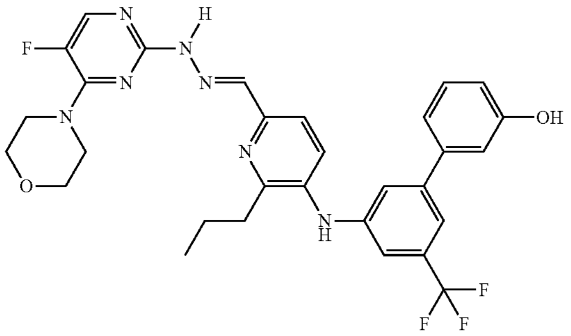

-continued
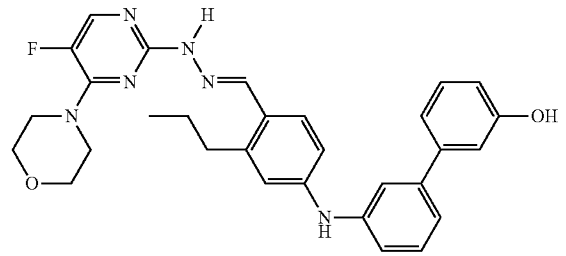
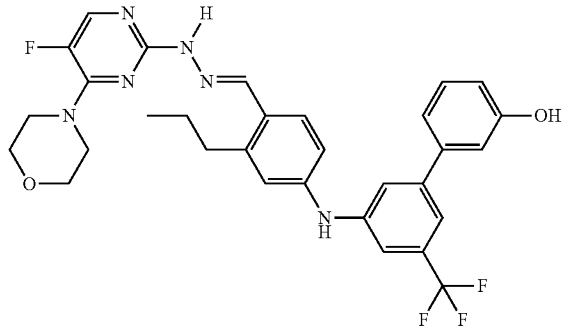
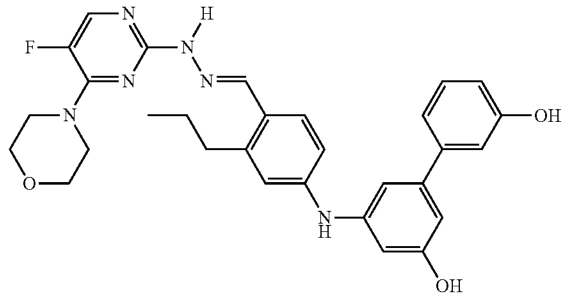
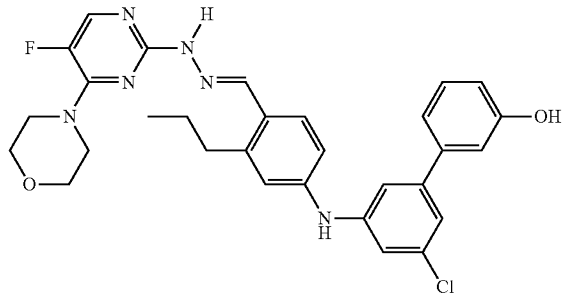
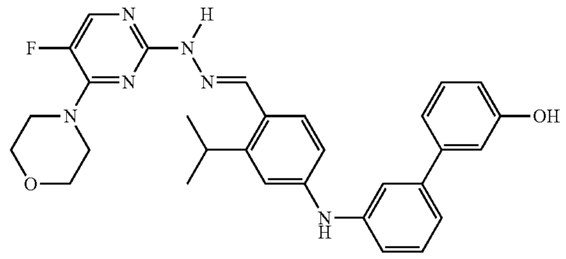
-continued
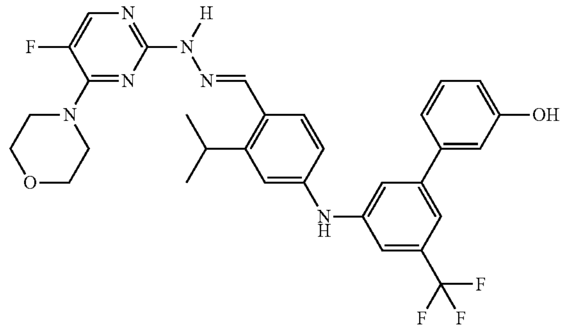
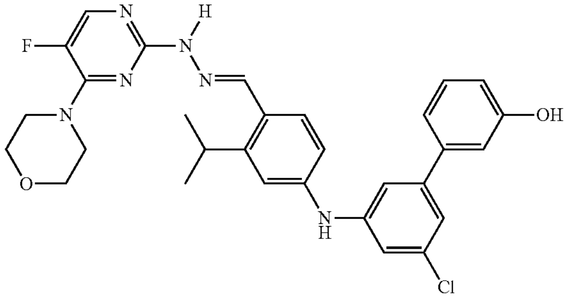
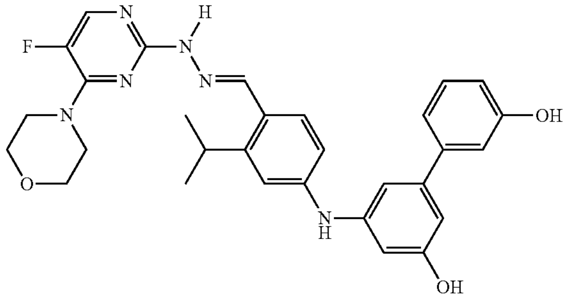
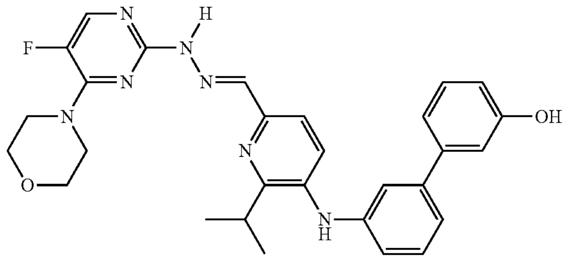
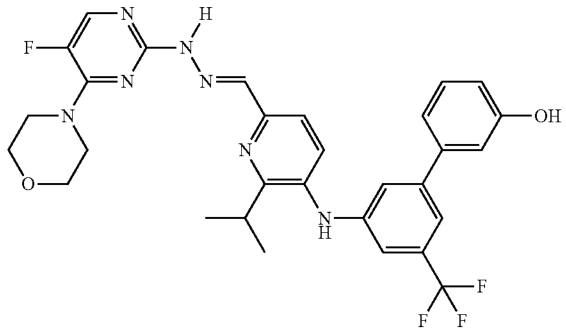

-continued
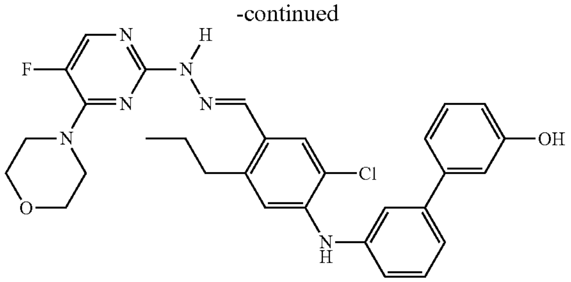
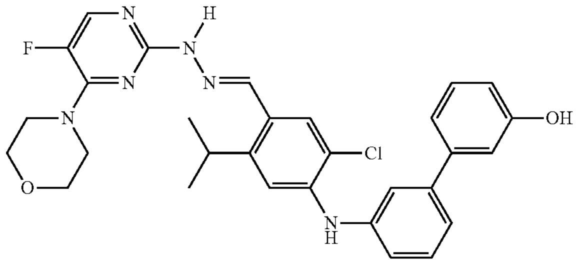
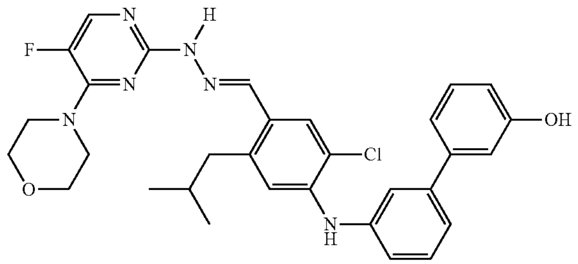
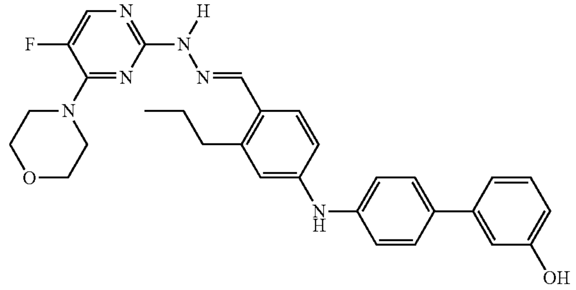
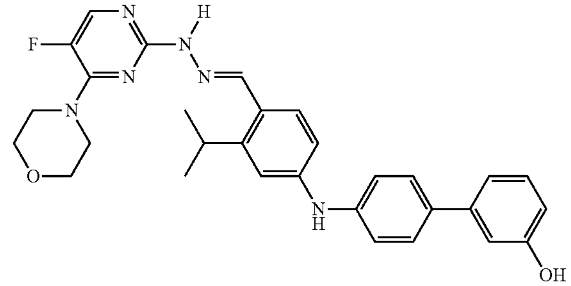
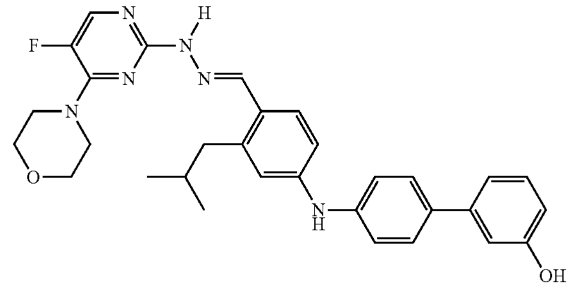

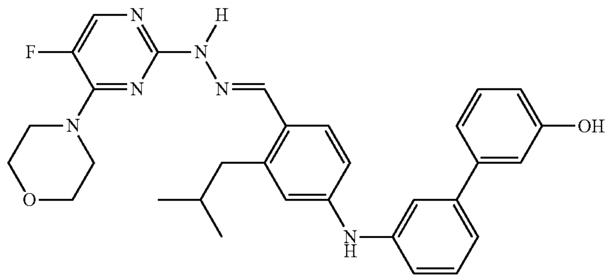
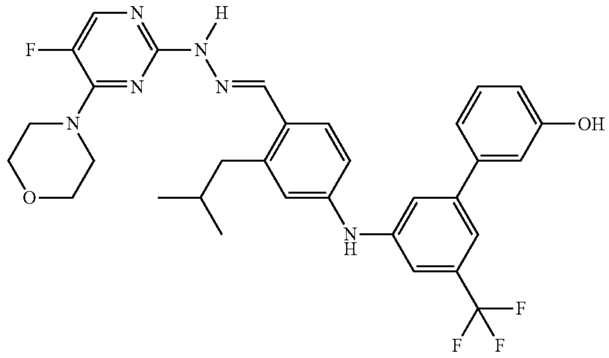
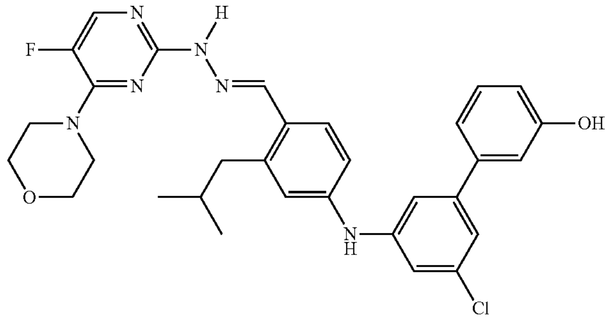
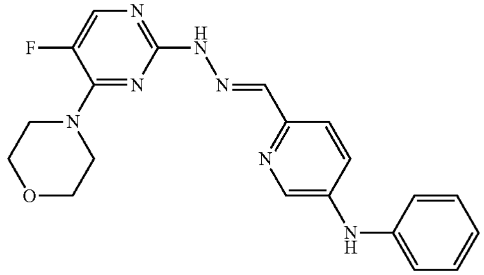
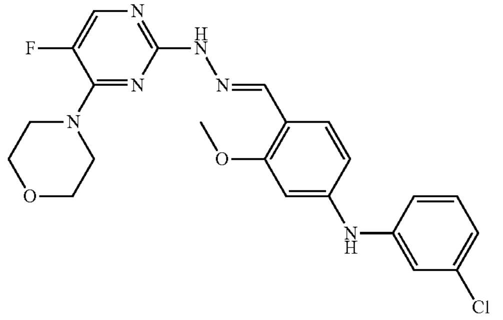
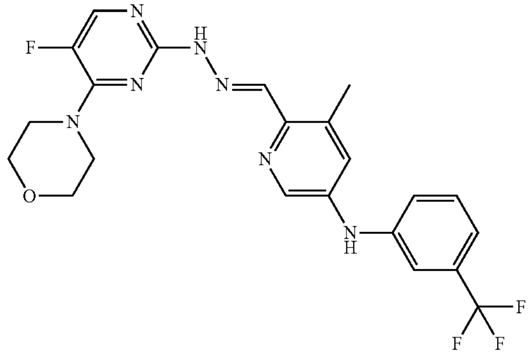
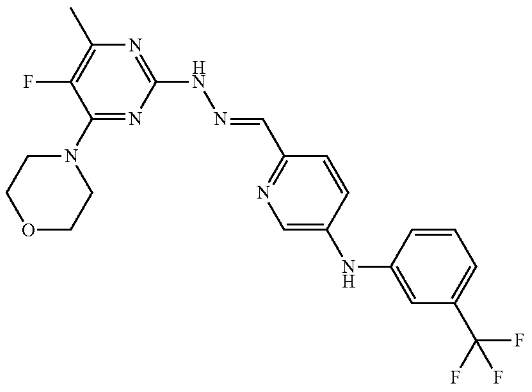

-continued
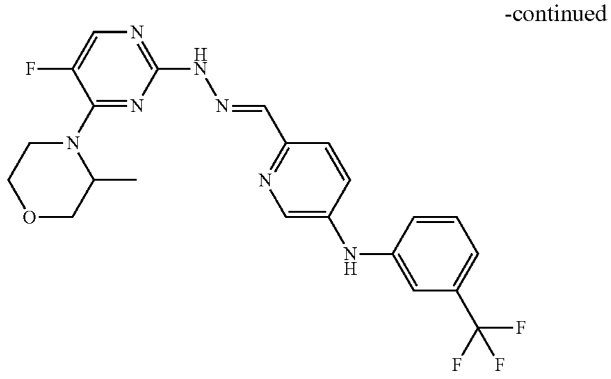
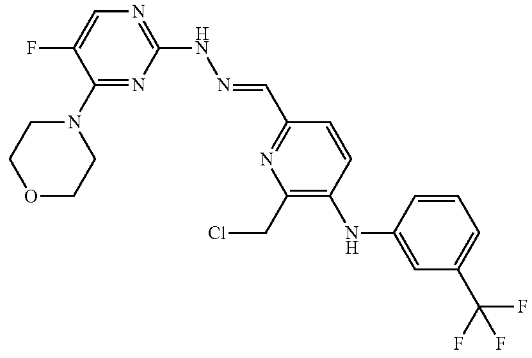
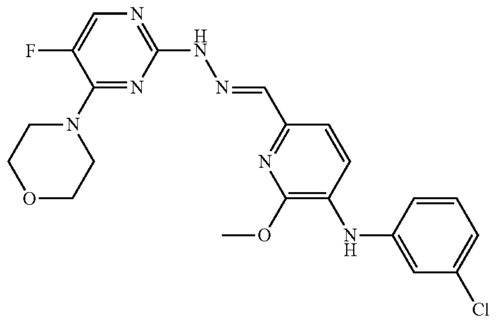
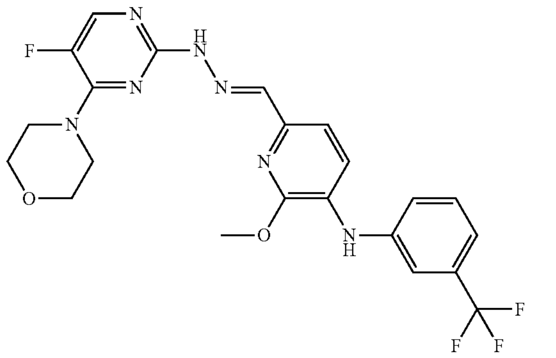
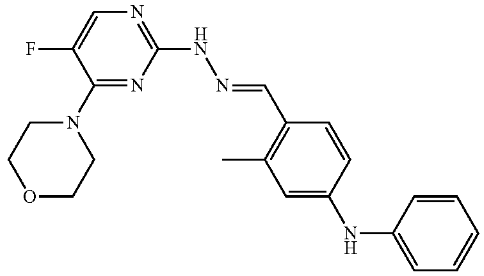
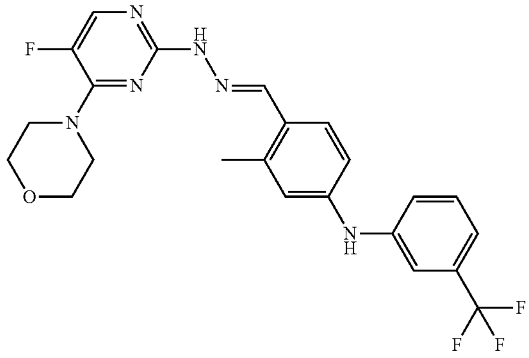
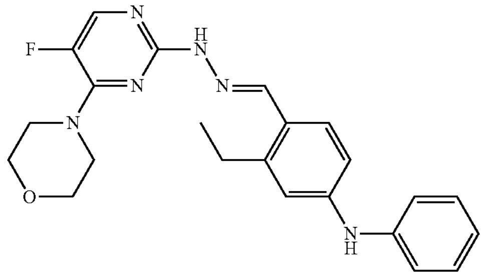
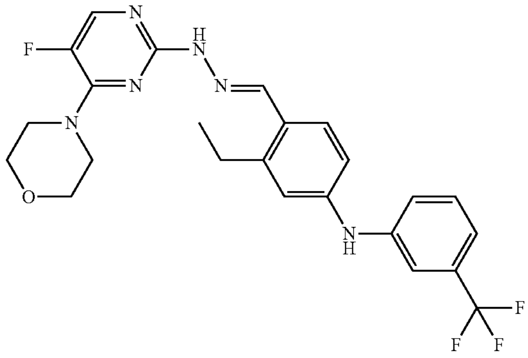

-continued
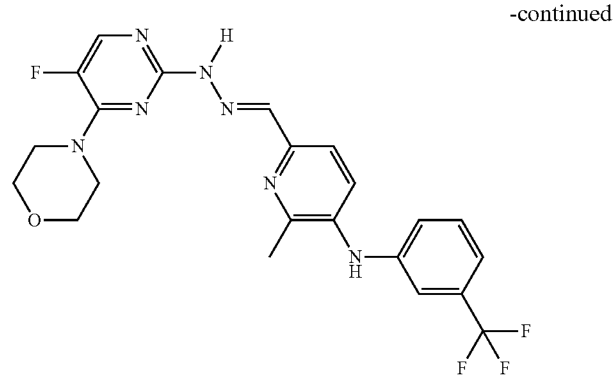
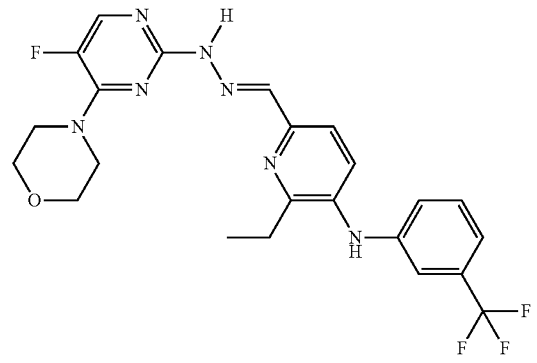
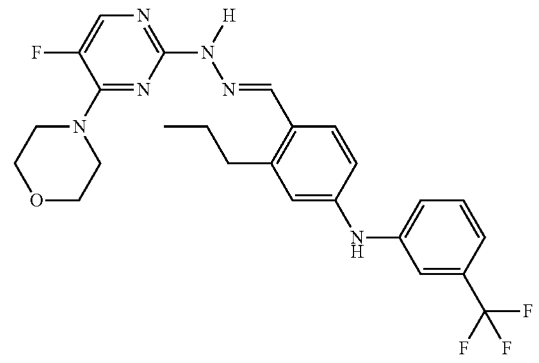
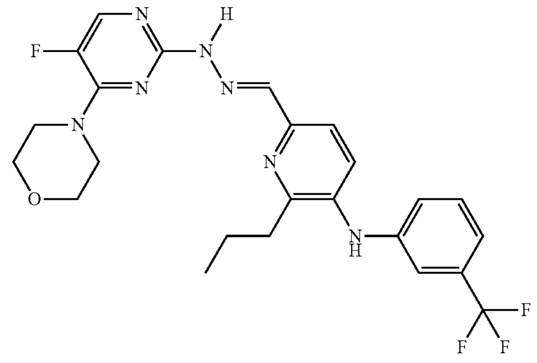
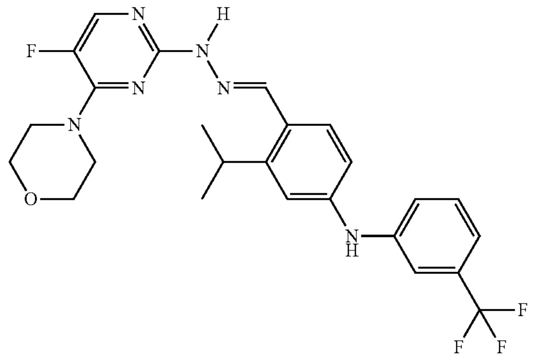
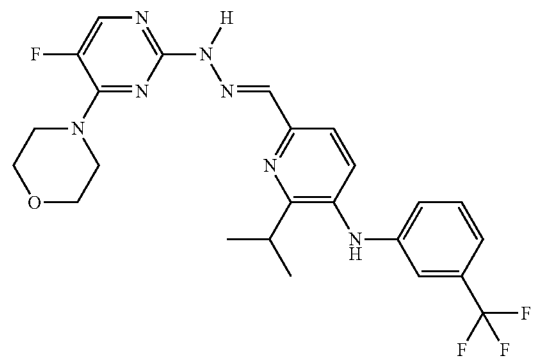
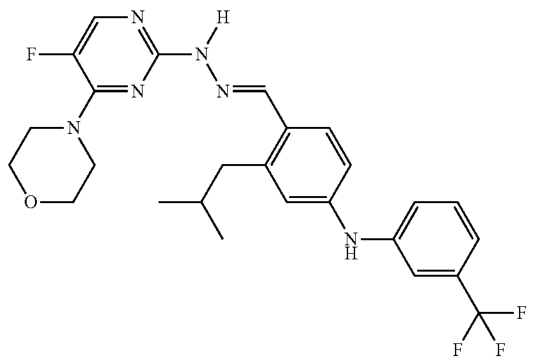

-continued
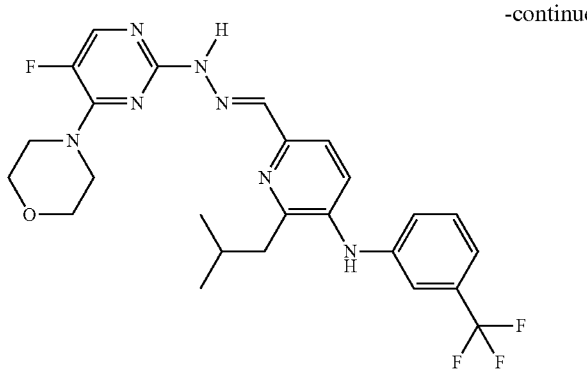
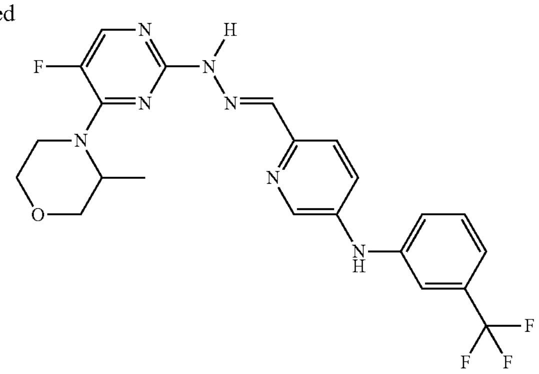
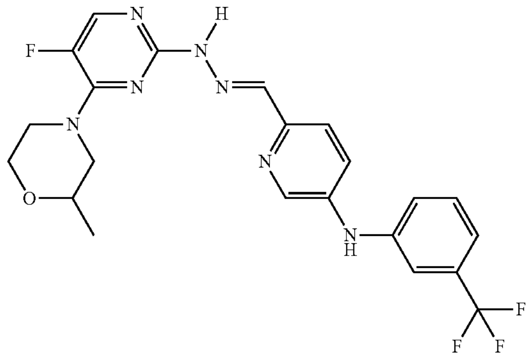
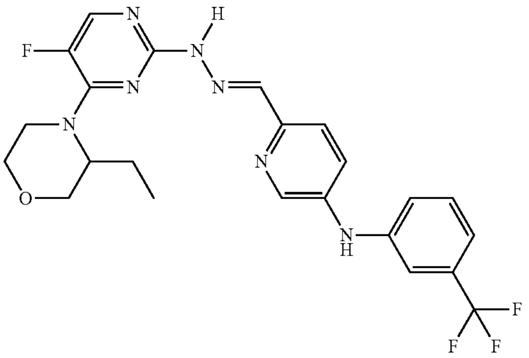
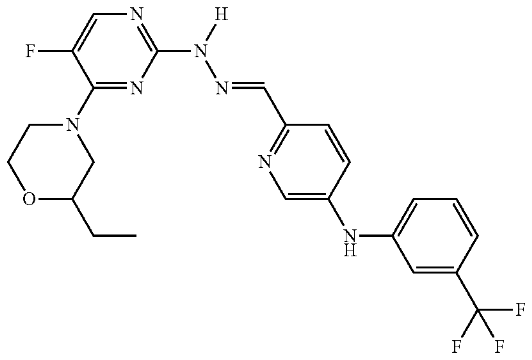
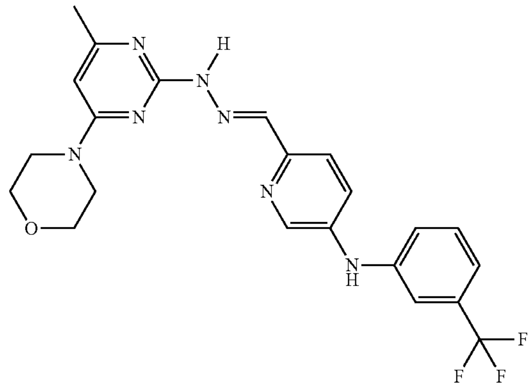
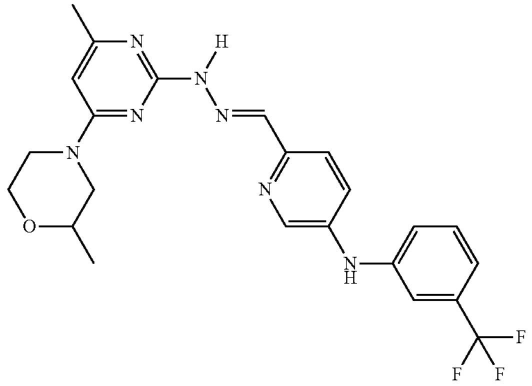
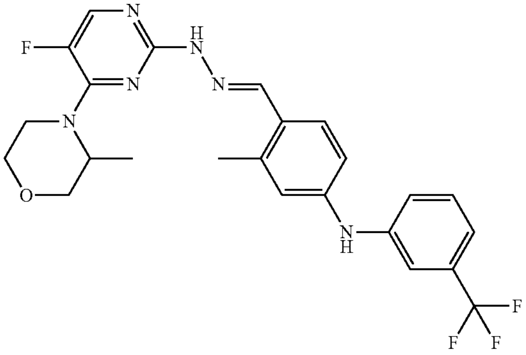

-continued
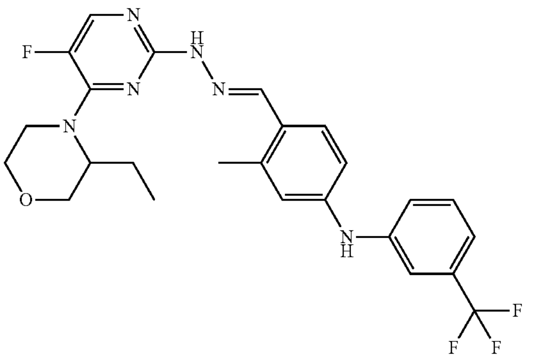
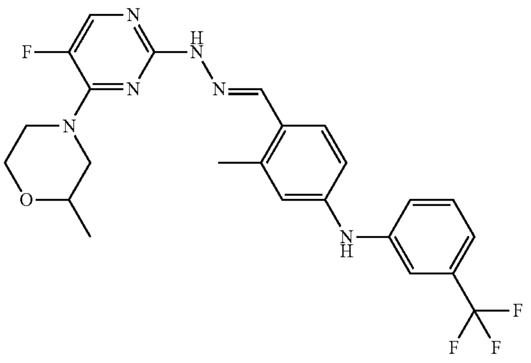
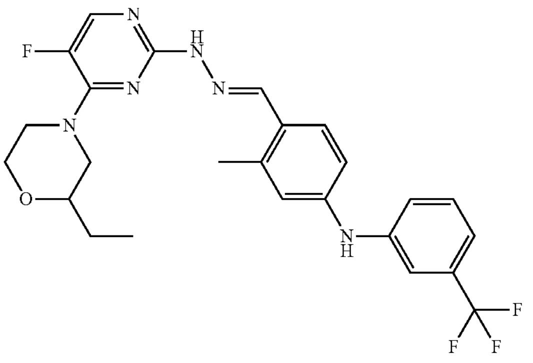
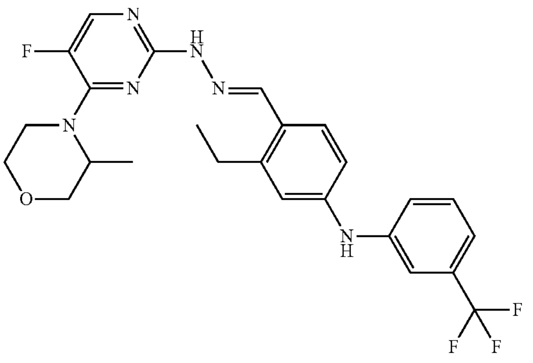
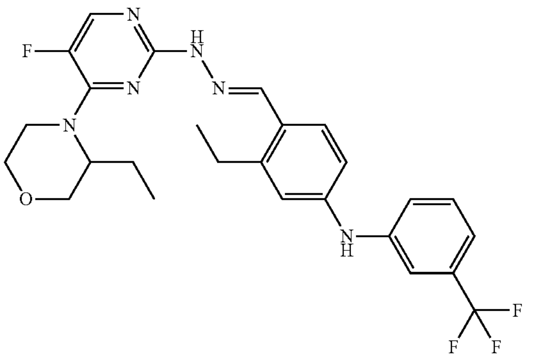
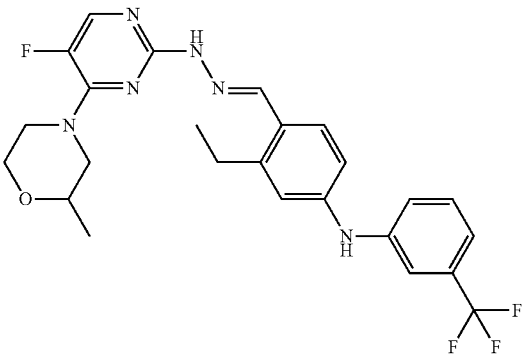
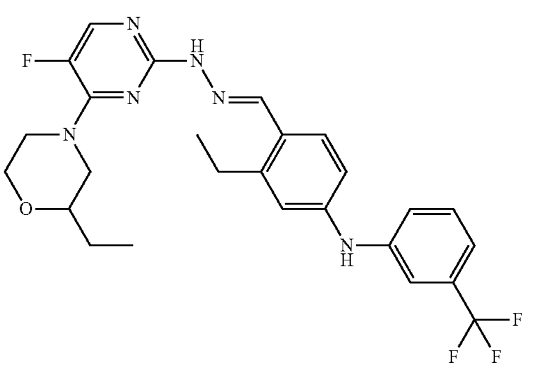
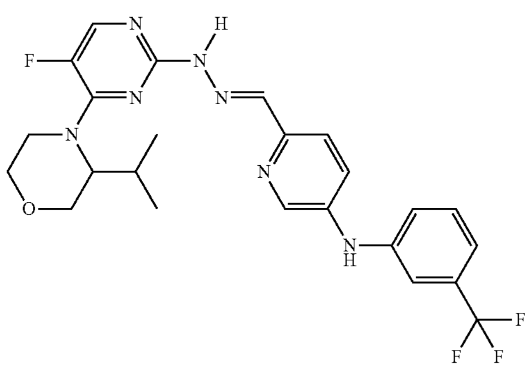

-continued
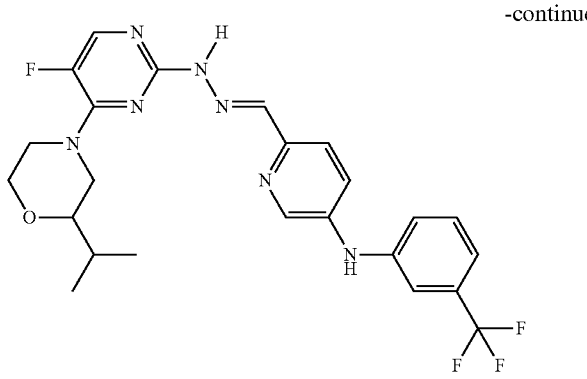
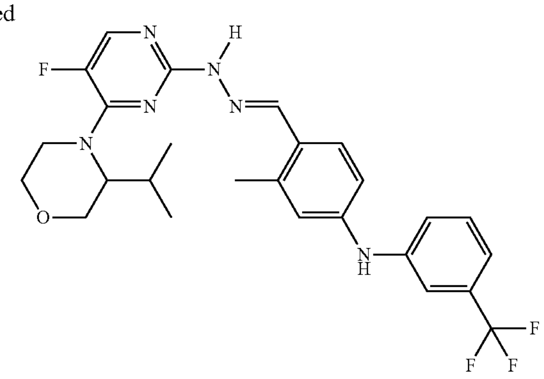
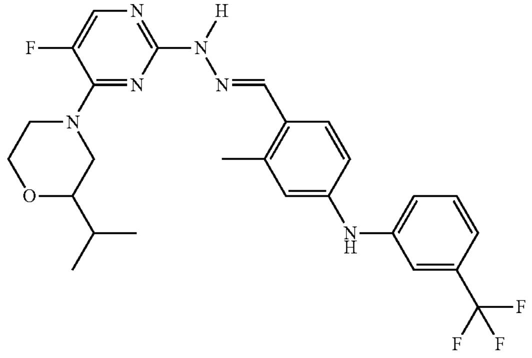
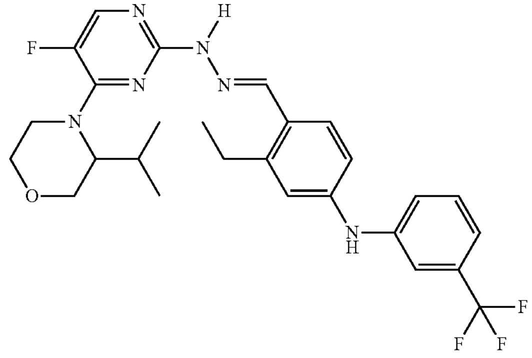
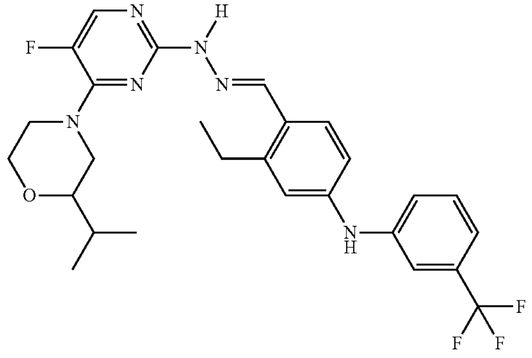
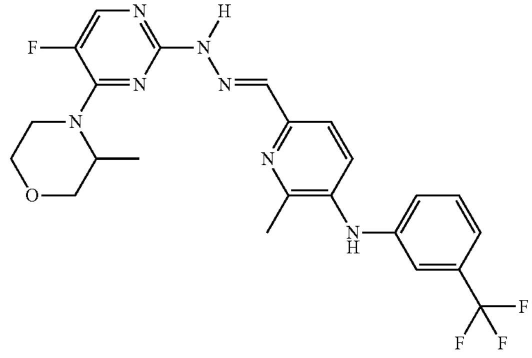
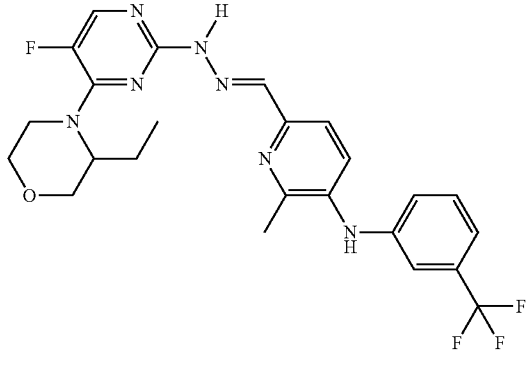
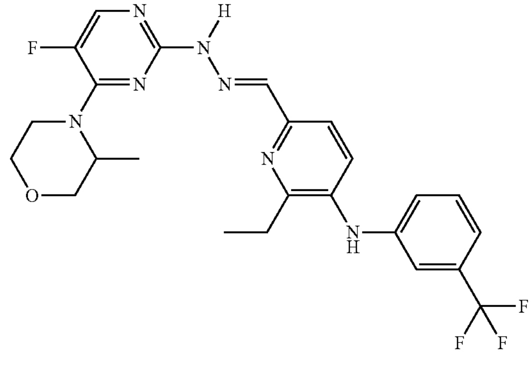

-continued
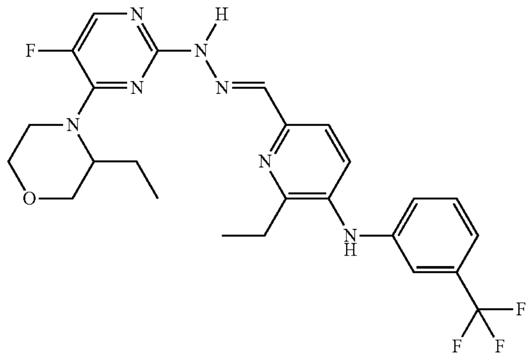
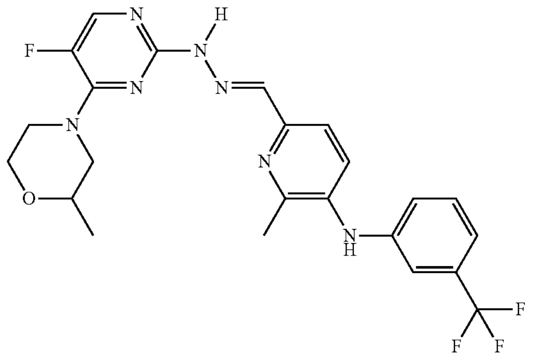
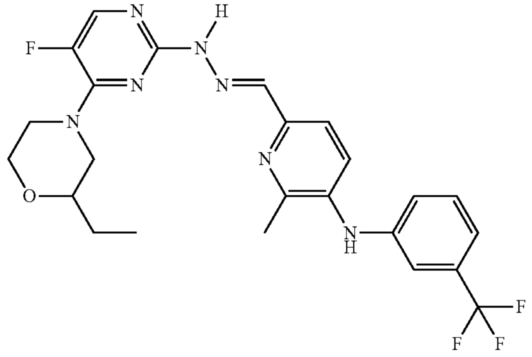
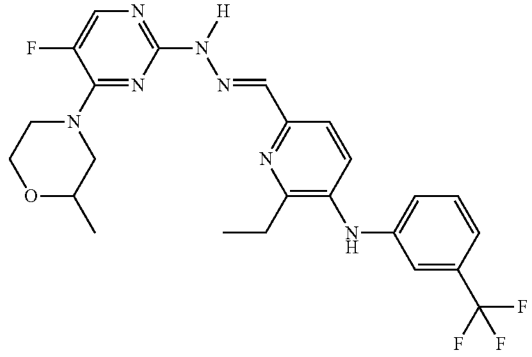
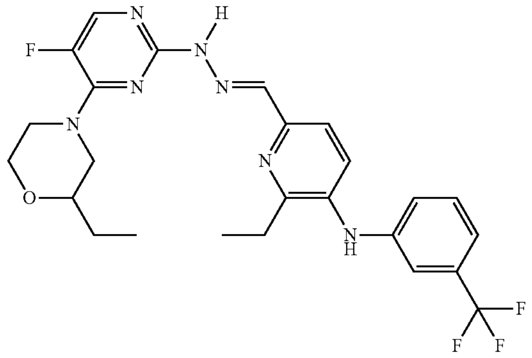
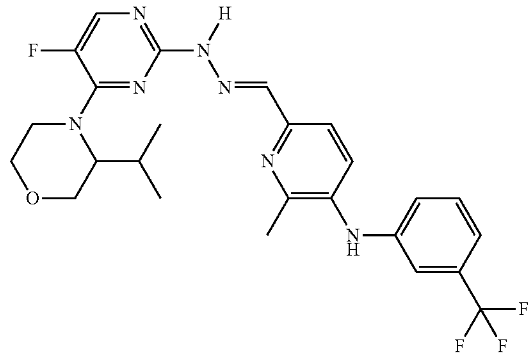
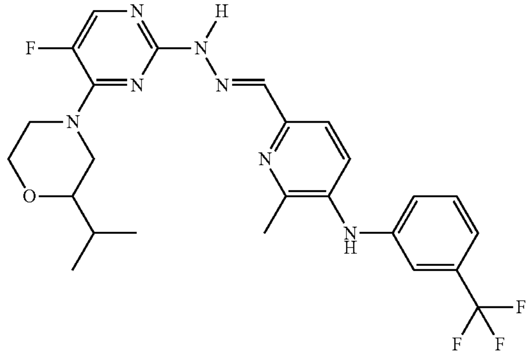
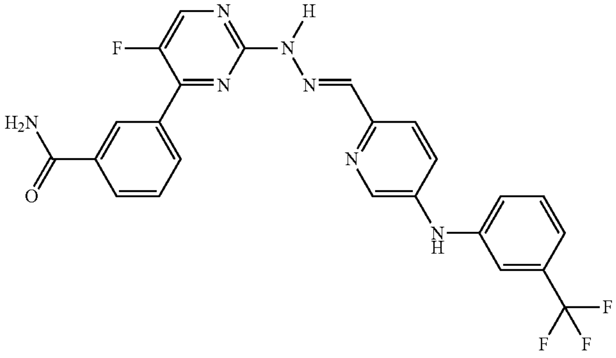

-continued
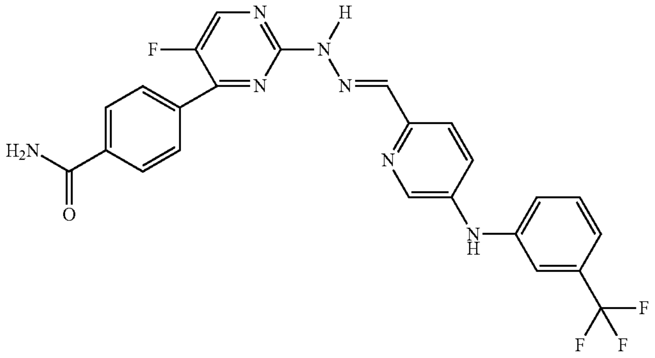
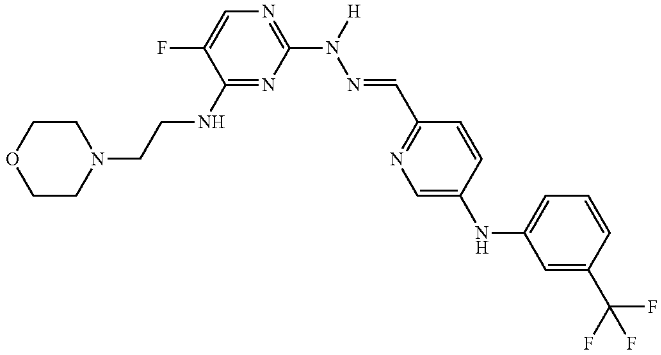
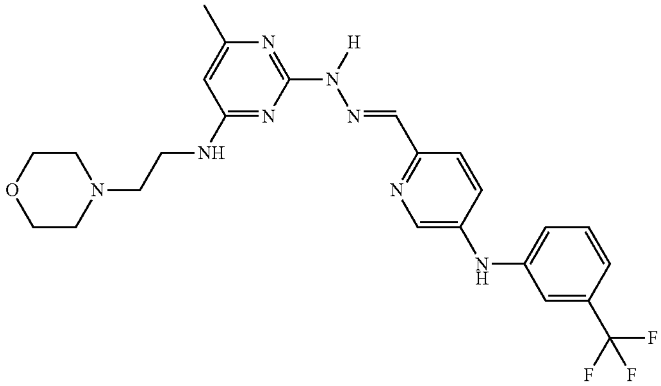
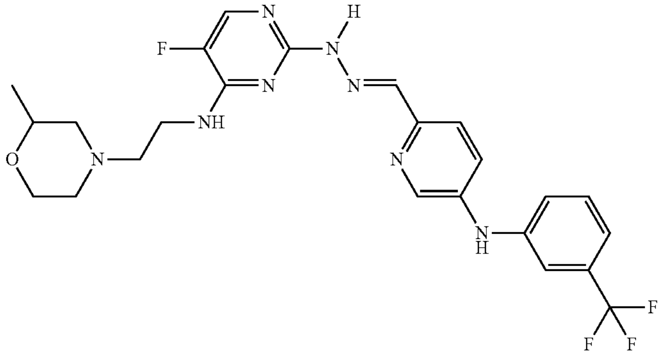

-continued
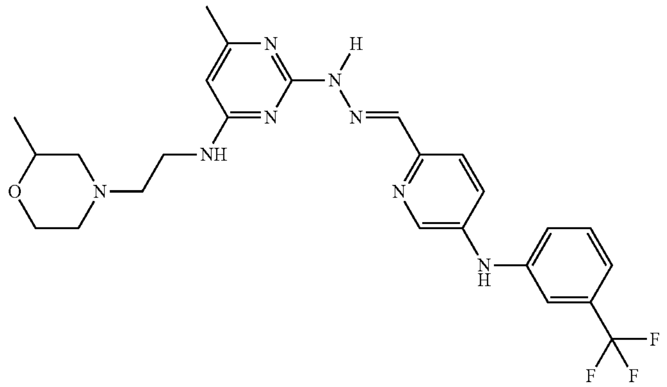
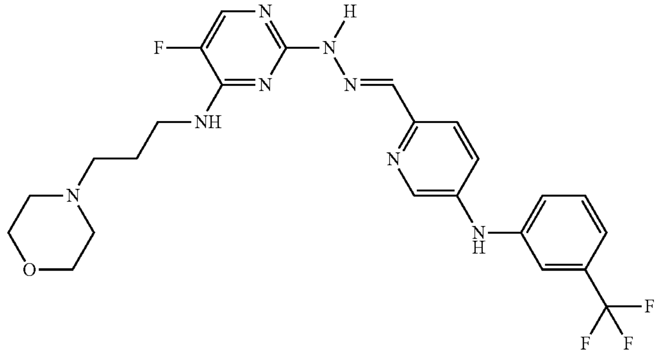
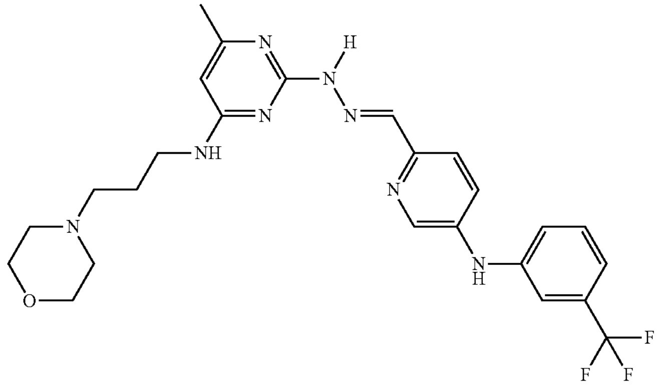
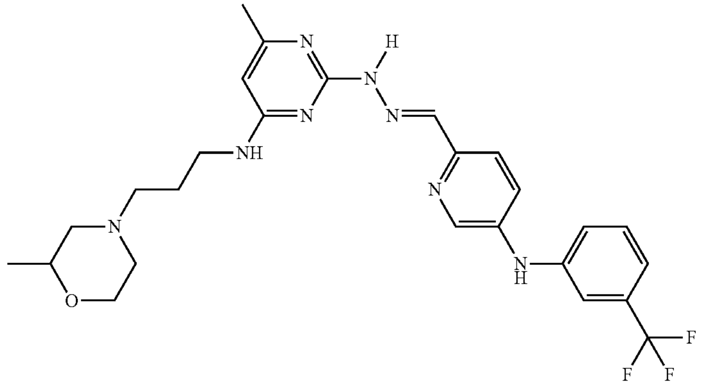

-continued
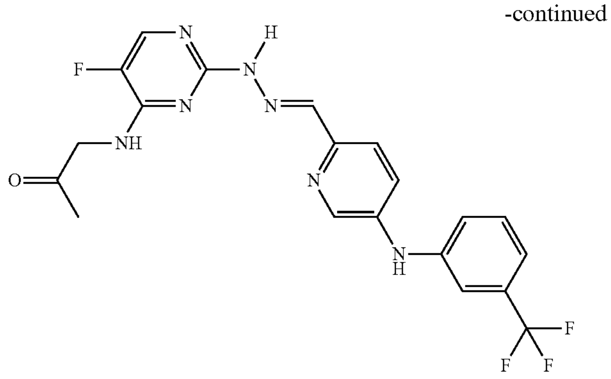
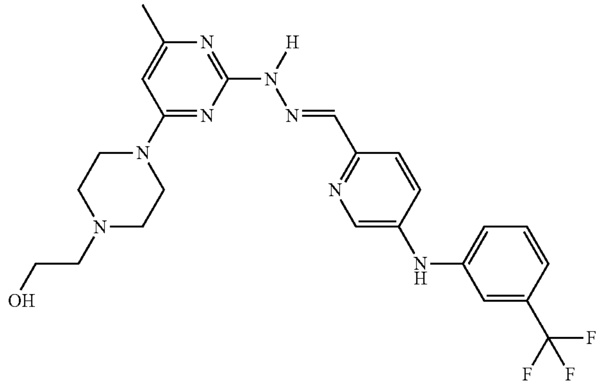
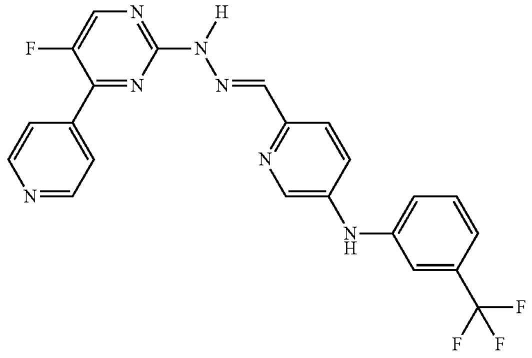
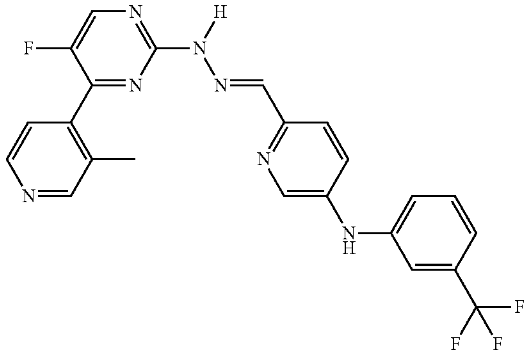
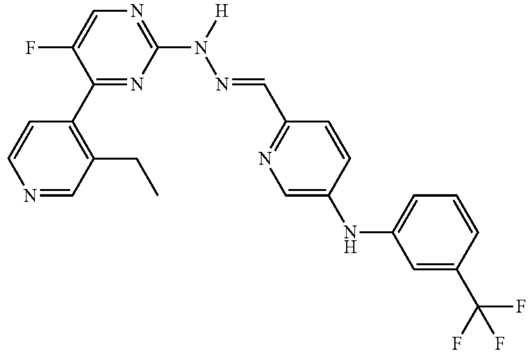
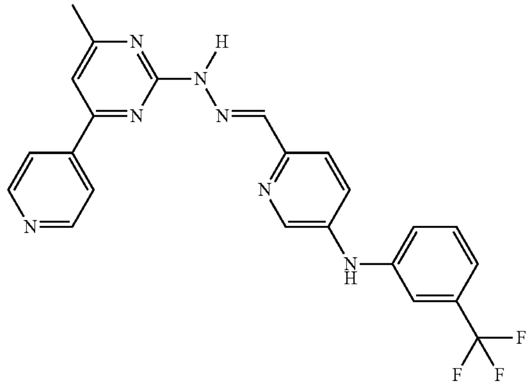

-continued
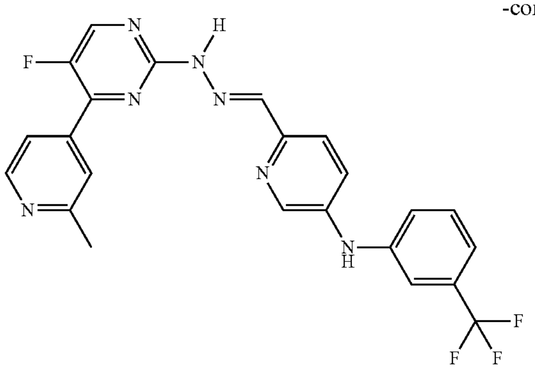
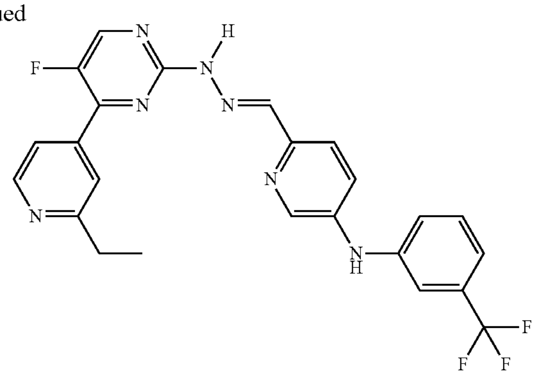
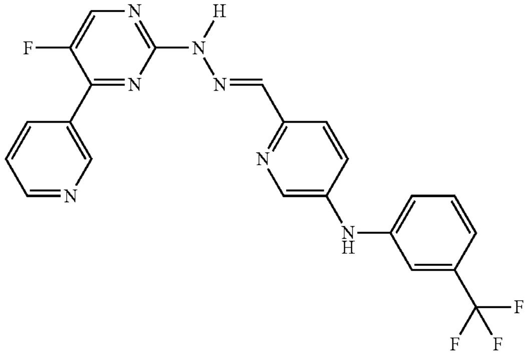
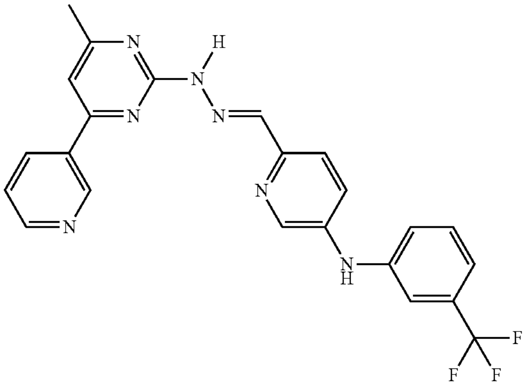
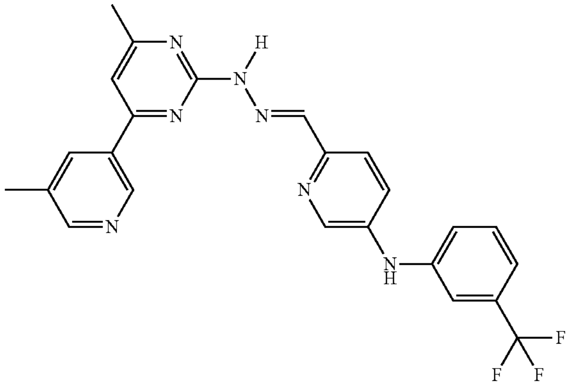
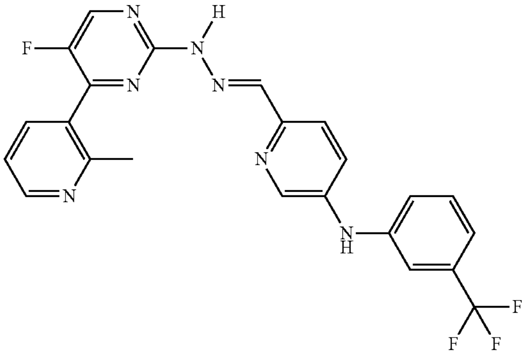
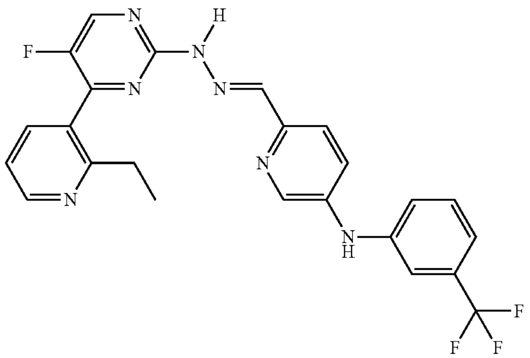
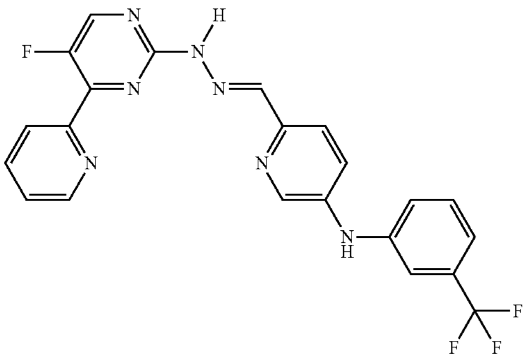

-continued
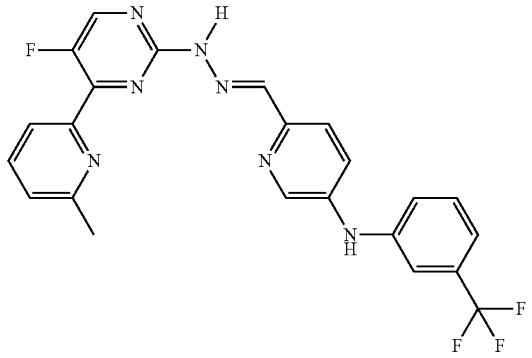
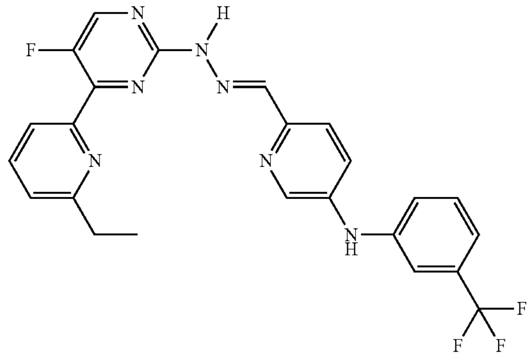
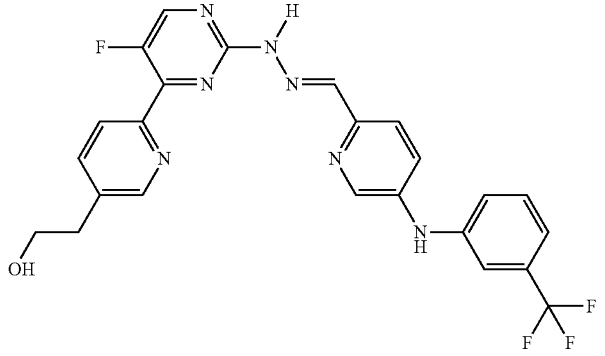
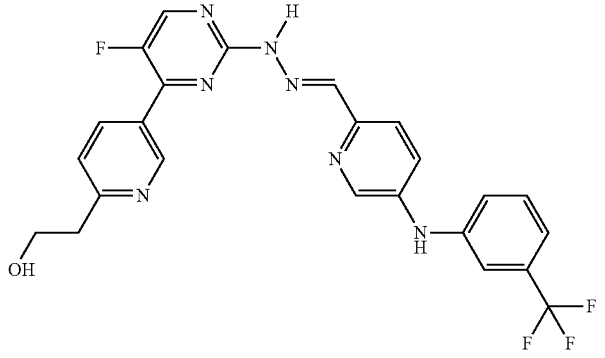
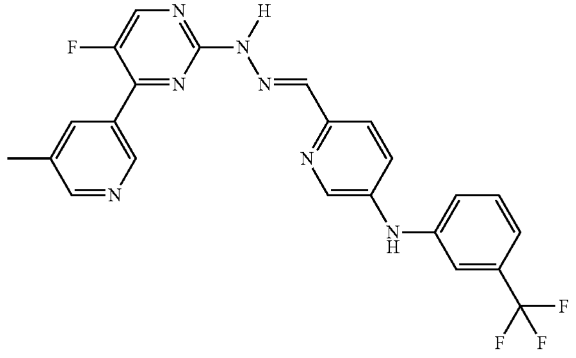
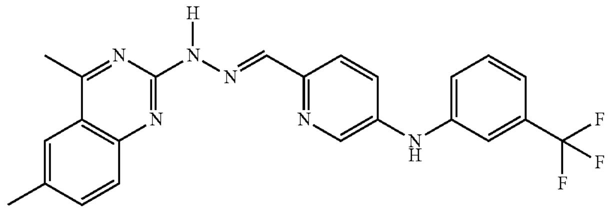

-continued
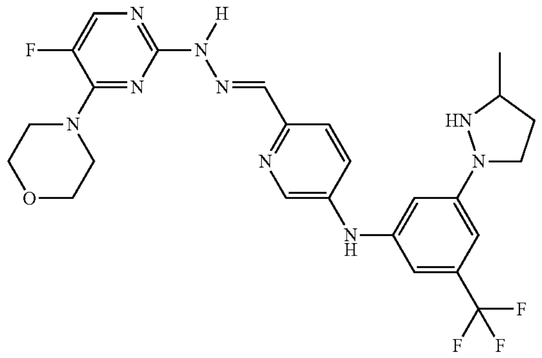
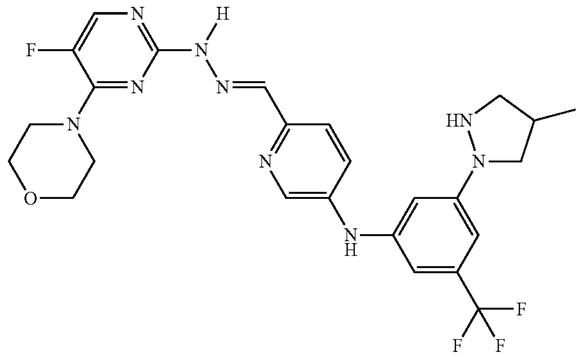
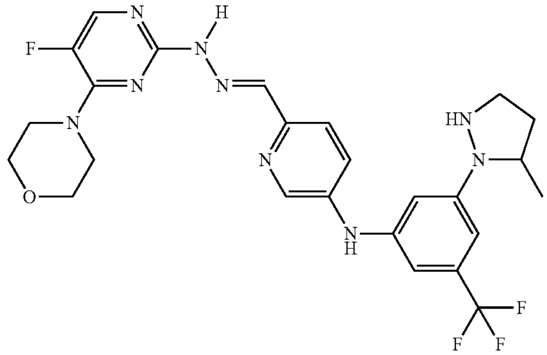
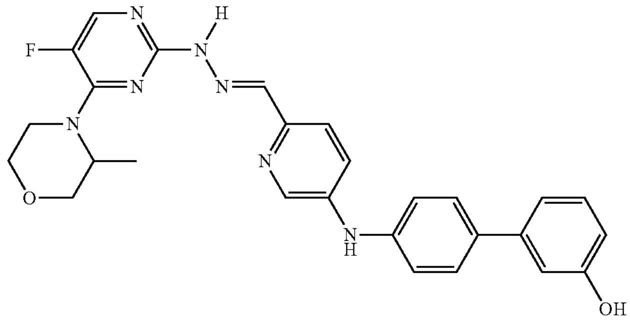
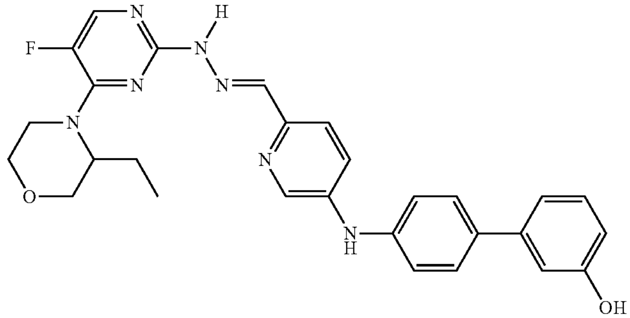
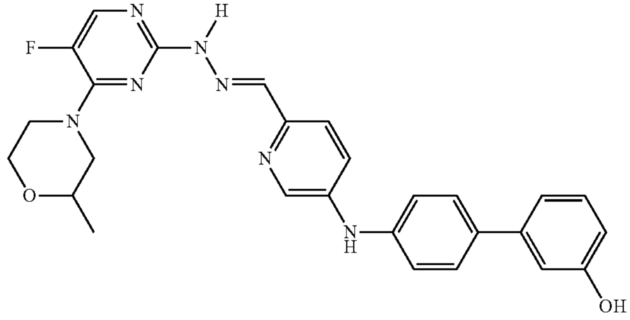

-continued
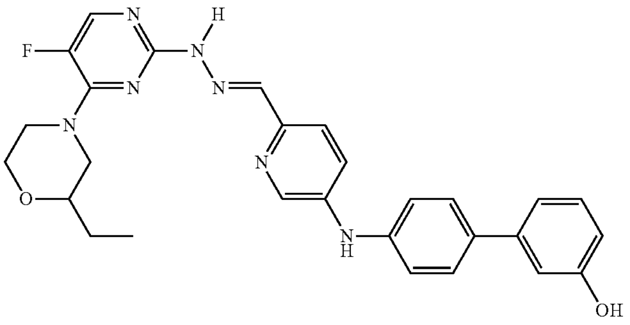
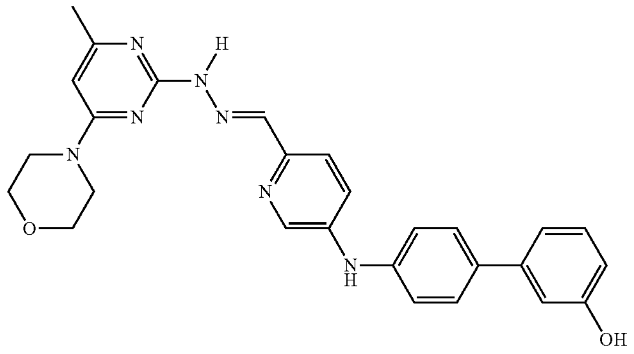
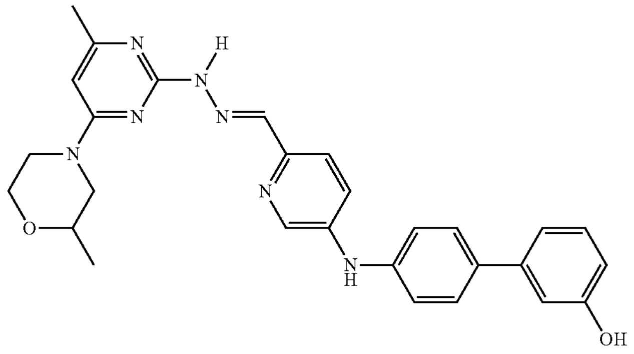
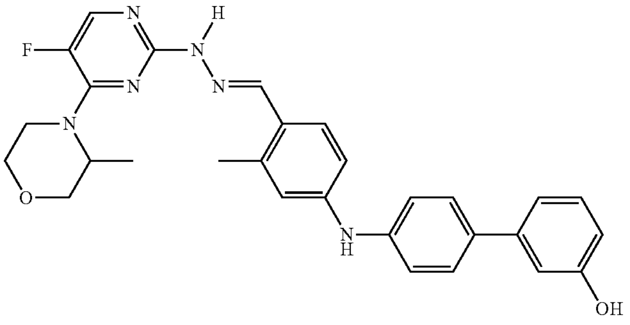
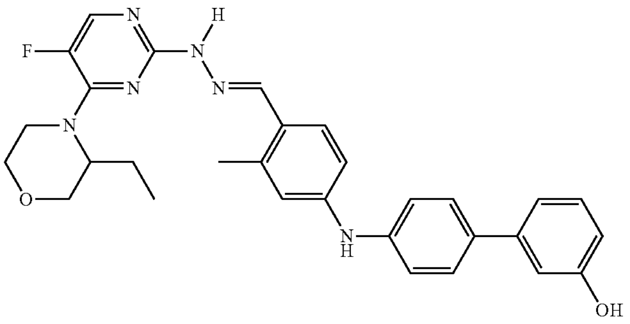

-continued
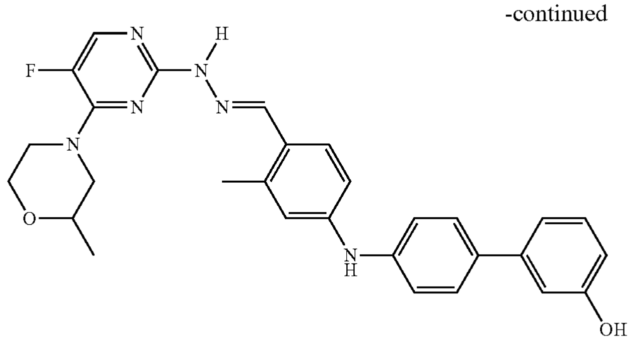
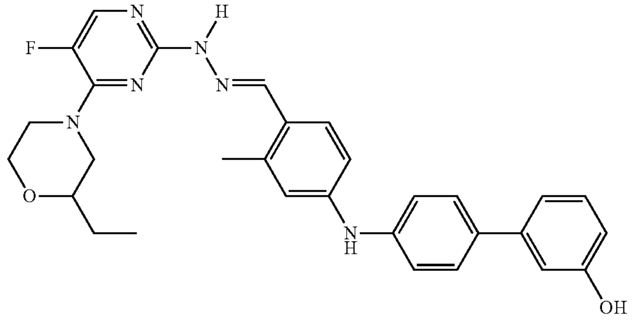
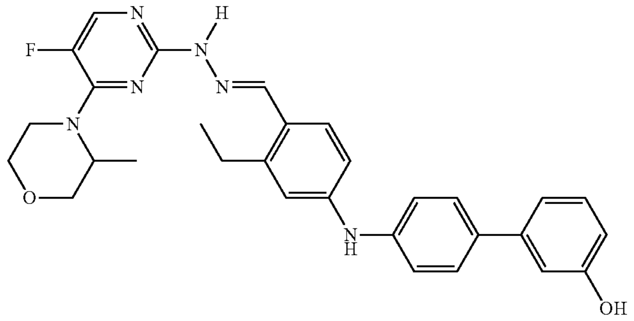
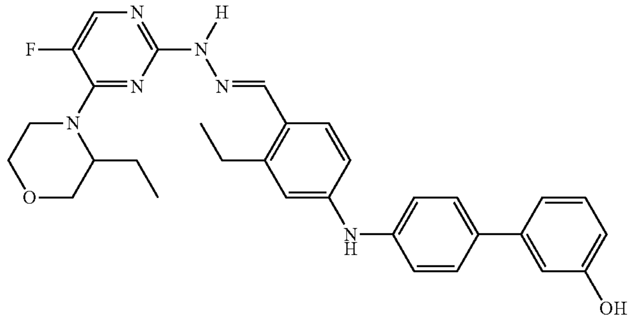
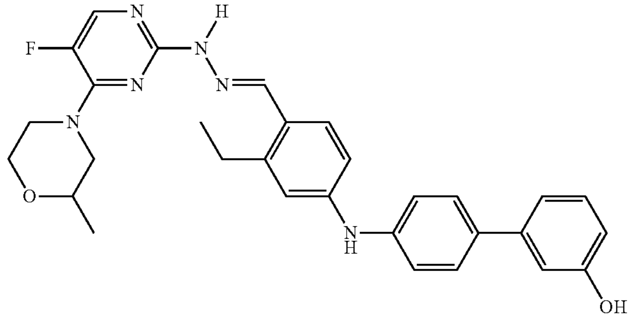

-continued
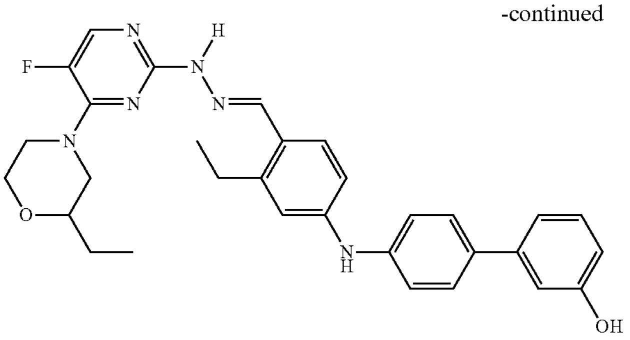
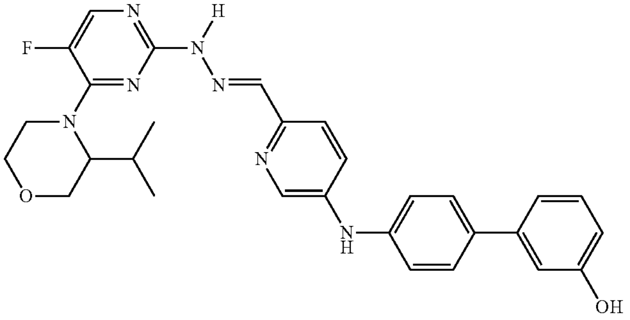
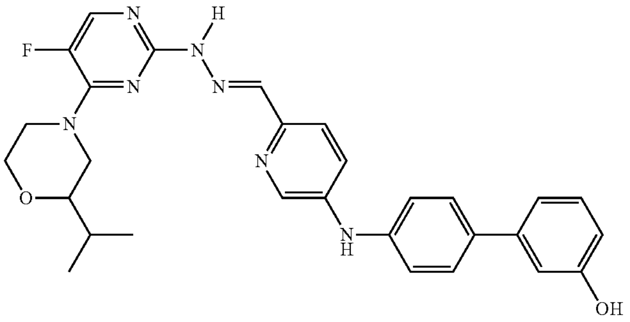
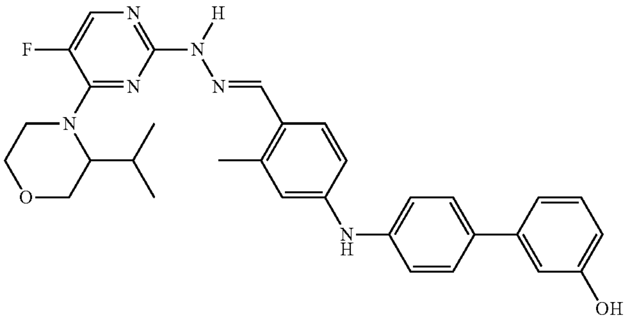
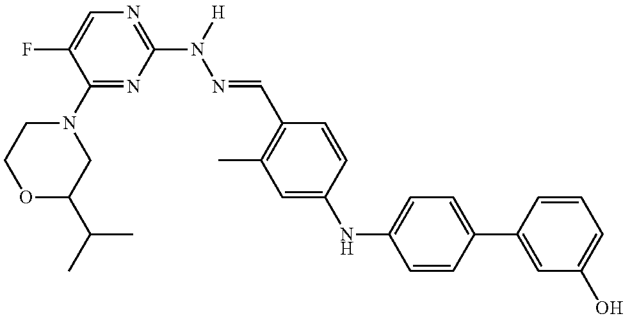

-continued
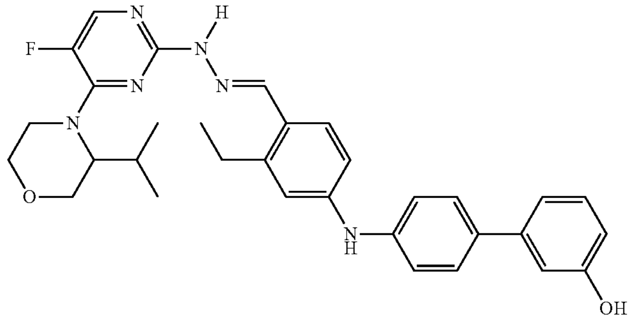
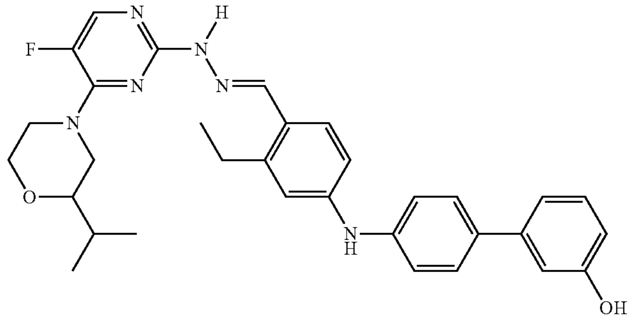
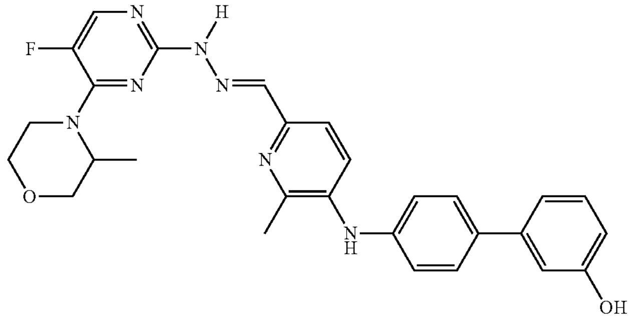
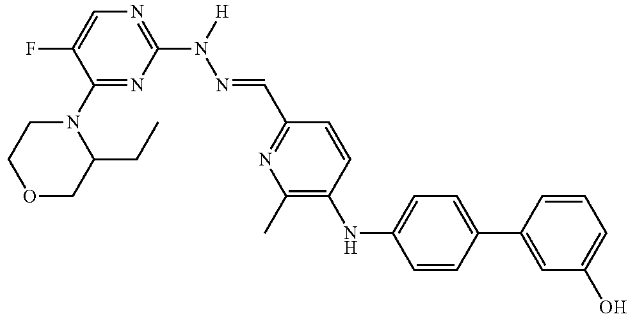
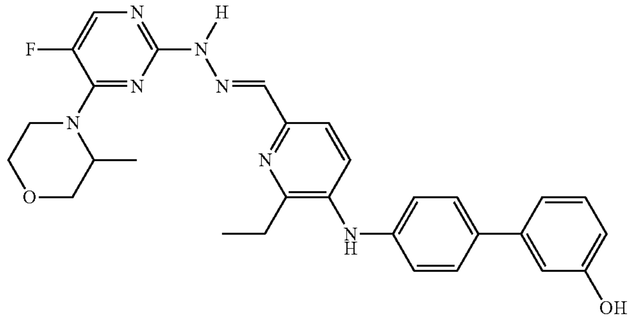

-continued
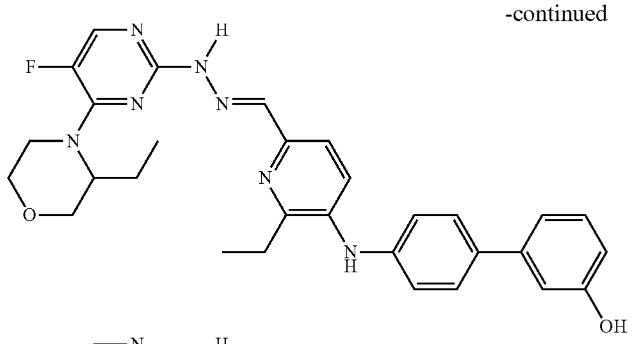
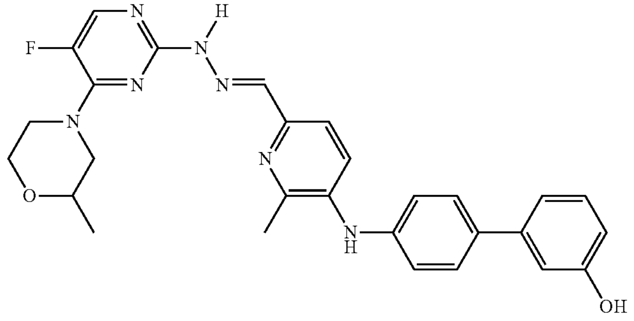
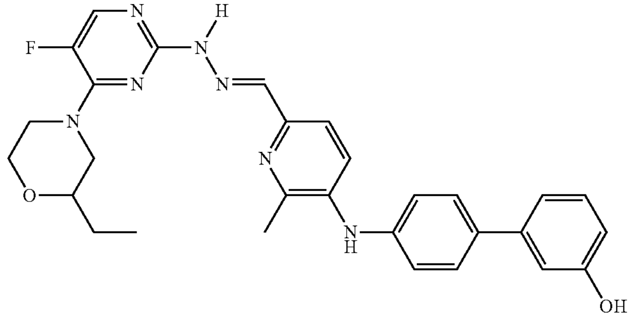
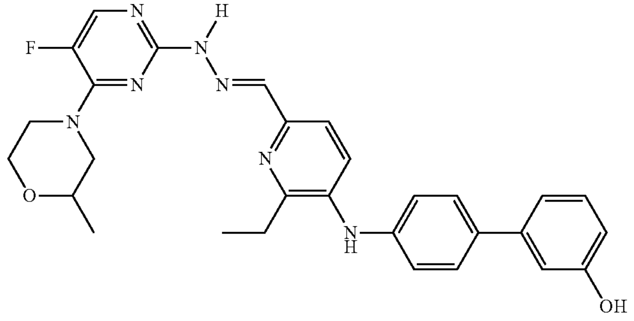
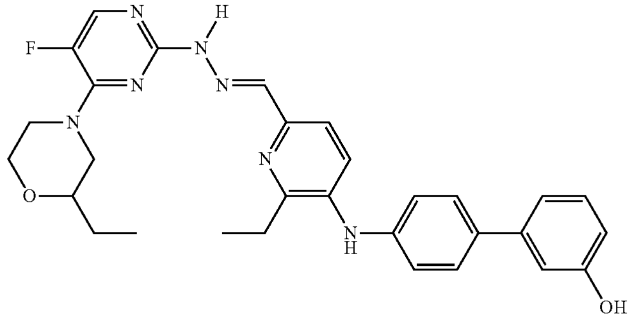

-continued
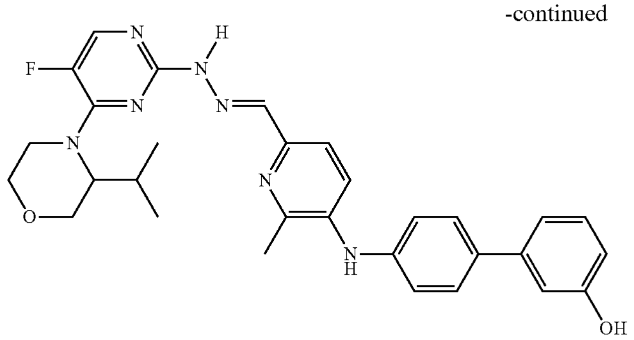
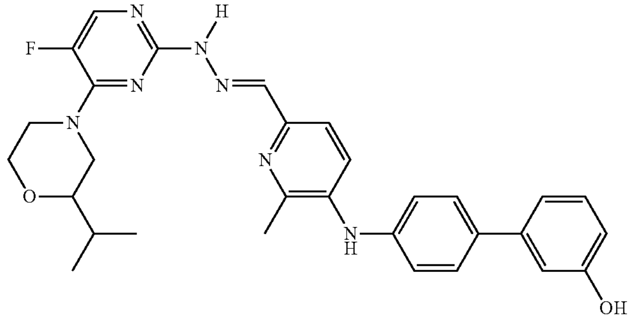
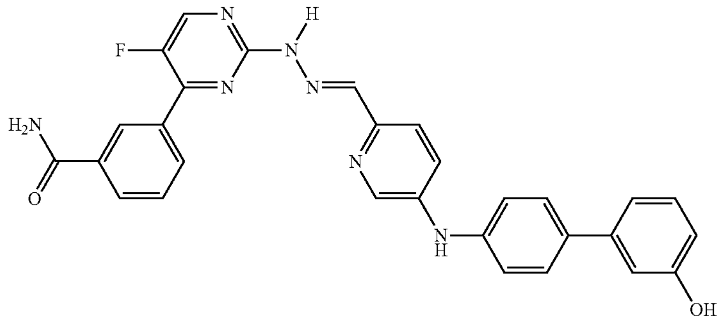
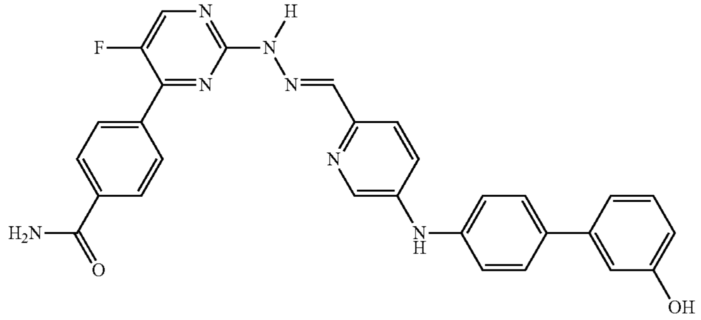
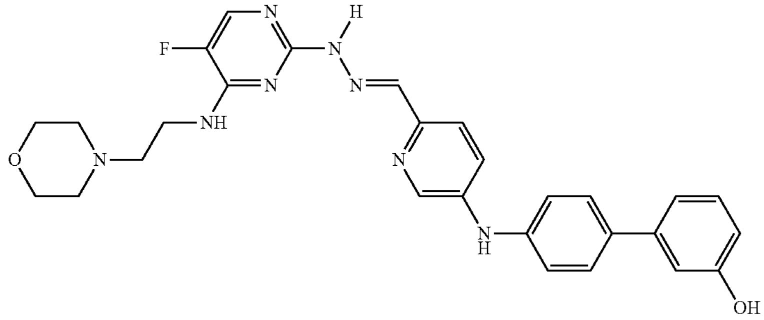

-continued
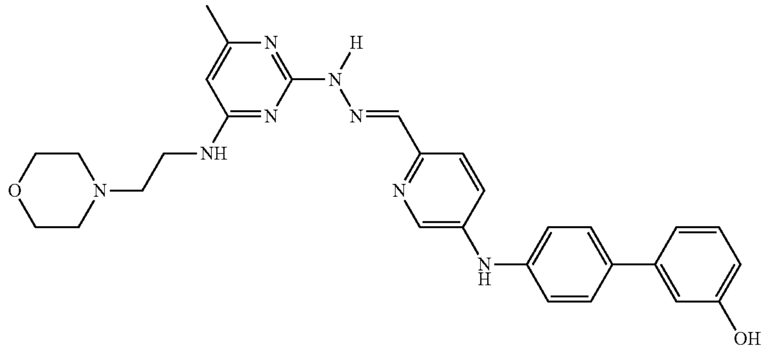
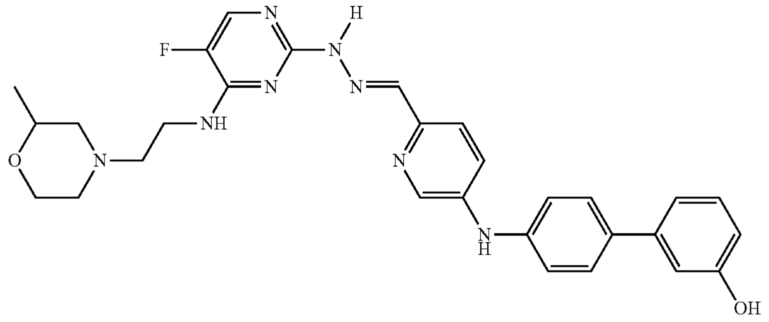
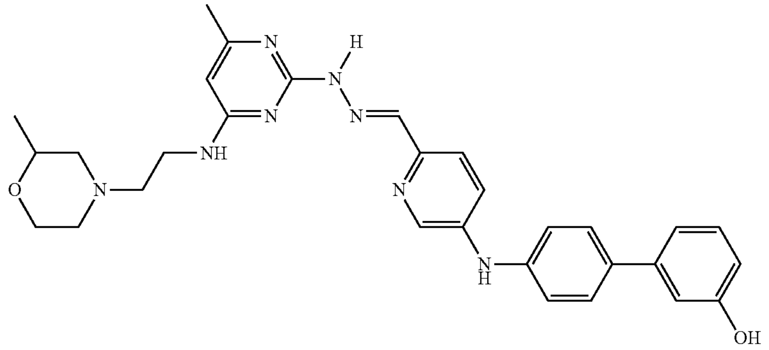
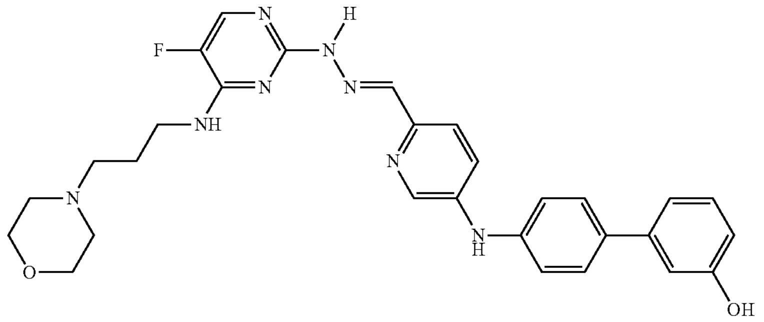
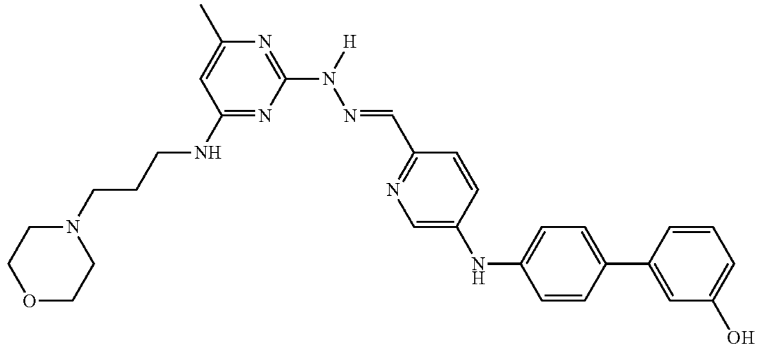

-continued
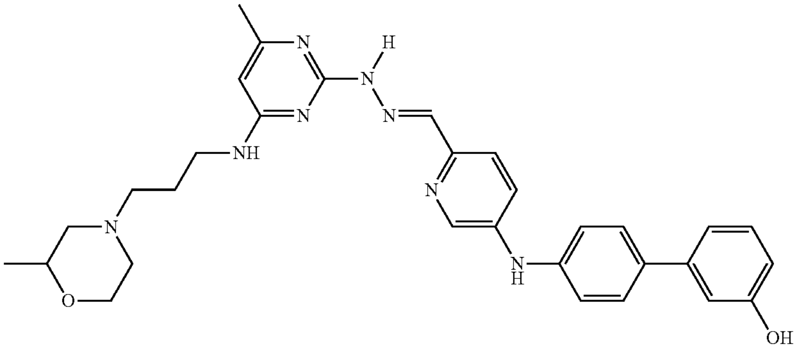
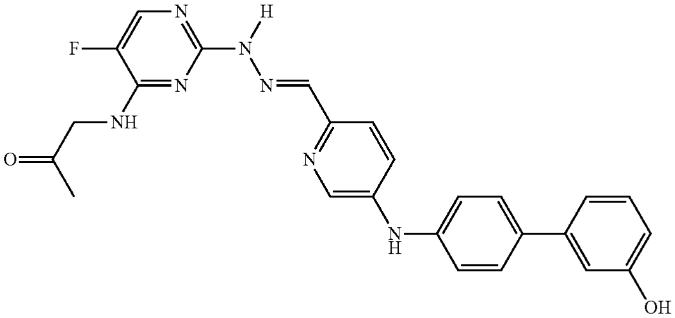
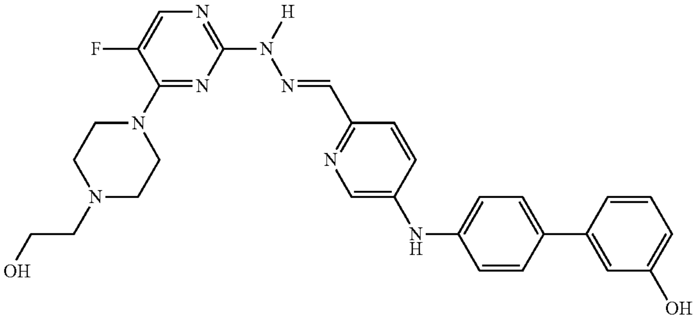
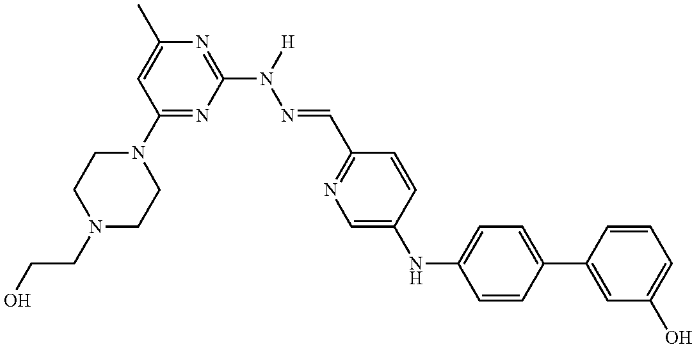
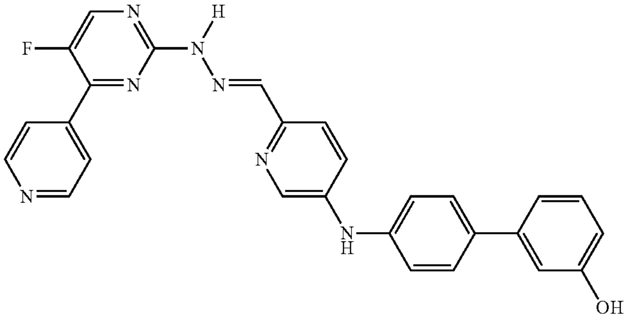

-continued
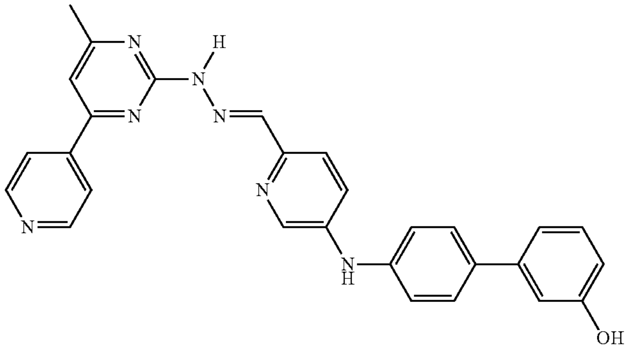
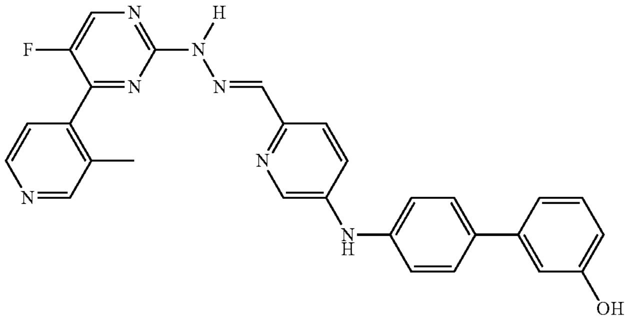
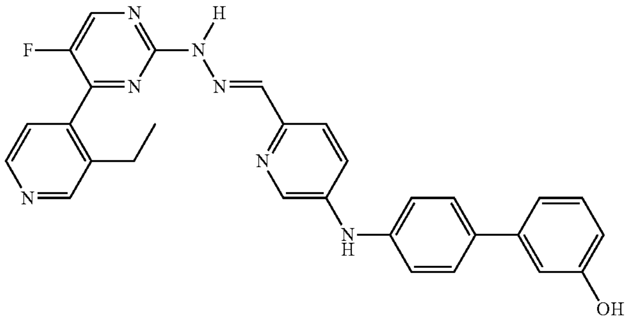
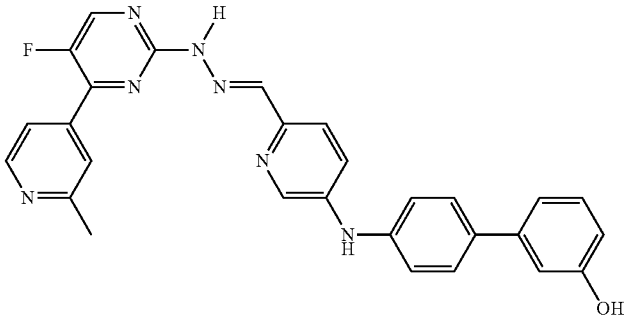
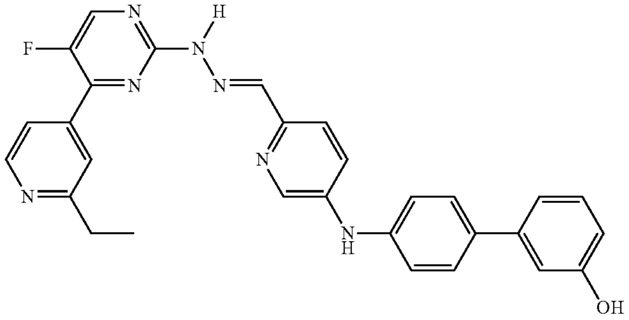

-continued
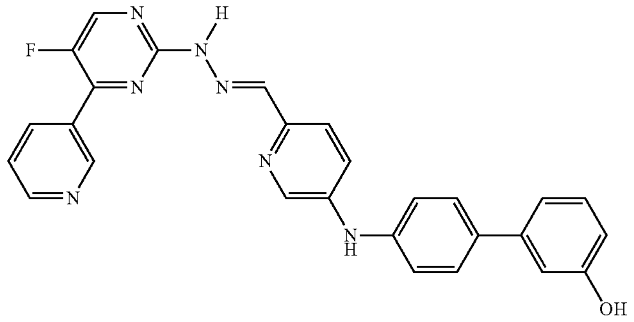
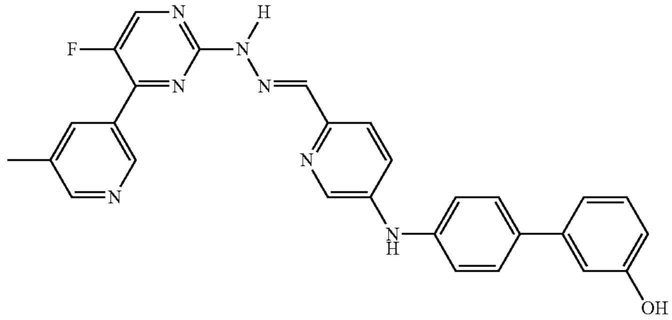
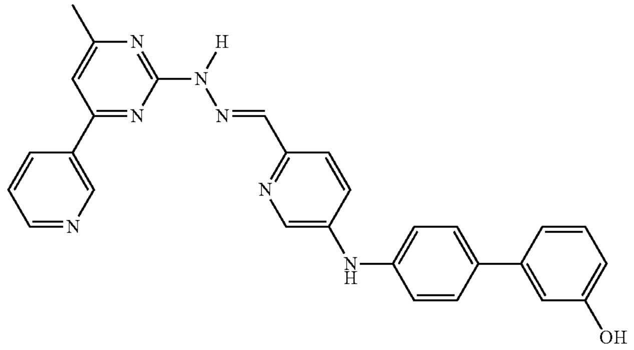
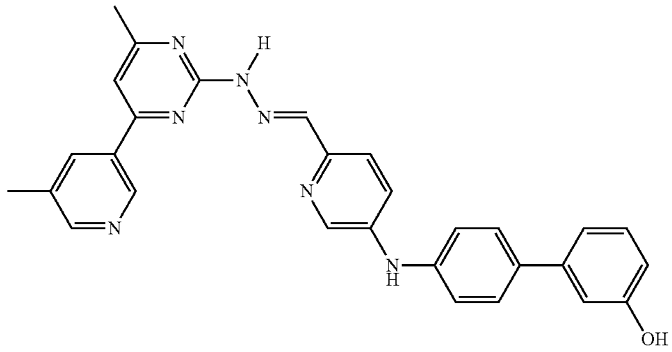
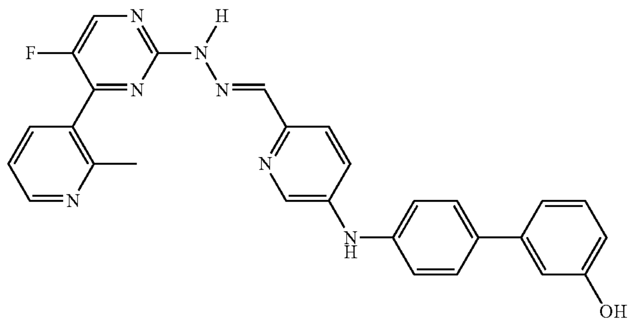

-continued
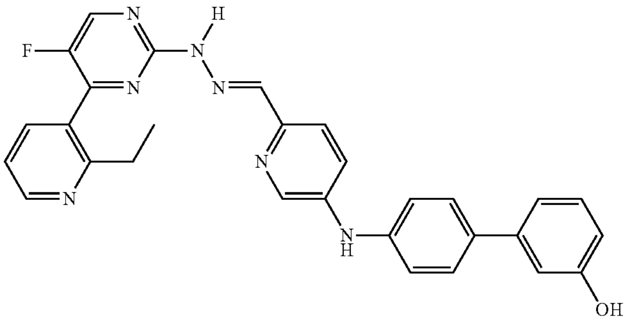
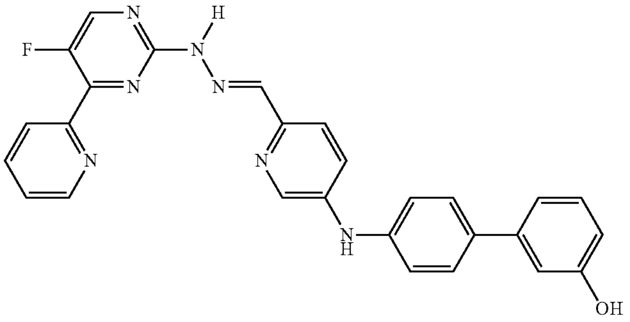
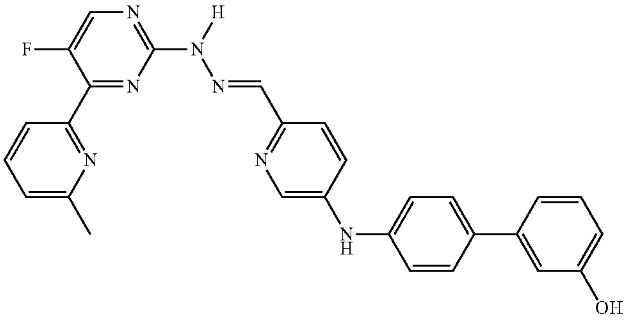
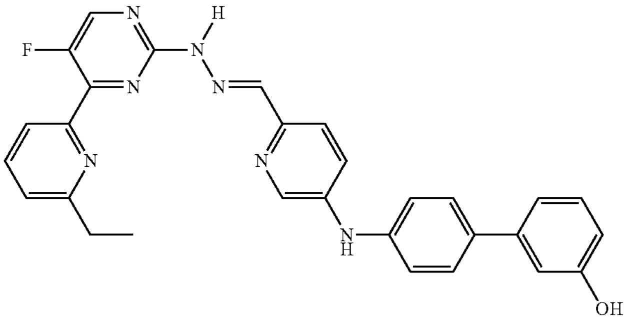
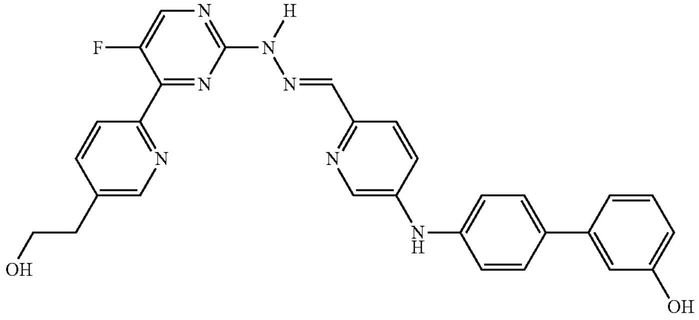

-continued
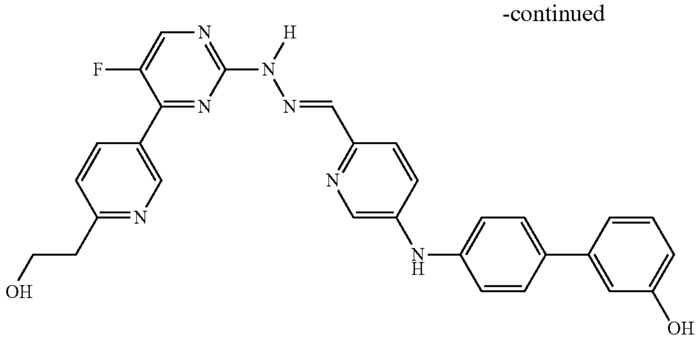
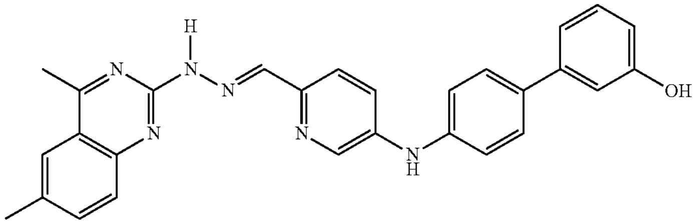
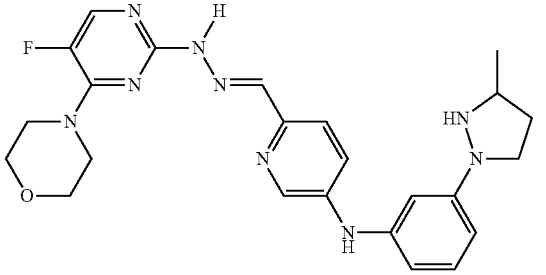
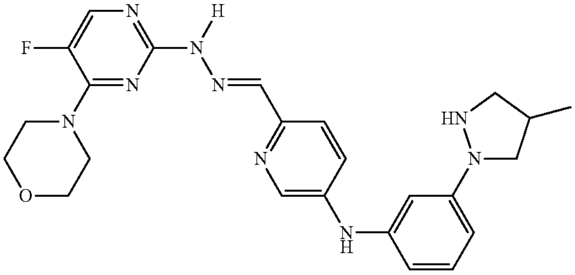
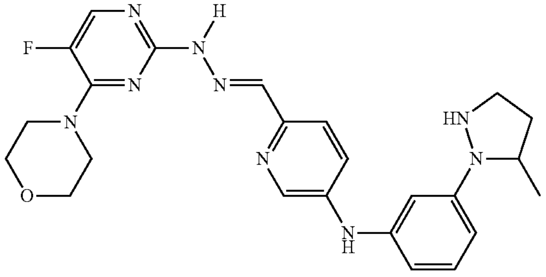
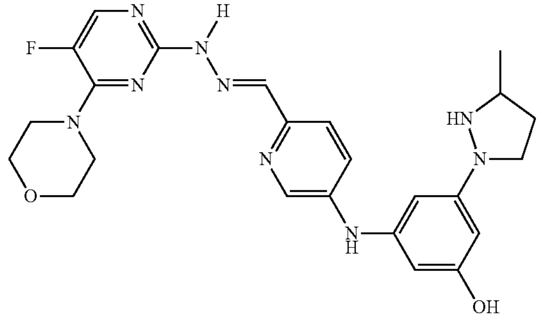
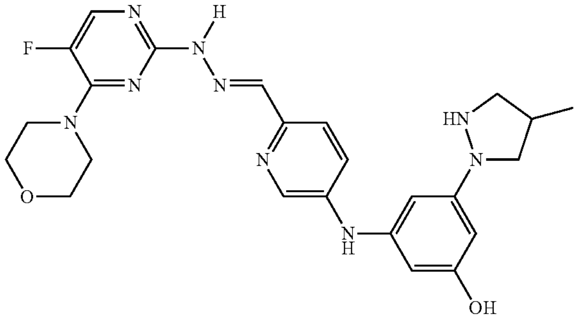
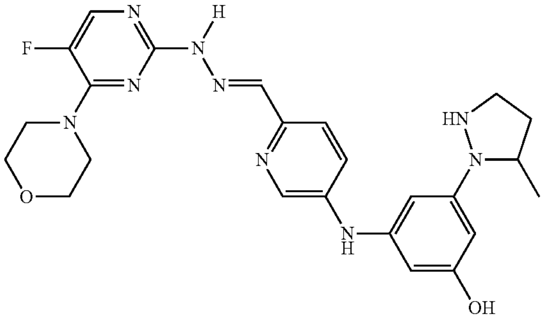
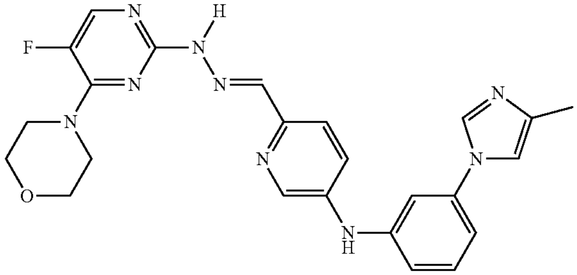

-continued
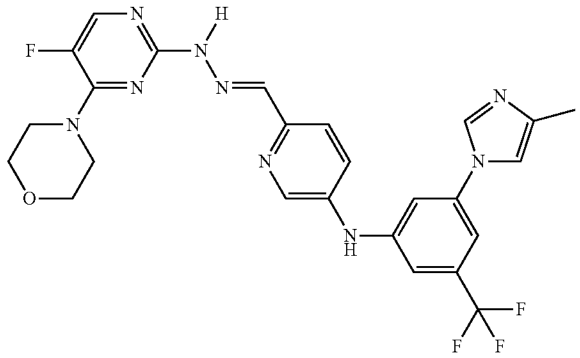
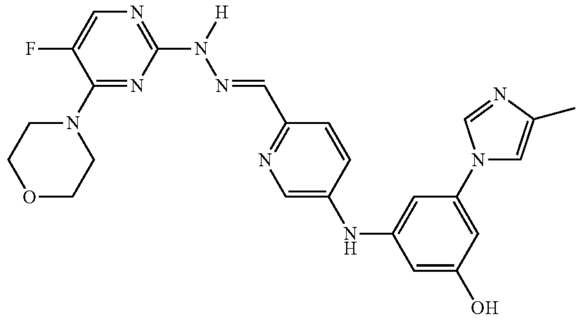
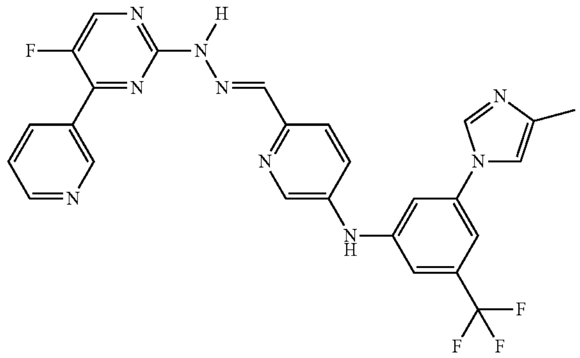
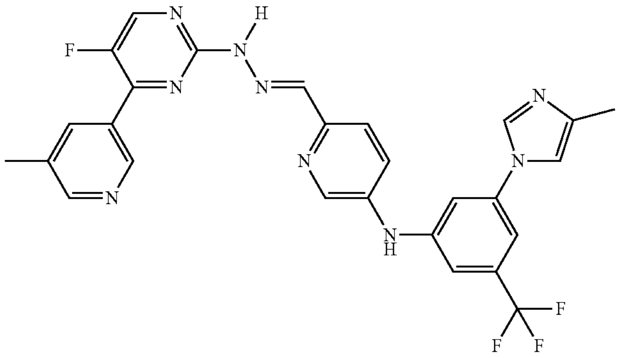

-continued
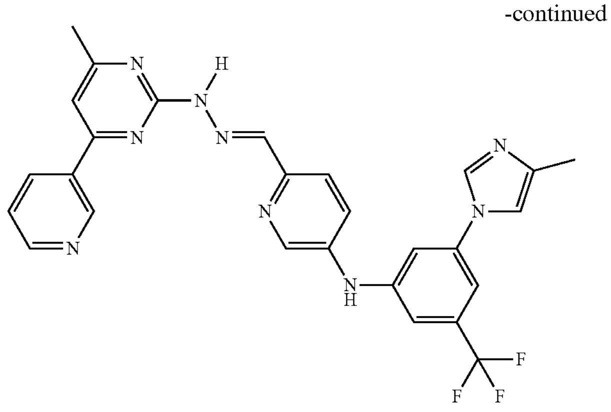
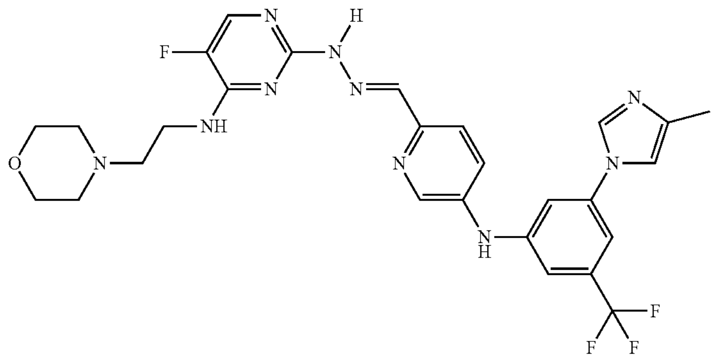
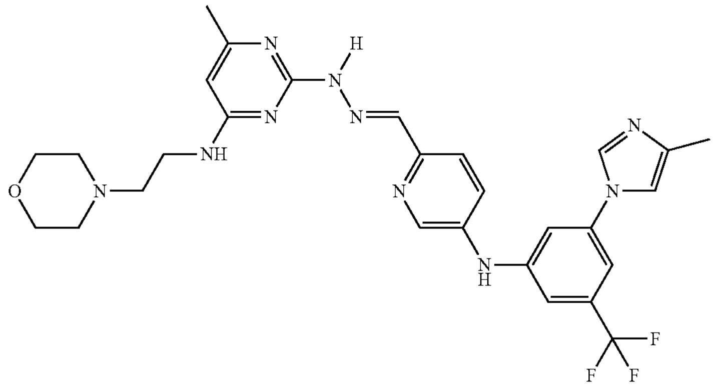
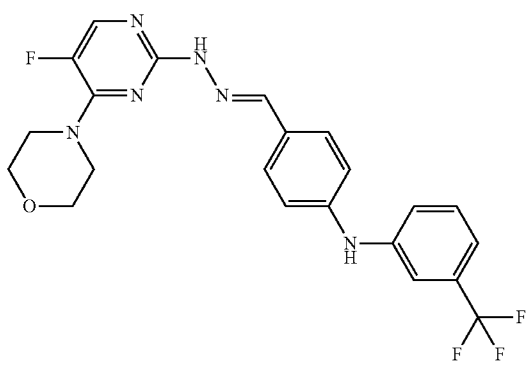
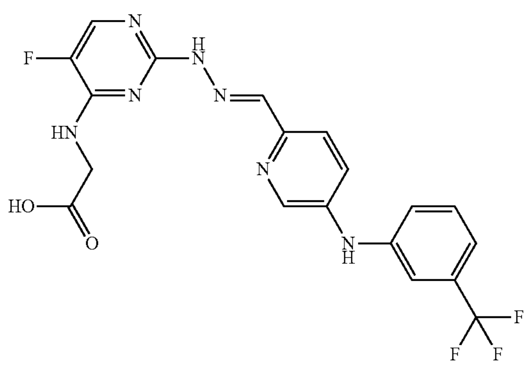

-continued
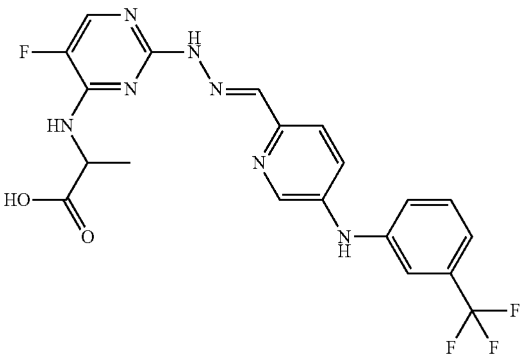
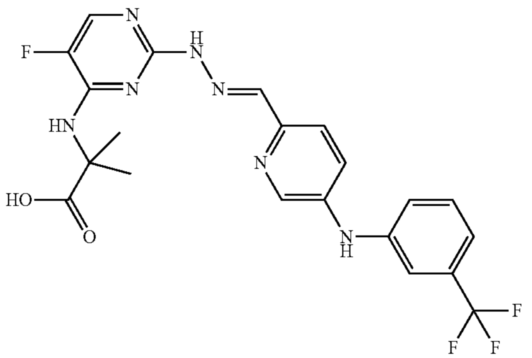
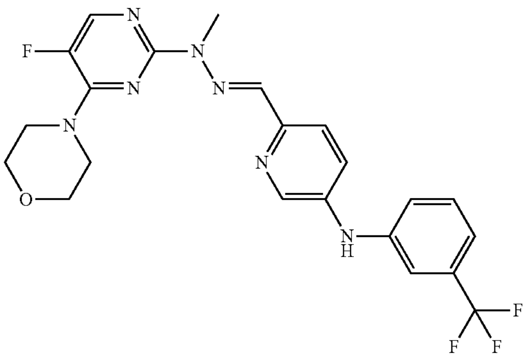
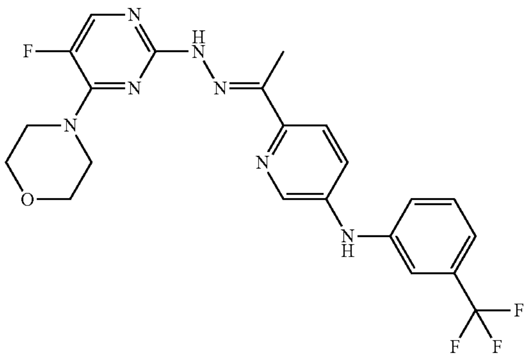
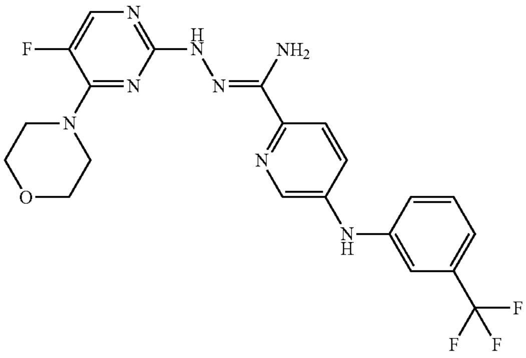
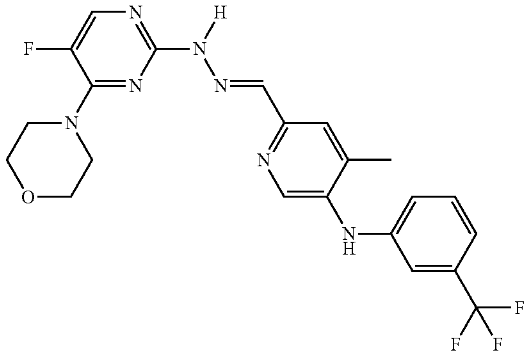
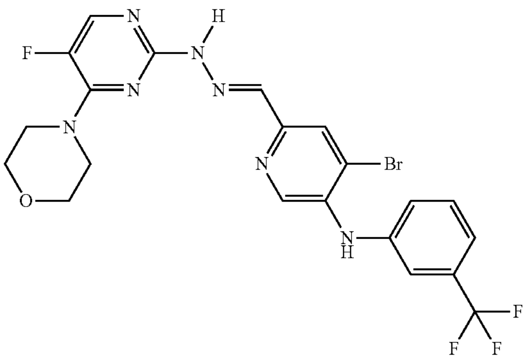
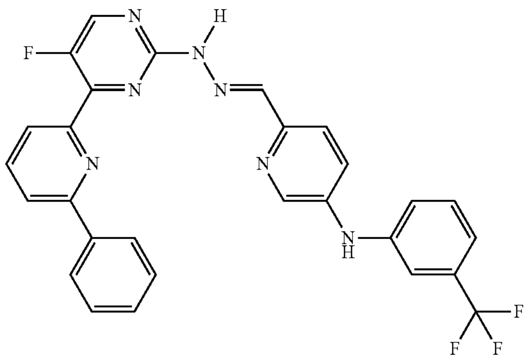

-continued
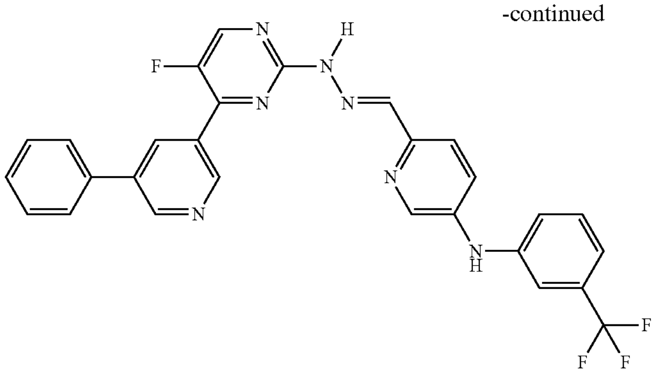
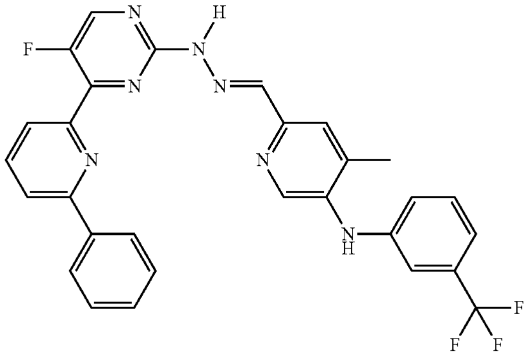
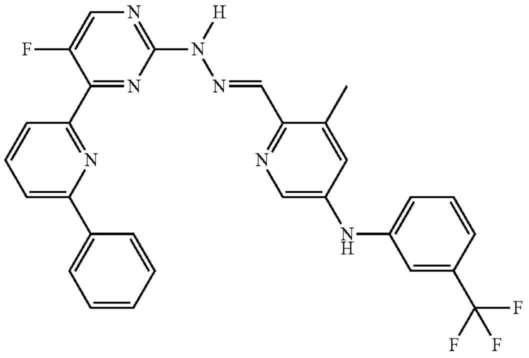
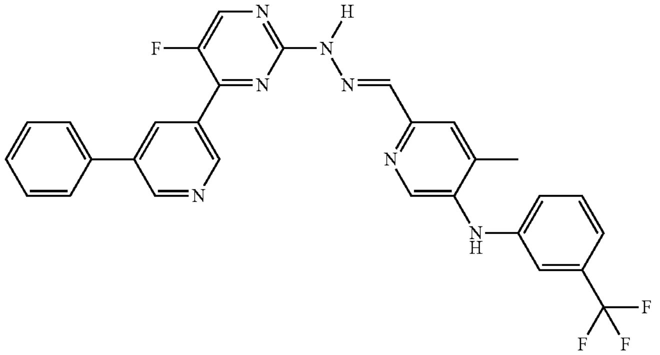
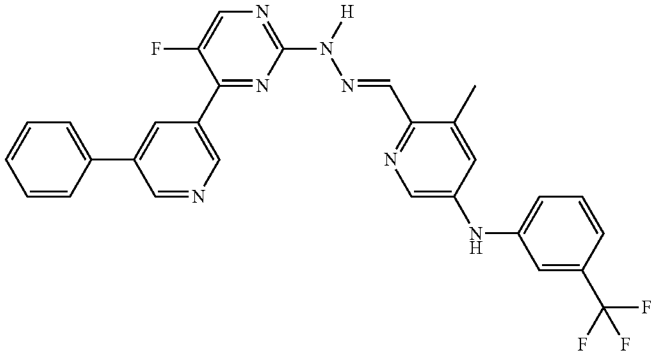

-continued
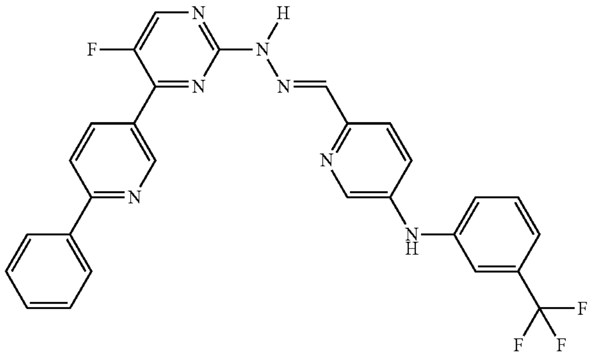
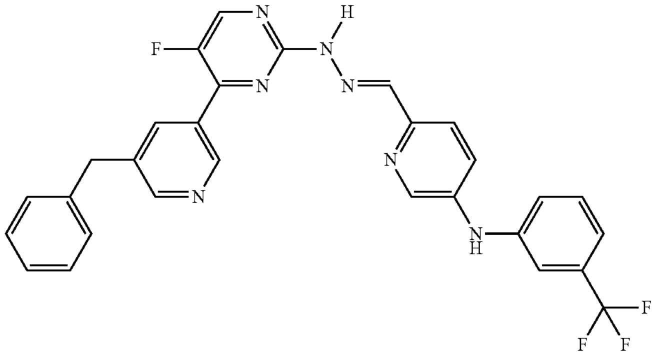
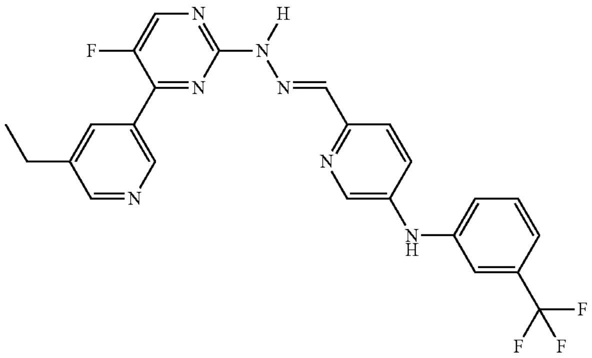
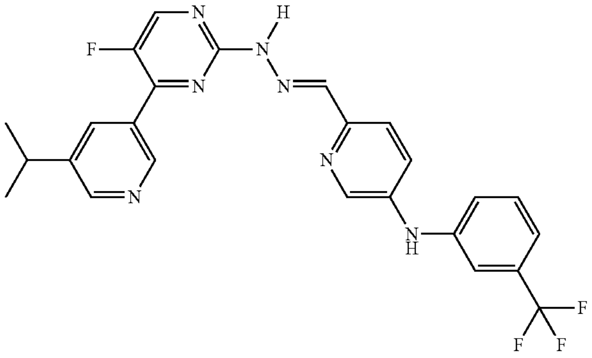

-continued
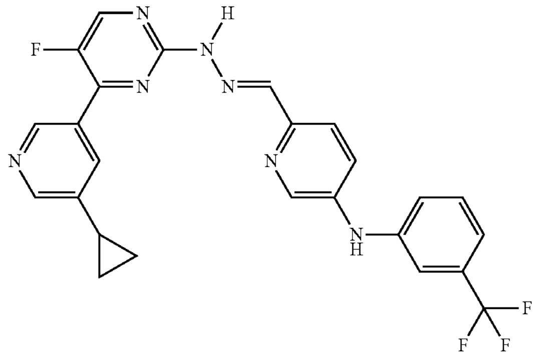
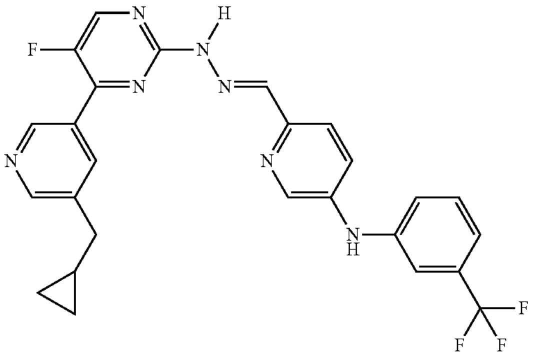
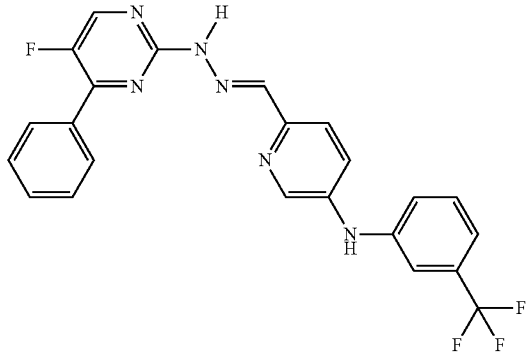
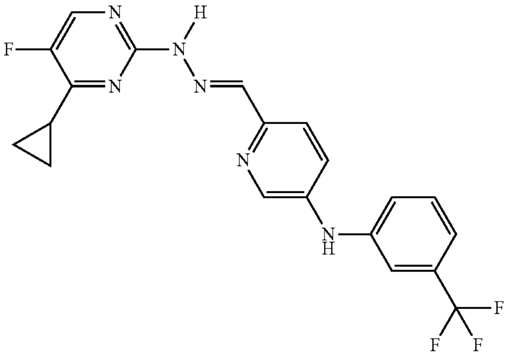
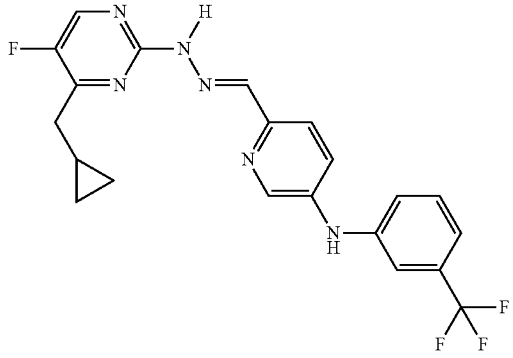
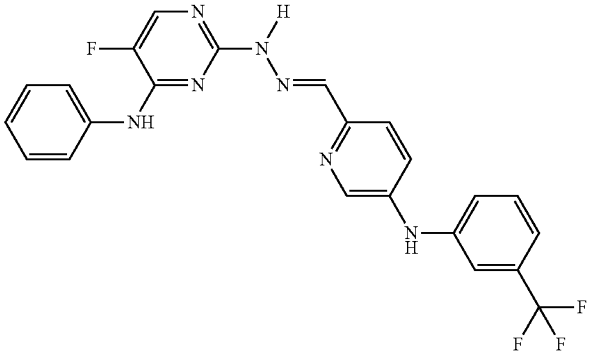
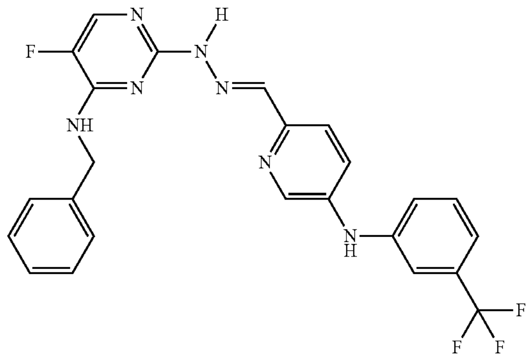
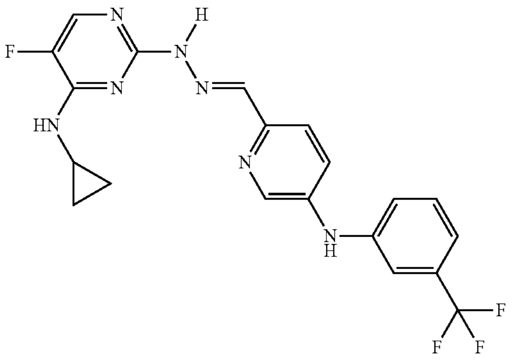

-continued
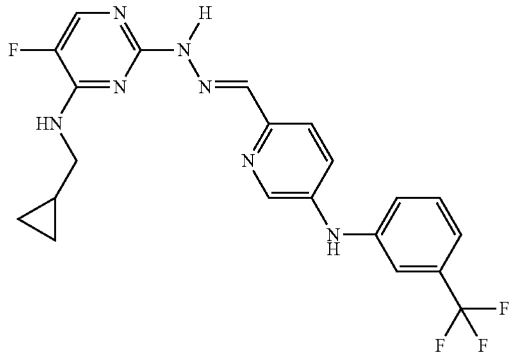
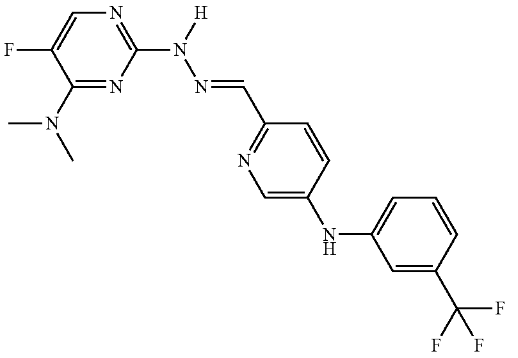
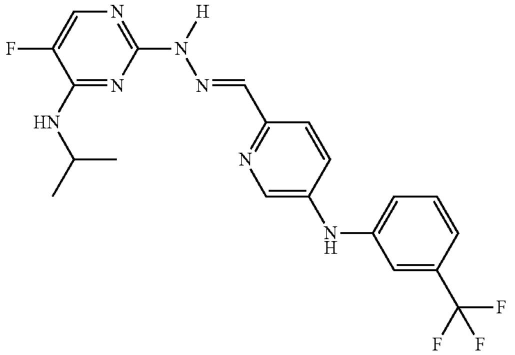
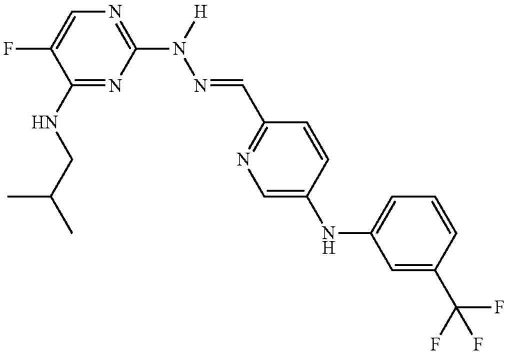
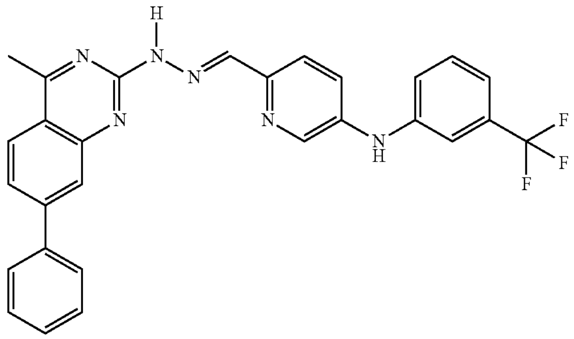
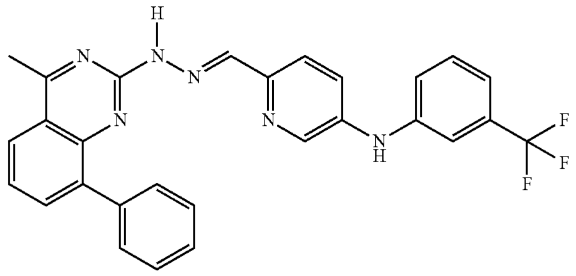
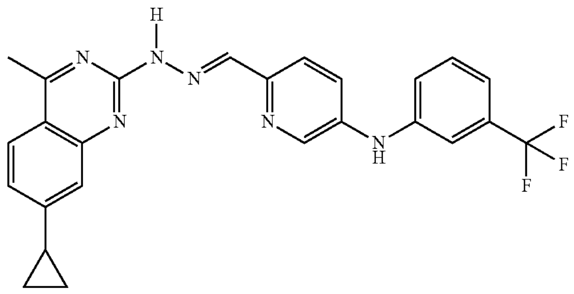
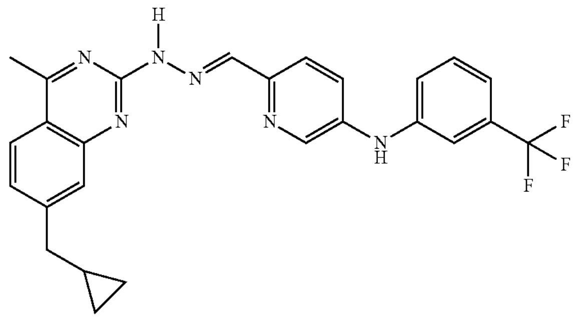
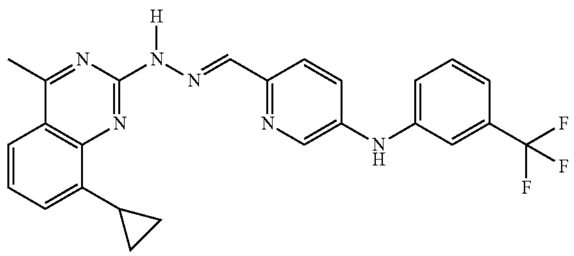
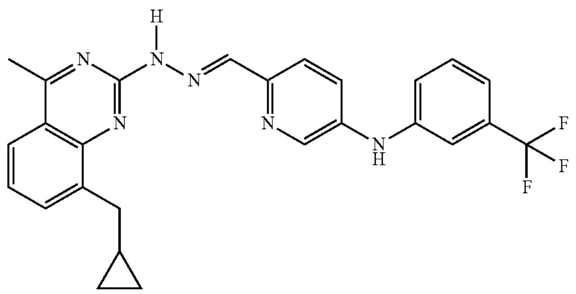

-continued
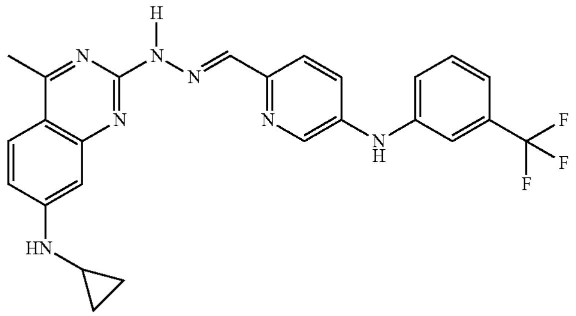
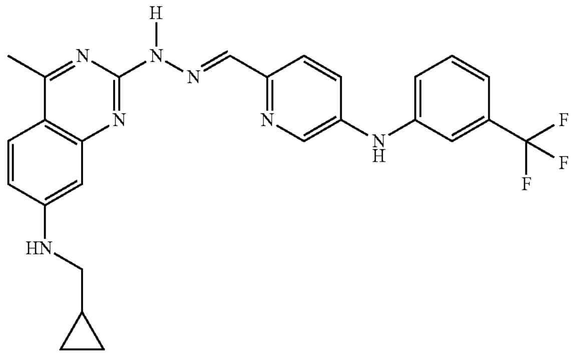
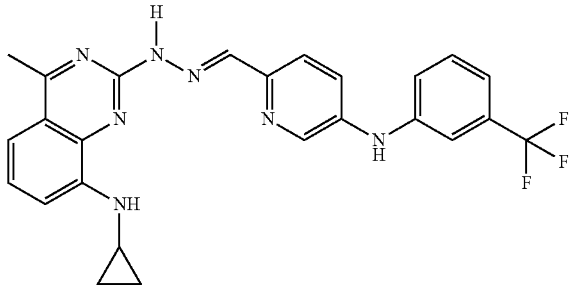
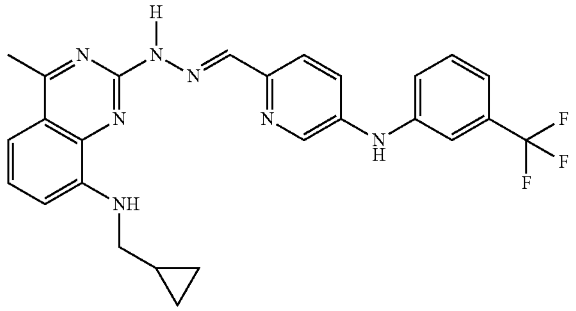
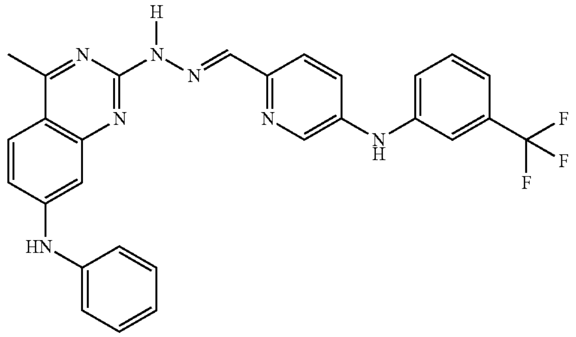
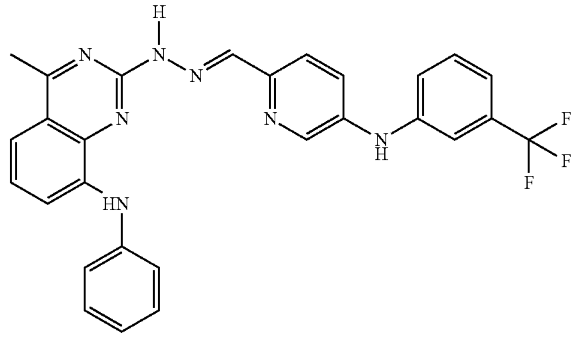
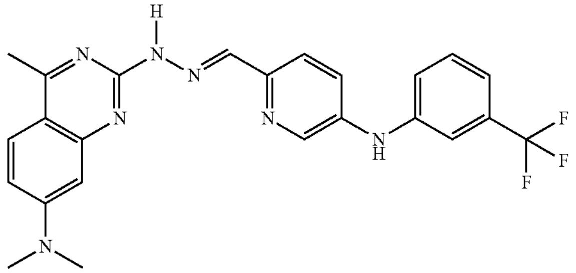
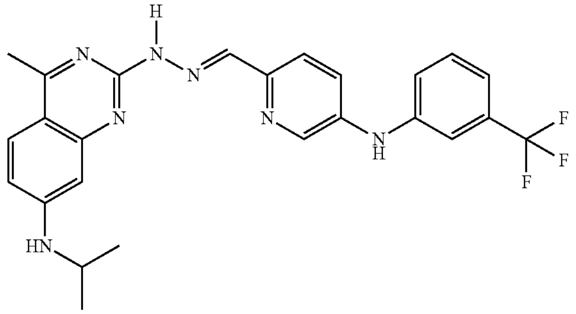
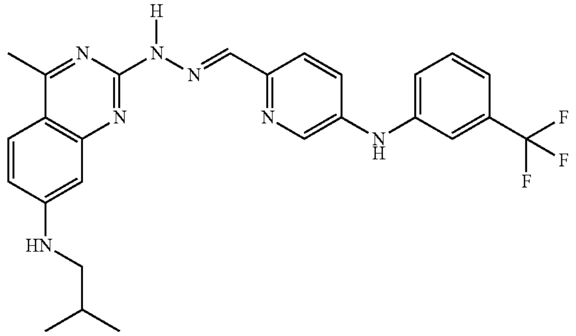
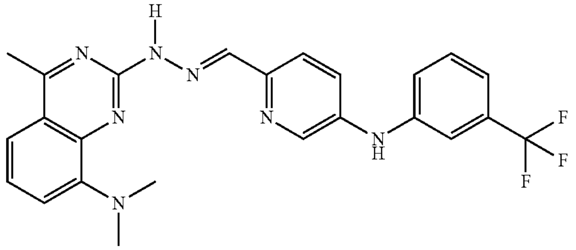

-continued

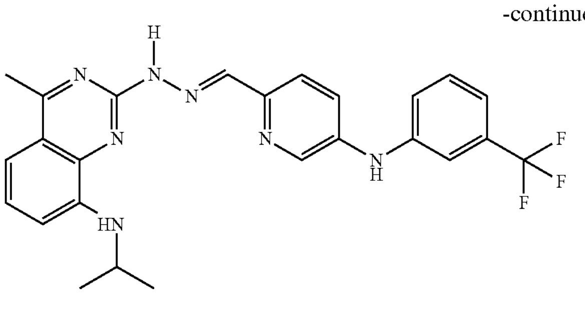

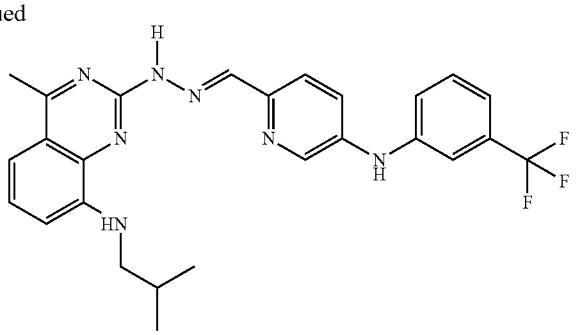

In a further preferred embodiment, the present invention provides inhibitors of the $P210^{BCR\text{-}ABL\text{-}T315I}$ theramutein having the formula III (III)

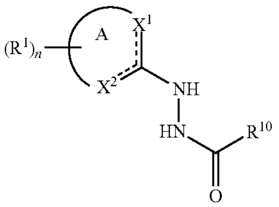

wherein ring A is a 5-, 6-, or 7-membered ring or a 7- to 12-membered fused bicyclic ring;

$X^1$ is selected from N, N—$R^0$ or C—$R^1$;

$X^2$ is selected from N, N—$R^0$ or C—$R^1$;

the dotted lines represent optional double bonds;

each $R^1$ is independently selected from the group consisting of H, alkyl, cycloalkyl, alkenyl, alkynyl, aralkyl, CN, $CF_3$, $NO_2$, $OR^{11}$, $—(CH_2)_pC(O)(CH_2)_qR^{11}$, $—(CH_2)_pC(O)N(R^{12})(R^{13})$, $—(CH_2)_pC(O)O(CH_2)_qR^{11}$, $—(CH_2)_pN(R^{11})C(O)R^{11}$, $—(CH_2)_pN(R^{12})(R^{13})$, $—N(R^{11})SO_2R^{11}$, $—OC(O)N(R^{12})(R^{13})$, $—SO_2N(R^{12})(R^{13})$, halo, aryl, and a heterocyclic ring, and additionally or alternatively, two $R^1$ groups on adjacent ring atoms form a 5- or 6-membered fused ring which contains from 0 to 3 heteroatoms;

n is to 6, each $R^{11}$ is independently selected from H, alkyl, cycloalkyl, alkenyl, alkynyl, aralkyl, aryl, and a heterocyclic ring;

each $R^{12}$ and $R^{13}$ are independently selected from H, alkyl, cycloalkyl, alkenyl, alkynyl, aralkyl, aryl, and a heterocyclic ring; or $R^{12}$ and $R^{13}$ may be taken together with the nitrogen to which they are attached form a 5- to 7-membered ring which may optionally contain a further heteroatom; wherein the 5- to 7-membered ring may optionally be substituted with one to three substituents that are independently selected from alkyl, cycloalkyl, alkenyl, alkynyl, aralkyl, CN, $CF_3$, $NO_2$, $OR^0$, $CO_2R^0$, $C(O)R^0$, halo, aryl, and a heterocyclic ring;

p is 0 to 4;

q is 0 to 4;

$R^{10}$ is selected from —Y'—$R^{18}$;

Y' is selected from a chemical bond, O, $NR^0$—, and a hydrocarbon chain having from 1 to 4 carbon atoms, and optionally substituted with one or more of halo, alkyl, cycloalkyl, alkenyl, alkynyl, aralkyl, $CO_2R^0$, $C(O)R^0$, $C(O)N(R^0)_2$, CN, $CF_3$, $N(R^0)_2$, $NO_2$, and $OR^0$;

$R^{18}$ is selected from the group consisting of H, alkyl, cycloalkyl, alkenyl, alkynyl, aralkyl, $CF_3$, aryl, and a heterocyclic ring; and each $R^0$ is independently selected from H, alkyl, cycloalkyl, aralkyl, aryl and a heterocyclic ring.

In a further preferred embodiment, the present invention provides inhibitors of the $P210^{BCR\text{-}ABL\text{-}T315I}$ theramutein having the formula $III_a$ ($III_a$)

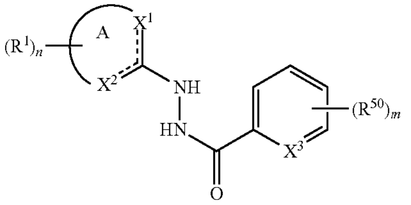

wherein:

ring A is a 5-, 6-, or 7-membered ring or a 7- to 12-membered fused bicyclic ring;

$X^1$ is selected from N, N—$R^0$ or C—$R^1$;

$X^2$ is selected from N, N—$R^0$ or C—$R^1$;

the dotted lines represent optional double bonds;

each $R^1$ is independently selected from the group consisting of H, alkyl, cycloalkyl, alkenyl, alkynyl, aralkyl, CN, $CF_3$, $NO_2$, $OR^{11}$, $—(CH_2)_pC(O)(CH_2)_qR^{11}$, $—(CH_2)_pC(O)N(R^{12})(R^{13})$, $—(CH_2)_pC(O)O(CH_2)_qR^{11}$, $—(CH_2)_pN(R^{11})C(O)R^{11}$, $—(CH_2)_pN(R^{12})(R^{13})$, $—N(R^{11})SO_2R^{11}$, $—OC(O)N(R^{12})(R^{13})$, $—SO_2N(R^{12})(R^{13})$, halo, aryl, and a heterocyclic ring, and additionally or alternatively, two $R^1$ groups on adjacent ring atoms form a 5- or 6-membered fused ring which contains from 0 to 3 heteroatoms;

n is 0 to 6, each $R^{11}$ is independently selected from H, alkyl, cycloalkyl, alkenyl, alkynyl, aralkyl, aryl, and a heterocyclic ring;

each $R^{12}$ and $R^{13}$ are independently selected from H, alkyl, cycloalkyl, alkenyl, alkynyl, aralkyl, aryl, and a heterocyclic ring; or $R^{12}$ and $R^{13}$ may be taken together with the nitrogen to which they are attached form a 5- to 7-membered ring which may optionally contain a further heteroatom, wherein the 5- to 7-membered ring may optionally be substituted with one to three substituents that are independently selected from alkyl, cycloalkyl, alkenyl, alkynyl, aralkyl, CN, $CF_3$, $NO_2$, $OR^0$, $CO_2R^0$, $C(O)R^0$, halo, aryl, and a heterocyclic ring;

p is 0 to 4;

q is 0 to 4;

$X^3$ is N, CH or C—$R^{50}$;

each $R^{50}$ is independently selected from the group consisting of alkyl, cycloalkyl, alkenyl, alkynyl, aralkyl, CN, $CF_3$, $NO_2$, $OR^{51}$, $-(CH_2)_rC(O)(CH_2)_sR^{51}$, $-(CH_2)_xC(O)N(R^{52})(R^{53})$, $-(CH_2)_rC(O)O(CH_2)_sR^{51}$, $-(CH_2)_rN(R^{51})C(O)R^{51}$, $-(CH_2)_rN(R^{52})(R^{53})$, $-N(R^{51})SO_2R^{51}$, $-OC(O)N(R^{52})(R^{53})$, $-SO_2N(R^{52})(R^{53})$, halo, aryl, and a heterocyclic ring, and additionally or alternatively, two $R^{50}$ groups on adjacent ring atoms form a 5- or 6-membered fused ring which contains from 0 to 3 heteroatoms;

$R^{51}$ is selected from H, alkyl, cycloalkyl, alkenyl, alkynyl, aralkyl, aryl, and a heterocyclic ring;

$R^{52}$ and $R^{53}$ are independently selected from H, alkyl, cycloalkyl, alkenyl, alkynyl, aralkyl, aryl, and a heterocyclic ring; or $R^{52}$ and $R^{53}$ may be taken together with the nitrogen to which they are attached form a 5- to 7-membered ring which may optionally contain a further heteroatom, wherein the 5- to 7-membered ring may optionally be substituted with one to three substituents that are independently selected from alkyl, cycloalkyl, alkenyl, alkynyl, aralkyl, CN, $CF_3$, $NO_2$, $OR^0$, $CO_2R^0$, $C(O)R^0$, halo, aryl, and a heterocyclic ring;

r is 0 to 4;

s is 0 to 4;

m is 0 to 4; to each $R^0$ is independently selected from H, alkyl, cycloalkyl, aralkyl, aryl and a heterocyclic ring.

In a further preferred embodiment, the present invention provides inhibitors of the $P210^{BCR-ABL-T315I}$ theramutein having the formula $III_b$

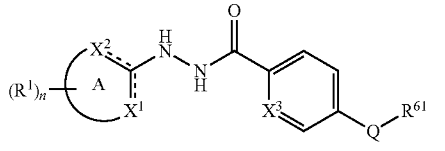

wherein:

ring A is a 5-, 6-, or 7-membered ring or a 7- to 12-membered fused bicyclic ring;

$X^1$ is selected from N, N—$R^0$ or C—$R^1$;

$X^2$ is selected from N, N—$R^0$ or C—$R^1$;

the dotted lines represent optional double bonds;

each $R^1$ is independently selected from the group consisting of H, alkyl, cycloalkyl, alkenyl, alkynyl, aralkyl, CN, $CF_3$, $NO_2$, $OR^{11}$, $-(CH_2)_pC(O)(CH_2)_qR^{11}$, $-(CH_2)_pC(O)N(R^{12})(R^{13})$, $-(CH_2)_pC(O)O(CH_2)_qR^{11}$, $-(CH_2)_pN(R^{11})C(O)R^{11}$, $(CH_2)_pN(R^{12})(R^{13})$, $-N(R^{11})SO_2R^{11}$, $-OC(O)N(R^{12})(R^{13})$, $-SO_2N(R^{12})(R^{13})$, halo, aryl, and a heterocyclic ring, and additionally or alternatively, two $R^1$ groups on adjacent ring atoms form a 5- or 6-membered fused ring which contains from 0 to 3 heteroatoms;

n is 0 to 6, each $R^{11}$ is independently selected from H, alkyl, cycloalkyl, alkenyl, alkynyl, aralkyl, aryl, and a heterocyclic ring;

each $R^{12}$ and $R^{13}$ are independently selected from H, alkyl, cycloalkyl, alkenyl, alkynyl, aralkyl, aryl, and a heterocyclic ring; or $R^{12}$ and $R^{13}$ may be taken together with the nitrogen to which they are attached form a 5- to 7-membered ring which may optionally contain a further heteroatom, wherein the 5- to 7-membered ring may optionally be substituted with one to three substituents that are independently selected from alkyl, cycloalkyl, alkenyl, alkynyl, aralkyl, CN, $CF_3$, $NO_2$, $OR^0$, $CO_2R^0$, $C(O)R^0$, halo, aryl, and a heterocyclic ring;

p is 0 to 4;

q is 0 to 4;

$X^3$ is N or CH;

$R^{61}$ is selected from aryl and a heterocyclic ring;

Q is selected from a chemical bond or a group having the formula —O—, $-(CH_2)_i-$, $-(CH_2)_iC(O)(CH_2)_j-$, $-(CH_2)_i-N(R^{62})-(CH_2)_j-$, $-(CH_2)_iC(O)-N(R^{62})-(CH_2)_j-$, $-(CH_2)_iC(O)O(CH_2)_j-$, $-(CH_2)_iN(R^{62})C(O)-(CH_2)_j-$, $-(CH_2)_iOC(O)N(R^{62})-(CH_2)_j-$, and $-O-(CH_2)_i-C(O)N(R^{62})-(CH_2)_j-$;

$R^{62}$ is selected from H, alkyl, aryl, and a heterocyclic ring;

each $R^0$ is independently selected from H, alkyl, cycloalkyl, aralkyl, aryl and a heterocyclic ring;

h is 0 to 4;

i is 0 to 4; and j is 0 to 4.

In a further preferred embodiment, the present invention provides inhibitors of the $P210^{BCR-ABL-T315I}$ theramutein having the formula $III_c$

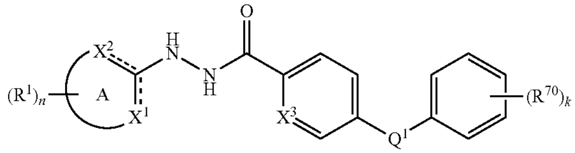

wherein:

ring A is a 5-, 6-, or 7-membered ring or a 7- to 12-membered fused bicyclic ring;

$X^1$ is selected from N, N—$R^0$ or C—$R^1$;

$X^2$ is selected from N, N—$R^0$ or C—$R^1$;

the dotted lines represent optional double bonds;

each $R^1$ is independently selected from the group consisting of H, alkyl, cycloalkyl, alkenyl, alkynyl, aralkyl, CN, $CF_3$, $NO_2$, $OR^{11}$, $-(CH_2)_pC(O)(CH_2)_qR^{11}$, $-(CH_2)_pC(O)N(R^{12})(R^{13})$, $-(CH_2)_pC(O)O(CH_2)_qR^{11}$, $-(CH_2)_pN(R^{11})C(O)R^{11}$, $-(CH_2)_pN(R^{12})(R^{13})$, $-N(R^{11})SO_2R^{11}$, $-OC(O)N(R^{12})(R^{13})$, $-SO_2N(R^{12})(R^{13})$, halo, aryl, and a heterocyclic ring, and additionally or alternatively, two $R^1$ groups on adjacent ring atoms form a 5- or 6-membered fused ring which contains from 0 to 3 heteroatoms;

n is 0 to 6, each $R^{11}$ is independently selected from H, alkyl, cycloalkyl, alkenyl, alkynyl, aralkyl, aryl, and a heterocyclic ring;

each $R^{12}$ and $R^{13}$ are independently selected from H, alkyl, cycloalkyl, alkenyl, alkynyl, aralkyl, aryl, mid a heterocyclic ring; or $R^{12}$ and $R^{13}$ may be taken together with the nitrogen to which they are attached form a 5- to 7-membered ring which may optionally contain a further heteroatom, wherein the 5- to 7-membered ring may optionally be substituted with one to three substituents that are independently selected from alkyl, cycloalkyl, alkenyl, alkynyl, aralkyl, CN, $CF_3$, $NO_2$, $OR^0$, $CO_2R^0$, $C(O)R^0$, halo, aryl, and a heterocyclic ring;

p is 0 to 4;

q is 0 to 4;

$X^3$ is N or CH;

each $R^0$ is independently selected from H, alkyl, cycloalkyl, aralkyl, aryl and a heterocyclic ring;

$Q^1$ is selected from a chemical bond or a group having the formula —O—, —$CH_2$—, —NH—, —C(O)—NH—, —C(O)O—, —NH—C(O)—, —OC(O)NH—, and —O—C(O)NH—;

each $R^{70}$ is selected from halo, alkyl, CN, $N(R^{71})_2$, cyclic-amino, $NO_2$, $OR^{71}$, and $CF_3$, each $R^{71}$ is selected from H, alkyl, aryl, aralkyl and a heterocyclic ring; and k is 0 to 4.

In a further preferred embodiment, the present invention provides inhibitors of the $P210^{BCR\text{-}ABL\text{-}T315I}$ theramutein having the formula $III_d$

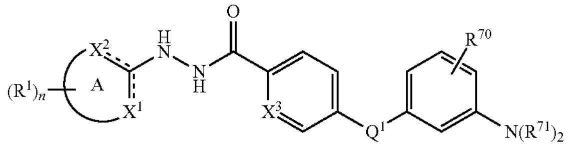

wherein:

ring A is a 5-, 6-, or 7-membered ring or a 7- to 12-membered fused bicyclic ring;

$X^1$ is selected from N, N—$R^0$ or C—$R^1$;

$X^2$ is selected from N, N—$R^0$ or C—$R^1$;

the dotted lines represent optional double bonds;

each $R^1$ is independently selected from the group consisting of H, alkyl, cycloalkyl, alkenyl, alkynyl, aralkyl, CN, $CF_3$, $NO_2$, $OR^{11}$, —$(CH_2)_pC(O)(CH_2)_qR^{11}$, —$(CH_2)_pC(O)N(R^{12})(R^{13})$, —$(CH_2)_pC(O)O(CH_2)_qR^{11}$, —$(CH_2)_pN(R^{11})C(O)R^{11}$, —$(CH_2)_pN(R^{12})(R^{13})$, —$N(R^{11})SO_2R^{11}$, —$OC(O)N(R^{12})(R^{13})$, —$SO_2N(R^{12})(R^{13})$, halo, aryl, and a heterocyclic ring, and additionally or alternatively, two $R^1$ groups on adjacent ring atoms form a 5- or 6-membered fused ring which contains from 0 to 3 heteroatoms;

n is 0 to 6, each $R^{11}$ is independently selected from H, alkyl, cycloalkyl, alkenyl, alkynyl, aralkyl, aryl, and a heterocyclic ring;

each $R^{12}$ and $R^{13}$ are independently selected from H, alkyl, cycloalkyl, alkenyl, alkynyl, aralkyl, aryl, and a heterocyclic ring; or $R^{12}$ and $R^{13}$ may be taken together with the nitrogen to which they are attached form a 5- to 7-membered ring which may optionally contain a further heteroatom, wherein the 5- to 7-membered ring may optionally be substituted with one to three substituents that are independently selected from alkyl, cycloalkyl, alkenyl, alkynyl, aralkyl, CN, $CF_3$, $NO_2$, $OR^0$, $CO_2R^0$, $C(O)R^0$, halo, aryl, and a heterocyclic ring;

p is 0 to 4;

q is 0 to 4;

each $R^0$ is independently selected from H, alkyl, cycloalkyl, aralkyl, aryl and a heterocyclic ring;

$R^8$ is selected from H and $CH_3$;

$X^3$ is N or CH;

$Q^1$ is selected from a chemical bond or a group having the formula —O—, —$CH_2$—, —NH—, —C(O)—NH—, —C(O)O—, —NH—C(O)—, —OC(O)NH—, and —O—C(O)NH—;

each $R^{70}$ is selected from halo, alkyl, CN, $N(R^{71})_2$, cyclic-amino, $NO_2$, $OR^{71}$, and $CF_3$; and each $R^{71}$ is selected from H and alkyl.

In a further preferred embodiment, the present invention provides inhibitors of the $P210^{BCR\text{-}ABL\text{-}T315I}$ theramutein having the formula $III_e$

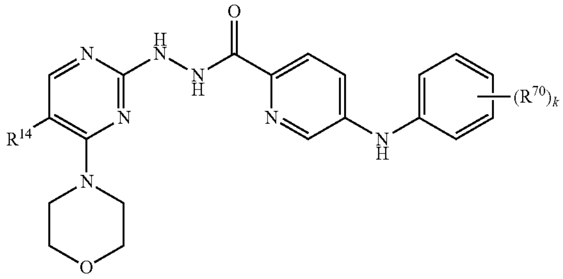

wherein $R^{14}$ is selected from H and F;

each $R^{70}$ is selected from halo, alkyl, CN, $N(R^{71})_2$, cyclic-amino, $NO_2$, $OR^{71}$, and $CF_3$, each $R^{71}$ is selected from H, alkyl, aryl, aralkyl and a heterocyclic ring; and k is 0 to 4.

Exemplary compounds of the formula III, $III_a$, $III_b$, $III_c$, $III_d$, or $III_e$ includes the following structures:

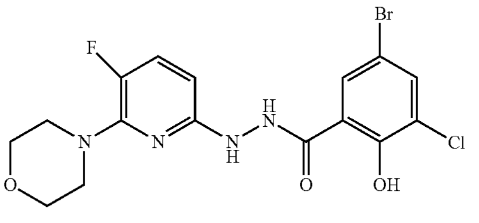

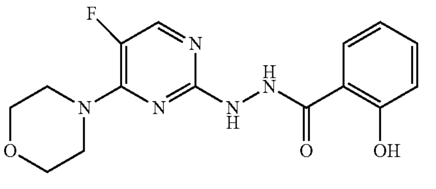

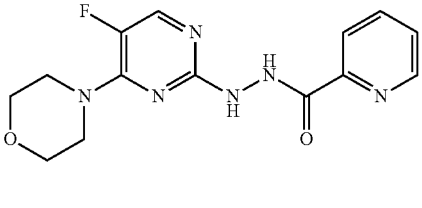

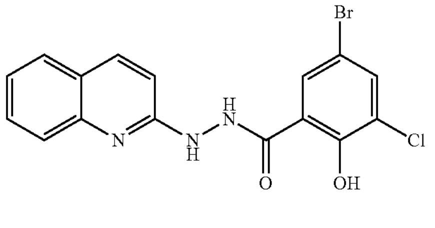

-continued
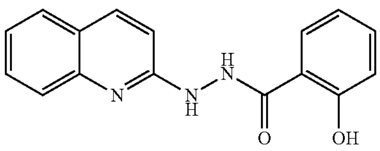
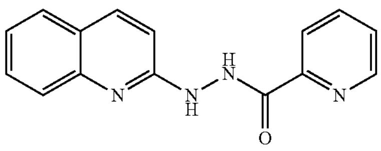
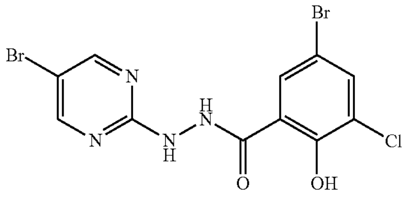
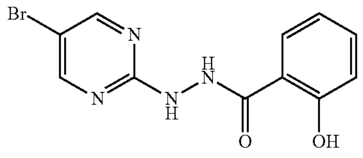
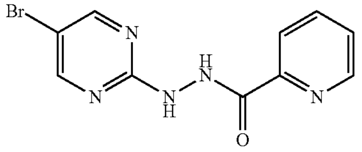
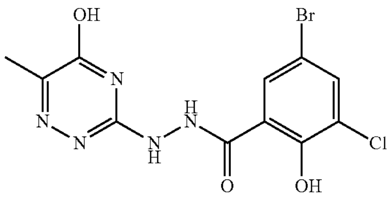
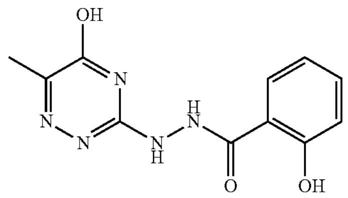
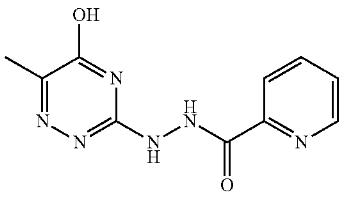
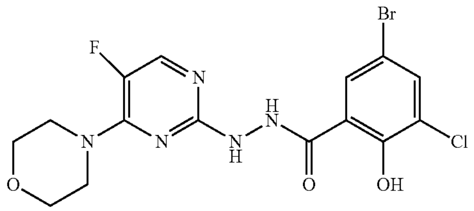
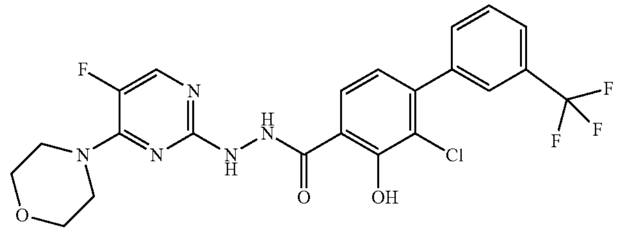
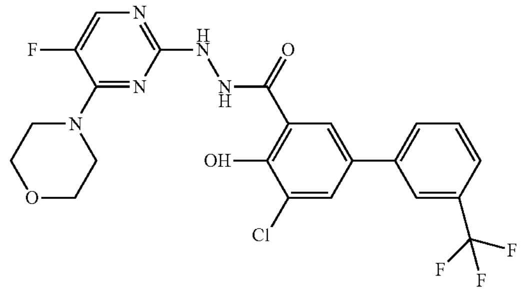
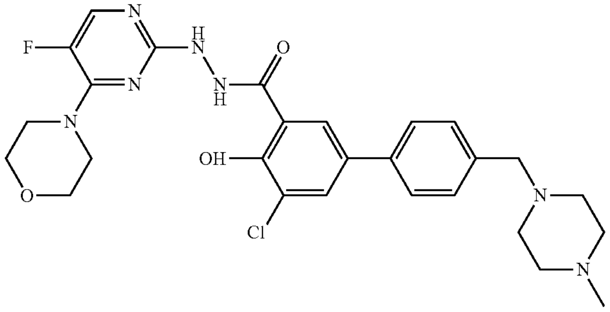
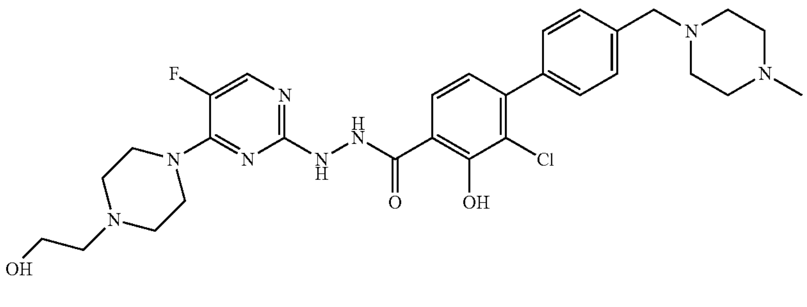

-continued
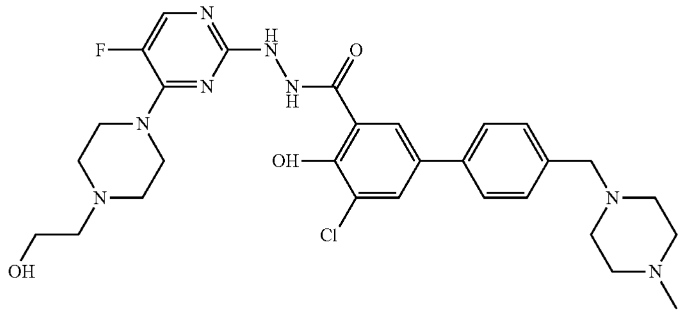
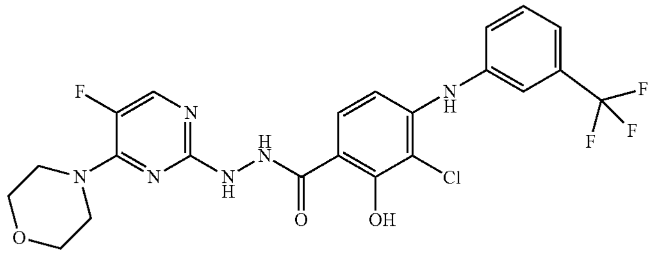
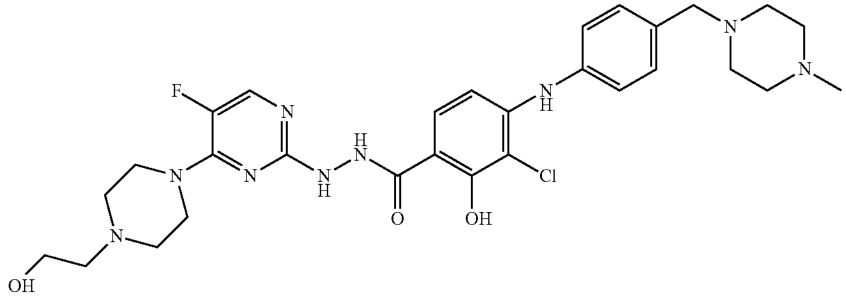
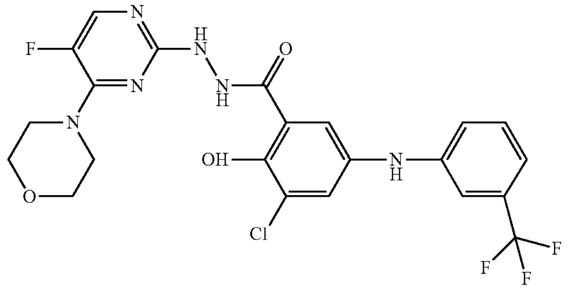
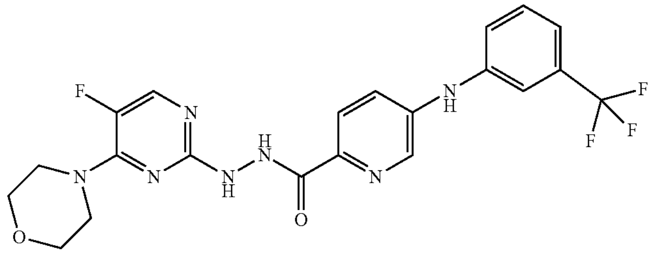
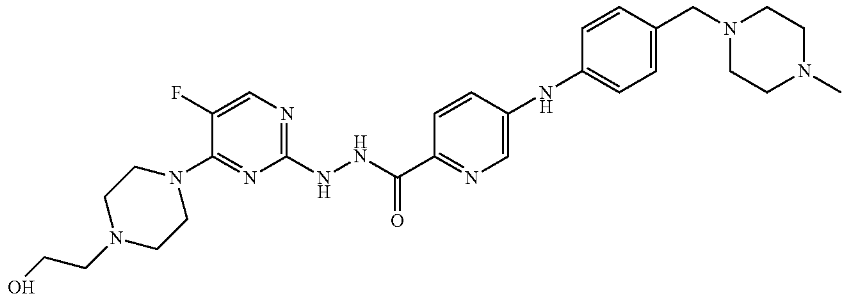

-continued
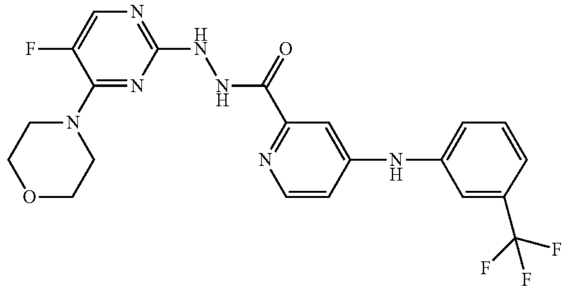
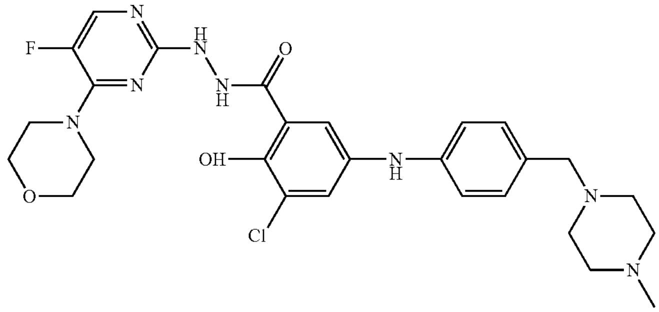
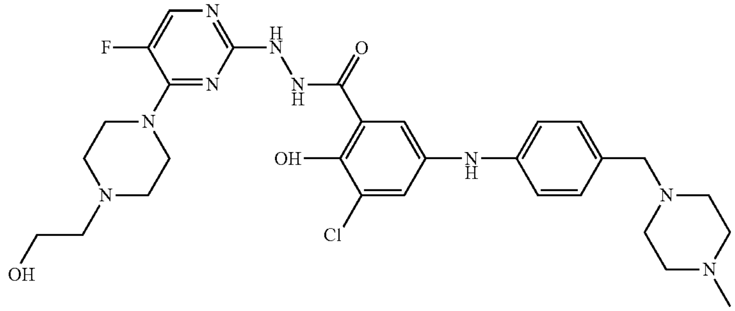
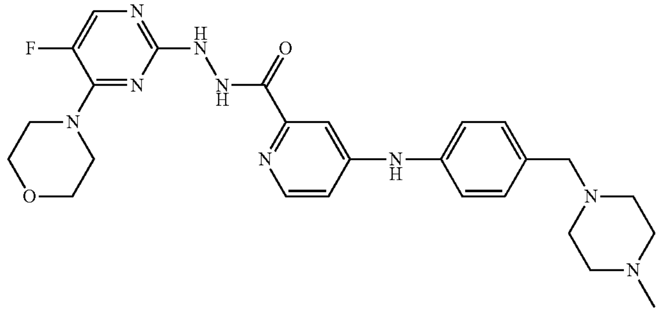
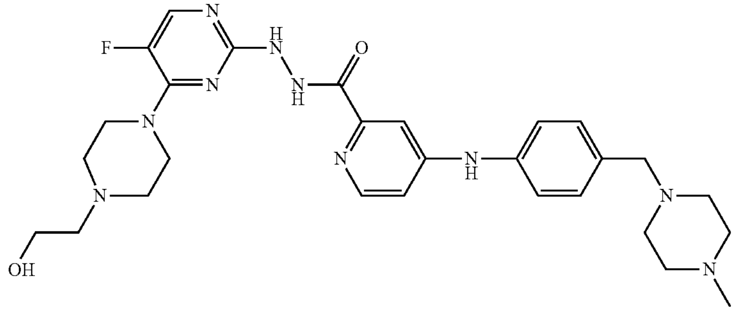

-continued
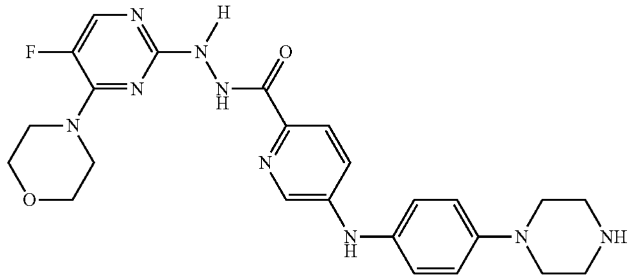
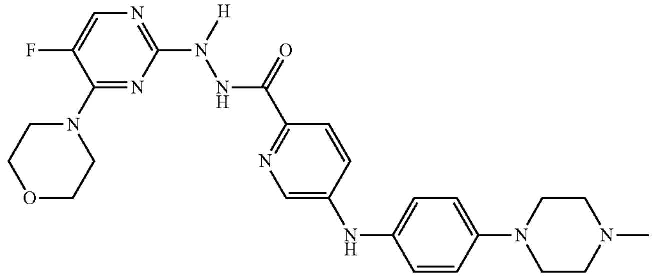
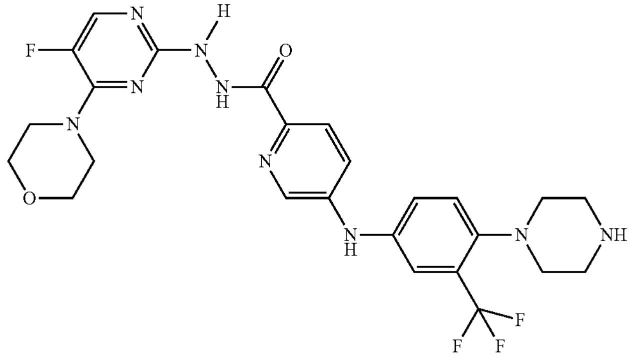
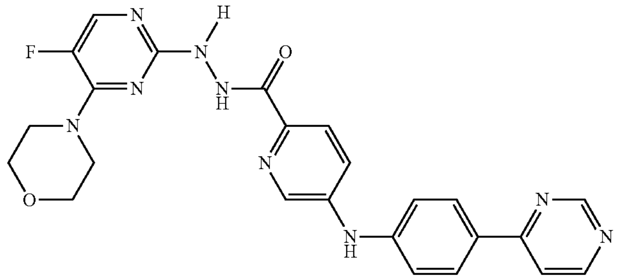
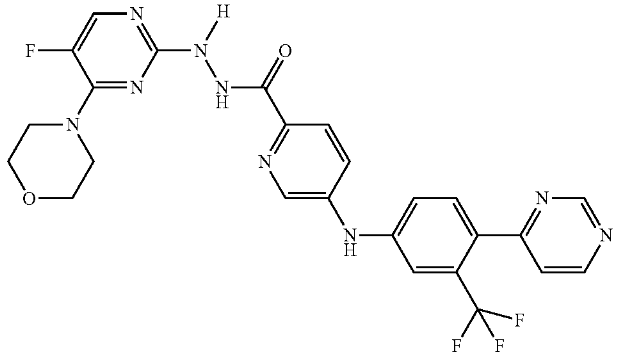

-continued
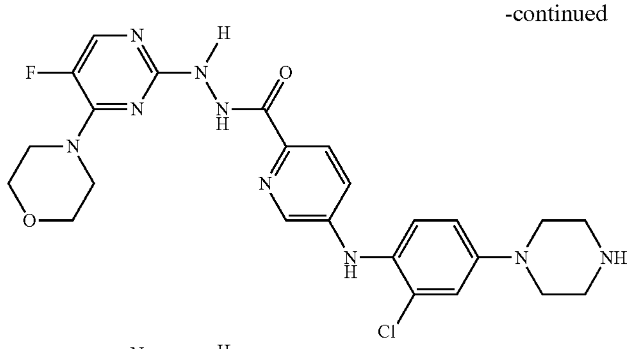
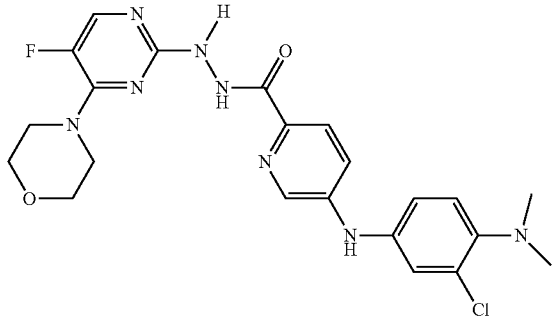
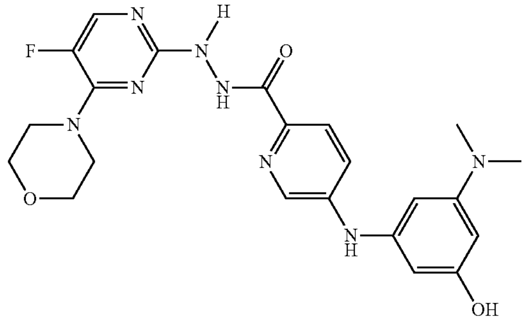
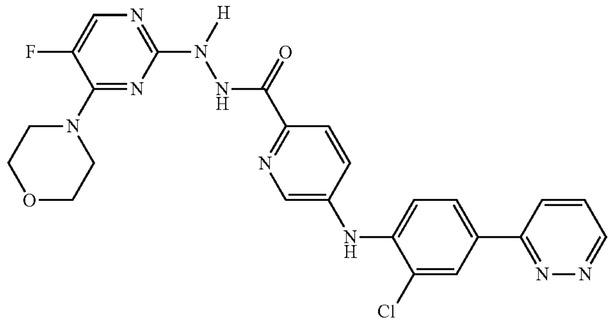
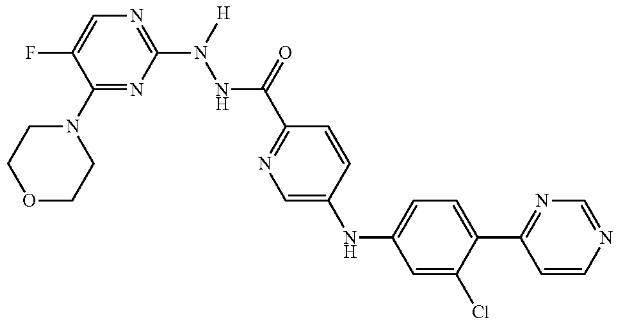
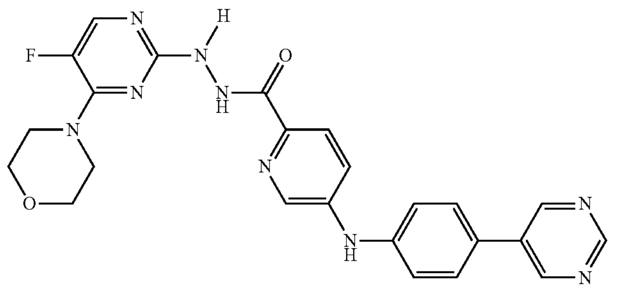

-continued
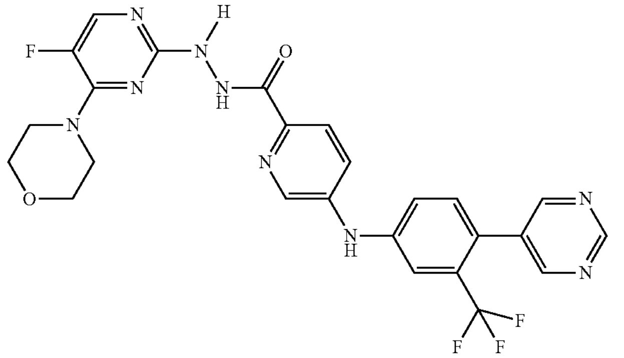
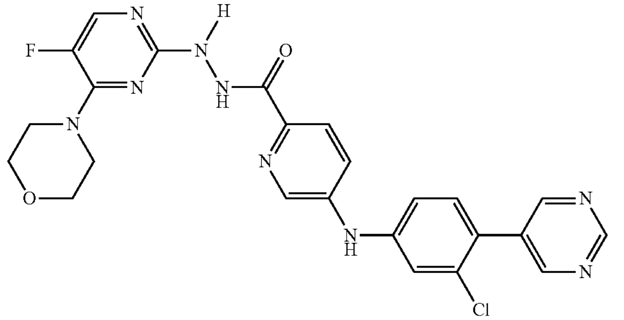
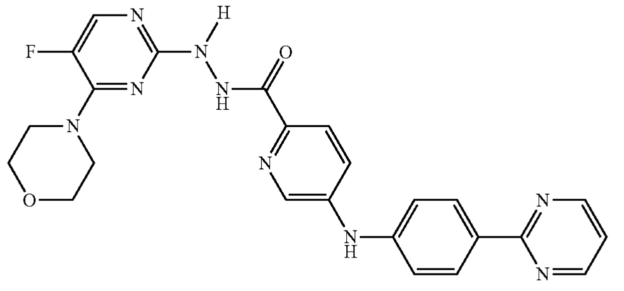
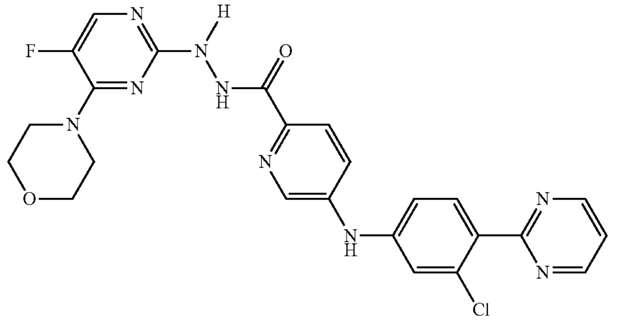
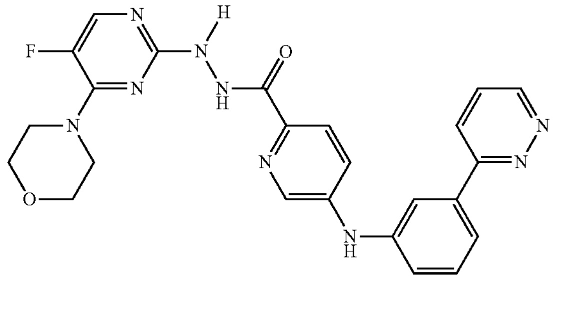
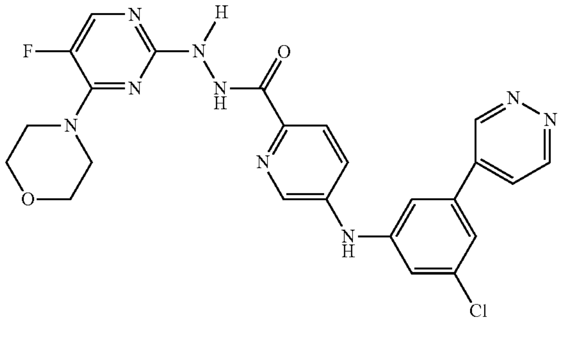

-continued
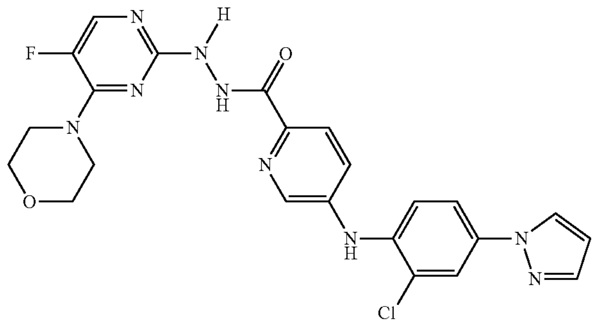
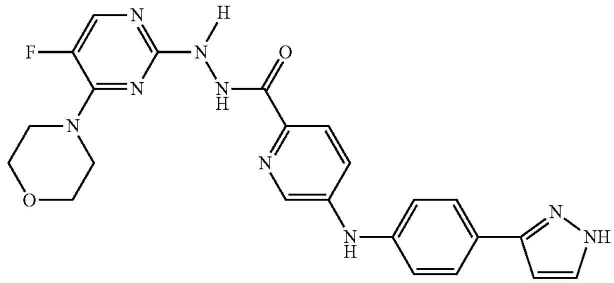
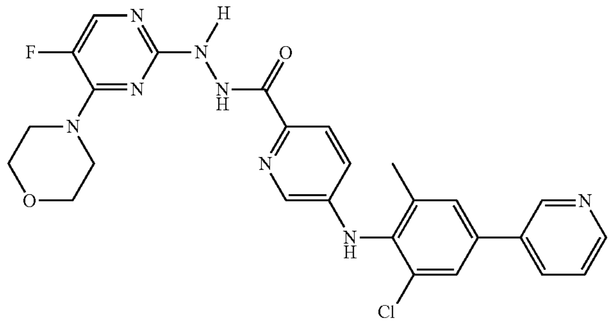
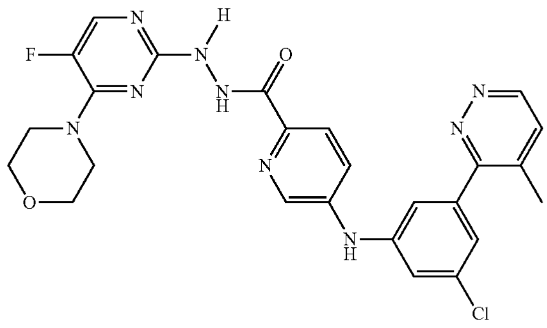
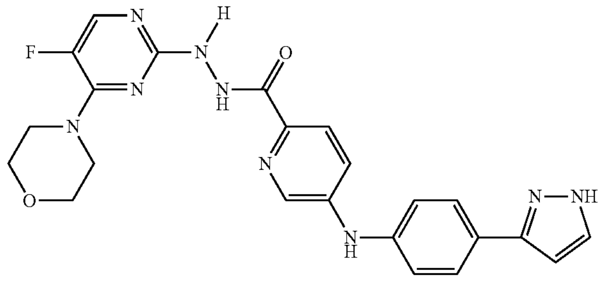

-continued
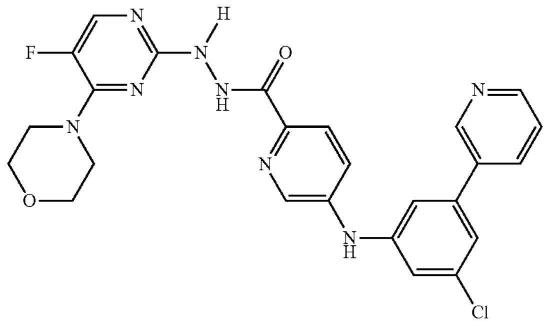
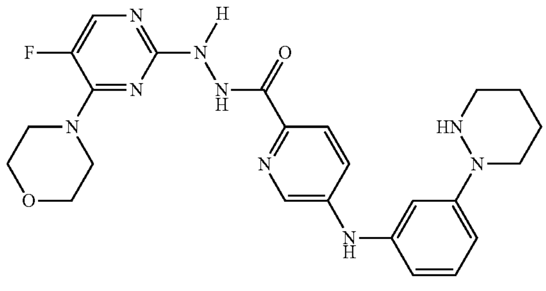
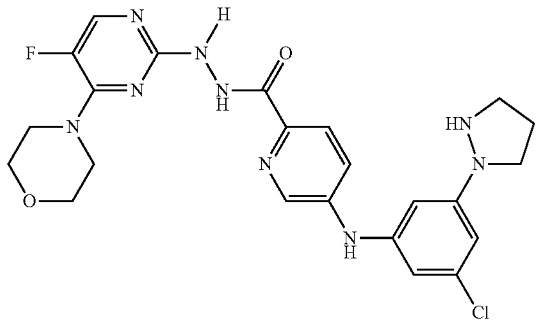
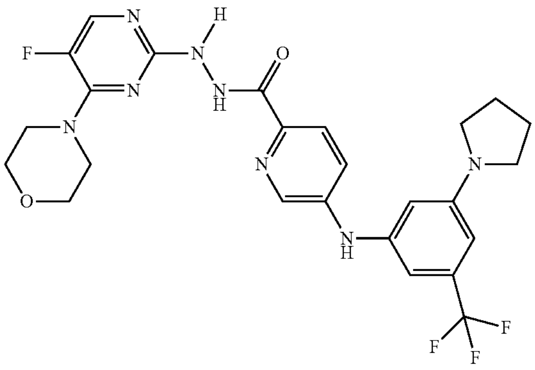
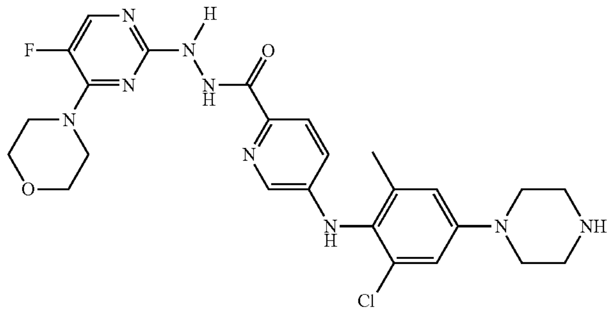
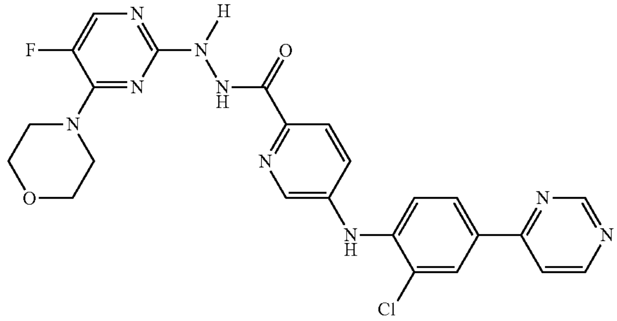
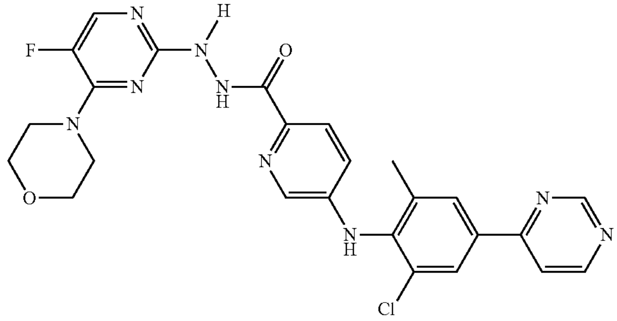

-continued
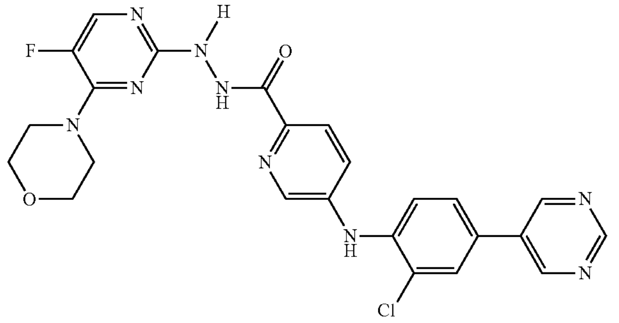
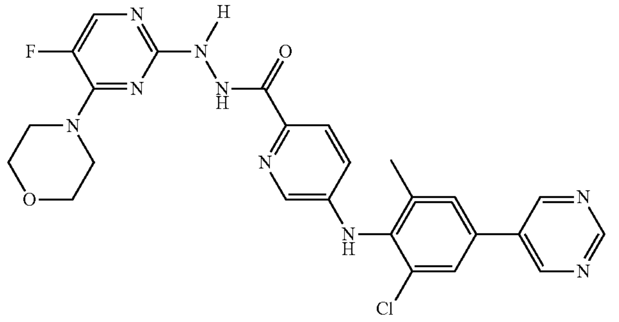
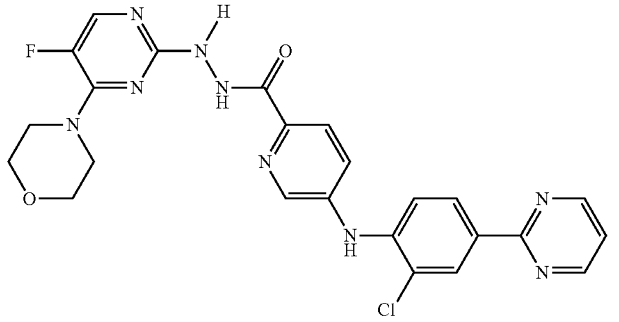
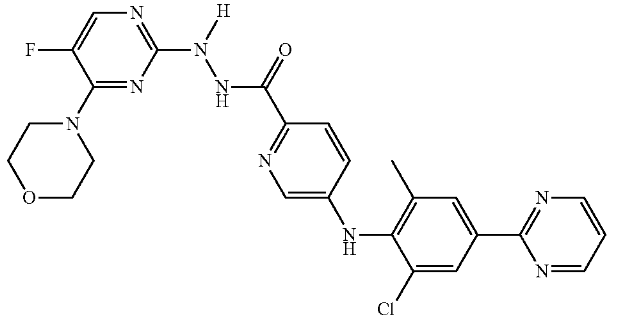
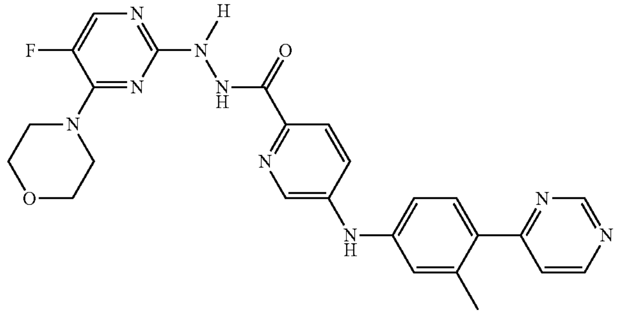

-continued
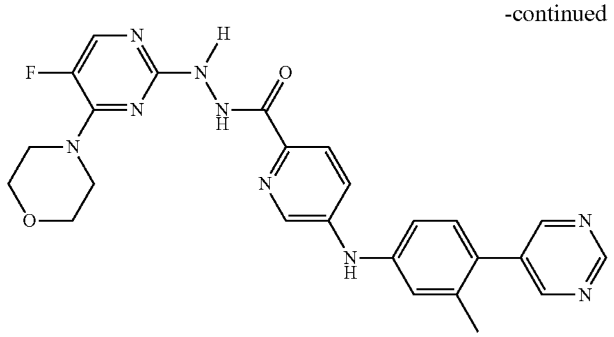
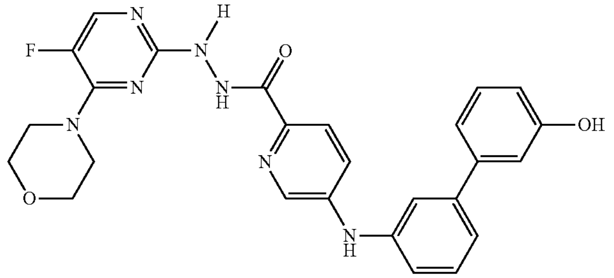
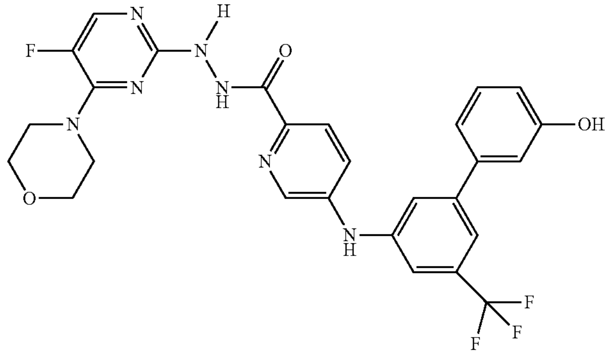
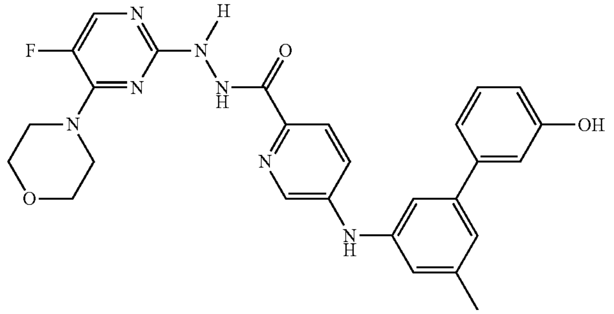
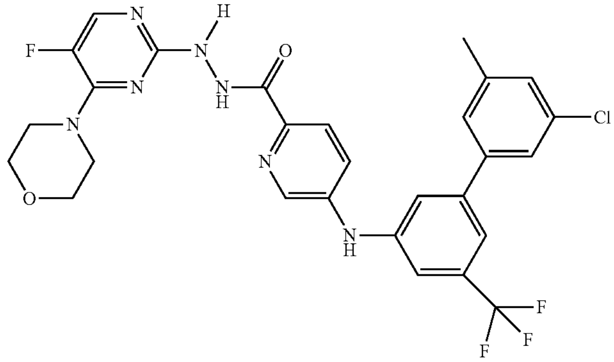

-continued
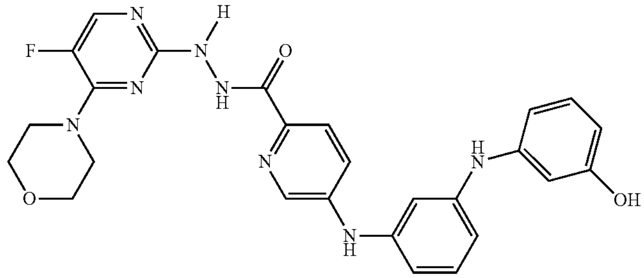
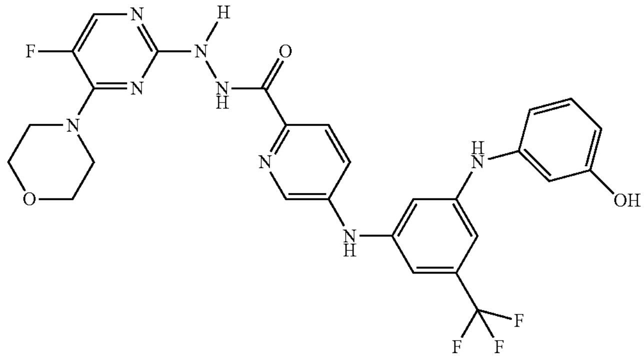
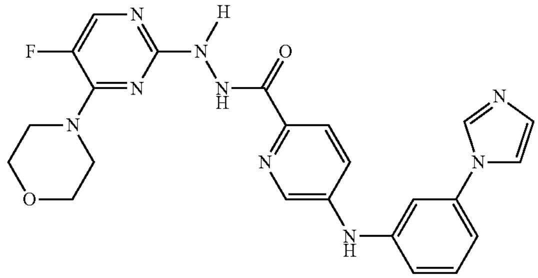
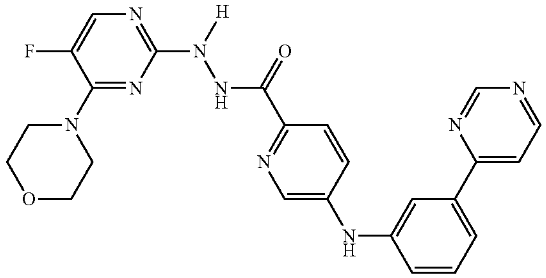
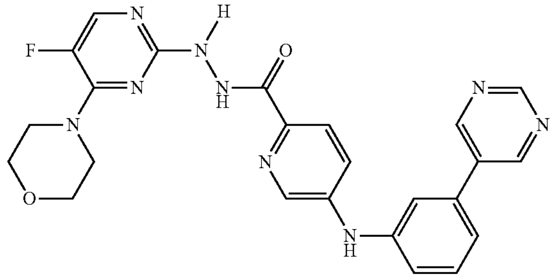
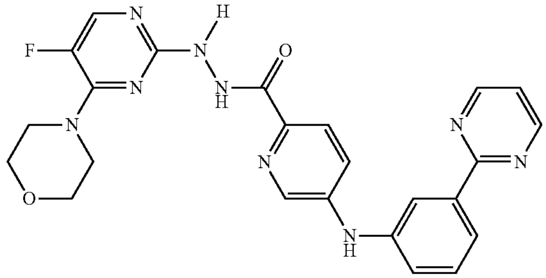
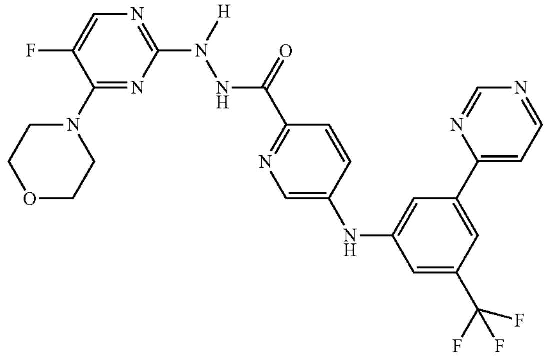
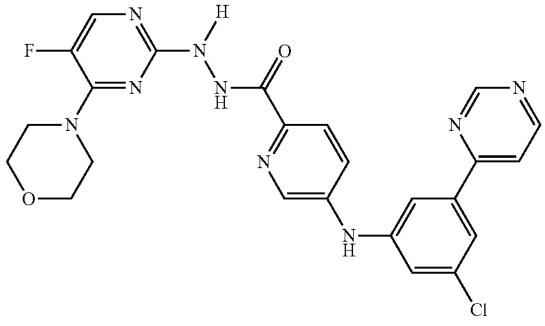

-continued
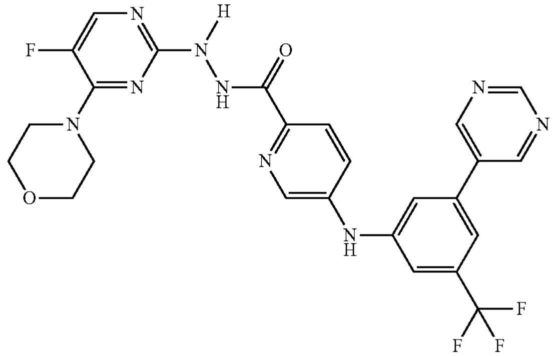
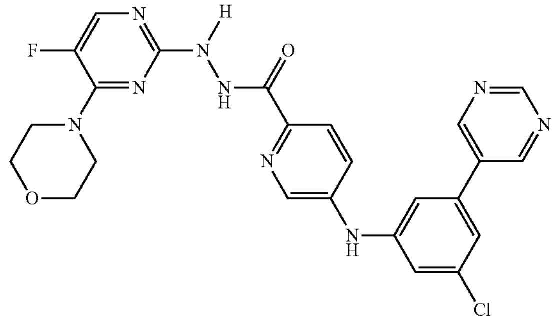
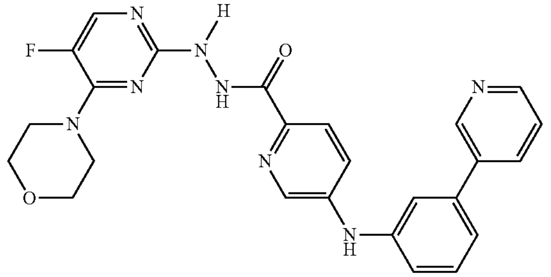
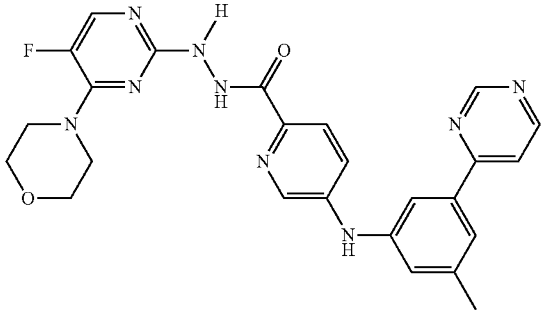
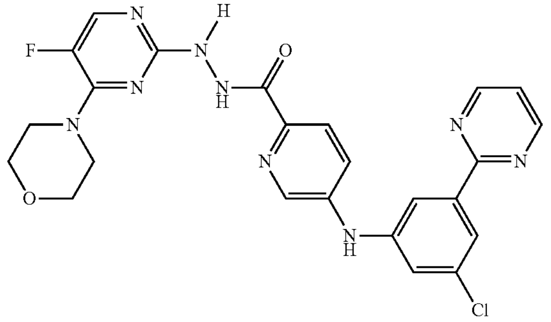
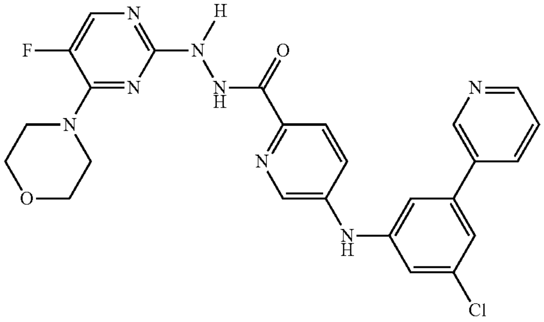
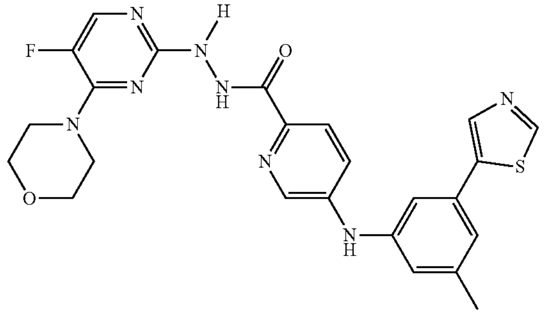
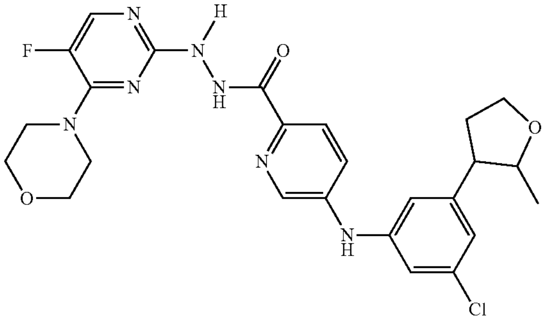
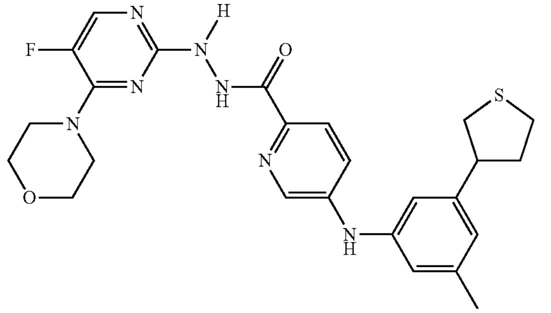
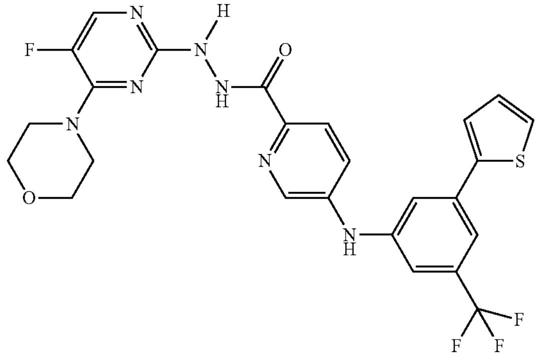

-continued
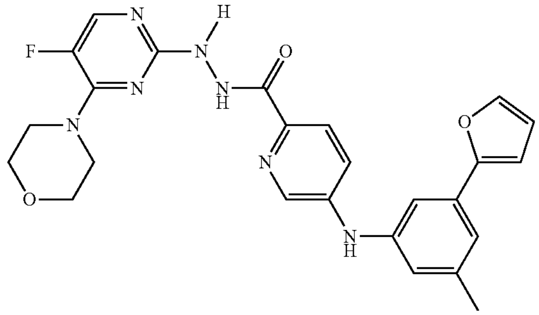
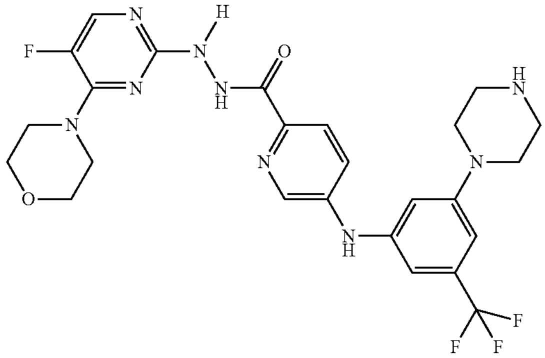
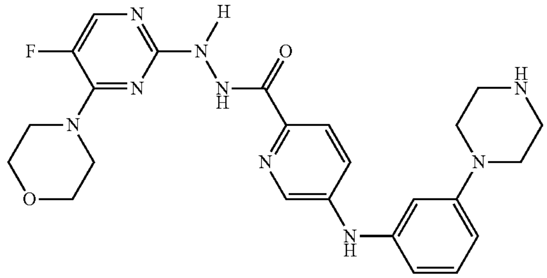
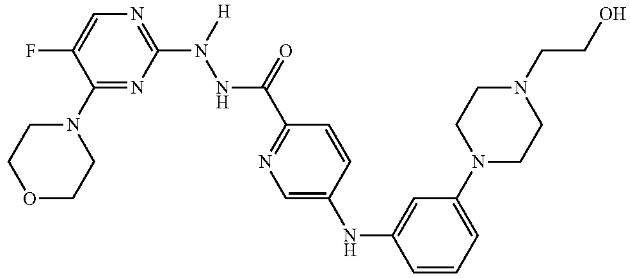
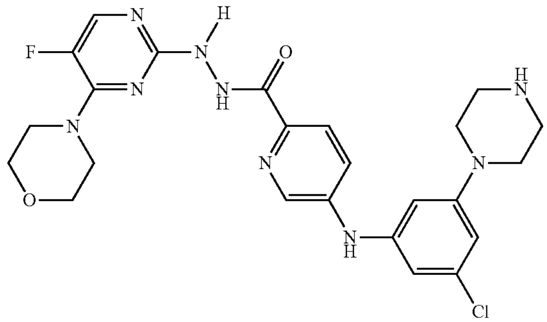
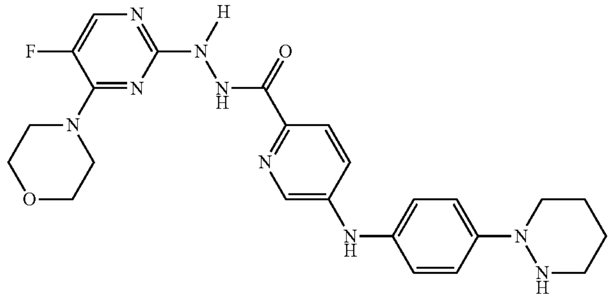

-continued
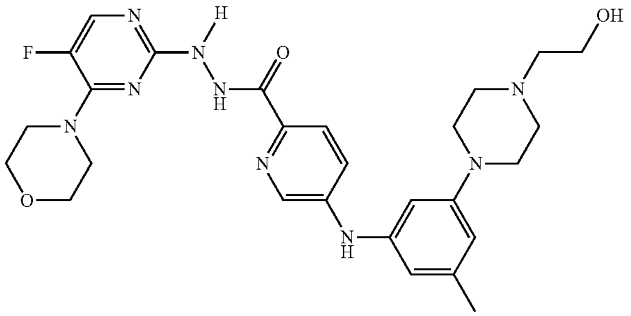
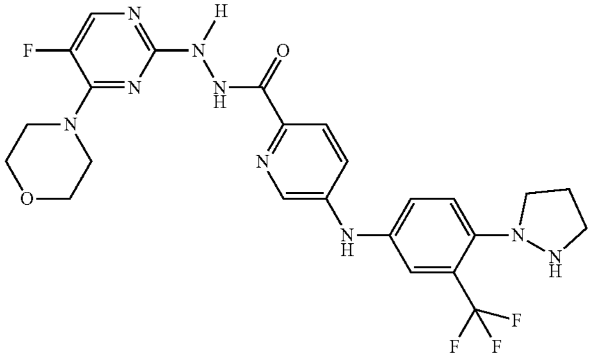
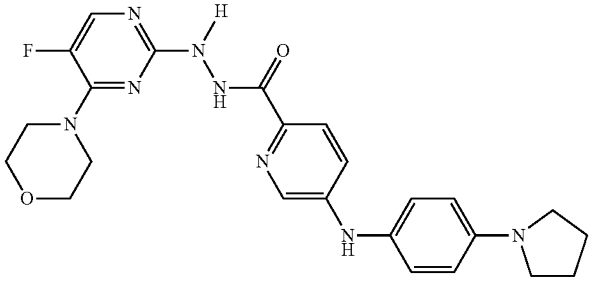
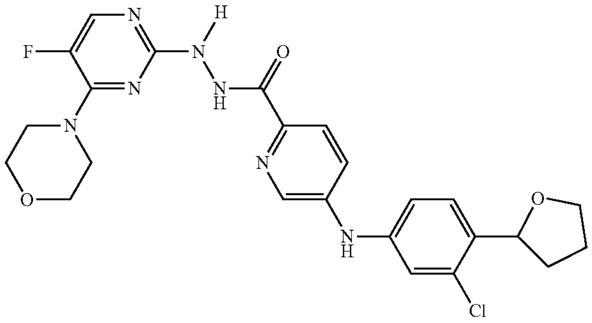
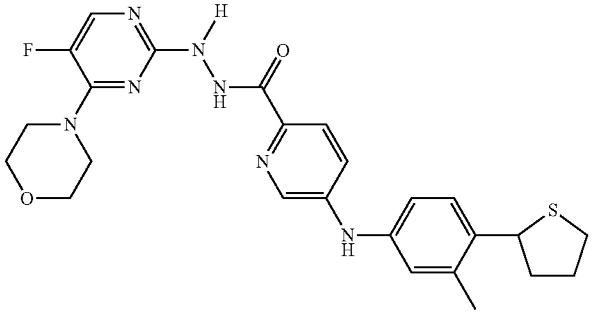

-continued
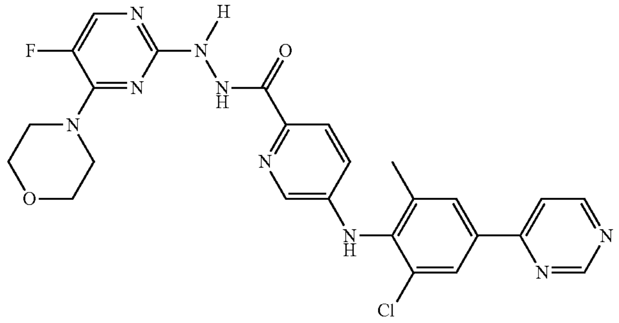
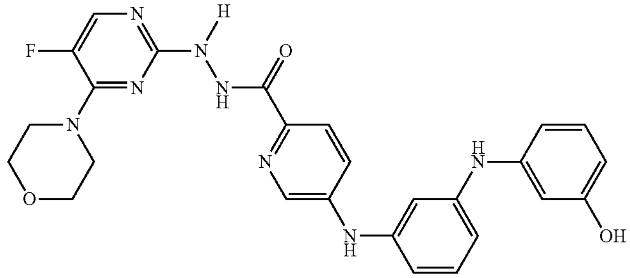
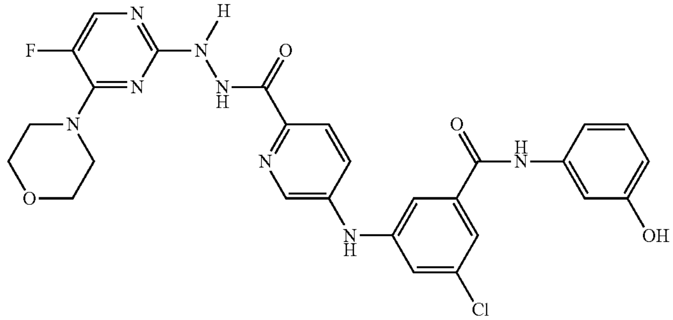
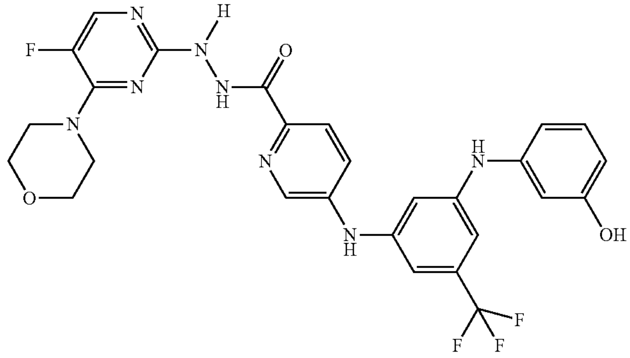
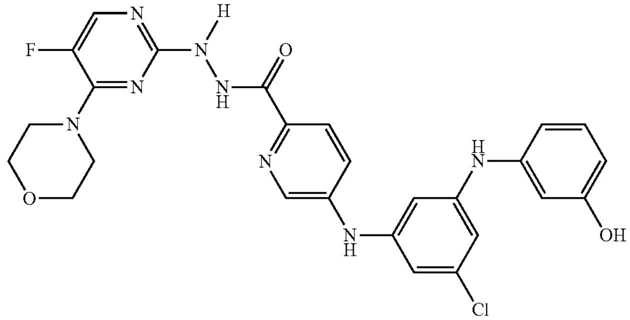

-continued
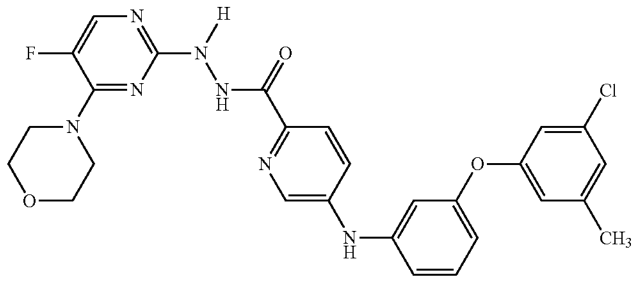
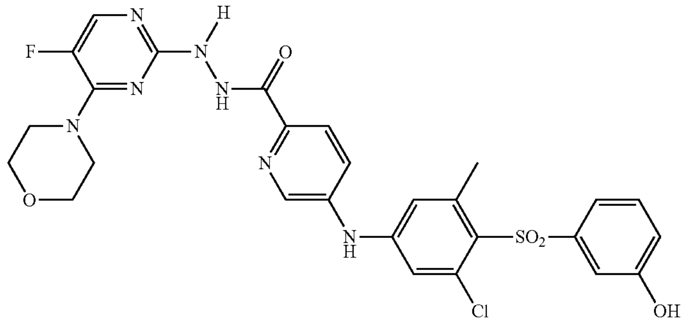
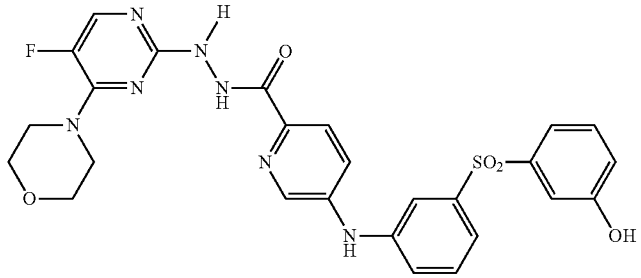
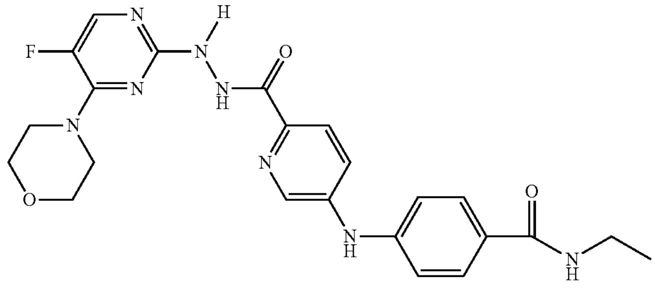
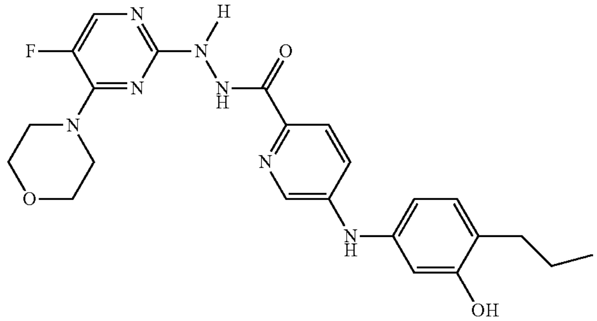

-continued
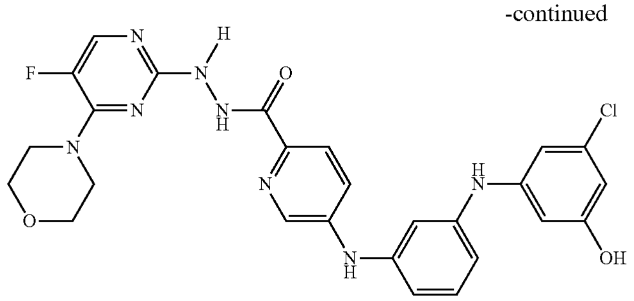
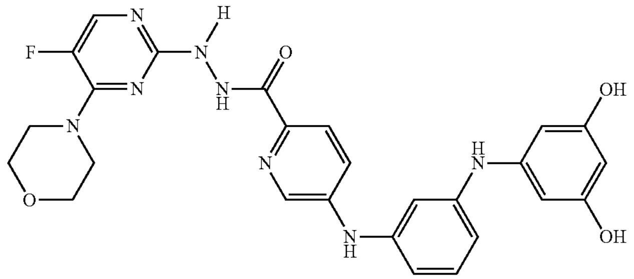
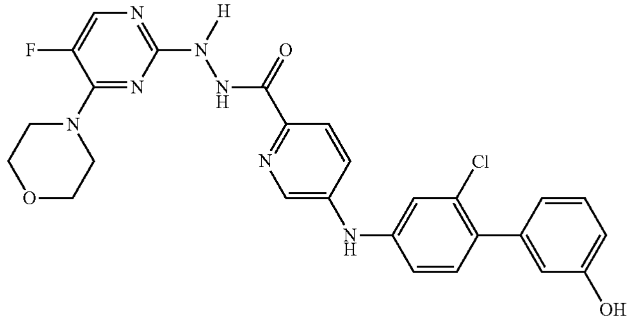
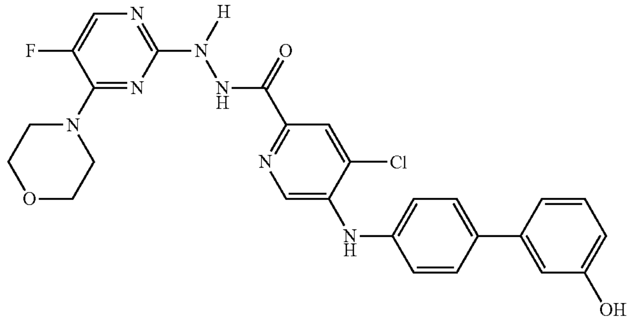
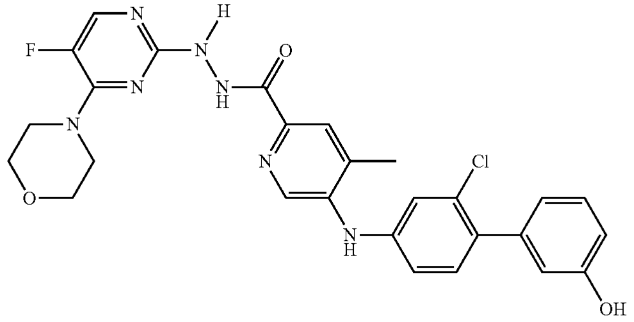

-continued
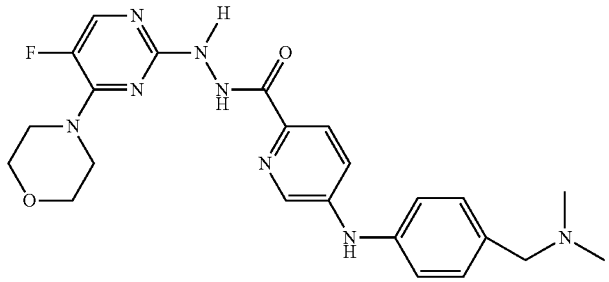
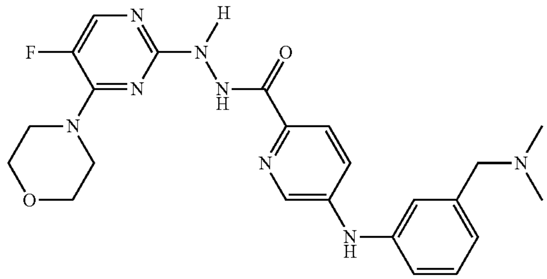
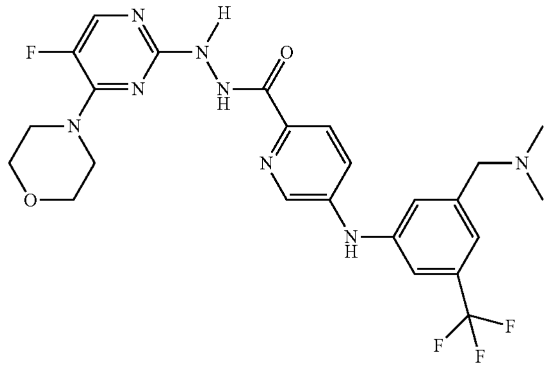
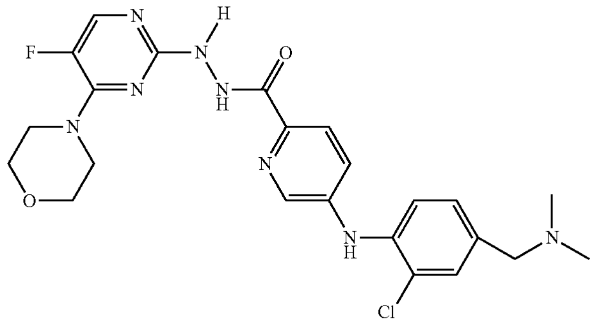
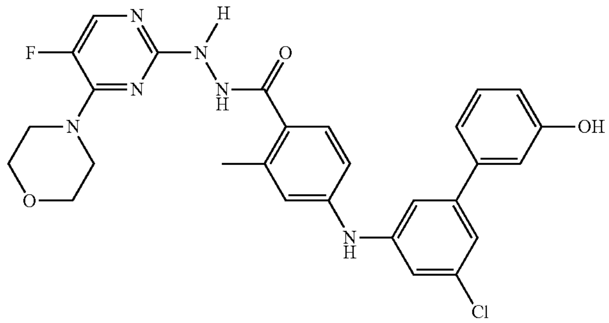
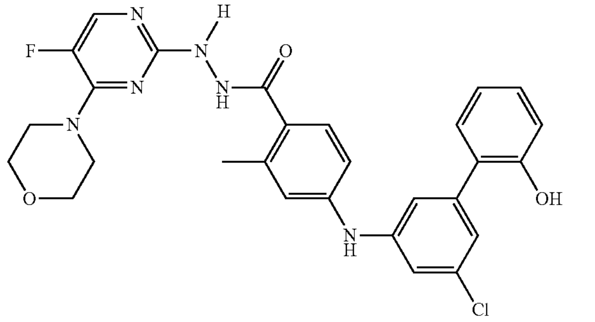

-continued
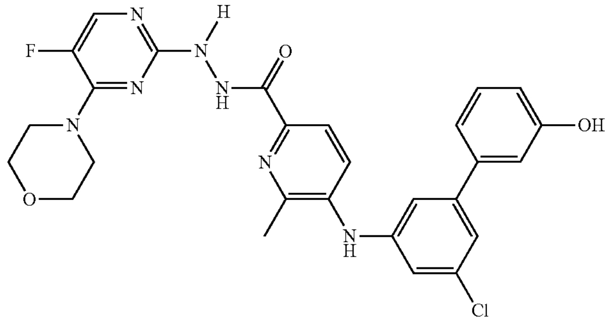
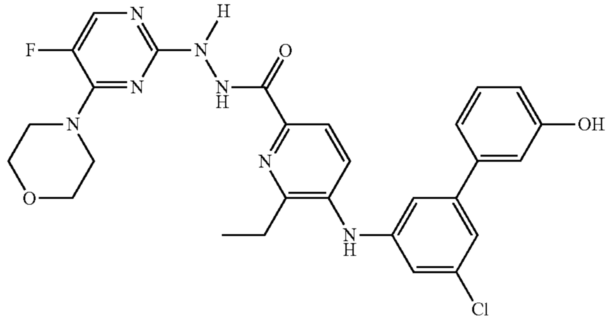
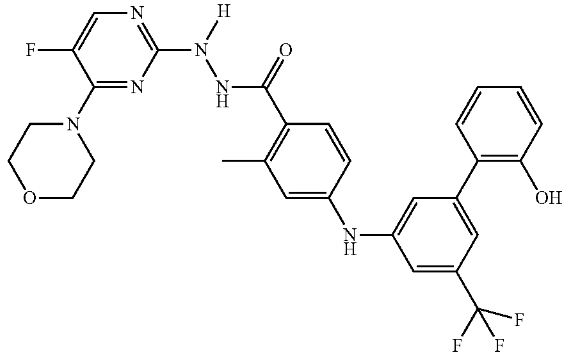
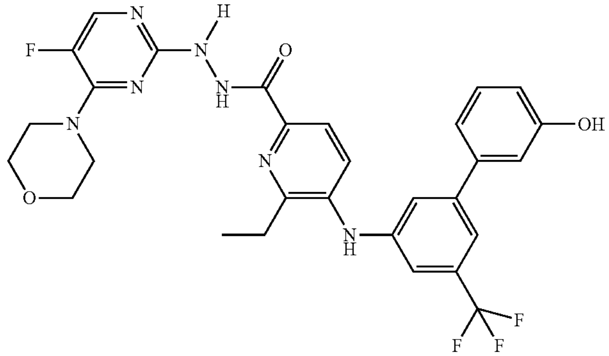
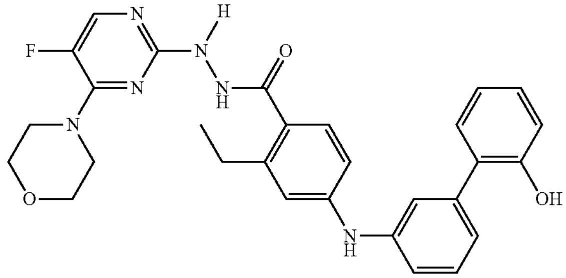
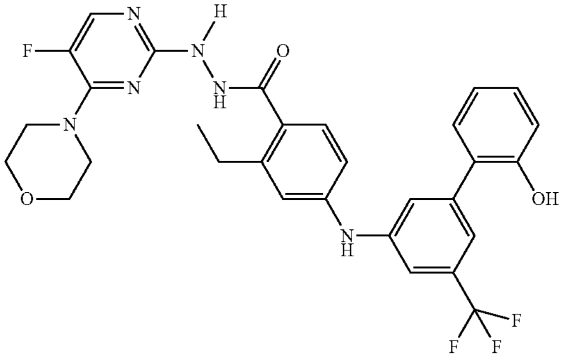

-continued
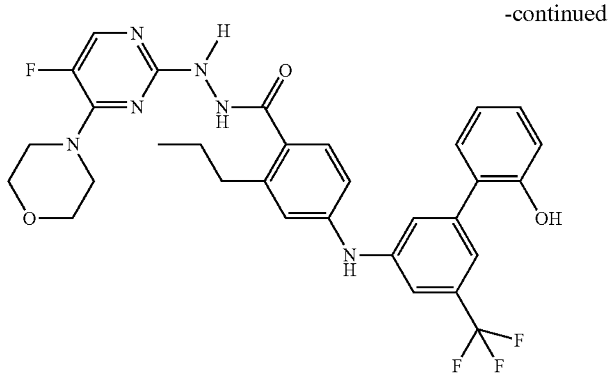
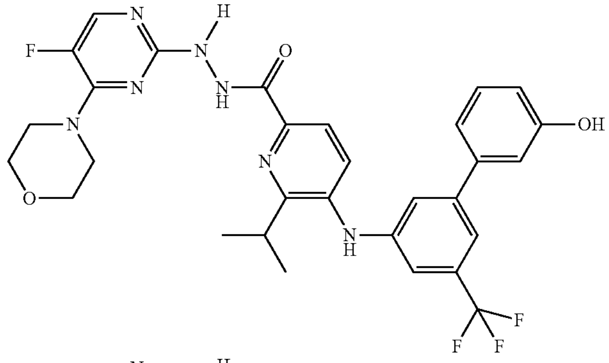
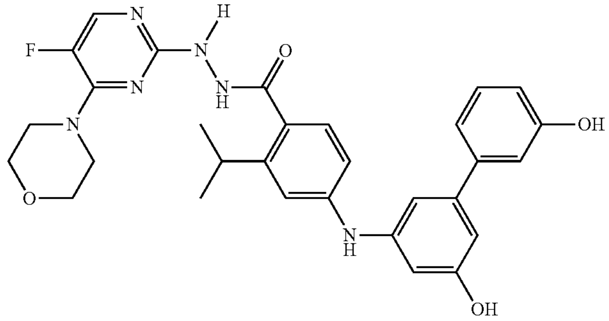
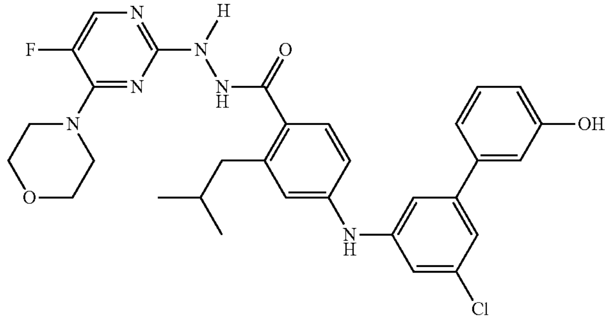
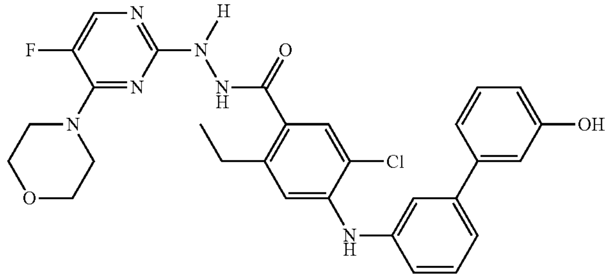

-continued
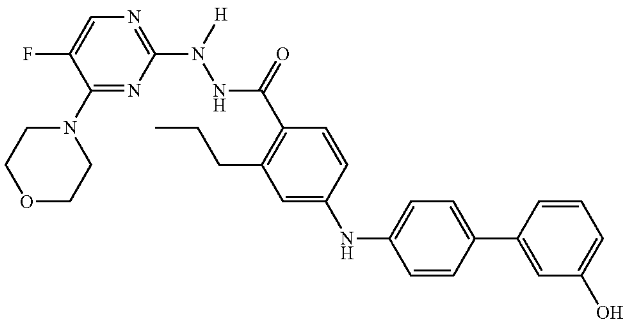
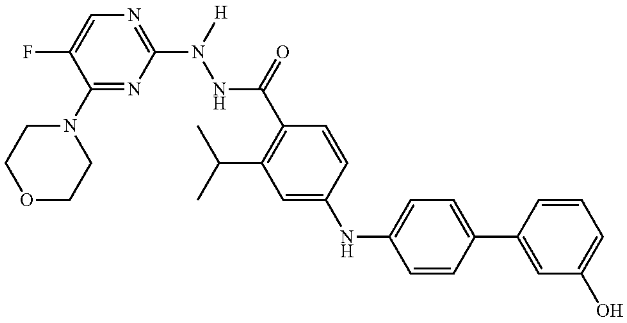
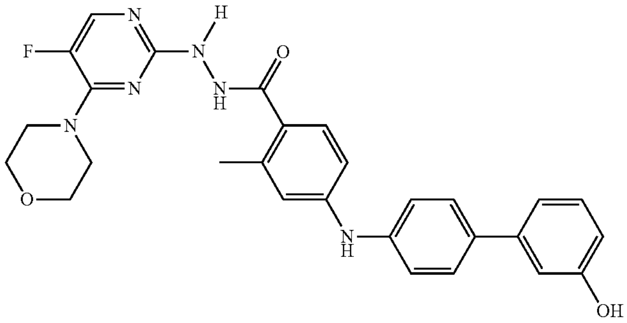
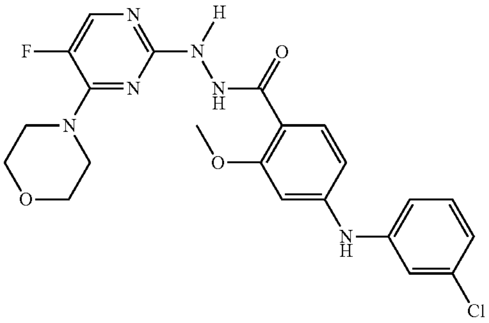
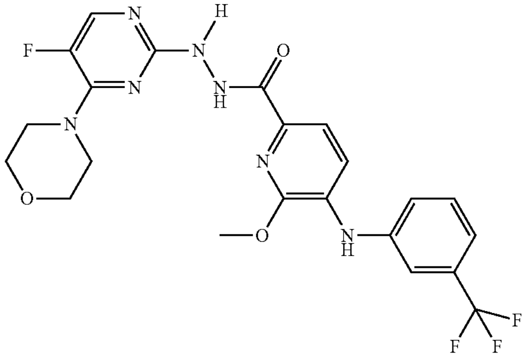
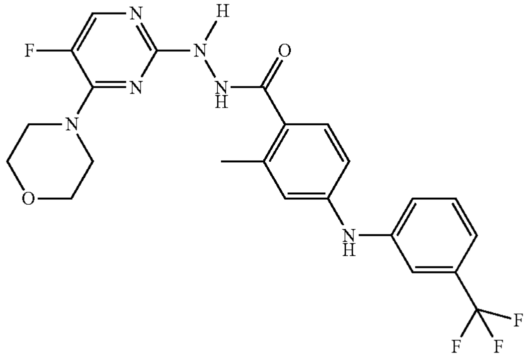
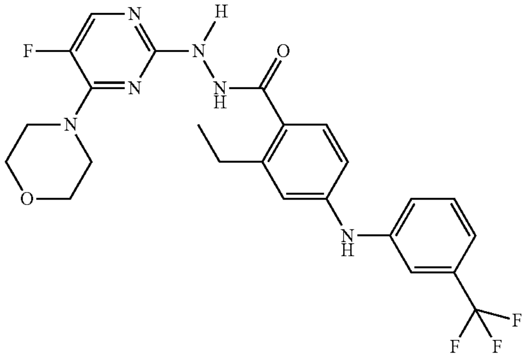
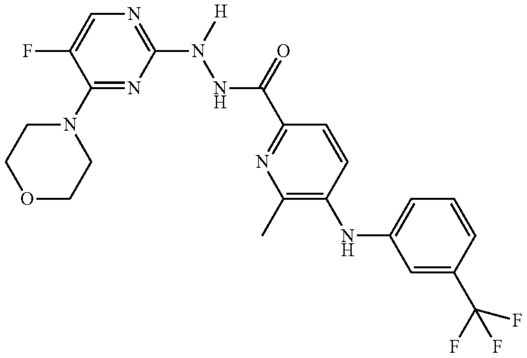

-continued
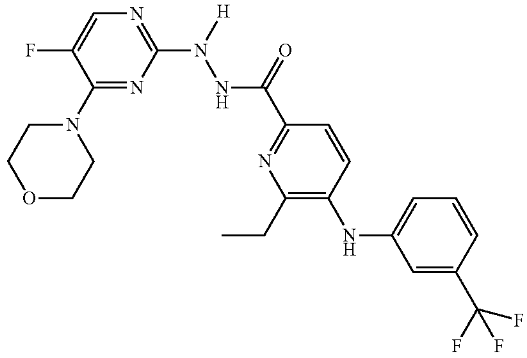
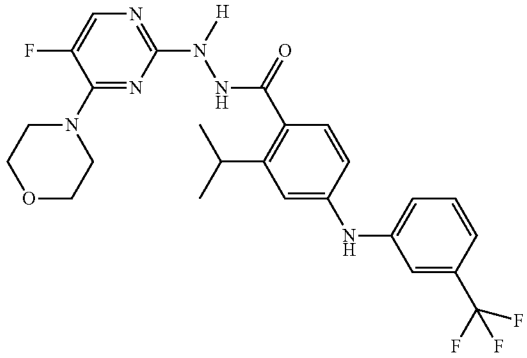
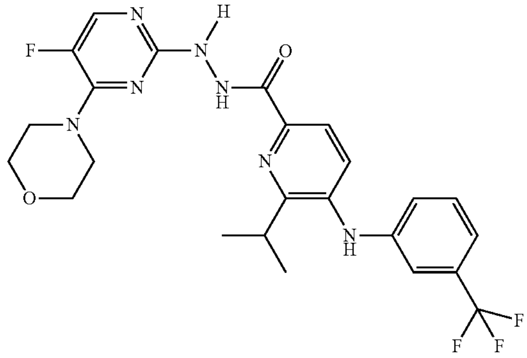
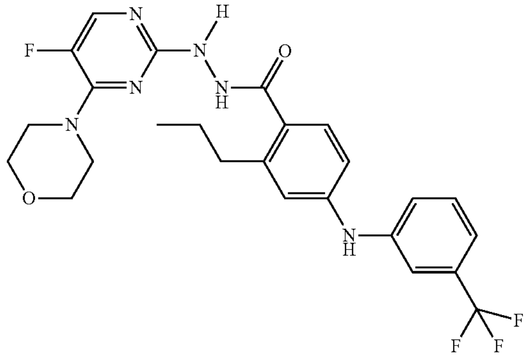
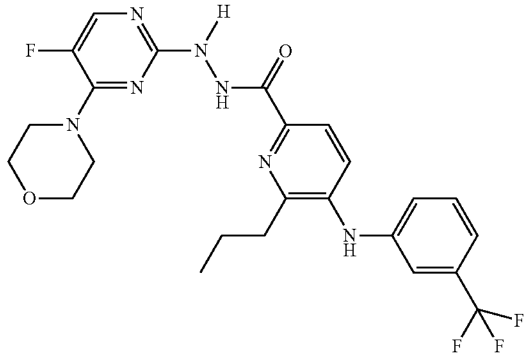
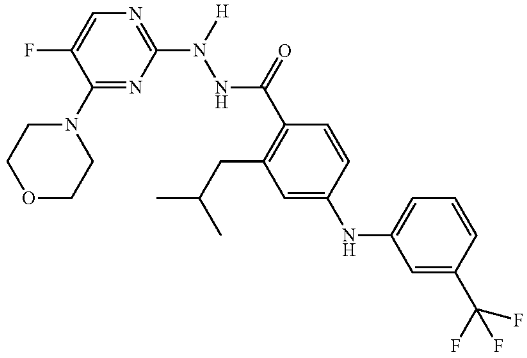
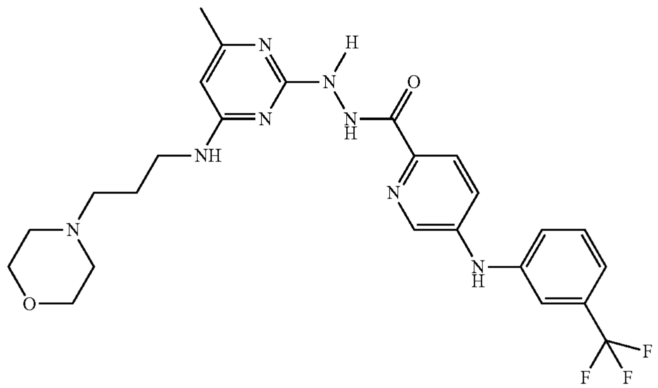

-continued
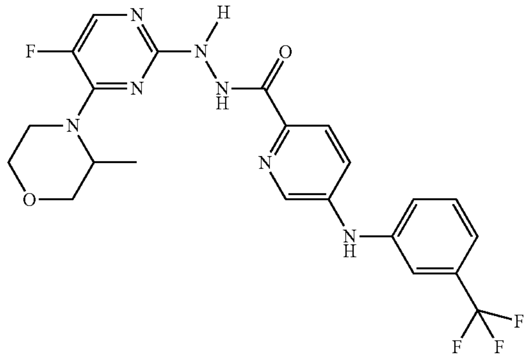
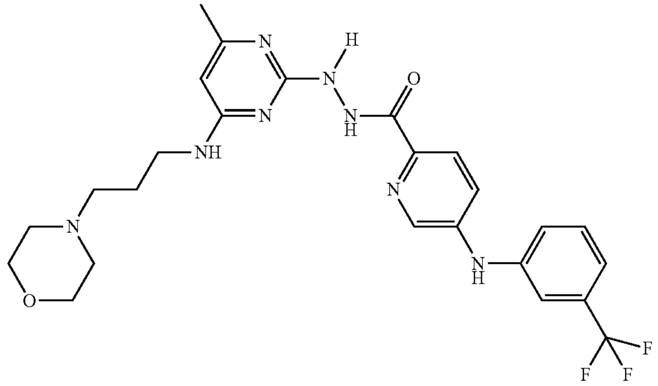
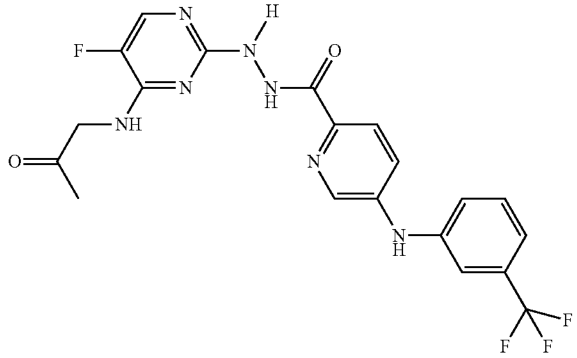
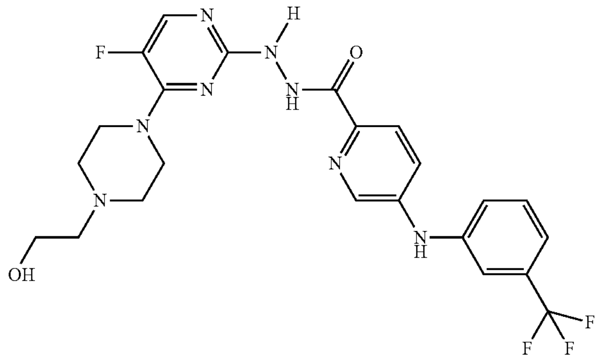

-continued
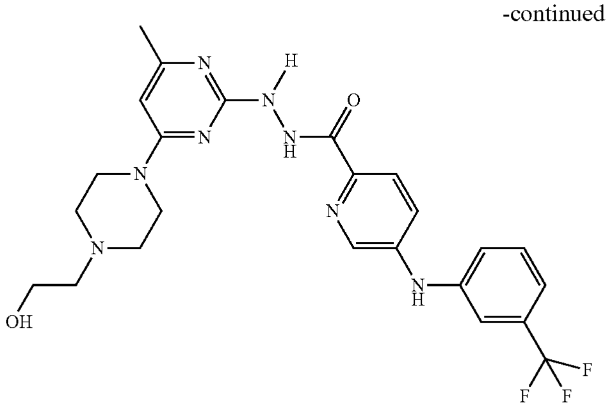
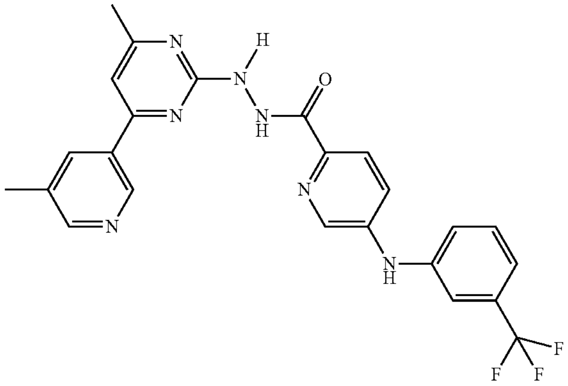
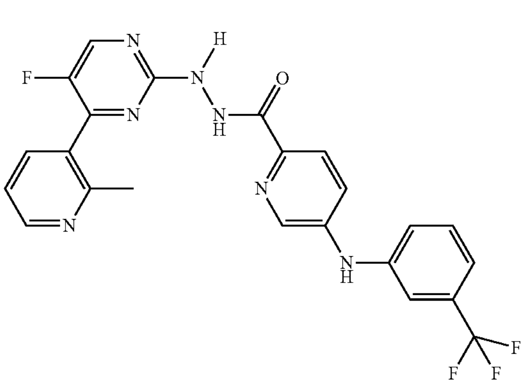
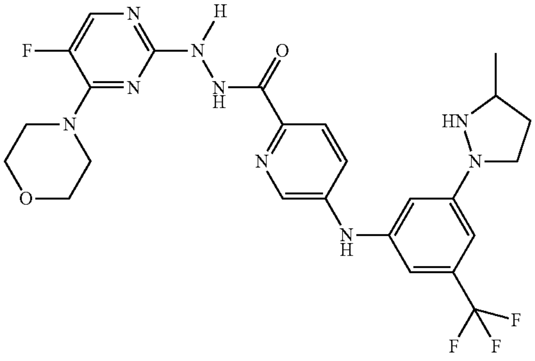
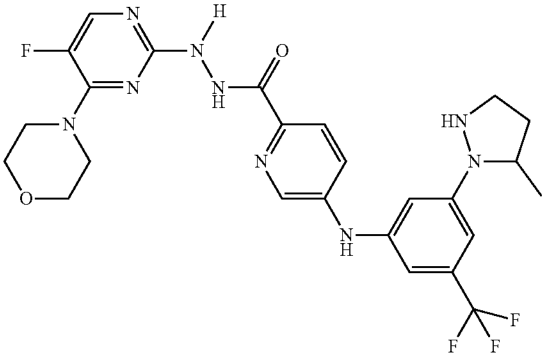
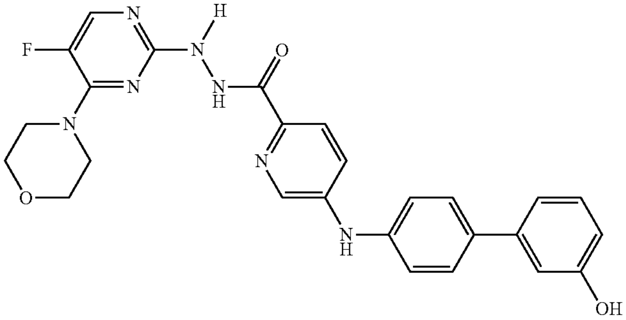

-continued
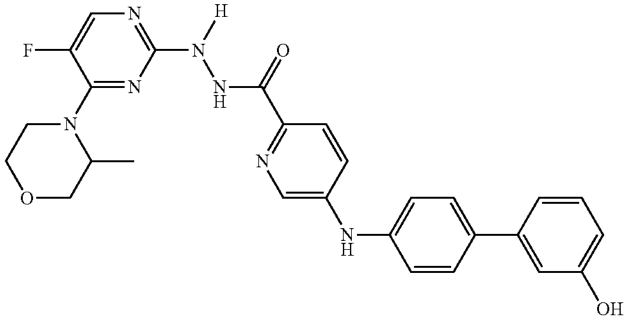
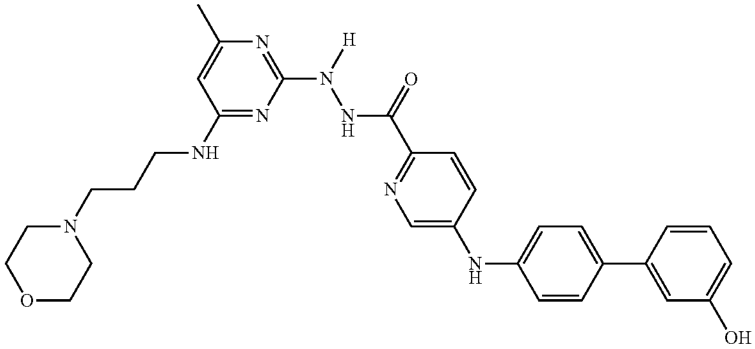
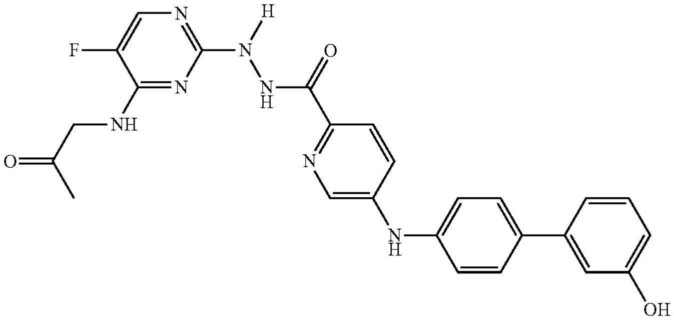
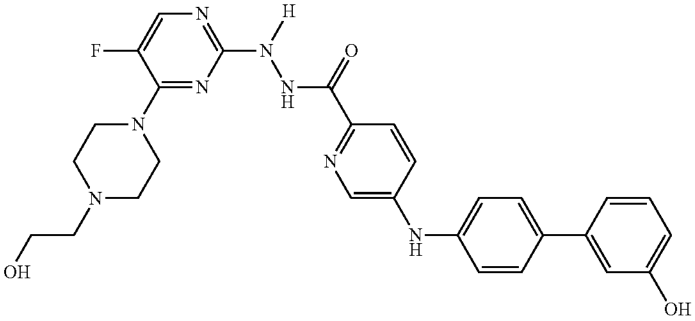
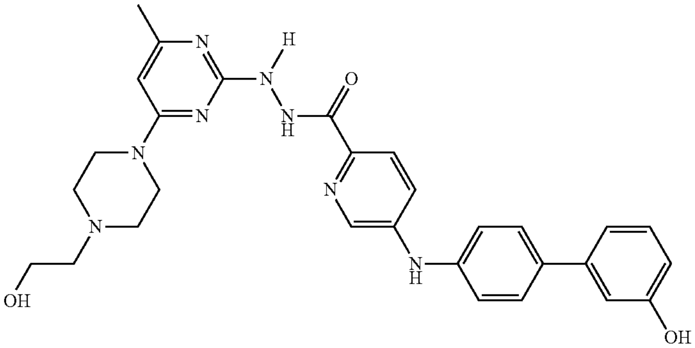

-continued
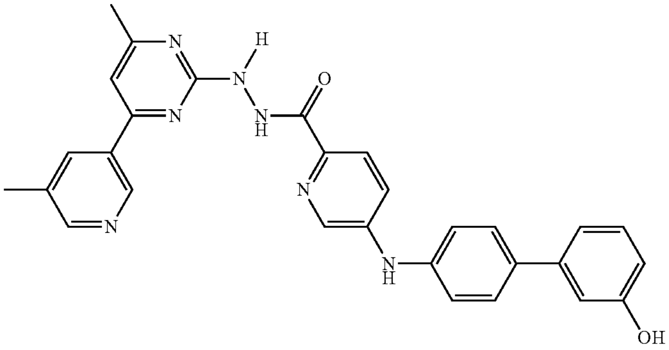
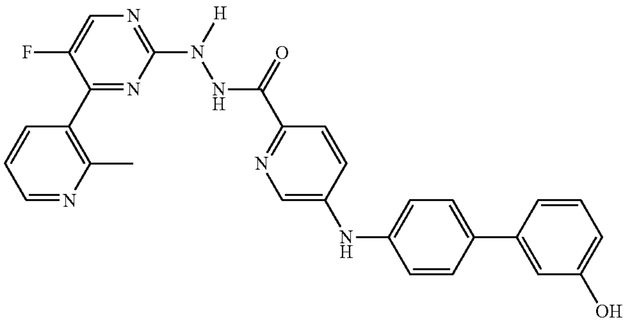
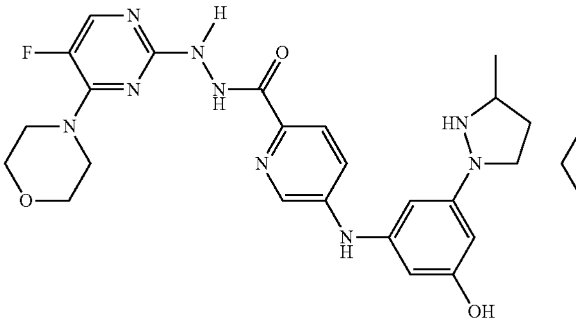
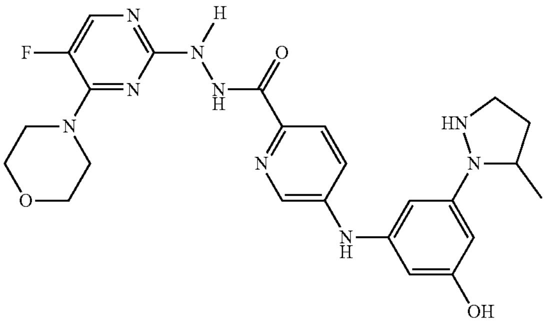
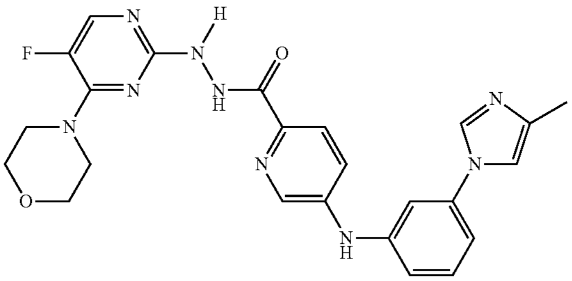
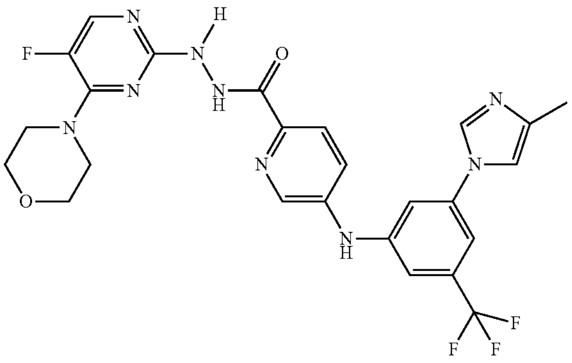

-continued
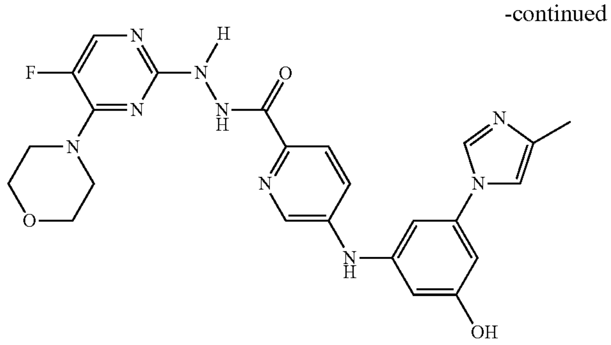
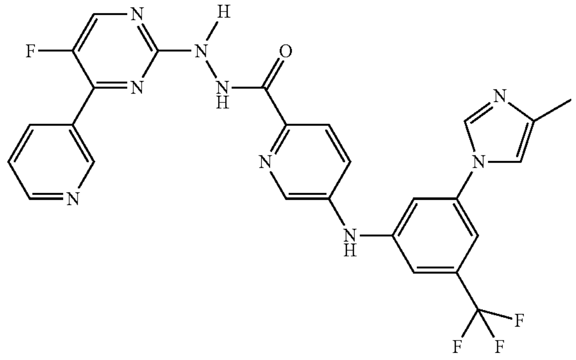
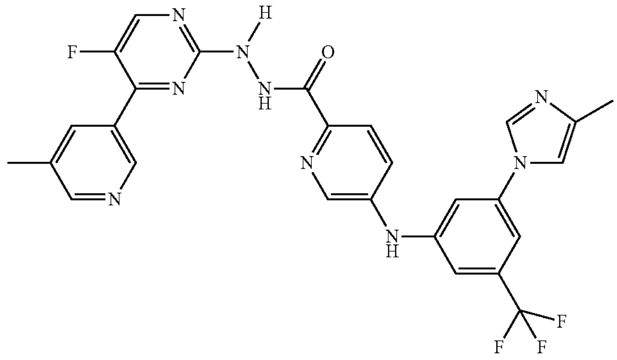
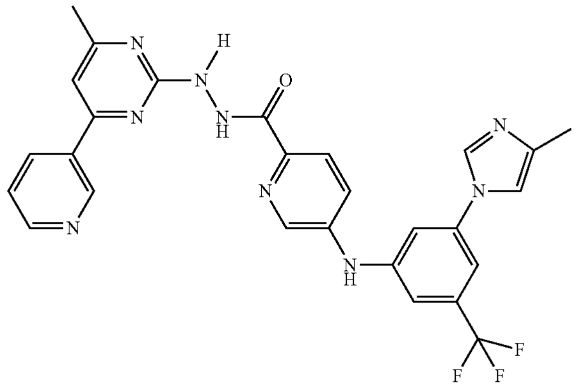

-continued
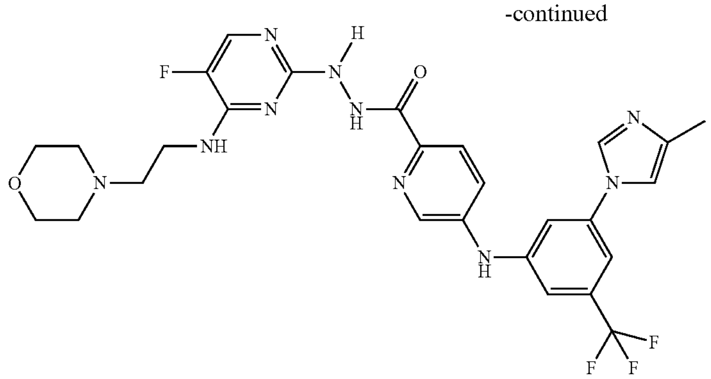
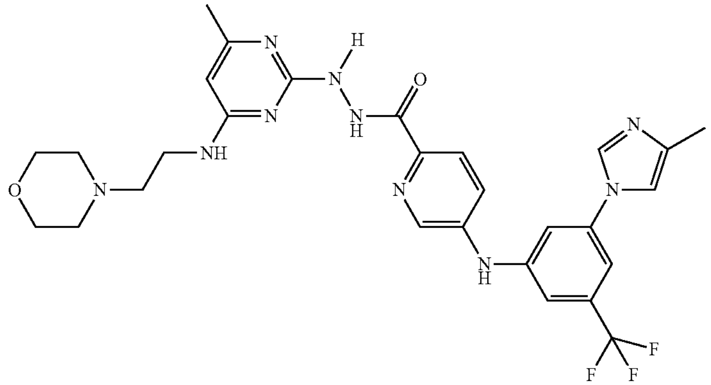
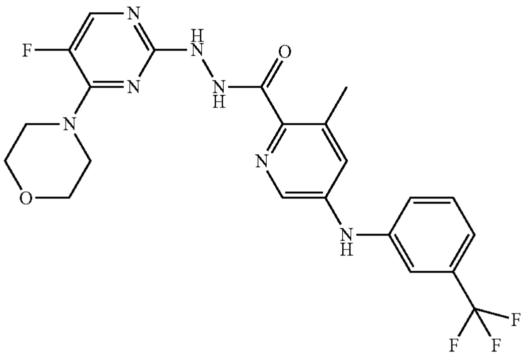
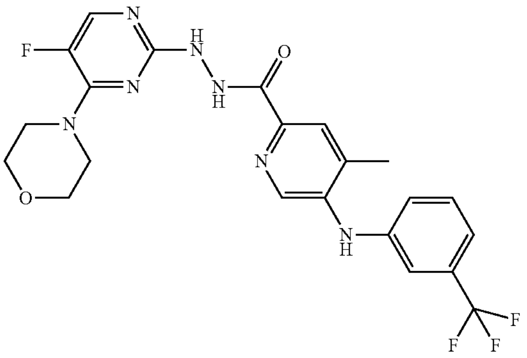
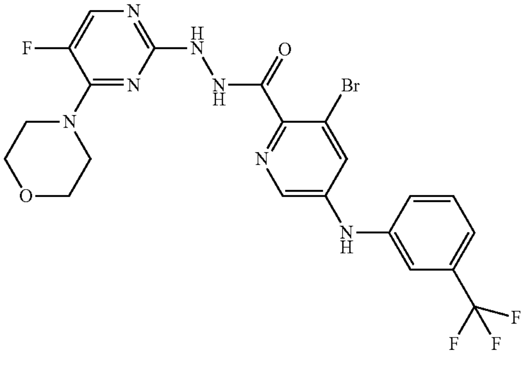
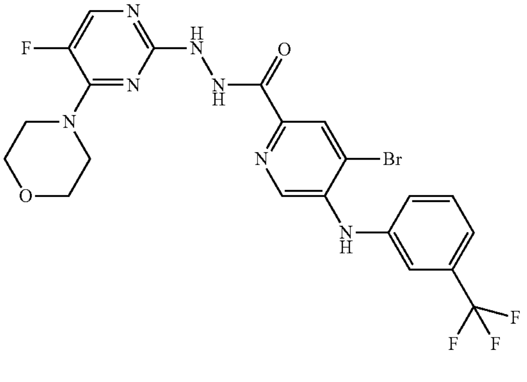

In a further embodiment, the present invention provides inhibitors of the $p210^{BCR-ABL-T315I}$ theramutein having the formula IV (IV)

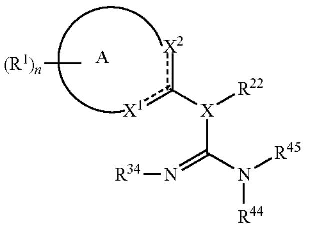

wherein:

ring A is a 5-, 6-, or 7-membered ring or a 7- to 12-membered fused bicyclic ring;

$X^1$ is selected from N, N—$R^0$ or C—$R^1$;

$X^2$ is selected from N, N—$R^0$ or C—$R^1$;

the dotted lines represent optional double bonds;

each $R^1$ is independently selected from the group consisting of H, alkyl, cycloalkyl, alkenyl, alkynyl, aralkyl, CN, $CF_3$, $NO_2$, $OR^{11}$, $—(CH_2)_pC(O)(CH_2)_qR^{11}$, $—(CH_2)_pC(O)N(R^{12})(R^{13})$, $—(CH_2)_pC(O)O(CH_2)_qR^{11}$, $—(CH_2)_pN(R^{11})C(O)R^{11}$, $—(CH_2)_pN(R^{12})(R^{13})$, $—N(R^{11})SO_2R^{11}$, $—OC(O)N(R^{12})(R^{13})$, $—SO_2N(R^{12})(R^{13})$, halo, aryl, and a heterocyclic ring, and additionally or alternatively, two $R^1$ groups on adjacent ring atoms form a 5- or 6-membered fused ring which contains from 0 to 3 heteroatoms;

n is 0 to 6, each $R^{11}$ is independently selected from H, alkyl, cycloalkyl, alkenyl, alkynyl, aralkyl, aryl, and a heterocyclic ring;

each $R^{12}$ and $R^{13}$ are independently selected from H, alkyl, cycloalkyl, alkenyl, alkynyl, aralkyl, aryl, and a heterocyclic ring; or $R^{12}$ and $R^{13}$ may be taken together with the nitrogen to which they are attached form a 5- to 7-membered ring which may optionally contain a further heteroatom;

p is 0 to 4;

q is 0 to 4;

$R^{22}$ is selected from H and $C_{1-3}$ alkyl;

$R^{34}$ is selected from H, $NO_2$, CN, alkyl, cycloalkyl, alkenyl, alkynyl, aralkyl, aryl and a heterocyclic ring;

$R^{44}$ is selected from H, alkyl, cycloalkyl, $—(C{=}O)R^0$, alkenyl, alkynyl, aralkyl, aryl, and a heterocyclic ring;

$R^{45}$ is selected from $—Y''—R^{19}$;

Y" is selected from a chemical bond, O, $NR^0$—, and a hydrocarbon chain having from 1 to 4 carbon atoms, and optionally substituted with one or more of halo, alkyl, cycloalkyl, alkenyl, alkynyl, aralkyl, $CO_2R^0$, $C(O)R^0$, $C(O)N(R^0)_2$, CN, $CF_3$, $N(R^0)_2$, $NO_2$, and $OR^0$;

$R^{19}$ is selected from the group consisting of H, alkyl, cycloalkyl, alkenyl, alkynyl, aralkyl, $CF_3$, aryl, and a heterocyclic ring; and each $R^0$ is independently selected from H, alkyl, cycloalkyl, aralkyl, aryl and a heterocyclic ring.

Exemplary compounds of the formula IV include the following structures:

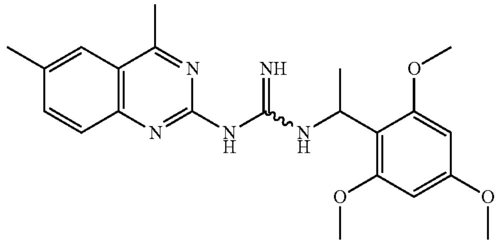

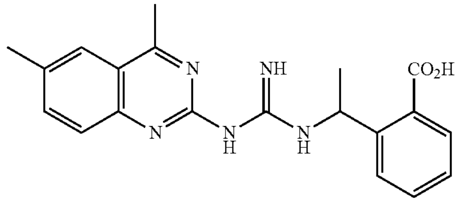

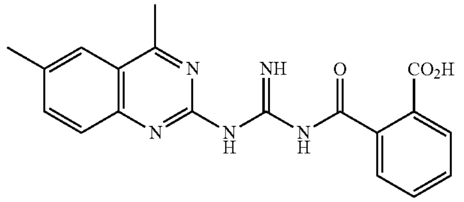

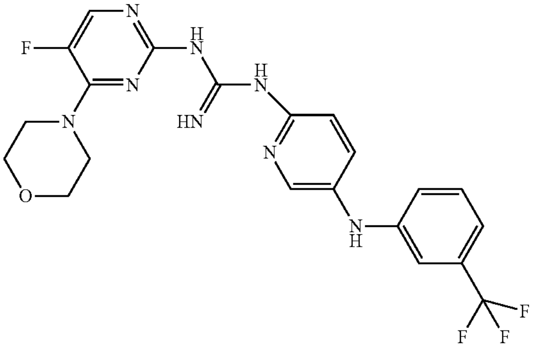

In a further embodiment, the present invention provides inhibitors of the $P210^{BCR-ABL-T315I}$ theramutein having the formula V (V)

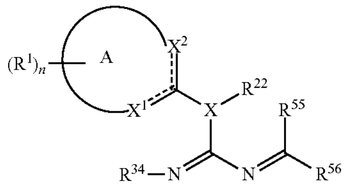

wherein:

ring A is a 5-, 6-, or 7-membered ring or a 7- to 12-membered fused bicyclic ring;

$X^1$ is selected from N, N—$R^0$ or C—$R^1$;

$X^2$ is selected from N, N—$R^0$ or C—$R^1$;

the dotted lines represent optional double bonds;

each $R^1$ is independently selected from the group consisting of H, alkyl, cycloalkyl, alkenyl, alkynyl, aralkyl, CN, $CF_3$, $NO_2$, $OR^{11}$, $—(CH_2)_pC(O)(CH_2)_qR^{11}$, $—(CH_2)_pC(O)N(R^{12})(R^{13})$, $—(CH_2)_pC(O)O(CH_2)_qR^{11}$, $—(CH_2)_pN$ $(R^{11})C(O)R^{11}$, $—(CH_2)_pN(R^{12})(R^{13})$, $—N(R^{11})SO_2R^{11}$, $—OC(O)N(R^{12})(R^{13})$, $—SO_2N(R^{12})(R^{13})$, halo, aryl, and a heterocyclic ring, and additionally or alternatively, two $R^1$ groups on adjacent ring atoms form a 5- or 6-membered fused ring which contains from 0 to 3 heteroatoms;

n is 0 to 6, each $R^{11}$ is independently selected from H, alkyl, cycloalkyl, alkenyl, alkynyl, aralkyl, aryl, and a heterocyclic ring;

each $R^{12}$ and $R^{13}$ are independently selected from H, alkyl, cycloalkyl, alkenyl, alkynyl, aralkyl, aryl, and a heterocyclic ring; or $R^{12}$ and $R^{13}$ may be taken together with the nitrogen to which they are attached form a 5- to 7-membered ring which may optionally contain a further heteroatom;

p is 0 to 4;

q is 0 to 4;

$R^{22}$ is selected from H and $C_{1-3}$ alkyl;

$R^{34}$ is selected from H, $NO_2$, CN, alkyl, cycloalkyl, alkenyl, alkynyl, aralkyl, aryl and a heterocyclic ring;

$R^{55}$ is selected from H, alkyl, cycloalkyl, alkenyl, alkynyl, aralkyl, aryl, and a heterocyclic ring;

$R^{56}$ is selected from $—Y''—R^{19}$;

Y'' is selected from a chemical bond; O, $NR^0—$, and a hydrocarbon chain having from 1 to 4 carbon atoms, and optionally substituted with one or more of halo, alkyl, cycloalkyl, alkenyl, alkynyl, aralkyl, $CO_2R^0$, $C(O)R^0$, $C(O)N(R^0)_2$, CN, $CF_3$, $N(R^0)_2$, $NO_2$, and $OR^0$;

$R^{19}$ is selected from the group consisting of H, alkyl, cycloalkyl, alkenyl, alkynyl, aralkyl, $CF_3$, aryl, and a heterocyclic ring; and each $R^0$ is independently selected from H, alkyl, cycloalkyl, aralkyl, aryl and a heterocyclic ring.

In a further embodiment, the present invention provides inhibitors of the $P210^{BCR-ABL-T315I}$ theramutein having the formula $V_a$ ($V_a$)

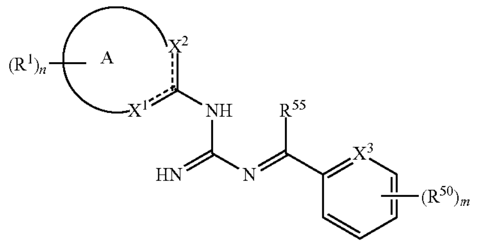

wherein:

ring A is a 5-, 6-, or 7-membered ring or a 7- to 12-membered fused bicyclic ring;

$X^1$ is selected from N, $N—R^0$ or $C—R^1$;

$X^2$ is selected from N, $N—R^0$ or $C—R^1$;

the dotted lines represent optional double bonds;

each $R^1$ is independently selected from the group consisting of H, alkyl, cycloalkyl, alkenyl, alkynyl, aralkyl, CN, $CF_3$, $NO_2$, $OR^{11}$, $—(CH_2)_pC(O)(CH_2)_qR^{11}$, $—(CH_2)_pC(O)NR^{12})(R^{13})$, $—(CH_2)_pC(O)O(CH_2)_qR^{11}$, $—(CH_2)_pN(R^{11})C(O)R^{11}$, $—(CH_2)_pN(R^{12})(R^{13})$, $—NR^{11})SO_2R^{11}$, $—OC(O)N(R^{12})(R^{13})$, $—SO_2N(R^{12})(R^{13})$, halo, aryl, and a heterocyclic ring, and additionally or alternatively, two $R^1$ groups on adjacent ring atoms form a 5- or 6-membered fused ring which contains from 0 to 3 heteroatoms;

n is 0 to 6, each $R^{11}$ is independently selected from H, alkyl, cycloalkyl, alkenyl, alkynyl, aralkyl, aryl, and a heterocyclic ring;

each $R^{12}$ and $R^{13}$ are independently selected from H, alkyl, cycloalkyl, alkenyl, alkynyl, aralkyl, aryl, and a heterocyclic ring; or $R^{12}$ and $R^{13}$ may be taken together with the nitrogen to which they are attached form a 5- to 7-membered ring which may optionally contain a further heteroatom;

p is 0 to 4;

q is 0 to 4;

$R^{55}$ is selected from H, alkyl, cycloalkyl, alkenyl, alkynyl, aralkyl, aryl, and a heterocyclic ring;

$X^3$ is N or $C—R^{50}$;

each $R^{50}$ is independently selected from the group consisting of alkyl, cycloalkyl, alkenyl, alkynyl, aralkyl, CN, $CF_3$, $NO_2$, $OR^{51}$, $—(CH_2)_rC(O)(CH_2)_sR^{51}$, $—(CH_2)_rC(O)N(R^{52})(R^{53})$, $—(CH_2)_rC(O)O(CH_2)_sR^{51}$, $—(CH_2)_rN(R^{51})C(O)R^{51}$, $—(CH_2)_rN(R^{52})(R^{53})$, $—N(R^{51})SO_2R^{51}$, $—OC(O)N(R^{52})(R^{53})$, $—SO_2N(R^{52})(R^{53})$, halo, aryl, and a heterocyclic ring, and additionally or alternatively, two $R^{50}$ groups on adjacent ring atoms form a 5- or 6-membered fused ring which contains from 0 to 3 heteroatoms;

$R^{51}$ is selected from H, alkyl, cycloalkyl, alkenyl, alkynyl, aralkyl, aryl, and a heterocyclic ring;

$R^{52}$ and $R^{53}$ are independently selected from H, alkyl, cycloalkyl, alkenyl, alkynyl, aralkyl, aryl, and a heterocyclic ring; or $R^{52}$ and $R^{53}$ may be taken together with the nitrogen to which they are attached form a 5- to 7-membered ring which may optionally contain a further heteroatom;

r is 0 to 4;

s is 0 to 4;

m is 0 to 4; and each $R^0$ is independently selected from H, alkyl, cycloalkyl, aralkyl, aryl and a heterocyclic ring.

Exemplary compounds of the formula V or $V_a$ include the following structures:

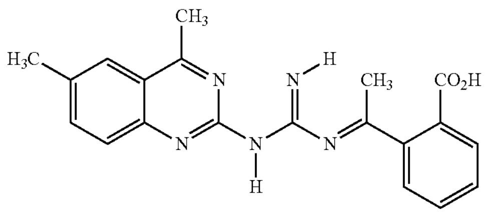

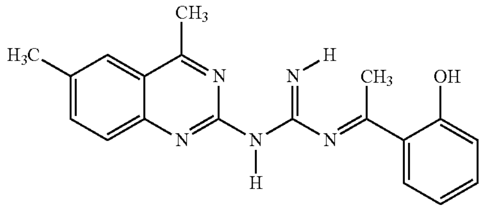

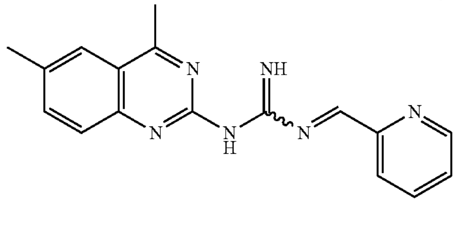

-continued

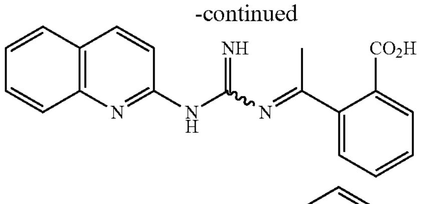

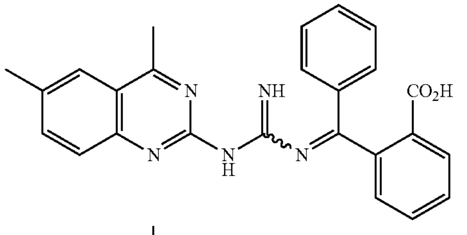

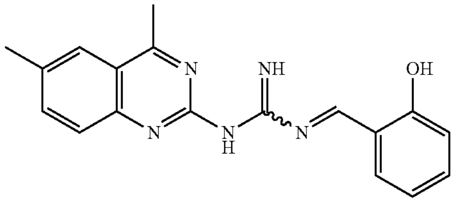

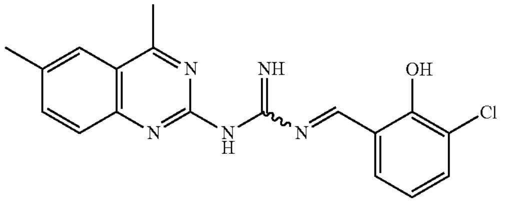

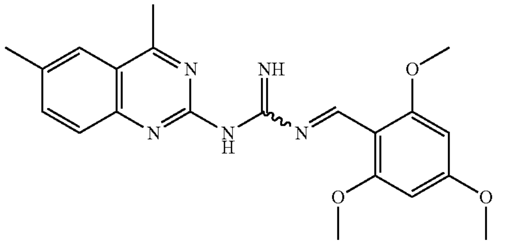

In a further embodiment, the present invention provides inhibitors of the $P210^{BCR\text{-}ABL\text{-}T315I}$ theramutein having the formula VI (VI)

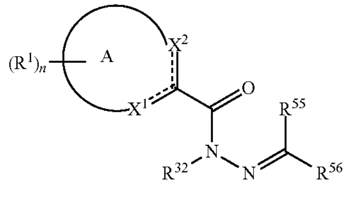

wherein:

ring A is a 5-, 6-, or 7-membered ring or a 7- to 12-membered fused bicyclic ring;

$X^1$ is selected from N, N—$R^0$ or C—$R^1$;

$X^2$ is selected from N, N—$R^0$ or C—$R^1$;

the dotted lines represent optional double bonds;

each $R^1$ is independently selected from the group consisting of H, alkyl, cycloalkyl, alkenyl, alkynyl, aralkyl, CN, $CF_3$, $NO_2$, $OR^{11}$, $—(CH_2)_pC(O)(CH_2)_qR^{11}$, $—(CH_2)_pC(O)N(R^{12})(R^{13})$, $—(CH_2)_pC(O)O(CH_2)_qR^{11}$, $—(CH_2)_pN(R^{11})C(O)R^{11}$, $—(CH_2)_pN(R^{12})(R^{13})$, $—N(R^{11})SO_2R^{11}$, $—OC(O)N(R^{12})(R^{13})$, $—SO_2N(R^{12})(R^{13})$, halo, aryl, and a heterocyclic ring, and additionally or alternatively, two $R^1$ groups on adjacent ring atoms form a 5- or 6-membered fused ring which contains from 0 to 3 heteroatoms;

n is 0 to 6, each $R^{11}$ is independently selected from H, alkyl, cycloalkyl, alkenyl, alkynyl, aralkyl, aryl, and a heterocyclic ring;

each $R^{12}$ and $R^{13}$ are independently selected from H, alkyl, cycloalkyl, alkenyl, alkynyl, aralkyl, aryl; and a heterocyclic ring; or $R^{12}$ and $R^{13}$ may be taken together with the nitrogen to which they are attached form a 5- to 7-membered ring which may optionally contain a further heteroatom;

p is 0 to 4;

q is 0 to 4;

$R^{55}$ is selected from H, alkyl, cycloalkyl, alkenyl, alkynyl, aralkyl, aryl, and a heterocyclic ring;

$R^{56}$ is selected from —Y"—$R^{19}$;

Y" is selected from a chemical bond, O, $NR^0$—, and a hydrocarbon chain having from 1 to 4 carbon atoms, and optionally substituted with one or more of halo, alkyl, cycloalkyl, alkenyl, alkynyl, aralkyl, $CO_2R^0$, $C(O)R^0$, $C(O)N(R^0)_2$, CN, $CF_3$, $N(R^0)_2$, $NO_2$, and $OR^0$;

$R^{19}$ is selected from the group consisting of H, alkyl, cycloalkyl, alkenyl, alkynyl, aralkyl, $CF_3$, aryl, and a heterocyclic ring; and each $R^0$ is independently selected from H, alkyl, cycloalkyl, aralkyl, aryl and a heterocyclic ring.

In a further embodiment, the present invention provides inhibitors of the $p210^{BCR\text{-}ABL\text{-}T315I}$ theramutein having the formula $VI_a$ (VIa)

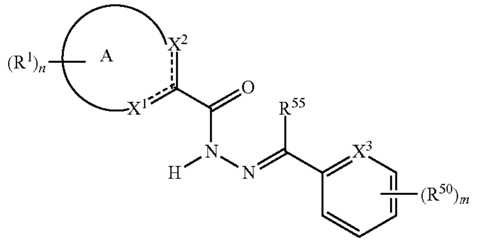

wherein:

ring A is a 5-, 6-, or 7-membered ring or a 7- to 12-membered fused bicyclic ring;

$X^1$ is selected from N, N—$R^0$ or C—$R^1$;

$X^2$ is selected from N, N—$R^0$ or C—$R^1$;

the dotted lines represent optional double bonds;

each $R^1$ is independently selected from the group consisting of H, alkyl, cycloalkyl, alkenyl, alkynyl, aralkyl, CN, $CF_3$, $NO_2$, $OR^{11}$, $—(CH_2)_pC(O)(CH_2)_qR^{11}$, $—(CH_2)_pC(O)N(R^{12})(R)^3)$, $—(CH_2)_pC(O)O(CH_2)_qR^{11}$, $—(CH_2)_pN(R^{11})C(O)R^{11}$, $—(CH_2)_pN(R^{12})(R^{13})$, $—N(R^{11})SO_2R^{11}$, $—OC(O)N(R^{12})(R^{13})$, $—SO_2N(R^{12})(R^{13})$, halo, aryl, and a heterocyclic ring, and additionally or alternatively, two $R^1$ groups on adjacent ring atoms form a 5- or 6-membered fused ring which contains from 0 to 3 heteroatoms;

n is 0 to 6, each $R^{11}$ is independently selected from H, alkyl, cycloalkyl, alkenyl, alkynyl, aralkyl, aryl, and a heterocyclic ring;

each $R^{12}$ and $R^{13}$ are independently selected from H, alkyl, cycloalkyl, alkenyl, alkynyl, aralkyl, aryl, and a heterocyclic ring; or $R^{12}$ and $R^{13}$ may be taken together with the nitrogen to which they are attached form a 5- to 7-membered ring which may optionally contain a further heteroatom;

p is 0 to 4;

q is 0 to 4;

$R^{55}$ is selected from H, alkyl, cycloalkyl, alkenyl, alkynyl, aralkyl, aryl, and a heterocyclic ring;

$X^3$ is N or C—$R^{50}$;

each $R^{50}$ is independently selected from the group consisting of alkyl, cycloalkyl, alkenyl, alkynyl, aralkyl, CN, $CF_3$, $NO_2$, $OR^{51}$, —$(CH_2)_r$C(O)$(CH_2)_s R^{51}$, —$(CH_2)_r$C(O)N$(R^{52})(R^{53})$, —$(CH_2)_r$C(O)O$(CH_2)_s R^{51}$, —$(CH_2)_r$N$(R^{51})$C(O)$R^{51}$, —$(CH_2)_r$N$(R^{52})(R^{53})$, —N$(R^{51})SO_2R^{51}$, —OC(O)N$(R^{52})(R^{53})$, —$SO_2$N$(R^{52})(R^{53})$, halo, aryl, and a heterocyclic ring, and additionally or alternatively, two $R^{50}$ groups on adjacent ring atoms form a 5- or 6-membered fused ring which contains from 0 to 3 heteroatoms;

$R^{51}$ is selected from H, alkyl, cycloalkyl, alkenyl, alkynyl, aralkyl, aryl, and a heterocyclic ring;

$R^{52}$ and $R^{53}$ are independently selected from H, alkyl, cycloalkyl, alkenyl, alkynyl, aralkyl, aryl, and a heterocyclic ring; or $R^{52}$ and $R^{53}$ may be taken together with the nitrogen to which they are attached form a 5- to 7-membered ring which may optionally contain a further heteroatom;

r is 0 to 4;

s is 0 to 4;

m is 0 to 4; and each $R^0$ is independently selected from H, alkyl, cycloalkyl, aralkyl, aryl and a heterocyclic ring.

Exemplary compounds of the formula VI or $VI_a$ include the following structures:

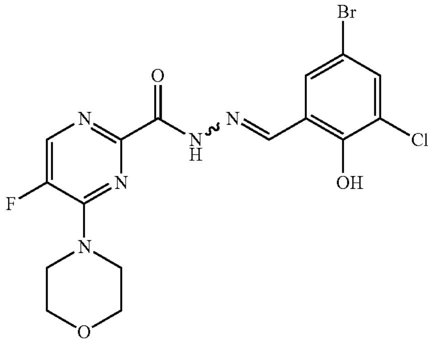

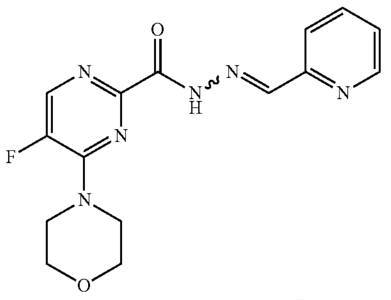

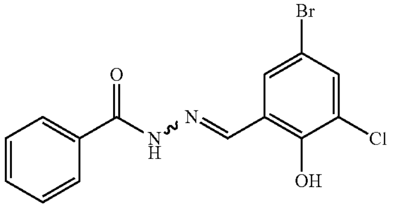

-continued

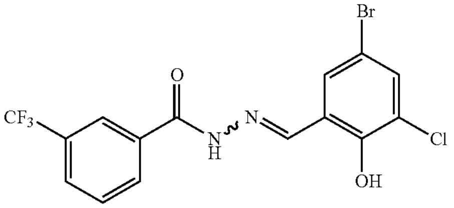

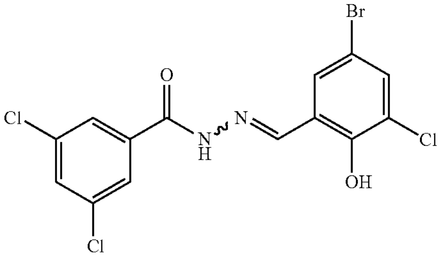

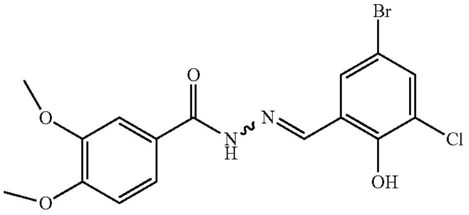

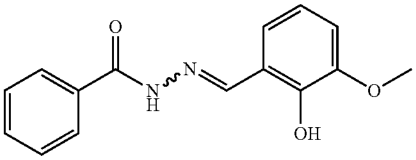

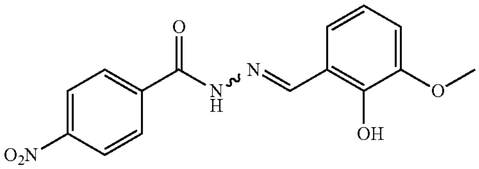

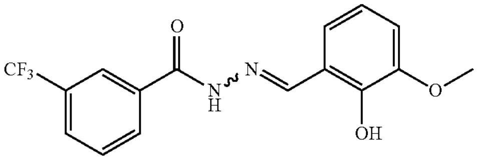

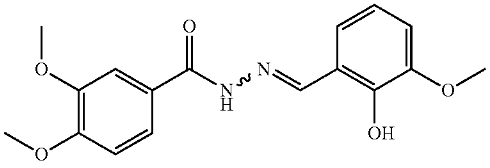

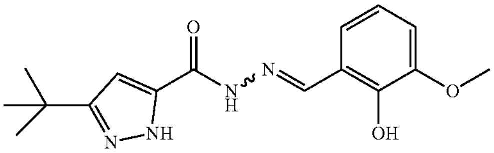

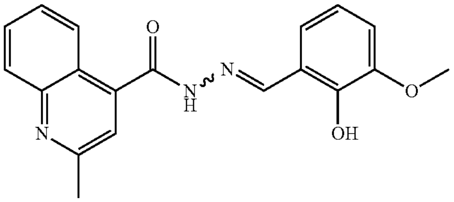

-continued

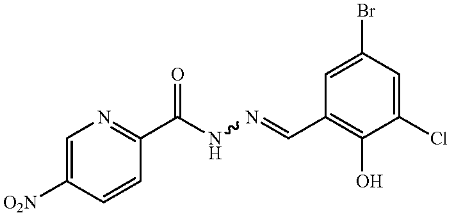

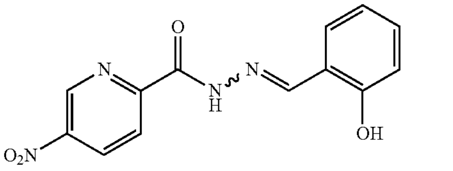

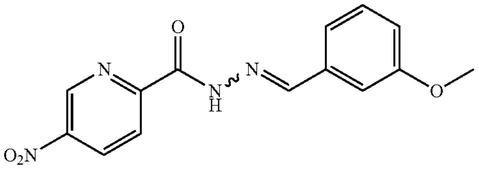

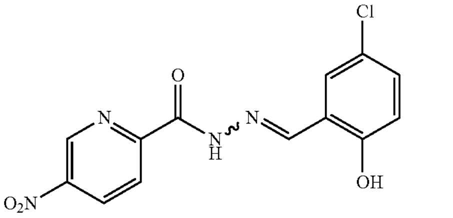

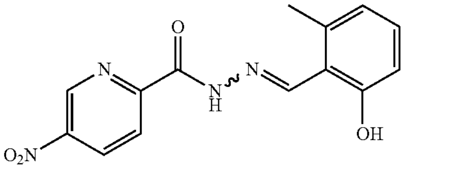

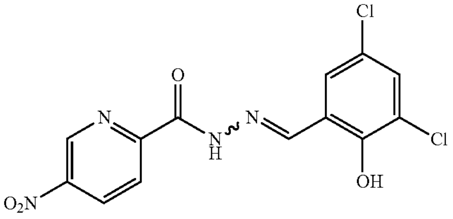

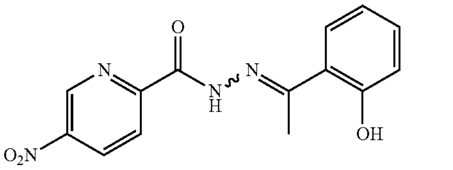

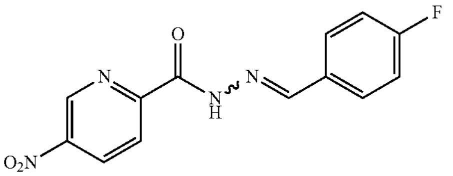

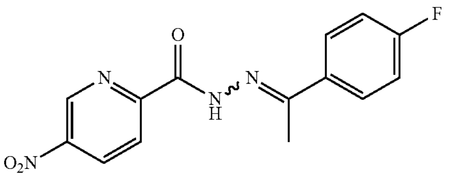

-continued

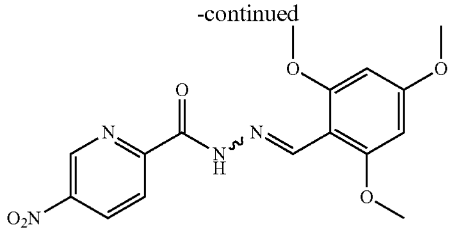

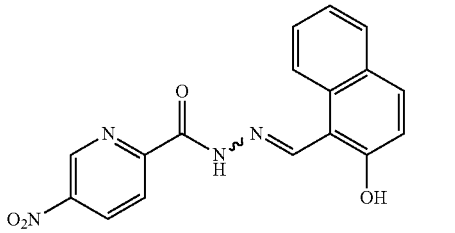

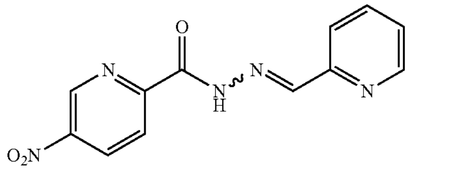

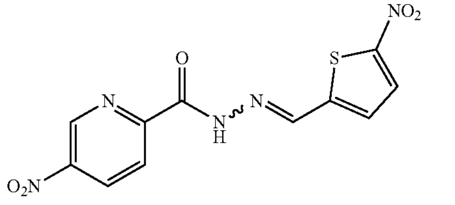

In a further preferred embodiment, the present invention provides inhibitors of the $P210^{BCR\text{-}ABL\text{-}T315I}$ theramutein having the formula VII

VII

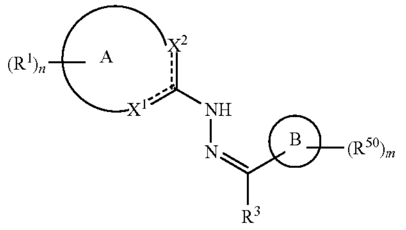

wherein:

ring A is a 5-, 6-, or 7-membered ring or a 7- to 12-membered fused bicyclic ring;

$X^1$ is selected from N, N—$R^0$ or C—$R^1$;

$X^2$ is selected from N, N—$R^0$ or C—$R^1$;

the dotted lines represent optional double bonds;

each $R^1$ is independently selected from the group consisting of H, alkyl, cycloalkyl, alkenyl, alkynyl, aralkyl, CN, $CF_3$, $NO_2$, $OR^{11}$, —$(CH_2)_pC(O)(CH_2)_qR^{11}$, —$(CH_2)_pC(O)N(R^{12})(R^{13})$, —$(CH_2)_pC(O)O(CH_2)_qR^{11}$, —$(CH_2)_pN(R^{11})C(O)R^{11}$, —$(CH_2)_pN(R^{12})(R^{13})$, —$N(R^{11})SO_2R^{11}$, —$OC(O)N(R^{12})(R^{13})$, —$SO_2N(R^{12})(R^{13})$, halo, aryl, and a heterocyclic ring, and additionally or alternatively, two $R^1$ groups on adjacent ring atoms form a 5- or 6-membered fused ring which contains from 0 to 3 heteroatoms;

n is 0 to 6, each $R^{11}$ is independently selected from H, alkyl, cycloalkyl, alkenyl, alkynyl, aralkyl, aryl, and a heterocyclic ring;

each $R^{12}$ and $R^{13}$ are independently selected from H, alkyl, cycloalkyl, alkenyl, alkynyl, aralkyl, aryl, and a heterocyclic ring; or $R^{12}$ and $R^{13}$ may be taken together with the nitrogen to which they are attached form a 5- to 7-membered ring which may optionally contain a further heteroatom;

p is 0 to 4;

q is 0 to 4;

ring B is selected from a cycloalkyl group having 5 or 6 ring atoms, and a heterocyclic group containing 5 or 6 ring atoms which includes one to three hetero atoms;

each $R^{50}$ is independently selected from the group consisting of alkyl, cycloalkyl, alkenyl, alkynyl, aralkyl, CN, $CF_3$, $NO_2$, $OR^{51}$, $—(CH_2)_rC(O)(CH_2)_sR^{51}$, $—(CH_2)_xC(O)N(R^{52})(R^{53})$, $—(CH_2)_rC(O)O(CH_2)_sR^{51}$, $—(CH_2)_rN(R^{51})C(O)R^{51}$, $—(CH_2)_rN(R^{52})(R^{53})$, $—N(R^{51})SO_2R^{51}$, $—OC(O)N(R^{52})(R^{53})$, $—SO_2N(R^{52})(R^{53})$, halo, aryl, and a heterocyclic ring, and additionally or alternatively, two $R^{50}$ groups on adjacent ring atoms form a 5- or 6-membered fused ring which contains from 0 to 3 heteroatoms;

$R^{51}$ is selected from H, alkyl, cycloalkyl, alkenyl, alkynyl, aralkyl, aryl, and a heterocyclic ring;

$R^{52}$ and $R^{53}$ are independently selected from H, alkyl, cycloalkyl, alkenyl, alkynyl, aralkyl, aryl, and a heterocyclic ring; or $R^{52}$ and $R^{53}$ may be taken together with the nitrogen to which they are attached form a 5- to 7-membered ring which may optionally contain a further heteroatom;

r is 0 to 4;

s is 0 to 4;

m is 0 to 4; and each $R^0$ is independently selected from H, alkyl, cycloalkyl, aralkyl, aryl and a heterocyclic ring.

Exemplary compounds of the formula VII include the following structures:

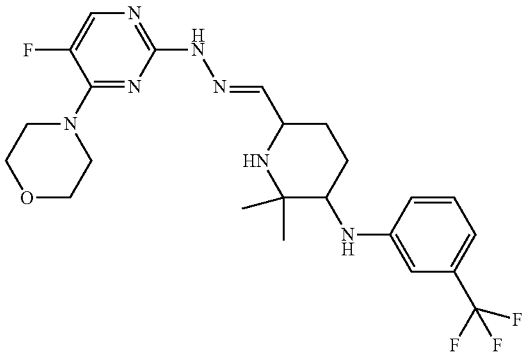

-continued

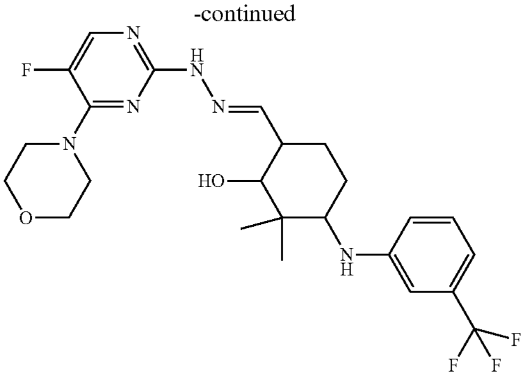

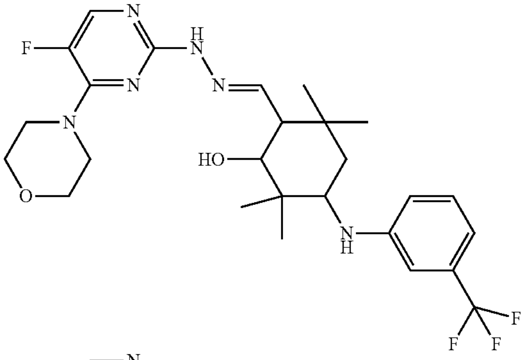

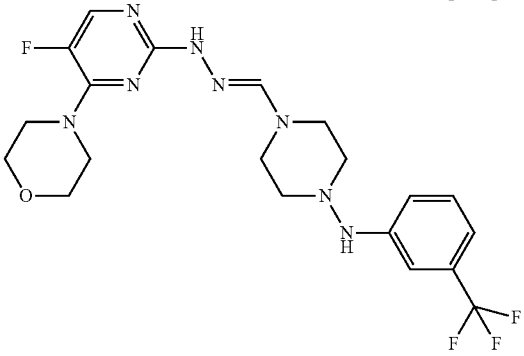

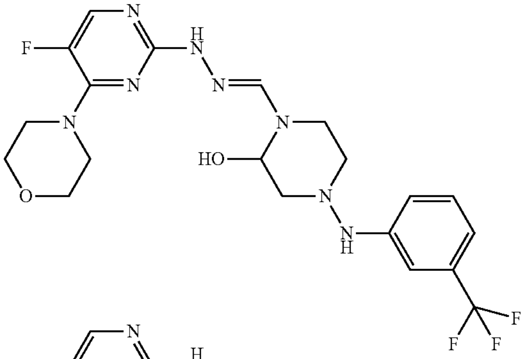

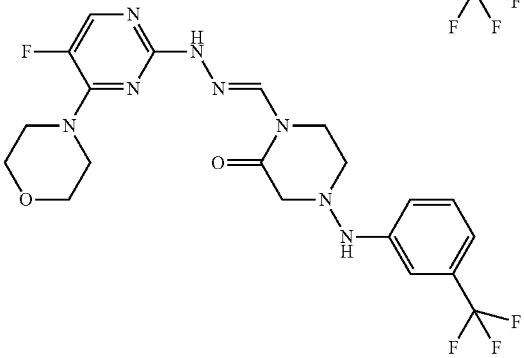

-continued

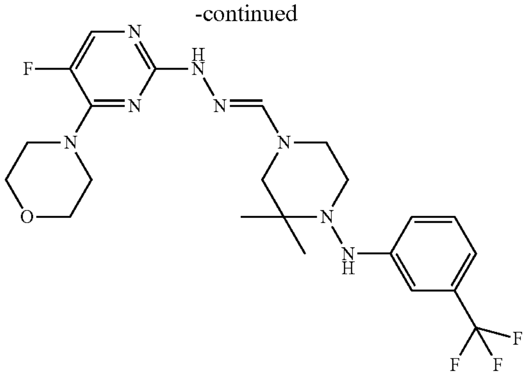

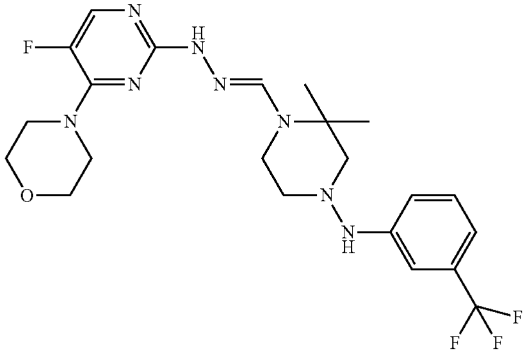

As used herein, the definition of each expression, e.g. alkyl, m, n, R, R' etc., when it occurs more than once in any structure, is intended to be independent of its definition elsewhere in the same structure.

For each of the above descriptions of compounds of the structures I, $I_a$, $I_b$, II, $II_a$, etc., each recitation of the terms halo, alkyl, cycloalkyl, alkenyl, alkynyl, aralkyl, aryl, heterocyclic group or heterocyclic ring, are independently selected from the definitions of these terms as provided in the beginning of this section.

It will be understood that chemical structures provided herein include the implicit proviso that substitution is in accordance with permitted valence of the substituted atom and the substituent(s), and that the substitution results in a stable compound, e.g., which does not spontaneously undergo transformation such as by rearrangement, cyclization, elimination, etc.

When one or more chiral centers are present in the compounds of the present invention, the individual isomers and mixtures thereof (e.g., racemates, etc.) are intended to be encompassed by the formulae depicted herein.

When one or more double bonds are present in the compounds of the present invention, both the cis- and trans-isomers are intended to be encompassed by the formulae depicted herein. Although chemical structures (such as, for example, structures II, $II_a$, V, $V_a$, VI, and $VI_a$) are depicted herein in either cis of trans configuration, both configurations are meant to be encompassed by the each of the formulae.

In certain embodiments, compounds of the invention may exist in several tautomeric forms. Accordingly, the chemical structures depicted herein encompass all possible tautomeric forms of the illustrated compounds.

The compounds of the invention may generally be prepared from commercially available starting materials and known chemical techniques. Embodiments of the invention may be synthesized as follows. One of skill in the art of medicinal or synthetic chemistry would be readily familiar with the procedures and techniques necessary to accomplish the synthetic approaches given below.

Compounds of the formula II may be prepared by reaction of an appropriate hydrazine compound, such as A, and an appropriate aldehyde, such as B, under conditions similar to those described on p. 562 of Gineinah, et al. (Arch. Pharm. Med. Chem. 2002, 11, 556-562).

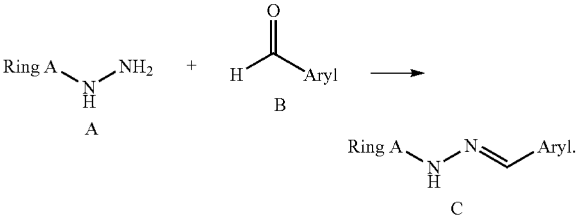

For example, heating A with 1.1 equivalents of B for 1 to 24 hours in a protic solvent such as a $C_1$ to $C_6$ alcohol, followed by cooling and collection of the precipitate, would afford C. Alternatively, product C may be isolated by evaporation of the solvent and purification by chromatography using silica gel, alumina, or $C_4$ to $C_{18}$ reverse phase medium. Similar methodology would be applicable in the cases where "Aryl" is replaced by other groups defined under $R^5$.

Compounds of the formula III ring may be prepared by reaction of an appropriate hydrazine compound, such as D, and an activated carboxylic acid such as E, wherein LG is a leaving group such as halo, 1-oxybenztriazole, pentafluorophenoxy, p-nitrophenoxy, or the like, or Compound E may also be a symmetrical carboxylic acid anhydride, whereby conditions similar to those described on p. 408 of Nair and Mehta (Indian J. Chem. 1967 5, 403-408) may be used.

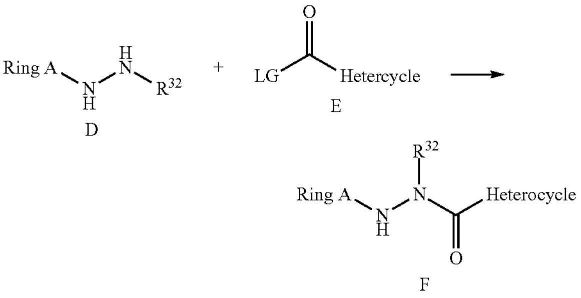

For example, treatment of D with an active ester such as Aryl-C(O)—$OC_6F_5$ in an inert solvent such as dichloromethane, 1,2-dichloroethane, or N,N-dimethylformamide, optionally in the presence of a base such as pyridine or another tertiary amine, and optionally in the presence of a catalyst such as 4-N,N-dimethylaminopyridine, at an appropriate temperature ranging from C to the boiling point of the solvent, would afford F, which may be isolated by evaporation of the solvent followed by chromatography using silica gel, alumina, or $C_4$ to $C_{18}$ reverse phase medium. The above active ester example of E would be readily prepared from the corresponding carboxylic acid and pentafluorophenol using a carbodiimide such as dicyclohexylcarbodiimide as a condensing agent.

Precursors such as A and D may be prepared by reaction of an appropriate nucleophile, for example, a hydrazine derivative, with a heteroaromatic compound bearing a halo substituent at a position adjacent to a nitrogen atom. For example, using methods analogous to those described by Wu, et al. (J. Heterocyclic Chem. 1990, 27, 1559-1563), Breshears, et al. (J. Am. Chem. Soc. 1959, 81, 3789-3792), or Gineinah, et al. (Arch. Pharm. Med. Chem. 2002, 11, 556-562), examples of compounds A and D may be prepared starting from, for example, a 2,4-dihalopyrimidine derivative, many of which are commercially available or are otherwise readily prepared by one skilled in the art. Thus, treatment of an appropriate 2,4-dihalopyrimidine derivative G with an amine or other nucleophile (Z), optionally in the presence of an added base, selectively displaces the 4-halo substituent on the pyrimidine ring. Subsequent treatment of the product with a second nucleophilic reagent such as hydrazine or a hydrazine derivative, optionally in a solvent such as a $C_1$ to $C_6$ alcohol and optionally in the presence of an added base, displaces the 2-halo substituent on the pyrimidine ring, to afford compounds that are examples of structures A and D above.

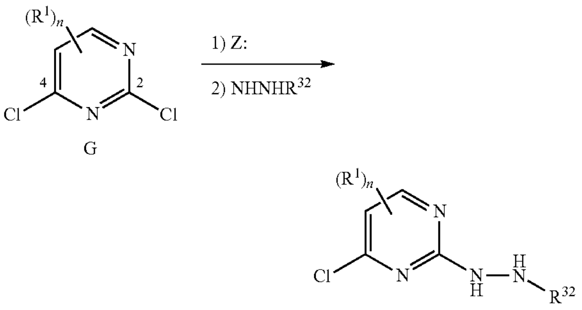

G

Embodiments wherein $R^2$ is —$NR^{22}$ and $R^3$ is —C(=$R^{33}$) can be synthesized by methods such as the following, or straightforward modifications thereof. The synthesis may be conducted starting from an appropriate ring A derivative J that bears a leaving group (LG) adjacent to the requisite ring nitrogen. Structure G above and the product of reaction of structure G with nucleophile Z, as illustrated above, are examples of such appropriate Ring A derivatives J. Suitable LG' groups are halo, alkylthio, alkylsulfonyl, alkylsulfonate or arylsulfonate. Treatment of J with an amine $R^{12}NH_2$ effects displacement of LG' to afford intermediates K. An example of this chemical transformation wherein $R^{12}$ is H and LG' is $CH_3SO_2$— is reported by Capps, et al. J. Agric. Food Chem. 1993, 41, 2411-2415, and an example wherein. $R^{12}$ is H and LG' is Cl is reported in Marshall, et al. J. Chem. Soc. 1951, 1004-1015.

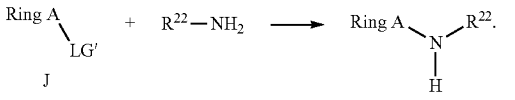

J K

Intermediates of structure K are transformed to compounds of the invention by simultaneous or sequential introduction of the elements, of $R^3$, $R^4$, and $R^5$. For example, treatment of intermediates of structure K with individual isocyanates $R^6$—N=C=O affords in a single step compounds of structure M, which are compounds of the invention wherein $R^2$=—$NR^{22}$—, $R^3$=—C=O—, $R^4$=—NH—, and $R^5$=-chemical bond-$R^6$. Alternative methods to convert compounds of structure K to compounds of structure M are well known to those skilled in the art, wherein $R^3$ together with a leaving group (for example p-nitrophenoxy or chloro) is first introduced, followed by subsequent displacement of the leaving group by, for example, an amine $R^6$—$NH_2$, to introduce $R^5$ and $R^6$.

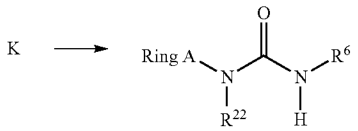

M

Alternatively, treatment of intermediates of structure K with a reagent such as cyanamide ($NH_2$—CN), typically under conditions of heating and optionally in the presence of acid in a solvent such as ethyl acetate or dioxane, affords intermediates N. Alternatives to cyanamide are nitroguanidine or amidinosulfonic acid ($NH_2$—C(=NH)—$SO_3H$). An example of such a transformation using cyanamide is reported by Latham et al., J. Org. Chem. 1950, 15, 884. An example using nitroguanidine is reported by Davis, Proc. Natl. Acad. Sci. USA 1925, 11, 72. Use of amidinosulfonic acid was reported by Shearer, et al. Bioorg. Med. Chem. Lett. 1997, 7, 1763.

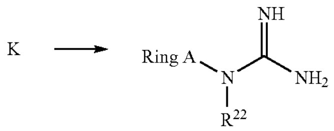

N

In analogy to the conversion of intermediates A or D to embodiments represented by C or F, intermediates K are converted, respectively, to compounds represented by P or Q, which are further embodiments of the invention.

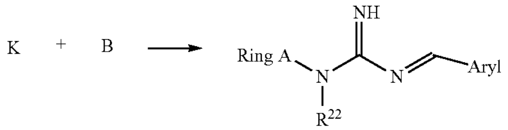

P

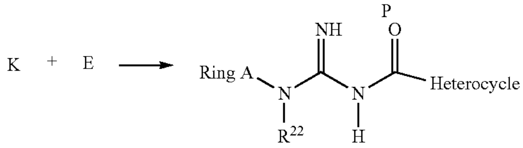

Q

Treatment of A or K with a ketone S, wherein R is as defined above, in place of an aldehyde B in the schemes above, affords compounds of structure T or U, respectively, which are further embodiments of the invention.

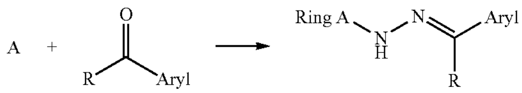

S T

-continued

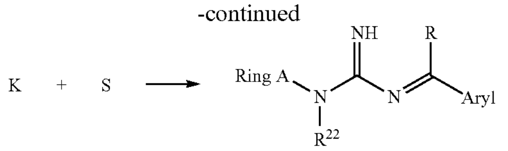

U

The non-guanidino carbon-nitrogen double bond of U can be selectively reduced by an appropriate reducing agent such as a metal (boron, aluminum, silicon, etc.) hydride reagents, preferably one with basic properties, to afford compounds V of the invention.

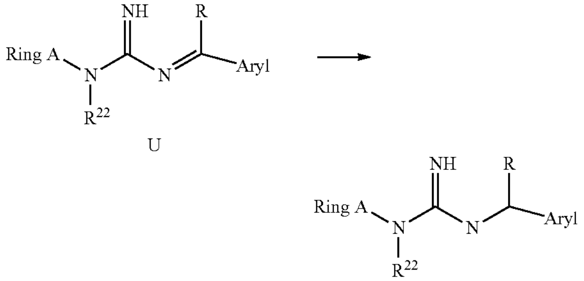

U

V

Embodiments of the invention wherein $R^2$═CO, $R^3$═—$NR^{32}$—, $R^4$═N—, and $R^5$═$ZR^7$, wherein Z is a hydrocarbon chain and $R^7$ is as defined above, may be prepared as follows. When $R^{32}$═H, a Ring A-derived carboxylic acid W is activated by conversion to the corresponding acid chloride, or alternatively to an active ester, or to an analogous activated derivative, many of which are well known in the art. Treatment of the activated carboxylic acid with hydrazine affords the corresponding hydrazide Y. Treatment of Y with an aldehyde or ketone (under conditions of heating and/or mild acid catalysis if necessary) affords the desired final product Z.

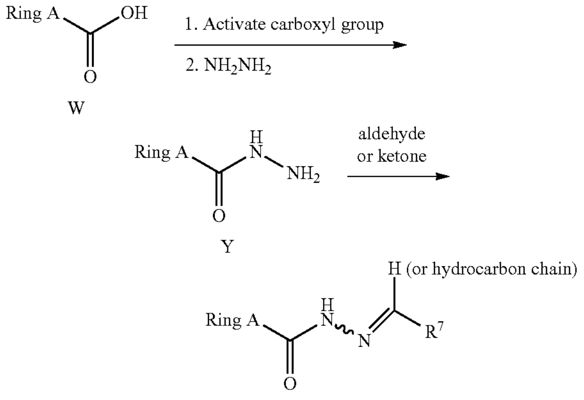

W

Y

Z

If not commercially available, Ring A-derived carboxylic acids W may be prepared by treatment of starting material J above with cyanide ion, optionally with heating or transition metal catalysis, to replace the leaving group LG' with a cyano residue. Basic or acidic hydrolysis of the cyano group affords the desired carboxylic acid intermediate W.

When $R^{32}$ is not H, then a protected form of monosubstituted hydrazine may be used in the above scheme in place of hydrazine. Thus, treatment of the activated carboxylic acid from W with $R^{32}$NHNH-PG, where PG is a nitrogen protecting group such as benzyloxycarbonyl or t-butyloxycarbonyl, followed by deprotection and treatment with an appropriate aldehyde or ketone as above affords Z', a further embodiment of the invention.

Z'

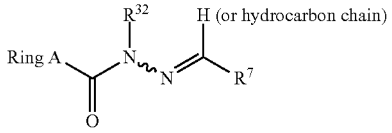

It will be apparent to a practitioner skilled in the art of organic molecule synthesis that the reaction processes illustrated above are representative of a broader set of methods that are logical extensions of the illustrated processes. Thus, additional embodiments of the invention that incorporate additional variants in $R^2$, $R^3$, $R^4$, and $R^5$ claimed by this invention are prepared by obvious modifications of the above processes.

As would be recognized by a person of ordinary skill, it may be advantageous to employ a temporary protecting group in achieving the final product. The phrase "protecting group" as used herein means temporary modifications of a potentially reactive functional group which protect it from undesired chemical transformations. Examples of such, protecting groups include esters of carboxylic acids, silyl ethers of alcohols, and acetals and ketals of aldehydes and ketones, respectively. The field of protecting group chemistry has been reviewed (Greene, T. W.; Wuts, P. G. M. *Protective Groups in Organic Synthesis*, $2^{nd}$ ed.; Wiley: New York, 1991).

One embodiment of this invention is directed to any endogenously occurring mammalian target protein selected by the skilled investigator to be of interest for the identification and/or optimization of a compound as an inhibitor or activator of said protein. In general such selected proteins will already be known to be involved in the etiology or pathogenesis of a human disease. In another embodiment, the invention is also directed toward mutant forms of such mammalian proteins. A "mutein" is a protein having an amino acid sequence that is altered as a result of a mutation that has occurred in its corresponding gene (Weigel et al, 1989). Such mutations may result in changes in one or more of the characteristics of the encoded protein. For example, an enzyme variant that has modified catalytic activity resulting from a change in one or more amino acids is a mutein.

This invention is concerned with proteins harboring an alteration of at least one amino acid residue (the terms "amino acid sequence change" or "amino acid sequence alteration" include changes, deletions, or additions, of at least one amino acid residue, or any combination of deletions, additions, changes) such that the resulting mutein has become (as a result of the mutation) resistant to a known therapeutic agent relative to the sensitivity of the non-mutated version of said protein to the therapeutic agent. This specialized class of muteins is hereinafter referred to as a theramutein, and the corresponding protein lacking the mutation is referred to herein as a prototheramutein.

As used herein, "prototheramutein" refers to an endogenously occurring protein in a cell that is susceptible to mutation that confers relative insensitivity (i.e. resistance) to a therapeutic compound which otherwise inhibits or activates the protein. Accordingly, "theramutein" refers to an endogenously occurring protein or portion of a protein in a cell that contains at least one amino acid sequence alteration relative to an endogenous form of the protein, wherein the amino acid sequence change is or was identified or becomes identifiable, and is or has been shown to be clinically significant for the development or progression of a given disease, following exposure of at least one human being to a substance that is known to inhibit or activate the prototheramutein. Solely for the purposes of defining the preceding sentence, a substance need not be limited to a chemical agent for the purposes of first defining the existence of a theramutein. Thus, by definition, a theramutein is a protein which harbors a mutation in its corresponding endogenous gene, wherein said mutation is associated with the development of clinical resistance in a patient to a drug that is normally able to activate or inhibit the non-mutated protein. With respect to a given theramutein, the term "corresponding prototheramutein" refers to the prototheramutein which, through mutation, gives rise to said theramutein. Similarly, with respect to a given prototheramutein, the "corresponding theramutein" refers to the theramutein which has arisen by mutation from said prototheramutein.

Accordingly, it is apparent to a skilled artisan that, as the genes which encode theramuteins are limited to endogenously occurring genes, the definition of a theramutein excludes proteins encoded by disease-causing infectious agents such as viruses and bacteria. As used herein, the term "endogenous gene" refers to a gene that has been present in the chromosomes of the organism at least in its unmutated form, since inception. The term "cell" as used herein refers to a living eukaryotic cell whether in an organism or maintained under appropriate laboratory tissue or organ culture conditions outside of an organism.

In one embodiment of the invention, the target protein (POI) may be any endogenously encoded mammalian protein. In another aspect of the invention, the POI is a theramutein, which is a protein that is altered for the first time with respect to a commonly occurring "wild type" form of the protein (i.e., a wild type protein is the prototheramutein from which the theramutein arises). In yet another aspect of the invention, a theramutein is a variant of a protein that is, itself, already a mutein (i.e., a mutein is the prototheramutein from which the theramutein arises). In still another embodiment, a theramutein may be further mutated as compared to a previously existing theramutein. In such instances, the first theramutein (such as the T315I mutant of p210 BCR-ABL (see below), may be thought of as a "primary" theramutein, whereas subsequent mutations of the (already mutated) T315I variant may be termed a secondary theramutein, tertiary theramutein, etc. As exemplified below, a mutein of the invention is a variant of Bcr-Abl tyrosine kinase that escapes inhibition by an inhibitor of the "wild type" Bcr-Abl. Such a Bcr-Abl mutein is altered with respect to a more common or "wild type" form of Bcr-Abl (which is also a mutein as well) in such a way that a property of the protein is altered.

It is understood that a protein of interest (POI) is an endogenously encoded mammalian protein. It will also be understood that a mutein of primary interest is a theramutein that may have the same, increased, or decreased specific activity relative to its prototheramutein, and that it is not inhibited or is poorly inhibited by an agent that is used to inhibit the prototheramutein. Likewise, another theramutein of primary interest is one that has the same, increased or decreased specific activity (relative to its prototheramutein) and that is not activated or is poorly activated by an agent that is used to activate the prototheramutein. Other variations are obvious to the skilled artisan. It will be further appreciated that theramuteins can include naturally occurring or commonly observed variants of a protein, for example, variants that are expressed from different alleles of a particular gene. In some cases such variants may be unremarkable with respect to their normal cellular function, with functional differences becoming apparent only in the presence of agents that differentially inhibit or activate the cellular function of the variants. For example, naturally occurring variants of a particular enzyme may have activity profiles that are not substantially different, but a therapeutic agent that modulates one may be ineffective in modulating the other.

It will be appreciated that one aspect of the invention is the identification of an agent that is active against a selected POI whose cellular function contributes to a given disease state such that activators or inhibitors of said POI would be expected to be therapeutically effective during the course of treatment for the disease. No limitation of any kind or nature is intended on the type of disease that may be treated, nor on the type of protein that may be targeted for modulation according to the teachings herein, provided that all other limitations stated herein are met, including the fact that any such protein that is selected for targeting must be an endogenous protein. Obviously, the skilled investigator may use non-endogenously occurring nucleic acids such as cDNAs in order to practice the method taught herein provided that the amino acid sequence corresponds to an endogenously occurring POI.

It will also be appreciated that, whereas one aspect of the invention is the identification of an agent that is active against a protein or theramutein that arises or becomes dominant (by any mechanism) prior to or during the course of a treatment for a given disease, another aspect is the identification of an agent that is active against a mutein that is common within a population of unafflicted individuals, but wherein said mutein is less susceptible to modulation by an approved drug, and where the variation in the activity profile of the mutein becomes important (and is therefore first identified as being a theramutein) in a disease state such as where it is overexpressed or participates in a signaling process which has otherwise become abnormally regulated. For example, a neoplastic disease may be caused by abnormal regulation of a cellular component other than the theramutein or its prototheramutein; and still be treatable with an inhibitor of the prototheramutein, whereas the same treatment would be less effective or ineffective where the theramutein was present. This can be an issue where it is observed that the response of a particular tumor type to an anticancer agent varies among individuals that express different variants of an enzyme against which the anticancer agent is directed (Lynch et al., 2004). Here, the variants would not have arisen or become predominant during the course of treatment of the disease, but are preexisting in the healthy population and are detected only by their altered responsiveness to a particular course of established therapeutic treatment.

As used herein, the terms "agonist" and "activator" of a protein are used interchangeably. An activator (agonist) is limited to a substance that binds to and activates the functioning of a given protein. Unless explicitly stated otherwise, an "activator", an "agonist", and an "activator of a protein" are identical in meaning. The activation by an activator may be partial or complete. Likewise, as used herein, the terms "antagonist" and "inhibitor" of a protein are used interchangeably. An inhibitor (antagonist) is limited to a substance that binds to and inhibits the functioning of a given protein. To state that a substance "inhibit(s)" a protein means the substance binds to the protein and reduce(s) the protein's activity in the cell without materially reducing the amount of the protein in the cell. Similarly, to state that a substance "activate(s)" a protein, such as a prototheramutein or theramutein, is to state that the substance increases the defined function of the protein in the cell without substantially altering the level of the protein in the cell. Unless explicitly stated otherwise, an "inhibitor", an "antagonist" and an "inhibitor of a protein" are also synonymous. The inhibition by an inhibitor may be partial or complete. A modulator is an activator or an inhibitor. By way of example, an "activator of $PKC_{\beta 1}$" should be construed to mean a substance that binds to and activates $PKC_{\beta 1}$. Similarly, an "inhibitor of $p210^{Bcr-Abl}$" is a substance that binds to and inhibits the functioning of $p210^{Bcr-Abl}$. To state that a substance "inhibits a protein" requires that the substance bind to the protein in order to exert its inhibitory effect. Similarly, to state that a substance "activates protein X" is to state that the substance binds to and activates protein X. The terms "bind(s)," "binding," and "binds to" have their ordinary meanings in the field of biochemistry in terms of describing the interaction between two substances (e.g., enzyme-substrate, protein-DNA, receptor-ligand, etc.). As used herein, the term "binds to" is synonymous with "interacts with" in the context, of discussing the relationship between a substance and its corresponding target protein. As used herein, to state that a substance "acts on" a protein, "affects" a protein, "exerts its effect on" a protein, etc., and all such related terms uniformly mean (as the skilled investigator is well aware) that said substance activates or inhibits said protein.

The concept of inhibition or activation of a mutated form of an endogenous protein to a greater extent than the corresponding non-mutated counterpart protein is defined for the first time and referred to herein as a positive "specificity gap." In general terms, and using an inhibitor case as an example, the specificity gap refers to the difference between the ability of a given substance, under comparable conditions to inhibit the theramutein in a cell-based assay system of the invention as compared to either:

a) the ability of the same substance under comparable conditions to inhibit the prototheramutein; or
b) the ability of a second substance (usually a known inhibitor of the prototheramutein) to inhibit the theramutein under comparable conditions; or
c) the ability of the second substance to inhibit the prototheramutein under comparable conditions.

When the comparison is made between the effects of two distinct substances (tested individually) on the theramutein alone, the result is termed a homologous specificity gap determination.

Alternatively, when a comparison is made between the effects of two distinct substances (generally, but not always), one of which is tested on the theramutein and the other on the prototheramutein, respectively, the result is termed a heterologous specificity gap (SG) determination. Thus, (a) and (c) as given above are examples of heterologous specificity gap (SG) determinations (although (a) uses the same substance in both instances), whereas (b) is an example of a homologous specificity gap determination.

Figure 3:
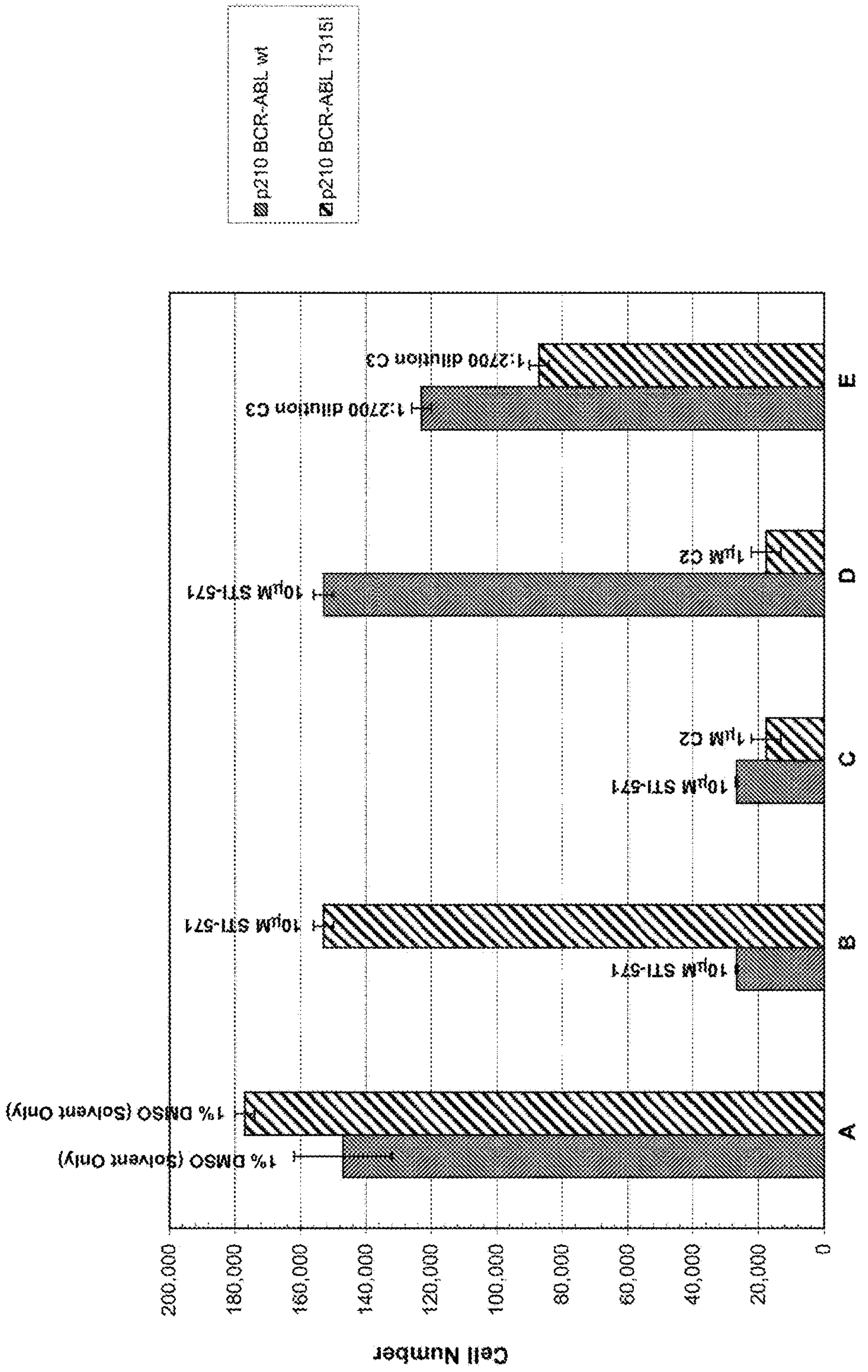
FIG. 3 shows various determinations of the specificity gap by comparing the effects of various compounds identified in the screen in terms of their effects on the prototheramutein- and theramutein-expressing cell lines. Compound 3 (C3) shows the best example of the ability of the method to identify a compound that exerts an even greater effect on the theramutein than on its corresponding prototheramutein. (Panel E). Panel A: control DMSO treatments; B: negative heterologous specificity gap; C: slightly positive heterologous specificity gap; D: large positive homologous specificity gap; E: positive heterologous specificity gap. See text for explanations.

Reference to FIG. 3 is informative in understanding and elucidating these concepts.

Analogous issues apply when the case concerns an activator. It will be immediately obvious to the skilled artisan that the term "comparable conditions" includes testing two different compounds, for example, at the same concentration (such as comparing two closely related compounds to determine relative potency), or by comparing the effects of two different compounds tested at their respective $IC_{50}$ values on the corresponding prototheramutein and theramutein. The skilled investigator will easily recognize other useful variations and comparable conditions.

Thus, in one embodiment of the application of this approach, substances that are more effective against a theramutein have a "positive specificity gap." A "zero, null or no" specificity gap indicates that there is no significant measurable difference between the effect of a substance on the theramutein as compared to its effect on the prototheramutein (however such compounds may be quite useful in their ability to inhibit or activate both a theramutein and its corresponding prototheramutein), and a "negative specificity gap" indicates a substance that at a given concentration is less effective against the given theramutein than against a form of the corresponding prototheramutein or other comparative form of the theramutein (such as one that may harbor a different mutation). The latter category is generally of lesser interest than the former categories of compounds, except in the case where the compound is so potent that its relatively lesser effect on the theramutein is of no real concern from the perspective of therapeutic efficacy. The skilled investigator can easily recognize a variety of approaches to quantifying the specificity gap assessment in a manner tailored to his or her needs. Such an analysis may assist the skilled investigator in classifying various compounds into discrete categories that may be helpful in guiding further lead optimization or biological profiling studies on such compounds.

The invention also provides a means for identifying compounds that exhibit a desired specificity gap. Such compounds can be identified and their ability to inhibit or activate the theramutein determined using an in vitro cell-based assay system where the effect of a substance on the cellular functioning of the mutated endogenous form of the protein is compared to the effect of the same drug on the cellular functioning of a non-mutated endogenous form of the protein.

Thus, the system enables the discovery of compounds capable of binding to a theramutein and exerting a greater modulatory effect on the cellular functioning of said theramutein than on its corresponding prototheramutein. Further, the system enables the discovery of compounds capable of binding to a theramutein and exerting at least as great or greater modulatory effect on the cellular functioning of a theramutein than previously known compounds are able to exert on the corresponding prototheramutein. In a particular embodiment of the invention, a compound may be screened for and identified that 1) is at least as effective against the theramutein as the original drug is against the prototheramutein, and/or 2) is similarly effective against the prototheramutein as against the theramutein (i.e., displays a small or essentially zero specificity gap).

In an embodiment of the invention, cells that overexpress a theramutein of interest are used to identify chemical agents that are inhibitors or activators of (i.e., that bind to and inhibit or that bind to and activate) at least the selected theramutein. The chemical agents may also be inhibitors or activators of the prototheramutein or even other theramuteins of the same prototheramutein. As used herein, the terms "chemical agent" and "compound" are used interchangeably, and both terms refer exclusively to substances that have a molecular weight up to, but not including, 2000 atomic mass units (Daltons). Such substances are sometimes referred to as "small molecules." Unless otherwise stated herein, the term substance as used herein refers exclusively to chemical agents/compounds, and does not refer to biological agents. As used herein, "biological agents," are molecules which include proteins, polypeptides, and nucleic acids, and have molecular weights equal to or greater than 2000 atomic mass units (Daltons).

In one embodiment of the invention, a theramutein is selected and used in a phenoresponse-based cellular assay system of the present invention designed to identify agents that are inhibitors or activators of the theramutein. Where two or more distinct theramuteins originating from the same prototheramutein are known, it is preferable to select the most resistant theramutein available for use in the assay system. In general, the degree of resistance of a theramutein to a given chemical agent is determined relative to its non-mutated counterpart (prototheramutein) using the drug that was first administered and known to inhibit or activate the prototheramutein and against which the theramutein "arose." The methods of determining the degree of such resistance, for example by analysis of $IC_{50}$ or $AC_{50}$ values, are well known and standard in the art and will not be reiterated herein. However, no causal relationship is necessary or should be inferred between the treatment of the patient with a given therapeutic agent per se and the subsequent appearance of a theramutein. Rather, what is required in order to practice the invention as it pertains to theramuteins is that a true theramutein be properly selected according to the teachings herein.

Thus, for example, randomly generated site directed mutants of known proteins that are created in the laboratory but that have not been shown to be clinically relevant are not appropriate muteins for use within the scope of this invention. Such muteins would not, of course, be properly classified as theramuteins either.

Figure 4:
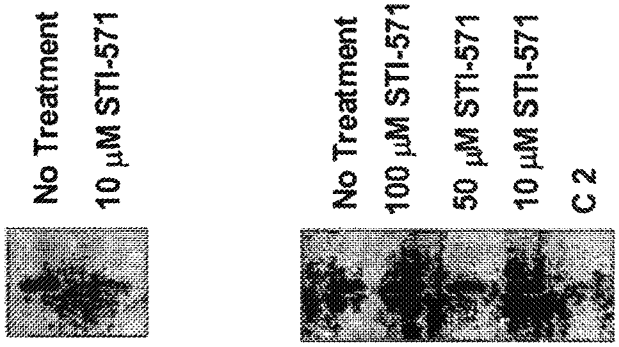
FIG. 4 shows an autoradiograph of recombinant P210 Bcr-Abl wild type and T315I mutant kinase domains assayed for autophosphorylation activity. 200 ng of protein were preincubated with test substances for 10 minutes under standard autophosphoryation reaction conditions and then radiolabelled ATP was added and the reactions proceeded for 30 minutes at 30° C., after which the samples were separated by SDS-PAGE. The gels were silver-stained, dried down under vacuum and exposed to X-ray film. Note that whereas 10 μM STI 571 is effective against wild type P210 Bcr-Abl, it is virtually ineffective against the T315I kinase domain, even at concentrations up to 100 μM. "P210 cell line" refers to cells expressing $p210^{BCR\text{-}ABL\text{-}wt}$. "T315I cell line" refers to cells expressing $p210^{BCR\text{-}ABL\text{-}T315I}$.
Figure 5:
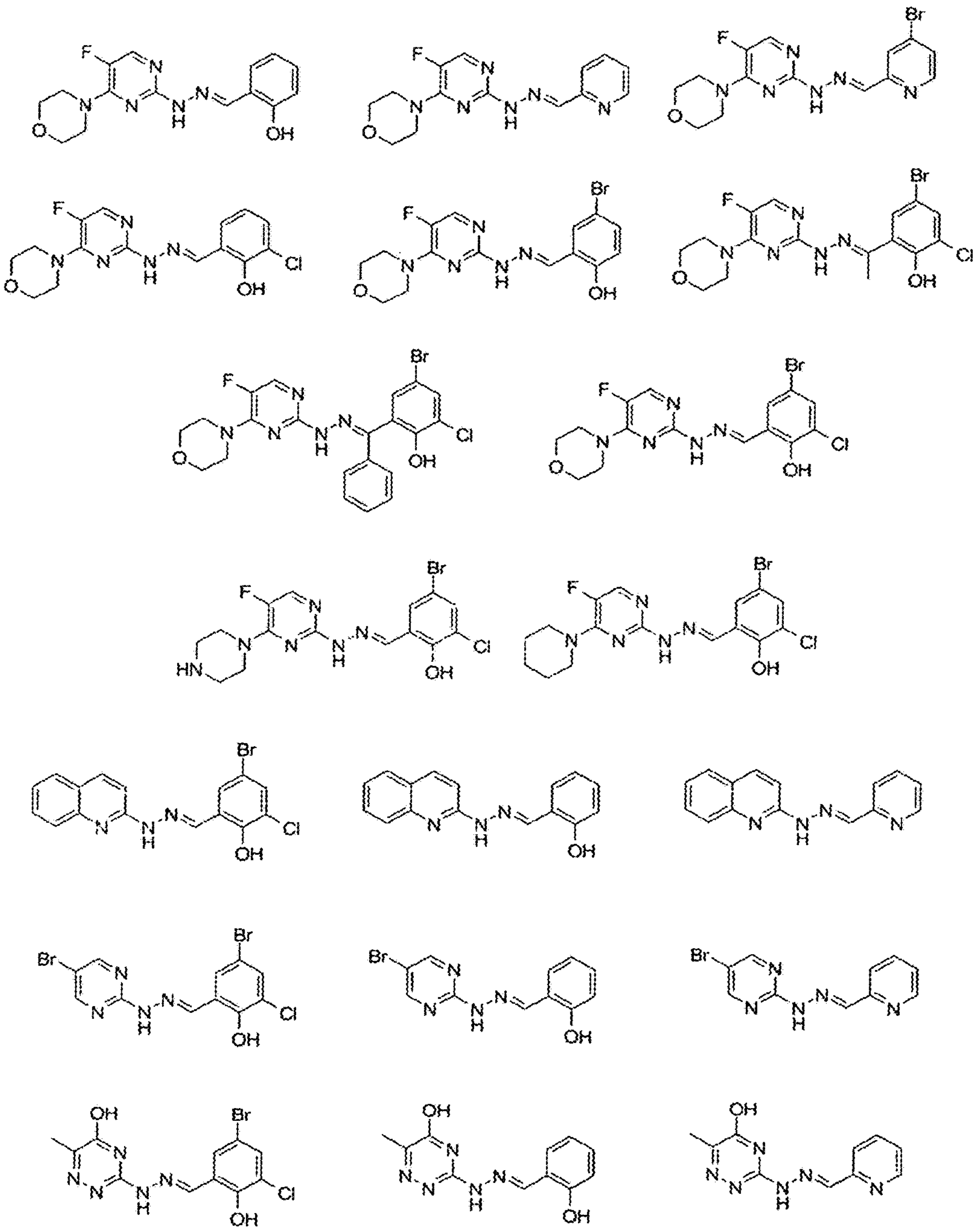
FIG. 5 shows the chemical structures of representative compounds of the present invention.
Figure 6:
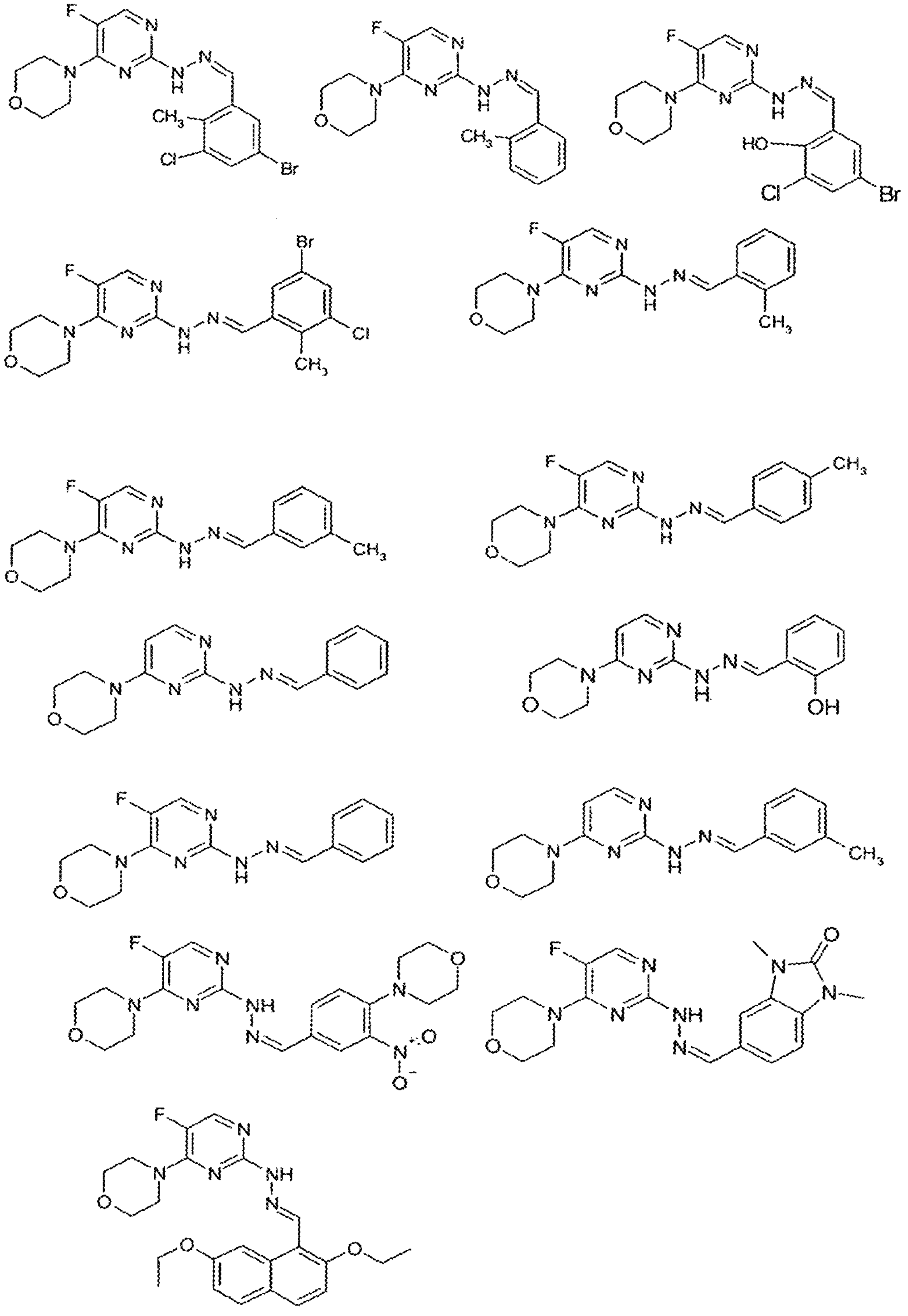
FIG. 6 shows the chemical structures of representative compounds of the present invention.
Figure 7:
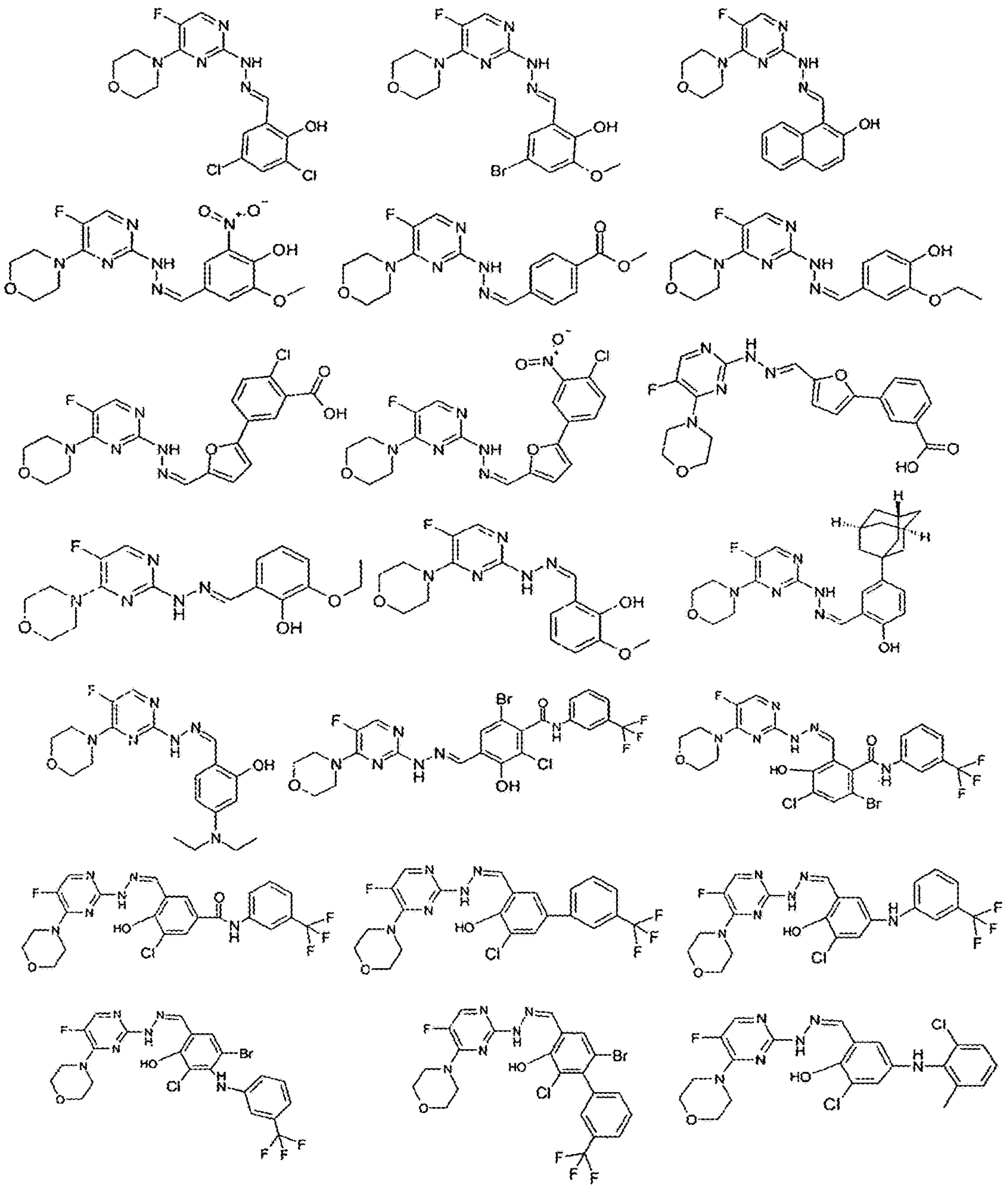
FIG. 7 shows the chemical structures of representative compounds of the present invention.
Figure 8:
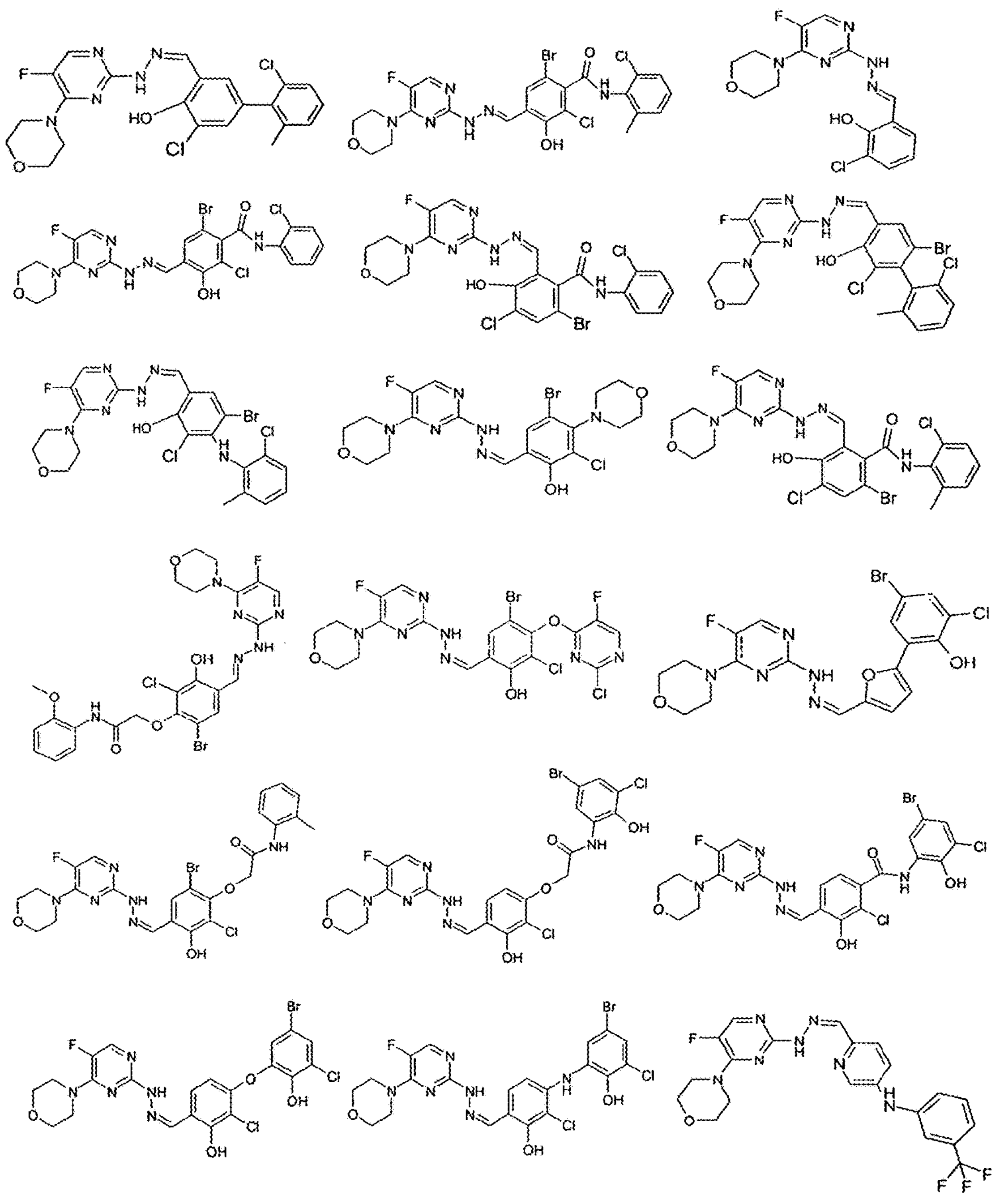
FIG. 8 shows the chemical structures of representative compounds of the present invention.
Figure 9:
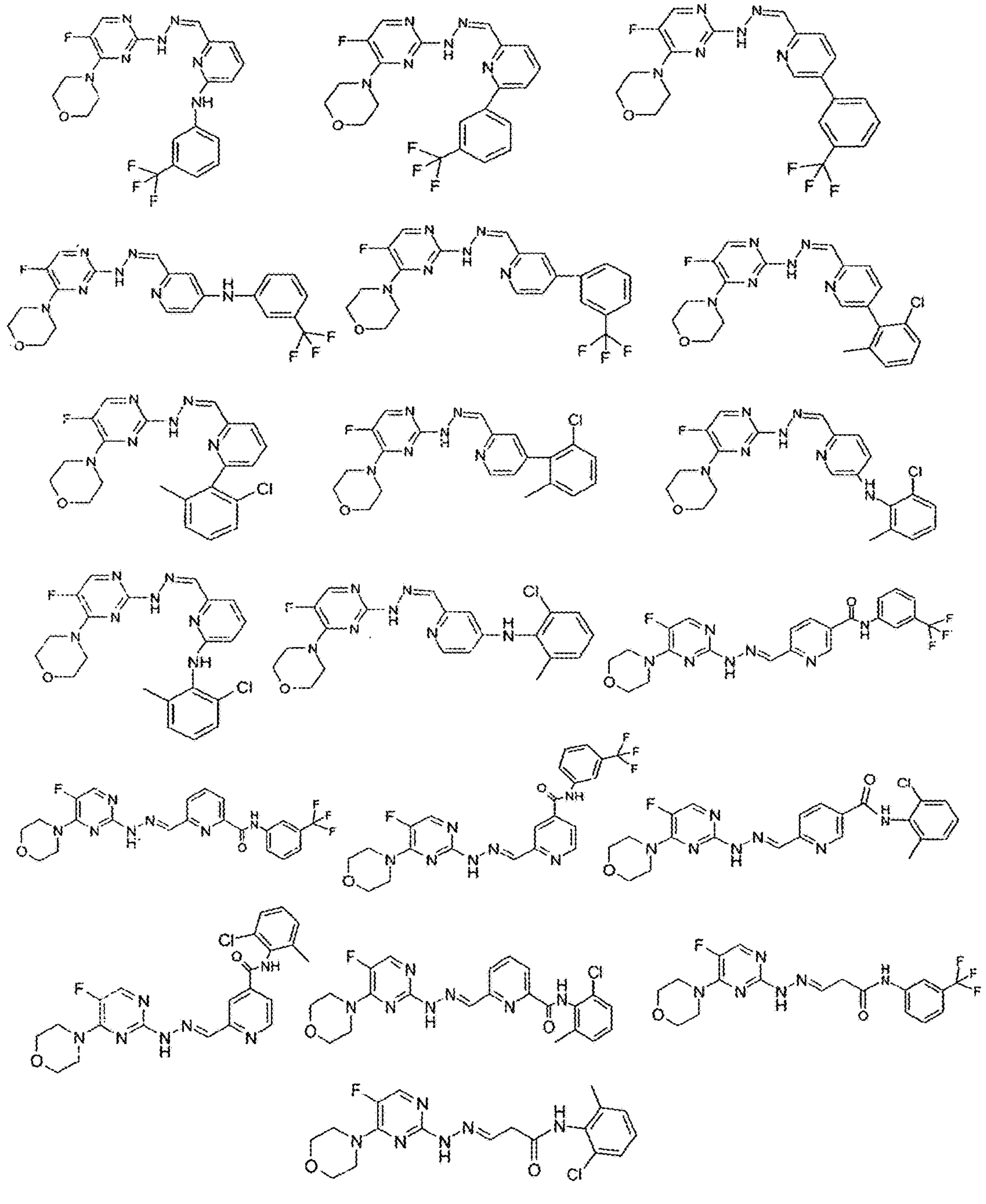
FIG. 9 shows the chemical structures of representative compounds of the present invention.
Figure 10:
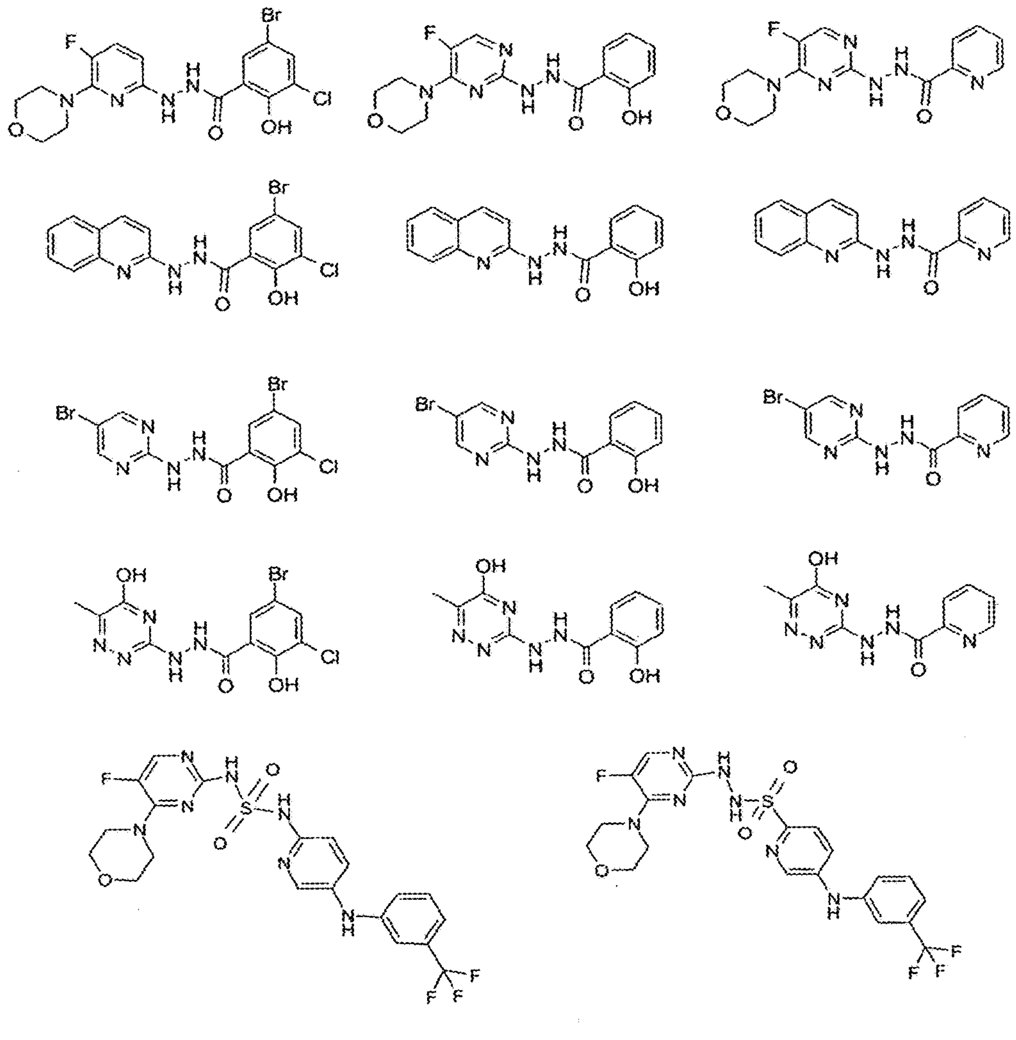
FIG. 10 shows the chemical structures of representative compounds of the present invention.
Figure 11:
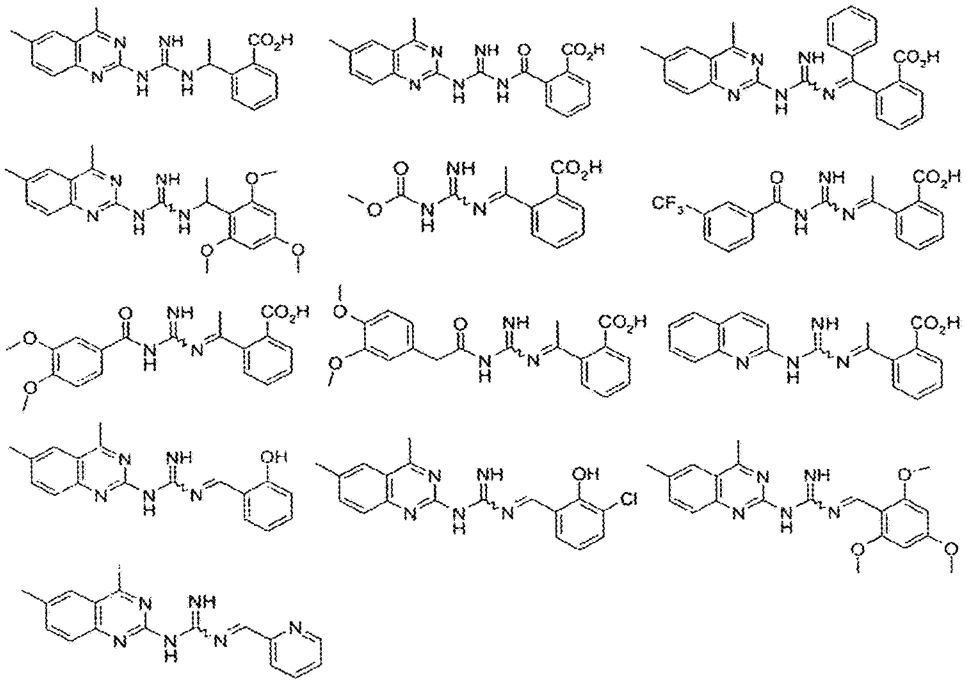
FIG. 11 shows the chemical structures of representative compounds of the present invention.
Figure 12:
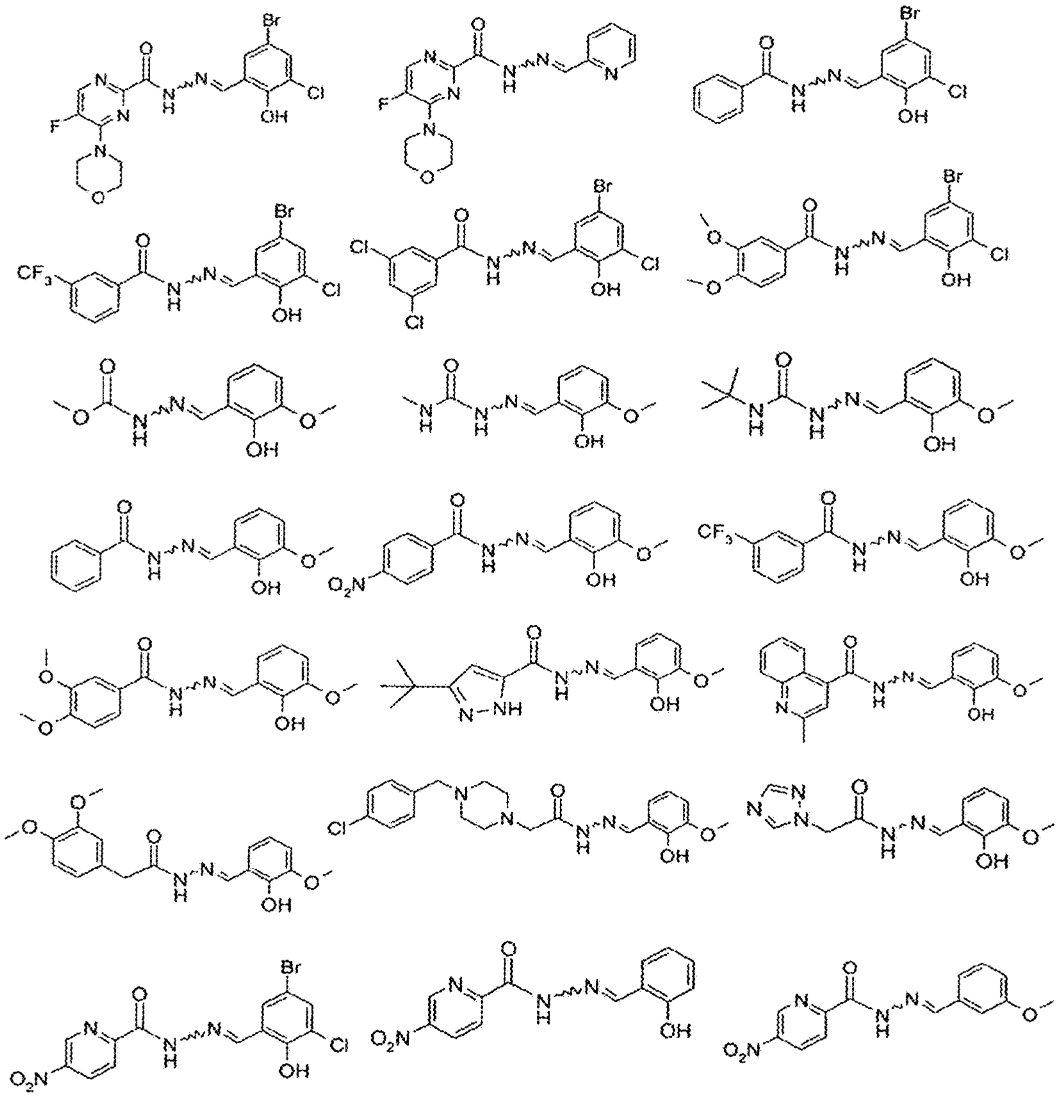
FIG. 12 shows the chemical structures of representative compounds of the present invention.
Figure 13:
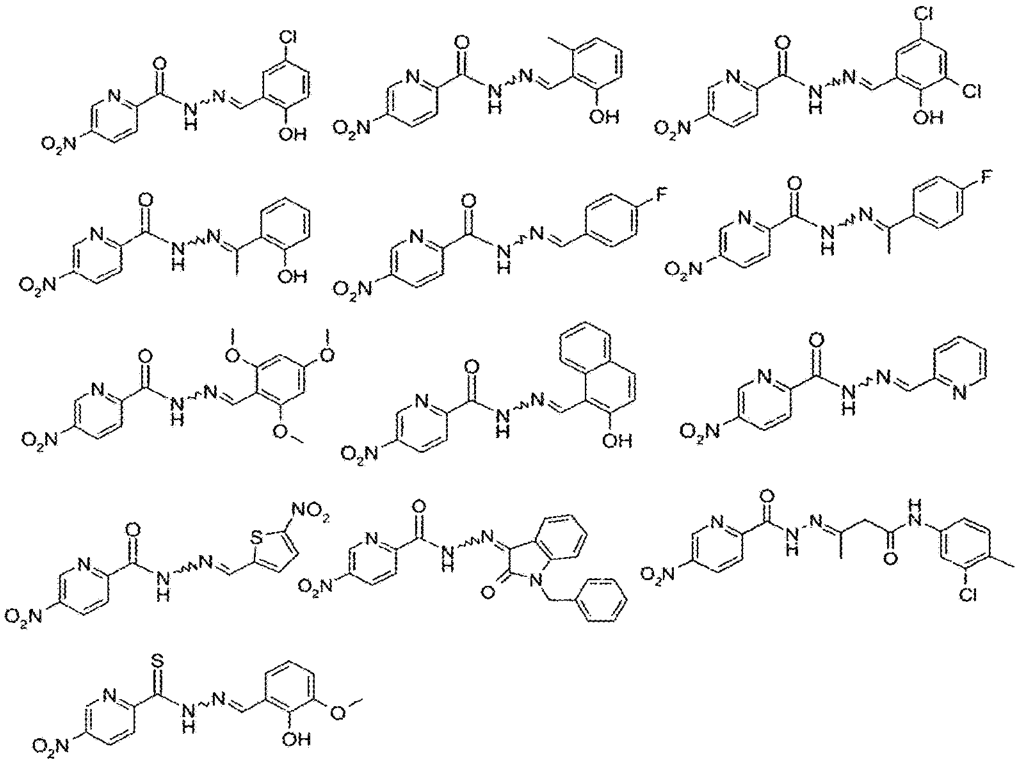
FIG. 13 shows the chemical structures of representative compounds of the present invention.

For example, in an effort to obtain potential inhibitors of mutants of $p210^{Bcr\text{-}Abl}$, Huron et al. (2003) used a recombinant c-abl preparation and screened a series of compounds known to inhibit c-src tyrosine kinase activity. The authors performed c-abl kinase assays on their compounds and identified the most potent compound as an 8 nM inhibitor against c-abl. When this compound (PD166326) was tested against various $p210^{Bcr\text{-}Abl}$ theramuteins, however, it showed activity against some of the mutants such as $p210^{Bcr\text{-}Abl\text{-}E255K}$, but the $p210^{Bcr\text{-}Abl\text{-}T315I}$ theramutein was found to remain 10 fold more resistant (Huron et al. 2003, Table 3). Furthermore, in each case the compound was still markedly less effective on the $p210^{Bcr\text{-}Abl}$ theramuteins than it was against the wild-type $p210^{Bcr\text{-}Abl}$. When the compound was tested against $p210^{Bcr\text{-}Abl\text{-}T315I}$ mutant activity, it was unable to inhibit the activity to any appreciable extent (p. 1270, left hand column, second paragraph; see also FIG. 4.). Thus, the disclosed compound was able to inhibit a theramutein that is partially resistant to STI-571, but had no activity against the T315I mutant of Bcr-Abl, which was already known at that time to be the theramutein that exhibited the most resistance to STI-571. Hence purely and simply, the Huron methodology failed to identify an effective inhibitor of the $p210^{Bcr\text{-}AblT315I}$ theramutein.

Indeed, prior to the disclosure of this invention, including both the detailed methodology described for the first time herein as well as the compositions provided herein, no one anywhere in the world has been successful in identifying a chemical agent, let alone a methodology that is capable of identifying a chemical agent that effectively inhibits the $p210^{Bcr\text{-}AblT315I}$ theramutein to an equal or greater extent than STI-571 is able to do with respect to the wild type $p210^{Bcr\text{-}Abl}$ protein. (See Shah et al., Science, July, 2004; O'Hare et al., Blood, 2004; Tipping et al., Leukemia, 2004; Weisberg et al., Leukemia, 2004).

It cannot be overemphasized that such compounds would be immensely useful, because at the present time there is no alternative for patients who progress to $p210^{Bcr\text{-}Abl\text{-}T315I}$ theramutein-mediated imatinib mesylate-resistant status. Once patients develop such resistance, there is no other effective alternative treatment available, and death is certain. The method described herein provides the first reported approach to identify, pharmacologically characterize and chemically synthesize effective inhibitors of the $p210^{Bcr\text{-}Abl\text{-}T315I}$ theramutein. Moreover, the skilled investigator will immediately recognize the applicability and generalizability of this approach to any highly drug-resistant theramutein. Finally, the skilled investigator will further recognize that linking a phenoresponse as defined herein to the increased presence and functional activity of a particular POI in the cell under appropriate conditions allows one to utilize the method with any given endogenous target protein for which a therapeutically effective compound is sought.

In the present invention, a test cell is used that displays a carefully selected phenotypic characteristic (as defined below) which is linked to the presence and functional activity of the particular protein-of-interest (POI) or theramutein-of-interest (TOI) in the cell under appropriate conditions. With respect to a theramutein, this should be qualitatively the same as the phenotypic characteristic displayed by a cell that expresses the prototheramutein. A phenotypic characteristic (i.e. a non-genotypic characteristic of the cell) is a property which is observed (measured), selected and/or defined for subsequent use in an assay method as described herein. Expression of the phenotypic characteristic is responsive to the total activity of the protein in the cell, and is a result of the absolute amount of the protein and its specific activity. Often, the phenotypic characteristic is observable as a result of elevated levels of protein activity and is not apparent in cells that express low amounts of the protein, or if the protein is also a theramutein, then the phenotypic characteristic will often not be apparent in cells expressing low amounts of either the theramutein or its corresponding prototheramutein. Further, it can often be demonstrated that the phenotypic characteristic is modulated by modulating the specific activity of the protein with an inhibitor or activator of the theramutein, although this is not always the case since an inhibitor or activator of the TOI may not always be available at the time the skilled investigator undertakes such a project. (However, clearly a known inhibitor or activator of a given prototheramutein will always exist as a result of the intrinsic definition of the nature of a theramutein itself.) Thus, for the purpose of defining the phenotypic characteristic to be subsequently used with a given test cell for assay purposes, the skilled investigator may also use a substance capable of increasing or decreasing the expression of the gene encoding a given POI (such as a theragene in the case of a theramutein), which will in turn lead to increases or decreases of the level of the corresponding theramutein. This allows the skilled investigator to simulate the effects of certain types of activators or inhibitors of the theramutein (such as a suicide inhibitor of the theramutein, which is a class of chemical agent which binds irreversibly and covalently modifies the TOI, rendering it permanently inactive), without actually having access to such a compound, for the purposes of refining the appropriate phenotypic characteristic for subsequently establishing a useful cellular assay system. Examples known to one of ordinary skill that would be helpful for such purposes include the use of anti-sense DNA oligonucleotides, small interfering RNAs, other RNA interference-based methodologies, and vector constructs containing inducible promoter systems. In this manner, the selected phenotypic characteristic is linked to the activity of the theramutein in the test cell. Notably for theramuteins, the selected phenotypic characteristic is usually also displayed by a cell that overexpresses the prototheramutein and in which the phenotypic characteristic is modulated by known inhibitors or activators of the prototheramutein.

A phenotypic characteristic is simply a characteristic of a cell other than a genotypic characteristic of the cell. Except for the specific requirements of a properly defined phenotypic characteristic as disclosed herein for the purposes of creating useful cellular assay systems according to the teachings of certain of the embodiments of the invention, no other limitation of the term phenotypic characteristic of any kind or nature is intended or appropriate in order to properly and effectively practice the invention. Indeed, the skilled artisan must be able to select any characteristic of the cell that maximizes the utility of establishing the proper cell-based assay for his or her needs. The phenotypic characteristic can be quantitative or qualitative and be observable or measurable directly (e.g., observable with the naked eye or with a microscope), but most commonly the characteristic is measured indirectly using standard automated laboratory equipment and assay procedures which are known to those of skill in the art. The term "observable" means that a characteristic may be measured or is otherwise detectable under appropriate conditions by any means whatsoever, including the use of any type of laboratory instrumentation available. The term "detectable" is not the same as "detected." A characteristic may be detectable to a skilled artisan without being detected at any given time, depending upon how the investigator chooses to design the assay system. For example, in searching for activators of a POI such as a prototheramutein (or theramutein), it may be desirable to have the relevant phenotypic characteristic detected only after the addition of a known activator or test substance capable of activating the POI. This provides the ability to maximize the intensity of the signal that is generated by the test cell in the assay.

Phenotypic characteristics include but are not limited to growth characteristics, transformation state, differentiation state, substrate phosphorylation state, catalytic activity, ion flux across the cell membrane (calcium, sodium, chloride, potassium, hydrogen ions, etc.), pH changes, fluctuations of second messenger molecules or other intracellular chemical species such as cAMP, phosphoinositides, cyclic nucleotides, modulations of gene expression, and the like. The characteristic of the cell may be observable or measurable continuously (e.g., growth rate of a cell), or after a period of time (e.g., terminal density of a cell culture), or transiently (e.g., modulation of a protein causes a transient change in phosphorylation of a substrate of the protein, or a transient flux in ion flow across the membrane, or elevations or reductions in intracellular cAMP levels). In certain embodiments, a selected phenotypic characteristic may be detected only in the presence of a modulator of the protein. No limitations are intended with respect to a characteristic that may be selected for measurement. As used herein, the terms "characteristic of a cell" and "phenotypic characteristic", and simply "characteristic", when used to refer to the particular measurable property of the intact cell or a sub-cellular fraction of the cell following the treatment of a test cell with a substance, are identical. For example, a phenotypic characteristic can be focus formation that becomes observable when a cell that over expresses a selected protein is cultured in the presence of an activator of the protein, or it may be a transient increase or decrease in the level of an intracellular metabolite or ion, such as cAMP, calcium, sodium, chloride, potassium, lithium, phosphatidylinositol, cGMP, bicarbonate, etc. It is obvious to one of ordinary skill in the art that after a cell is exposed to a test substance, the characteristic so measured (assayed) may be determined on a sub-cellular fraction of the cell. However, the initial treatment of the cell with a substance, which thereby causes the substance to come into contact with the cell, must be performed on the intact cell, not a sub-cellular fraction.

The characteristic selected for measurement within the cell must not be an intrinsic physical or chemical property of the protein (or theramutein or prototheramutein) itself (such as the mere amount (mass) of the protein inside the cell), but rather must be a characteristic that results from the activity of the protein (or theramutein or prototheramutein) inside the cell, thus affecting a characteristic of the cell which is distinct from the theramutein itself, as discussed in detail above. For example, where the theramutein is a protein kinase that is capable of undergoing autophosphorylation, a process whereby the enzyme is capable of catalyzing the phosphorylation of itself by transferring a terminal phosphate group from ATP onto itself, it would NOT be appropriate to select the phosphorylation state of the TOI as an appropriate phenotypic characteristic of the cell for measurement. This is because such a characteristic does not reflect the activity of the TOI on other cellular components. As the skilled investigator knows, autophosphorylation is not necessarily reflective of the activity of a protein kinase in a cell, since mutants of protein kinases are known that retain enzymatic activity sufficient to undergo autophosphorylation, yet have lost the capability to engage in signal transduction events within the cell. The classic paper by White et al. (1988) is both educational and noteworthy in this respect.

The term "responsive phenotypic characteristic" means a characteristic of the cell which is responsive to inhibitors or activators of a given protein (including, e.g., a prototheramutein or theramutein). The term "known therapeutic agent" is defined as any agent that has been administered to a human being for the treatment of a disease in a country of the world.

A useful phenotypic characteristic, as exemplified herein in association with $p210^{Bcr\text{-}Abl}$ and theramuteins thereof, is disregulation of cell growth and proliferation. It is noted that the same or similar assay may be appropriate for use with many different proteins of interest. For example, disregulations of growth, proliferation, and/or differentiation are common phenotypic characteristics that may result from overexpression of a variety of different cellular proteins. It is an important teaching of this invention that by overexpressing a selected protein in order to cause the appearance of such a phenotypic characteristic, the characteristic becomes linked to the presence, amount, and specific activity of that selected protein under suitable conditions, and this linkage allows the skilled investigator to identify inhibitors or activators of a protein of interest (POI) as desired. Accordingly, the phenotypic characteristic is responsive to changes in the level and/or specific activity of the selected protein. Such a responsive phenotypic characteristic, when also demonstrated to be responsive to a known modulator of the POI is referred to herein as a "phenoresponse." In the special case of a theramutein which has no known modulator, a modulator of the prototheramutein must be utilized to establish a phenorespone to be used with the theramutein. The conception and recognition of this highly useful property of a cell represents one of the substantial advances of this invention over the prior art, including Applicant's own prior original work in the general area of cell-based assays (U.S. Pat. Nos. 4,980,281; 5,266,464; 5,688,655; 5,877,007). The identification and selection of the phenoresponse provides the skilled investigator with a cellular assay system that is extremely sensitive in terms of its ability to identify inhibitors or activators of the POI, and therefore identifies such chemical agents with a much higher degree of assurance than any other related assay method disclosed in the prior art.

Though not always necessary, it will often be advantageous to employ cells that express high levels of the POI, and to select a phenotypic characteristic that results from overexpression of the POI. This is because phenotypic characteristics linked to the functioning of the POI generally become more distinguishable (easier to measure) as a POI is overexpressed to a greater extent. Further, phenoresponses that are observed in response to modulators of the POI are often amplified as the functional level of the POI is increased. Expressed another way, the selected phenoresponse observed in cells that overexpress the protein (or theramutein) is particularly sensitive to modulators of the protein (or theramutein).

Preferably, the protein is stably expressed in a test cell. Stable expression results in a level of the protein in the cell that remains relatively unchanged during the course of an assay. For example, stimulation or activation of a component of a signaling pathway may be followed by a refractory period during which signaling is inhibited due to down-regulation of the component. For proteins of the invention, such down-regulation is usually sufficiently overcome by artificially overexpressing the protein. Expressed another way, the expression is sufficiently maintained that changes in a phenotypic characteristic that are observed during the course of an assay are due primarily to inhibition or activation of the protein, rather than a change in its level, even if down-modulation of the protein subsequently occurs. For these reasons, although stable expression of the protein is preferred, transfection followed by transient expression of the protein may be employed provided that the selected phenotypic characteristic is measurable and the duration of the assay system is short relative to the progressive decline in the levels of the transiently expressed protein that is to be expected in such systems over time. For these reasons, stably expressing cell lines are preferred (U.S. Pat. No. 4,980,281).

The term "cellular specificity" means the ability of a compound, at a given concentration, to modulate a selected phenoresponse of the Test cell without affecting the Control Cell to the same extent, if at all. The term "cellular specificity gap" ("CSG") means a measurement of the ability of a selected compound to modulate the selected phenoresponse corresponding to a given target protein (not limited to a theramutein) in a test cell relative to the ability of said compound to modulate the same phenoresponse in a corresponding control cell. For the purposes of applying the CSG technique to non-theramutein endogenous target proteins, the selected phenoresponse must have been previously defined using a known inhibitor or activator of the target protein.

Determination of the CSG provides the skilled investigator with a method of comparing the relative potential therapeutic value of different compounds within a group of compounds (two or more) by comparing their relative cross-reactivity with control cells irrespective of the potency against the target protein of any given compound within the group. Compounds that exhibit the greatest "specificity" in their activity against test cells relative to control cells are generally the most desirable compounds, since a "wide" CSG will assist in selecting a compound that may reasonably be assumed to have minimal potential side effects in patients as compared to other compounds within the aforementioned group that have "narrow" CSGs. The effects of the CSG measurement are seen most easily when comparing cell-based assay generated dose-response curves in their entirety, however the following hypothetical example is also instructive.

Consider the following table of hypothetical compounds and their corresponding $IC_{50}$ values using a cell-free assay system. This example uses a protein kinase as the target protein. This is the sort of situation that investigators skilled in the art are faced with on a daily basis when dealing with the problem of trying to perform lead optimization on a selected compound or group of compounds for the purpose of identifying a potential optimized lead candidate compound for subsequent pre-clinical (animal) and clinical studies.

TABLE 1

Cell-Free Purified Protein Kinase Inhibition Assay.

| Compound | $IC_{50}$ against Target Protein Kinase (nM) | $IC_{50}$ against a Non-Target Protein Kinase (nM) | $IC_{50}$ Ratio |
|---|---|---|---|
| A | 0.2 | 10,000 | 50,000 |
| B | 3 | 10,000 | 3,333 |
| C | 250 | 10,000 | 40 |
| D | 500 | 10,000 | 20 |

A standard approach in the art at the present time is to identify compounds that exhibit a high degree of potency with respect to inhibition of the target protein kinase's enzymatic activity in a cell-free assay system without showing significant inhibitory activity against a distinct but closely related protein kinase. As the results of the cell-free assay system shown above in Table 1 indicate, compound A is the most potent of the series of compounds (A,B,C,D) and also shows the largest difference between its $IC_{50}$ against the target protein relative to its effect on the non-target protein. For example, if one were interested in identifying inhibitors of the Abl kinase, one might use another protein kinase, such as the EGF receptor, c-kit, or c-Src, as a "negative" control kinase in such an assay. As with c-Abl, all of these latter enzymes are tyrosine protein kinases. Indeed, it is commonplace in the field at the present time to use so-called "panels" of protein kinases, including serine/threonine kinases, tyrosine kinases, and dual-specificity kinases, in order to identify compounds that inhibit as few protein kinases as possible (other than the target protein kinase itself). The reasoning behind this approach is that the fewer the number of kinases that are inhibited in a cell-free system by a given compound, the less likely the compound is to have untoward side effects in the patient. However, there is very little clinical evidence that actually supports this view.

Furthermore, in some cases it has been argued by others that compounds that target more than one kinase may have additional therapeutic effects as compared to those compounds that are highly specific for only a single target protein. There is some evidence for this being true in the case of imatinib, whose cross-reactivity with c-kit has resulted in beneficial effects for patients with certain histologic types of carcinoma of the small intestine, as discussed previously herein. Despite this cross-reactivity with c-kit, however, imatinib displays a high degree of cellular specificity in the assay systems of the present invention, which is consistent with its high degree of clinical efficacy and relatively modest side effect profile within the first three years of treatment. However, as the specificity of a given compound drops in the cellular systems of the present invention, the increased cross-reactivity with other targets such as (in this example) other protein kinase family members may result in untoward side effects in the patient. This is discussed in further detail below.

TABLE 2

Results from Applying the Method(s) of the Invention by Utlitizing a Phenoresponse-Based Cellular Assay System and Measuring the Cellular Specificity Gap (CSG)

| Compound | $IC_{50}$ against Test Cells (nM) | $IC_{50}$ against Control Cells (nM) | CSG |
|---|---|---|---|
| A | 1 | 1 | 1 |
| B | 10 | 100 | 10 |
| C | 500 | 20,000 | 40 |
| D | 10 | 200 | 20 |

Figure 14:
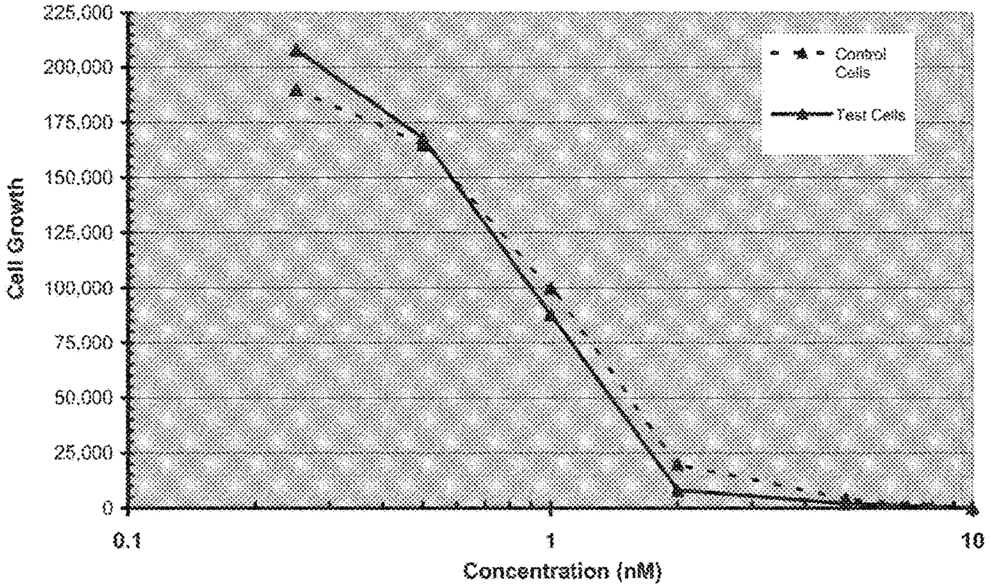
FIG. 14 shows the inhibitory effect on growth rate of a hypothetical compound having a cellular specificity gap of 1 with respect to a test cell and a control cell.
Figure 15:
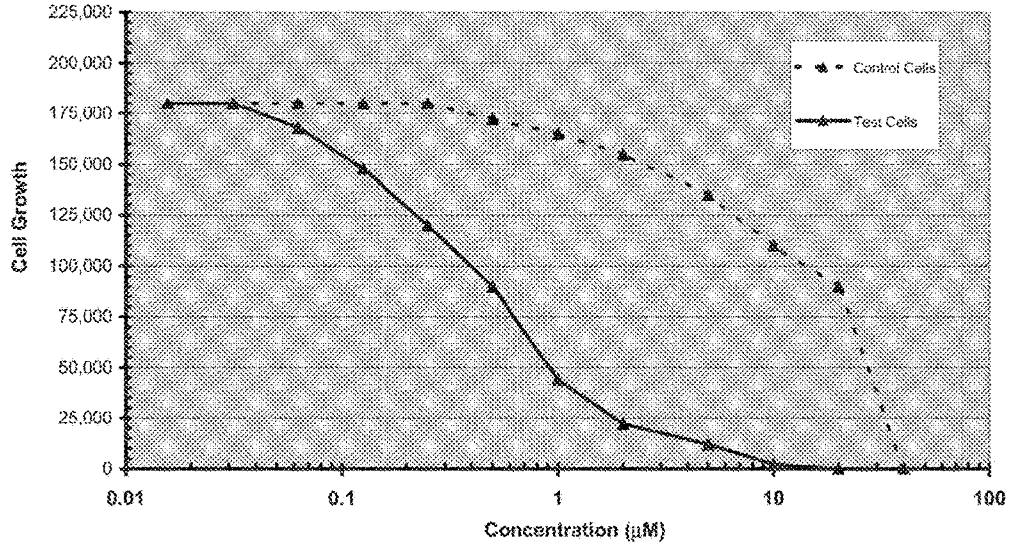
FIG. 15 shows the inhibitory effect on growth rate of a hypothetical compound having a cellular specificity gap of 40 with respect to a test cell and a control cell.

The conclusion that would be drawn by the investigator from the results of the cell-free assay shown in Table 1 above is that compound A is the most potent compound, showing a 50% inhibitory concentration ($IC_{50}$) value of 0.2 nanomolar (0.2 nM). As shown in Table 2 and FIG. 14, however, this compound, shows no specificity for the Test cells relative to the Control Cells, since it's $IC_{50}$ for the Control cells is also 1 nanomolar. Similarly, compounds B and D are still quite potent, with both having $IC_{50}$'s of 10 nM against the Test cells, whereas compound D is more specific than B since its $IC_{50}$ for the Control cells is higher (200 nM). The CSG measurements of compounds B and D immediately reflect that compound D would be the preferred compound between these two, all other considerations being equal. Most importantly, however, is that compound C is shown in this example to be the best compound of the group in terms of its CSG, at 40 (Table 2, FIG. 15). This means that compound C shows the greatest specificity for the Test cells relative the Control cells, and would be expected to have the lowest incidence of inducing unwanted side effects in patients, since this finding is derived from a direct testing of the compound in a living cellular system, the ultimate point of pharmacological action for the overwhelming majority of medicines. The important point in this example is that the CSG measurement allows the skilled investigator to rank order the potential therapeutic value of a series of compounds independently of their potency in cell-free systems. Thus, although compound C is the least potent compound, it is the most specific in its ability to inhibit the Test cells while leaving the Control cells relatively unaffected over wide concentration range. This is reflected in its CSG of 40, and demonstrates that compound C, rather than compound A, is the compound that should be given the highest priority for further pre-clinical and clinical development efforts.

Use of the method of present invention in this manner provides for an ability to rank order and prioritize the pharmaceutical discovery and development process in a manner which was not possible previously. Through iterative application of the approach given above, the skilled investigator working together with medicinal chemists may synthesize analogus of compounds that score positively in the assay systems described herein, test such compounds in the assay methods of the invention, rank order the compounds according to their CSG values, select the best ones for further development, and repeat the process as many times as necessary in order to fully develop and optimize compounds that exhibit a high degree of specificity against a given Test cell relative to its corresponding Control cell. Once a given compound has been optimized using the system described herein, which generally means that the CSG between Control and Test cells (if measured using the cellular $IC_{50}$ ratio method described above) is at least three to five fold, the skilled investigator can then proceed to complete the lead optimization process through additional chemical modifications of the compound selected in this way and tested for properties such as plasma half-life, oral bioavailability, and related parameters using appropriate animal models. Of course, the likelihood of such compounds having the desired effects on the target protein in the cellular environment is virtually assured as a result of the process of optimizing said compounds according to the methods described herein, rather than with older, cell-free methods.

It will be immediately apparent to the skilled investigator that analogous approaches may also be utilized with activators of a given target protein. It will also be apparent to the skilled investigator that there are other ways of determining the CSG. For example, using the inhibitor example given above, another useful approach to determine the CSG is to measure the ratio of the highest concentration of a compound which results in 50% growth inhibition of the control cell line, divided by the lowest concentration of the compound at which at least 90% of the test cell line is inhibited. Other obvious modifications of this approach may be utilized as well, including computing the logarithm of the concentrations at which compounds show a given percentage of activity, normalization of either the control or test cell responses relative to one another, etc. No limitation is intended on the nature of the computed or observed comparison of the control cell responsiveness to the test cell responsiveness for the purposes of determining the CSG.

If one uses the $IC_{50}$-ratio of control cells/test cells method as described above, then compounds with CSG values less than or equal to 1 would not generally be considered to be good clinical candidate compounds, whereas compounds with CSG values of greater than approximately 10 would be quite promising and worthy of further consideration.

This example also highlights the distinctions between the effects of a given compound in a cell-free system versus the more medically and physiologically relevant cell-based system of the present invention.

In an embodiment of the invention, compound profiling is used to identify and/or minimize side effects associated with administration of a compound to a patient. The cell-based lead optimization method allows early identification of potential side effects as compared to the cell-free approach. For example, imatinib shows a wide cellular specificity gap according to the methods of the invention described herein. This is consistent with imatinib's significant advance in the area of anti-cancer drugs. However, it is not without side effects. Recent evidence demonstrates that imatinib is associated with cardiac toxicity in a small percentage of patients (Kerkelä et al., 2006). This group may increase over time as patients take imatinib for longer periods of time.

Figure 16:
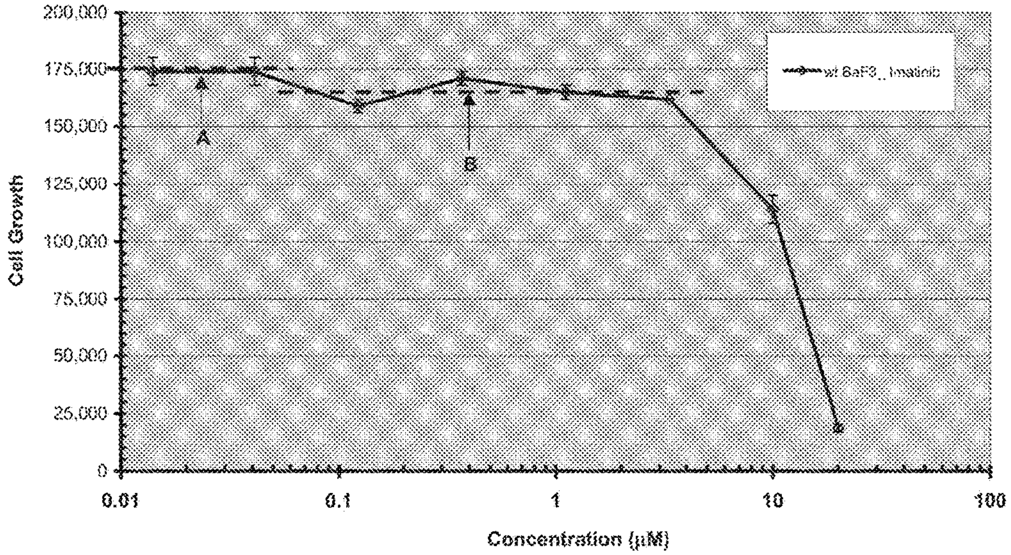
FIG. 16 shows the growth inhibitory effect of imatinib mesylate at concentrations significantly below the apparent $IC_{50}$ for cellular toxicity.

Through the use of the methods of the invention, FIG. 16 shows that imatinib tested at various concentrations on the wild type Ba/F3 cell line shows a slight but significant growth inhibitory effect at concentrations that are substantially below the apparent $IC_{50}$ for cellular toxicity (about 10 μM) on the control cell line that imatinib exhibits at markedly higher concentrations. Such results become even more evident when the comparison of the effects of other compounds on the Control cell line are compared to those of imatinib.

In still another implementation of the method, compounds which may show promising activity in a cell-free system but have small CSG values (as discussed above) would be expected to have higher potential side effects in patients, especially over longer treatment periods. Compounds having low CSG values have been reported by others with respect to certain targets such at p210 Bcr-Abl$^{T315I}$ mutant (Carter et al., 2005), and still other groups have even entered such compounds into clinical trials. However, based upon the teachings of this invention it may be expected that such compounds will have an increased incidence of untoward side effects in patients.

A preferred drug screening method of the present invention involves the following:

1) Identification of a protein of interest (POI), such as a theramutein for which a novel inhibitor or activator is desired. Often, the POI is implicated or suspected to be implicated in establishment or maintenance of a disease state, perhaps due to inappropriate expression or a mutation-induced change in specific activity. Identification of an appropriate theramutein, for example, may be performed using standard techniques (See, Gone et al., Science, 2001; see also PCT/US02/18729). Briefly, patients that have been given a course of a therapeutically effective treatment using an activator or inhibitor of a known or suspected prototheramutein and have subsequently shown clinical signs and symptoms consistent with disease relapse are identified, and cells or tissue samples derived from such patients are obtained. Using standard laboratory techniques such as RT-PCR, the sequence of the prototheramutein is determined and compared to the previously determined nucleic acid sequence of the known prototheramutein gene or cDNA sequence. Mutations, if present, are identified and are correlated with functional resistance of the prototheramutein's function either in cell-based or, more commonly, cell-free assay systems, again using standard methodology. Once resistance-inducing mutations are confirmed, then said one or more confirmed mutants comprise a defined theramutein which may be used in the subsequent methods as described herein.

2) Provision of a test cell that expresses the POI and displays an observable (measurable) phenotypic characteristic that is linked to expression of the POI. In the case of a theramutein, the phenotypic characteristic is usually one which has been previously shown to be responsive to inhibitors or activators of the theramutein or, more commonly, the corresponding prototheramutein. Such a phenotypic characteristic that is linked to expression of the POI and has been previously shown to be responsive to inhibitors or activators of the POI (or the prototheramutein-of-interest (pTOI)) is defined herein as a "phenoresponse." One embodiment of this invention is the definitive use of the phenoresponse for the purpose of identifying compounds that are likely to be inhibitors or activators of the TOI. This may be accomplished through the use of a high-throughput screen using a cell line overproducing a given TOT and for which an appropriate phenoresponse has been identified and characterized. Alternatively, one may utilize a high-throughput primary screen using a more generic phenotypic characteristic of a cell line (that does not qualify as a phenoresponse according to the teachings herein) and then utilize a secondary screen according to the teachings herein to distinguish between compounds that are true positive "hits", i.e. inhibitors or activators of the theramutein of interest, from false positive compounds that are not inhibitors or activators of the theramutein of interest. In one embodiment, a cell is selected that naturally expresses the theramutein such that a responsive phenotypic characteristic is present under suitable culture conditions which are obvious to one of ordinary skill in the art. In other embodiments, the theramutein is overexpressed, in some instances in a host cell that does not otherwise express the theramutein at all. This usually involves construction of an expression vector from which the theramutein can be introduced into a suitable host cell and overexpressed using standard vector systems and methodology. (Gorre et al., 2001; Housey et al., 1988). In one embodiment, overexpression results in a level of the theramutein that is at least about 3 times the amount of the protein usually present in a cell. Alternatively, the amount is at least about 10 times the amount usually present in a cell. In another embodiment, the amount is at least about 20 times or more preferably at least about 50 times the amount usually present in a cell.

3) Provision of a control cell that expresses the POI to a lesser extent or not at all (e.g., an unmodified host cell or host cell harboring an expression vector that does not express the POI). In the case of a theramutein of interest, the control cell can also be a cell expressing the prototheramutein corresponding to the theramutein of interest.

As some of the muteins that are described herein are also enzymes, they usually retain catalytic activity, and therefore the control cell usually displays substantially the same phenotypic characteristic as the test cell. The phenotypic characteristic need not be quantitatively alike in both cells, however. For example, a mutation that leads to reactivation of the prototheramutein may also increase, decrease, or otherwise affect its specific activity with respect to one or more of its substrates in the cell. As a result, it may exhibit the selected phenotypic characteristic to a greater or lesser extent. Accordingly, it may be desirable in some cases to adjust expression of either or both of the prototheramutein and the theramutein such that test and control cells exhibit the phenotypic characteristic to approximately the same degree. This may be done, for example, by expressing the proteins from promoters whose activity can be adjusted by adjusting the amount of inducer present, all using standard methodology (see, for example, Sambrook et al. 1989 and 2001).

It will be obvious to one of ordinary skill in the art that a properly defined phenoresponse may be quantitatively different between the prototheramutein- and the theramutein-expressing cell lines as a result of differences in the specific activity (if any) between the theramutein and its corresponding prototheramutein. Theramutein-inducing mutations may increase or decrease the specific activity of said theramutein relative to the corresponding prototheramutein. When comparing a theramutein expressing cell line with a prototheramutein expressing cell line, it is preferable that the selected phenoresponse is qualitatively the same in both cell types. Thus, the skilled investigator may choose to normalize the activity of the theramutein-expressing cell line to that of the prototheramutein-expressing cell line, or vice versa. Such normalization methods are standard in the art. See, for example, Bolstad et al. (2003).

Alternatively, the skilled investigator may also wish to use unmodified host cells or host cells harboring the expression vector only as control cells for certain experimental procedures. (The host cells are the cells into which an expression vector encoding the theramutein was introduced in order to generate the test cells.) This may be the case where the investigator is only interested in identifying a specific inhibitor or activator of the theramutein of interest, irrespective of whether or not said compound is also effective against the prototheramutein of interest (pTOI).

4) The test and control cells are then maintained or propagated (although not necessarily at the same time) in growth media (or even in intact animals) under suitable conditions such that the phenoresponse may be expressed and assayed. Control cells that are expressing the prototheramutein may be treated with a known modulator of the prototheramutein, or with a test substance, and test cells are treated with test compounds to determine whether they are active against the theramutein, as measured by the ability of said substances to modulate the phenoresponse in the expected manner. Alternatively, control cells not expressing the prototheramutein may also be substituted, depending upon the particular phenoresponse that the skilled investigator has chosen for study. Substances may then be assayed on the test cells and, optionally, on the control cells at the same time, or at another time, and the results compared.

In one embodiment of the invention, substances that are active with regard to the test cells can be rapidly identified by their ability to modulate the phenoresponse of the test cells in the same manner as, for example, the known modulator of the prototheramutein alters the phenoresponse of prototheramutein-expressing control cells. In another embodiment, active substances may be identified by their ability to modulate the activity of the theramutein in the test cells while having little or no effect on the unmodified (prototheramutein and/or theramutein non-expressing) control cells. The skilled investigator will readily appreciate the many variations of this approach that may be utilized to identify, for example, modulators that are more effective against the theramutein, or that are equally effective against both the prototheramutein and one or more corresponding specific theramuteins.

Other phenoresponses can be observed and/or measured and include, for example, detection of substrates of the prototheramutein, and detection of gene expression changes that are regulated by the activity of the theramutein. In the simplest terms, any characteristic of the cell that the skilled investigator has previously correlated with the functional activity of the theramutein may be suitable for use with such methods. However, in selecting a given characteristic, the skilled investigator must first verify that said characteristic fulfills the criteria of being a phenoresponse according the teachings as given in detail herein. The skilled investigator may also wish to normalize the phenoresponse with the theramutein expressing cells to that of the prototheramutein expressing cells.

Characteristics suitable for detection may be measured by a variety of methods very well known to those of skill in the art. Such methods include, but are not limited to, detection of fluorescence of suitably labeled proteins (FACS), immunohistochemistry (IHC) for detection of protein expression, competitive radioligand binding assays, solid matrix blotting techniques, such as Northern, Southern, and Western blots of cell extracts, reverse transcriptase polymerase chain reaction (RT-PCR), enzyme linked immunosorbent assays (ELISA), phosphorylation assays, gel retardation assays, membrane potential perturbations, and the like. The relevant phenotypic characteristic may be detected either on the intact cell after treatment with a test substance or, alternatively, on a subcellular fraction of the cell after treatment of the intact cell with a test substance.

Once compounds are identified that have the desired effect on the theramutein expressing test cells, it may be desirable (but not necessary) to independently verify that the compounds identified are exerting their effects on the theramutein through a direct binding mechanism, i.e. that the compounds fulfill the criteria of being inhibitors or activators (as desired) of the theramutein according to the teachings of the invention (the reader is referred to the definitions of the terms "activator" and "inhibitor" as given above). This may be accomplished with numerous standard binding assays that are known to one of ordinary skill in the art, involving either purified protein samples or intact cellular binding assays using cells transfected with the appropriate prototheramutein or theramutein together with appropriate controls as dictated by sound scientific methods. Since such methods are well established in the art they will not be reiterated here. Numerous reference texts comprehensively discuss such techniques (see, for example, Foreman and Johansen, 2002; Enna S. J. et al. (1991) Current Protocols in Pharmacology, Wiley & Sons, Incorporated; Bonifacino, J. S. et al. (1999) Current Protocols in Cell Biology, Wiley & Sons, Incorporated). See also Housey, G. M. 1988, Chapter 4, and references therein; see also Horowitz et al., 1981.

In a particular embodiment of the invention, the method is used to identify substances that are inhibitors of the $p210^{Bcr\text{-}Abl\text{-}T315I}$ theramutein. The prototheramutein and theramutein are each expressed in Ba/F3 (murine) cells using standard methodology and the phenoresponses that are observed are growth characteristics (terminal cell density for a carefully defined cell culture, and growth in the absence of Interleukin-3 (IL-3). Unmodified host cells, or host cells containing the expression vector only or both, may optionally also be used. In still another embodiment, the test cells alone may be used with or without reference to a known inhibitor or activator.

Another useful assay is the determination of the state of phosphorylation of a direct substrate of $p210^{Bcr\text{-}Abl\text{-}T315I}$. One such substrate is Crkl (Gone et al., *Science* 293:876-80 (2001)), an adapter protein which mediates the connection between Bcr-Abl and Ras. The phosphorylation state of CRKL is representative of the signaling activity of $p210^{Bcr\text{-}Abl}$ in a cell. Another downstream substrate is p62DOK. Any such substrate would suffice for these purposes, provided of course that phosphorylation of said substrate has been shown to occur inside the cell, and is not simply an autophosphorylation event of the TOI or PTOI as discussed above. Other signal transduction cascade components may also be monitored, including src family kinases, STATS, PI3 Kinase, raf kinase, RAS, MEK, ERK1 and ERK2, JNK1, 2 and 3, MLK1, 2 and 3, MKK4, MKK7, AKT, mTOR, HSP90, and others.

As exemplified herein, inhibitors of the T315I theramutein have been identified. Furthermore, these inhibitors are also active to differing extents against the wild type prototheramutein $p210^{Bcr\text{-}Abl\text{-}wt}$.

According to the present invention, a therapeutically effective amount of one or more compounds that modulate the functional activity of a $p210^{Bcr\text{-}Abl}$ theramutein is administered to a mammal in need thereof. The term "administering" as used herein means delivering the compounds of the present invention to a mammal by any method that may achieve the result sought. They may be administered, for example, orally, parenterally (intravenously or intramuscularly), topically, transdermally or by inhalation. The term "mammal" as used herein is intended to include, but is not limited to, humans, laboratory animals, domestic pets and farm animals. "Therapeutically effective amount" means an amount of a compound that, when administered to a mammal, is effective in producing the desired therapeutic effect, such as inhibiting kinase activity, inhibiting cancer cell growth and division, etc.

The invention provides a method of treating disease in a mammal by administering to the mammal an effective amount of a modulator of a theramutein. Suitable diseases to be treated according to the present invention include, but are not limited to, relapsing neoplastic or other proliferative disorders that have become resistant to previously administered drugs. The method is also useful for overcoming variation among individuals with respect to susceptibility to drug treatment that results from allelic differences among therapy targets. For example, the role of $p210^{Bcr-Abl}$ tyrosine kinase signaling in CML has been extensively demonstrated, as has the role of theramuteins of $p210^{Bcr-Abl}$ in drug resistant recurrence of CML. Further, different muteins of $p210^{Bcr-Abl}$ exhibit varying sensitivity to inhibitors of $p210^{Bcr-Abl}$. Although some theramuteins arise during drug therapy, others may preexist in the population. These latter examples will not be recognized as theramuteins until such time as the disease state ensues and is followed by treatment with a known class of therapeutic agents. Only after said treatment will such preexisting theramuteins reveal themselves as being clinically significant in terms of relative non-responsiveness leading to the progression of the disease in the patient harboring the theramutein.

In an embodiment of the invention, theramutein modulators are administered in combination with one or more other anti-neoplastic agents. Any suitable anti-neoplastic agent can be used, such as a chemotherapeutic agent, radiation or combinations thereof. The anti-neoplastic agent can be an alkylating agent or an anti-metabolite. Examples of alkylating agents include, but are not limited to, cisplatin, cyclophosphamide, melphalan, and dacarbazine. Examples of anti-metabolites include, but not limited to, doxorubicin, daunorubicin, and paclitaxel, gemcitabine, and topoisomerase inhibitors irinotecan (CPT-11), aminocamptothecin, camptothecin, DX-8951f, topotecan (topoisomerase I inhibitor), and etoposide (VP-16; topoisomerase II inhibitor) and teniposide (VM-26; topoisomerase II inhibitor). When the anti-neoplastic agent is radiation, the source of the radiation can be either external (external beam radiation therapy—EBRT) or internal (brachytherapy—BT) to the patient being treated. The dose of anti-neoplastic agent administered depends on numerous factors, including, for example, the type of agent, the type and severity of the tumor being treated and the route of administration of the agent. It should be emphasized, however, that the present invention is not limited to any particular dose, route of administration, or combination of chemotherapeutic agents or other therapeutic regimens that are combined with the administration of protein modulators.

Anti-neoplastic agents which are presently known in the art or being evaluated can be grouped into a variety of classes including, for example, mitotic inhibitors, alkylating agents, anti-metabolites, intercalating antibiotics, growth factor inhibitors, cell cycle inhibitors, enzymes, topoisomerase inhibitors, anti survival agents, biological response modifiers, anti-hormones, and anti-angiogenesis agents, all of which can be administered with inhibitors or activators of theramuteins.

A modulator of a theramutein can be administered with antibodies that neutralize other receptors involved in tumor growth. Further, a modulator of a theramutein can be administered with a compound that otherwise modulates a component of a signal transduction pathway, preferably a component of the signal transduction pathway in which the theramutein is active and which is common to one or more other signal transduction pathways. In an embodiment of the invention, a theramutein modulator is used in combination with a receptor antagonist that binds specifically to the Epidermal Growth Factor Receptor (EGFR). Particularly preferred are antigen-binding proteins that bind to the extracellular domain of EGFR and block binding of one or more of its ligands and/or neutralize ligand-induced activation of EGFR. An EGFR antagonist can be an antibody that binds to EGFR or a ligand of EGFR and inhibits binding of EGFR to its ligand. Ligands for EGFR include, for example, EGF, TGF-α, amphiregulin, heparin-binding EGF (HB-EGF) and betacellulin. EGF and TGF-α are thought to be the main endogenous ligands that result in EGFR-mediated stimulation, although TGF-α has been shown to be more potent in promoting angiogenesis. It should be appreciated that the EGFR antagonist can bind externally to the extracellular portion of EGFR, which can or can not inhibit binding of the ligand, or internally to the tyrosine kinase domain in the case of chemical agents. Examples of EGFR antagonists that bind EGFR include, without limitation, biological agents such as antibodies (and functional equivalents thereof) specific for EGFR, and chemical agents (small molecules), such as synthetic kinase inhibitors that act directly on the cytoplasmic domain of EGFR.

Other examples of growth factor receptors involved in tumorigenesis are the receptors for vascular endothelial growth factor (VEGFR-1 and VEGFR-2), platelet-derived growth factor (PDGFR), nerve growth factor (NGFR), fibroblast growth factor (FGFR), and others.

In a combination therapy, the theramutein inhibitor is administered before, during, or after commencing therapy with another agent, as well as any combination thereof, i.e., before and during, before and after, during and after, or before, during and after commencing the anti-neoplastic agent therapy. For example, the theramutein inhibitor can be administered between 1 and 30 days, preferably 3 and 20 days, more preferably between 5 and 12 days before commencing radiation therapy. In a preferred embodiment of the invention, chemotherapy is administered prior to, concurrently with or, more preferably, subsequent to antibody therapy.

In the present invention, any suitable method or route can be used to administer theramutein inhibitors of the invention, and optionally, to co-administer anti-neoplastic agents and/or antagonists of other receptors. The anti-neoplastic agent regimens utilized according to the invention, include any regimen believed to be optimally suitable for the treatment of the patient's neoplastic condition. Different malignancies can require use of specific anti-tumor antibodies and specific anti-neoplastic agents, which will be determined on a patient to patient basis. Routes of administration include, for example, oral, intravenous, intraperitoneal, subcutaneous, or intramuscular administration. The dose of antagonist administered depends on numerous factors, including, for example, the type of antagonists, the type and severity of the tumor being treated and the route of administration of the antagonists. It should be emphasized, however, that the present invention is not limited to any particular method or route of administration.

Suitable carriers include, for example, one or more of water, saline, phosphate buffered saline, dextrose, glycerol, ethanol and the like, as well as combinations thereof. Carriers can further comprise minor amounts of auxiliary substances, such as wetting or emulsifying agents, preservatives or buffers, which enhance the shelf life or effectiveness of the theramutein modulator as the active ingredient.

The compositions can, as is well known in the art, be formulated so as to provide quick, sustained or delayed release of the active ingredient after administration to the mammal.

The compositions of this invention can be in a variety of forms. These include, for example, solid, semi-solid and liquid dosage forms, such as tablets, pills, powders, liquid solutions, dispersions or suspensions, liposomes, suppositories, injectable and infusible solutions. The preferred form depends on the intended mode of administration and therapeutic application.

Such compositions of the present invention are prepared in a manner well known in the pharmaceutical art. In making the composition the active ingredient will usually be mixed with a carrier, or diluted by a carrier and/or enclosed within a carrier which can, for example, be in the form of a capsule, sachet, paper or other container. When the carrier serves as a diluent, it can be a solid, semi-solid, or liquid material, which acts as a vehicle, excipient or medium for the active ingredient. Thus, the composition can be in the form of tablets, lozenges, sachets, cachets, elixirs, suspensions, aerosols (as a solid or in a liquid medium), ointments containing, for example, up to 10% by weight of the active compound, soft and hard gelatin capsules, suppositories, injection solutions, suspensions, sterile packaged powders and as a topical patch.

It should be appreciated that the methods and compositions of the present invention can be administered to any suitable mammal, such as a rabbit, rat, or mouse. More preferably, the mammal is a human.

The compounds according to the invention may also be present as salts. In the context of the invention, preference is given to pharmaceutically acceptable salts. Pharmaceutically acceptable salts refers to an acid addition salt or a basic addition salt of a compound of the invention in which the resulting counter ion is understood in the art to be generally acceptable for pharmaceutical uses. Pharmaceutically acceptable salts can be salts of the compounds according to the invention with inorganic or organic acids. Preference is given to salts with inorganic acids, such as, for example, hydrochloric acid, hydrobromic acid, phosphoric acid or sulfuric acid, or to salts with organic carboxylic or sulfonic acids, such as, for example, acetic acid, maleic acid, fumaric acid, malic acid, citric acid, tartaric acid, lactic acid, benzoic acid, or methanesulfonic acid, ethanesulfonic acid, phenylsulfonic acid, toluenesulfonic acid or naphthalenedisulfonic acid. Pharmaceutically acceptable salts can also be metal or ammonium salts of the compounds according to the invention. Particular preference is given to, for example, sodium, potassium, magnesium or calcium salts, and also to ammonium salts which are derived from ammonia or organic amines, such as, for example, ethylamine, di- or triethylamine, di- or triethanolamine, dicyclohexylamine, dimethylaminoethanol, arginine, lysine, ethylenediamine or 2-phenylethylamine. (see, Berge et al. *J. Pharm. Sci.* 1977, 66, 1-19).

Throughout this application, various publications, reference texts, textbooks, technical manuals, patents, and patent applications have been referred to. The teachings and disclosures of these publications, patents, patent applications and other documents in their entireties are hereby incorporated by reference into this application to more fully describe the state of the art to which the present invention pertains.

It is to be understood and expected that variations in the principles of invention herein disclosed may be made by one skilled in the art and it is intended that such modifications are to be included within the scope of the present invention.

The following examples further illustrate the invention, but should not be construed to limit the scope of the invention in any way. Detailed descriptions of conventional methods, such as those employed in the construction of vectors and plasmids, the insertion of genes encoding polypeptides into such vectors and plasmids, the introduction of plasmids into host cells, and the expression and determination thereof of genes and gene products can be obtained from numerous publications, including Sambrook, J et al., (1989) Molecular Cloning: A Laboratory Manual, $2^{nd}$ ed., Cold Spring Harbor Laboratory Press; Coligan, J. et al. (1994) Current Protocols in Immunology, Wiley & Sons, Incorporated; Enna, S. J. et al. (1991) Current Protocols in Pharmacology, Wiley & Sons, Bonifacino, J. S. et al. (1999) Current Protocols in Cell Biology, Wiley & Sons, and U.S. Pat. No. 4,980,281. All references mentioned herein are incorporated in their entirety.

EXAMPLES

It is to be understood and expected that variations in the principles of the invention herein disclosed may be made by one skilled in the art and it is intended that such modifications are to be included within the scope of the present invention.

Examples of the invention which follow are set forth to further illustrate the invention and should not be construed to limit the invention in any way.

Example 1: Identification of a Protein Modulator $p210^{Bcr\text{-}Abl\text{-}T315I}$ is a theramutein of the p210Bcr-Abl protein ($p210^{Bcr\text{-}Abl}$) that is resistant to inhibition by imatinib mesylate (Gleevec, STI-571). The mutation at position 315 converts a threonine to an isoleucine residue and is one of several mutations that are observed among resistant or relapsed patients. This particular mutant, however, is the most resistant such theramutein yet identified.

A phenoresponse was determined for a Ba/F3 cell line engineered to overexpress the $p210^{Bcr\text{-}Abl\text{-}T315I}$ theramutein. The phenoresponse was determined relative to non-transformed Ba/F3 cells and Ba/F3 cells that express the $p210^{Bcr\text{-}Abl\text{-}wt}$ prototheramutein. The phenoresponse was the ability of the T315I mutants to grow to a higher cell saturation density under analogous culture conditions as compared to the control non-transformed Ba/F3 cell line, and to grow in the absence of interleukin 3 (IL-3), which is required for maintenance of the control non-transformed Ba/F3 cell line. The phenoresponse was defined and characterized according to the teachings given above.

The detection system utilized was a high speed cell imaging and counting system in which 3 μl sample volumes of cells were sequentially injected through a 5 μl optical microcell, digitally imaged and electronically stored, scanned, and then counted, all under a microcomputer-based control system. The system has the capacity to perform direct cell counts on samples from cultures as small as 500 μl and provides statistically significant total cell counts from culture samples containing as few as 12,500 cells. All of the figures displaying cell count and viability assays utilized this system for data acquisition and analysis. Simultaneously with the cell count performed, the system is also capable of determining overall cell viability by distinguishing counted, imaged cells that have excluded trypan blue (counted as "viable" cells) from cells which have taken up the trypan blue dye (counted as "non-viable" cells). Injection of trypan blue into the cell sample occurs immediately prior to the sample being sequentially injected into the microcell for simultaneous cell counting and imaging.

The system may be integrated into the workflow of high-throughput screening devices to provide a sensitive and precise cell counting and cell viability assay system that is more reliable and less prone to confounding effects of metabolic viability-based cellular assays such as XTT or Alamar blue.

Initially, approximately 113,000 compounds were screened at concentrations generally ranging from 10 to 20 μM to identify a subset that was capable of affecting growth of Ba/F3 cells (Ba/F3 T315I cells) overexpressing the $p210^{Bcr\text{-}Abl\text{-}T315I}$ theramutein by any means.

A total of approximately 11,760 compounds showed greater than 50% growth inhibition, which were thought to correspond to approximately 4500 distinct chemical classes. Retesting of these compounds with the same cell line yielded a database of compound responsiveness which was then sorted and rank ordered according to those compounds exhibiting the highest overall growth inhibition. From this rank ordered database, the highest scoring 130 compounds (based upon the greatest degree of growth inhibition observed at the lowest concentrations that compounds were tested) were then rescreened in a defined cell-based assay system using Ba/F3 T315I as test cells and wild type Ba/F3 as control cells according to the methods of the present invention. Compounds of interest were those that differentially inhibited growth of Ba/F3 cells expressing the $p210^{Bcr\text{-}Abl\text{-}T315I}$ theramutein relative to non-transformed wild type Ba/F3 cells. Six compounds were identified that fulfilled the desired criteria, and some of these compounds were analyzed in further detail using the Ba/F3 $p210^{Bcr\text{-}Abl\text{-}wt}$ cells line (Ba/F3 P210 cells) as well. One compound was unavailable for further testing due to lack of availability of additional material from the chemical supplier. The remaining five compounds were independently evaluated in additional cell-based assays using the aforementioned cell lines as well as in a cell-free purified protein kinase assay using human recombinantly produced 120 Kd kinase domain fragments isolated from both wild type P210 Bcr-Abl as well as P210 T315I mutant kinase domain.

All five compounds inhibited $p210^{Bcr\text{-}Abl\text{-}T315I}$ 120 Kd activity as measured by inhibition of autophosphorylation activity. Thus, of the 6 highest scoring compounds out of more than 113,000 compounds screened, at least 5 of the six directly inhibited the $p210^{Bcr\text{-}AblT315I}$ mutant directly. One compound appeared to spread the recombinant protein band out on the SDS page gel. This was also evident on the silver-stained gel (data not shown). It is possible that this compound may actually be a "suicide" inhibitor that is able to covalently cross-link the POI in order to permanently inhibit its activity, but this will require further study.

Taken together, the teachings and the results described herein provide conclusive proof that the system is capable of identifying inhibitors or activators of the selected theramutein, and the skilled investigator will immediately recognize that such a system may be easily applied to any other theramutein or other protein with only obvious, minor modifications.

Figure 2:
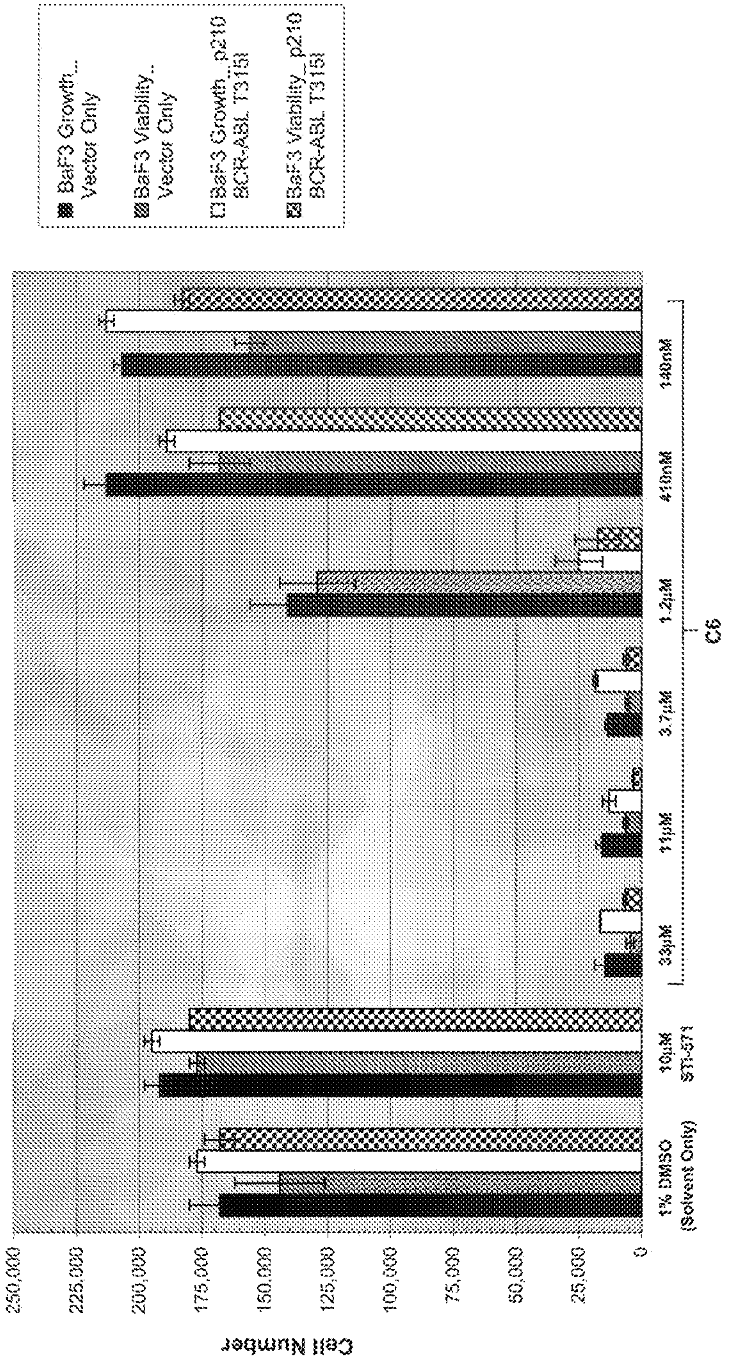
FIG. 2 shows the effect on growth and viability of different concentrations of Compound 6 (C6) for non-transformed vector control Ba/F3 cells as well as Ba/F3 cells expressing the $p210^{Bcr\text{-}Abl\text{-}T315I}$ drug resistant mutant. All other details are as per FIG. 1.

Representative examples of the cell-based assay results demonstrating selective inhibition of growth of the Ba/F3 T315I cell line relative to the wild type non-transformed Ba/F3 cells are shown in FIGS. 1 and 2. The compounds inhibited growth and reduced the viability of cells expressing the T315I theramutein at concentrations tinder which the growth and viability of the wild type Ba/F3 non-transformed cells (not expressing either $p210^{Bcr\text{-}Abl\text{-}wt}$ or $p210^{Bcr\text{-}Abl\text{-}T315I}$) were relatively unaffected, whereas cells expressing both the prototheramutein as well as the theramutein were substantially inhibited. In some instances, the T315I expressing cells were inhibited to an even greater extent than the P210 prototheramutein expressing cells. (See, for example, FIG. 3, right hand side, Compound 3 results against P210 and T315I cells.

In summary, the methods presented herein provide a fundamental advance in the form of a generalizable approach for creating or identifying modulators of any given theramutein. The results demonstrate conclusively the power of the method to identify critically needed compounds to overcome a specific type of acquired drug resistance that is uniformly fatal in certain patient populations and is presently untreatable. Furthermore, it is evident to one of skill in this art that the techniques and methods described herein may, using obvious modifications, be straighforwardly generalized to any potential theramutein or other disease associated protein of clinical significance.

It is remarkable that out of a primary screen of more than 100,000 compounds where approximately 10,000 compounds exhibited some degree of growth inhibition, when the most potent growth inhibitory substances were rescreened using the Method described in detail herein, 6 distinct compounds were identified and all of the compounds that were subsequently tested exhibited inhibitory activity in a cell-free purified protein kinase assay using the T315I mutant (one compound was unavailable for further testing). Based upon such remarkable results, it becomes immediately clear to the skilled artisan that the method may be effectively applied toward the identification of inhibitors or activators of any protein based upon the proper selection and definition of the phenoresponse according to the teachings in the sections given above and the documents incorporated by reference herein. For example, with knowledge of the foregoing, one of ordinary skill in the art could easily design an assay system to identify inhibitors of theramuteins derived from other prototheramuteins known to exhibit mutations that confer drug resistance such as the c-kit gene product or the Epidermal Growth Factor (EGF) Receptor (EGFR), or the Platelet Derived Growth Factor (PDGF) Receptor α and β. No limitation should be inferred upon the utility of the method with respect to its ability to be utilized with any given protein, including theramuteins and protothermuteins, expressed in any mammalian cell type for which a corresponding phenoresponse is detectable.

Example 2: Phenoresponse-Based Optimization of a Protein Modulator

In this example, a compound previously identified according to the teachings of this invention is optimized for activity against its selected protein target. However, unlike methods typically used in the prior art, the optimization process herein is also performed entirely through the use of the phenoresponse-based cellular assay system. For completeness sake and to demonstrate the power of the methodology to refine, a cell-free assay system using recombinantly produced target enzyme is also used to independently demonstrate that the compounds that score positively in the phenoresponse-based cellular assay indeed also score positively in a cell-free assay system format that is standard in the art and uses recombinantly produced enzyme.

Compound C2 which was originally identified as an inhibitor of the T315I theramutein was subjected to a novel lead optimization program as follows. Various chemical modifications were introduced into the basic scaffold structure of compound C2 using standard medicinal chemistry synthetic methods. Once synthesized, the various analogues (chemical variants) were tested using the phenoresponse-based cellular assay system described above in Example 1.

Based upon the original structure of compound C2, the contribution(s) to pharmacological activity arising from the phenyl ring that contained the bromo, chloro, and hydroxyl substituents were analyzed. An initial series of analogues were synthesized that consisted of either the unsubstituted phenyl ring (C2-01), or various substituents on the phenyl ring, such as bromo, chloro, and hydroxyl, etc. located various positions around the phenyl ring. Detailed chemical structures are shown in Table 3.

TABLE 3

Optimization of C2 Compounds

| | | |
|---|---|---|
| | $R_1$ = 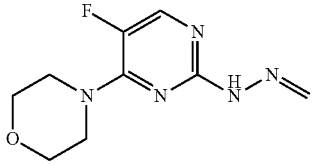 | |
| C2 | 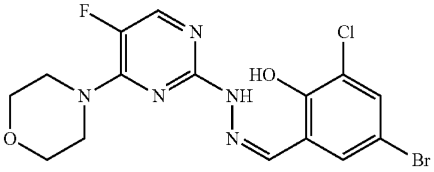 | 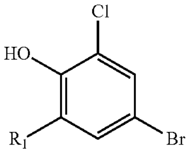 |
| C2-27 | 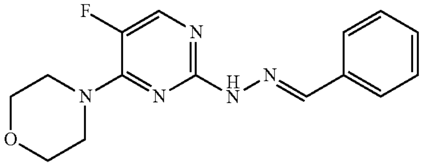 | 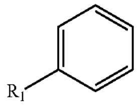 |
| C2-21 | 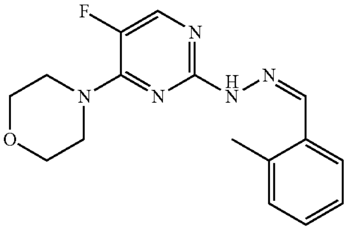 | 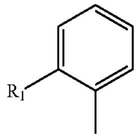 |
| C2-01 | 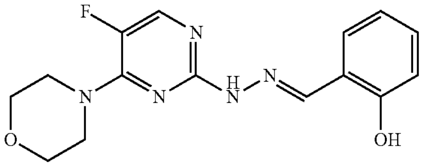 | 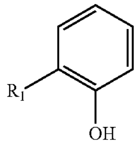 |
| C2-02 | 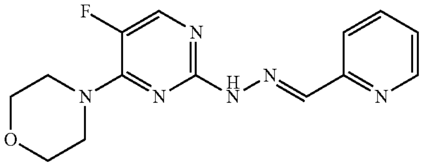 | 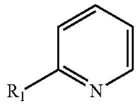 |
| C2-05 | 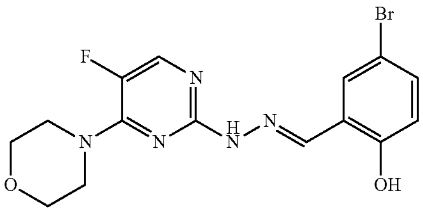 | 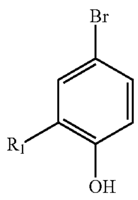 |

TABLE 3-continued
| Optimization of C2 Compounds | | |
|---|---|---|
| C2-86 | 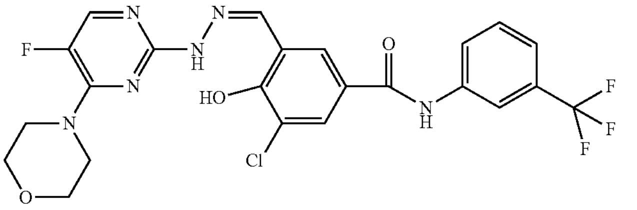 [SMILES: O=C(Nc1cccc(C(F)(F)F)c1)c1cc(Cl)c(O)c(/C=N\Nc2ncc(F)c(N3CCOCC3)n2)c1] | 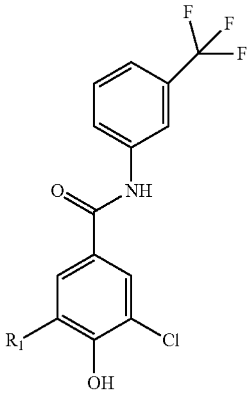 |
| C2-87 | 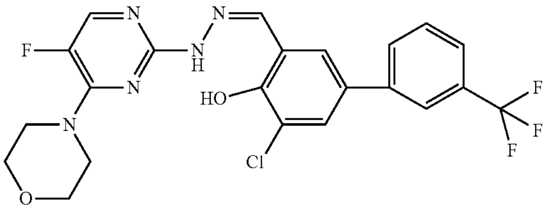 [SMILES: Oc1c(Cl)cc(-c2cccc(C(F)(F)F)c2)cc1/C=N\Nc1ncc(F)c(N2CCOCC2)n1] | 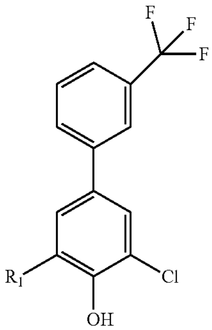 |
| C2-109 | 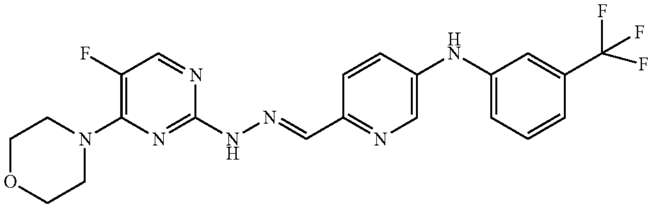 [SMILES: Fc1cnc(N/N=C/c2ccc(Nc3cccc(C(F)(F)F)c3)cn2)nc1N1CCOCC1] | 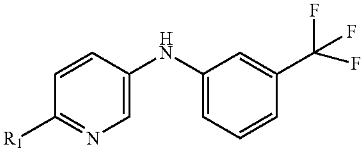 |
| C2-112 | 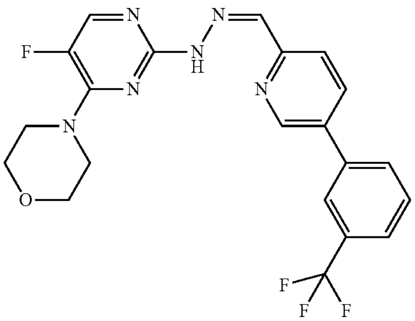 [SMILES: Fc1cnc(N/N=C\c2ccc(-c3cccc(C(F)(F)F)c3)cn2)nc1N1CCOCC1] | 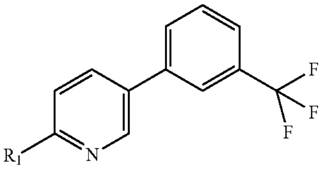 |
| C2-121 | 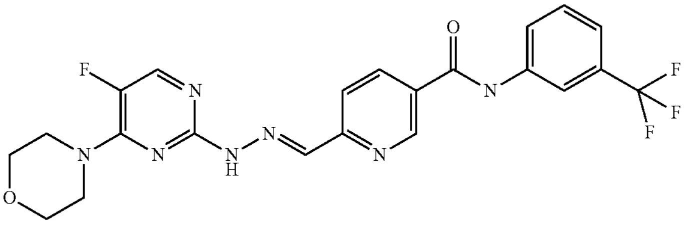 [SMILES: O=C(Nc1cccc(C(F)(F)F)c1)c1ccc(/C=N/Nc2ncc(F)c(N3CCOCC3)n2)nc1] | 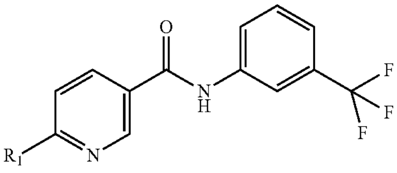 |

TABLE 3-continued

| Optimization of C2 Compounds | | |
|---|---|---|
| C2-122 | 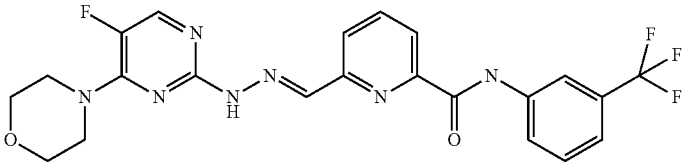 [SMILES: O=C(Nc1cccc(C(F)(F)F)c1)c1cccc(/C=N/Nc2ncc(F)c(N3CCOCC3)n2)n1] | 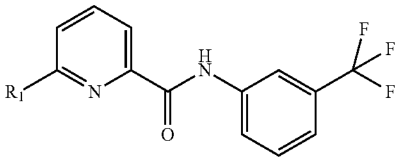 |
| C2-128 | 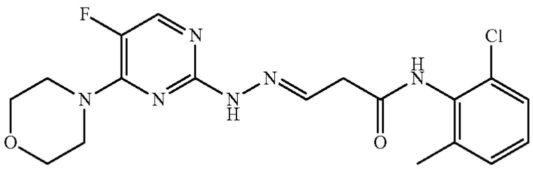 [SMILES: Cc1cccc(Cl)c1NC(=O)C/C=N/Nc1ncc(F)c(N2CCOCC2)n1] | 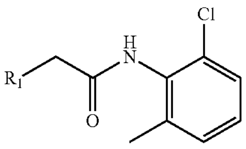 |

Figure 17:
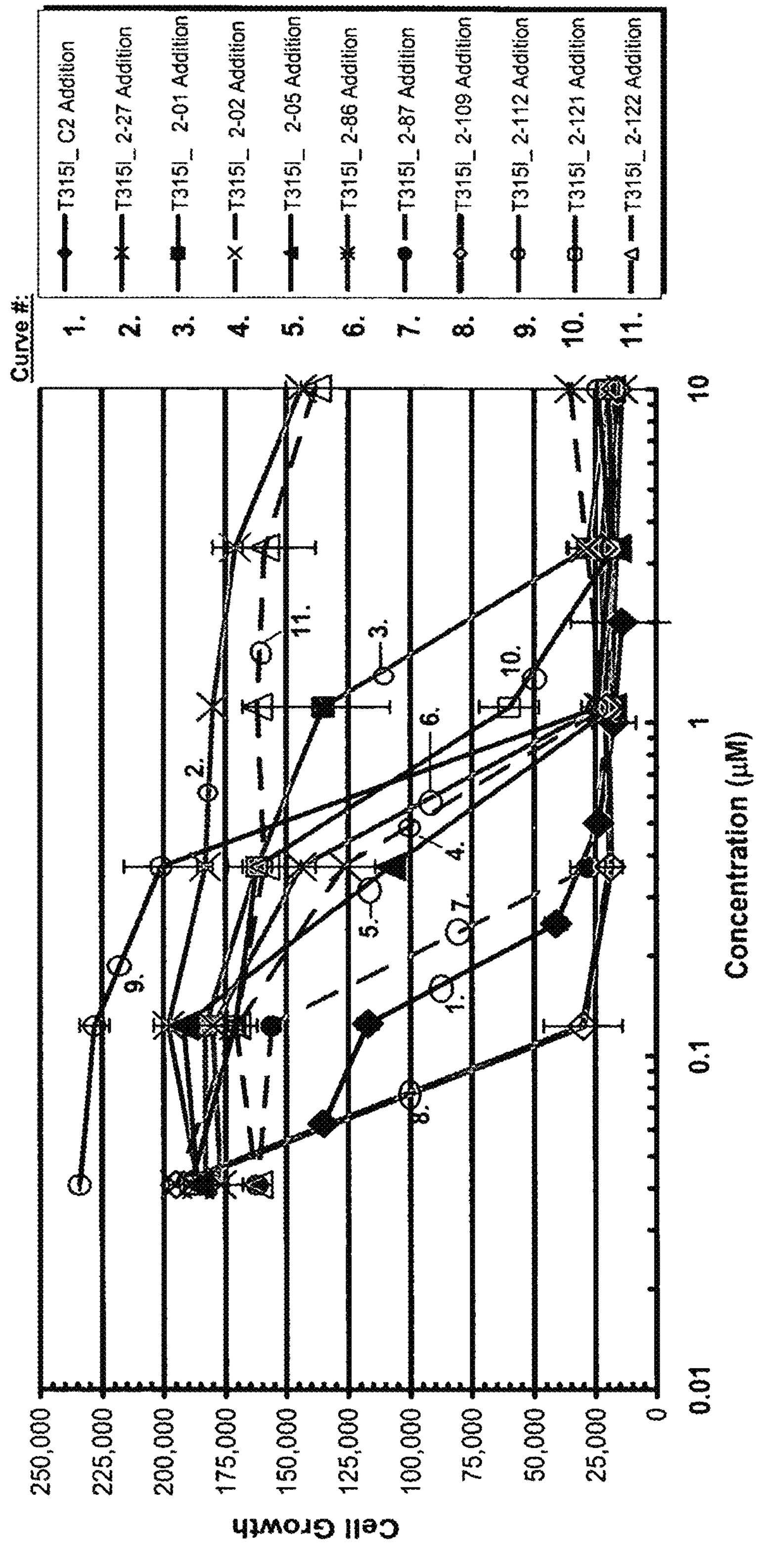
FIG. 17 shows the effect on growth of different concentrations of C2 and various C2 analogues for Ba/F3 cells expressing the $p210^{Bcr\text{-}Abl\text{-}T315I}$ drug resistant mutant.
Figure 18:
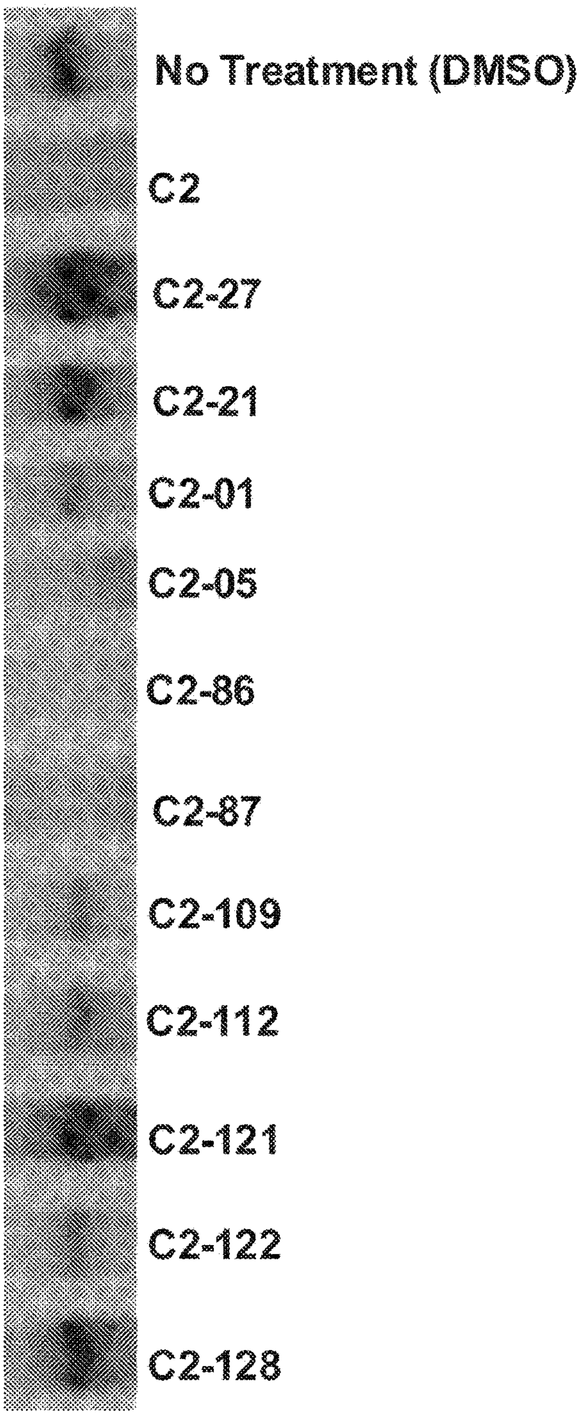
FIG. 18 shows the results of a standard cell free protein kinase autophosphorylation assay for T315I mutant kinase domains in the presence of C2 and various C2 analogues at a concentration of 20 μM.

These compounds were then tested in the phenoresponse-based cellular assay system, as shown in FIG. 17. Each of the compounds was also tested in a standard cell free protein kinase autophosphorylation assay at a concentration of 20 μM as shown in FIG. 18. As a comparison of FIG. 17 and FIG. 18 will indicate, there was a striking, essentially complete qualitative correlation between the activity of the compounds in the phenoresponse based (cellular) assay system and their corresponding activity in the cell free purified protein kinase autophosphorylation assay.

Additional chemical modifications were made to the same phenyl ring discussed above for a variety of medicinal chemistry purposes and for reasons that are beyond the scope of this invention, but were related to enhancing potency against the $p210^{Bcr\text{-}Abl\text{-}T315I}$ target while simultaneously limiting cross-reactivity with the control wild type Ba/F3 non-transformed cells (not expressing either $p210^{Bcr\text{-}Abl\text{-}wt}$ or $p210^{Bcr\text{-}Abl\text{-}T315I}$), as well as to improve selectivity, minimize potential side effects in the patient, etc. As shown in FIGS. 17 and 18 taken together with Table 3, additional compounds synthesized and tested included C2-109, C2-112, C2-122, and C2-128. A detailed comparison of FIGS. 17 and 18 reveals once again that all of the compounds that score positively in the cellular assay system also exhibited protein kinase inhibitory activity in the cell free system, whereas those that were essentially inactive in the phenoresponse-based cellular assay were also essentially inactive in the cell-free system. These results conclusively demonstrate that the compounds showing inhibitory activity in the phenoresponse-based assay system were entirely consistent qualitatively with the results obtained in the cell free protein kinase autophosphorylation assay.

Furthermore, where there are modest differences in relative potency between the cell free assay results and the phenoresponse-based assay results (see for example, compound C2-122 which appears to be more potent in the cell-free assay than in the phenoresponse-based cellular system, such distinctions point out the enhanced ability of the cellular assay system to predict in vivo efficacy of a given compound as compared to classical cell-free assay systems. Using a classical cell-free screen, one might have considered C2-122 to be an important compound, yet the phenoresponse-based assay immediately rules it out as being less potent than several of the other compounds tested. This type of lead optimization strategy employing a cellular system without dependence and reliance upon a cell-free radioligand or other binding assay has not been reported before in the prior art.

In summary, the present invention provides the skilled investigator with a powerful and rapid method for lead optimization which supplants the necessity for repeated cell free in vitro verifications of the ability of a compound to hit its corresponding target. Thus the optimization process may be performed essentially entirely with reliance upon the phenoresponse-based assay systems results, obviating the need for repetitive confirmatory cell free assay determinations. While such confirmatory experiments may be performed if the skilled investigator chooses to do so, they are generally unnecessary with this method, as the results given above unequivocally demonstrate.

The skilled investigator is well aware that no assay system of any kind or nature, whether it be a radioligand binding assay, ELISA, ligand binding assay, or cellular assay, is free of false-positive results. This assay system, while surprisingly robust, will not be free of the possibility of false positive results either, and the skilled investigator knows that independent verification of unusual results is simply good science and should be taken into consideration where appropriate.

Example 3: Phenoresponse-Based Profiling of a Protein Modulator

The phenoresponse-based assay system of the invention can be used to profile the biological activity of a given compound with respect to its ability to inhibit or activate multiple distinct protein targets to differing extents. For example, in certain instances the skilled artisan may be interested in identifying or optimizing modulators of a given target protein where additional proteins are known that are distinct but highly related to the target POI. Such protein families may consist of two or more members that share a high degree of homology at both the DNA and amino acid sequence levels, yet the family members may have distinct functions within the cell. Through iterative application of the phenoresponse-based system described herein, one could create individual Test Cells expressing each of the distinct family members and then utilize three or four or more distinct Test Cell lines with corresponding defined phenoresponses to identify or optimize compounds that are selective for one particular family member.

In yet another embodiment of the present invention, the skilled artisan may also choose to express two or three or even four distinct protein targets in a single Test Cell (or Test Cell line) and create a phenoresponse-based assay system useful for identifying compounds that are NOT selective among individual isozymes of a given protein family. In certain therapeutic situations, lack of selectivity among individual family members may be preferable. Ibuprofen, for example, is an established, low-cost safe and effective non-steroidal anti-inflammatory drug that does not significantly discriminate between the cyclooxygenase type 1 (COX-1) and COX-2 family members. Such lack of discrimination may in some instances be beneficial and may reduce the likelihood of certain unwanted side effects that may occur with an overly selective chemical agent.

Profiling the biological effects of a given compound with respect to its ability to inhibit or activate certain related protein targets, whether or not such targets are members of the same protein family, also has substantial value from the perspective of understanding the molecular and cellular mechanism(s) of action of a given chemical agent. For example, in the case of imatinib, not only does the compound inhibit the wild type version of the P210 Bcr/Abl protein ($p210^{Bcr\text{-}Abl\text{-}wt}$), it also cross reacts with and is capable of inhibiting the c-kit oncoprotein as well. As discussed above in the background of the invention, this cross-reactive inhibition of the kit oncoprotein is serendipitous, because gastrointestinal stromal tumors (GIST), a type of tumor arising in the small intestine, are driven by kit activity and are thus responsive to imatinib treatment as well (NEJM paper). Thus, such cross reactivity with other related proteins need not always be associated with toxicity of a drug. In some instances such cross-reactivities can be therapeutically effective.

Representative Compounds of the Invention corresponding to the various chemical formulae given above were tested in the cellular assay system described elsewhere herein (see Example 1) and assigned activity categories as shown in Table 4. The assigned activity categories are represented by the following designations, wherein the $IC_{50}$ for a given cell line is the concentration at which a given compound inhibits the growth of that cell line by 50% in the cellular assay system. Compounds tested on a given cell line that exhibited an $IC_{50}$ value that was <300 nM (less than 300 nanomolar) were designated, as Category "A" compounds. Compounds tested on a given cell line that exhibited an $IC_{50}$ value that was <1 μM (less than 1 micromolar) were designated as Category "B" compounds. Compounds tested on a given cell line that exhibited an $IC_{50}$ value that was <10 μM (less than 10 micromolar) were designated as Category "C" compounds. Compounds tested on a given cell line that exhibited an $IC_{50}$ value that was ≥10 μM (greater than or equal to 10 micromolar) were designated as Category "D" compounds.

TABLE 4

| Structure: | wt BaF3 | T315I |
|---|---|---|
| 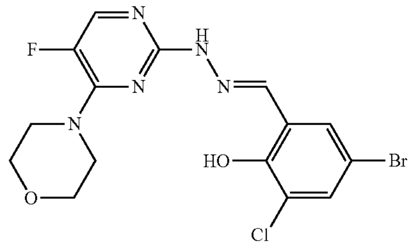 [SMILES: Oc1c(Cl)cc(Br)cc1/C=N/Nc1ncc(F)c(N2CCOCC2)n1] | B | A |
| 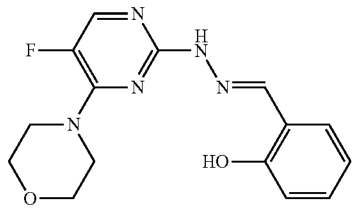 [SMILES: Oc1ccccc1/C=N/Nc1ncc(F)c(N2CCOCC2)n1] | C | C |
| 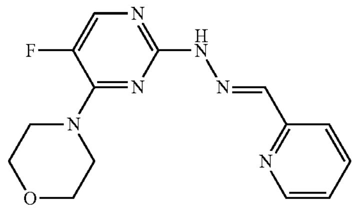 [SMILES: Fc1cnc(N/N=C/c2ccccn2)nc1N1CCOCC1] | B | B |
| 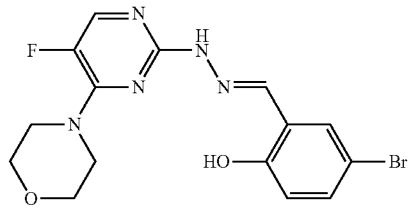 [SMILES: Oc1ccc(Br)cc1/C=N/Nc1ncc(F)c(N2CCOCC2)n1] | B | B |

TABLE 4-continued
| Structure: | wt BaF3 | T315I |
|---|---|---|
| 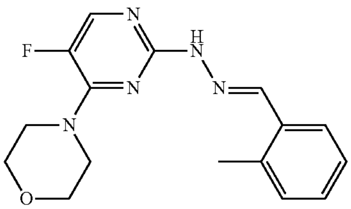 [SMILES: Cc1ccccc1/C=N/Nc1ncc(F)c(N2CCOCC2)n1] | D | D |
| 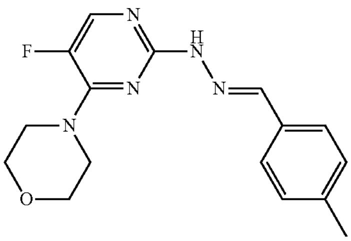 [SMILES: Cc1ccc(/C=N/Nc2ncc(F)c(N3CCOCC3)n2)cc1] | D | D |
| 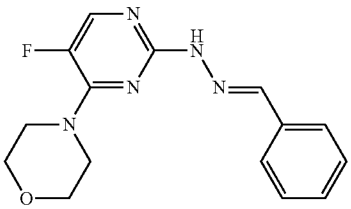 [SMILES: Fc1cnc(N/N=C/c2ccccc2)nc1N1CCOCC1] | D | D |
| 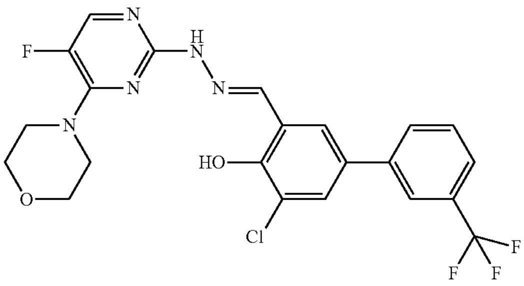 [SMILES: Oc1c(Cl)cc(-c2cccc(C(F)(F)F)c2)cc1/C=N/Nc1ncc(F)c(N2CCOCC2)n1] | B | A |
| 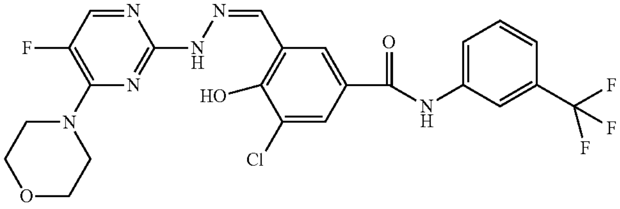 [SMILES: O=C(Nc1cccc(C(F)(F)F)c1)c1cc(Cl)c(O)c(/C=N\Nc2ncc(F)c(N3CCOCC3)n2)c1] | B | B |

TABLE 4-continued
| Structure: | wt BaF3 | T315I |
|---|---|---|
| 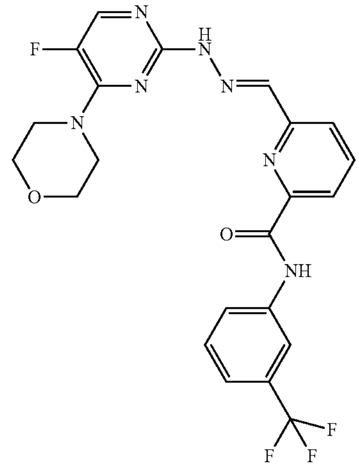 [SMILES: O=C(Nc1cccc(C(F)(F)F)c1)c1cccc(/C=N/Nc2ncc(F)c(N3CCOCC3)n2)n1] | D | D |
| 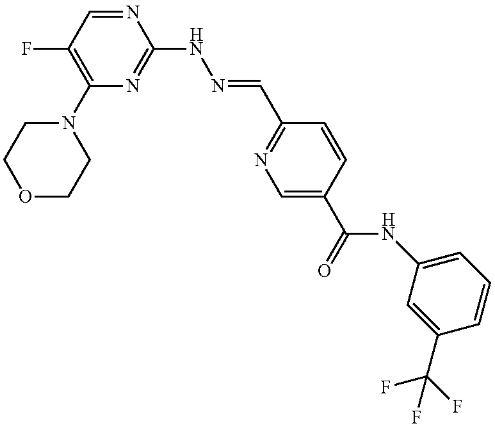 [SMILES: O=C(Nc1cccc(C(F)(F)F)c1)c1ccc(/C=N/Nc2ncc(F)c(N3CCOCC3)n2)nc1] | C | B |
| 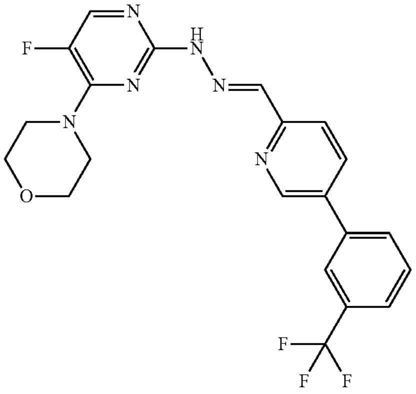 [SMILES: Fc1cnc(N/N=C/c2ccc(-c3cccc(C(F)(F)F)c3)cn2)nc1N1CCOCC1] | B | B |
| 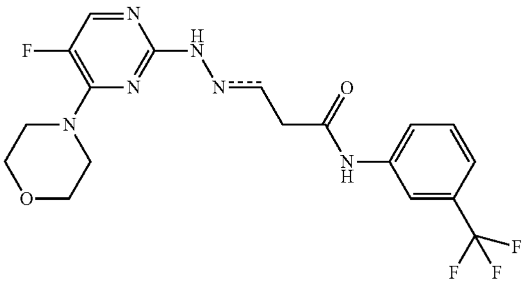 | D | D |

TABLE 4-continued
| Structure: | wt BaF3 | T315I |
|---|---|---|
| 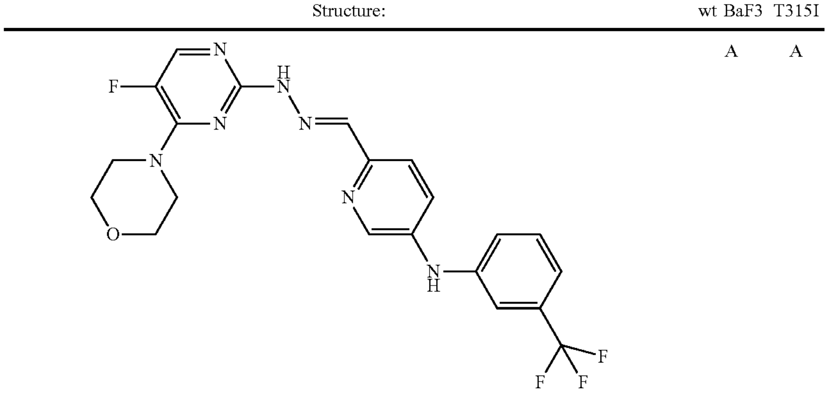 | A | A |
| 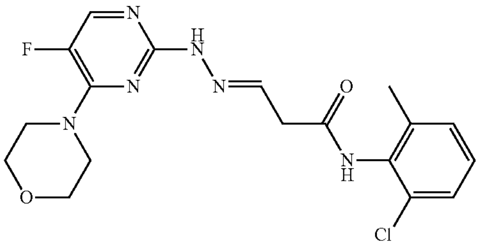 [SMILES: Cc1cccc(Cl)c1NC(=O)C/C=N/Nc1ncc(F)c(N2CCOCC2)n1] | D | D |
| 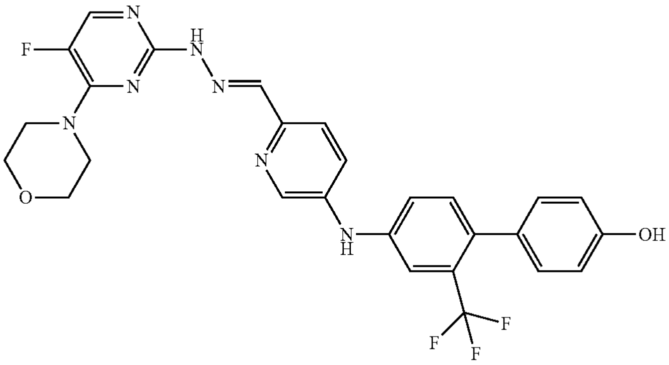 [SMILES: Oc1ccc(-c2ccc(Nc3ccc(/C=N/Nc4ncc(F)c(N5CCOCC5)n4)nc3)cc2C(F)(F)F)cc1] | A | A |
| 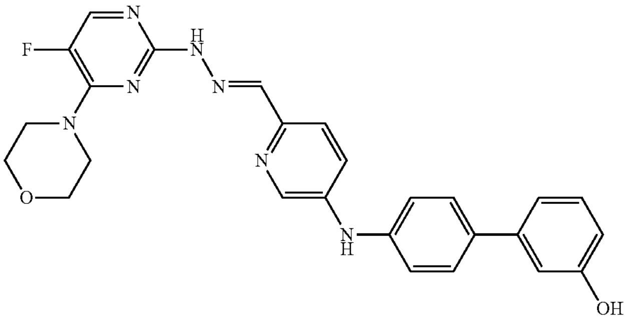 [SMILES: Oc1cccc(-c2ccc(Nc3ccc(/C=N/Nc4ncc(F)c(N5CCOCC5)n4)nc3)cc2)c1] | A | A |
| 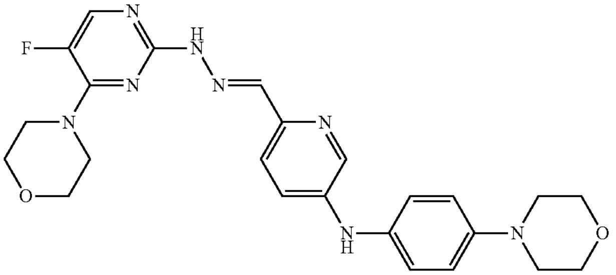 [SMILES: Fc1cnc(N/N=C/c2ccc(Nc3ccc(N4CCOCC4)cc3)cn2)nc1N1CCOCC1] | B | B |

TABLE 4-continued
| Structure: | wt BaF3 | T315I |
|---|---|---|
| 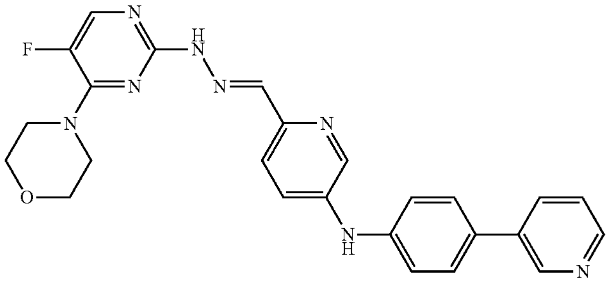 [SMILES: Fc1cnc(N/N=C/c2ccc(Nc3ccc(-c4cccnc4)cc3)cn2)nc1N1CCOCC1] | B | A |
| 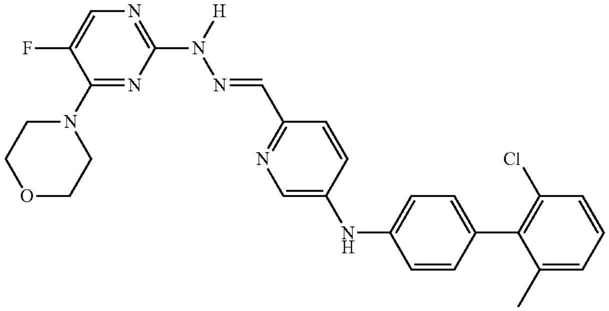 [SMILES: Cc1cccc(Cl)c1-c1ccc(Nc2ccc(/C=N/Nc3ncc(F)c(N4CCOCC4)n3)nc2)cc1] | A | A |
| 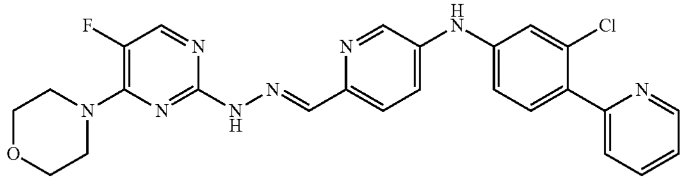 [SMILES: Fc1cnc(N/N=C/c2ccc(Nc3ccc(-c4ccccn4)c(Cl)c3)cn2)nc1N1CCOCC1] | B | B |
| 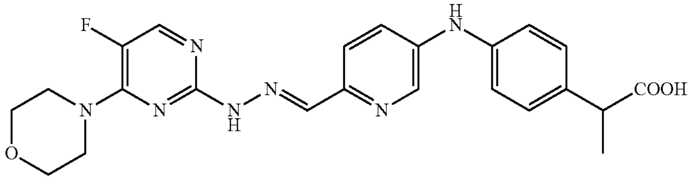 [SMILES: CC(C(=O)O)c1ccc(Nc2ccc(/C=N/Nc3ncc(F)c(N4CCOCC4)n3)nc2)cc1] | D | D |
| 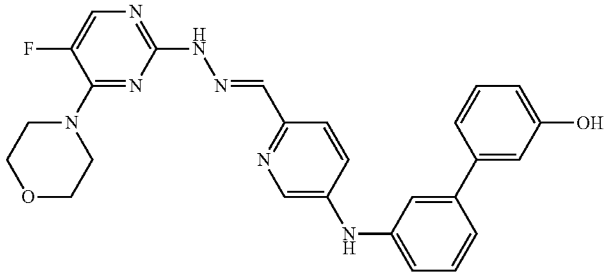 [SMILES: Oc1cccc(-c2cccc(Nc3ccc(/C=N/Nc4ncc(F)c(N5CCOCC5)n4)nc3)c2)c1] | B | A |
| 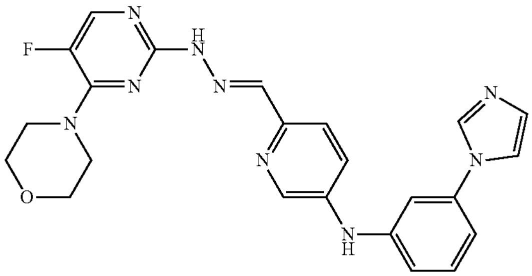 [SMILES: Fc1cnc(N/N=C/c2ccc(Nc3cccc(-n4ccnc4)c3)cn2)nc1N1CCOCC1] | B | B |

TABLE 4-continued
| Structure: | wt BaF3 | T315I |
|---|---|---|
| 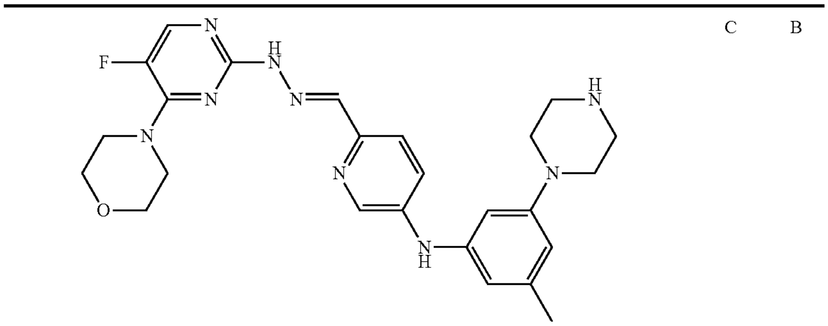 | C | B |
| 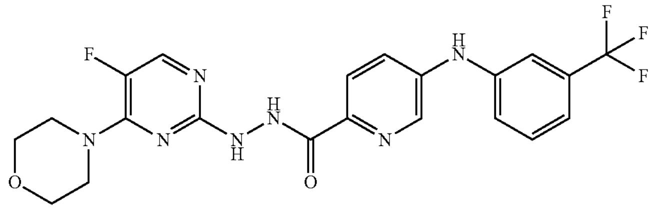 [SMILES: O=C(NNc1ncc(F)c(N2CCOCC2)n1)c1ccc(Nc2cccc(C(F)(F)F)c2)cn1] | B | B |
| 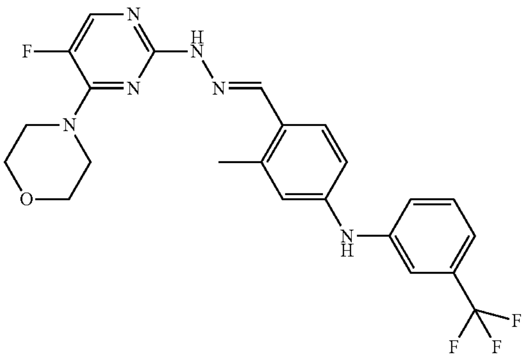 [SMILES: Cc1cc(Nc2cccc(C(F)(F)F)c2)ccc1/C=N/Nc1ncc(F)c(N2CCOCC2)n1] | D | D |
| 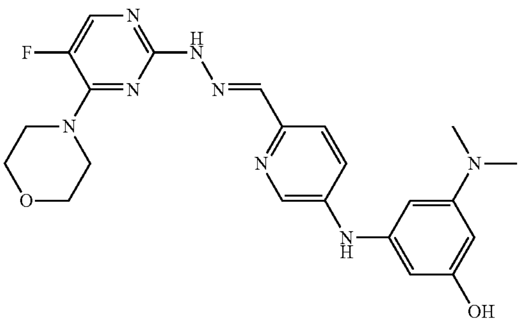 [SMILES: CN(C)c1cc(O)cc(Nc2ccc(/C=N/Nc3ncc(F)c(N4CCOCC4)n3)nc2)c1] | C | B |
| 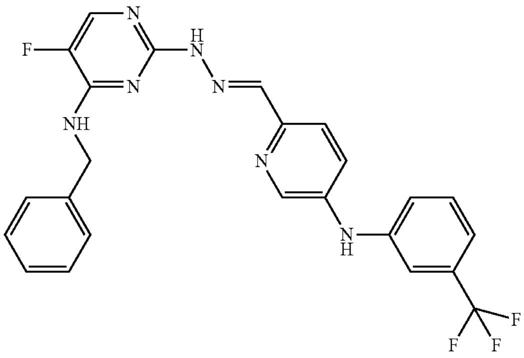 [SMILES: Fc1cnc(N/N=C/c2ccc(Nc3cccc(C(F)(F)F)c3)cn2)nc1NCc1ccccc1] | A | A |

TABLE 4-continued
| Structure: | wt BaF3 | T315I |
|---|---|---|
| 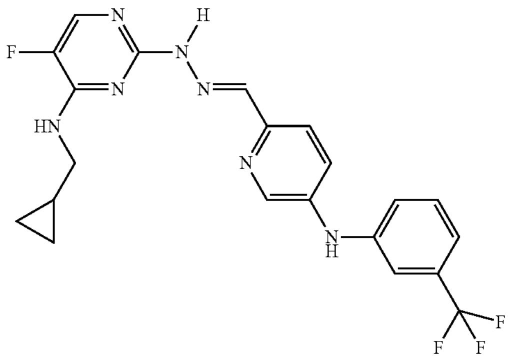 [SMILES: Fc1cnc(N/N=C/c2ccc(Nc3cccc(C(F)(F)F)c3)cn2)nc1NCC1CC1] | A | A |
| 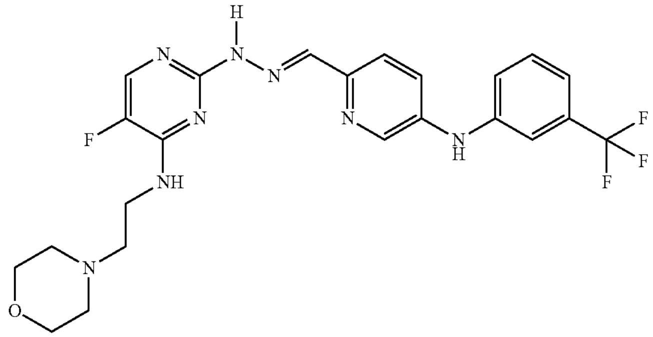 [SMILES: Fc1cnc(N/N=C/c2ccc(Nc3cccc(C(F)(F)F)c3)cn2)nc1NCCN1CCOCC1] | A | A |
| 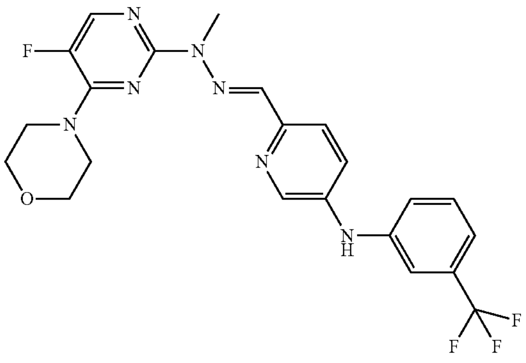 [SMILES: CN(/N=C/c1ccc(Nc2cccc(C(F)(F)F)c2)cn1)c1ncc(F)c(N2CCOCC2)n1] | A | A |
| 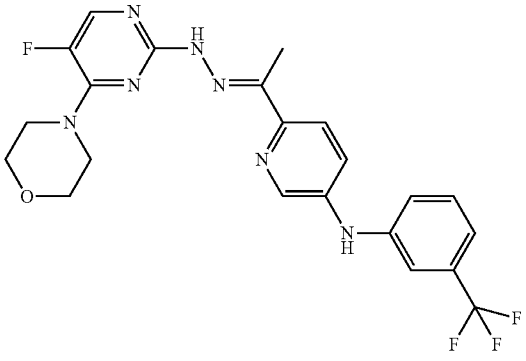 [SMILES: C/C(=N\Nc1ncc(F)c(N2CCOCC2)n1)c1ccc(Nc2cccc(C(F)(F)F)c2)cn1] | A | A |

TABLE 4-continued

| Structure: | wt BaF3 | T315I |
|---|---|---|
| 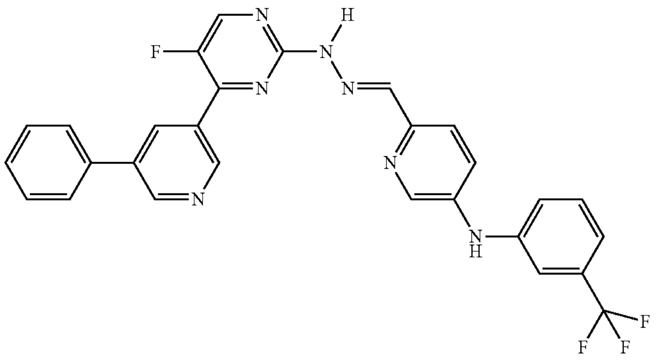 [SMILES: Fc1cnc(N/N=C/c2ccc(Nc3cccc(C(F)(F)F)c3)cn2)nc1-c1cncc(-c2ccccc2)c1] | B | B |
| 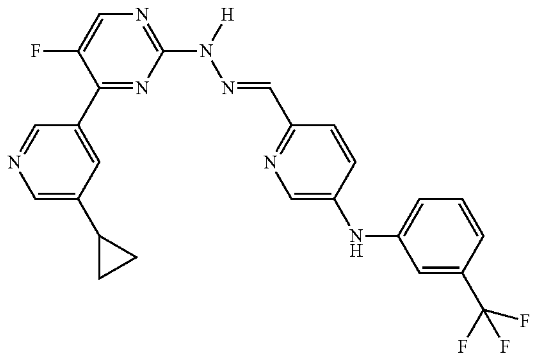 [SMILES: Fc1cnc(N/N=C/c2ccc(Nc3cccc(C(F)(F)F)c3)cn2)nc1-c1cncc(C2CC2)c1] | C | C |
| 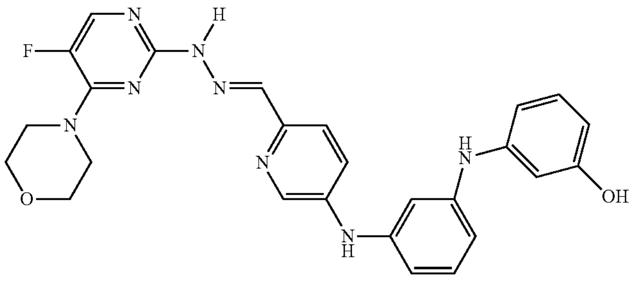 [SMILES: Oc1cccc(Nc2cccc(Nc3ccc(/C=N/Nc4ncc(F)c(N5CCOCC5)n4)nc3)c2)c1] | B | B |

Example 4

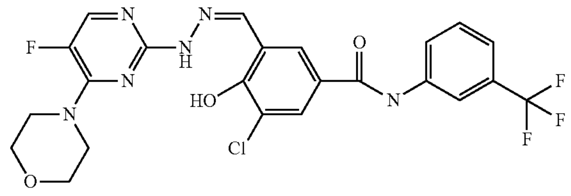 [SMILES: O=C(Nc1cccc(C(F)(F)F)c1)c1cc(Cl)c(O)c(/C=N\Nc2ncc(F)c(N3CCOCC3)n2)c1]

Reaction Scheme:

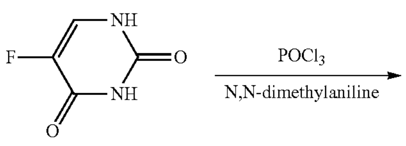

1

-continued

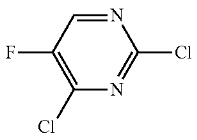

2

Experimental Details:

The mixture of compound 1 (25 g) and N, N-dimethylaniline (24.2 g) in $POCl_3$ (110 mL) was refluxed for 5 h. $POCl_3$ was removed by evaporation at reduced pressure and the residue was poured into ice-water (500 g) cautiously and stirred for 1 h. The mixture was then filtered and the solid was washed with water to give compound 2 as a yellow solid.

2. Reaction Scheme:

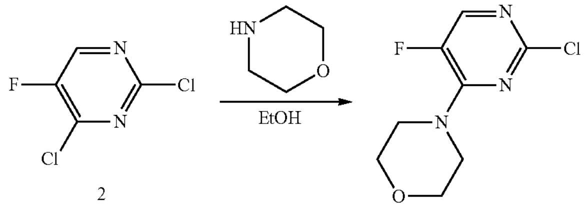

2

3

Experimental Details:

To a solution of compound 2 (1.04 g) in 15 ml of ethanol, 1.08 g (2 eq) of morphine was added dropwise at −10° C. in 15 min. The mixture was stirred for 0.5 h and heated at 50° C. for 15 min. After cooling and dilution with water (50 ml), compound 3 was obtained as a yellow solid powder after filtration.

3. Reaction Scheme:

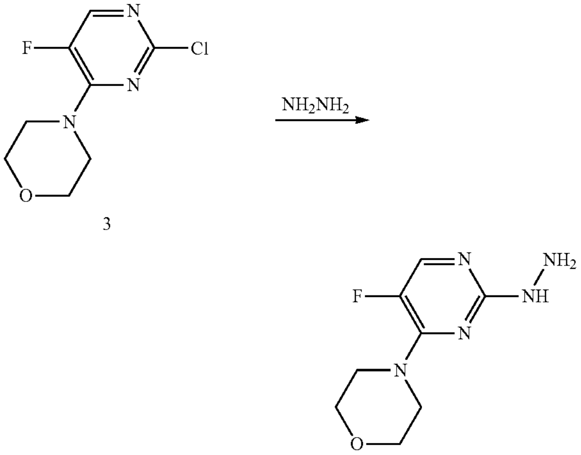

3

4

Experimental Details:

To 1.1 g of compound 3 was added 8 ml of $NH_2NH_2.H_2O$. The mixture was refluxed for 2 h. After cooling, the crude product was obtained after filtration. Purification by column chromatography gave pure compound 4 as a light yellow solid.

4. Reaction Scheme:

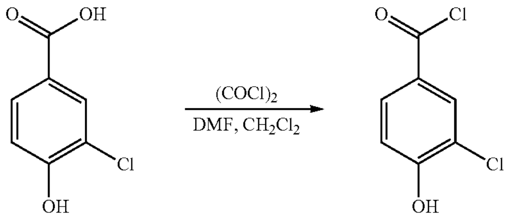

5

6

Experimental Details:

To the solution of compound 5 (1.0 g, 1.0 eq) and DMF (0.05 g, cat. amount) in 20 mL of dichloromethane was added $(COCl)_2$ (0.81 g, 1.1 eq) dropwise. The reaction mixture was stirred at r.t. for 2 h and then concentrated to give 1.2 g of crude product of compound 6, which was used for the next step without further purification.

5. Reaction Scheme:

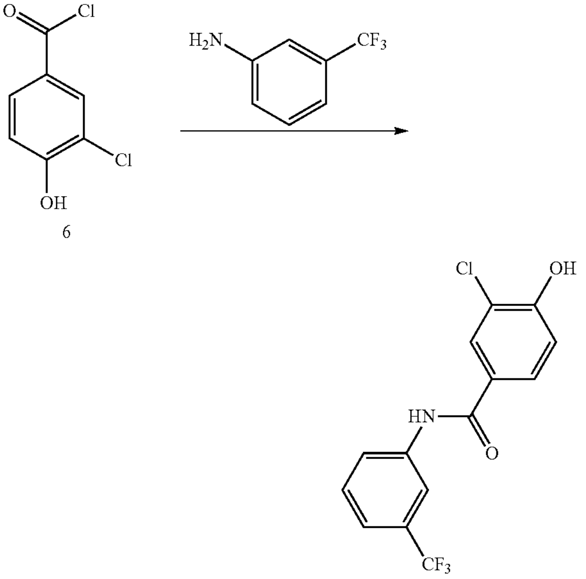

6

7

Experimental Details:

To the crude product of compound 6 (1.2 g, 1.0 eq) in 20 mL of dichloromethane was added 3-trifluoromethyl-phenylamine (0.94 g, 1.0 eq) and triethylamine (0.71 g, 1.2 eq). The reaction mixture was stirred at r.t. overnight, washed with 1 N NaOH solution, 1 N HCl solution and brine. The organic layer was collected, dried over $Na_2SO_4$, and concentrated to give crude product of compound 7. After purification by column chromatography, 1.1 g of compound 7 was obtained.

6. Reaction Scheme:

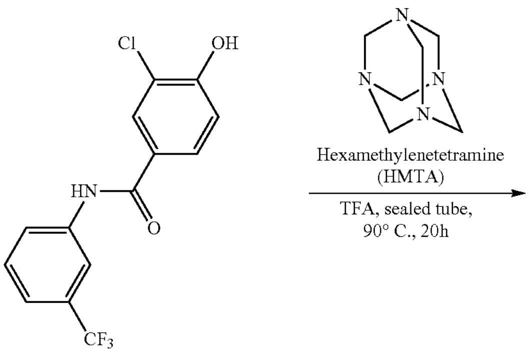

7

-continued

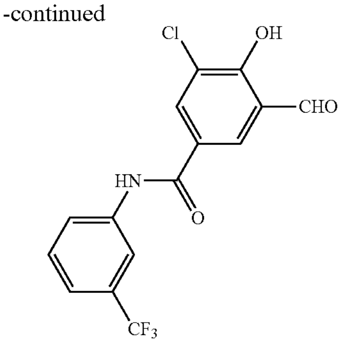

8

Experimental Details:

To the mixture of compound 7 (0.3 g, 1.0 eq) and 3 mL of trifluoroacetic acid was added hexamethylenetetramine (0.53 g, 4.0 eq). The reaction mixture was immediately sealed and heated to 90° C. for 20 h. After cooling, the reaction mixture was adjusted to pH 8 with 1 N NaOH solution, extracted with dichloromethane and the organic phase was dried, concentrated to give a brown solid. Purification by preparative TLC gave compound 8 as a yellow solid.

7. Reaction Scheme:

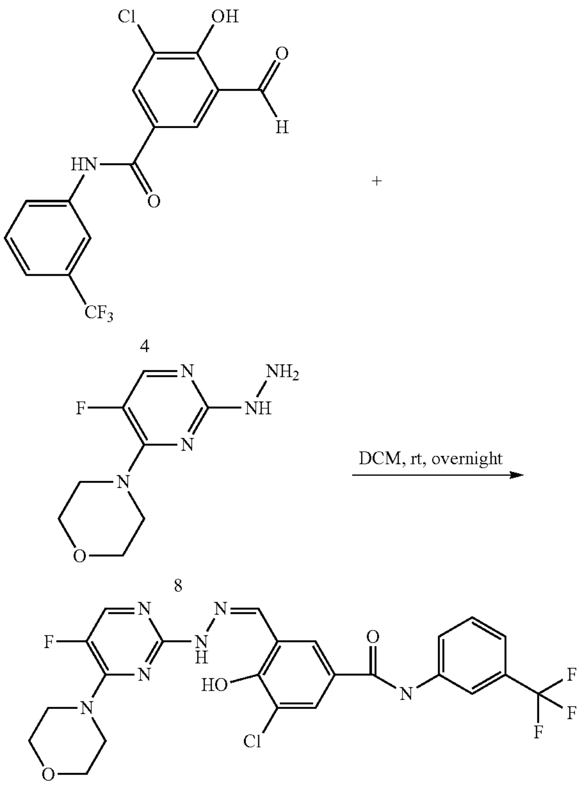

Experimental Details:

The mixture of compound 4 (30 mg, 1.0 eq) and compound 8 (19 mg, 1.0 eq) in 5 mL of dichloromethane was stirred at r.t. overnight. The precipitates were collected and washed with dichloromethane thoroughly, dried under vacuum to give the desired compound.

Example 5

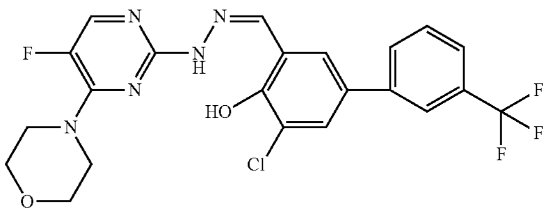 [SMILES: Oc1c(Cl)cc(-c2cccc(C(F)(F)F)c2)cc1/C=N\Nc1ncc(F)c(N2CCOCC2)n1]

1. Reaction Scheme:

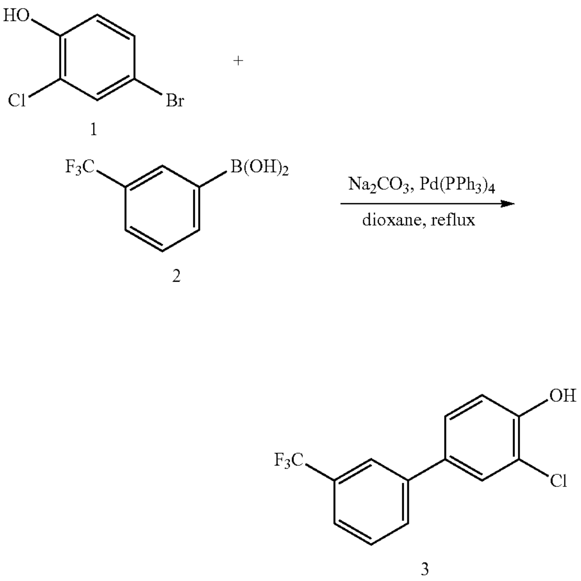

Experimental Details:

To the mixture of compound 1 (1.0 g, 1.0 eq), compound 2 (0.92 g, 1.0 eq), $Na_2CO_3$ (0.77 g, 1.5 eq) in 15 mL of dioxane was added $Pd(PPh_3)_4$ (0.56 g, 0.1 eq), and the reaction mixture was refluxed under $N_2$ for 16 h. After cooling, the mixture was filtered and the filtrate was evaporated to dryness and purified by column chromatography to give compound 3.

2. Reaction Scheme:

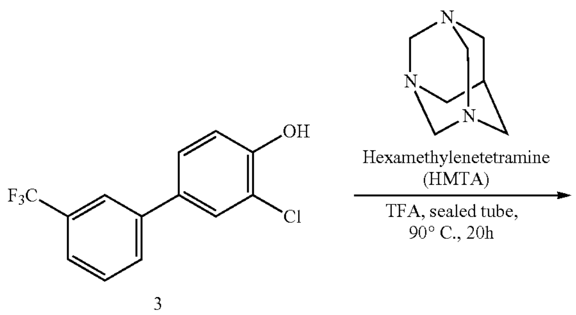

3

-continued

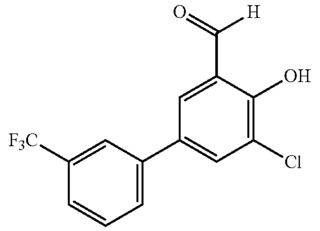

4

Experimental Details:

To the mixture of compound 3 (0.3 g, 1.0 eq) and 3 mL of trifluoroacetic acid was added hexamethylenetetramine (0.62 g, 4.0 eq). The reaction mixture was immediately sealed and heated to 90° C. for 20 h. After cooling, the reaction mixture was adjusted to pH 8 with 1 N NaOH solution, extracted with dichloromethane and the organic phase was dried, concentrated to give a brown solid. Purification by preparative TLC gave compound 4 as a yellow solid.

3. Reaction Scheme:

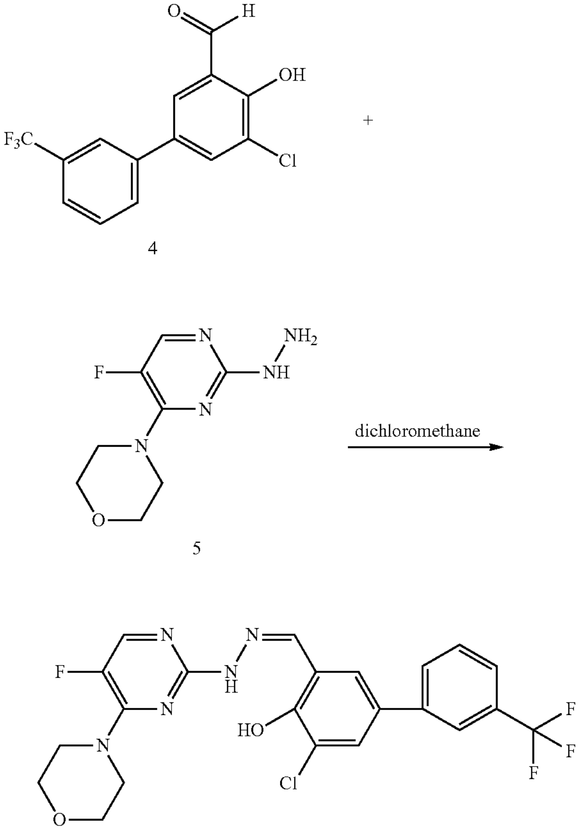

4

5

Experimental Details:

The mixture of compound 4 (30 mg, 1.0 eq) and compound 5 (19 mg, 1.0 eq) in 5 mL of dichloromethane was stirred at r.t. overnight. The precipitates were collected and washed with dichloromethane, dried under vacuum to give the desired compound.

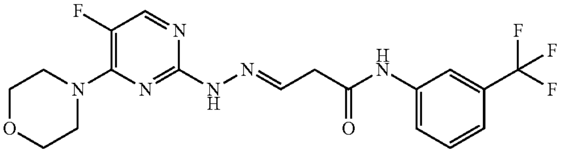 [SMILES: O=C(C/C=N/Nc1ncc(F)c(N2CCOCC2)n1)Nc1cccc(C(F)(F)F)c1]

Example 6

1. Reaction Scheme:

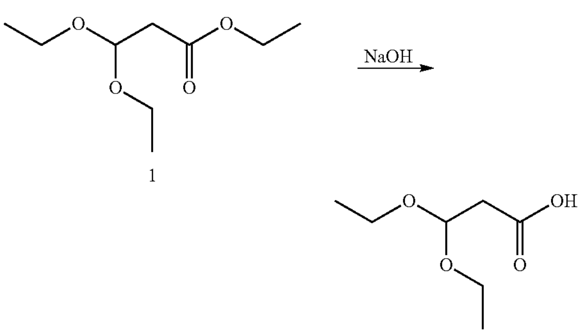

1

2

Experimental Details:

To the solution of compound 1 (0.6 g, 1.0 eq) in 10 mL of methanol was added 4 mL of 1 N NaOH solution, and the mixture was stirred at r.t. overnight. Solvent was evaporated and the residue was acidified to pH 6 with 5% citric acid, extracted with dichloromethane. The organic layer was dried, concentrated to give compound 2.

2. Reaction Scheme:

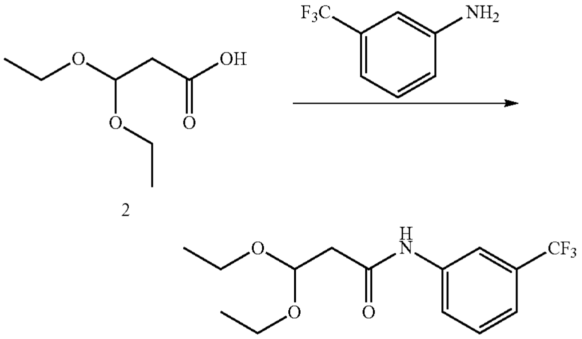

2

3

Experimental Details:

The mixture of compound 2 (0.4 g, 1.0 eq), trifluoromethyl phenylamine (0.39 g, 1.0 eq), EDC (0.71 g, 1.5 eq), HOBt (33 mg, 0.1 eq) in 10 mL of dichloromethane was stirred at r.t. overnight. The mixture was washed with 1 N NaOH solution, water, extracted with dichloromethane. The organic layer was dried over $Na_2SO_4$, concentrated to dryness, and purified by column chromatography to give compound 3.

3. Reaction Scheme:

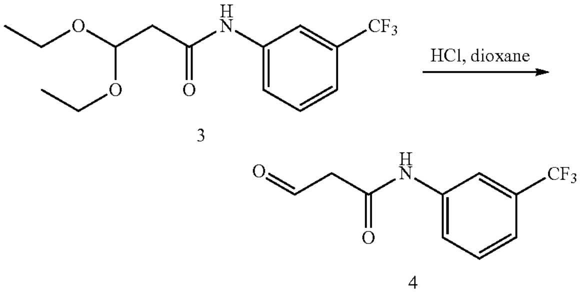

3

4

Experimental Details:

The solution of compound 3 (0.2 g, 1.0 eq) in 10 mL of dioxane was treated with 4 mL of 1 N HCl, and the mixture was heated to 60° C. for 2 h. After cooled, pH was adjusted to 8 by addition of $NaHCO_3$. The mixture was extracted with dichloromethane, washed the organic layer with water, dried with $Na_2SO_4$ and evaporated to dryness. The crude product was purified by column chromatography to give compound 4.

4. Reaction Scheme:

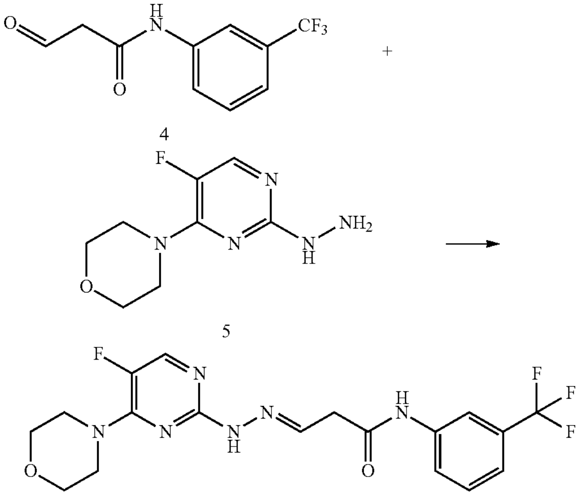

4

5

Experimental Details:

The mixture of compound 4 (40 mg, 1.0 eq) and compound 5 (30 mg, 1.0 eq) in 5 mL of dichloromethane was stirred at r.t. overnight. The mixture was concentrated to dryness and purified by preparative HPLC to give the desired compound.

Example 7

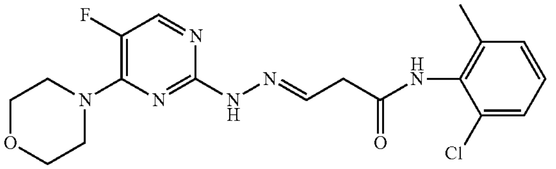 [SMILES: Cc1cccc(Cl)c1NC(=O)C/C=N/Nc1ncc(F)c(N2CCOCC2)n1]

1. Reaction Scheme:

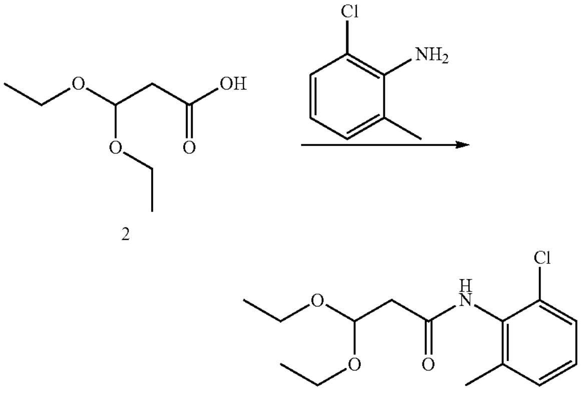

2

3

Experimental Details:

The mixture of compound 2 (0.3 g, 1.0 eq), 2-chloro-6-methyl-phenylamine (0.26 g, 1.0 eq), EDC (0.53 g, 1.5 eq), HOBt (25 mg, 0.1 eq) in 10 mL of dichloromethane was stirred at r.t. overnight. The mixture was washed with 1 N NaOH solution, water, and extracted with dichloromethane. The organic layer was dried over $Na_2SO_4$, concentrated to dryness, purified by column chromatography to give compound 3.

2. Reaction Scheme:

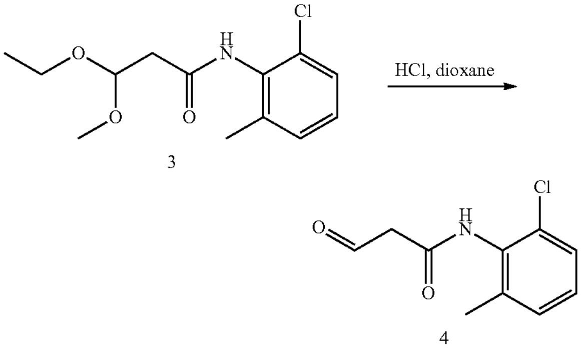

3

4

Experimental Details:

The solution of compound 3 (0.2 g, 1.0 eq) in 10 mL of dioxane was treated with 4 mL of 1 N HCl, and the mixture was heated to 60° C. for 2 h. After cooling, the pH was adjusted to 8 by addition of $NaHCO_3$. The mixture was extracted with dichloromethane, washed the organic layer with water, dried with $Na_2SO_4$ and evaporated to dryness. The crude product was purified by column chromatography to give compound 4.

3. Reaction Scheme:

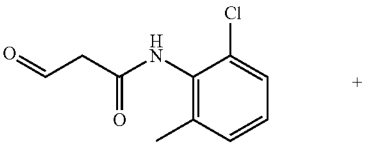

4

-continued

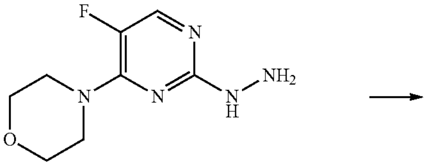

5

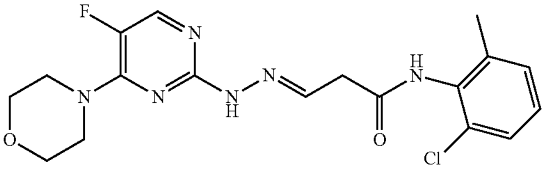

Experimental Details:

The mixture of compound 4 (40 mg, 1.0 eq) and compound 5 (30 mg, 1.0 eq) in 5 mL of dichloromethane was stirred at r.t. overnight. The mixture was concentrated to dryness and purified by preparative HPLC to give the desired compound.

Example 8

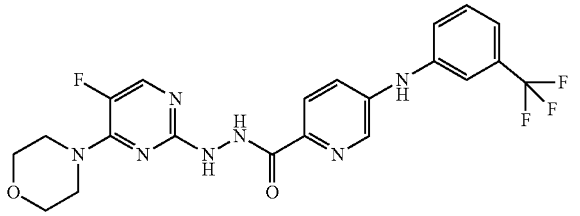 [SMILES: O=C(NNc1ncc(F)c(N2CCOCC2)n1)c1ccc(Nc2cccc(C(F)(F)F)c2)cn1]

1. Reaction Scheme:

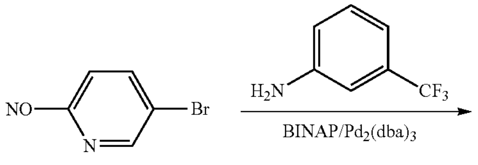

1

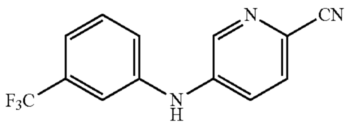

2

Experimental Details:

To a solution of 1 g (5.5 mmol) of 5-bromo-2-cyanopyridine, 0.97 g of (6.05 mmol 1.1 eq) 3-(trifluoromethyl)aniline in 100 ml of toluene was added 3 eq of t-BuONa, 0.2 eq of BINAP and 0.1 eq of $Pd_2(dba)_3$. Then the solution was heated to reflux overnight. The reaction was monitored by LC/MS. The volatiles were removed under reduced pressure. The crude product was purified by flash chromatography to afford compound 2.

2. Reaction Scheme:

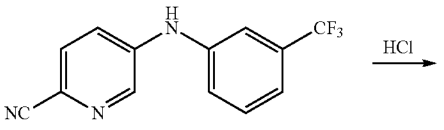

2

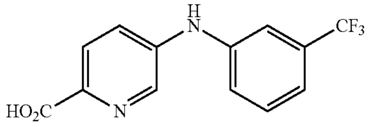

3

Experimental Details:

250 mg (0.95 mmol) of compound 2 was added to 20 mL of concentrated HCl, then the solution was heated to reflux until the starting material disappeared. The mixture was concentrated under reduced pressure to obtain compound 3 as a yellow solid without purification.

3. Reaction Scheme:

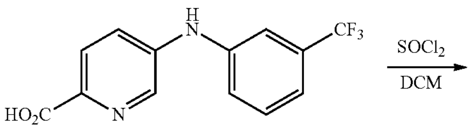

3

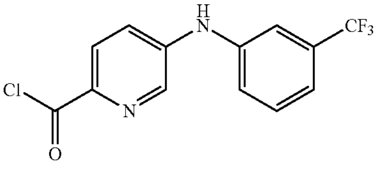

4

Experimental Details:

A solution of 50 mg (0.18 mmol) of compound 3 in 3 mL of dichloromethane was added to 0.5 mL of thionyl dichloride. The mixture was heated and stirred for 3 h. Finally the solution was evaporated under reduced pressure. Compound. 4 was obtained and used in next step without purification.

4. Reaction Scheme:

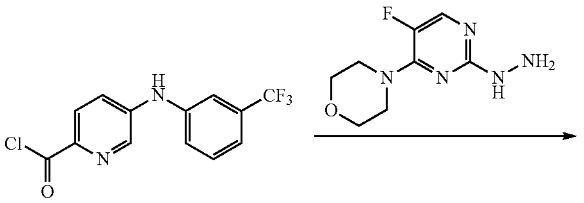

4

-continued

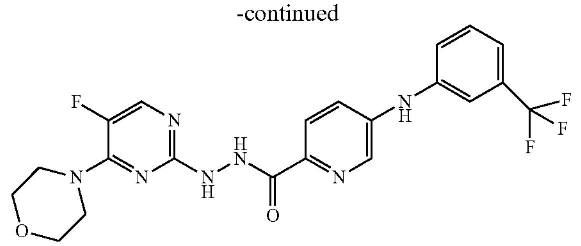

Experimental Details:

A solution of 50 mg of compound 4 and 43 mg (1.2 eq) of hydrazine in 5 mL of DCM was stirred at 25° C. for 3 hours. The reaction mixture was concentrated and the residue was purified by preparative HPLC to give the desired compound.

Example 9

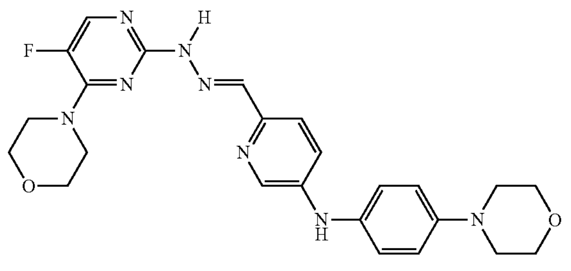 [SMILES: Fc1cnc(N/N=C/c2ccc(Nc3ccc(N4CCOCC4)cc3)cn2)nc1N1CCOCC1]

1. Reaction Scheme:

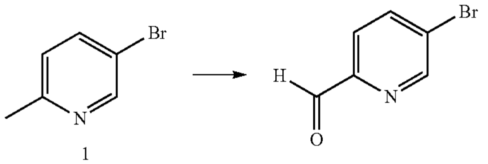

1 2

Experimental Details:

A suspension of compound 1 (25 g, 0.145 mol) and $SeO_2$ (27.5 g, 0.247 mol) in acetic acid (1200 mL) was heated to reflux for 12 h. The reaction mixture was concentrated under reduced pressure to dryness. The residue was dissolved into water and brought to pH=9 by adding $K_2CO_3$. The resulted mixture was extracted with EA (100 mL×3). The combined EA was dried over $Na_2SO_4$. After filtrating off the $Na_2SO_4$, the filtrate was concentrated under reduced pressure to give the crude product 2, which was used in next step without purification.

2. Reaction Scheme:

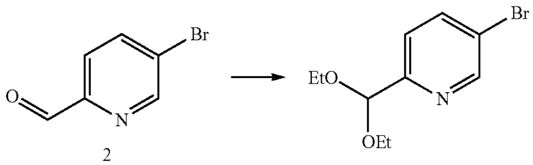

2 3

Experimental Details:

A solution of 2 above prepared in ethanol triethyl orthoformate (10 mL) was refluxed 4 h. After removing off the solvent, the residue was separated by column to give the product 3 as oil.

3. Reaction Scheme:

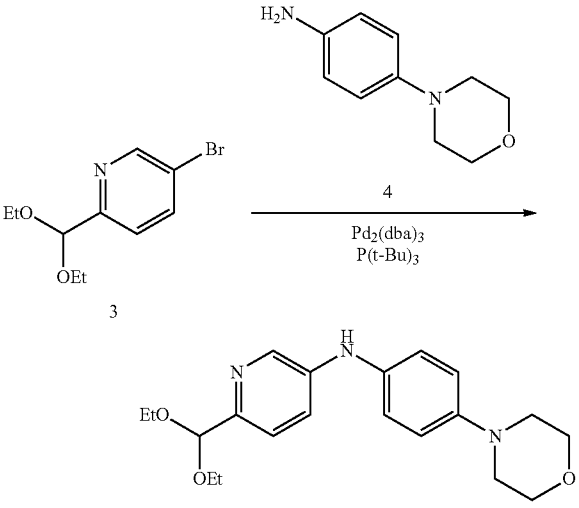

3 5

Experimental Details:

To a stirred and degassed mixture of compound 3 (73 mg, 0.28 mmol) and compound 4 (50 mg, 0.28 mmol), and tBuONa (27 mg, 0.56 mmol) and BINAP (70.4 mg, 1.12 mol) in toluene (15 mL) was added $Pd_2(dba)_3$ (26 mg, 0.028 mmol) under $N_2$ atmosphere and stirred at 80° C. for 48 h. After filtering off the solid, the filtrate was concentrated to give the crude product 5 which was used in the next step without purification.

4. Reaction Scheme:

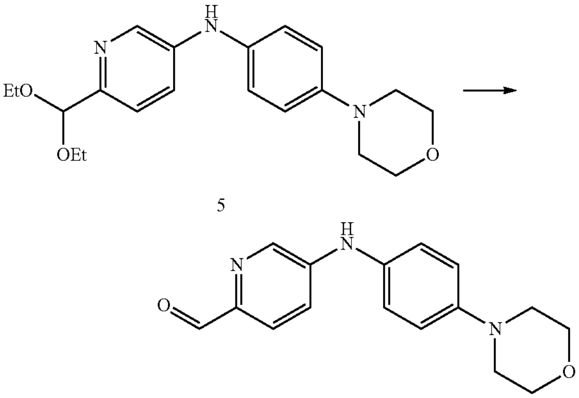

5 6

Experimental Details:

A solution of compound 5 (335 mg, 0.1 mmol) in dichloromethane (10 mL) was treated with $BBr_3$ (146 mg, 0.6 mmol) at −30° C. under $N_2$ atmosphere, then was stirred at room temperature for 4 h. The reaction was poured unto ice-water and then was brought by adding $Na_2CO_3$. The resulting mixture was extracted with dichloromethane (25 mL×3), the combined organic layer was dried over $Na_2SO_4$. After filtrating off the $Na_2SO_4$, the filtrate was concentrated to give the crude product 6 which was done next step without purification.

5. Reaction Scheme:

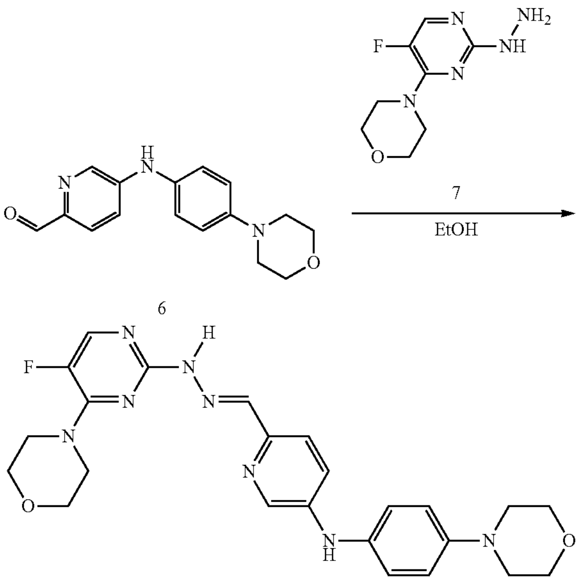

6

Experimental Details:

A solution of compound 6 (27.74 mg, 0.1 mmol) and compound 7 (21 mg, 0.1 mmol) in anhydrous $CH_2Cl_2$ (300 mL) was stirred under reflux for 6 h. The solvent was removed under reduced pressure. The residue was separated by prep-TLC to give the desired compound.

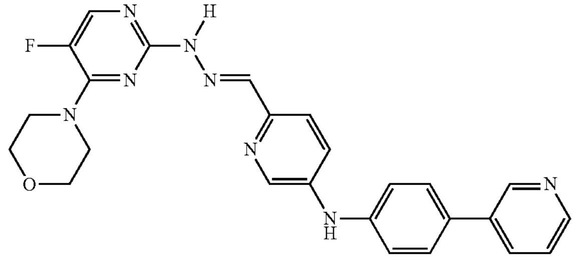 [SMILES: Fc1cnc(N/N=C/c2ccc(Nc3ccc(-c4cccnc4)cc3)cn2)nc1N1CCOCC1]

Example 10

1. Reaction Scheme:

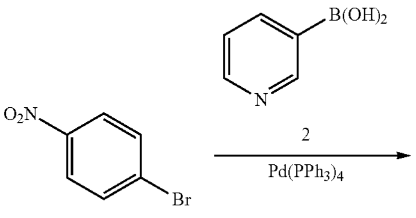

1

-continued

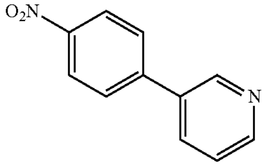

3

Experimental Details:

To a stirred and degassed mixture of compound 1 (5 g, 25 mmol) and compound 2 (3.4 g, 27 mmol) in DMF (50 mL) and aqueous $Na_2CO_3$ (20 mL, 2 M) was added $Pd_2(dbbf)_3$ (26 mg, 0.028 mmol) under $N_2$ atmosphere and stirred at 100° C. for 18 h. After cooling to room temperature and filtrating off the solid, the filtrate was extracted with EA (200 mL). The organic layer was concentrated to dryness. The residue was purified by column to give the crude product 3.

2. Reaction Scheme:

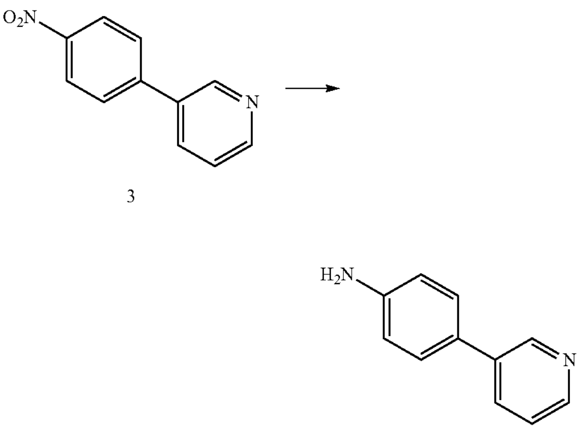

3

4

Experimental Details:

A mixture of compound 3 (2 g, 0.1 mol) and $Na_2S_2O_4$ (5.2 g, 0.3 mol) in methanol (80 mL) and $H_2O$ (20 mL) was heated to reflux for 3 h. The reaction was concentrated to dryness under reduced pressure. The residue was dissolved into water and then was extracted with EA (150 mL). The organic layer was washed with brine twice and dried over $Na_2SO_4$. After filtrating off the $Na_2SO_4$, the filtrate was concentrated to give the product 4.

3. Reaction Scheme:

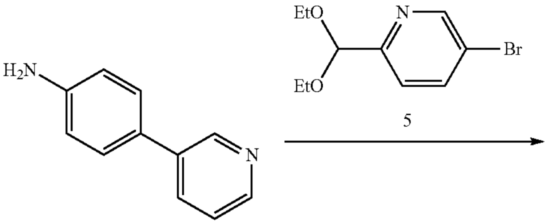

4

-continued

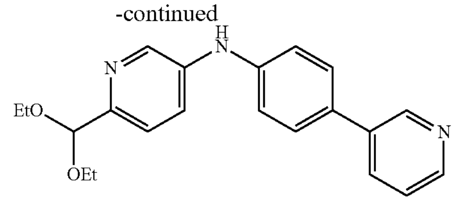

6

Experimental Details:

To a stirred and degassed mixture of compound 5 (228 mg, 88 mmol) and compound 4 (150 mg, 88 mmol), and $_t$BuONa (170 mg, 176 mmol) and BINAP (210 mg, 176 mmol) in toluene (25 mL) was added $Pd_2(dba)_3$ (79 mg, 0.88 mmol) under $N_2$ atmosphere and stirred at 80° C. for 48 h. After filtering off the solid, the filtrate was concentrated to give the crude product 6.

4. Reaction Scheme:

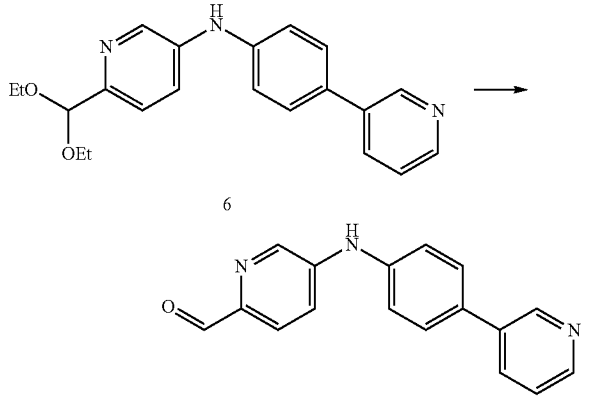

6

7

Experimental Details:

A solution of compound 6 (140 mg, 4 mmol) in dichloromethane (20 mL) was treated with $BBr_3$ (600 mg, 10.6 mmol) at −30° C. under $N_2$ atmosphere, then was stirred at room temperature for 4 h. The reaction was poured unto ice-water and then was brought pH=9 by adding $Na_2CO_3$. The resulting mixture was extracted with dichloromethane (25 mL×3), the combined organic layer was dried over $Na_2SO_4$. After filtrating off the $Na_2SO_4$, the filtrate was concentrated to dryness. The residue was purified by column to give the product 7.

5. Reaction Scheme:

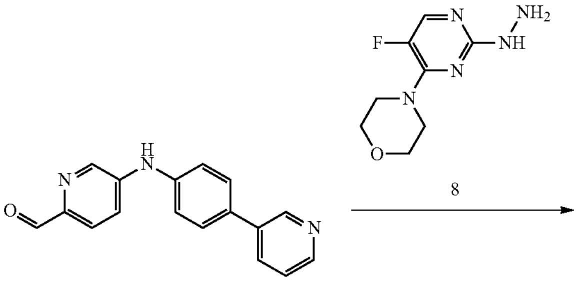

8

7

-continued

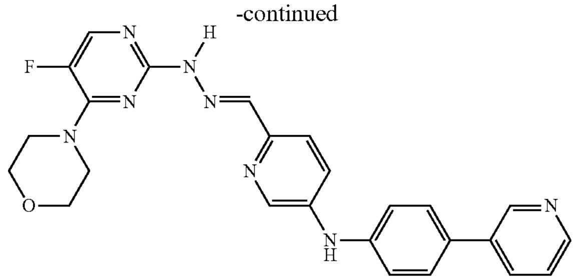

Experimental Details:

A solution of compound 7 (98 mg, 0.36 mmol) and compound 8 (64 mg, 0.3 mmol) in anhydrous $CH_2Cl_2$ (300 mL) was stirred under reflux for 6 h. The solvent was removed under reduced pressure. The residue was separated by prep-TLC to give the desired compound.

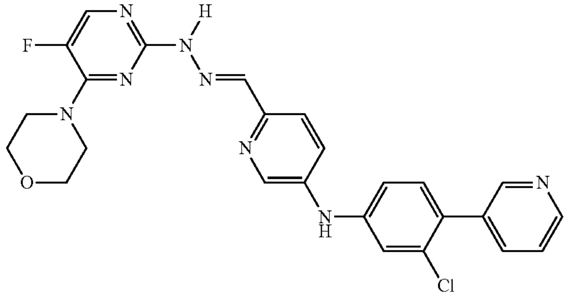 [SMILES: Fc1cnc(N/N=C/c2ccc(Nc3ccc(-c4cccnc4)c(Cl)c3)cn2)nc1N1CCOCC1]

Example 11

1. Reaction Scheme:

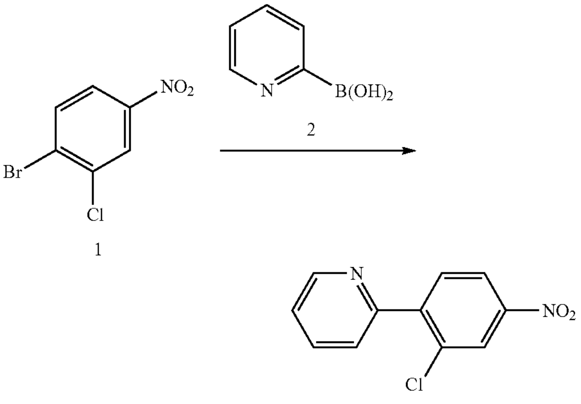

2

1

3

Experimental Details:

To a stirred and degassed mixture of compound 1 (5.9 g, 25 mmol) and compound 2 (3.3 g, 27 mmol) in DMF (50 mL) and aqueous $Na_2CO_3$ (20 mL, 2 M) was added $Pd_2(dbbf)_3$ (26 mg, 0.028 mmol) under $N_2$ atmosphere and stirred at 100° C. for 18 h. After cooling to room temperature and filtrating off the solid, the filtrate was extracted with EA (200 mL). The organic layer was concentrated to give the crude product 3 which is done next step without purification.

2. Reaction Scheme:

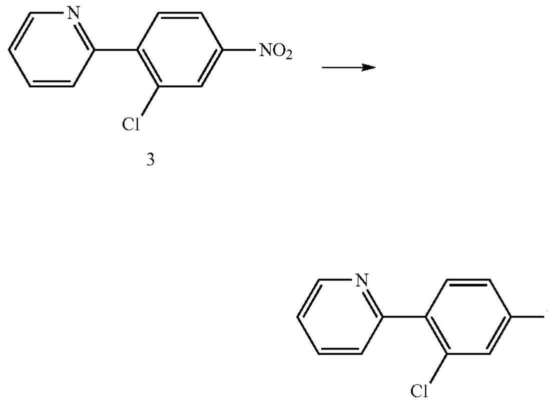

3

4

Experimental Details:

A mixture of 3 (6.5 g, 27.9 mmol) and $Pd(OH)_2$ (10%, 0.5 g) in ethanol (200 mL) was stirred under hydrogen atmosphere (20 psi) at room temperature for 2 hour. The catalyst was filtrated off, and the filtrate was removed under vacuum to afford the product 4 as a colorless oil.

3. Reaction Scheme:

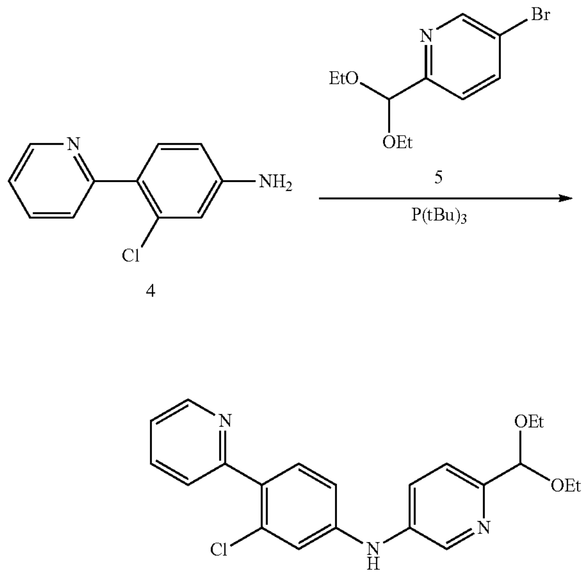

4

5

6

Experimental Details:

To a stirred and degassed mixture of compound 4 (406 mg, 20 mmol) and compound 5 (520 mg, 20 mmol), and $_t$BuONa (170 mg, 176 mmol) and BINAP (210 mg, 176 mmol) in toluene (25 mL) was added $Pd_2(dba)_3$ (79 mg, 0.88 mmol) under $N_2$ atmosphere and stirred at 80° C. for 48 h. After filtrating off the solid, the filtrate was concentrated to give the crude product 6 which is used in next step without purification.

4. Reaction Scheme:

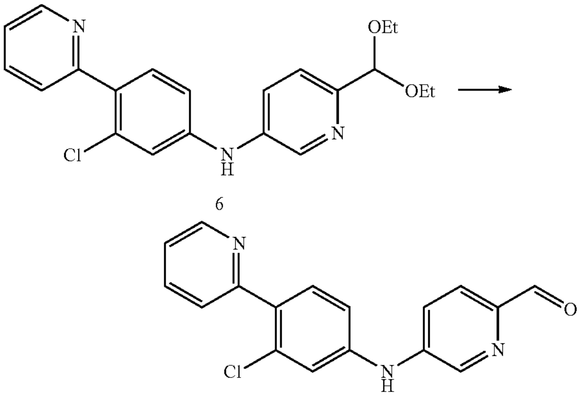

6

7

Experimental Details:

A solution of compound 6 (383 mg, 10 mmol) in dichloromethane (20 mL) was treated with $BBr_3$ (600 mg, 10.6 mmol) at −30° C. under $N_2$ atmosphere, then was stirred at room temperature for 4 h. The reaction was poured unto ice-water and then was brought to pH 9 by adding $Na_2CO_3$. The resulting mixture was extracted with dichloromethane (25 mL×3), the combined organic layer was dried over $Na_2SO_4$. After filtrating off the $Na_2SO_4$, the filtrate was concentrated to dryness. The residue was purified by column to give the product 7.

5. Reaction Scheme:

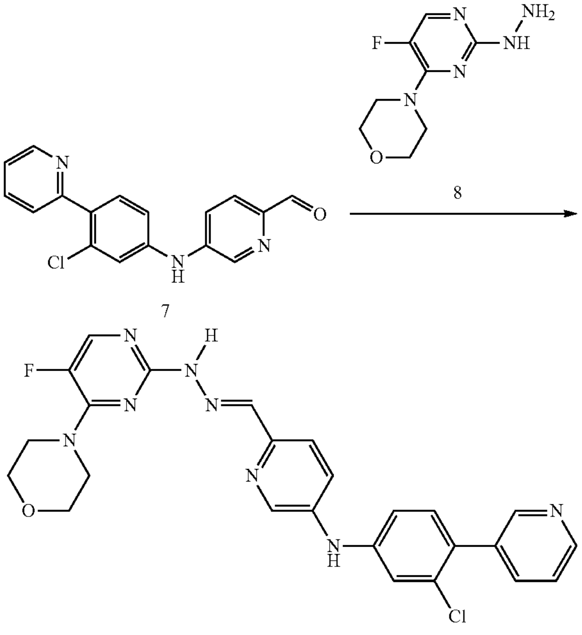

8

7

Experimental Details:

A mixture of 7 (60 mg, 0.22 mmol) nicotinaldehyde (33 mg, 0.15 m mol) in dichloromethane (10 mL) was heated to reflux for 3 hr. After removing off solvent, the residue was purified by chromatography to give the desired compound.

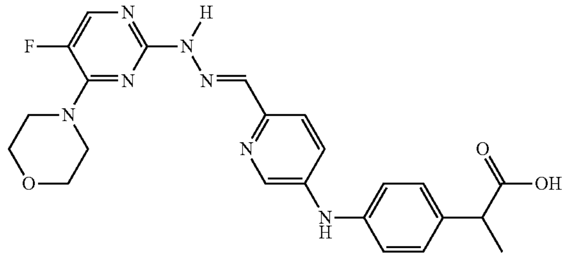 [SMILES: CC(C(=O)O)c1ccc(Nc2ccc(/C=N/Nc3ncc(F)c(N4CCOCC4)n3)nc2)cc1]

Example 12

1. Reaction Scheme:

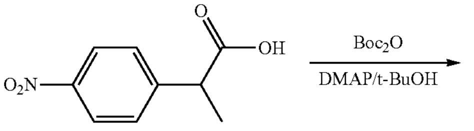

1

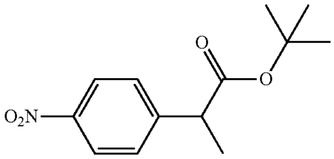

2

Experimental Details:

A solution of DMAP (9.3 g, 0.077 mol) and compound 1 (10 g, 0.051 mol) and $Boc_2O$ (12 g, 0.051 mol) in tBuOH (200 mL) was stirred at room temperature overnight. The solvent was removed under reduced pressure and the residue was purified by flash chromatography on silica gel. (ethyl acetate/petroleum ether=10:1) to give 2 as a colorless oil.

2. Reaction Scheme:

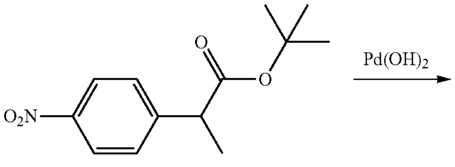

2

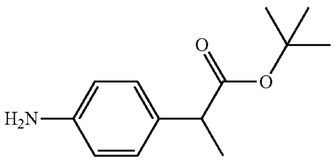

3

Experimental Details:

A mixture of 2 (6.17 g, 27.9 mmol) and $Pd(OH)_2$ (10%, 1 g) in ethanol (200 mL) was stirred under hydrogen atmosphere (50 psi) at room temperature for 4 hour. The catalyst was filtrated off, and the filtrate was removed under vacuum to afford the product 3 as a colorless oil.

3. Reaction Scheme:

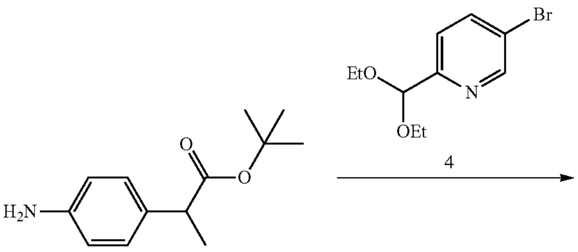

3

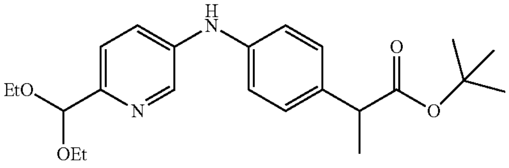

5

Experimental Details:

A mixture of compound 3 (2.65 g, 12 mmol) and compound 4 (2.6 g, 10 mmol) and $_t$BuONa (1.34 g, 14 mmol,) and $Pd_2(dba)_3$ (46.5 mg, 50 mmol,) and DCHPB (70 mg, 0.2 mmol) in dry toluene (50 mL) was heated to 80-90° C. under $N_2$ for 24 hours. The precipitation was filtrated and the filtrate was removed in vacuo and the residue was purified by chromatography on silica gel (ethyl acetate/petroleum ether=1.0:1) to give afford 5 as a yellow oil.

4. Reaction Scheme:

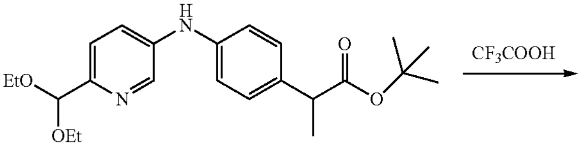

5

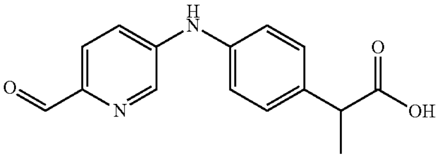

6

Experimental Details:

To a solution of 5 (0.9 g, 2.24 mmol) in $CHCl_3$ (50 mL), $CF_3COOH$ (40 mL) was added at 0° C. After addition complete, the resulting mixture was stirred at room temperature overnight. The solvent was removed under reduced pressure to dryness. The residue was recrystallized from ether to yield an off-white solid. The solid was dissolve in ammonia (10 mL). The mixture was brought the pH=7.0 by adding 1M HCl and precipitated. The precipitate was collected and washed with cold water (5 mL), and dried under reduced pressure to afford 6 as a dark solid.

5. Reaction Scheme:

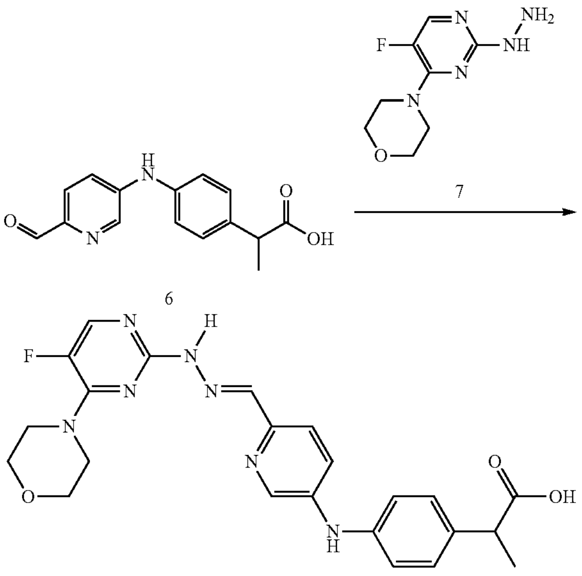

7

6

Experimental Details:

A mixture of 6 (60 mg, 0.22 mmol), nicotinaldehyde (33 mg, 0.15 m mol) in dichloromethane (10 mL) was heated to reflux for 3 hr. After removing off solvent, the residue was purified by chromatography to give the desired compound as a yellow solid.

Example 13

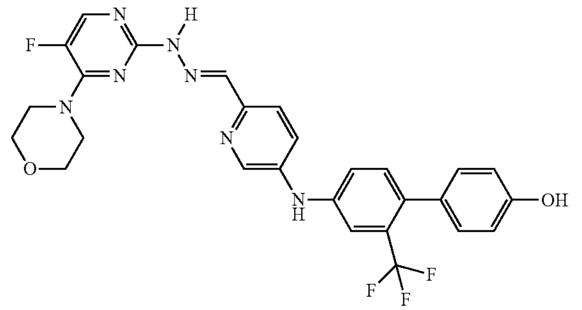 [SMILES: Oc1ccc(-c2ccc(Nc3ccc(/C=N/Nc4ncc(F)c(N5CCOCC5)n4)nc3)cc2C(F)(F)F)cc1]

1. Reaction Scheme:

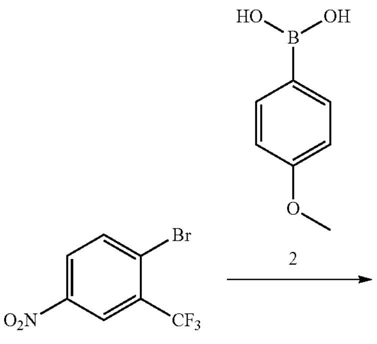

2

1

-continued

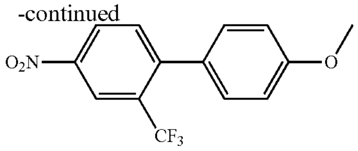

3

Experimental Details:

To a stirred and degassed mixture of compound 1 (6.7 g, 25 mmol) and compound 2 (4.1 g, 27 mmol) in DMF (50 mL) and aqueous $Na_2CO_3$ (20 mL, 2 M) was added $Pd_2(dbbf)_3$ (26 mg, 0.028 mmol) under $N_2$ atmosphere and stirred at 100° C. for 18 h. After cooling to room temperature and filtrating off the solid, the filtrate was extracted with EA (200 mL). The organic layer was concentrated to give the crude product 3.

2. Reaction Scheme:

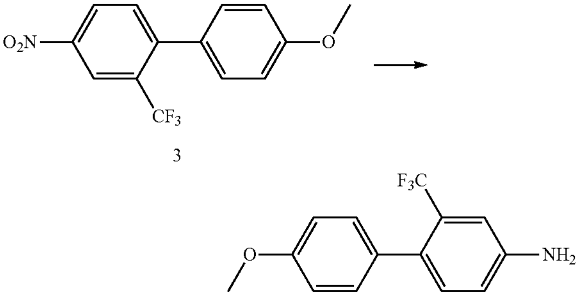

3

4

Experimental Details:

A mixture of 3 (3.2 g, 10 mmol) and $Pd(OH)_2$ (10%, 0.5 g) in ethanol (200 mL) was stirred under hydrogen atmosphere (20 psi) at room temperature for 2 hour. The catalyst was filtrated off, and the filtrate was removed under vacuum to afford the product 4 as colorless oil.

3. Reaction Scheme:

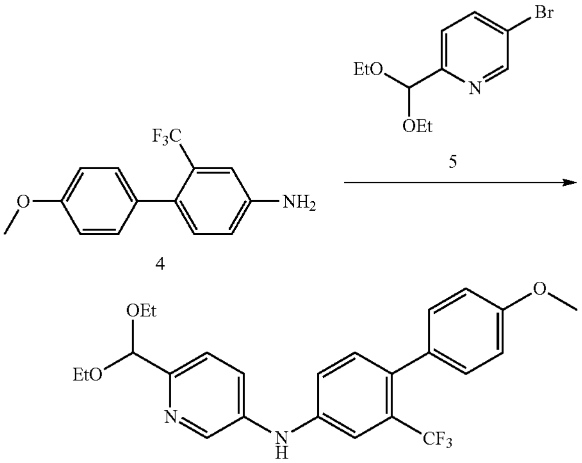

5

4

6

Experimental Details:

To a stirred and degassed mixture of compound 4 (297 mg, 10 mmol) and compound 5 (259 mg, 10 mmol), and $_t$BuONa (170 mg, 17.6 mmol) and BINAP (210 mg, 17.6 mmol) in toluene (25 mL) was added $Pd_2(dba)_3$ (79 mg, 0.88 mmol) under $N_2$ atmosphere and stirred at 80° C. for 48 h. After filtrating off the solid, the filtrate was concentrated to give the crude product 6 which is done next step without purification.

4. Reaction Scheme:

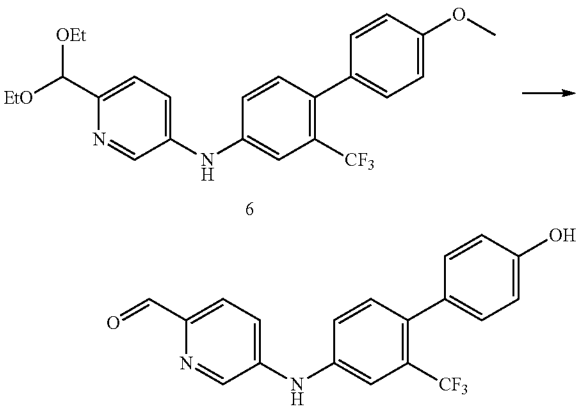

6

7

Experimental Details:

A solution of compound 6 (446 mg, 10 mmol) in dichloromethane (20 mL) was treated with $BBr_3$ (600 mg, 10.6 mmol) at −30° C. under $N_2$ atmosphere, then was stirred at room temperature for 4 h. The reaction was poured unto ice-water and then was brought pH=9 by adding $Na_2CO_3$. The resulting mixture was extracted, with dichloromethane (25 mL×3), the combined organic layer was dried over $Na_2SO_4$. After filtrating off the $Na_2SO_4$, the filtrate was concentrated to dryness. The residue was purified by column to give the product 7.

5. Reaction Scheme:

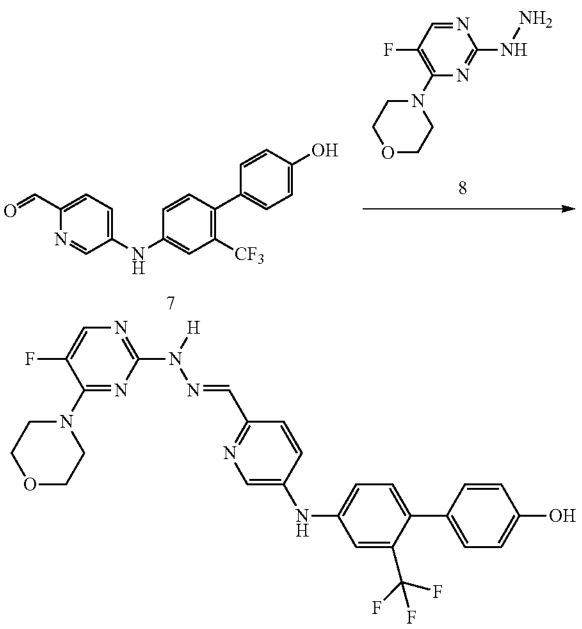

8

7

Experimental Details:

A mixture of 7 (67 mg, 0.15 mmol), nicotinaldehyde (33 mg, 0.15 m mol) in dichloromethane (10 mL) was heated to reflux for 3 hr. After removing off solvent, the residue was purified by chromatography to give the desired compound as a yellow solid.

Example 14

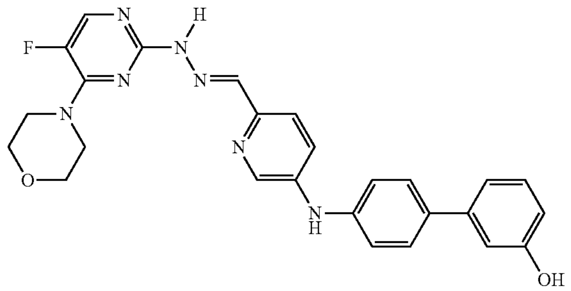 [SMILES: Oc1cccc(-c2ccc(Nc3ccc(/C=N/Nc4ncc(F)c(N5CCOCC5)n4)nc3)cc2)c1]

1. Reaction Scheme:

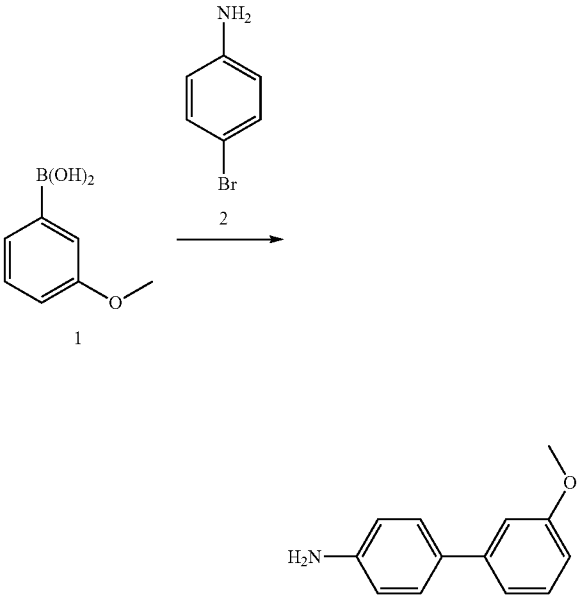

2

1

3

Experimental Details:

To a stirred and degassed mixture of compound 1 (3 g, 0.02 mol) and compound 2 (3.4 g, 0.02 mol), and KOH (5.28 g, 0.1 mol) and TBBA (6.44 g, 0.02 mol) in anhydrous THF (100 mL) was added Pd $(PPh_3)_4$ (2.31 g, 2 mmol) under $N_2$ atmosphere and stirred under reflux for 12 h. After filtrating off the solid, the filtrate was concentrated to dryness. The residue was purified by column to give the product 3, which is used in next step without purification.

2. Reaction Scheme:

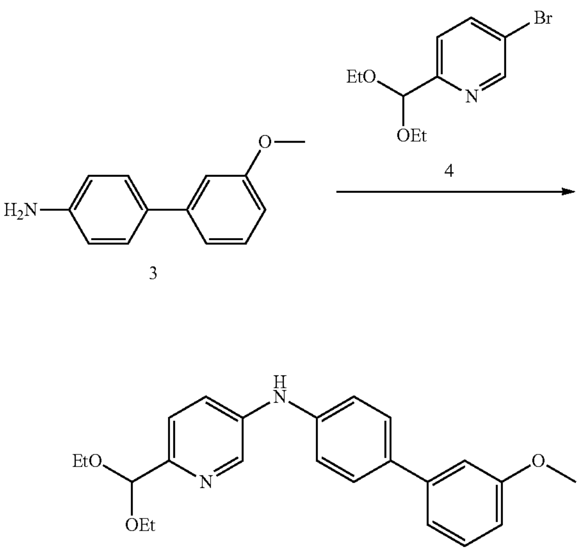

3

4

5

Experimental Details:

To a stirred and degassed mixture of compound 3 (334 mg, 1.7 mmol) and compound 4 (434 mg, 1.7 mmol), and t-BuONa (322 mg, 3.4 mmol) and BINAP (420 mg, 0.67 mol) in toluene (60 mL) was added $Pd_2(dba)_3$ (156 mg, 0.017 mmol) under $N_2$ atmosphere and stirred at 80° C. for 48 h. After filtrating off the solid, the filtrate was concentrated to dryness. The residue was purified by column to give the product 5.

3. Reaction Scheme:

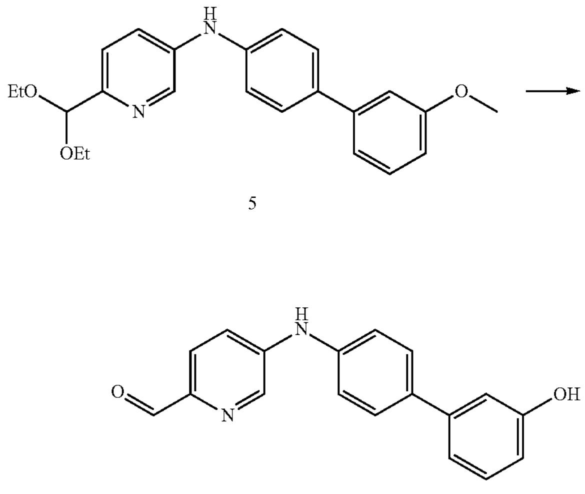

5

6

Experimental Details:

A solution of compound 5 (100 mg, 0.3 mmol) in dichloromethane (10 mL) was treated with $BBr_3$ (393 mg, 0.6 mmol) at −30° C. under $N_2$ atmosphere, then was stirred at room temperature for 4 h. The reaction was poured unto ice-water and then was brought by adding $Na_2CO_3$. The resulting mixture was extracted with dichloromethane (25 mL×3), the combined organic layer was dried over $Na_2SO_4$. After filtrating off the $Na_2SO_4$, the filtrate was concentrated to give the crude product 6.

4. Reaction Scheme:

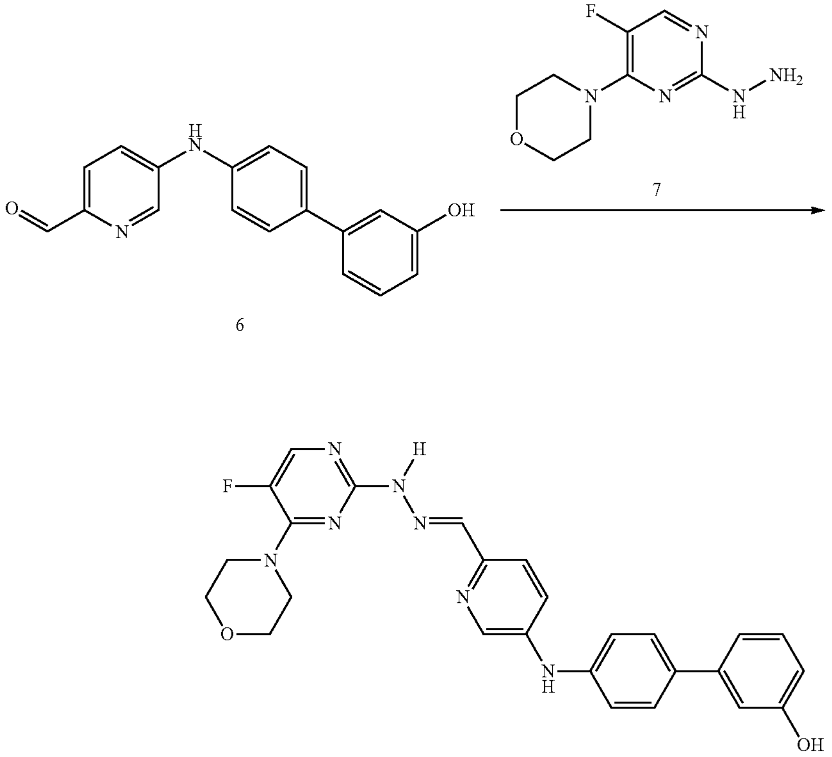 [SMILES: O=Cc1ccc(Nc2ccc(-c3cccc(O)c3)cc2)cn1 ; NNc1ncc(F)c(N2CCOCC2)n1 ; Oc1cccc(-c2ccc(Nc3ccc(/C=N/Nc4ncc(F)c(N5CCOCC5)n4)nc3)cc2)c1]

7

6

Experimental Details:

A mixture of 6 (39 mg, 0.13 mmol), nicotinaldehyde (29 mg, 0.13 m mol) in dichloromethane (10 mL) was heated to reflux for 3 hr. After removing off solvent, the residue was purified by chromatography to give the desired compound as a yellow solid.

Example 15

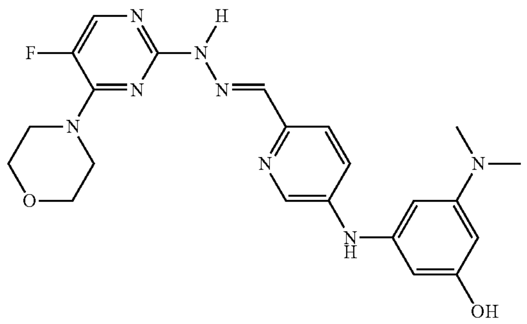 [SMILES: CN(C)c1cc(O)cc(Nc2ccc(/C=N/Nc3ncc(F)c(N4CCOCC4)n3)nc2)c1]

1. Reaction Scheme:

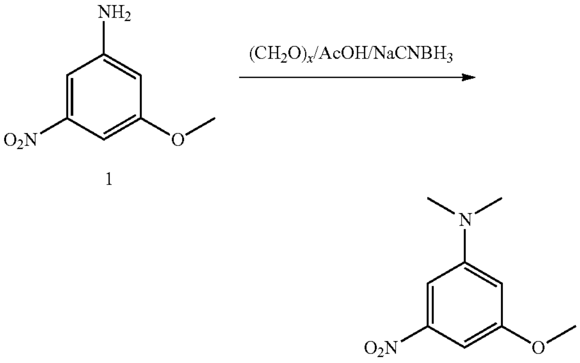

1

2

Experimental Details:

Paraformaldehyde (1.8 g, 59.3 mmol) was added to a solution of compound 1 (1.0 g, 5.9 mmol) in acetic acid (40 mL), followed by $NaCNBH_3$ (1.8 g, 28.8 mmol) at 10° C. After stirring of 16 h at room temperature, the solution was poured into ice/water (100 mL), and the PH adjusted to 10 with concentrated NaOH. The solution was extracted with DCM (3×100 mL). The combined organic layers were dried ($MgSO_4$), filtrated and concentrated in vacuo to give compound 2.

2. Reaction Scheme:

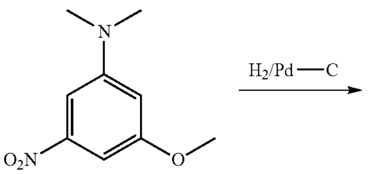

2

-continued

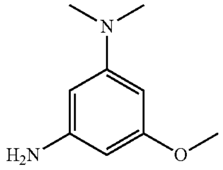

3

Experimental Details:

0.84 g (4.3 mmol) of compound 2 was hydrogenated under 1 atm hydrogen with Pd/C for 16 hour. The reaction mixture was filtered and the filtrate was concentrated to afford compound 3 without further purification.

3. Reaction Scheme:

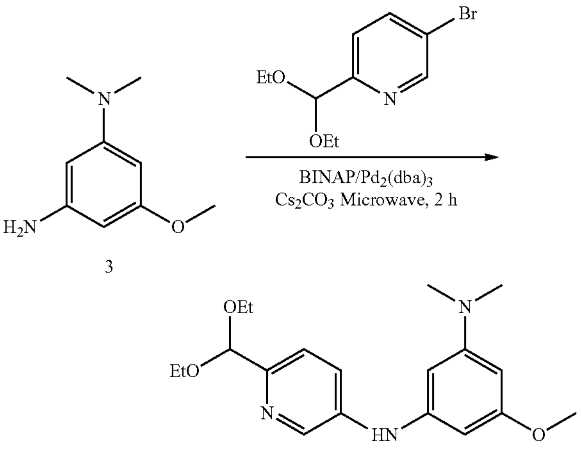

3

4

Experimental Details:

A solution of 250 mg (1.51 mmol) of compound 3, 0.2 eq of BINAP, 0.1 eq of $Pd_2(dba)_3$, 3 eq of $Cs_2CO_3$ and 5-Bromo-2-diethoxymethyl-pyridine (0.783 g, 3.01 mmol) in 10 mL of 1,4-dioxane was reacted at 150° C. under microwave for 2 hours. The reaction was monitored by LC-Ms. The mixture was concentrated and the residue was purified by preparative TLC to afford compound 4.

4. Reaction Scheme:

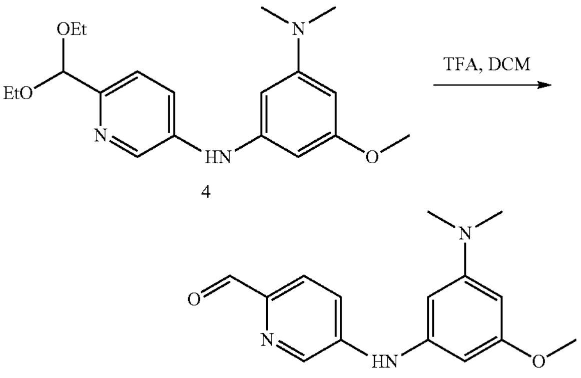

4

5

Experimental Details:

A solution of 300 mg (0.55 mmol) of compound 4 in 5 mL of DCM was added 4 mL of TFA. The reaction mixture was stirred for 30 min at r.t. The mixture was added ice/water and basified by $NaHCO_3$ to PH=10 and extracted with DCM (15 mL*3). The combined organic layer was washed with water and brine, dried over $MgSO_4$, filtered and concentrated to afford compound 5.

5. Reaction Scheme:

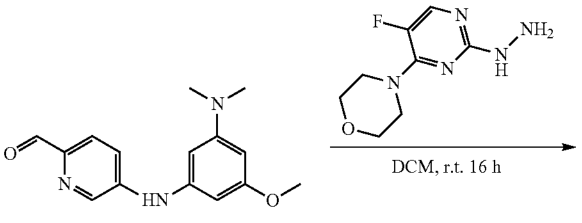

5

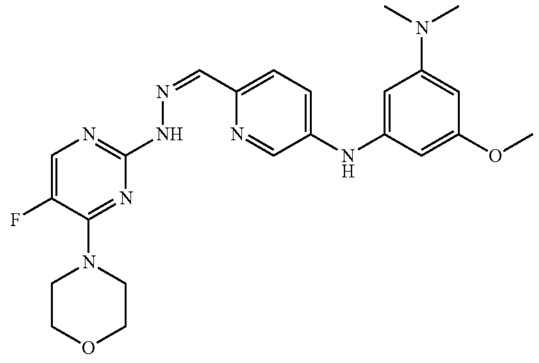

6

Experimental Details:

A solution of 80 mg (0.295 mmol) of compound 5 and (5-Fluoro-4-morpholin-4-yl-pyrimidin-2-yl)-hydrazine (125 mg, 0.59 mmol) in 10 mL of DCM was stirred at 25° C. for 15 hours. The reaction mixture was concentrated and the residue was purified by preparative HPLC to afford compound 6.

6. Reaction Scheme:

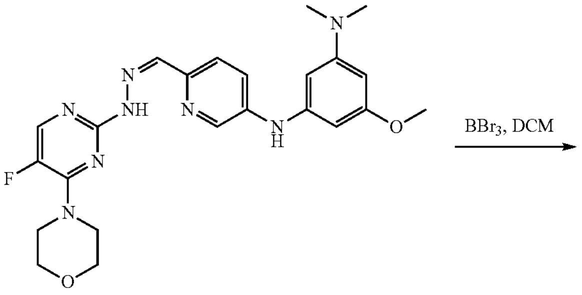

6

-continued

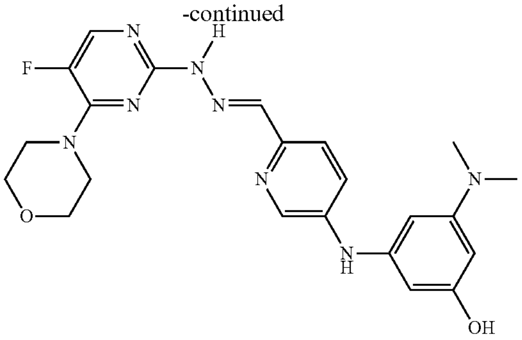

Experimental Details:

To a solution of compound 6 (40 mg, 0.086 mmol) in dry DCM (5 mL) was added drop wise BBr (22 mg, 0.258 mmol) at 0° C. The reaction mixture was stirred for 3 h at r.t. The reaction was quenched with methanol, and the mixture was concentrated. The residue was purified by preparative HPLC to give the desired compound.

Example 16

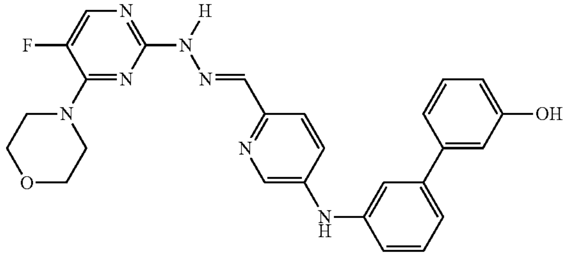 [SMILES: Oc1cccc(-c2cccc(Nc3ccc(/C=N/Nc4ncc(F)c(N5CCOCC5)n4)nc3)c2)c1]

1. Reaction Scheme:

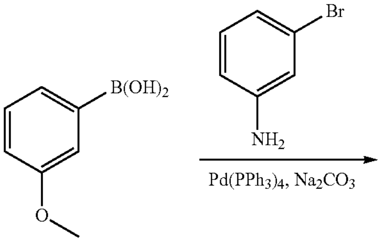

1

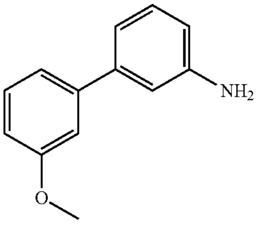

2

Experimental Details:

To a stirred solution of 3-Bromoaniline (0.86 g) in 30 ml of toluene were added 0.1 eq of $Pd(PPh_3)_4$, 5 ml of sat. aq. of $Na_2CO_3$ and a solution of 3-methoxyphenyl boronic acid (0.75 g) in 10 ml of EtOH under $N_2$ atmosphere. The mixture was vigorously stirred under reflux for 15 h and cooled, 10 ml of $H_2O$ was added, and the mixture was extracted with $CH_2Cl_2$ (20 ml×3). The combined organic layers were dried over $Na_2SO_4$ and concentrated. The residue was purified by column chromatography (PE/EA=10:1) to get pure compound 2.

2. Reaction Scheme:

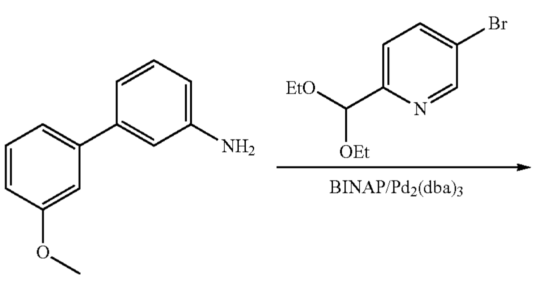

2

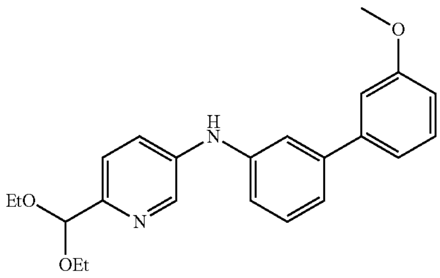

3

Reaction Details:

A mixture of compound 2 (59.5 mg), 5-bromo-2-diethoxymethyl-pyridine (116.7 mg), t-BuONa (86.4 mg), BINAP (36.7 mg) and $Pd_2(dba)_3$ (27.4 mg) in dioxane (2 ml) was microwaved for 2 hs at 150° C., the solution was filtered and concentrated. The residue was purified by preparative TLC to afford compound 3.

3. Reaction Scheme:

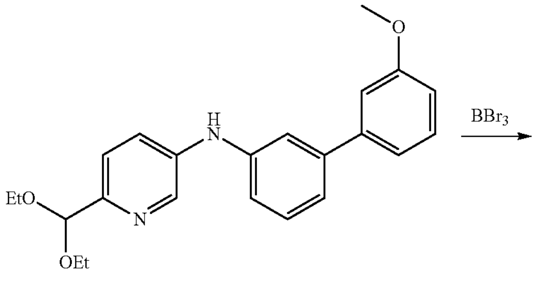

3

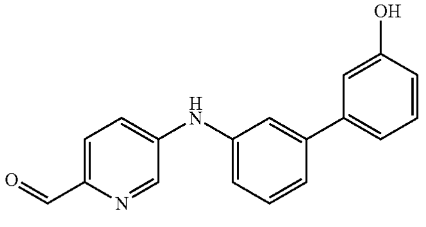

4

Reaction Details:

To a solution of compound 3 (120 mg) in 5 ml of DCM was added 1 ml of $BBr_3$, the reaction was stirred overnight at r.t. Then added 5 ml of $H_2O$ to the mixture, extracted with EtOAc and concentrated. The crude product was purified by pre. TLC to afford compound 4.

4. Reaction Scheme:

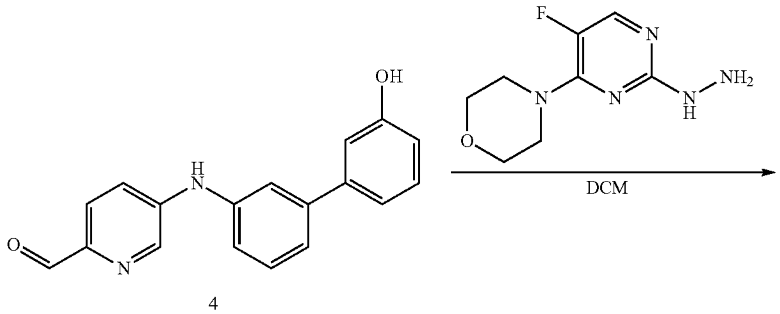

4

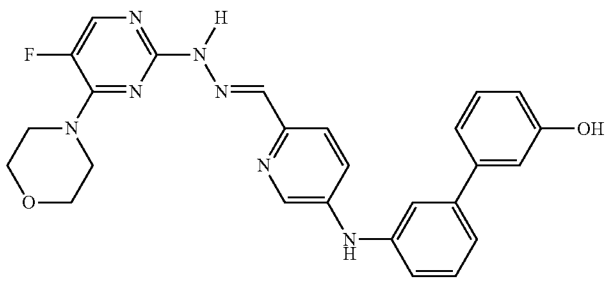

Experimental Details:

A mixture of 43.5 mg of compound 4 and 32 mg of hydrazine in 5 ml DCM was stirred overnight at r.t. and concentrated. The crude product was purified by preparative TLC to afford the desired compound.

Example 17

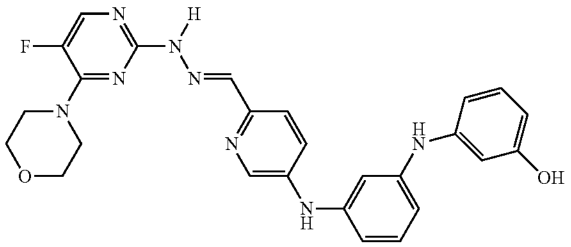 [SMILES: Oc1cccc(Nc2cccc(Nc3ccc(/C=N/Nc4ncc(F)c(N5CCOCC5)n4)nc3)c2)c1]

1. Reaction Scheme:

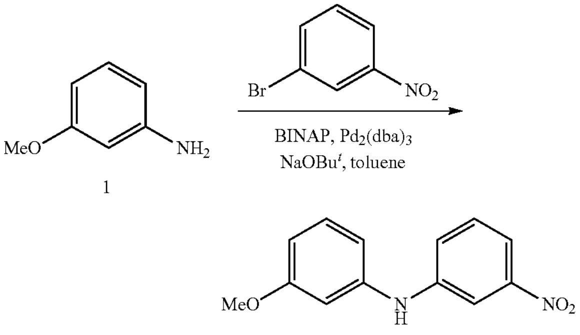

1 2

Experimental Details:

A solution of 2.0 g (16.2 mmol, 1.0 eq) of compound 1, 0.05 eq of BINAP, 0.05 eq of $Pd_2(dba)_3$, 1.2 eq of t-BuONa and 1-Bromo-3-nitro-benzene (3.28 g, 16.2 mmol, 1.0 eq) in 20 mL of anhydrous toluene was reacted at 100° C. for 24 hours. The reaction was monitored by LC-MS. The mixture was concentrated and the residue was purified by column chromatography to afford compound 2.

2. Reaction Scheme:

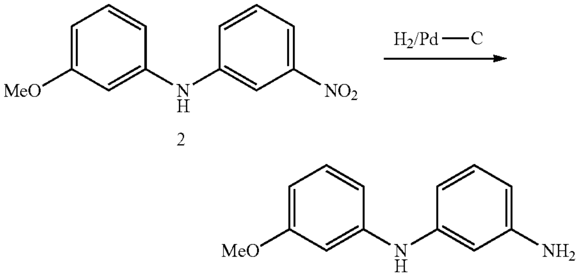

2 3

Experimental Details:

2.5 g of compound 2 was hydrogenated under 1 atm of hydrogen with Pd/C (0.25 g) for 16 hour. The reaction mixture was filtered and the filtrate was concentrated to afford compound 3 without further purification.

3. Reaction Scheme:

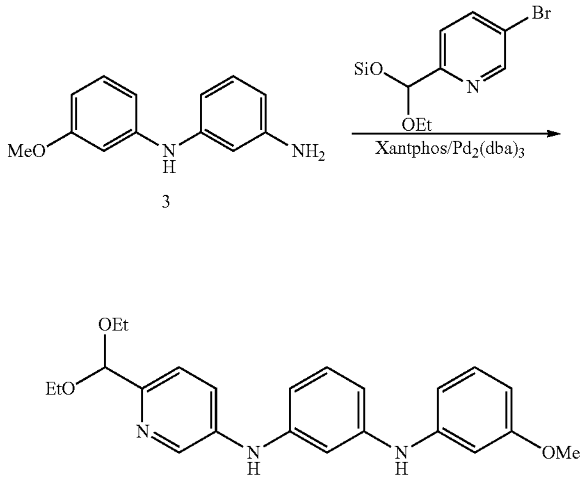

3 4

Experimental Details:

A solution of 500 mg (2.33 mmol) of compound 3, 5-Bromo-2-diethoxymethylpyridine (607 mg, 2.33 mmol), 0.05 eq of xantphos, 0.05 eq of $Pd_2(dba)_3$ and 1.5 eq of t-BuONa in 10 mL of toluene was refluxed at 100° C. for 24 hours. The reaction was monitored by LC-MS. The mixture was concentrated and the residue was purified by column chromatography to afford compound 4.

4. Reaction Scheme:

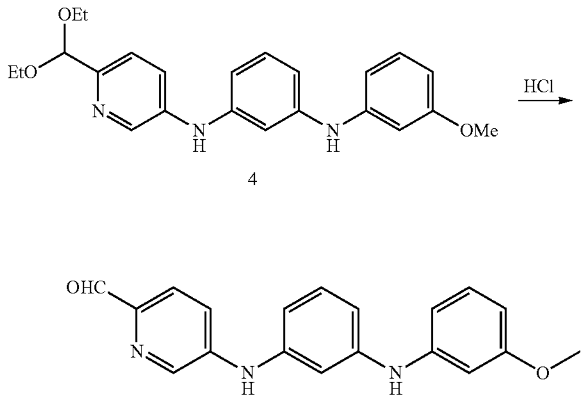

4 5

Experimental Details:

100 mg of compound 4 was treated with 1 mL of HCl (1N aqueous solution) and 10 mL of dioxane. The mixture was stirred at rt for 4 h, adjusted to pH 8-9 with 0.5 N NaOH solution. After extracted with DCM, dried organic layer with $Na_2SO_4$ and concentrated to give compound 5.

5. Reaction Scheme:

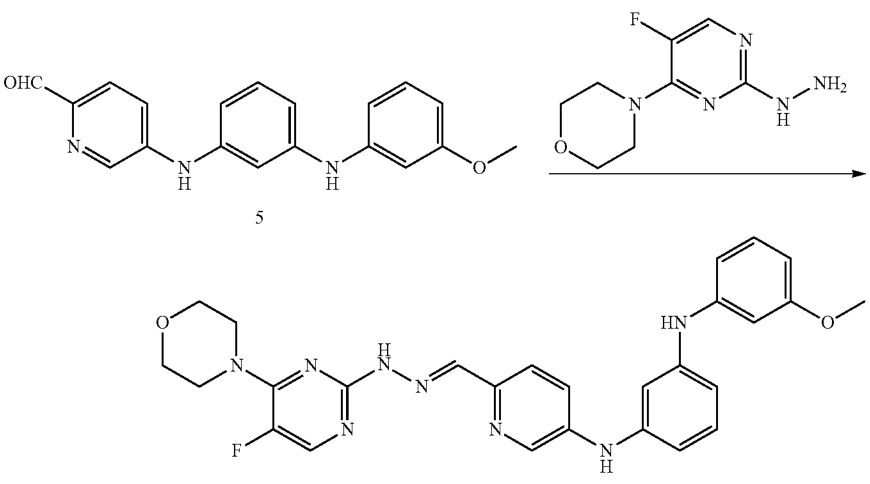

5

6

Experimental Details:

A solution of 50 mg (0.16 mmol) of compound 5 and (5-Fluoro-4-morpholin-4-ylpyrimidin-2-yl)-hydrazine (50 mg, 0.23 mmol) in 5 mL of DCM was stirred at 25° C. for 15 hours. The reaction mixture was concentrated and the residue was purified by preparative HPLC to afford compound 6.

6. Reaction Scheme:

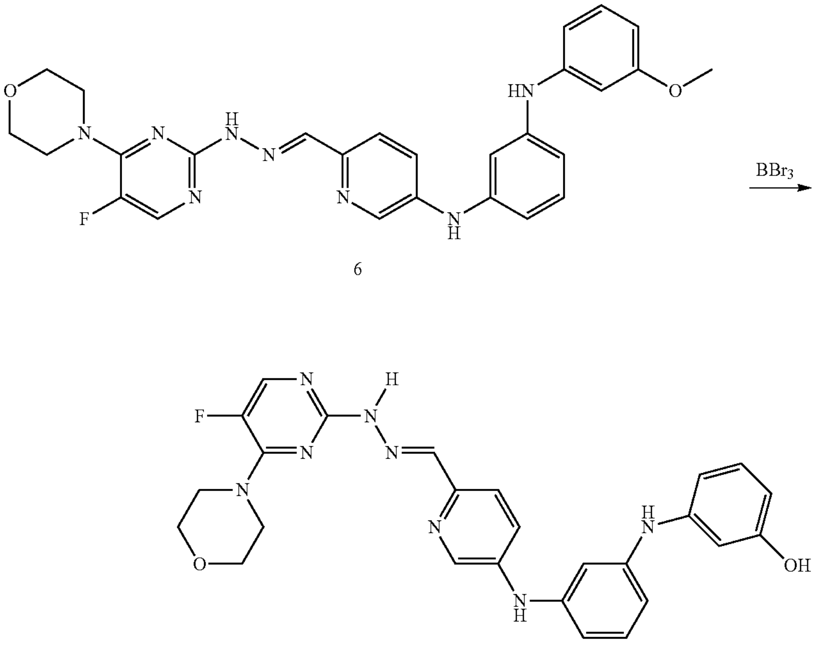

6

Experimental Details:

To a solution of compound 6 (50 mg, 0.09 mmol) in dry DCM (5 mL) was added dropwise $BBr_3$ (20 mg, 0.25 mmol) at 0° C. The reaction mixture was stirred for 3 hr at r.t. The reaction was quenched with methanol, and the mixture was concentrated. The residue was purified by preparative HPLC to give the desired compound.

Example 18

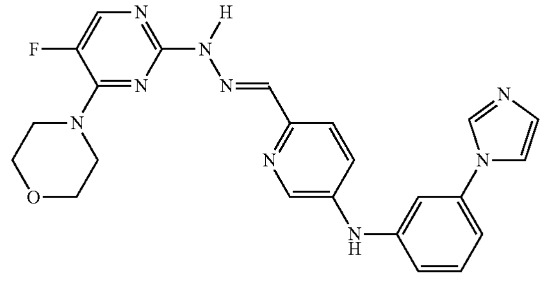 [SMILES: Fc1cnc(N/N=C/c2ccc(Nc3cccc(-n4ccnc4)c3)cn2)nc1N1CCOCC1]

1. Reaction Scheme:

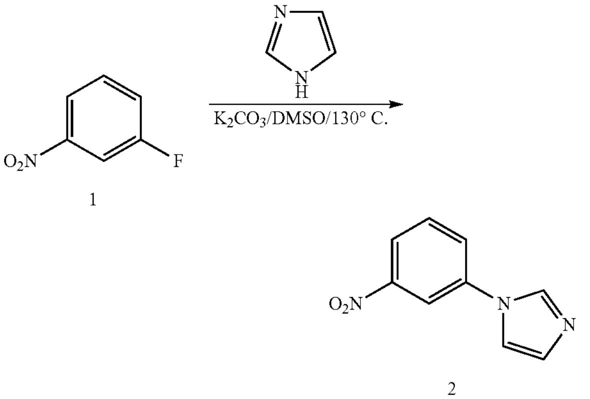

1

2

Experimental Details:

A solution of 10 g (70.92 mmol) of 3-fluoro-nitrobenzene, 1 eq imidazole and 2 eq $K_2CO_3$ in 100 ml of DMSO was heated at 130° C. for 5 hours. The reaction was monitored by LC-MS. Then 500 mL of water was added and the precipitate was filtered and the solid was washed with water and dried to afford compound 2 without further purification.

2. Reaction Scheme:

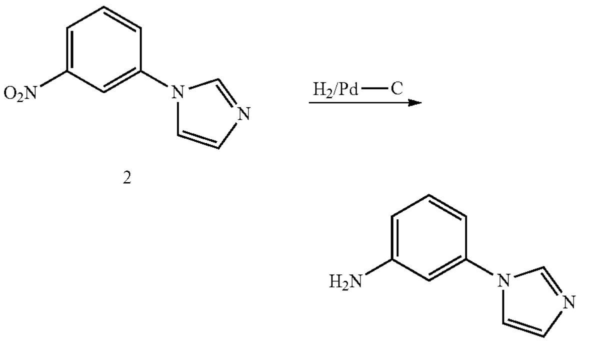

2

3

Experimental Details:

5 g (31.4 mmol) of compound 2 was hydrogenated under 1 atm hydrogen with Pd/C for 0.5 hour. The reaction mixture was filtered and the filtrate was concentrated to afford compound 3 without further purification.

3. Reaction Scheme:

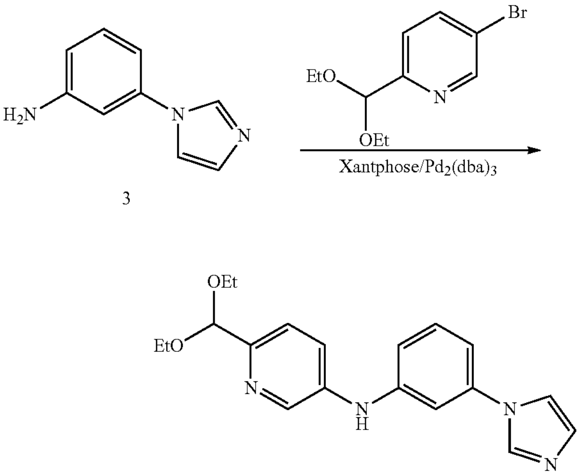

3

4

Experimental Details:

A solution of 500 mg (3.14 mmol) of compound 3, 0.1 eq of xantphose, 0.1 eq of $Pd_2(dba)_3$ and 1.5 eq of t-BuONa in 10 mL of toluene was refluxed at 130° C. for 15 hours. The reaction was monitored by LC-Ms and washed with water and extracted with EtOAc. The combined organic layer was washed with brine and dried over $MgSO_4$. Filtered and concentrated, residue was purified by preparative TLC to afford compound 4.

4. Reaction Scheme:

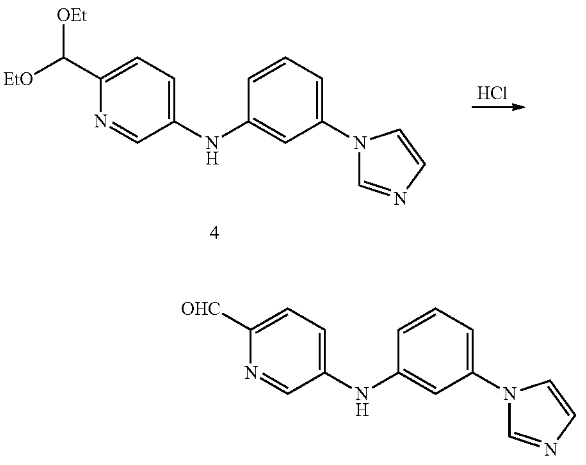

4

5

Experimental Details:

A solution of 200 mg of compound 4 in 5 mL of 1,4-dioxane was added 8 mL of 4N HCl and heated at 80° C. for 2 hours. The reaction mixture was basified by 2N NaOH to ph=10 and extracted with DCM (15 mL*3). The combined organic layer was washed with water and brine, dried over $MgSO_4$, filtered and concentrated to afford 250 mg of crude product. The crude product was purified by preparative TLC to afford compound 5.

5. Reaction Scheme:

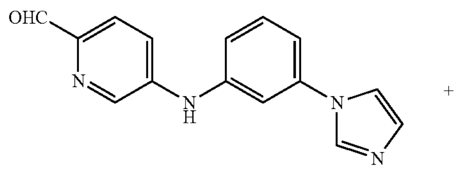

5

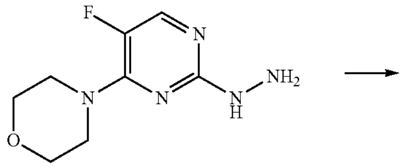

6

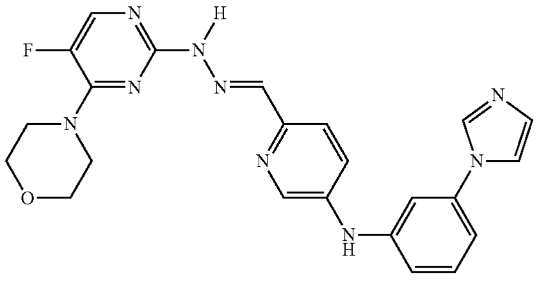

Experimental Details:

A solution of 80 mg of compound 5 and 1 eq of compound 6 in 5 mL of DCM was stirred at 25° C. for 15 hours. The reaction mixture was concentrated and the residue was purified by preparative HPLC to afford the desired compound.

Example 19

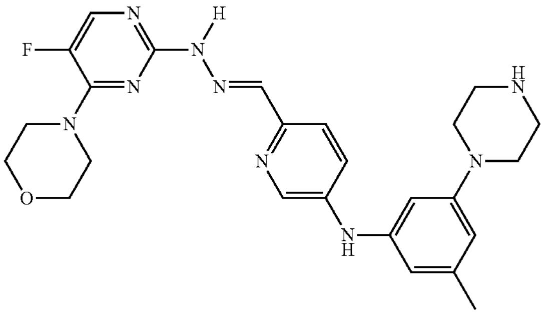 [SMILES: Cc1cc(Nc2ccc(/C=N/Nc3ncc(F)c(N4CCOCC4)n3)nc2)cc(N2CCNCC2)c1]

1. Reaction Scheme:

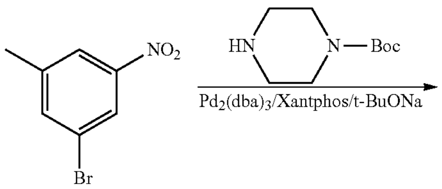

-continued

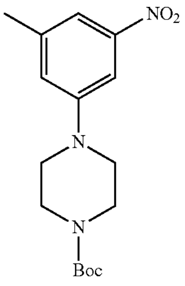

1

Experimental Details:

A solution of 1.50 g of 1-Bromo-3-methyl-5-nitro-benzene and 1.60 g (1.2 eq) of Piperazine-1-carboxylic acid tert-butyl ester, 0.1 eq of xantphos, 0.1 eq of $Pd_2(dba)_3$ and 1.5 eq of t-BuONa in 20 mL of toluene was refluxed at 130° C. for 4 hours. The reaction was monitored by LC-Ms and washed with water and extracted with EtOAc. The combined organic layer was washed with brine and dried over $Na_2SO_4$. Filtered and concentrated, residue was purified with column chromatography on silica gel using 10:1 PA:EA as an eluant. The appropriate fractions were combined and concentrated under reduced pressure, to give intermediate 1.

2. Reaction Scheme:

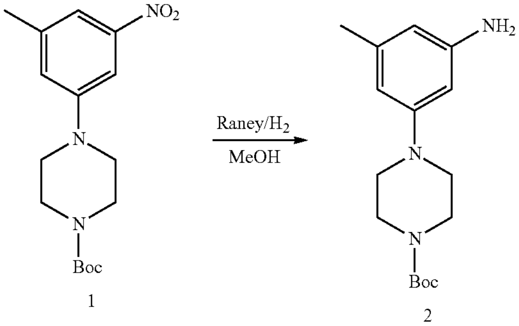 [SMILES: "MeOH" ; Cc1cc(N2CCN(C(=O)OC(C)(C)C)CC2)cc([N+](=O)[O-])c1 ; Cc1cc(N)cc(N2CCN(C(=O)OC(C)(C)C)CC2)c1]

1 2

Experimental Details:

1.6 g of intermediate of 1 was hydrogenated under 1 atm hydrogen with Raney/Ni for 2 hours. The reaction mixture was filtered and the filtrate was concentrated to afford intermediate 2 without further purification.

3. Reaction Scheme:

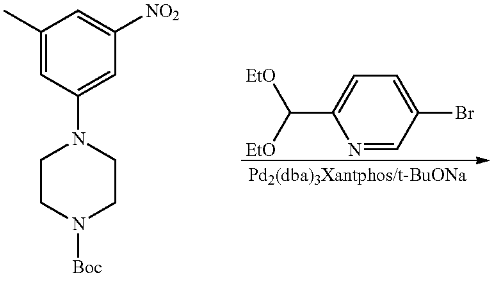

2

-continued

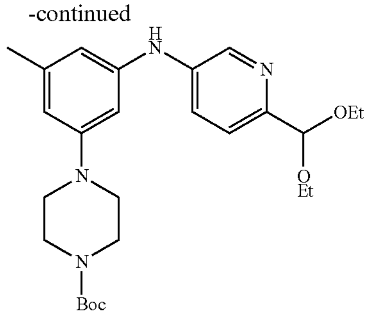

3

Experimental Details:

A solution of 1.20 g of Intermediate of 2, and 1.30 g (1.20 eq) of 5-Bromo-2-diethoxymethyl-pyridine, 0.1 eq of xantphose, 0.1 eq of $Pd_2(dba)_3$ and 1.5 eq of t-BuONa in 20 mL of toluene was refluxed at 130° C. for 4 hours. The reaction was monitored by LC-MS and washed with water and extracted with EtOAc. The combined organic layer was washed with brine and dried over $Na_2SO_4$. Filtered and concentrated, residue was purified with column chromatography on silica gel using 4:1 PA:EA as an eluant. The appropriate fractions were combined and concentrated under reduced pressure to give intermediate 3.

4. Reaction Scheme:

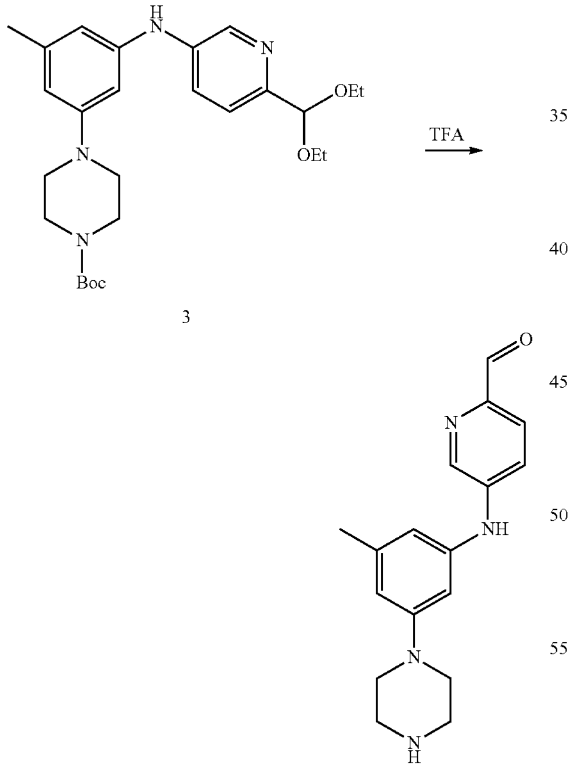

3

4

Experimental Details:

200 mg of intermediate 3 was dissolved in 10 ml of DCM. 130 mg of TFA was added to the reaction mixture solution dropwise and stirred for 3 h at r.t. The reaction mixture was based with $NaHCO_3$ solution to neutral and brine, dried over $Na_2SO_4$, filtered and concentrated to afford 220 mg of crude product. The crude product was purified by preparative TLC to afford intermediate 4.

5. Reaction Scheme:

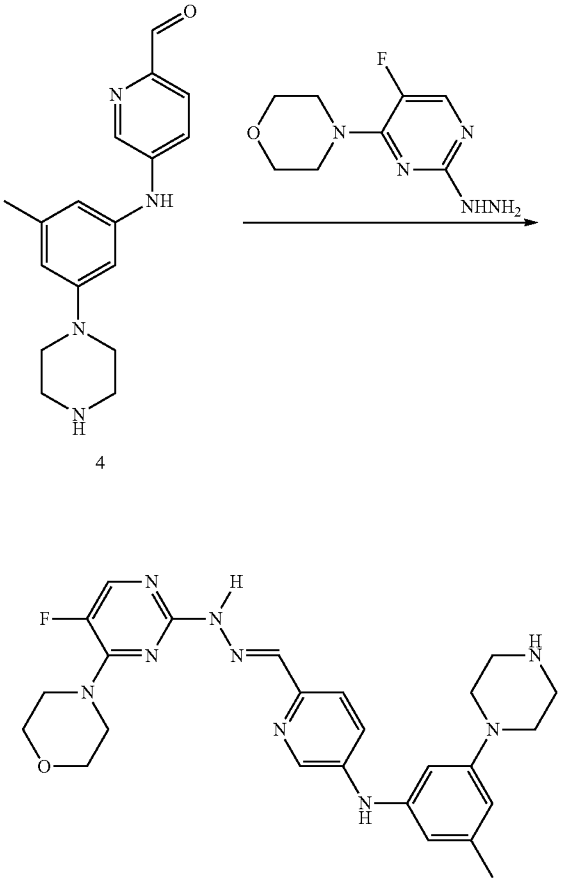

4

Experimental Details:

A solution of 50 mg of intermediate 4 and 1.0 eq of (5-Fluoro-4-morpholin-4-ylpyrimidin-2-yl)-hydrazine in 5 mL of DCM was stirred at r.t. for 3 hours. The reaction mixture was washed with water and brine, concentrated it to give the residue and purified by preparative HPLC to afford the desired compound.

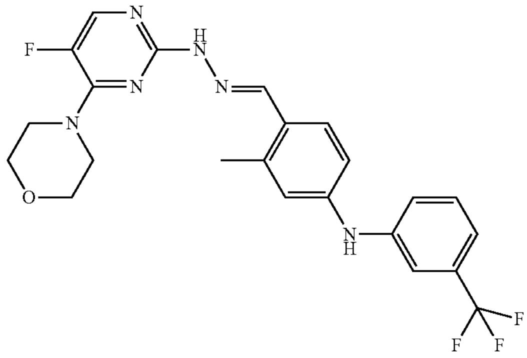 [SMILES: Cc1cc(Nc2cccc(C(F)(F)F)c2)ccc1/C=N/Nc1ncc(F)c(N2CCOCC2)n1]

Example 20

1. Reaction Scheme:

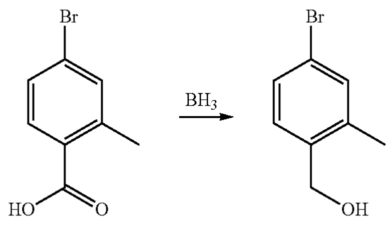

1 2

Experimental Details:

15 ml of 1M $BH_3$/THF was added dropwise into a solution of 3 g (13.95 mmol) of 4-bromo-2-methyl-benzoic acid in 20 ml of THF at 0° C. The reaction solution was allowed to reach room temperature for 1 hour and quenched by the dropwise addition of 50 ml of 50% aqueous THF. The mixture was treated with $Na_2CO_3$ and concentrated. The residue was extracted with $Et_2O$. The organic layer was dried to give compound 2.

2. Reaction Scheme:

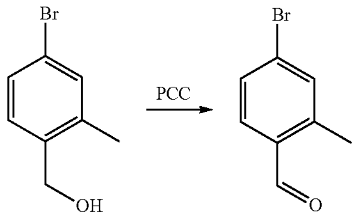

2 3

Experimental Details:

A solution of 2.4 g (11.9 mmol) of compound 2 in 20 ml of DCM was added a slurry of 5.1 g (23.8 mmol) of PCC in 60 ml of DCM. The reaction solution was stirred for 1 hour at r.t. diluted with 300 ml of $Et_2O$ and filtered. The filtrate was concentrated to give compound 3.

3. Reaction Scheme:

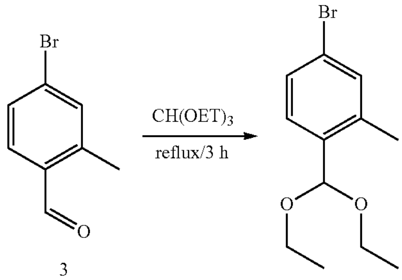

3

4

Experimental Details:

A solution of 2.1 g (14 mmol) was added into a solution of ethanol which containing 1.9 g (9.55 mmol) of compound 3. The reaction solution was heated to reflux for 3 hours, and then concentrated. The solid was washed with $NaHCO_3$ and extracted with acetic ether. The organic layer was dried to give compound 4.

4. Reaction Scheme:

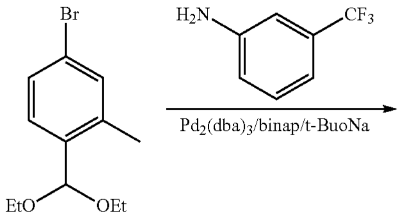

4

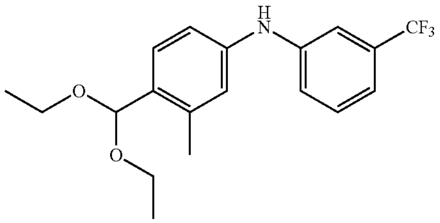

5

Experimental Details:

0.7 g of compound 4, 0.41 g of 3-trifluromethyl-phenylamine 0.32 g of $Pd_2(dba)_3$, 0.21 g of binap and 0.02 g of t-BuONa were added into 35 ml of toluene. The reaction solution was heated to reflux overnight, and concentrated. The crude product was purified by column chromatography (ethyl acetate/hexane=1:1) to give compound 5.

5. Reaction Scheme:

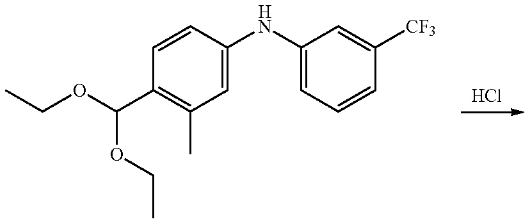

5

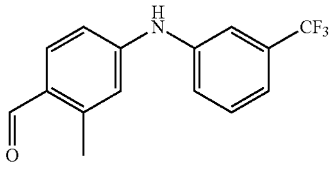

6

Experimental Details:

The solution of compound 5 (0.2 g, 1.0 eq) in 10 mL of dioxane was treated with 4 mL of 1 N HCl, and the mixture was heated to 60° C. for 2 h. After cooling, the pH was adjusted to 8 by addition of $NaHCO_3$. The mixture was extracted with dichloromethane, washed the organic layer with water, dried with $Na_2SO_4$ and evaporated to dryness. The crude product was purified by column chromatography to give compound 6.

6. Reaction Scheme:

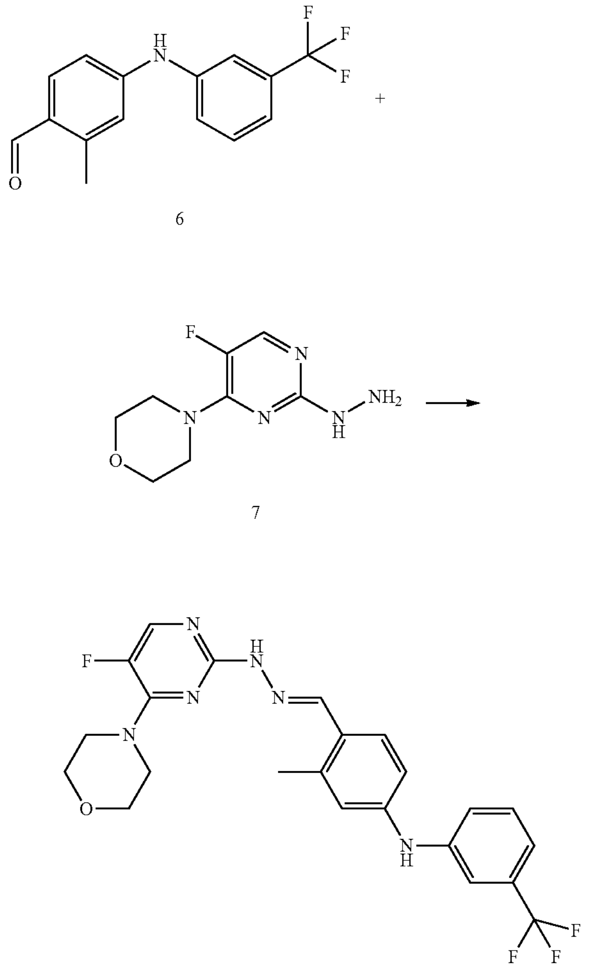

6, 7

Experimental Details:

A solution of 80 mg of compound 6 and 1 eq of compound 7 in 5 mL of DCM was stirred at 25° C. for 15 hours. The reaction mixture was concentrated and the residue was purified by preparative HPLC to afford the desired compound.

Example 21

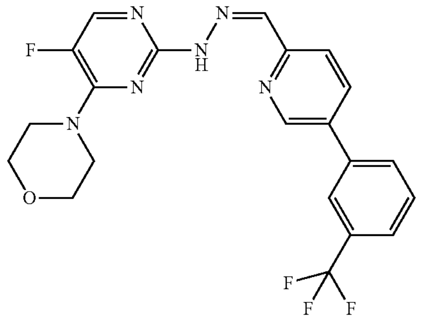

1. Reaction Scheme:

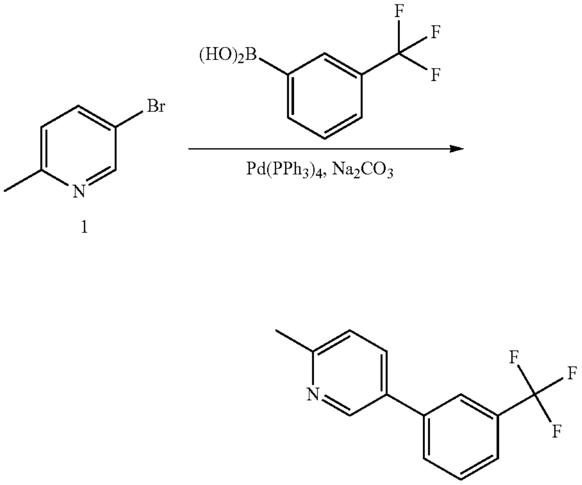

1, 2

Experimental Details:

To the mixture of compound 1 (0.5 g, 1.0 eq), 3-trifluoromethyl phenyl boronic acid (0.63 g, 1.0 eq), $Na_2CO_3$ (0.46 g, 1.5 eq) in 15 mL of dioxane was added $Pd(PPh_3)_4$ (0.33 g, 0.1 eq), and the reaction mixture was refluxed under $N_2$ for 16 h. After cooling, the mixture was filtered and the filtrate was evaporated to dryness and purified by column chromatography to give compound 2.

2. Reaction Scheme:

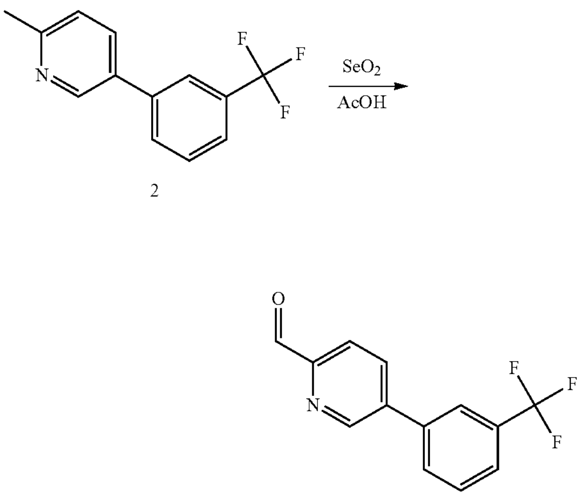

2, 3

Experimental Details:

A mixture of compound 2 (0.2 g, 1.0 eq), $SeO_2$ (0.19 g, 2.0 eq) in 10 mL of acetic acid was refluxed under $N_2$ for 48 h. Solvent was removed by evaporation and the residue was dissolved in water and adjusted to pH 6 with saturated $NaHCO_3$ solution, extracted with dichloromethane. The organic layers were collected, dried and evaporated to dryness. The crude product was purified by column chromatography give compound 3.

3. Reaction Scheme:

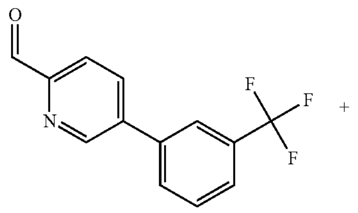

3

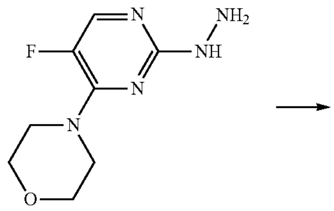

4

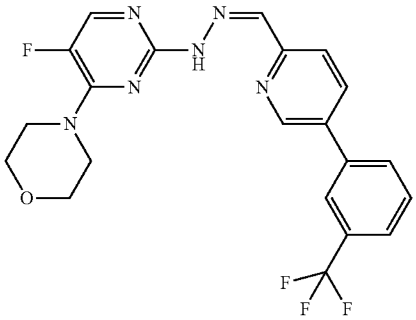 [SMILES: Fc1cnc(N/N=C\c2ccc(-c3cccc(C(F)(F)F)c3)cn2)nc1N1CCOCC1]

Experimental Details:

The mixture of compound 3 (30 mg, 1.0 eq) and compound 4 (19 mg, 1.0 eq) in 5 mL of dichloromethane was stirred at r.t. overnight. The mixture was concentrated to dryness and purified by preparative HPLC to give the desired compound.

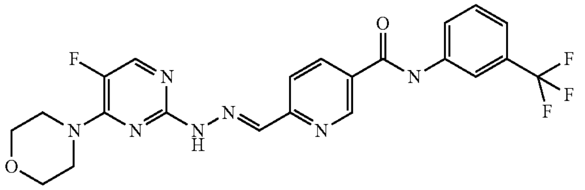

Example 22

1. Reaction Scheme:

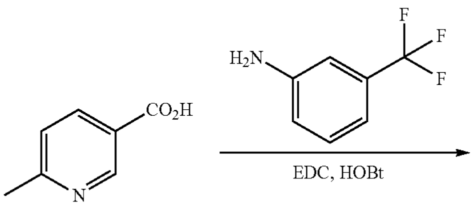

1

-continued

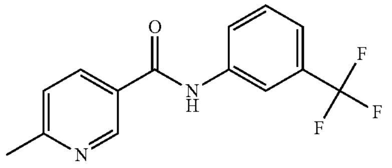

2

Experimental Details:

The mixture of compound 1 (0.5 g, 1.0 eq), trifluoromethyl phenylamine (0.58 g, 1.0 eq), EDC (1.05 g, 1.5 eq), HOBt (50 mg, 0.1 eq) in 15 mL of dichloromethane was stirred at r.t. overnight. The mixture was washed with 1 N NaOH solution, water, extracted with dichloromethane. The organic layer was dried over $Na_2SO_4$, concentrated to dryness, purified by column chromatography to give compound 2.

2. Reaction Scheme:

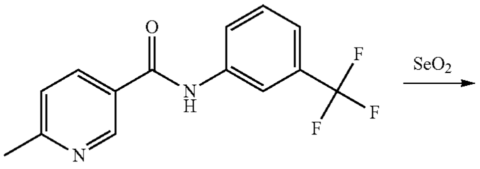

2

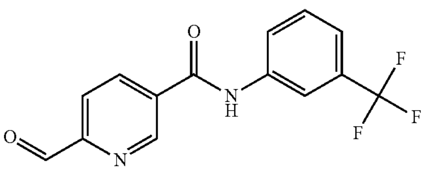

3

Experimental Details:

A mixture of compound 2 (0.2 g, 1.0 eq), $SeO_2$ (0.16 g, 2.0 eq) in 10 mL of acetic acid was refluxed under $N_2$ for 48 h. Solvent was removed by evaporation and the residue was dissolved in water and adjusted to pH 6 with saturated $NaHCO_3$ solution, extracted with dichloromethane. The organic layers were collected, dried and evaporated to dryness. The crude product was purified by column chromatography to give compound 3.

3. Reaction Scheme:

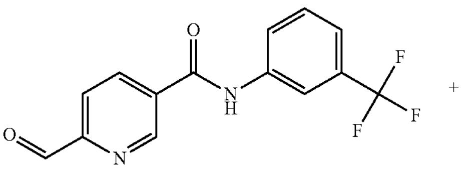

3

-continued

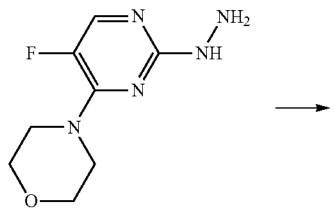

4

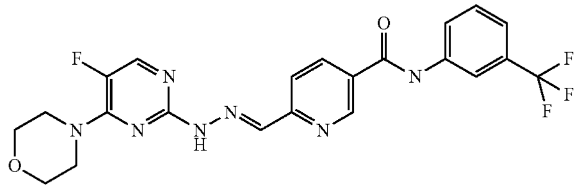 [SMILES: O=C(Nc1cccc(C(F)(F)F)c1)c1ccc(/C=N/Nc2ncc(F)c(N3CCOCC3)n2)nc1]

Experimental Details:

The mixture of compound 3 (40 mg, 1.0 eq) and compound 4 (30 mg, 1.0 eq) in 5 mL of dichloromethane was stirred at r.t. overnight. The precipitates were collected and washed with dichloromethane, dried under vacuum to give the desired compound.

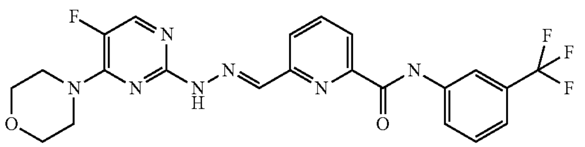 [SMILES: O=C(Nc1cccc(C(F)(F)F)c1)c1cccc(/C=N/Nc2ncc(F)c(N3CCOCC3)n2)n1]

Example 23

1. Reaction Scheme:

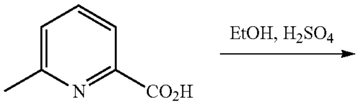

1

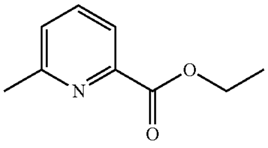

2

Experimental Details:

The solution of compound 1 (3.0 g, 1.0 eq) and 2 mL 98% $H_2SO_4$ in 10 mL of EtOH was refluxed for 4 h, cooled to r.t., evaporated to dryness, diluted with water, adjusted to pH 8 with $NaHCO_3$, extracted with dichloromethane. The organic layer was dried and concentrated to give compound 2.

2. Reaction Scheme:

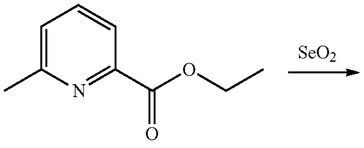

2

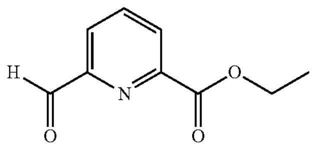

3

Experimental Details:

A mixture of compound 2 (1.7 g, 1.0 eq), $SeO_2$ (2.29 g, 2.0 eq) in 80 mL of acetic acid was refluxed under $N_2$ for 48 h. Solvent was removed by evaporation and the residue was dissolved in water and, adjusted to pH 6 with saturated $NaHCO_3$ solution, extracted with dichloromethane. The organic layers were collected, dried and evaporated to dryness. The crude product was purified by column chromatography to give compound 3.

3. Reaction Scheme:

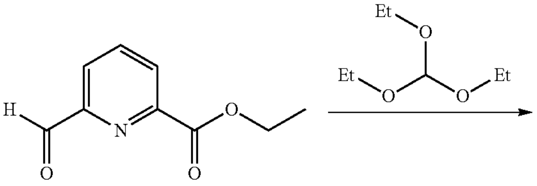

3

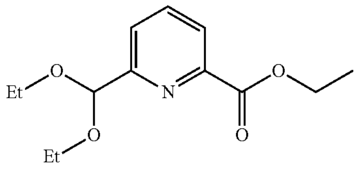

4

Experimental Details:

The solution of compound 3 (1.1 g, 1.0 eq), diethoxymethoxy-ethane (2.3 g, 2.5 eq) and $TsOH.H_2O$ (0.12 g, 0.1 eq) in 20 mL of ethanol was refluxed for 5 h. The solvent was evaporated and the solid was dissolved in EtOAc, washed with water. The organic layer was dried over $Na_2SO_4$ and evaporated to give compound 4.

4. Reaction Scheme:

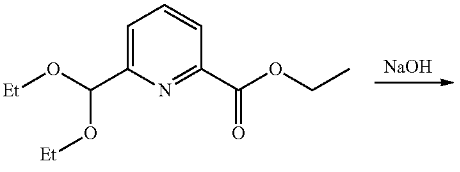

4

-continued

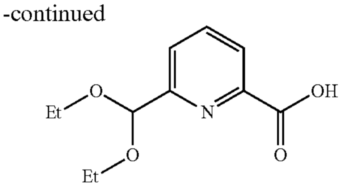

5

Experimental Details:

To the solution of compound 4 (0.6 g, 1.0 eq) in 10 mL of methanol was added 4 mL of 1 N NaOH solution, and the mixture was stirred at r.t. overnight. Solvent was evaporated and the residue was acidified to pH 6 with 5% citric acid, extracted with dichloromethane. The organic layer was dried, concentrated to give compound 5.

5. Reaction Scheme:

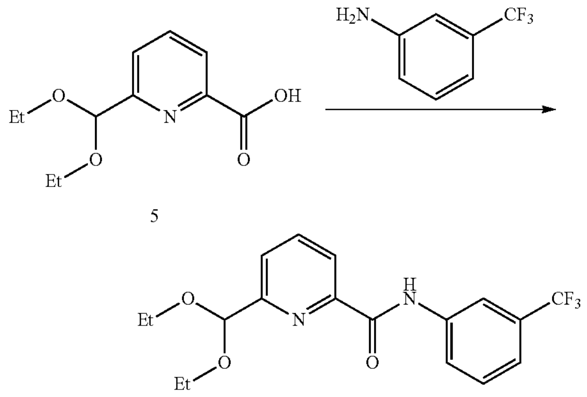

5

6

Experimental Details:

The mixture of compound 5 (0.4 g, 1.0 eq), trifluoromethyl phenylamine (0.29 g, 1.0 eq), EDC (0.51 g, 1.5 eq), HOBt (25 mg, 0.1 eq) in 10 mL of dichloromethane was stirred at r.t. overnight. The mixture was washed with 1 N NaOH solution, water, extracted with dichloromethane. The organic layer was dried over $Na_2SO_4$, concentrated to dryness, purified by column chromatography to give compound 6.

6. Reaction Scheme:

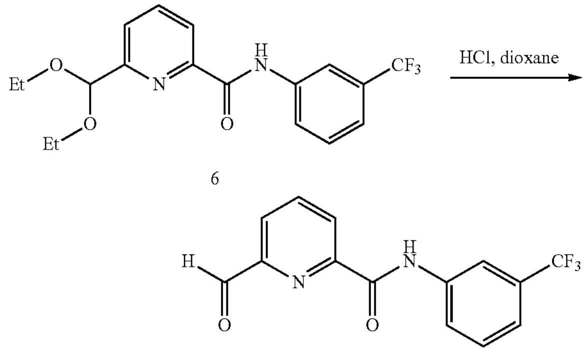

6

7

Experimental Details:

The solution of compound 6 (0.2 g, 1.0 eq) in 10 mL of dioxane was treated with 4 mL of 1 N HCl, and the mixture was heated to 60° C. for 2 After cooling, pH was adjusted to 8 by addition of $NaHCO_3$. The mixture was extracted With dichloromethane, washed the organic layer with water, dried with $Na_2SO_4$ and evaporated to dryness. The crude product was purified by column chromatography to give compound 7.

7. Reaction Scheme:

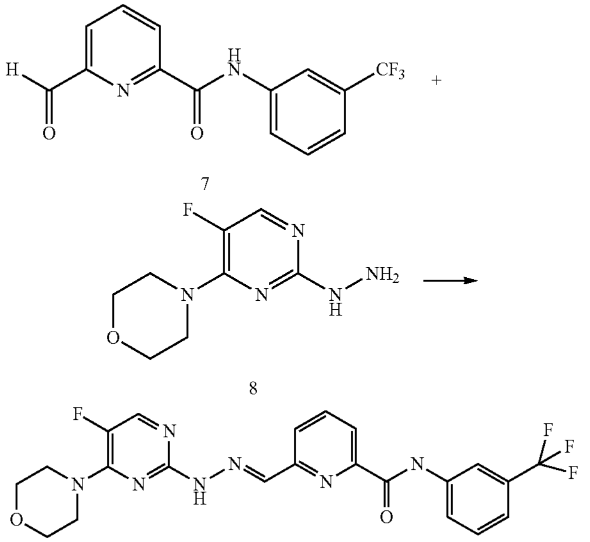

7

8

Experimental Details:

The mixture of compound 7 (30 mg, 1.0 eq) and compound 8 (19 mg, 1.0 eq) in 5 mL of dichloromethane was stirred at r.t. overnight. The precipitates were collected and washed with dichloromethane, dried under vacuum to give the desired compound.

Example 24

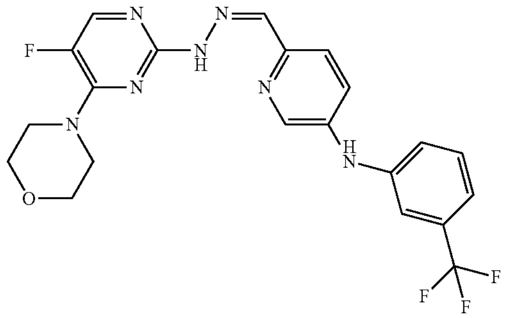 [SMILES: Fc1cnc(N/N=C\c2ccc(Nc3cccc(C(F)(F)F)c3)cn2)nc1N1CCOCC1]

1. Reaction Scheme:

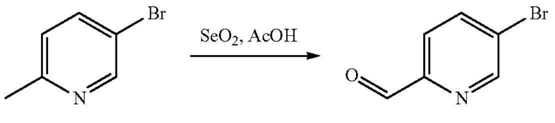

1

2

Experimental Details:

A mixture of compound 1 (2.0 g, 1.0 eq), $SeO_2$ (2.6 g, 2.0 eq) in 80 mL of acetic acid was refluxed under $N_2$ for 36 h. Solvent was removed by evaporation and the residue was dissolved in water and adjusted to pH 6 with saturated $NaHCO_3$ solution, extracted with dichloromethane. The organic layers were collected, dried and evaporated to dryness. The crude product was purified by column chromatography to give compound 2.

2. Reaction Scheme:

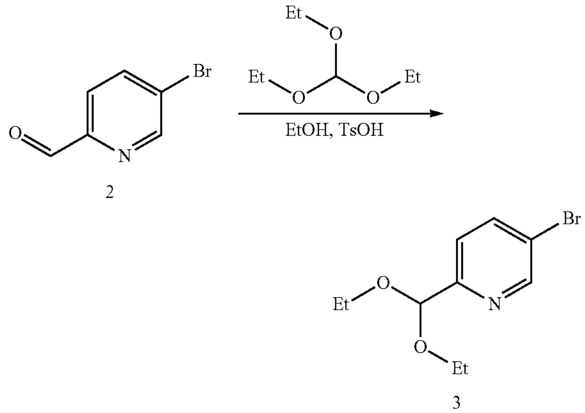

2

3

Experimental Details:

The solution of compound 2 (0.5 g, 1.0 eq), diethoxymethoxy-ethane (1.0 g, 2.5 eq) and $TsOH.H_2O$ (0.05 g, 0.1 eq) in 8 mL of ethanol was refluxed for 3 h. The solvent was evaporated and the solid was dissolved in EtOAc, washed with water. The organic layer was dried over $Na_2SO_4$ and evaporated to give compound 3.

3. Reaction Scheme:

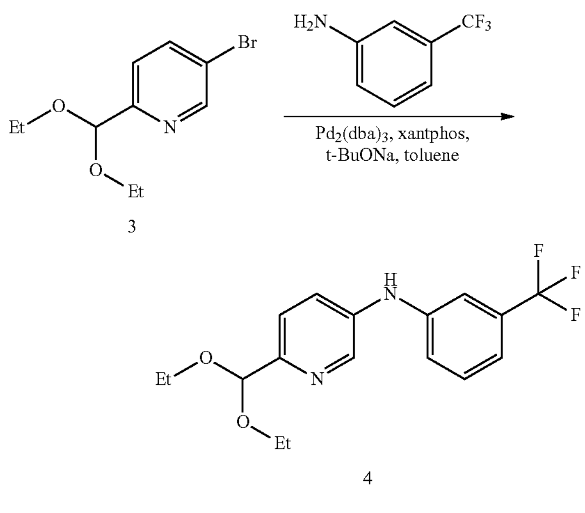

3

4

Experimental Details:

To the mixture of compound 3 (0.6 g, 1.0 eq), 3-trifluoromethyl-phenylamine (0.37 g, 1.0 eq), t-BuONa (0.26 g, 1.2 eq) in 15 mL of toluene was added under $N_2$ $Pd_2(dba)_3$ (42 mg, 0.02 eq) and xantphos (28 mg, 0.02 eq). The mixture was refluxed under $N_2$ for 16 h, cooled, filtered. The filtrate was concentrated and purified by column chromatography to give compound 4.

4. Reaction Scheme:

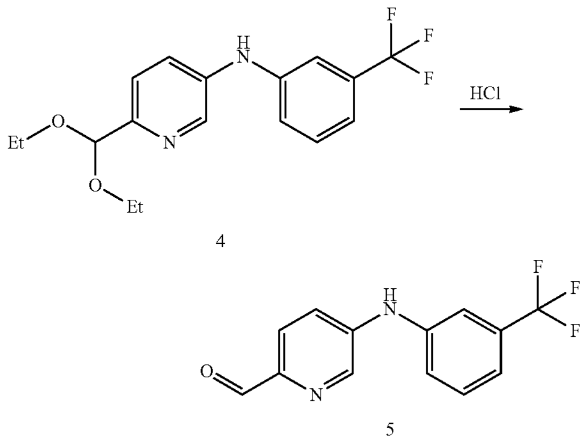

4

5

Experimental Details:

The solution of compound 4 (0.25 g, 1.0 eq) in 10 mL of dioxane was treated with 4 mL of 1 N HCl, and the mixture was heated to 60° C. for 2 h. After cooling, the pH was adjusted to 8 by addition of $NaHCO_3$. The mixture was extracted with dichloromethane, washed the organic layer with water, dried with $Na_2SO_4$ and evaporated to dryness. The crude product was purified by column chromatography to give compound 5.

5. Reaction Scheme:

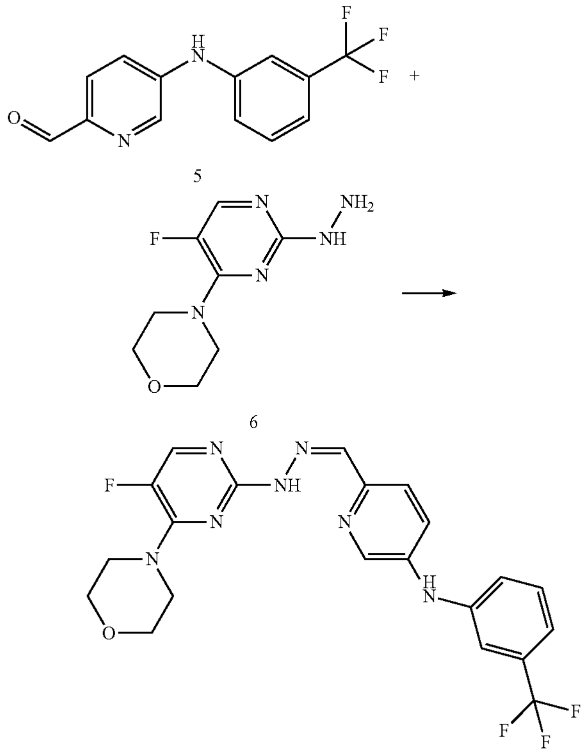

5

6

Experimental Details:

The mixture of compound 5 (30 mg, 1.0 eq) and compound 6 (19 mg, 1.0 eq) in 5 mL of dichloromethane was stirred at r.t. overnight. The precipitates were collected and washed with dichloromethane, dried under vacuum to give the desired compound.

Example 25

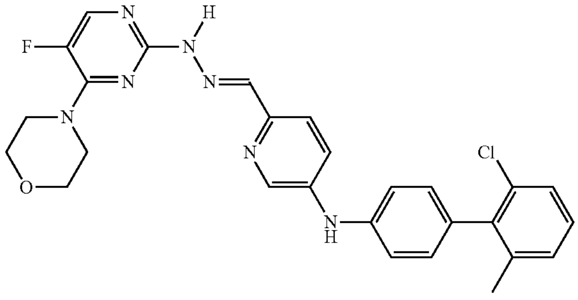 [SMILES: Cc1cccc(Cl)c1-c1ccc(Nc2ccc(/C=N/Nc3ncc(F)c(N4CCOCC4)n3)nc2)cc1]

1. Reaction Scheme:

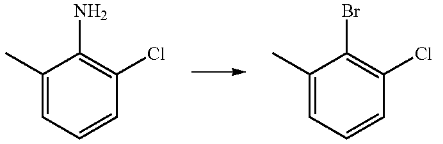

1 2

Experimental Details:

To a solution of compound 1 (14 g, 0.1 mol) in aqueous HBr (30 mL) was added a solution of $NaNO_2$ (8.3 g 0.15 mol) in $H_2O$ (10 mL) at 0° C. over a period of 30 min. After stirring for 60 min, the reaction mixture was added to a solution of CuBr (14 g, 0.1 mol) in aqueous HBr (16 mL) at 80° C. After complete addition, the reaction mixture was stirred at the same temperature for 2 h. After cooling to room temperature, the reaction mixture was extracted with EA (100 mL×3). The combined organic layer were washed with brine and dried over $Na_2SO_4$. After filtrating off the $Na_2SO_4$, the filtrate was concentrated to dryness. The residue was purified by column to give the product 2.

2. Reaction Scheme:

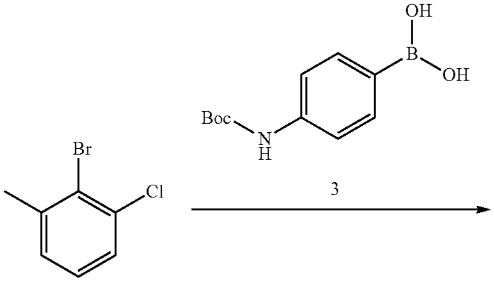

3

2

-continued

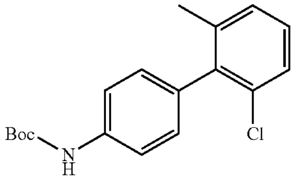

4

Experimental Details:

To a stirred and degassed mixture of compound 2 (4.11 g, 0.02 mol) and compound 3 (4.74 g, 0.02 mol), and KOH (5.28 g, 0.1 mol) and TBBA (6.44 g, 0.02 mol) in anhydrous THF (100 mL) was added Pd $(PPh_3)_4$ (2.31 g, 2 mmol) under $N_2$ atmosphere and stirred under reflux for 12 h. After filtrating off the solid, the filtrate was concentrated to dryness. The residue was purified by column to give the product 4.

3. Reaction Scheme:

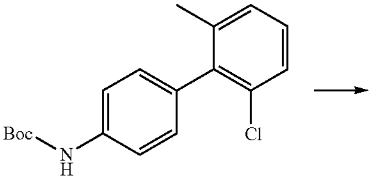

4

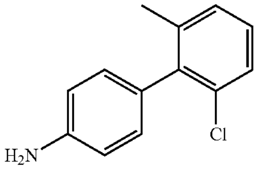

5

Experimental Details:

A solution of 4 (1 g, 3 mmol) in dichloromethane (10 mL) was treated with TFA (1 mL) and then stirred for 6 h at room temperature. The solvent was removed under reduced pressure to give the product 5 which is done next step without purification.

4. Reaction Scheme:

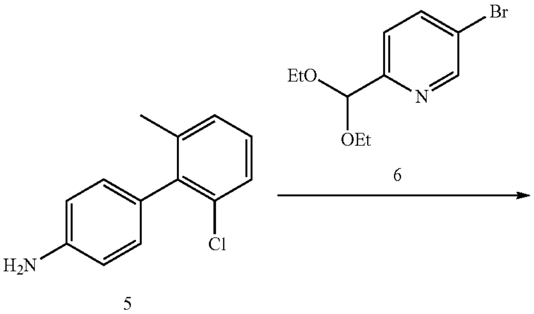

6

5

-continued

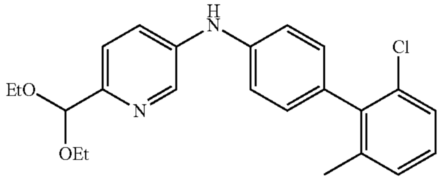

7

Experimental Details:

To a stirred and degassed mixture of compound 5 (619 mg, 2.4 mmol) and compound 6 (520 mg, 2.4 mmol), and t BuONa (460 mg, 4.8 mmol) and BINAP (599 mg, 6.9 mol) in toluene (60 mL) was added $Pd_2(dba)_3$ (221 mg, 0.024 mmol) under $N_2$ atmosphere and stirred at 80° C. for 48 h. After filtrating off the solid, the filtrate was concentrated to dryness. The residue was purified by column to give the product 7.

5. Reaction Scheme:

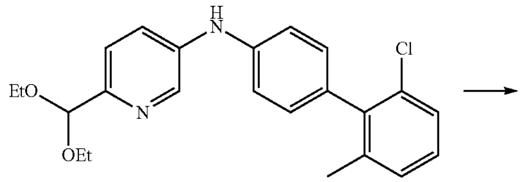

7

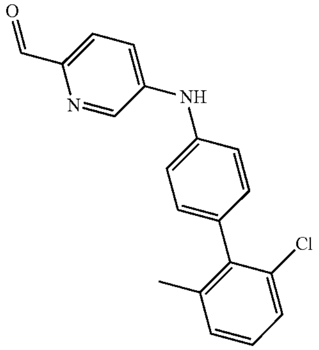

8

Experimental Details:

A solution of compound 7 (396 mg, 0.1 mmol) in dichloromethane (10 mL) was treated with $BBr_3$ (146 mg, 0.6 mmol) at −30° C. under $N_2$ atmosphere, then was stirred at room temperature for 4 h. The reaction was poured unto ice-water and then was brought by adding $Na_2CO_3$. The resulting mixture was extracted with dichloromethane (25 mL×3), the combined organic layer was dried over $Na_2SO_4$. After filtrating off the $Na_2SO_4$, the filtrate was concentrated to give the crude product 8, which was done next step without purification.

6. Reaction Scheme:

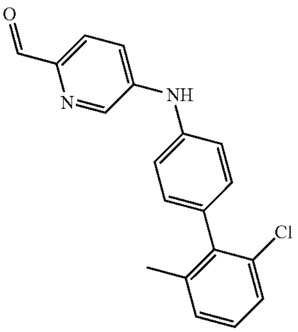

8

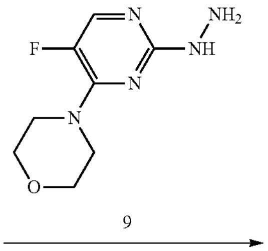

9

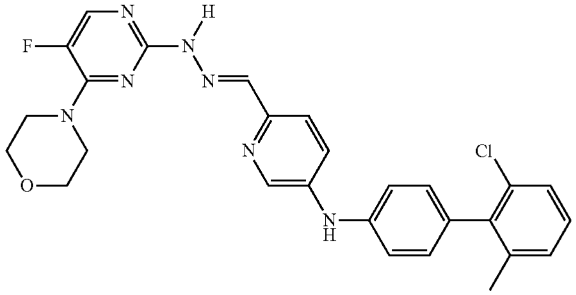

Experimental Details:

A solution of compound 8 (32.2 mg, 0.1 mmol) and compound 9 (21 mg, 0.1 mmol) in anhydrous $CH_2Cl_2$ (300 mL) was stirred under reflux for 6 h. The solvent was removed under reduced pressure. The residue was separated by prep-TLC to give the desired compound.

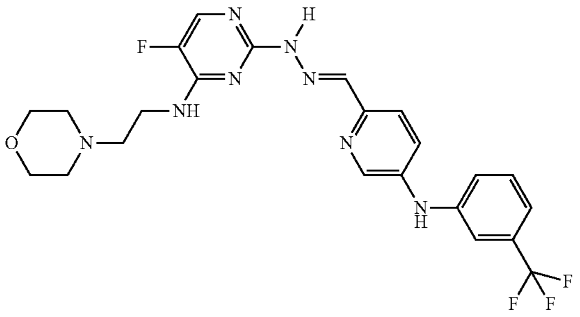 [SMILES: Fc1cnc(N/N=C/c2ccc(Nc3cccc(C(F)(F)F)c3)cn2)nc1NCCN1CCOCC1]

Example 26

1. Reaction Scheme:

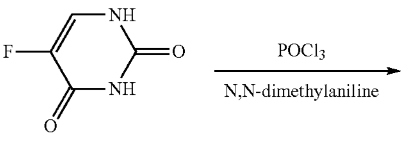

1

-continued

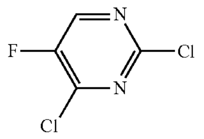

2

Experimental Details:

A solution of 5-fluoro-1H-pyrimidine-2,4-dione (113 g, 0.5 mol) in N,N-dimethylaniline (70 mL) was treated with $POCl_3$ (500 mL), then was reflux for 2 h. After cooling to room temperature, the reaction mixture was poured onto ice-water. The resulting mixture was extracted with ethyl acetate (100 mL×3). The combined organic layers were washed with saturated aqueous of $NaHCO_3$, then brine. The solvent was removed under reduced pressure to give compound 2.

2. Reaction Scheme:

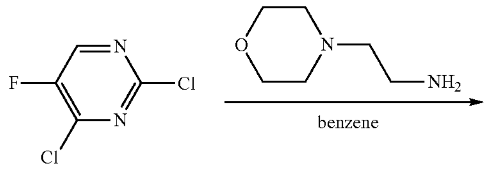

2

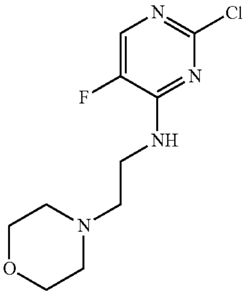

3

Experimental Details:

To a solution of compound 2 (20.8 g, 0.194 mol) in ethanol (300 mL) was added morpholine (21.6 g, 0.25 mol) drop wise at −10° C. over a period of 15 min. This mixture was stirred at room temperature for 0.5 h, heated then to 50° C. for 15 min. After cooling to room temperature and dilution with water, solid was precipitated. The solid was collected by filtrate and washed with water to give compound 3.

3. Reaction Scheme:

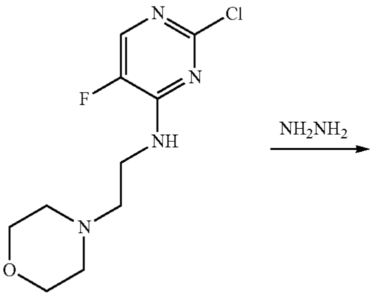

3

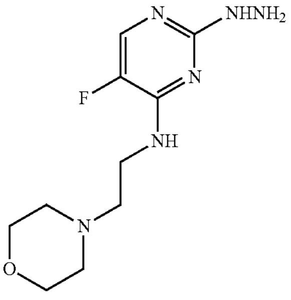

4

Experimental Details:

A solution of 3 (4.6 g, 17.5 mmol) and hydrazine (8.75 g, 87.5 mmol) in ethanol (40 mL) was heated to reflux for 6 h. After cooling and precipitating, the precipitate was collected by filtrate and washed with ethanol to give compound 4.

4. Reaction Scheme:

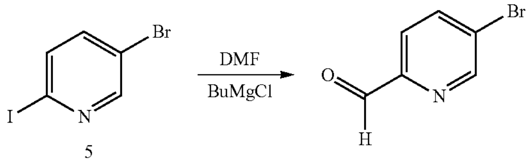

5

6

Experimental Details:

A solution of compound 5 (14 g, 50 mmol) in anhydrous THF (100 mL) was treated with BuMgCl (37.5 mL, 60 mmol) at −15° C. under $N_2$ atmosphere. After complete addition, this mixture was stirred at this temperature for 1 h. Anhydrous DMF (0.54 g, 75 mmol) was added to the reaction mixture at 0° C. over a period of 30 min, warmed then to room temperature for 1 h. The reaction mixture was quenched by adding 2 M HCl (80 mL). The result mixture was extracted with ethyl acetate (50 mL×3). The combined organic layers were dried over $Na_2SO_4$. The solvent was concentrated to dryness. The residue was separated by column to give compound 6.

5. Reaction Scheme:

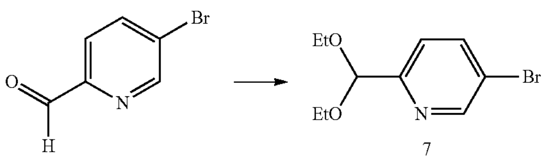

6

7

Experimental Details:

A solution of compound 6 (4.5 g, 22.5 mmol) in triethyl orthoformate (15 mL) was heated in the presence of a trace of TsOH over night. The reaction mixture was diluted with ethyl acetate (100 mL) and washed with an aqueous of 5% $Na_2CO_3$. The organic layer was separated and dried over $Na_2SO_4$. The solvent was concentrated to give compound 7.

6. Reaction Scheme:

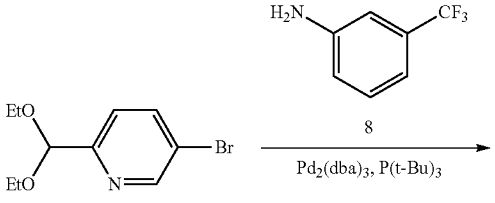

8

7

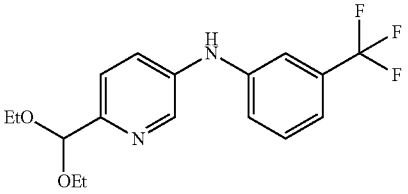

9

Experimental Details:

To a stirred and degassed mixture of compound 7 (1.3 g, 5 mmol) and compound 8 (0.97 g, 6 mmol), and t BuONa (0.7 g, 7 mmol) and $P(t\text{-}Bu)_3$ (15 mg) in toluene (60 mL) was added $Pd_2(dba)_3$ (23 mgl) under $N_2$ atmosphere and stirred under reflux for 12 h. After filtrating off the solid, the filtrate was concentrated to dryness. The residue was purified by column to give product 9.

7. Reaction Scheme:

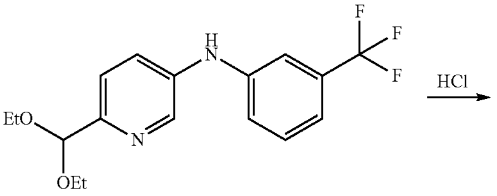

9

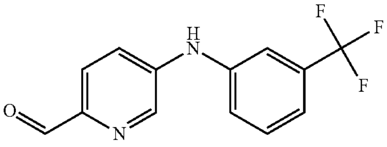

10

Experimental Details:

A solution of compound 9 (200 mg, 0.58 mmol) in dichloromethane (10 mL) was treated with $BBr_3$ (146 mg, 0.6 mmol) at −30° C. under $N_2$ atmosphere, then was stirred at room temperature for 4 h. The reaction was poured unto ice-water and then was brought by adding $Na_2CO_3$. The resulting mixture was extracted with dichloromethane (25 mL×3), the combined organic layer was dried over $Na_2SO_4$. After filtrating off the $Na_2SO_4$, the filtrate was concentrated to give the crude product 10.

8. Reaction Scheme:

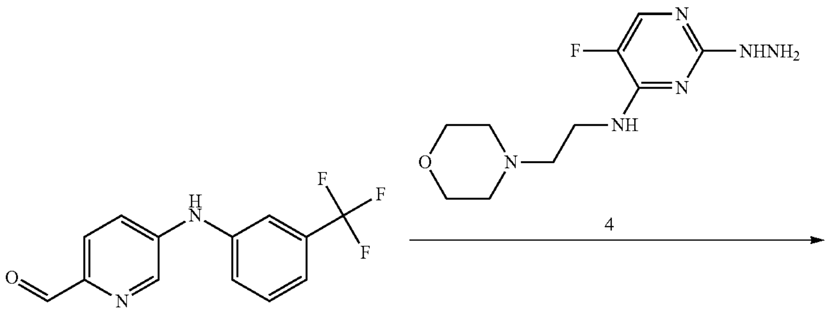

4

10

-continued

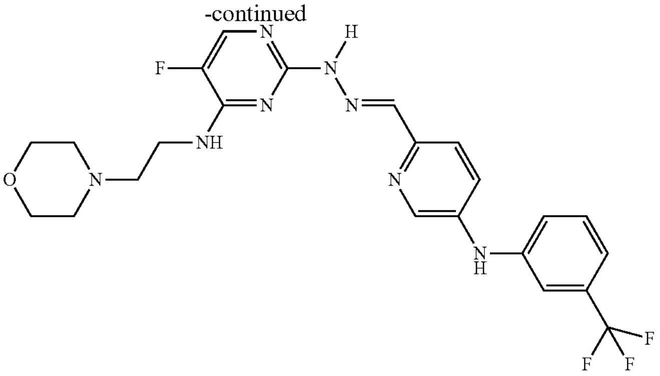

Experimental Details:

A solution of compound 10 (48.7 mg, 0.2 mmol) and compound 4 (63 mg, 0.2 mmol) in anhydrous $CH_2Cl_2$ (300 mL) was stirred under reflux for 6 h. The solvent was removed under reduced pressure. The residue was separated by prep-TLC to give the desired compound.

Example 27

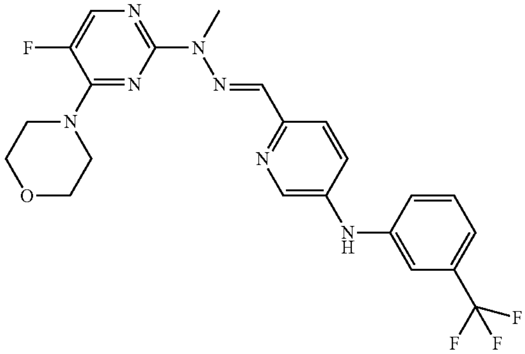 [SMILES: CN(/N=C/c1ccc(Nc2cccc(C(F)(F)F)c2)cn1)c1ncc(F)c(N2CCOCC2)n1]

1. Reaction Scheme:

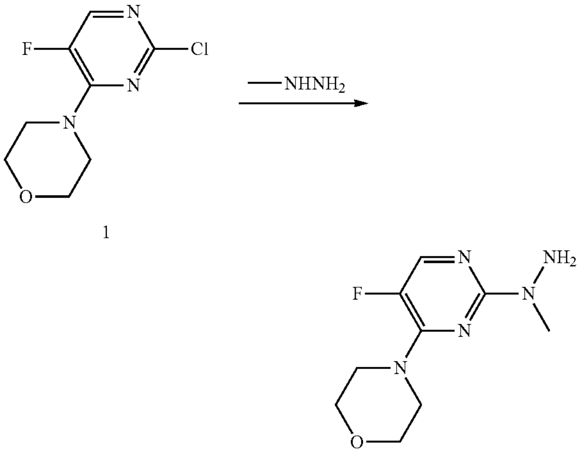

1

2

Experimental Details:

A solution of 3 (2.4 g, 11 mmol) and methylhydrazine (2 g, 45 mmol) in ethanol (40 mL) was heated to reflux for 6 h. After cooling and precipitating, the precipitate was collected by filtrate and washed with ethanol to give compound 2.

2. Reaction Scheme:

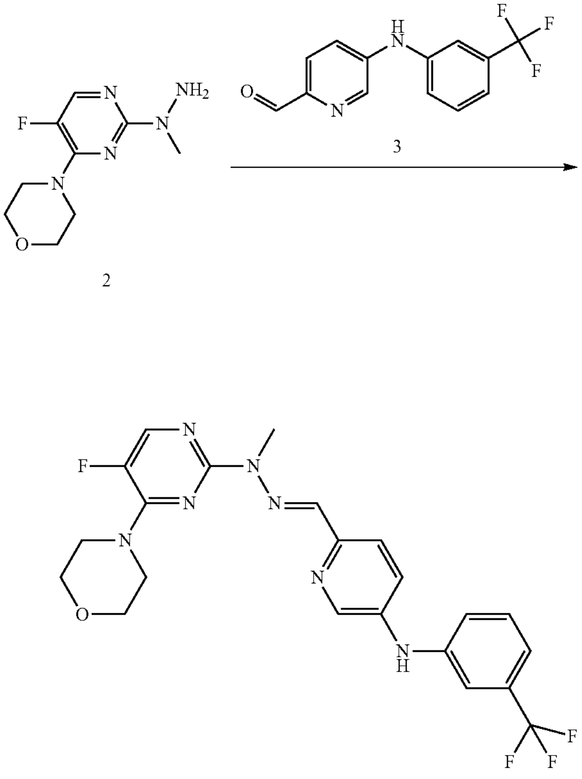

2

3

Experimental Details:

A solution of compound 2 (28 mg, 0.1 mmol) and compound 3 (37 mg, 0.1 mmol) in anhydrous $CH_2Cl_2$ (300 mL) was stirred under reflux for 6 h. The solvent was removed under reduced pressure. The residue was separated by prep-TLC to give the desired compound.

Example 28

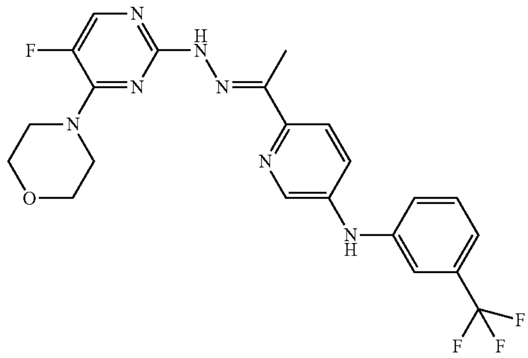 [SMILES: C/C(=N\Nc1ncc(F)c(N2CCOCC2)n1)c1ccc(Nc2cccc(C(F)(F)F)c2)cn1]

1. Reaction Scheme:

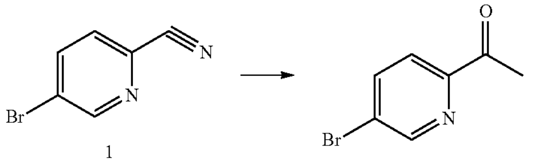

1 2

Experimental Details:

A solution of 1 (2 g, 0.011 mol) in anhydrous THF (100 mL) was treated with MeMgCl (15 mL. 0.038 mol), at −20° C. and stirred for 2 h at this temperature. This reaction mixture was quenched by adding the saturated aqueous of $NH_4Cl$. The resulting mixture was extracted with ethyl acetate (100 mL×3). The combined organic layers were washed with brine. The solvent was removed under reduced pressure to give compound 2.

2. Reaction Scheme:

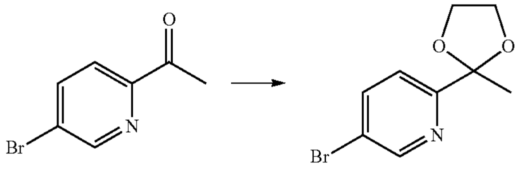

2 3

Experimental Details:

A solution of compound 2 (2 g, 0.01 mol) and ethylene glycol (3 g, 0.048 mol) in anline (100 mL) was heated in the presence of a trace of TsOH for 3 h. The reaction mixture was diluted with ethyl acetate (100 mL) and washed with an aqueous of 5% $Na_2CO_3$. The organic layer was separated and dried over $Na_2SO_4$. The solvent was concentrated to give compound 3.

3. Reaction Scheme:

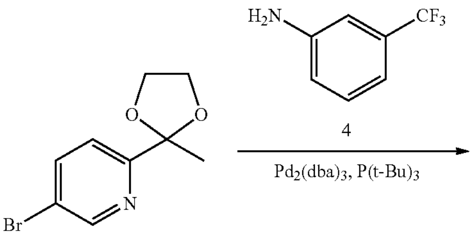

3

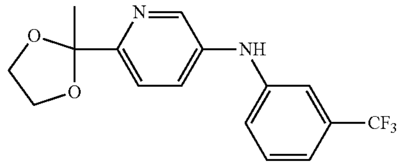

5

Experimental Details:

To a stirred and degassed mixture of compound 3 (0.4 g, 1.6 mmol) and compound 4 (0.3 g, 1.9 mmol), and t BuONa (0.22 g, 2 mmol) and $P(t\text{-}Bu)_3$ (59 mg) in toluene (30 mL) was added $Pd_2(dba)_3$ (29 mgl) under $N_2$ atmosphere and stirred under reflux for 12 h. After filtrating off the solid, the filtrate was concentrated to dryness. The residue was purified by column to give product 5.

4. Reaction Scheme:

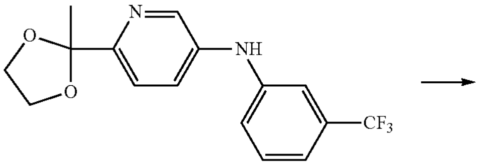

5

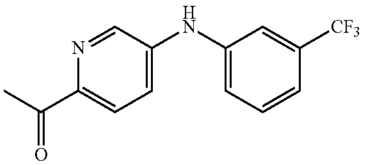

6

Experimental Details:

A solution of compound 5 (100 mg, 0.3 mmol) in dichloromethane (10 mL) was treated with $BBr_3$ (146 mg, 0.6 mmol) at −30° C. under $N_2$ atmosphere, then was stirred at room temperature for 4 h. The reaction was poured unto ice-water and then was brought by adding $Na_2CO_3$. The resulting mixture was extracted with dichloromethane (25 mL×3), the combined organic layer was dried over $Na_2SO_4$. After filtrating off the $Na_2SO_4$, the filtrate was concentrated to give the crude product 6.

5. Reaction Scheme:

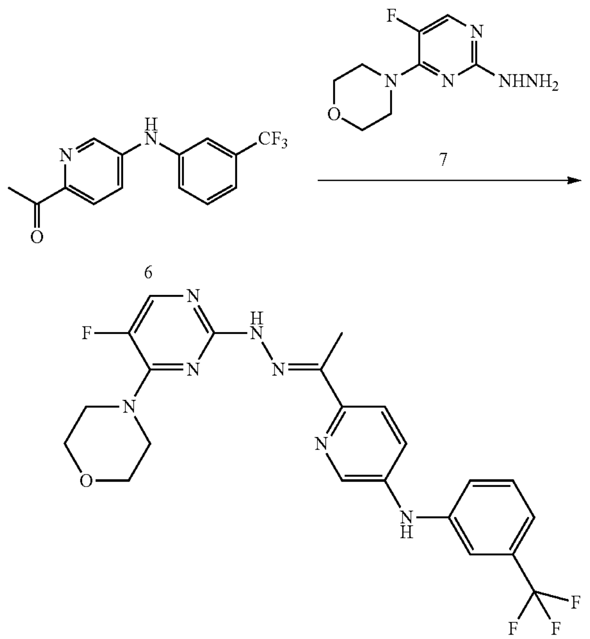

6

Experimental Details:

A solution of compound 6 (64 mg, 0.2 mmol) and compound 7 (45 mg, 0.2 mmol) in anhydrous $CH_2Cl_2$ (300 mL) was stirred under reflux for 6 h. The solvent was removed under reduced pressure. The residue was separated by prep-TLC to give the desired compound.

Example 29

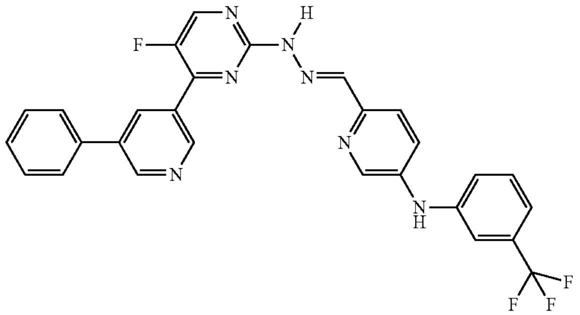 [SMILES: Fc1cnc(N/N=C/c2ccc(Nc3cccc(C(F)(F)F)c3)cn2)nc1-c1cncc(-c2ccccc2)c1]

1. Reaction Scheme:

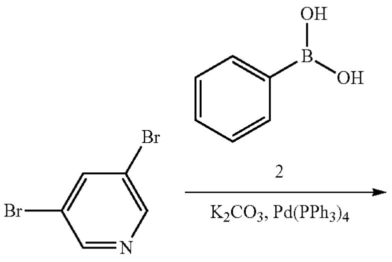

1

-continued

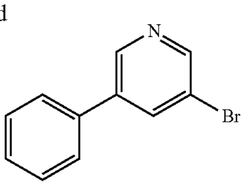

3

Experimental Details:

A mixture of 1 (5.2 g, 22 mmol) and 2 (2.44 g, 20 mmol) in an aqueous of 2 M $Na_2CO_3$ (25 mL) and toluene (40 mL) was stirred with $Pd(PPh_3)_4$ (0.57 g, 0.05 mmol) under reflux over night. The reaction mixture was extracted with ethyl acetate (100 mL×3). The combined organic layers were washed with brine. The solvent was removed under reduced pressure to dryness. The residue was purified by column to give 3.

2. Reaction Scheme:

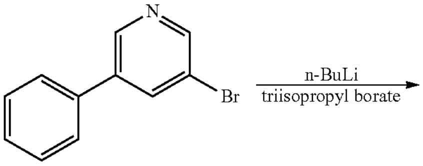

3

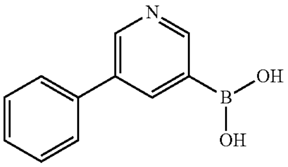

4

Experimental Details:

A solution of compound 3 (0.78 g, 3.3 mmol) and triisopropyl borate (1 mL, 4 mmol) in anhydrous toluene (50 mL) was treated with n-BuLi (1.5 mL, 3.75 mmol) at −60° C. under $N_2$ atmosphere. After complete addition, this mixture was stirred at −10° C. for 1 h. The reaction mixture was quenched by adding aqueous of 2 M HCl, and washed with toluene. The aqueous layer was brought pH=8 by adding $Na_2CO_3$, extracted then with ethyl acetate (50 mL×3). The combined organic layers were washed with brine. The solvent was removed under reduced pressure to dryness. The residue was separated by column to give 4.

3. Reaction Scheme:

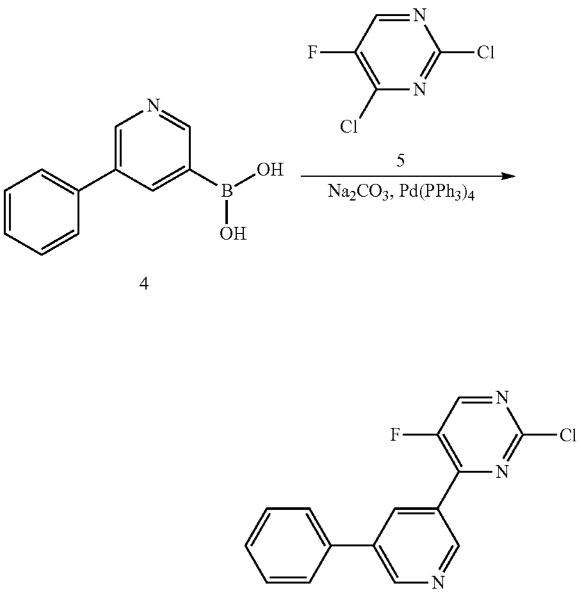

4

6

Experimental Details:

To a stirred and degassed mixture of compound 4 (2.8 g, 14 mmol) and compound 5 (7 g, 42 mmol) in an aqueous of 2 M $Na_2CO_3$ (250 mL) and -toluene (40 mL) was stirred with $Pd(PPh_3)_4$ (0.57 g, 0.05 mmol) under reflux over night. The reaction mixture was extracted with ethyl acetate (100 mL×3). The combined organic layers were washed with brine. The solvent was removed under reduced pressure to dryness. The residue was separated by column to give 6.

4. Reaction Scheme:

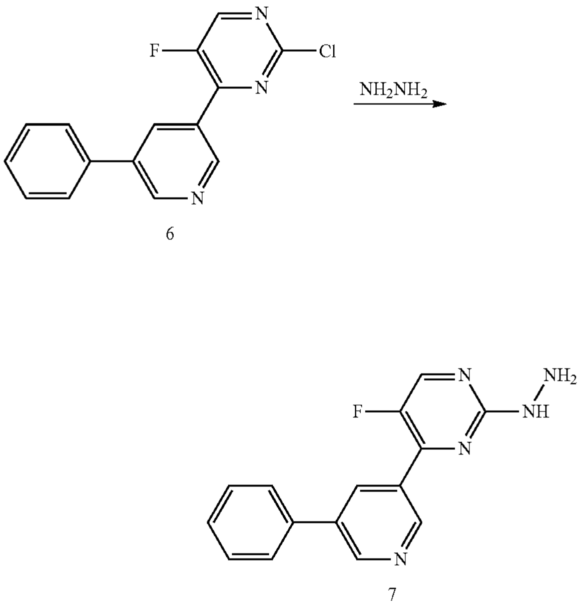 [SMILES: Fc1cnc(Cl)nc1-c1cncc(-c2ccccc2)c1 ; "NH2NH2" ; NNc1ncc(F)c(-c2cncc(-c3ccccc3)c2)n1]

6

7

Experimental Details:

A solution of 6 (0.53 g, 1.9 mmol) and hydrazine (0.52 g, 8.8 mmol) in ethanol (50 mL) was stirred under reflux for 6 h. After cooling and precipitating, the precipitate was collected by filtrate and washed with ethanol to give compound 7.

5. Reaction Scheme:

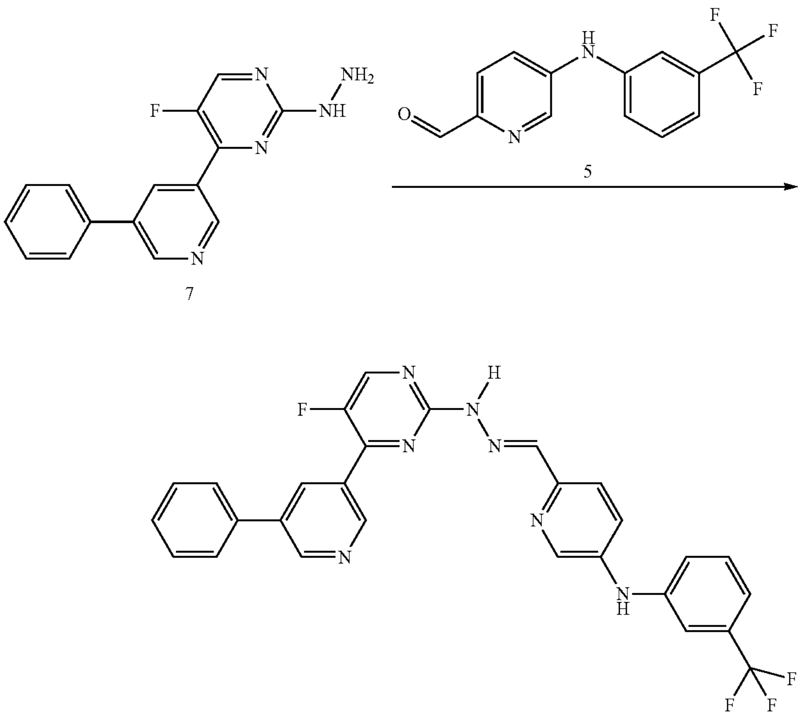

7

Experimental Details:

A solution of compound 7 (53 mg, 0.13 mmol) and compound 8 (79 mg, 0.13 mmol) in anhydrous $CH_2Cl_2$ (300 mL) was stirred under reflux for 6 h. The solvent was removed under reduced pressure. The residue was purified by prep-TLC to give the desired compound.

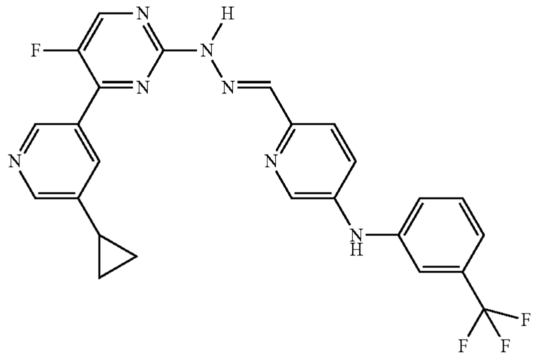 [SMILES: Fc1cnc(N/N=C/c2ccc(Nc3cccc(C(F)(F)F)c3)cn2)nc1-c1cncc(C2CC2)c1]

Example 30

1. Reaction Scheme:

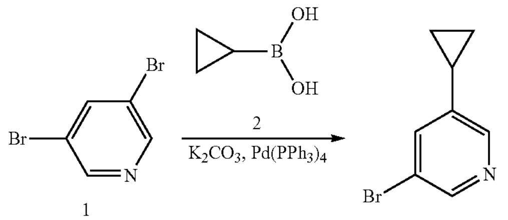

1

3

Experimental Details:

A mixture of 1 (3.1 g, 13 mmol) and 2 (1 g, 12 mmpl) in an aqueous of 2 M $Na_2CO_3$ (15 mL) and toluene (30 mL) was stirred with $Pd(PPh_3)_4$ (0.4 g, 0.029 mmol) under reflux over night. The reaction mixture was extracted with ethyl acetate (100 mL×3). The combined organic layers were washed with brine. The solvent was removed under reduced pressure to dryness. The residue was separated by column to give 3.

2. Reaction Scheme:

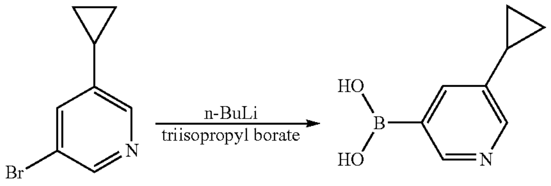

3

4

Experimental Details:

A solution of compound 3 (2.0 g, 10 mmol) and triisopropyl borate (7 mL, 30 mmol) in anhydrous toluene (50 mL) was treated with n-BuLi (12 mL, 30 mmol) at −60° C. under $N_2$ atmosphere. After complete addition, this mixture was stirred at −10° C. for 1 h. The reaction mixture was quenched by adding an aqueous of 2 m HCl, and washed with toluene. The aqueous layer was brought pH=8 by adding $Na_2CO_3$, extracted then with ethyl acetate (50 mL×3). The combined organic layers were washed with brine. The solvent was removed under reduced pressure to dryness. The residue was separated by column to give 4.

3. Reaction Scheme:

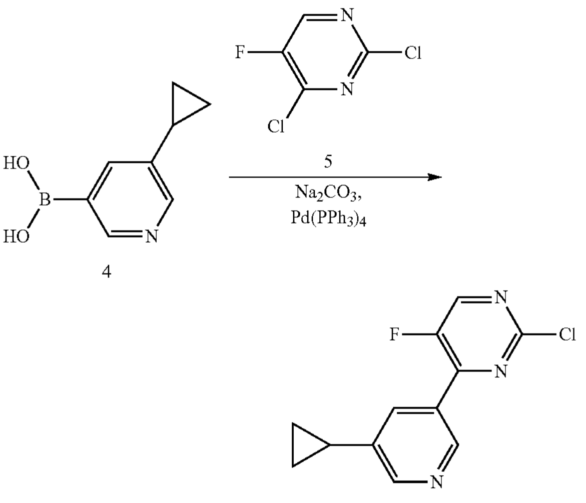

4

6

Experimental Details:

To a stirred and degassed mixture of compound 4 (0.5 g, 3 mmol) and compound 5 (1.5 g, 9 mmol) in an aqueous of 2 M $Na_2CO_3$ (3.5 mL) and toluene (40 mL) was stirred with $Pd(PPh_3)_4$ (94 mg, 0.003 mmol) under reflux over night. The reaction mixture was extracted with ethyl acetate (100 mL×3). The combined organic layers were washed with brine. The solvent was removed under reduced pressure to dryness. The residue was purified by column to give 6.

4. Reaction Scheme:

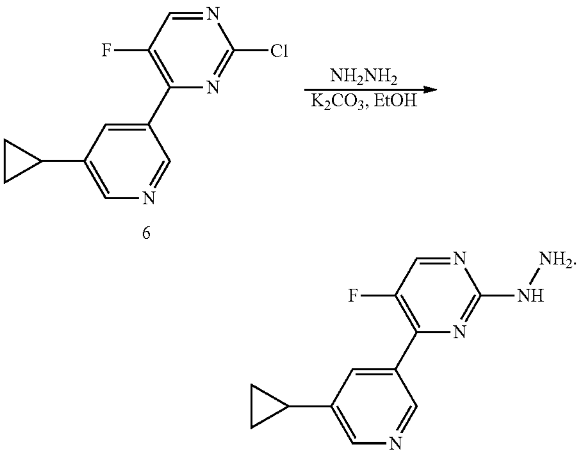

6

7

Experimental Details:

A solution of 6 (0.24 g, 1 mmol) and hydrazine (03 g, 4.7 mmol) in ethanol (50 mL) was stirred under reflux for 6 h. After cooling and precipitating, the precipitate was collected by filtrate and washed with ethanol to give compound 7.

5. Reaction Scheme:

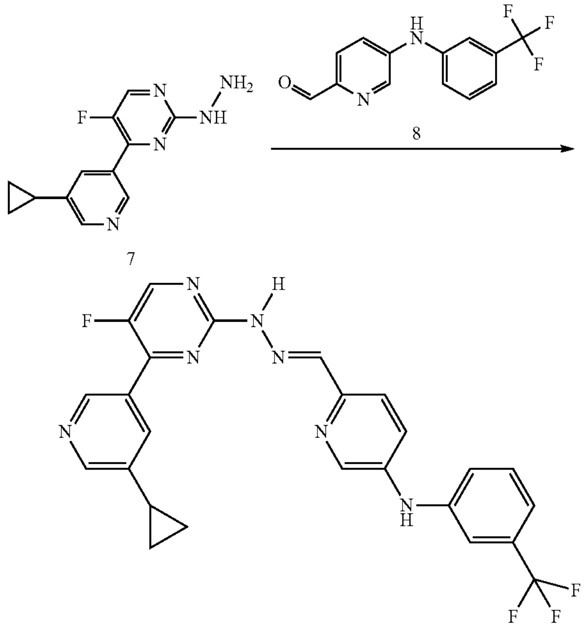

8

7

Experimental Details:

A solution of compound 7 (70 mg, 0.29 mmol) and compound 8 (83 mg, 0.3 mmol) in anhydrous $CH_2Cl_2$ (300 mL) was stirred under reflux for 6 h. The solvent was removed under reduced pressure. The residue was purified by prep-TLC to give the desired compound.

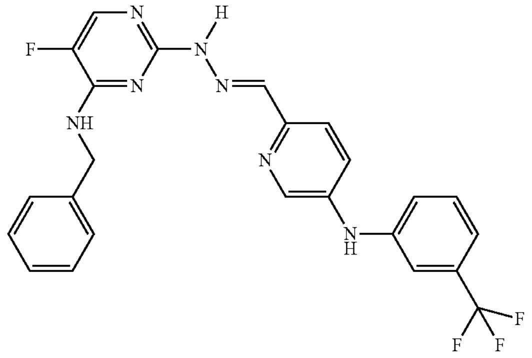

Example 31

1. Reaction Scheme:

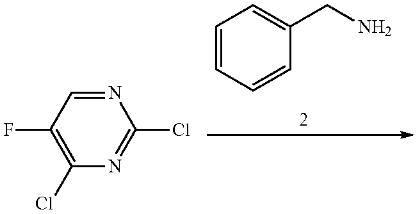

2

1

-continued

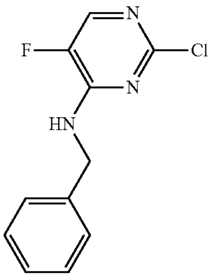

3

Experimental Details:

To a solution of compound 2 (0.83 g, S mmol) in ethanol (100 mL) was added benzylamine (0.54 g, 5 mmol) drop wise. After stirring for 2 h, the reaction mixture was diluted with water. The resulting mixture was extracted with ethyl acetate (50 mL×3). The combined organic layers were dried over $Na_2SO_4$. The solvent was concentrated to give compound 3.

2. Reaction Scheme:

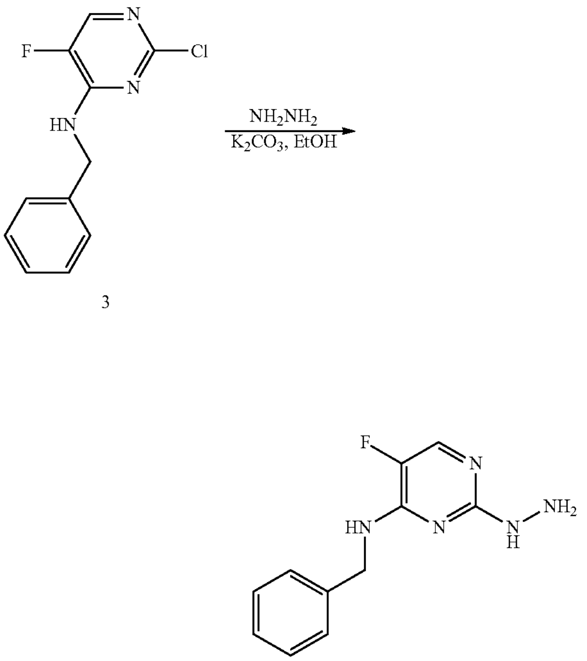

3

4

Experimental Details:

A solution of 3 (1.18 g, 5 mmol) and hydrazine (5 ml) in ethanol (40 mL) was heated to reflux for 6 h. After cooling and precipitating, the precipitate was collected by filtrate and washed with ethanol to give compound 4.

3. Reaction Scheme:

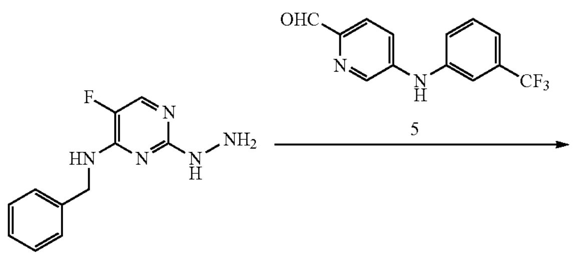

4

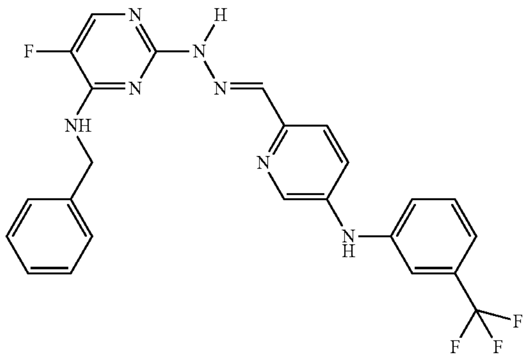 [SMILES: Fc1cnc(N/N=C/c2ccc(Nc3cccc(C(F)(F)F)c3)cn2)nc1NCc1ccccc1]

Experimental Details:

A solution of compound 4 (48.7 mg, 2 mmol) and compound 5 (63 mg, 0.2 mmol) in anhydrous $CH_2Cl_2$ (300 mL) was stirred under reflux for 6 h. The solvent was removed under reduced pressure. The residue was separated by prep-TLC to give the desired compound.

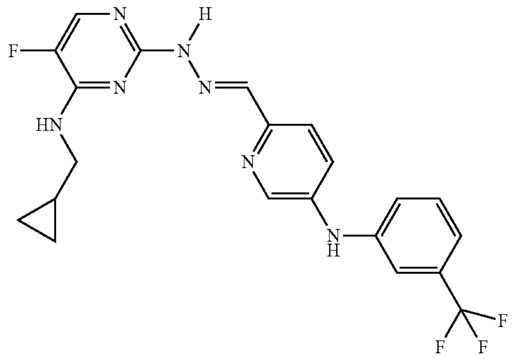 [SMILES: Fc1cnc(N/N=C/c2ccc(Nc3cccc(C(F)(F)F)c3)cn2)nc1NCC1CC1]

Example 32

1. Reaction Scheme:

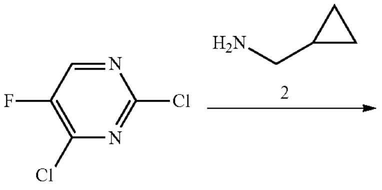

1

-continued

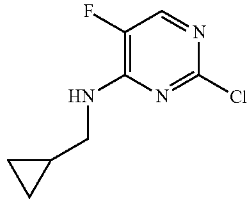

3

Experimental Details:

To a solution of compound 2 (0.83 g, 5 mmol) in ethanol (100 mL) was added compound 2 (0.35 g, 5 mmol) dropwise. After stirring for 2 h, the reaction mixture was diluted with water. The resulting mixture was extracted with ethyl acetate (50 mL×3). The combined organic layers were dried over $Na_2SO_4$. The solvent was concentrated to give compound 3.

2. Reaction Scheme:

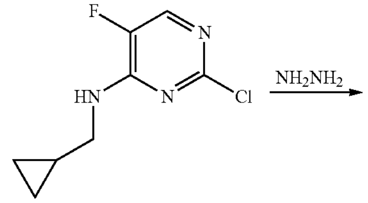

3

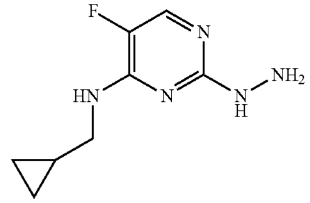

4

Experimental Details:

A solution of 3 (1.0 g, 5 mmol) and hydrazine (5 mL) in ethanol (40 mL) was heated to reflux for 6 h. After cooling and precipitating, the precipitate was collected by filtrate and washed with ethanol to give compound 4.

3. Reaction Scheme:

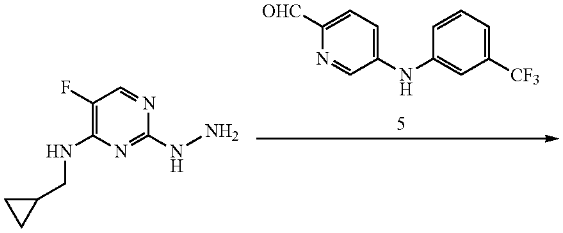

4

-continued

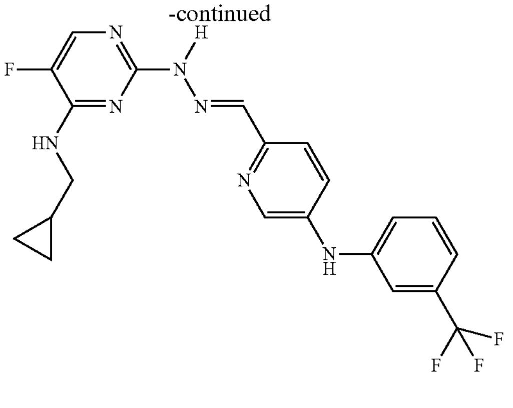

Experimental Details:

A solution of compound 4 (480 mg, 2 mmol) and compound 5 (60 mg, 0.2 mmol) in anhydrous $CH_2Cl_2$ (300 mL) was stirred under reflux for 6 h. The solvent was removed under reduced pressure. The residue was separated by prep-TLC to give the desired compound.

All references to any publication, patent, or other citation are hereby incorporated by reference.

REFERENCES

Adcock, I. M., Lane, S. J. Mechanisms of Steroid Action and Resistance in Inflammation. Journal of Endocrinology, Volume 178 (September 2003) Pages 347-355

Allen, P. B., Wiedemann, L. M. An Activating Mutation in the ATP Binding Site of the ABL Kinase Domain. The Journal of Biological Chemistry, Volume 271 (Aug. 9, 1996) Pages 19585-19591

Barthe, C., Cony-Makhoul, P., Melo, J. V., Reiffers, J., Mahon, F, X. Roots of Clinical Resistance to STI-571 Cancer Therapy. Science, Volume 293 (Sep. 21, 2001) Page 2163a Branford, S., Rudzki, Z., Walsh, S., Grigg, A., Arthur, C., Taylor, K., Hermann, R., Lynch, K. P., Hughes, T. P. High Frequency of Point Mutations Clustered Within the Adenosine Triphosphate-Binding Region of BCR/ABL in Patients with Chronic Myeloid Leukemia or Ph-positive Acute Lymphoblastic Leukemia Who Develop Imatinib (STI571) Resistance. Blood, Volume 99 (May 1, 2002) Pages 3472-3475

Burbaum, J. J., Ohlmeyer, M. H., Reader, J. C., Henderson, I., Dillard, L. W., Li, G., Randle, T. L., Sigal, N. H., Chelsky, D., Baldwin, J. J. A paradigm for drug discovery employing encoded combinatorial libraries. Proceedings of the National Academy of Science USA, Volume 92 (Jun. 20, 1995) Pages 6027-6031.

Carter, T. A., Wodicka, L. M., Shah, N. P., Velasco, A. M., Fabian, M. A., Treiber; D. K., Milanov, Z. V., Atteridge, C. E., Biggs, W. H. 3rd, Edeen, P. T., Floyd, M., Ford, J. M., Grotzfeld, R. M., Herrgard, S., Insko, D. E., Mehta, S. A., Patel, H. K., Pao, W., Sawyers, C I., Varmus, H., Zarrinkar, P. P., Lockhart, D. J. Inhibition of drug-resistant mutants of ABL, KIT, and EGF receptor kinases. Proceedings of the National Academy of Science USA, Volume 102 (Aug. 2, 2005) Pages 11011-11016.

Corbin, A. S., Buchdunger, E., Pascal, F., Druker, B. J. Analysis of the Structural Basis of Specificity of Inhibition of the Abl Kinase by STI571. The Journal of Biological Chemistry, Volume 277 (Aug. 30, 2002) Pages 32214-32219

Cunningham, B. C., De Vos, A. M., Mulkerrin, M. G., Ultsch, M, Wells, J. A. Selecting Ligand Agonists and Antagonists. U.S. Pat. No. 5,506,107 (Apr. 9, 1996)

Cunningham, B. C., Wells, J. A., Clark, R. G., Olson, K., Fuh, G. G. Method for Inhibiting Growth Hormone Action. U.S. Pat. No. 6,004,931 (Dec. 21, 1999)

Daley, G. Q., Van Etten, R. A., Baltimore, D. Induction of Chronic Myelogenous Leukemia in Mice by the $P210^{brc/abl}$ Gene of the Philadelphia Chromosome. Science, Volume 247 (Feb. 16, 1990) Pages 824-830

Druker, B. J., M. D., Talpaz, M., M. D., Resta, D. J., R. N., Peng, B., Ph.D., Buchdunger, E., Ph.D., Ford, J. M., M. D., Lydon, N. B., Ph.D., Kantarjian, H., M. D., Capdeville, R., M. D., Ohno-Jones, S., B. S., Sawyers, C. L., M. D. Efficacy and Safety of a Specific Inhibitor of the BCR-ABL Tyrosine Kinase in Chronic Myeloid Leukemia. The New England Journal of Medicine, Volume 344 (Apr. 5, 2001) Pages 1031-1037

Druker, B. J., Tamura, S., Buchdunger, E., Ohno, S., Segal, G. M., Fanning, S., Zimmermann, J., Lydon, N. B. Effects of a Selective Inhibitor of the Abl Tyrosine Kinase on the Growth of Bcr-Abl Positive Cells. Nature Medicine, Volume 2 (May 1996) Pages 561-566

Druker, B. J., M. D., Sawyers, C. L., M. D., Kantarjian, H., M. D., Resta, D. J., R. N., Reese, S. F., M. D., Ford, J. M., M. D., Capdeville, R., M. D., Talpaz, M., M. D. Activity of a Specific Inhibitor of the BCR-ABL Tyrosine Kinase in the Blast Crisis of Chronic Myeloid Leukemia and Acute Lymphoblastic Leukemia with the Philadelphia Chromosome. The New England Journal of Medicine, Volume 344 (Apr. 5, 2001) Pages 1038-1042

Faderl, S., M. D., Talpaz, M., M. D., Estrov, Z., M. D., O'Brien, S., M. D., Kurzrock, R., M. D., Kantarjian, H. M., M. D. The Biology of Chronic Myeloid Leukemia. The New England Journal of Medicine, Volume 341 (Jul. 15, 1999) Pages 164-172

Foreman, J. C. and Johansen, T. Textbook of Receptor Pharmacology. CRC Press, 2002; Boca Raton Gambacorti-Passerini, C., Barni, R., Le Coutre, P., Zucchetti, M., Cabrita, G., Cleris, L., Rossi, F., Gianazza, E., Brueggen, J., Cozens, R., Pioltelli, P., Pogliani, E., Corneo, G., Formelli, F., D'Incalci, M. Role of α1 Acid Glycoprotein in the In Vivo Resistance of Human BCR-$ABL^+$. Leukemic Cells to the Abl Inhibitor STI571. Journal of the National Cancer Institute, Volume 92 (Oct. 18, 2000) Pages 1641-1650.

Goodnow, R. A., Jr., Guba, W., Haap, W. Library design practices for success in lead generation with small molecule libraries. Combinatorial Chemistry and High Throughput Screening, Volume 6 (November 2003) Pages 649-660.

Gorre, M. E., Mohammed, M., Ellwood, K., Hsu, N., Paquette, R., Rao, P. N., Sawyers, C. L. Clinical Resistance to STI-571 Cancer Therapy Caused by BCR-ABL Gene Mutation or Amplification. Science, Volume 293 (Aug. 3, 2001) Pages 876-880.

Hanke, J. H., Gardner, J. P., Dow, R. L., Changelian, P. S., Brissette, W. H., Weringer, E. J., Pollok, B. A., Connelly, P. A. Discovery of a novel, potent, and Src family-selective tyrosine kinase inhibitor. Study of Lck- and FynT-dependent T cell activation. Journal of Biological Chemistry, Volume 271 (January 1996) Pages 695-701.

Hofmann, W. K., Jones, L. C., Lemp, N. A., DeVos, S., Gschaidmeier, H., Hoelzer, D., Ottmann, O. G., Koeffler, H. P. $Ph^+$ Acute Lymphoblastic Leukemia Resistant to the Tyrosine Kinase Inhibitor STI571 has a Unique BCR-ABL Gene Mutation. Blood, Volume 99 (Mar. 1, 2002) Pages 1860-1862.

Hou, Y. Y., Tan, Y. S., Sun, M. H., Wei, Y. K., Xu, J. F., Lu, S. H., A-Ke-Su, S. J., Zhou, Y. N., Gao, F., Zheng, A. H., Zhang, T. M., Hou, W. Z., Wang, J., Du, X., Zhu, X. Z. C-kit Gene Mutation in Human Gastrointestinal Stromal Tumors. World Journal of Gastroenterology, Volume 10 (May 1, 2004) Pages 1310-1314.

Housey G M. Method of Screening for Protein Inhibitors and Activators. U.S. Pat. No. 4,980,281 (Dec. 25, 1990)

Housey G M, Johnson M D, Hsiao W L, O'Brian C A, Murphy J P, Kirschmeier P, Weinstein L B. Overproduction of protein kinase C causes disordered growth control in rat fibroblasts. Cell, Volume 52 (Feb. 12, 1988) Pages 343-54.

Kerkelä, R., Grazette, L., Yacobi, R., Iliescu, C., Patten, R., Beahm, C., Walters, B., Shevtsov, S., Pesant, S., Clubb, F. J., Rosenzweig, A., Salomon, R. N., Van Etten, R. A., Alroy, J., Durand, J. B., Force, T. Cardiotoxicity of the cancer therapeutic agent imatinib mesylate. Nature Medicine, Volume 12 (August 2006) Pages 908-916.

Knight, Z. A., Shokat, K. M. Features of Selective Kinase Inhibitors. Chemistry and Biology, Volume 12 (June 2005) Pages 621-637.

La Rosee, P., Corbin, A. S., Stoffregen, E. P., Deininger, M. W., Druker, B. J. Activity of the Bcr-Abl Kinase Inhibitor PD180970 Against Clinically Relevant Bcr-Abl Isoforms That Cause Resistance to Imatinib Mesylate (Gleevec, STI-571). Cancer Research, Volume 62 (Dec. 15, 2002) Pages 7149-7153

Le Coutre, P., Tassi, E., Varella-Garcia, M., Barni, R., Mologni, L., Cabrita, G., Marchesi, E., Supino, R., Gambacorti-Passerini, C. Induction of Resistance to the Abelson Inhibitor STI571 in Human Leukemic Cells Through Gene Amplification. Blood, Volume 95 (Mar. 1, 2000) Pages 1758-1766

Leonard, G. D., Fojo, T., Bates, S. E. The Role of ABC Transporters in Clinical Practice. The Oncologist, Volume 8 (2003) Pages 411-424

Loutfy, M. R., Walmsley, S. L. Salvage Antiretroviral Therapy in HIV Infection. Expert Opinion, Volume 3 (February 2002) Pages 81-90

Lynch, T. J., M. D., Bell, D. W., Ph.D., Sordella, R., Ph.D., Gurubhagavatula, S., M. D., Okimoto, R. A., B. S., Brannigan, B. W., B. A., Harris, P. L., M. S., Haserlat, S. M., B. A., Supko, J. G., Ph.D., Haluska, F. G., M. D., Ph.D., Louis, D. N., M. D., Christiani, D. C., M. D., Settleman, J., Ph.D., Haber, D. A., M. D., Ph.D. Activating Mutations in the Epidermal Growth Factor Receptor Underlying Responsiveness of Non-Small-Cell Lung Cancer to Gefitinib. The New England Journal of Medicine, Volume 350 (May 20, 2004) Pages 2129-2139

Mahon, F. X., Deininger, M. W. N., Schultheis, B., Chabrol, J., Reiffers, J., Goldman, J. M., Melo, J. V. Selection and Characterization of BCR-ABL Positive Cell Lines with Differential Sensitivity to the Tyrosine Kinase Inhibitor STI571: Diverse Mechanisms of Resistance. Blood, Volume 96 (Aug. 1, 2000) Pages 1070-1079

Marx, J. Why a New Cancer Drug Works Well in Some Patients. Science, Volume 304 (Apr. 30, 2004) Pages 658-659

Melo J V, Myint H, Galton D A, Goldman J M. P190BCR-ABL chronic myeloid leukaemia: the missing link with chronic myelomonocytic leukaemia? Leukemia, Volume 8 (January 1994) Pages 208-11

Noble, M. E. M., Endicott, J. A., Johnson, L. N. Protein Kinase Inhibitors: Insights into Drug Design from Structure. Science, Volume 303 (Mar. 19, 2004) Pages 1800-1805

O'Hare T, Pollock R, Stoffregen E P, Keats J A, Abdullah O M, Moseson E M, Rivera V M, Tang H, Metcalf C A 3rd, Bohacek R S, Wang Y, Sundaramoorthi R, Shakespeare W C, Dalgarno D, Clackson T, Sawyer T K, Deininger M W, Druker B J. Inhibition of wild-type and mutant Bcr-Abl by AP23464, a potent ATP-based oncogenic protein kinase inhibitor: implications for CML. Blood, Volume 104 (Oct. 15, 2004) Pages 2532-2539

Paez, J. G., Jänne, P. A., Lee, J. C., Tracy, S., Greulich, H., Gabriel, S., Herman, P., Kaye, F J., Lindeman, N., Boggon, T. J., Naoki, K., Sasaki, H., Fujii, Y., Eck, M. J., Sellers, W. R., Johnson, B. E., Meyerson, M. EGFR Mutations in Lung Cancer: Correlation with Clinical Response to Gefitinib Therapy. Sciencexpress (Apr. 29, 2004) Pages 1-4

Ravandi F, Cortes J, Albitar M, Arlinghaus R, Qiang Guo J, Talpaz M, Kantarjian H M. Chronic myelogenous leukaemia with p185(BCR/ABL) expression: characteristics and clinical significance. British Journal of Haematology, Volume 107 (December 1999) Pages 581-586

Sambrook and Russell, Molecular Cloning: A Laboratory Manual. Cold Spring Harbor Laboratory Press, New York, 2001, Volumes 1-3

Sawyers, C. L. M.D. Chronic Myeloid Leukemia. The New England Journal of Medicine, Volume 340 (Apr. 29, 1999) Pages 1330-1340.

Sawyers, C. L., Gone, M. E., Shah, N. P., Nicoll, J. Mutations in the BCR-ABL Tyrosine Kinase Associated with Resistance to STI-571. WO 02/102976 A2 Published Dec. 27, 2002 (PCT/US02/18729 Filed Jun. 14, 2002)

Schindler, T., Bornmann, W., Pellicena, P., Miller, W. T., Clarkson, B., Kuriyan, J. Structural Mechanism for STI-571 Inhibition of Abelson Tyrosine Kinase. Science, Volume 289 (Sep. 15, 2000) Pages 1938-1942

Senechal, K., Halpern, J., Sawyers, C. L. The CRKL Adaptor Protein Transforms Fibroblasts and Functions in Transformation by the BCR-ABL Onocogene. The Journal of Biological Chemistry, Volume 271 (Sep. 20, 1996) Pages 23255-23261

Senechal, K., Heaney, C., Druker, B., Sawyers, C. L. Structural Requirements for Function of the Crkl Adapter Protein in Fibroblasts and Hematopoietic Cells. Molecular and Cellular Biology, Volume 18 (September 1998) Pages 5082-5090.

Tipping A J, Baluch S, Barnes D J, Veach D R, Clarkson B M, Bornmann W G, Mahon F X, Goldman J M, Melo J V. Efficacy of dual-specific Bcr-Abl and Src-family kinase inhibitors in cells sensitive and resistant to imatinib mesylate. Leukemia, Volume 18 (August 2004) Pages 1352-1356

Von Bubnoff, N., Schneller, F., Peschel, C., Duyster, J. BCR-ABL Gene Mutations in Relation to Clinical Resistance of Philadelphia-Chromosome-Positive Leukemia to STI571: A Prospective Study. The Lancet, Volume 359 (Feb. 9, 2002) Pages 487-491

Von Bubnoff, N., Veach D R, Van Der Kuip H, Aulitzky W E, Sanger J, Seipel P, Bornmann W G, Peschel C, Clarkson B, Duyster J. A cell-based screen for resistance of Bcr-Abl positive leukemia identifies the mutation pattern for PD166326, an alternative Abl kinase inhibitor. Blood, Volume 105 (Feb. 15, 2005) Pages 1652-1659

Wakai, T., Kanda, T., Hirota, S., Ohashi, A., Shirai, Y. Hatakeyama, K. Late Resistance to Imatinib Therapy in a Metastatic Gastrointestinal Stromal Tumour is Associated With a Second KIT Mutation. British Journal of Cancer, Volume 90 (Jun. 1, 2004) Pages 2059-2061

Warmuth, M., Mathes, R., Hallek, M. Method for Selecting Enzyme Inhibitors. U.S. Patent Application 2003/0162222 A1 (Aug. 28, 2003)

Weigel, U., Meyer, M., Sebald, W. Mutant Proteins of Human Interleukin 2: Renaturation Yield, Proliferative Activity and Receptor Binding. European Journal of Biochemistry, Volume 180 (Mar. 15, 1989) Pages 295-300.

Weisberg E, Catley L, Kujawa J, Atadja P, Remiszewski S, Fuerst P, Cavazza C, Anderson K, Griffin J D. Histone deacetylase inhibitor NVP-LAQ824 has significant activity against myeloid leukemia cells in vitro and in vivo. Leukemia, Volume 18 (December 2004) Pages 1951-1963

Weisberg, E., Griffin, J. D. Mechanism of Resistance to the ABL Tyrosine Kinase Inhibitor STI 571 in BCR/ABL-Transformed Hematopoietic Cell Lines. Blood, Volume 95 (Jun. 1, 2000) Pages 3498-3505

Weisberg B, Manley P W, Breitenstein W, Bruggen J, Cowan-Jacob S W, Ray A, Huntly B, Fabbro D, Fendrich G, Hall-Meyers E, Kung A L, Mestan J, Daley G Q, Callahan L, Catley L, Cavazza C, Azam M, Neuberg D, Wright R D, Gilliland D G, Griffin J D. Characterization of AMN107, a selective inhibitor of native and mutant Bcr-Abl. Cancer Cell, Volume 7 (February 2005) Pages 129-41

White, M F, Livingston, J M, Backer, Lauris, V, Dull, T J, Ullrich A, Kahn, C R. Mutation of the Insulin Receptor at Tyrosine 960 Inhibits Signal Transmission but Does Not Affect Its Tyrosine Kinase Activity. Cell, Volume 54 (Aug. 26, 1988) Pages 641-649

What is claimed is:

1. A method of testing cellular specificity of a chemical agent, the method comprising:

a) providing a test cell which expresses a target protein and is capable of manifesting a phenoresponse linked to the presence and functional activity of the target protein in the cell and wherein the phenoresponse is also capable of being modulated by a known modulator;

b) providing a control cell which expresses the target protein at a lower level than the test cell or does not express the target protein, the control cell being capable of manifesting the phenoresponse to a lesser extent than the test cell or not at all;

c) measuring modulation of the phenoresponse of the test cell treated with the known modulator;

d) measuring modulation of the phenoresponse of the control cell treated with the known modulator;

e) measuring modulation of the phenoresponse of the test cell treated with a chemical agent;

f) measuring modulation of the phenoresponse of the control cell treated with the chemical agent;

g) determining the cellular specificity of the chemical agent using the test cell and the control cell, and the cellular specificity of the known modulator using the test cell and the control cell;

h) comparing the cellular specificity of the chemical agent to the cellular specificity of the known modulator and, if the cellular specificity of the chemical agent is greater than the cellular specificity of the known modulator, determining that the cellular specificity of the chemical agent is improved compared to the cellular specificity of the known modulator.

2. The method of claim 1, wherein the chemical agent is an inhibitor of the target protein.

3. The method of claim 2, wherein comparing the cellular specificity of the chemical agent to the cellular specificity of the known modulator comprises comparing i) a first ratio of $IC_{50}$ for the control cell over $IC_{50}$ for the test cell, determined using the chemical agent, to ii) a second ratio of $IC_{50}$ for the control cell over $IC_{50}$ for the test cell, determined using the known modulator.

4. The method of claim 1, wherein the chemical agent is an activator of the target protein.

5. The method of claim 4, wherein comparing the cellular specificity of the chemical agent to the cellular specificity of the known modulator comprises comparing i) a first ratio of $AC_{50}$ for the test cell over $AC_{50}$ for the control cell, determined using the chemical agent, to ii) a second ratio of $AC_{50}$ for the test cell over $AC_{50}$ for the control cell, determined using the known modulator.

6. The method of claim 1, wherein the modulation of the phenoresponses of the test cells and control cells are measured at the same time.

7. The method of claim 1, wherein the modulation of the phenoresponses of the test cells and control cells are measured at different times.

8. The method of claim 1, wherein the target protein is an enzyme.

9. The method of claim 1, wherein the target protein is a theramutein.

10. The method of claim 1, wherein the target protein is a cell cycle control protein.

11. The method of claim 1, wherein the target protein is a docking protein.

12. The method of claim 1, wherein the target protein is a cell surface receptor.

13. The method of claim 1, wherein the phenoresponse of the test cell comprises a growth characteristic of the test cell and the phenoresponse of the control cell comprises the growth characteristic of the control cell.

14. The method of claim 1, wherein the phenoresponse of the test cell comprises proliferation of the test cell and the phenoresponse of the control cell comprises proliferation of the control cell.

15. The method of claim 1, wherein the phenoresponse of the test cell comprises a transformation state of the test cell and the phenoresponse of the control cell comprises the transformation state of the control cell.

16. The method of claim 1, wherein the phenoresponse of the test cell comprises a differentiation state of the test cell and the phenoresponse of the control cell comprises the differentiation state of the control cell.

17. The method of claim 1, wherein the phenoresponse of the test cell comprises a phosphorylation state of a second protein in the test cell that is not the target protein and the phenoresponse of the control cell comprises the phosphorylation state of the second protein in the control cell.

18. The method of claim 1, wherein the phenoresponse of the test cell comprises a change of an ion flux across a membrane of the test cell and the phenoresponse of the control cell comprises a change of the ion flux across the membrane of the control cell.

19. The method of claim 18, wherein the ion flux comprises flux of at least one of the ions selected from the group consisting of calcium ions, sodium ions, chloride ions, potassium ions, and hydrogen ions.

20. The method of claim 1, wherein the phenoresponse of the test cell comprises a change of pH within the test cell and the phenoresponse of the control cell comprises a change of pH within the control cell.

21. The method of claim 1, wherein the phenoresponse of the test cell comprises a change in concentration of an intracellular chemical species in the test cell and the phenoresponse of the control cell comprises a change in the concentration of the intracellular chemical species within the control cell.

22. The method of claim 21, wherein the intracellular chemical species comprises at least one of a phosphoinositide and a cyclic nucleotide.

23. The method of claim 22, wherein the cyclic nucleotide comprises cyclic adenosine monophosphate (cAMP).

* * * * *